(12) United States Patent
Kakumanu et al.

(10) Patent No.: US 12,109,196 B2
(45) Date of Patent: *Oct. 8, 2024

(54) NON-SEDATING DEXMEDETOMIDINE TREATMENT REGIMENS

(71) Applicant: BioXcel Therapeutics, Inc., New Haven, CT (US)

(72) Inventors: Vasukumar Kakumanu, Guntur (IN); David Christian Hanley, Brookfield, CT (US); Frank Yocca, Clinton, CT (US); Chetan Dalpatbhai Lathia, Woodbridge, CT (US); Lavanya Rajachandran, New Haven, CT (US); Robert Risinger, New Haven, CT (US)

(73) Assignee: BioXcel Therapeutics, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,689

(22) Filed: Feb. 16, 2024

(65) Prior Publication Data

US 2024/0197684 A1 Jun. 20, 2024

Related U.S. Application Data

(63) Continuation of application No. 18/216,890, filed on Jun. 30, 2023, which is a continuation of application No. 17/993,422, filed on Nov. 23, 2022, now Pat. No. 11,890,272, which is a continuation of application No. 17/628,021, filed as application No. PCT/US2020/042618 on Jul. 17, 2020.

(60) Provisional application No. 63/037,759, filed on Jun. 11, 2020, provisional application No. 62/977,554, filed on Feb. 17, 2020, provisional application No. 62/970,411, filed on Feb. 5, 2020, provisional application No. 62/963,769, filed on Jan. 21, 2020, provisional application No. 62/943,022, filed on Dec. 3, 2019, provisional application No. 62/877,056, filed on Jul. 22, 2019, provisional application No. 62/876,371, filed on Jul. 19, 2019.

(51) Int. Cl.

| | | |
|---|---|---|
| A61K 31/4174 | (2006.01) |
| A61K 9/00 | (2006.01) |
| A61K 9/06 | (2006.01) |
| A61K 9/20 | (2006.01) |
| A61K 9/70 | (2006.01) |
| A61K 47/10 | (2017.01) |
| A61K 47/26 | (2006.01) |
| A61K 47/34 | (2017.01) |
| A61K 47/38 | (2006.01) |
| A61K 47/44 | (2017.01) |
| A61P 25/18 | (2006.01) |
| A61P 25/20 | (2006.01) |
| A61P 25/36 | (2006.01) |

(52) U.S. Cl.
CPC .......... *A61K 31/4174* (2013.01); *A61K 9/006* (2013.01); *A61K 9/06* (2013.01); *A61K 9/2013* (2013.01); *A61K 9/2018* (2013.01); *A61K 9/7007* (2013.01); *A61K 9/7015* (2013.01); *A61K 47/10* (2013.01); *A61K 47/26* (2013.01); *A61K 47/34* (2013.01); *A61K 47/38* (2013.01); *A61K 47/44* (2013.01); *A61P 25/18* (2018.01); *A61P 25/20* (2018.01); *A61P 25/36* (2018.01)

(58) Field of Classification Search
CPC ..... A61K 9/006; A61K 9/7007; A61K 9/7015
See application file for complete search history.

(56) References Cited

U.S. PATENT DOCUMENTS

| | | |
|---|---|---|
| 3,912,743 A | 10/1975 | Christensen et al. |
| 4,007,196 A | 2/1977 | Christensen et al. |
| 4,085,225 A | 4/1978 | Welle et al. |
| 4,136,193 A | 1/1979 | Bogeso et al. |
| 4,314,081 A | 2/1982 | Molloy et al. |
| 4,407,957 A | 10/1983 | Lim |
| 4,478,836 A | 10/1984 | Mouzin et al. |
| 4,670,455 A | 6/1987 | Virtanen et al. |
| 4,760,093 A | 7/1988 | Blank et al. |
| 4,760,094 A | 7/1988 | Blank et al. |
| 4,761,501 A | 8/1988 | Husbands et al. |
| 4,767,789 A | 8/1988 | Blank et al. |
| 4,839,170 A | 6/1989 | Sarnoff et al. |
| 4,943,590 A | 7/1990 | Boegesoe et al. |
| 4,956,388 A | 9/1990 | Robertson et al. |

(Continued)

FOREIGN PATENT DOCUMENTS

| | | |
|---|---|---|
| AU | 2007201370 B2 | 9/2009 |
| AU | 2009238370 B2 | 7/2011 |

(Continued)

OTHER PUBLICATIONS

Aantaa, et al., "Intramuscular dexmedetomidine, a novel alpha2-adrenoceptor agonist, as premedication for minor gynaecological surgery", Acta Anaesthesiologica Scandinavica (1991); 35(4): 283-288.

Abdelaziz, et al., "Effect of intranasal dexmedetomidine or intranasal midazolam on prevention of emergence agitation in pediatric strabismus surgery: A randomized controlled study", Egyptian Journal of Anaesthesia (2016) 32: 285-291.

Abdel-Ghaffar, et al., "Oral trans-mucosal dexmedetomidine for controlling of emergence agitation in children undergoing tonsillectomy: a randomized controlled trial", Revista Brasileira de Anestesiologia (2019); 69(5): 469-476.

(Continued)

*Primary Examiner* — Genevieve S Alley
(74) *Attorney, Agent, or Firm* — COOLEY LLP

(57) ABSTRACT

Disclosed herein are methods of administering relatively high doses of dexmedetomidine or a pharmaceutically acceptable salt thereof to a human subject, without also inducing significant sedation. The disclosed methods are particularly suitable for the treatment of agitation, especially when associated with neurodegenerative and/or neuropsychiatric diseases such as schizophrenia, bipolar illness such as bipolar disorder or mania, dementia, depression, or delirium.

25 Claims, 31 Drawing Sheets

(56) References Cited

U.S. PATENT DOCUMENTS

| | | |
|---|---|---|
| 5,039,540 A | 8/1991 | Ecanow |
| 5,178,878 A | 1/1993 | Wehling et al. |
| 5,188,825 A | 2/1993 | Iles et al. |
| 5,217,718 A | 6/1993 | Colley et al. |
| 5,330,763 A | 7/1994 | Gole et al. |
| 5,395,907 A | 3/1995 | Zajaczkowski |
| 5,508,367 A | 4/1996 | Zajaczkowski |
| 5,520,639 A | 5/1996 | Peterson et al. |
| 5,565,268 A | 10/1996 | Zajaczkowski |
| 5,605,911 A | 2/1997 | Olney et al. |
| 5,631,023 A | 5/1997 | Kearney et al. |
| 5,654,007 A | 8/1997 | Johnson et al. |
| 5,700,873 A | 12/1997 | Zajaczkowski et al. |
| 5,704,911 A | 1/1998 | Parsons |
| 5,712,301 A | 1/1998 | Jaatinen et al. |
| 5,726,250 A | 3/1998 | Zajaczkowski |
| 5,729,958 A | 3/1998 | Kearney et al. |
| 5,731,387 A | 3/1998 | Zajaczkowski |
| 5,780,014 A | 7/1998 | Eljamal et al. |
| 5,798,113 A | 8/1998 | Dionne et al. |
| 5,814,607 A | 9/1998 | Patton |
| 5,817,332 A | 10/1998 | Urtti et al. |
| 5,820,875 A | 10/1998 | Fallon et al. |
| 5,827,541 A | 10/1998 | Yarwood et al. |
| 5,837,287 A | 11/1998 | Yarwood et al. |
| 5,846,233 A | 12/1998 | Lilley et al. |
| 5,879,327 A | 3/1999 | Moreau DeFarges et al. |
| 5,951,999 A | 9/1999 | Therriault et al. |
| 5,976,577 A | 11/1999 | Green et al. |
| 6,149,938 A | 11/2000 | Bonadeo et al. |
| 6,156,339 A | 12/2000 | Grother et al. |
| 6,174,546 B1 | 1/2001 | Therriault et al. |
| 6,200,604 B1 | 3/2001 | Pather et al. |
| 6,212,791 B1 | 4/2001 | Thompson et al. |
| 6,221,392 B1 | 4/2001 | Khankari et al. |
| 6,239,228 B1 | 5/2001 | Zajaczkowski et al. |
| 6,269,615 B1 | 8/2001 | Amborn et al. |
| 6,284,270 B1 | 9/2001 | Lagoviyer et al. |
| 6,297,240 B1 | 10/2001 | Embleton |
| 6,316,029 B1 | 11/2001 | Jain et al. |
| 6,413,549 B2 | 7/2002 | Green et al. |
| 6,465,010 B1 | 10/2002 | Lagoviyer et al. |
| 6,471,992 B1 | 10/2002 | Yoo et al. |
| 6,509,040 B1 | 1/2003 | Murray et al. |
| 6,709,669 B1 | 3/2004 | Murray et al. |
| 6,716,867 B1 | 4/2004 | Aantaa et al. |
| 6,726,928 B2 | 4/2004 | Yarwood et al. |
| 6,753,782 B2 | 6/2004 | Power |
| 6,814,978 B2 | 11/2004 | Bunick et al. |
| 6,908,626 B2 | 6/2005 | Cooper et al. |
| 6,982,251 B2 | 1/2006 | Ghosal et al. |
| 7,001,609 B1 | 2/2006 | Matson et al. |
| 7,282,217 B1 | 10/2007 | Grimshaw et al. |
| 7,357,891 B2 | 4/2008 | Yang et al. |
| 7,425,292 B2 | 9/2008 | Yang et al. |
| 7,425,341 B1 | 9/2008 | Grimshaw et al. |
| 7,470,397 B2 | 12/2008 | Meathrel et al. |
| 7,579,019 B2 | 8/2009 | Tapolsky et al. |
| 7,580,798 B2 | 8/2009 | Brunner et al. |
| 7,630,758 B2 | 12/2009 | Lapinlampi et al. |
| 7,666,337 B2 | 2/2010 | Yang et al. |
| 7,727,466 B2 | 6/2010 | Meathrel et al. |
| 7,897,080 B2 | 3/2011 | Yang et al. |
| 7,939,105 B2 | 5/2011 | Parikh et al. |
| 7,972,618 B2 | 7/2011 | Fuisz et al. |
| 7,972,621 B2 | 7/2011 | Wong et al. |
| 7,993,674 B2 | 8/2011 | Weibel |
| 8,048,449 B2 | 11/2011 | Kashid et al. |
| 8,127,516 B2 | 3/2012 | Lee et al. |
| 8,158,152 B2 | 4/2012 | Palepu |
| 8,221,480 B2 | 7/2012 | Boyden et al. |
| 8,241,661 B1 | 8/2012 | Fuisz et al. |
| 8,242,158 B2 | 8/2012 | Roychowdhury et al. |
| 8,256,233 B2 | 9/2012 | Boyden et al. |
| 8,282,954 B2 | 10/2012 | Bogue et al. |
| 8,313,768 B2 | 11/2012 | Kriksunov et al. |
| 8,324,260 B1 | 12/2012 | Garcia Da Rocha et al. |
| 8,338,470 B1 | 12/2012 | Roychowdhury et al. |
| 8,364,221 B2 | 1/2013 | Mannheimer et al. |
| 8,414,922 B2 | 4/2013 | Bryson et al. |
| 8,436,033 B1 | 5/2013 | Roychowdhury et al. |
| 8,455,527 B1 | 6/2013 | Roychowdhury et al. |
| 8,568,777 B2 | 10/2013 | Fuisz |
| 8,617,589 B2 | 12/2013 | Fuisz et al. |
| 8,648,106 B2 | 2/2014 | Roychowdhury et al. |
| 8,663,687 B2 | 3/2014 | Myers et al. |
| 8,663,696 B2 | 3/2014 | Myers et al. |
| 8,685,437 B2 | 4/2014 | Yang et al. |
| 8,846,074 B2 | 9/2014 | Bryson et al. |
| 8,882,684 B2 | 11/2014 | Halperin et al. |
| 8,882,703 B2 | 11/2014 | Hickle |
| 8,900,498 B2 | 12/2014 | Yang et al. |
| 8,936,825 B2 | 1/2015 | Myers et al. |
| 9,073,294 B2 | 7/2015 | Kumar et al. |
| 9,192,580 B2 | 11/2015 | Green et al. |
| 9,248,146 B2 | 2/2016 | Barnhart et al. |
| 9,283,219 B2 | 3/2016 | Bryson et al. |
| 9,303,918 B2 | 4/2016 | Li |
| 9,320,712 B2 | 4/2016 | Roychowdhury et al. |
| 9,346,601 B2 | 5/2016 | Bogue et al. |
| 9,427,412 B2 | 8/2016 | Bryson et al. |
| 9,441,142 B2 | 9/2016 | Malik et al. |
| 9,545,376 B2 | 1/2017 | Musho et al. |
| 9,561,191 B2 | 2/2017 | Myers et al. |
| 9,572,773 B2 | 2/2017 | Dormady et al. |
| 9,585,961 B2 | 3/2017 | Barnhart et al. |
| 9,616,049 B2 | 4/2017 | Roychowdhury et al. |
| 9,649,296 B1 | 5/2017 | Pizza |
| 9,662,297 B2 | 5/2017 | Musho et al. |
| 9,662,301 B2 | 5/2017 | Musho et al. |
| 9,717,796 B1 | 8/2017 | Pizza |
| 9,775,819 B2 | 10/2017 | Bahl et al. |
| 9,795,559 B2 | 10/2017 | Henwood et al. |
| 9,814,674 B2 | 11/2017 | Musho et al. |
| 9,855,221 B2 | 1/2018 | Myers et al. |
| 9,901,650 B2 | 2/2018 | Nedergaard et al. |
| 9,931,305 B2 | 4/2018 | Yang et al. |
| 9,937,122 B2 | 4/2018 | Zhu et al. |
| 9,937,123 B2 | 4/2018 | Barnhart et al. |
| 9,974,754 B2 | 5/2018 | Yamazaki et al. |
| 9,993,428 B2 | 6/2018 | Gerard et al. |
| 10,130,684 B2 | 11/2018 | Rubin et al. |
| 10,130,766 B1 | 11/2018 | Bibian et al. |
| 10,137,245 B2 | 11/2018 | Melker et al. |
| 10,285,953 B2 | 5/2019 | Bryson et al. |
| 10,314,503 B2 | 6/2019 | Prerau et al. |
| 10,383,574 B2 | 8/2019 | Purdon et al. |
| 10,548,839 B2 | 2/2020 | Tian |
| 10,602,978 B2 | 3/2020 | Purdon et al. |
| 10,792,246 B2 | 10/2020 | Kakumanu et al. |
| 11,116,723 B2 | 9/2021 | Temtsin-Krayz |
| 11,478,422 B2 | 10/2022 | Kakumanu et al. |
| 11,497,711 B2 | 11/2022 | Kakumanu et al. |
| 11,517,524 B2 | 12/2022 | Kakumanu et al. |
| 11,554,106 B2 | 1/2023 | Petitjean et al. |
| 11,559,484 B2 | 1/2023 | Kakumanu et al. |
| 11,786,508 B2 | 10/2023 | Nandabalan et al. |
| 11,806,334 B1 | 11/2023 | Kakumanu et al. |
| 11,806,429 B2 | 11/2023 | Kakumanu et al. |
| 11,839,604 B2 | 12/2023 | Nandabalan et al. |
| 11,890,272 B2 | 2/2024 | Kakumanu et al. |
| 2002/0037977 A1 | 3/2002 | Feldstein et al. |
| 2002/0192287 A1 | 12/2002 | Mooney et al. |
| 2003/0096012 A1 | 5/2003 | Besse et al. |
| 2003/0124191 A1 | 7/2003 | Besse et al. |
| 2003/0145854 A1 | 8/2003 | Hickle |
| 2003/0158242 A1 | 8/2003 | Kugelmann |
| 2004/0138312 A1 | 7/2004 | Wheeler et al. |
| 2004/0156894 A1 | 8/2004 | Grother et al. |
| 2005/0037055 A1 | 2/2005 | Yang et al. |
| 2005/0118217 A1 | 6/2005 | Barnhart et al. |
| 2005/0222270 A1 | 10/2005 | Olney et al. |
| 2006/0058590 A1 | 3/2006 | Shaw et al. |
| 2006/0058700 A1 | 3/2006 | Marro et al. |

(56) References Cited

U.S. PATENT DOCUMENTS

| | | |
|---|---|---|
| 2006/0069086 A1 | 3/2006 | Michalow |
| 2006/0199805 A1 | 9/2006 | Pyke et al. |
| 2007/0117835 A1 | 5/2007 | Hung |
| 2007/0184099 A1 | 8/2007 | Nowak |
| 2007/0281003 A1 | 12/2007 | Fuisz et al. |
| 2008/0026040 A1 | 1/2008 | Farr et al. |
| 2008/0124381 A1 | 5/2008 | Barnhart et al. |
| 2008/0280947 A1 | 11/2008 | Blondino et al. |
| 2008/0299005 A1 | 12/2008 | Meathrel et al. |
| 2008/0306980 A1 | 12/2008 | Brunner et al. |
| 2009/0076156 A1 | 3/2009 | Husain et al. |
| 2009/0099480 A1 | 4/2009 | Salgo et al. |
| 2009/0142850 A1 | 6/2009 | Meathrel et al. |
| 2009/0226522 A1 | 9/2009 | Howes et al. |
| 2009/0275853 A1 | 11/2009 | Sarkela |
| 2010/0029706 A1 | 2/2010 | Miller et al. |
| 2010/0130566 A1 | 5/2010 | Purpura et al. |
| 2010/0137937 A1 | 6/2010 | John et al. |
| 2010/0196286 A1 | 8/2010 | Armer et al. |
| 2011/0021588 A1 | 1/2011 | Henwood et al. |
| 2011/0066004 A1 | 3/2011 | Sullivan et al. |
| 2011/0172262 A1 | 7/2011 | Deftereos et al. |
| 2011/0245633 A1 | 10/2011 | Goldberg et al. |
| 2011/0269777 A1 | 11/2011 | Bachurin et al. |
| 2011/0290694 A1 | 12/2011 | Fuisz et al. |
| 2012/0076921 A1 | 3/2012 | Myers et al. |
| 2012/0100278 A1 | 4/2012 | Nowak et al. |
| 2012/0195955 A1 | 8/2012 | Bryson et al. |
| 2012/0309804 A1 | 12/2012 | Horn |
| 2012/0325209 A1 | 12/2012 | Quintin |
| 2012/0328688 A1 | 12/2012 | Fuisz et al. |
| 2013/0072532 A1 | 3/2013 | Henwood et al. |
| 2013/0095156 A1 | 4/2013 | Barnhart et al. |
| 2013/0096172 A1 | 4/2013 | Garcia Da Rocha et al. |
| 2013/0116215 A1 | 5/2013 | Coma et al. |
| 2013/0178465 A1 | 7/2013 | Henwood et al. |
| 2013/0225626 A1 | 8/2013 | Bryson et al. |
| 2014/0010873 A1 | 1/2014 | Tygesen et al. |
| 2014/0163080 A1 | 6/2014 | Horn |
| 2014/0203480 A1 | 7/2014 | Musho et al. |
| 2014/0261990 A1 | 9/2014 | Dadey et al. |
| 2014/0275194 A1 | 9/2014 | Dadey et al. |
| 2014/0287181 A1 | 9/2014 | Malik et al. |
| 2014/0316217 A1 | 10/2014 | Purdon et al. |
| 2014/0323898 A1 | 10/2014 | Purdon et al. |
| 2014/0328898 A1 | 11/2014 | Hood et al. |
| 2014/0377329 A1 | 12/2014 | Bryson et al. |
| 2015/0098980 A1 | 4/2015 | Pongpeerapat et al. |
| 2015/0098981 A1 | 4/2015 | Pongpeerapat et al. |
| 2015/0098982 A1 | 4/2015 | Pongpeerapat et al. |
| 2015/0098983 A1 | 4/2015 | Pongpeerapat et al. |
| 2015/0098997 A1 | 4/2015 | Pongpeerapat et al. |
| 2015/0141772 A1 | 5/2015 | LeBOEUF et al. |
| 2015/0250957 A1 | 9/2015 | Albalat |
| 2015/0258067 A1 | 9/2015 | Kokkonen et al. |
| 2016/0000945 A1 | 1/2016 | Nedergaard et al. |
| 2016/0113885 A1 | 4/2016 | Myers et al. |
| 2016/0151299 A1 | 6/2016 | Bryson et al. |
| 2016/0310441 A1 | 10/2016 | Yamazaki et al. |
| 2016/0324446 A1 | 11/2016 | Prerau et al. |
| 2016/0338972 A1 | 11/2016 | Bryson et al. |
| 2016/0374588 A1 | 12/2016 | Shariff et al. |
| 2017/0087084 A1 | 3/2017 | Musho et al. |
| 2017/0087097 A1 | 3/2017 | Musho et al. |
| 2017/0128358 A1 | 5/2017 | Barnhart et al. |
| 2017/0128421 A1 | 5/2017 | Sura et al. |
| 2017/0165235 A1 | 6/2017 | Roychowdhury et al. |
| 2017/0231556 A1 | 8/2017 | Purdon et al. |
| 2017/0239221 A1 | 8/2017 | Negi et al. |
| 2017/0246108 A1 | 8/2017 | Musho et al. |
| 2017/0252294 A1 | 9/2017 | Musho et al. |
| 2017/0273611 A1 | 9/2017 | Purdon et al. |
| 2017/0274174 A1 | 9/2017 | Purdon et al. |
| 2017/0296482 A1 | 10/2017 | Myers et al. |
| 2018/0055764 A1 | 3/2018 | Henwood et al. |
| 2018/0065767 A1 | 3/2018 | Bogue et al. |
| 2018/0098937 A1 | 4/2018 | Horn |
| 2018/0110897 A1 | 4/2018 | Bush et al. |
| 2018/0117012 A1 | 5/2018 | Shudo et al. |
| 2018/0147201 A1 | 5/2018 | Toledano |
| 2018/0177797 A1 | 6/2018 | Berdahl et al. |
| 2018/0360736 A1 | 12/2018 | Obeid et al. |
| 2019/0022397 A1 | 1/2019 | Srivastava et al. |
| 2019/0183729 A1 | 6/2019 | Sura et al. |
| 2019/0209022 A1 | 7/2019 | Sobol et al. |
| 2019/0216345 A1 | 7/2019 | Scheib |
| 2019/0216389 A1 | 7/2019 | Scheib |
| 2019/0276707 A1 | 9/2019 | Wong et al. |
| 2019/0314274 A1 | 10/2019 | Masto et al. |
| 2019/0365715 A1 | 12/2019 | Nandabalan et al. |
| 2019/0374158 A1 | 12/2019 | Brown et al. |
| 2020/0000708 A1 | 1/2020 | Barnhart et al. |
| 2020/0000717 A1 | 1/2020 | Kakumanu et al. |
| 2020/0069650 A1 | 3/2020 | Korpivaara et al. |
| 2020/0093800 A1 | 3/2020 | Pongpeerapat et al. |
| 2020/0138721 A1 | 5/2020 | Grother et al. |
| 2020/0168340 A1 | 5/2020 | Park et al. |
| 2020/0172768 A1 | 6/2020 | Nolen et al. |
| 2020/0243196 A1 | 7/2020 | Ohno et al. |
| 2020/0265950 A1 | 8/2020 | Hosoi et al. |
| 2020/0345635 A1 | 11/2020 | Kakumanu et al. |
| 2021/0077388 A1 | 3/2021 | Kakumanu et al. |
| 2021/0267944 A1 | 9/2021 | Yocca et al. |
| 2022/0031663 A1 | 2/2022 | Nandabalan et al. |
| 2022/0110864 A1 | 4/2022 | Kakumanu et al. |
| 2022/0142918 A1 | 5/2022 | Kakumanu et al. |
| 2022/0160629 A1 | 5/2022 | Kakumanu et al. |
| 2022/0202373 A1 | 6/2022 | Yocca et al. |
| 2022/0226288 A1 | 7/2022 | Adedoyin et al. |
| 2022/0276034 A1 | 9/2022 | Kinney et al. |
| 2022/0395222 A1 | 12/2022 | Yocca et al. |
| 2023/0081503 A1 | 3/2023 | Nandabalan et al. |
| 2023/0093109 A1 | 3/2023 | Nandabalan et al. |
| 2023/0118091 A1 | 4/2023 | Kakumanu et al. |
| 2023/0140624 A1 | 5/2023 | Kakumanu et al. |
| 2023/0218580 A1 | 7/2023 | Nandabalan et al. |
| 2023/0338339 A1 | 10/2023 | Kakumanu et al. |
| 2023/0381099 A1 | 11/2023 | Kakumanu et al. |
| 2023/0390190 A1 | 12/2023 | Kakumanu et al. |
| 2023/0414572 A1 | 12/2023 | Negi et al. |
| 2024/0024288 A1 | 1/2024 | Kakumanu et al. |
| 2024/0024289 A1 | 1/2024 | Yocca et al. |

FOREIGN PATENT DOCUMENTS

| | | |
|---|---|---|
| AU | 2014227693 B2 | 6/2018 |
| CA | 2324967 A1 | 5/2002 |
| CA | 3026783 A1 | 12/2017 |
| CN | 101365373 A | 2/2009 |
| CN | 101496801 A | 8/2009 |
| CN | 102657635 A | 9/2012 |
| CN | 103284945 A | 9/2013 |
| CN | 104161760 A | 11/2014 |
| CN | 104470516 A | 3/2015 |
| CN | 104784174 A | 7/2015 |
| CN | 105168122 A | 12/2015 |
| CN | 105287519 A | 2/2016 |
| CN | 105534891 A | 5/2016 |
| CN | 106038538 A | 10/2016 |
| CN | 106539778 A | 3/2017 |
| CN | 106727443 A | 5/2017 |
| CN | 106727524 A | 5/2017 |
| CN | 107028880 A | 8/2017 |
| CN | 107137399 A | 9/2017 |
| CN | 107412152 A | 12/2017 |
| CN | 107412204 A | 12/2017 |
| CN | 107693485 A | 2/2018 |
| CN | 108498469 A | 9/2018 |
| CN | 109620802 A | 4/2019 |
| CN | 110893186 A | 3/2020 |
| CN | 111481506 A | 8/2020 |
| CN | 112138250 A | 12/2020 |
| EP | 1549305 B1 | 4/2009 |
| EP | 2243468 A1 | 10/2010 |

(56) References Cited

FOREIGN PATENT DOCUMENTS

| | | |
|---|---|---|
| EP | 2252290 A1 | 11/2010 |
| EP | 1169314 B2 | 6/2011 |
| EP | 1695094 B1 | 6/2013 |
| EP | 3326612 A1 | 5/2018 |
| JP | 2009526829 A | 7/2009 |
| JP | 5921928 B2 | 5/2016 |
| JP | 2016154598 A | 9/2016 |
| JP | 2019048091 A | 3/2019 |
| KR | 101859486 B1 | 6/2018 |
| KR | 20190109310 A | 9/2019 |
| RU | 2635532 C1 | 11/2017 |
| SU | 1138164 A1 | 2/1985 |
| TW | 201801670 A | 1/2018 |
| WO | WO-9514746 A2 | 6/1995 |
| WO | WO-9830207 A1 | 7/1998 |
| WO | WO-9837111 A1 | 8/1998 |
| WO | WO-9938496 A1 | 8/1999 |
| WO | WO-0044351 A1 | 8/2000 |
| WO | WO-02089794 A1 | 11/2002 |
| WO | WO-2004032913 A1 | 4/2004 |
| WO | WO-2005032519 A1 | 4/2005 |
| WO | WO-2005039499 A2 | 5/2005 |
| WO | WO-2006031209 A1 | 3/2006 |
| WO | WO-2006090371 A2 | 8/2006 |
| WO | WO-2008079721 A1 | 7/2008 |
| WO | WO-2008091588 A1 | 7/2008 |
| WO | WO-2009005771 A1 | 1/2009 |
| WO | WO-2009048606 A1 | 4/2009 |
| WO | WO-2009076165 A1 | 6/2009 |
| WO | WO-2010132882 A2 | 11/2010 |
| WO | WO-2011039686 A1 | 4/2011 |
| WO | WO-2011127586 A1 | 10/2011 |
| WO | WO-2012009144 A2 | 1/2012 |
| WO | WO-2012075373 A2 | 6/2012 |
| WO | WO-2012083269 A1 | 6/2012 |
| WO | WO-2012177326 A1 | 12/2012 |
| WO | WO-2013090278 A2 | 6/2013 |
| WO | WO-2013103378 A1 | 7/2013 |
| WO | WO-2013130577 A2 | 9/2013 |
| WO | WO-2013173317 A1 | 11/2013 |
| WO | WO-2014120936 A2 | 8/2014 |
| WO | WO-2014130777 A1 | 8/2014 |
| WO | WO-2014153489 A1 | 9/2014 |
| WO | WO-2014176444 A1 | 10/2014 |
| WO | WO-2015054058 A1 | 4/2015 |
| WO | WO-2015054059 A2 | 4/2015 |
| WO | WO-2015054061 A1 | 4/2015 |
| WO | WO-2015054063 A1 | 4/2015 |
| WO | WO-2016061413 A1 | 4/2016 |
| WO | WO-2016061554 A1 | 4/2016 |
| WO | WO-2016075365 A1 | 5/2016 |
| WO | WO-2016089997 A1 | 6/2016 |
| WO | WO-2017117627 A1 | 7/2017 |
| WO | WO-2018072015 A1 | 4/2018 |
| WO | WO-2018086498 A1 | 5/2018 |
| WO | WO-2018109272 A1 | 6/2018 |
| WO | WO-2018116202 A1 | 6/2018 |
| WO | WO-2018118673 A2 | 6/2018 |
| WO | WO-2018126182 A1 | 7/2018 |
| WO | WO-2018162845 A1 | 9/2018 |
| WO | WO-2019036253 A1 | 2/2019 |
| WO | WO-2019044619 A1 | 3/2019 |
| WO | WO-2019070929 A1 | 4/2019 |
| WO | WO-2019073927 A1 | 4/2019 |
| WO | WO-2019158810 A1 | 8/2019 |
| WO | WO-2020006073 A1 | 1/2020 |
| WO | WO-2020006092 A1 | 1/2020 |
| WO | WO-2020006119 A1 | 1/2020 |
| WO | WO-2020259440 A1 | 12/2020 |
| WO | WO-2021016112 A2 | 1/2021 |
| WO | WO-2021055595 A1 | 3/2021 |
| WO | WO-2021163482 A1 | 8/2021 |
| WO | WO-2022076818 A1 | 4/2022 |
| WO | WO-2022147537 A1 | 7/2022 |
| WO | WO-2022183029 A1 | 9/2022 |
| WO | WO-2023278824 A1 | 1/2023 |

OTHER PUBLICATIONS

Abdelmageed, et al., "Intramuscular dexmedetomidine for prevention of shivering after general anesthesia in patients undergoing arthroscopic anterior cruciate ligament reconstruction." Ain-Shams Journal of Anesthesiology (2014); 7(2): 156-162.

Adami, et al., "Combinations of dexmedetomidine and alfaxalone with butorphanol in cats: application of an innovative stepwise optimization method to identify optimal clinical doses for intramuscular anaesthesia", Journal of Feline Medicine and Surgery (2016); 18 (10): 846-853.

Ahmad, et al., "Effects of Midazolam or Midazolam-Fentanyl on Sedation and Analgesia Produced by Intramuscular Dexmedetomidine in Dogs", Asian Journal of Animal Sciences (2011); 5 (5): 302-316.

Aho, et al., "Intramuscularly administered dexmedetomidine attenuates hemodynamic and stress hormone responses to gynecologic laparoscopy", Anesthesia & Analgesia (1992); 75(6): 932-939.

Aich, et al., "A Comparison of Intranasal Dexmedetomidine and Intranasal Midazolam for Premedication in Children Undergoing Elective Surgeries", International Journal of Science and Research (IJSR) (2016); 5 (7): 1730-1737.

Aikaterini, et al. "Bradycardia leading to asystole following dexmedetomidine infusion during cataract surgery: dexmedetomidine-induced asystole for cataract surgery", Case Reports in Anesthesiology (2018); 2018(2896032); 2 pages.

Akin, et al., "Dexmedetomidine vs midazolam for premedication of pediatric patients undergoing anesthesia", Pediatric Anesthesia (2012); 22(9): 871-876.

Albertson, et al., "Is It Prime Time for Alpha2-Adrenocepter Agonists in the Treatment of Withdrawal Syndromes?", Journal of Medical Toxicology (2014) 10: 369-381.

Ali, et al., "Prevention of sevoflurane related emergence agitation in children undergoing adenotonsillectomy: A comparison of dexmedetomidine and propofol", Saudi Journal of Anaesthesia (2013); 7(3): 296-300.

Ambi, et al., "Intranasal dexmedetomidine for paediatric sedation for diagnostic magnetic resonance imaging studies", Indian Journal of Anaesthesia (2012); 56(6): 587-588.

Ansah, et al., "Comparison of three doses of dexmedetomidine with medetomidine in cats following intramuscular administration." Veterinary Pharmacology and Therapeutics (1998); 21(5): 380-387.

Antonino, et al., "Effectiveness Of Intramuscular Dexmedetomidine And Methadone In Combination To Intratesticular Lidodaine For Orquiectomy In Dogs—Preliminary Study", Investigação (2017); 16(7); English abstract only; 2 pages.

Anttila, et al., "Bioavailability of dexmedetomidine after extravascular doses in healthy subjects", British Journal of Clinical Pharmacology (2003); 56(6): 691-693.

Anusua, et al., "Efficacy of Dexmedetomidine in Reducing Emergence Agitation After Sevoflurane Anaesthesia in Indian Paediatric Population", International Journal of Scientific Research (2015); 4(7): 458-461.

ANZCTR Clinical Trial ID: ACTRN12616001522404, "Does ketamine improve the quality of sedation of intranasal dexmedetomidine premedication in children", Fujian Provincial Hospital (Date Registered: Nov. 4, 2016, Date Last Updated: Jan. 29, 2018) [online] https://www.anzctr.org.au/Trial/Registration/TrialReview.aspx?id=369976 (Access Date: May 6, 2018); 5 pages.

Aravindhanthan, et al., "Sublingual spray: a new technology oriented formulation with multiple benefits", International Journal of Research in Pharmaceutical Sciences (2019); 10(4): 2875-2885.

Assad, et al., "Comparative study between prophylactic single dose of fentanyl and dexmedetomidine in the management of agitation after sevoflurane anesthesia in children", Egyptian Journal of Anaesthesia (2011); 27(1): 31-37.

(56) References Cited

OTHER PUBLICATIONS

Aungst, et al., "Comparison of nasal, rectal, buccal, sublingual and intramuscular insulin efficacy and the effects of a bile salt absorption promoter", Journal of Pharmacology and Experimental Therapeutics (1988); 244(1): 23-27.

[Author Unknown] Assessment Report ([Trade Name] Precedex Injection 200μg [Abott] and [Maruishi], Date of Application: Dec. 7, 2001), Oct. 22, 2003, p. 1-57; 29 pages.

[Author Unknown] "Dexmedetomidine", Alzheimer's Drug Discovery Foundation, Cognitive Vitality.org (Mar. 19, 2019); 11 pages.

Ayeko, et al., "Prevention and treatment of sevoflurane emergence agitation and delirium in children with dexmedetomidine", Saudi Journal of Anaesthesia (2014); 8(4): 570-571.

Baddigam, et al., "Dexmedetomidine in the Treatment of Withdrawal Syndromes in Cardiothoracic Surgery Patients", Journal of Intensive Care Medicine (2005); 20(2):118-123.

Bajwa, et al., "Dexmedetomidine: An Adjuvant Making Large Inroads into Clinical Practice", Annals of Medical and Health Sciences Research (Oct.-Dec. 2013); 3(4): 475-483.

Bakri, et al., "Comparison of dexmedetomidine or ondansetron with haloperidol for treatment of postoperative delirium in trauma patients admitted to intensive care unit: randomized controlled trial", Anaesth Pain & Intensive Care (2015); 19(2): 118-123.

Bala, et al., "Orally dissolving strips: A new approach to oral drug delivery system", International Journal of Pharmaceutical Investigation (Apr. 2013); 3(2): 67-76.

Barends, et al., "Intranasal dexmedetomidine in elderly subjects with or without beta blockade: a randomised double-blind single-ascending-dose cohort study", British Journal of Anaesthesia (2020); 124 (4): 411-419.

Barr, et al., "Clinical practice guidelines for the management of pain, agitation, and delirium in adult patients in the intensive care unit", Critical Care Medicine (2013); 41(1): 263-306.

Bartlett, et al., "Understanding the Oral Mucosal Absorption and Resulting Clinical Pharmacokinetics of Asenapine", AAPS PharmSciTech (Dec. 2012); 13(4): 1110-1115.

Batandier, et al., "Acute stress delays brain mitochondrial permeability transition", Journal of Neurochemistry (2014); 131: 314-322.

Battegay, et al., "Double-blind comparative study of paroxetine and amitriptyline in depressed patients of a university psychiatric outpatient clinic (pilot study)", Neuropsychobiology (1985); 13(1-2): 31-37.

Behrle, et al., "Intranasal Dexmedetomidine as a Sedative for Pediatric Procedural Sedation", The Journal of Pediatric Pharmacology and Therapeutics (2017); 22(1): 4-8.

Belgrade, et al., "Dexmedetomidine Infusion for the Management of Opioid-Induced Hyperalgesia", Pain Medicine (2010);11: 1819-1826.

Belkin, et al., "Alpha-2 receptor agonists for the treatment of posttraumatic stress disorder", Drugs in Context (2015); 4(212286); 5 pages.

Benfield, et al., "Fluvoxamine: a review of its pharmacodynamic and pharmacokinetic properties, and therapeutic efficacy in depressive illness", Drugs (1986); 32: 313-334.

Bergese, et al., "A Phase IIIb, Randomized, Double-blind, Placebo-controlled, Multicenter Study Evaluating the Safety and Efficacy of Dexmedetomidine for Sedation During Awake Fiberoptic Intubation", American Journal of Therapeutics (2010); 17, 586-595.

Bharati, et al., "Incidence of cardiac arrest increases with the indiscriminate use of dexmedetomidine: a case series and review of published case reports", Acta Anaesthesiologica Taiwanica (2011); 49(4): 165-167.

Bhardwaj, et al., "Abstract PR227: Comparison of Nasal Dexmedetomidine with Oral Midazolam for Premedication in Children Effect on Psychomotor Recovery", Anesthesia & Analgesia (2016); 123(3S_Suppl): p. 288.

Bhat, et al., "Comparison of intranasal dexmedetomidine and dexmedetomidine-ketamine for premedication in pediatrics patients: A randomized double-blind study", Anesth Essays Res. (2016); 10 (2): 349-355.

Bienvenu, et al., "Treatment of four psychiatric emergencies in the intensive care unit", Critical Care Medicine (2012); 40(9): 2662-2670.

Biermann, et al., "Sedative, cardiovascular, haematologic and biochemical effects of four different drug combinations administered intramuscularly in cats", Veterinary Anaesthesia and Analgesia (2012); 39(2): 137-150.

BioXcel Therapeutics, Inc., "BioXcel Therapeutics Announces BXCL501 Program Initiative for Prevention and Treatment of Acute Agitation using Wearable Digital Devices", (Sep. 18, 2019) [online] https://www.globenewswire.com/en/news-release/2019/09/18/1917334/0/en/BioXcel-Therapeutics-Announces-BXCL501-Program-Initiative-for-Prevention-and-Treatment-of-Acute-Agitation-using-Wearable-Digital-Devices.html (Access Date: Aug. 1, 2022); 3 pages.

BioXcel Therapeutics, Inc., "BioXcel Therapeutics Announces FDA Approval of IGALMI™ (dexmedetomidine) Sublingual Film for Acute Treatment of Agitation Associated with Schizophrenia or Bipolar I or II Disorder in Adults", Press Release (Apr. 6, 2022); 5 pages.

BioXcel Therapeutics, Inc., "BioXcel Therapeutics Announces First Patient Enrolled in Phase 1b/2 Study of BXCL501 for Acute Treatment of Agitation Associated with Dementia", (Jan. 7, 2020) [online] https://www.globenewswire.com/news-release/2020/01/07/1967125/0/en/BioXcel-Therapeutics-Announces-First-Patient-Enrolled-in-Phase-1b-2-Study-of-BXCL501-for-Acute-Treatment-of-Agitation-Associated-with-Dementia.html (Access Date: Aug. 1, 2022); 3 pages.

BioXcel Therapeutics, Inc., "BioXcel Therapeutics Announces Positive Topline Results From Tranquility II Phase 3 Trial of BXCL501 for Acute Treatment of Alzheimer's Disease-Related Agitation", Press Release (Jun. 29, 2023); 4 pages.

BioXcel Therapeutics, Inc., "BioXcel Therapeutics Announces Promising Topline Results from Part 1 of Pivotal Serenity III Trial of BXCL501 for At-Home Use in Acute Treatment of Agitation in Bipolar Disorders or Schizophrenia", Press Release (May 25, 2023); 5 pages.

BioXcel Therapeutics, Inc., "BioXcel Therapeutics, Inc. (BTAI) CEO Vimal Mehta on Q2 2018 Results—Earnings Call Transcript," Seeking Alpha (Aug. 12, 2018) [online] https://seekingalpha.com/article/4198129-bioxcel-therapeutics-inc-btai-ceo-vimal-mehta-q2-2018-results-earnings-call-transcript?part=single (Access Date: Jul. 39, 2019); 13 pages.

BioXcel Therapeutics, Inc., "BioXcel Therapeutics Provides Update on the Clinical Advancement of BXCL501 for the Acute Treatment of Agitation," Globe Newswire (Oct. 30, 2018) [online] https://www.globenewswire.com/news-release/2018/10/30/1638858/0/en/BioXcel-Therapeutics-Provides-Update-on-the-Clinical-Advancement-of-BXCL501-for-the-Acute-Treatment-of-Agitation.html (Access Date: Jul. 22, 2019); 2 pages.

BioXcel Therapeutics, Inc., "BioXcel Therapeutics Reports Positive Results from Study in Agitated Schizophrenia Patients Supporting BXCL501 Clinical Development", Globe Newswire (Nov. 14, 2018) [online] https://www.globenewswire.com/news-release/2018/11/14/1651151/0/en/BioXcel-Therapeutics-Reports-Positive-Results-from-Study-in-Agitated-Schizophrenia-Patients-Supporting-BXCL501-Clinical-Development.html (Access Date: Jul. 22, 2019); 3 pages.

BioXcel Therapeutics, Inc., "BioXcel Therapeutics Reports Second Quarter 2018 Financial Results and Provides Business Update", Press Release (Aug. 8, 2018); 7 pages.

BioXcel Therapeutics, Inc., "BioXcel Therapeutics Reports Third Quarter 2018 Quarterly Results and Provides Business Update", Press Release (Nov. 9, 2018); 8 pages.

BioXcel Therapeutics, Inc., "BioXcel Therapeutics to Host Second Quarter 2018 Financial Results and Business Update", Press Release (Aug. 2, 2018); 2 pages.

BioXcel Therapeutics, Inc., "Next Wave of Medicines Utilizing AI", Presentation (Jun. 2020) [online] https://d1io3yog0oux5.cloudfront.

(56) References Cited

OTHER PUBLICATIONS net/_ec77451d0911d660fb193909a0a1ba0e/bioxceltherapeutics/db/445/3421/pdf/BioXcel+Therapeutics+Presentation_June+11.pdf; 30 pages.

BioXcel Therapeutics, Inc., United States Securities and Exchange Commission, Form 10-K, Annual Report Pursuant to Section 13 or 15(d) of the Securities Exchange Act of 1934, For the year ended Dec. 31, 2019, 135 pages.

Blevins, et al., "Effects of acute and chronic ethanol exposure on heteromeric N-methyl-d-aspartate receptors expressed in HEK 293 cells", Journal of Neurochemistry (1997); 69(6): 2345-2354.

Bonanno, et al., "Effectiveness of preoperative intranasal dexmedetomidine compared with oral midazolam for the prevention of emergence delirium in pediatric patients undergoing general anesthesia: a systematic review protocol", JBI Database of Systematic Reviews and Implementation Reports (2016); 14(8): 70-79.

Bond, et al., "Dexmedetomidine Nasal Sedation Produces More Oculocardiac Reflex During Strabismus Surgery", Journal of Pediatric Ophthalmology and Strabismus (2016); 53 (5): 318.

Boriosi, et al., "Safety and Efficacy of Buccal Dexmedetomidine for MRI Sedation in School-Aged Children", Hospital Pediatrics (May 2019); 9(5): 348-354.

Boyer, "Calming patient agitation with dexmedetomidine", Nursing Critical Care (2010); 5(1): 30-34.

Boyer, "Treating agitation with dexmedetomidine in the ICU", Dimensions of Critical Care Nursing (2009); 28(3): 102-109.

Brandt, "The Hopkins Verbal Learning Test: Development of a new memory test with six equivalent forms", The Clinical Neuropsychologist (1991); 5(2): 125-142.

Browning, et al., "A single dose of citalopram increases fear recognition in healthy subjects", Journal of Psychopharmacology (2007); 21(7): 684-690.

Bryson, et al., "Treatment-resistant postictal agitation after electroconvulsive therapy (ECT) controlled with dexmedetomidine", The Journal of ECT (2013); 29(2): e18; 1 page.

Candiotti, et al., "Monitored Anesthesia Care with Dexmedetomidine: A Prospective, Randomized, Double-Blind, Multicenter Trial", Anesthesia & Analgesia (2010); 110(1): 47-56.

Canfrán, et al., "Comparison of sedation scores and propofol induction doses in dogs after intramuscular administration of dexmedetomidine alone or in combination with methadone, midazolam, or methadone plus midazolam", The Veterinary Journal (2016); 210: 56-60.

Carrasco, et al., "Dexmedetomidine for the Treatment of Hyperactive Delirium Refractory to Haloperidol in Nonintubated ICU Patients: A Nonrandomized Controlled Trial", Critical Care Medicine (2016); 44: 1295-1306.

Carter, et al., "Onset and quality of sedation after intramuscular administration of dexmedetomidine and hydromorphone in various muscle groups in dogs." Journal of the American Veterinary Medical Association (2013); 243(11): 1569-1572.

Center for Drug Evaluation and Research, Application No. 21-038, Medical Review(s), Drug Name: Precedex (dexmedetomidine hcl injection), Applicant: Abbott Laboratories, Chemical & Therapeutic Class: 1S, Original Application Date: Dec. 18, 1998; 183 pages.

Center for Drug Evaluation and Research, Application No. 21-038, Pharmacology Review(s), Drug Name: Precedex (dexmedetomidine hcl injection), Dec. 18, 1998, 184 pages.

Center for Drug Evaluation and Research, Application No. 215390Orig1s000, Multi-Discipline Review, NDA/BLA Multi-disciplinary Review and Evaluation NDA 215390, Drug Name: IGALMI (dexmedetomidine hydrochloride orally dissolving film), Submit Date: Mar. 1, 2021; 159 pages.

Changlu, et al., "Determination of Effective Dosage in Intranasal Dexmedetomidine Sedation for MRI Scanning with Modified Dixon's Up-and-Down Method in Children", China Pharmaceuticals (2015); 24(22): 22-24; 3 pages with English Abstract.

Charney, et al., "Noradrenergic neuronal dysregulation in panic disorder: the effects of intravenous yohimbine and clonidine in panic disorder patients", Acta Psychiatrica Scandinavica (1992); 86(4): 273-282.

Charney, et al., "The psychobiology of resilience and vulnerability to anxiety disorders: implications for prevention and treatment", Dialogues in Clinical Neuroscience (2003); 5(3): 207-221.

Chen, et al., "Dexmedetomidine alleviated isoflurane-induced neurotoxicity in aged rats", International Journal of Clinical and Experimental Medicine (2018); 11(4): 3686-3692.

Chen, et al., "Effect of dexmedetomidine on emergence agitation after oral and maxillofacial surgery", Shanghai Journal of Stomatology (2013); 22(6): 698-701; 6 pages with English Abstract.

Chen, et al., "Protective role of dexmedetomidine in unmethylated CpG-induced inflammation responses in BV2 microglia cells", Folia Neuropathologica (2016); 54(4): 382-391.

Cheon, et al., "[NM-250] Use of dexmedetomidine for prevention of post-operative agitation in a 14 year-old male with Angelman's Syndrome", University of Chicago, Chicago, IL (2014); 1 page.

Cheung, et al., "Analgesic and sedative effects of intranasal dexmedetomidine in third molar surgery under local anaesthesia", British Journal of Anaesthesia (2011); 107(3): 430-437.

Cheung, et al., "Evaluation of the Analgesic Efficacy of Local Dexmedetomidine Application", The Clinical Journal of Pain (Jun. 2011); 27(5): 377-382.

Cheung, et al., "Intranasal dexmedetomidine in combination with patient-controlled sedation during upper gastrointestinal endoscopy: a randomised trial", Acta Anestheologica Scandinavica (2015); 59 (2): 215-223.

Chokroverty, et al., "Overview of sleep & sleep disorders", Indian Journal of Medical Research (Feb. 2010); 131: 126-140.

Chowdhury, et al., "General intensive care for patients with traumatic brain injury: An update", Saudi Journal of Anaesthesia (2014); 8(2): 256-263.

Christiansen, et al., "Sedation of red porgy (*Pagrus pagrus*) and black sea bass (*Centropristis striata*) using ketamine (K), dexmedetomidine (D) and midazolam (M) delivered via intramuscular injection." Journal of Zoo and Aquarium Research (2014); 2 (3): 62-68.

Cimen, et al., "Comparison of buccal and nasal dexmedetomidine premedication for pediatric patients", Paediatric Anaesthesia (2013); 23(2): 134-138.

Citrome, et al., "Sublingual Dexmedetomidine for Agitation Associated with Schizophrenia or Bipolar Disorder: A Post Hoc Analysis of Number Needed to Treat, Number Needed to Harm, and Likelihood to be Helped or Harmed", Advances in Therapy (Oct. 2022); 39: 4821-4835.

Claassen, et al., "Fluvoxamine, a specific 5-hydroxytryptamine uptake inhibitor", British Journal of Pharmacology (1977); 60(4): 505-516.

ClinicaiTrials.gov Identifier: NCT00417664, Is Dexmedetomidine Associated With a Lower Incidence of Postoperative Delirium When Compared to Propofol or Midazolam in Cardiac Surgery Patients, First Posted—Jan. 4, 2007, Last Update Posted—Jan. 4, 2007, retrieved from https://clinicaltrials.gov/ct2/show/NCT00417664, 5 pages.

Clinical Trial Registration No. ChiCTR-IOR-17012415, "Effect of nasal dexmedetomidine on the prevention of emergence agitation in children undergoing day surgery with desoflurane anesthesia." Guangzhou Women and Children Medical Center, Date of Registration: Aug. 18, 2017, Estimated Trial End Date: Mar. 31, 2018, http://www.chictr.org.cn/showprojen.aspx?proj=21174, downloaded May 5, 2018, 3 pages.

ClinicalTrials.gov Identifier: NCT00095251, MENDS Study: Trial in Ventilated ICU Patients Comparing an Alpha2 Agonist Versus a Gamma Aminobutyric Acid (GABA)-Agonist to Determine Delirium Rates, Efficacy of Sedation, Analgesia and Discharge Cognitive Status, First Posted—Nov. 2, 2004, Last Update Posted—Sep. 11, 2018, retrieved from https://clinicaltrials.gov/ct2/show/NCT00095251, 8 pages.

ClinicalTrials.gov Identifier: NCT00351299, Randomized Controlled Trial of Dexmedetomidine for the Treatment of Intensive

(56) References Cited

OTHER PUBLICATIONS

Care Unit (ICU) Delirium, Jul. 12, 2006, Last Update Posted—Jun. 9, 2017, retrieved from https://clinicaltrials.gov/ct2/show/NCT00351299, 15 pages.
ClinicalTrials.gov Identifier: NCT00455143, Cognitive Protection—Dexmedetomidine and Cognitive Reserve, First Posted—Apr. 3, 2007, Last Update Posted—Jul. 17, 2019, retrieved from https://clinicaltrials.gov/ct2/show/NCT00455143, 20 pages.
ClinicalTrials.gov Identifier: NCT00460473, A Research Study to Evaluate the Effectiveness of Dexmedetomidine in Preventing Delirium After Hip Fracture Repair Surgery, First Posted—Apr. 16, 2007, Last Update Posted—Jul. 24, 2015, retrieved from https://clinicaltrials.gov/ct2/show/NCT00460473, 7 pages.
ClinicalTrials.gov Identifier: NCT00464763, A Research Study to Evaluate the Effectiveness of Dexmedetomidine in Preventing Delirium After Heart Surgery, First Posted—Apr. 24, 2007, Last Update Posted—Mar. 21, 2017, retrieved from https://clinicaltrials.gov/ct2/show/NCT00460473, 7 pages.
ClinicalTrials.gov Identifier: NCT00468052, Decrease Emergence Agitation and Provide Pain Relief for Children Undergoing Tonsillectomy & Adenoidectomy, First Posted—May 1, 2007, Last Update Posted—Dec. 5, 2016, retrieved from https://clinicaltrials.gov/ct2/show/NCT00468052, 24 pages.
ClinicalTrials.gov Identifier: NCT00505804, A Comparison of Dexmedetomidine and Haloperidol in Patients With Intensive Care Unit (ICU)-Associated Agitation and Delirium (Dex), First Posted—Jul. 25, 2007, Last Update Posted—Jan. 24, 2013, retrieved from https://clinicaltrials.gov/ct2/show/NCT00505804, 6 pages.
ClinicalTrials.gov Identifier: NCT00561678, Perioperative Cognitive Function—Dexmedetomidine and Cognitive Reserve, First Posted—Nov. 21, 2007, Last Update Posted—Apr. 23, 2018, retrieved from https://clinicaltrials.gov/ct2/show/NCT00561678, 23 pages.
ClinicalTrials.gov Identifier: NCT00654329, Dexmedetomidine vs Fentanyl for BMT (DexBMT). Children's Research Institute, First Posted Apr. 8, 2018, Results First Posted Apr. 25, 2011, Last Update Posted Apr. 25, 2011, Study Start Date Aug. 2005, https://clinicaltrials.gov/ct2/show/NCT00654329, downloaded May 5, 2018, 6 pages.
ClinicalTrials.gov Identifier: NCT00778063, Study Using Dexmedetomidine to Decreases Emergence Delirium in Pediatric Patients (PED-DEX). Ochsner Health System, First Posted Oct. 23, 2008, Last Update Posted Mar. 15, 2013, Study Start Date Mar. 2009, https://clinicaltrials.gov/ct2/show/NCT00778063, downloaded May 6, 2018, 8 pages.
ClinicalTrials.gov Identifier: NCT00837187, Bioavailability of Dexmedetomidine After Intranasal Administration (INDEX). University of Turku, First Posted Feb. 5, 2009, Last Update Posted Jan. 13, 2010, Study Start Date Mar. 2009, https://clinicaltrials.gov/ct2/show/NCT00837187, downloaded May 6, 2018, 6 pages.
ClinicalTrials.gov Identifier: NCT00857727, Use of Dexmedetomidine to Reduce Emergence Delirium Incident in Children (DexPeds), First Posted—Mar. 9, 2009, Last Update Posted—Nov. 27, 2018, retrieved from https://clinicaltrials.gov/ct2/show/NCT00857727, 18 pages.
ClinicalTrials.gov Identifier: NCT01065701, Comparison of Two Doses of Intranasal Dexmedetomidine as Premedication in Children. The University of Hong Kong, First Posted Feb. 9, 2010, Last Update Posted Oct. 26, 2017, Study Start Date Jul. 2009, https://clinicaltrials.gov/ct2/show/NCT01065701, downloaded May 6, 2018, 5 pages.
ClinicalTrials.gov Identifier: NCT01132794, A Study to Assess the Analgesia and Sedation Using Intranasal Dexmedetomidine in Third Molar Surgery Under Local Anaesthesia. The University of Hong Kong, First Posted May 28, 2010, Last Update Posted Jun. 16, 2010, https://clinicaltrials.gov/ct2/show/NCT01132794, downloaded May 5, 2018, 6 pages.
ClinicalTrials.gov Identifier: NCT01140529, Dexmedetomidine for the Treatment of Delirium After Heart Surgery (DexinDelir), First Posted—Jun. 9, 2010, Last Update Posted—Nov. 1, 2016, retrieved from https://clinicaltrials.gov/ct2/show/NCT01140529, 5 pages.

ClinicalTrials.gov Identifier: NCT01151865, Dexmedetomidine to Lessen Intensive Care Unit (ICU) Agitation (DahLIA), First Posted—Jun. 29, 2010, Last Update Posted—Jan. 21, 2015, retrieved from https://clinicaltrials.gov/ct2/show/NCT01151865, 9 pages.
ClinicalTrials.gov Identifier: NCT01188551, Dexmedetomidine Versus Fentanyl Following Pressure Equalization Tube Placement. Nationwide Children's Hospital, First Posted Aug. 25, 2010, Last Update Posted Apr. 1, 2014, Study Start Date Jan. 2011, https://clinicaltrials.gov/ct2/show/NCT01188551, downloaded May 5, 2018, 6 pages.
ClinicalTrials.gov Identifier: NCT01255904, A Trial Of Oral Chloral Hydrate Versus Intranasal Dexmedetomidine For Sedated Abr Exams. Baylor College of Medicine, First Posted Dec. 8, 2010, Last Update Posted May 16, 2016, Study Start Date Aug. 2011, https://clinicaltrials.gov/ct2/show/NCT01255904, downloaded May 6, 2018, 5 pages.
ClinicalTrials.gov Identifier: NCT01283412, Dexmedetomidine on Postoperative Delirium and Quality of Recovery in Geriatric Patients, First Posted—Jan. 26, 2011, Last Update Posted—Nov. 20, 2013, retrieved from https://clinicaltrials.gov/ct2/show/NCT01283412, 4 pages.
ClinicalTrials.gov Identifier: NCT01353378, Use of Dexmedetomidine in Children Undergoing Oral Maxillofacial Surgery to Decrease Emergence Delirium, First Posted—May 13, 2011, Last Update Posted—May 5, 2017, retrieved from https://clinicaltrials.gov/ct2/show/NCT01353378, 5 pages.
ClinicalTrials.gov Identifier: NCT01362205, Dexmedetomidine (Precedex) for Severe Alcohol Withdrawal Syndrome (AWS) and Alcohol Withdrawal Delirium (AWD), First Posted—May 30, 2011, Last Update Posted—Nov. 6, 2017, retrieved from https://clinicaltrials.gov/ct2/show/NCT01362205, 36 pages.
ClinicalTrials.gov Identifier: NCT01374737, ED50 of Dexmedetomidine to Prevent Emergence Agitation in Children, First Posted—Jun. 16, 2011, Last Update Posted—Jun. 16, 2011, downloaded Feb. 11, 2018 https://clinicaltrials.gov/ct2/show/NCT01374737, 5 pages.
ClinicalTrials.gov Identifier: NCT01378741, Reducing Delirium After Cardiac Surgery: A Multifaceted Approach Of Perioperative Care, First Posted—Jun. 22, 2011, Last Update Posted—Apr. 21, 2015, retrieved from https://clinicaltrials.gov/ct2/show/NCT01378741, 5 pages.
ClinicalTrials.gov Identifier: NCT01512355, The Effect of Dexmedetomidine on Decreasing Emergence Agitation and Delirium in Pediatric Patients Undergoing Strabismus Surgery, First Posted—Jan. 19, 2012, Last Update Posted—Jul. 16, 2015, retrieved from https://clinicaltrials.gov/ct2/show/NCT01512355, 5 pages.
ClinicalTrials.gov Identifier: NCT01513772, The Effect of Dexmedetomidine on the Emergence Agitation in Nasal Surgery, First Posted—Jan. 20, 2012, Last Update Posted—Aug. 9, 2012, retrieved from https://clinicaltrials.gov/ct2/show/NCT01513772, 4 pages.
ClinicalTrials.gov Identifier: NCT01517438, Effects of Serotonin Inhibitors on Patient-controlled Analgesia Related Nausea and Vomiting, First Posted—Jan. 25, 2012, Last Update Posted—Jan. 25, 2012, retrieved from https://clinicaltrials.gov/ct2/show/NCT01517438, 4 pages.
ClinicalTrials.gov Identifier: NCT01517932, Effects of Dexmedetomidine on Stress Response and Postoperative Analgesia, First Posted—Jan. 25, 2012, Last Update Posted—Mar. 20, 2013, retrieved from https://clinicaltrials.gov/ct2/show/NCT01517932, 6 pages.
ClinicalTrials.gov Identifier: NCT01524367, Effect of Single-dose Dexmedetomidine on Emergence Excitement in Adults With Nasotracheal Intubation After Orthognathic Surgery, First Posted—Feb. 2, 2012, Last Update Posted—Feb. 6, 2015, retrieved from https://clinicaltrials.gov/ct2/show/NCT01524367, 6 pages.
ClinicalTrials.gov Identifier: NCT01528891, Dexmedetomidine as a Rapid Bolus in Children for Emergence Agitation, First Posted—Feb. 8, 2012, Last Update Posted—Jan. 20, 2016, downloaded Feb. 11, 2018 https://clinicaltrials.gov/ct2/show/results/NCT01528891, 6 pages.
ClinicalTrials.gov Identifier: NCT01528891, Dexmedetomidine as a Rapid Bolus in Children for Emergence Agitation, First Posted—

(56) References Cited

OTHER PUBLICATIONS

Feb. 8, 2012, Last Update Posted—Mar. 8, 2018, retrieved from https://clinicaltrials.gov/ct2/show/results/NCT01528891, 15 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Feb. 17, 2012, Study Start Date—Jun. 2010, Estimated Study Completion Date—Jan. 2013, 9 pages.
ClinicalTrials.gov Identifier: NCT01535287, The Effect of Intramuscular Dexmedetomidine on Emergence Agitation in Children Undergoing With or Without Tube Insertion Under General Anesthesia. First Posted—Feb. 17, 2012, Last Update Posted—Jul. 9, 2018, retrieved from https://clinicaltrials.gov/ct2/show/NCT01535287, 24 pages.
ClinicalTrials.gov Identifier: NCT01578161, The Effect of Dexmedetomidine on Emergence Agitation in Children Undergoing a Surgery Under Desflurane Anesthesia, First Posted—Apr. 16, 2012, Last Update Posted—Apr. 16, 2012, downloaded Feb. 11, 2018 https://clinicaltrials.gov/ct2/show/NCT01578161, 6 pages.
ClinicalTrials.gov Identifier: NCT01691001, Effect of Dexmedetomidine on Sevoflurane Requirements and Emergence Agitation in Children Undergoing Ambulatory Surgery, First Posted—Sep. 24, 2012, Last Update Posted—Sep. 24, 2012, retrieved from https://clinicaltrials.gov/ct2/show/NCT01691001, 4 pages.
ClinicalTrials.gov Identifier: NCT01739933, The MENDS2 Study, Maximizing the Efficacy of Sedation and Reducing Neurological Dysfunction and Mortality in Septic Patients With Acute Respiratory Failure (MENDS2), First Posted—Dec. 4, 2012, Last Update Posted—Apr. 5, 2019, retrieved from https://clinicaltrials.gov/ct2/show/NCT01739933, 11 pages.
ClinicalTrials.gov Identifier: NCT01791296, Does Nightly Dexmedetomidine Improve Sleep and Reduce Delirium in ICU Patients? (SKY-DEX), First Posted—Feb. 13, 2013, Last Update Posted—Mar. 17, 2017, retrieved from https://clinicaltrials.gov/ct2/show/NCT01791296, 8 pages.
ClinicalTrials.gov Identifier: NCT01887184, Sedation Using Intranasal Dexmedetomidine in Upper Gastrointestinal Endoscopy. The University of Hong Kong, First Posted Jun. 26, 2013, Last Update Posted Oct. 28, 2014, Study Start Date Jan. 2009, https://clinicaltrials.gov/ct2/show/NCT01887184, downloaded May 5, 2018, 7 pages.
ClinicalTrials.gov Identifier: NCT01895023, Effects of Dexmedetomidine Premedication on Emergence Agitation After Strabismus Surgery in Children. Yao Yusheng, First Posted Jul. 10, 2013, Last Update Posted Jan. 6, 2015, Study Start Date Sep. 2013, https://clinicaltrials.gov/ct2/show/NCT01895023, downloaded May 5, 2018, 7 pages.
ClinicalTrials.gov Identifier: NCT01900405, Intranasal Dexmedetomidine Sedation for Pediatric CT Imaging. University of Sao Paulo, First Posted Jul. 16, 2013, Last Update Posted Jul. 16, 2013, Study Start Date Apr. 2013, downloaded https://clinicaltrials.gov/ct2/show/NCT01900405, downloaded May 6, 2018, 7 pages.
ClinicalTrials.gov Identifier: NCT01901588, Efficacy of Single-Shot Dexmedetomidine Versus Placebo in Preventing Pediatric Emergence Delirium in Strabismus Surgery, First Posted—Mar. 8, 2016, Last Update Posted—Last Update Posted—Jul. 11, 2016, retrieved from https://clinicaltrials.gov/ct2/show/NCT01901588, 5 pages.
ClinicalTrials.gov Identifier: NCT01904760, Dexmedetomidine to Prevent Agitation After Free Flap Surgery, First Posted—Jul. 22, 2013, Last Update Posted—Nov. 13, 2014, retrieved from https://clinicaltrials.gov/ct2/show/NCT01904760, 6 pages.
ClinicalTrials.gov Identifier: NCT01934049, Postoperative Recovery in Elderly Patients Undergoing Hip Hemi-arthroplasty, First Posted—Sep. 4, 2013, Last Update Posted—Sep. 10, 2013, retrieved from https://clinicaltrials.gov/ct2/show/NCT01934049, 7 pages.
ClinicalTrials.gov Identifier: NCT01937611, Intramuscular Dexmedetomidine as Premedication. First Posted—Sep. 9, 2013, Last Update Posted—Sep. 9, 2013, Study Start Date—Mar. 2013, Estimated Study Completion Date—Oct. 2013, 8 pages.

ClinicalTrials.gov Identifier: NCT01966315, The Comparison of Dexmedetomidine and Midazolam for the Sleep in Intensive Care Unit, First Posted—Oct. 21, 2013, Last Update Posted—Apr. 23, 2019, retrieved from https://clinicaltrials.gov/ct2/show/NCT01966315, 5 pages.
ClinicalTrials.gov Identifier: NCT02007798, Small-dose Dexmedetomidine Effects on Recovery Profiles of Supratentorial Tumors Patients From General Anesthesia, First Posted—Dec. 11, 2013, Last Update Posted—Jan. 14, 2014, retrieved from https://clinicaltrials.gov/ct2/show/NCT02007798, 8 pages.
ClinicalTrials.gov Identifier: NCT02072083, Intranasal Dexmedetomidine vs Midazolam-ketamine Combination for Premedication of Pediatric Patients. TC Erciyes University, First Posted Feb. 26, 2014, Last Update Posted Apr. 14, 2015, Study Start Date Feb. 2014, https://clinicaltrials.gov/ct2/show/NCT02072083, downloaded May 5, 2018, 6 pages.
ClinicalTrials.gov Identifier: NCT02077712, Intranasal Dexmedetomidine Sedation for Ophthalmic Examinations in Children (DEX-EYE). Sun Yat-sen University, First Posted Mar. 4, 2014, Last Update Posted May 3, 2016, Study Start Date Feb. 2014, https://clinicaltrials.gov/ct2/show/NCT02077712, downloaded May 5, 2018, 7 pages.
ClinicalTrials.gov Identifier: NCT02080169, Safety and Efficacy of Combined Sedation With Midazolam and Dexmedetomidine in ICU Patients, First Posted—Mar. 6, 2014, Last Update Posted—Mar. 6, 2014, retrieved from https://clinicaltrials.gov/ct2/show/NCT02080169, 8 pages.
ClinicalTrials.gov Identifier: NCT02096068, Neuroprotection With Dexmedetomidine in Patients Undergoing Elective Cardiac or Abdominal Surgery (Neuprodex), First Posted—Mar. 26, 2014, Last Update Posted—Aug. 22, 2018, retrieved from https://clinicaltrials.gov/ct2/show/NCT02096068, 9 pages.
ClinicalTrials.gov Identifier: NCT02104297, Effect of Deksmedetomidine and Remifentanil in Extubation Agitation (EA), First Posted—Apr. 4, 2014, Last Update Posted—Apr. 4, 2014, retrieved from https://clinicaltrials.gov/ct2/show/NCT02104297, 5 pages.
ClinicalTrials.gov Identifier: NCT02108171, Intranasal Dexmedetomidine Premedication. Guangzhou First People's Hospital, First Posted Apr. 9, 2014, Last Update Posted Mar. 14, 2016, Study Start Date Mar. 2014, https://clinicaltrials.gov/ct2/show/NCT02108171, downloaded May 5, 2018, 24 pages.
ClinicalTrials.gov Identifier: NCT02117726, Impact of Various Sedation Regimens on the Incidence of Delirium, First Posted—Apr. 21, 2014, Last Update Posted—Jul. 16, 2014, retrieved from https://clinicaltrials.gov/ct2/show/NCT02117726, 7 pages.
ClinicalTrials.gov Identifier: NCT02168439, Intranasal Dexmedetomidine vs Intranasal Midazolam as Anxiolysis Prior to Pediatric Laceration Repair. University of Pittsburgh, Results First Posted Mar. 10, 2017, Last Update Posted Mar. 10, 2017, Study Start Date Jun. 2014, https://clinicaltrials.gov/ct2/show/NCT02168439, downloaded May 6, 2018, 6 pages.
ClinicalTrials.gov Identifier: NCT02169336, Placebo-Controlled Evaluation of Intranasal Dexmedetomidine for Postoperative Analgesia Following Bunionectomy. Recro Pharma, Inc., First Posted Jun. 23, 2014, Last Update Posted Dec. 10, 2015, Study Start Date Jun. 2014, https://clinicaltrials.gov/ct2/show/NCT02169336, downloaded May 6, 2018, 7 pages.
ClinicalTrials.gov Identifier: NCT02169843, Minimizing ICU Neurological Dysfunction With Dexmedetomidine-induced Sleep (MINDDS), First Posted—Jun. 23, 2014, Last Update Posted—Jun. 23, 2014, retrieved from https://clinicaltrials.gov/ct2/show/NCT02169843, 6 pages.
ClinicalTrials.gov Identifier: NCT02211118, Sedation and Physiological Effects of Intranasal Dexmedetomidine in Severe COPD. Dayton VA Medical Center, First Posted Aug. 7, 2014, Last Update Posted Feb. 8, 2017, Study Start Date Oct. 2014, https://clinicaltrials.gov/ct2/show/NCT02211118, 6 pages.
ClinicalTrials.gov Identifier: NCT02222636, The Clinical Research of Intranasal Dexmedetomidine Used in Plastic Surgery of Children. Xijing Hospital, First Posted Aug. 21, 2014, Last Update Posted Aug. 21, 2014, Study Start Date Sep. 2014, https://clinicaltrials.gov/ct2/show/NCT02222636, downloaded May 6, 2018, 6 pages.

(56) References Cited

OTHER PUBLICATIONS

ClinicalTrials.gov Identifier: NCT02225210, Effects of Dexmedetomidine Sedation on Delirium and Haemodynamic in Mechanical Ventilated Elderly Patients, First Posted—Aug. 26, 2014, Last Update Posted—Aug. 26, 2014, retrieved from https://clinicaltrials.gov/ct2/show/NCT02225210, 6 pages.

ClinicalTrials.gov Identifier: NCT02239445, Intranasal Dexmedetomidine VS Oral Chloral Hydrate for Rescue Sedation During Magnetic Resonance Imaging. Guangzhou Women and Children's Medical Center, First Posted Sep. 12, 2014, Last Update Posted May 12, 2015, Study Start Date Sep. 2014, https://clinicaltrials.gov/ct2/show/NCT02239445, downloaded May 6, 2018, 7 pages.

ClinicalTrials.gov Identifier: NCT02245256, Efficacy of Low-dose Dexmedetomidine to Prevent Delirium in Liver Transplant Patients, First Posted—Sep. 19, 2014, Last Update Posted—Jan. 25, 2018, retrieved from https://clinicaltrials.gov/ct2/show/NCT02245256, 5 pages.

ClinicalTrials.gov Identifier: NCT02250703, Intranasal Dexmedetomidine Premedication in Children. Results First Posted Jul. 7, 2017, Last Update Posted Jul. 7, 2017, Study Start Date Sep. 2014, downloaded https://clinicaltrials.gov/ct2/show/NCT02250703, downloaded May 6, 2018, 8 pages.

ClinicalTrials.gov Identifier: NCT02253199, The Effect of Age on the Median Effective Dose (ED50) of Intranasal Dexmedetomidine for Rescue Sedation Following Failed Sedation With Oral Chloral Hydrate During Magnetic Resonance Imaging. Guangzhou Women and Children's Medical Center, First Posted Oct. 1, 2014, Last Update Posted Mar. 29, 2016, Study Start Date Oct. 2014, https://clinicaltrials.gov/ct2/show/NCT02253199, downloaded May 5, 2018, 7 pages.

ClinicalTrials.gov Identifier: NCT02267538, Dexmedetomidine and Delirium in Patients After Cardiac Surgery, First Posted—Feb. 2, 2018, Last Update Posted—Mar. 5, 2018, retrieved from https://clinicaltrials.gov/ct2/show/NCT02267538, 12 pages.

ClinicalTrials.gov Identifier: NCT02275182, Impact of Dexmedetomidine on the Post-Operative Cognition Dysfunction(POCD) in Geriatric Patients, First Posted—Oct. 27, 2014, Last Update Posted—Apr. 25, 2018, retrieved from https://clinicaltrials.gov/ct2/show/NCT02275182, 8 pages.

ClinicalTrials.gov Identifier: NCT02284243, Placebo-Controlled Evaluation of Intranasal Dexmedetomidine for Postoperative Analgesia Following Bunionectomy Surgery. Recro Pharma, Inc., First Posted Nov. 5, 2014, Last Update Posted May 2, 2017, Study Start Date Oct. 2014, https://clinicaltrials.gov/ct2/show/NCT02284243, downloaded May 6, 2018, 8 pages.

ClinicalTrials.gov Identifier: NCT02299232, Dexmedetomidine in Children for Magnetic Resonance Imaging (MRI) Sedation (DEX). Sisli Hamidiye Etfal Training and Research Hospital, First Posted Nov. 24, 2014, Last Update Posted Oct. 25, 2017, Study Start Date Feb. 2014, https://clinicaltrials.gov/ct2/show/NCT02299232, downloaded May 6, 2018, 6 pages.

ClinicalTrials.gov Identifier: NCT02366299, Comparison of Dexmedetomidine and Propofol on the Delirium and Neuroinflammation in Patients With SIRS, First Posted—Feb. 19, 2015, Last Update Posted—Feb. 19, 2015, retrieved from https://clinicaltrials.gov/ct2/show/NCT02366299, 4 pages.

ClinicalTrials.gov Identifier: NCT02394418, Effect of Sevoflurane, Propofol and Dexmedetomidine on Delirium & Neuroinflammation in Mechanically Ventilated Patients, First Posted—Mar. 20, 2015, Last Update Posted—Jul. 5, 2017, retrieved from https://clinicaltrials.gov/ct2/show/NCT02394418, 5 pages.

ClinicalTrials.gov Identifier: NCT02412150, Effect of Dexmedetomidine After Thyroidectomy, First Posted—Apr. 9, 2015, Last Update Posted—Mar. 6, 2019, retrieved from https://clinicaltrials.gov/ct2/show/NCT02412150, 4 pages.

ClinicalTrials.gov Identifier: NCT02459509, A Comparison of Two Doses of Intranasal Dexmedetomidine for Premedication in Children. The University of Hong Kong, First Posted Jun. 2, 2015, Last Update Posted Apr. 18, 2016, Study Start Date Jun. 2015, https://clinicaltrials.gov/ct2/show/NCT02459509, downloaded May 6, 2018, 8 pages.

ClinicalTrials.gov Identifier: NCT02509949, Effects of Dexmedetomidine on Delirium After Living Donor Renal Transplantation in Adult Patients, First Posted—Jul. 28, 2015, Last Update Posted—Jun. 12, 2018, retrieved from https://clinicaltrials.gov/ct2/show/NCT02509949, 4 pages.

ClinicalTrials.gov Identifier: NCT02528513, Midazolam Used Alone or Sequential Use of Midazolam and Propofol/Dexmedetomidine in Mechanically Ventilated Patients, First Posted—Aug. 19, 2015, Last Update Posted—Apr. 28, 2016, retrieved from https://clinicaltrials.gov/ct2/show/NCT02528513, 9 pages.

ClinicalTrials.gov Identifier: NCT02544906, Propofol Versus Dexmedetomidine for Prevention of Sevoflurane Agitation in Recipients of Living Donor Liver Transplantation (Agitation), First Posted—Sep. 9, 2015, Last Update Posted—Sep. 9, 2015, retrieved from https://clinicaltrials.gov/ct2/show/NCT02544906, 4 pages.

ClinicalTrials.gov Identifier: NCT02546765, Dexmedetomidine and IV Acetaminophen for the Prevention of Postoperative Delirium Following Cardiac Surgery (DEXACET), First Posted—Sep. 11, 2015, Last Update Posted—Aug. 1, 2018, retrieved from https://clinicaltrials.gov/ct2/show/NCT02546765, 9 pages.

ClinicalTrials.gov Identifier: NCT02548923, Dexmedetomidine Versus Propofol for Prolonged Sedation in Critically Ill Trauma and Surgical Patients, First Posted—Sep. 14, 2015, Last Update Posted—Sep. 14, 2015, retrieved from https://clinicaltrials.gov/ct2/show/NCT02548923, 5 pages.

ClinicalTrials.gov Identifier: NCT02573558, Intraoperative Sedation and Postoperative Delirium, First Posted—Oct. 12, 2015, Last Update Posted—Apr. 6, 2016, retrieved from https://clinicaltrials.gov/ct2/show/NCT02573558, 5 pages.

ClinicalTrials.gov Identifier: NCT02675049, Efficacy and Optimal Dose Selection of Intranasal Dexmedetomidine During Breast Lumpectomy Under Local Anaesthesia. Tianjin Medical University Cancer Institute and Hospital, First Posted Feb. 5, 2016, Last Update Posted Mar. 1, 2016, Study Start Date Jan. 2016, https://clinicaltrials.gov/ct2/show/NCT02675049, downloaded May 5, 2018, 6 pages.

ClinicalTrials.gov Identifier: NCT02699801, Dexmedetomidine Use in ICU Sedation and Postoperative Recovery in Elderly Patients and Post-cardiac Surgery (DIRECT), First Posted—Mar. 4, 2016, Last Update Posted—Nov. 3, 2016, retrieved from https://clinicaltrials.gov/ct2/show/NCT02699801, 8 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Dec. 27, 2017, downloaded Feb. 11, 2018 https://clinicaltrials.gov/ct2/show/NCT02720705, 7 pages.

ClinicalTrials.gov Identifier: NCT02720705, Transbucal Dexmedetomidine for Prevention of Sevoflurane Emergence Agitation in Pre-school Children, First Posted—Mar. 28, 2016, Last Update Posted—Nov. 1, 2018, retrieved from https://clinicaltrials.gov/ct2/show/NCT02720705, 6 pages.

ClinicalTrials.gov Identifier: NCT02757495, Can Caudal Dexmedetomidine Prevents Sevoflurane Induced Emergence Agitation in Children, First Posted—May 2, 2016, Last Update Posted—Feb. 27, 2019, retrieved from https://clinicaltrials.gov/ct2/show/NCT02757495, 6 pages.

ClinicalTrials.gov Identifier: NCT02773797, Placebo Controlled Evaluation of Sedation and Physiological Response to Intranasal Dexmedetomidine in Severe COPD. Dayton VA Medical Center, First Posted—May 16, 2016, Last Update Posted—May 16, 2016, Study Start Date Aug. 2016, https://clinicaltrials.gov/ct2/show/NCT02773797, 7 pages.

ClinicalTrials.gov Identifier: NCT02780427, ED50 and ED95 of Intranasal Dexmedetomidine in Pediatric Patients Undergoing Transthoracic Echocardiography Study. Guangzhou Women and Children's Medical Center, First Posted May 23, 2016, Last Update Posted Nov. 21, 2017, Study Start Date Jun. 2016, https://clinicaltrials.gov/ct2/show/NCT02780427, downloaded May 6, 2018, 8 pages.

ClinicalTrials.gov Identifier: NCT02793986, Dexmedetomidine vs Propofol Sedation Reduces Postoperative Delirium in Patients Receiv-

(56) References Cited

OTHER PUBLICATIONS ing Hip Arthroplasty, First Posted—Jun. 8, 2016, Last Update Posted—Jun. 29, 2017, retrieved from https://clinicaltrials.gov/ct2/show/NCT02793986, 6 pages.
ClinicalTrials.gov Identifier: NCT02809937, Dexmedetomidine and Long-term Outcome in Elderly Patients After Surgery, First Posted—Jun. 22, 2016, Last Update Posted—Jun. 16, 2017, retrieved from https://clinicaltrials.gov/ct2/show/NCT02809937, 10 pages.
ClinicalTrials.gov Identifier: NCT02818569, Repurposing Dexmedetomidine as an Orally Administered Sleep Therapeutic, First Posted—Jun. 29, 2016, Last Update Posted—Aug. 17, 2018, retrieved from https://clinicaltrials.gov/ct2/show/NCT02818569, 5 pages.
ClinicalTrials.gov Identifier: NCT02836431, Pharmacokinetic Study of Dexmedetomidine After Intra-nasal Dosing in Children. Children's Hospital Medical Center, First Posted Jul. 19, 2016, Last Update Posted Aug. 1, 2017, Study Start Date Jan. 2016, https://clinicaltrials.gov/ct2/show/NCT02836431, downloaded May 6, 2018, 8 pages.
ClinicalTrials.gov Identifier: NCT02836431, Pharmacokinetic Study of Dexmedetomidine After Intra-nasal Dosing in Children, First Posted—Jul. 19, 2016, Last Update Posted—Jul. 30, 2018, retrieved from https://clinicaltrials.gov/ct2/show/NCT02836431, 8 pages.
ClinicalTrials.gov Identifier: NCT02856594, Minimizing ICU Neurological Dysfunction With Dexmedetomidine-induced Sleep (MINDDS), First Posted—Aug. 5, 2016, Last Update Posted—Jan. 8, 2019, retrieved from https://clinicaltrials.gov/ct2/show/NCT02856594, 6 pages.
ClinicalTrials.gov Identifier: NCT02903407, Pain, Agitation and Delirium (PAD) Protocol in the Duke CICU, First Posted—Sep. 16, 2016, Last Update Posted—Oct. 18, 2018, retrieved from https://clinicaltrials.gov/ct2/show/NCT02903407, 9 pages.
ClinicalTrials.gov Identifier: NCT02917018, Effect of Dexmedetomidine on Stress Response and Emergence Agitation During Laparoscopic Surgery, First Posted—Sep. 28, 2016, Last Update Posted—Jan. 4, 2017, downloaded Feb. 11, 2018 https://clinicaltrials.gov/ct2/show/NCT02917018, 6 pages.
ClinicalTrials.gov Identifier: NCT02923128, Whether Dexmedetomidine Can Improve the Prognosis of Elderly Patients With Postoperative Cognitive Dysfunction, First Posted—Oct. 4, 2016, Last Update Posted—Oct. 11, 2016, retrieved from https://clinicaltrials.gov/ct2/show/NCT02923128, 7 pages.
ClinicalTrials.gov Identifier: NCT02951793, Abuse and Addiction in ICU, First Posted—Nov. 1, 2016, Last Update Posted—May 19, 2017, retrieved from https://clinicaltrials.gov/ct2/show/NCT02951793, 7 pages.
ClinicalTrials.gov Identifier: NCT02955732, Pharmacological Characteristics of Intranasally Given Dexmedetomidine in Paediatric Patients (PINDEX), First Posted Nov. 4, 2016, Last Update Posted—Sep. 12, 2018, retrieved from https://clinicaltrials.gov/ct2/show/NCT02955732, 5 pages.
ClinicalTrials.gov Identifier: NCT02955732, Pharmacological Characteristics of Intranasally Given Dexmedetomidine in Paediatric Patients (PINDEX). Turku University Hospital, First Posted Nov. 4, 2016, Last Update Posted Dec. 14, 2017, Study Start Date Jan. 1, 2017, https://clinicaltrials.gov/ct2/show/NCT02955732, downloaded May 6, 2018, 6 pages.
ClinicalTrials.gov Identifier: NCT02985697, Safety and Efficacy of Intranasal Dexmedetomidine. Bon Secours Pediatric Dental Associates, First Posted Dec. 7, 2016, Last Update Posted Dec. 7, 2016, Study Start Date Jan. 2017, https://clinicaltrials.gov/ct2/show/NCT02985697, downloaded May 6, 2018, 8 pages.
ClinicalTrials.gov Identifier: NCT03012984, Dexmedetomidine Supplemented Analgesia and Incidence of Postoperative Delirium, First Posted—Jan. 6, 2017, Last Update Posted—Jul. 31, 2018, retrieved from https://clinicaltrials.gov/ct2/show/NCT03012984, 13 pages.
ClinicalTrials.gov Identifier: NCT03069638, Intranasal Dexmedetomidine Sedation During Intraarticular Joint Injections in Pediatric Population, First Posted—Mar. 3, 2017, Last Update Posted—May 12, 2021, retrieved from https://clinicaltrials.gov/ct2/show/NCT03069638, 8 pages.
ClinicalTrials.gov Identifier: NCT03069638, Intranasal Dexmedetomidine Sedation During Intra-articular Joint Injections in Pediatric Population. University of Oulu, First Posted Mar. 3, 2017, Last Update Posted Mar. 15, 2018, Actual Study Start Date Feb. 1, 2017, https://clinicaltrials.gov/ct2/show/NCT03069638, downloaded May 6, 2018, 7 pages.
ClinicalTrials.gov Identifier: NCT03078946, Dexmedetomidine Versus Morphine and Midazolam in Prevention and Treatment of Delirium After Adult Cardiac Surgery, First Posted—Mar. 14, 2017, Last Update Posted—Mar. 14, 2017, retrieved from https://clinicaltrials.gov/ct2/show/NCT03078946, 6 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Apr. 19, 2017, downloaded Feb. 11, 2018 https://clinicaltrials.gov/ct2/show/NCT03120247, 7 pages.
ClinicalTrials.gov Identifier: NCT03120247, Pharmacokinetics and Pharmacodynamics of Oral Transmucosal Dexmedetomidine. (OTM/DEX/PK), First Posted—Apr. 19, 2017, Last Update Posted—Oct. 2, 2018, retrieved from https://clinicaltrials.gov/ct2/show/NCT03120247, 6 pages.
ClinicalTrials.gov Identifier: NCT03120442, Postoperative Delirium After Total Knee Arthroplasty Under Regional Anesthesia, First Posted—Apr. 19, 2017, Last Update Posted—Mar. 26, 2019, retrieved from https://clinicaltrials.gov/ct2/show/NCT03120442, 12 pages.
ClinicalTrials.gov Identifier: NCT03131375, Dexmedetomidine Reduces Emergence Delirium in Children Undergoing Tonsillectomy With Propofol Anesthesia, First Posted—Apr. 27, 2017, Last Update Posted—Jul. 9, 2018, retrieved from https://clinicaltrials.gov/ct2/show/NCT03131375, 7 pages.
ClinicalTrials.gov Identifier: NCT03151863, Intranasal Dexmedetomidine for Procedural Pain Management in Elderly Adults in Palliative Care (INDEX). Walid HABRE, First Posted May 12, 2017, Last Update Posted May 16, 2017, Estimated Study Start Date Jul. 1, 2017, https://clinicaltrials.gov/ct2/show/NCT03151863, downloaded May 5, 2018, 9 pages.
ClinicalTrials.gov Identifier: NCT03171740, Premedication With Intranasal Dexmedetomidine or Midazolam for Prevention of Emergence Agitation in Children. Brasilia University Hospital, First Posted May 31, 2017, Last Update Posted Sep. 13, 2017, Study Start Date Jun. 1, 2017, https://clinicaltrials.gov/ct2/show/NCT03171740, downloaded May 5, 2018, 8 pages.
ClinicalTrials.gov Identifier: NCT03171740, Premedication With Intranasal Dexmedetomidine or Midazolam for Prevention of Emergence Agitation in Children, First Posted—May 31, 2017, Last Update Posted—Jul. 13, 2018, retrieved from https://clinicaltrials.gov/ct2/show/NCT03171740, 7 pages.
ClinicalTrials.gov Identifier: NCT03172897, Low-dose Dexmedetomidine in Mechanically Ventilated ICU Patients, First Posted—Jun. 1, 2017, Last Update Posted—Jun. 21, 2019, retrieved from https://clinicaltrials.gov/ct2/show/NCT03172897, 10 pages.
ClinicalTrials.gov Identifier: NCT03174678, Dexmedetomidine Premedication in Children, First Posted—Jun. 2, 2017, Last Update Posted—Jun. 2, 2017, retrieved from https://clinicaltrials.gov/ct2/show/NCT03174678, 6 pages.
ClinicalTrials.gov Identifier: NCT03220880, Intranasal Dexmedetomidine Sedation in Children for Non-painful Procedures. Columbia University, First Posted Jul. 18, 2017, Last Update Posted Apr. 10, 2018, Study Start Date Nov. 1, 2018, https://clinicaltrials.gov/ct2/show/NCT03220880, downloaded May 5, 2018, 9 pages.
ClinicalTrials.gov Identifier: NCT03251222, Intranasal Sedation With Dexmedetomidine. University Medical Centre Ljubljana, First Posted Aug. 16, 2017, Last Update Posted Aug. 16, 2017, Actual Study Start Date Jan. 1, 2017, https://clinicaltrials.gov/ct2/show/NCT03251222, downloaded May 6, 2018, 8 pages.
ClinicalTrials.gov Identifier: NCT03251651, Intraoperative Sedatives and Postoperative Delirium, First Posted—Aug. 16, 2017, Last Update Posted—Apr. 24, 2018, retrieved from https://clinicaltrials.gov/ct2/show/NCT03251651 , 6 pages.

(56) References Cited

OTHER PUBLICATIONS

ClinicalTrials.gov Identifier: NCT03262090, Effect of Dexmedetomidine on the Prevention of Emergence Agitation in Children Undergoing Day Surgery, First Posted—Aug. 25, 2017, Last Update Posted—Jun. 25, 2019, retrieved from https://clinicaltrials.gov/ct2/show/NCT03262090, 6 pages.

ClinicalTrials.gov Identifier: NCT03290625, Intranasal Sedation With Dexmedetomidine and Ketamine in Pediatric Dentistry (Naso II). Universidade Federal de Goias, First Posted Sep. 25, 2017, Last Update Posted Feb. 20, 2018, Actual Study Start Date Nov. 9, 2017, https://clinicaltrials.gov/ct2/show/NCT03290625, downloaded May 6, 2018, 10 pages.

ClinicalTrials.gov Identifier: NCT03293277, Safety, Pharmacokinetics and Pharmacodynamics of Intranasal Dexmedetomidine in Healthy Subjects. Jiangsu HengRui Medicine Co., Ltd., First Posted Sep. 26, 2017, Last Update Posted Jan. 23, 2018, Study Start Date Jul. 26, 2017, https://clinicaltrials.gov/ct2/show/NCT03293277, downloaded May 5, 2018, 7 pages.

ClinicalTrials.gov Identifier: NCT03293927, Polypharmacy-related Adverse Events in Critically Ill Children, First Posted—Sep. 26, 2017, Last Update Posted—Jul. 18, 2019, retrieved from https://clinicaltrials.gov/ct2/show/NCT03293927, 5 pages.

ClinicalTrials.gov Identifier: NCT03317067, Effects of Dexmedetomidine on Delirium Duration of Non-intubated ICU Patients (4D Trial) (4D), First Posted—Oct. 23, 2017, Last Update Posted—Feb. 4, 2019, retrieved from https://clinicaltrials.gov/ct2/show/NCT03317067, 7 pages.

ClinicalTrials.gov Identifier: NCT03323593, Pharmacokinetics of Different Mode Administration of Intranasal Dexmedetomidine. The University of Hong Kong, First Posted Oct. 27, 2017, Last Update Posted Oct. 27, 2017, Study Start Date May 2013, https://clinicaltrials.gov/ct2/show/NCT03323593, downloaded May 6, 2018, 5 pages.

ClinicalTrials.gov Identifier: NCT03337672, Comparison of Dexmedetomidine and Midazolam for Prevention of Emergence Delirium in Children, First Posted—Nov. 9, 2017, Last Update Posted—Jan. 9, 2019, retrieved from https://clinicaltrials.gov/ct2/show/NCT03337672, 6 pages.

ClinicalTrials.gov Identifier: NCT03346226, How Different Sedatives Affect Hip Fracture Patient's Postoperative Delirium, First Posted—Nov. 17, 2017, Last Update Posted—Dec. 13, 2017, retrieved from https://clinicaltrials.gov/ct2/show/NCT03346226, 9 pages.

ClinicalTrials.gov Identifier: NCT03394430, Comparison of Midazolam or Dexmedetomidine on Epileptiform EEG During Sevoflurane Mask Induction. First Posted Jan. 9, 2018, Last Update Posted Feb. 13, 2018, Estimated Study Start Date Apr. 1, 2018, https://clinicaltrials.gov/ct2/show/NCT03394430, downloaded May 5, 2018, 8 pages.

ClinicalTrials.gov Identifier: NCT03399838, Comparing in Dexmedetomidine With po/pr Midazolam for Procedural Sedation in the Pediatric Emergency Department (PedINDEX). University Hospital Inselspital, Berne, First Posted Jan. 16, 2018, Last Update Posted Jan. 16, 2018, https://clinicaltrials.gov/ct2/show/NCT03399838, downloaded May 6, 2018, 6 pages.

ClinicalTrials.gov Identifier: NCT03417999, Pharmacokinetic Study of Intranasal Dexmedetomidine in Pediatric Patients With Congenital Heart Disease. Children's Hospital of Philadelphia, First Posted Jan. 31, 2018, Last Update Posted Apr. 12, 2018, Estimated Study Start Date May 2018, https://clinicaltrials.gov/ct2/show/NCT03417999, downloaded May 6, 2018, 7 pages.

ClinicalTrials.gov Identifier: NCT03477994, Efficacy of Dexmedetomidine Versus Clonidine to Control Delirium in Patients Undergoing CABG, First Posted—Mar. 27, 2018, Last Update Posted—Jul. 11, 2019, retrieved from https://clinicaltrials.gov/ct2/show/NCT03477994, 6 pages.

ClinicalTrials.gov Identifier: NCT03596775, Effect of Dexmedetomidine on Emergence Agitation and Postoperative Behavior Changes in Children, First Posted—Jul. 24, 2018, Last Update Posted—Sep. 7, 2018, retrieved from https://clinicaltrials.gov/ct2/show/NCT03596775?cond=Dexmedetomidine&sfpd_s=07%2F14%2F2018&sfpd_e=11%2F20%2F2018&rank=29, 7 pages.

ClinicalTrials.gov Identifier: NCT03600727, Propofol and Dexmedetomidine on Inflammation, First Posted—Jul. 26, 2018, Last Update Posted—Jul. 26, 2018, retrieved from https://clinicaltrials.gov/ct2/show/NCT03600727?cond=Dexmedetomidine&sfpd_s=07%2F14%2F2018&sfpd_e=11%2F20%2F2018&rank=21, 6 pages.

ClinicalTrials.gov Identifier: NCT03624595, Low-dose Dexmedetomidine and Postoperative Delirium After Cardiac Surgery, First Posted—Aug. 10, 2018, Last Update Posted—Apr. 24, 2019, retrieved from https://clinicaltrials.gov/ct2/show/NCT03624595?cond=Dexmedetomidine&sfpd_s=07%2F14%2F2018&sfpd_e=11%2F20%2F2018&rank=2, 12 pages.

ClinicalTrials.gov Identifier: NCT03629262, Dexmedetomidine Supplemented Intravenous Analgesia in Elderly After Orthopedic Surgery, First Posted—Aug. 14, 2018, Last Update Posted—Dec. 11, 2018, retrieved from https://clinicaltrials.gov/ct2/show/NCT03629262?cond=Dexmedetomidine&sfpd_s=07%2F14%2F2018&sfpd_e=11%2F20%2F2018&rank=3, 11 pages.

ClinicalTrials.gov Identifier: NCT03629483, Dexmedetomidine Combined With Ropivacaine for Postoperative Continuous Femoral Nerve Block, First Posted—Aug. 14, 2018, Last Update Posted—Dec. 11, 2018, retrieved from https://clinicaltrials.gov/ct2/show/NCT03629483?cond=Dexmedetomidine&sfpd_s=07%2F14%2F2018&sfpd_e=11%2F20%2F2018&rank=4, 10 pages.

ClinicalTrials.gov Identifier: NCT03655847, Acceptable Hemodynamic Changes in Dexmedetomidine for Single Intravenous Bolus Injection, First Posted—Aug. 31, 2018, Last Update Posted—Feb. 15, 2019, retrieved from https://clinicaltrials.gov/ct2/show/NCT03655847?cond=Dexmedetomidine&sfpd_s=07%2F14%2F2018&sfpd_e=11%2F20%2F2018&rank=9, 7 pages.

ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—May 18, 2021, retrieved from https://clinicaltrials.gov/ct2/show/study/NCT03668951, 8 pages.

ClinicalTrials.gov Identifier: NCT03668951, Pharmacokinetic Study of Dexmedetomidine After Intra-Nasal and Buccal Dosing in Children (DexPK), First Posted—Sep. 13, 2018, Last Update Posted—Sep. 13, 2018, retrieved from https://clinicaltrials.gov/ct2/show/NCT03668951?term=buccal&cond=dexmedetomidine&sfpd_s=07%2F01%2F2018&rank=1, 7 pages.

ClinicalTrials.gov Identifier: NCT03708315, Precedex for Schizophrenia (DEX), First Posted—Oct. 17, 2018, Last Update Posted—Oct. 17, 2018, retrieved from https://clinicaltrials.gov/ct2/show/NCT03708315?cond=Dexmedetomidine&sfpd_s=07%2F14%2F2018&sfpd_e=11%2F20%2F2018&rank=33, 6 pages.

ClinicalTrials.gov Identifier: NCT03742180, Sublingual Ketorolac Compared to Intranasal Dexmedetomidine for Postoperative Analgesia in Pediatric Patients Undergoing Bilateral Myringotomy, First Posted—Nov. 15, 2018, Last Update Posted—Nov. 15, 2018, retrieved from https://clinicaltrials.gov/ct2/show/NCT03742180?term=sublingual&cond=dexmedetomidine&sfpd_s=07%2F01%2F2018&rank=1, 6 pages.

ClinicalTrials.gov Identifier: NCT03779282, KETODEX for Emergence Delirium in Children Undergoing Outpatient Strabismus Surgery, First Posted—Dec. 18, 2018, Last Update Posted—Dec. 18, 2018, retrieved from https://clinicaltrials.gov/ct2/show/NCT03779282?term=dexmedetomidine&cond=Agitation%2C+Emergence, 5 pages.

ClinicalTrials.gov Identifier: NCT03806777, Intra-nasal Dexmedetomidine for Children Undergoing MRI Imaging (DexmedMRI), First Posted—Jan. 16, 2019, Last Update Posted—Jan. 25, 2019, retrieved from https://clinicaltrials.gov/ct2/show/NCT03806777, 7 pages.

ClinicalTrials.gov Identifier: NCT03877120, Treatment Of Alcohol Withdrawal Syndrome: Dexmedetomidine Vs Diazepam In A Hospital O'horn, First Posted—Mar. 15, 2019, Last Update Posted—Mar. 15, 2019, retrieved from https://clinicaltrials.gov/ct2/show/NCT03877120, 6 pages.

ClinicalTrials.gov Identifier: NCT03926663, Intranasal Injection of Dexmedetomidine and Bupivacaine in Septoplasty Surgeries, First Posted—Apr. 24, 2019, Last Update Posted—Aug. 1, 2019, retrieved from https://clinicaltrials.gov/ct2/show/NCT03926663, 7 pages.

(56) References Cited

OTHER PUBLICATIONS

ClinicalTrials.gov Identifier: NCT03938831, Dexmedetomidine and Delirium in Elderly Patients, First Posted—May 6, 2019, Last Update Posted—May 6, 2019, retrieved from https://clinicaltrials.gov/ct2/show/NCT03938831, 5 pages.
ClinicalTrials.gov Identifier: NCT03957304, Intranasal Dexmedetomidine Dose-finding Study, First Posted—May 21, 2019, Last Update Posted—May 7, 2021, retrieved from https://clinicaltrials.gov/ct2/show/NCT03957304, 9 pages.
ClinicalTrials.gov Identifier: NCT04010305, Sub-Lingual Dexmedetomidine in Agitation Associated With Schizophrenia, First Posted—Jul. 8, 2019, Access Date—Jun. 9, 2023, retrieved from https://clinicaltrials.gov/ct2/show/NCT04010305, 9 pages.
ClinicalTrials.gov Identifier: NCT04200235, A Trial of Dexmedetomidine Hydrochloride Nasal Spray in Preoperative Sedation of Children, First Posted—Dec. 16, 2019, Last Update Posted—Sep. 9, 2020, retrieved from https://clinicaltrials.gov/ct2/show/NCT04200235, 8 pages.
ClinicalTrials.gov Identifier: NCT04268303, Dexmedetomidine in the Treatment of Agitation Associated With Schizophrenia (Serenity I), First Posted—Feb. 13, 2020; Access Date Apr. 27, 2023, retrieved from https://clinicaltrials.gov/ct2/show/NCT04268303; 9 pages.
ClinicalTrials.gov Identifier: NCT04270708, Intranasal Dexmedetomidine vs Oral Triclofos Sodium for EEG in Children With Autism, First Posted—Feb. 17, 2020, Last Update Posted—Feb. 17, 2020, retrieved from https://clinicaltrials.gov/ct2/show/NCT04270708, 8 pages.
ClinicalTrials.gov Identifier: NCT04276883, Dexmedetomidine in the Treatment of Agitation Associated With Bipolar Disorder (Serenity II), First Posted—Feb. 19, 2020, Access Date—May 30, 2023, retrieved from https://clinicaltrials.gov/ct2/show/NCT04276883, 21 pages.
ClinicalTrials.gov Identifier: NCT04383418, A Trial of Dexmedetomidine Hydrochloride Nasal Spray in Preoperative Sedation of Adults, First Posted—May 12, 2020, Last Update Posted—Jul. 15, 2021, retrieved from https://clinicaltrials.gov/ct2/show/NCT04383418, 7 pages.
ClinicalTrials.gov Identifier: NCT04509414, Intranasal Dexmedetomidine for Deep-sedated Pediatric Dental Patients, First Posted—Aug. 12, 2020, Last Update Posted—Aug. 12, 2020, retrieved from https://clinicaltrials.gov/ct2/show/NCT04509414, 8 pages.
ClinicalTrials.gov Identifier: NCT04665453, Dexmedetomidine and Melatonin for Sleep Induction for EEG in Children (MeloDex), First Posted—Dec. 11, 2020, Last Update Posted—Dec. 16, 2020, retrieved from https://clinicaltrials.gov/ct2/show/NCT04665453, 9 pages.
ClinicalTrials.gov Identifier: NCT04669457, Pediatric Delirium, First Posted—Dec. 16, 2020, Last Update Posted—May 11, 2021, retrieved from https://clinicaltrials.gov/ct2/show/NCT04669457, 8 pages.
ClinicalTrials.gov Identifier: NCT04859283, Premedication With Intranasal Dexmedetomidine in Sedation of Patients Undergoing Total Knee Arthroplasty (TKADEX), First Posted—Apr. 26, 2021, Last Update Posted—Sep. 10, 2021, retrieved from https://clinicaltrials.gov/ct2/show/NCT04859283, 7 pages.
ClinicalTrials.gov Identifier: NCT05065775, Bioavailability of Intranasal Dexmedetomidine (INDEX), First Posted—Oct. 4, 2021, Last Update Posted—Oct. 12, 2021, retrieved from https://clinicaltrials.gov/ct2/show/NCT05065775, 7 pages.
ClinicalTrials.gov Identifier: NCT05111431, A Trial of Dexmedetomidine Hydrochloride Nasal Spray in Preoperative Sedation of Children, First Posted—Nov. 8, 2021, Last Update Posted—Dec. 16, 2021, retrieved from https://clinicaltrials.gov/ct2/show/NCT05111431, 7 pages.
Cohen, et al., "Intranasal Dexmedetomidine for Sedation during CT Scanning", Anesthesiology (2008); 109(A998); 1 page.
Cohen, et al., "Oral transmucosal administration of dexmedetomidine for sedation in 4 dogs", Canadian Veterinary Journal (Nov. 2015); 56(11): 1144-1148.
Cohen, et al., "Treatment of post-electroconvulsive therapy agitation with dexmedetomidine", The Journal of ECT (2013); 29(2): e23-e24.
Congdon, et al., "Evaluation of the sedative and cardiovascular effects of intramuscular administration of dexmedetomidine with and without concurrent atropine administration in dogs", Journal of the American Veterinary Medical Association (2011); 239(1): 81-89.
Co-pending U.S. Appl. No. 17/628,021, inventors Kakumanu; Vasukumar et al., filed on Jan. 18, 2022.
Co-pending U.S. Appl. No. 18/278,786, inventors De Vivo; Michael et al., filed on Aug. 24, 2023.
Co-pending U.S. Appl. No. 18/430,003, inventors Kakumanu; Vasukumar et al., filed on Feb. 1, 2024.
Co-pending U.S. Appl. No. 18/436,589, inventors Nandabalan; Krishnan et al., filed on Feb. 8, 2024.
Co-pending U.S. Appl. No. 18/574,404, inventors Risinger; Robert et al., filed on Dec. 27, 2023.
Cozzi, et al., "Intranasal Dexmedetomidine Sedation as Adjuvant Therapy in Acute Asthma Exacerbation With Marked Anxiety and Agitation", Annals of Emergency Medicine (2016); 69(1): 125-127.
Czinn, et al., "Effectiveness of Intramuscular Dexmedetomidine for Sedation in Young Children Undergoing Diagnostic Testing", The Anesthiology Annual Meeting, American Society of Anestheologists (2011); Abstract A578, 2 pages.
Darrouj, et al. "Dexmedetomidine infusion as adjunctive therapy to benzodiazepines for acute alcohol withdrawal", Annals of Pharmacotherapy (2008); 42(11): 1703-1705.
De Assis Brasil, et al., "The blockade of the serotoninergic receptors 5-HT5A, 5-HT6 and 5-HT7 in the basolateral amygdala, but not in the hippocampus facilitate the extinction of fear memory", Behavioural Brain Research (2019); 372(112055); 7 pages.
De Wilde, et al., "Fluvoxamine and chlorimipramine in endogenous depression", Journal of Affective Disorders (1982); 4(3): 249-259.
Detke, et al., "Active behaviors in the rat forced swimming test differentially produced by serotonergic and noradrenergic antidepressants", Psychopharmacology (1995); 121(1): 66-72.
Dewhirst, et al., "Pain management following myringotomy and tube placement: Intranasal dexmedetomidine versus intranasal fentanyl", International Journal of Pediatric Otorhinolaryngology (2014); 78(7): 1090-1094.
Diaper, et al., "Pharmacological strategies for detoxification", British Journal of Clinical Pharmacology (2013); 77(2): 302-314.
Djaiani, et al., "Dexmedetomidine versus Propofol Sedation Reduces Delirium after Cardiac Surgery", Anesthesiology (2016); 124:362-368.
Dogru, et al., "The Effectiveness of Intramuscular Dexmedetomidine on Hemodynamic Responses During Tracheal Intubation and Anesthesia Induction of Hypertensive Patients: A Randomized, Double-Blind, Placebo-Controlled Study", Current Therapeutic Research (2007); 68(5): 292-302.
D'orazi, et al., "Citalopram/opiate alkaloids Serotonin syndrome, treated with dexmedetomidine: case report", Reactions Weekly, (Nov. 2015); 1579(1): p. 117.
Dua, et al., "Comparative evaluation of dexmedetomidine as a premedication given intranasally vs orally in children between 1 to 8 years of age undergoing minor surgical procedures", Pediatric Anesthesia and Critical Care Journal (2016); 4(1): 13-17.
Dundar, et al., "Pharmacological treatment of acute agitation associated with psychotic and bipolar disorder: a systematic review and meta-analysis", Human Psychopharmacology: Clinical and Experimental (2016); 31: 268-285.
Dyck, et al., "The pharmacokinetics and hemodynamic effects of intravenous and intramuscular dexmedetomidine hydrochloride in adult human volunteers", Anesthesiology (1993); 78(5): 813-820.
Ebert, et al., "The Effects of Increasing Plasma Concentrations of Dexmedetomidine in Humans", Anesthesiology (2000); 93:382-394.
Economopoulos, "BioXcel Therapeutics CEO Says Wearable Devices Are Another Tool To Combat Alzheimer's Agitation", Benzinga (Apr. 15, 2020) [online] https://www.benzinga.com/general/biotech/20/04/15808398/bioxcel-therapeutics-ceo-says-wearable-devices-are-another-tool-to-combat-alzheimers-agitation (Access Date: Aug. 1, 2022); 4 pages.

(56) References Cited

OTHER PUBLICATIONS

El-Gohary, et al., "Dexmedetomidine for Emergence Agitation after Sevoflurane Anesthesia in Preschool Children Undergoing Day Case Surgery: Comparative Dose-Ranging Study", The Medical Journal of Cairo University (2011); 79(2): 17-23.
El-Hamid, et al., "Effect of intranasal dexmedetomidine on emergence agitation after sevoflurane anesthesia in children undergoing tonsillectomy and/or adenoidectomy", Saudi Journal of Anesthesia (2017); 11(2): 137-143.
Ellermann, et al., "Safe electrophysiologic profile of dexmedetomidine in different experimental arrhythmia models", Scientific Reports (2021); 11(1): 23940; 11 pages.
Ely, et al., "Monitoring sedation status over time in ICU patients: reliability and validity of the Richmond Agitation-Sedation Scale (RASS)", Jama (2003); 289(22): 2983-2991.
Emerick, "Automatic pain pathways", Dr. Darren R. Emerick (Apr. 2019); 1 page.
Emerick, "SUMO Pharma Version 1.4", Dr. Darren R. Emerick (Apr. 2019); 3 pages.
Emerick, "SUMO Pharma Version 1.4a", Dr. Darren R. Emerick (Apr. 2019); 1 page.
Emerick, "SUMO Pharma Version 1.5", Dr. Darren R. Emerick (Apr. 2019); 2 pages.
Emerick, "SUMO Pharma Version 1.6", Dr. Darren R. Emerick (Apr. 2019); 1 page.
Emery, et al., "Sedative Effects of Intranasal Midazolam and Dexmedetomidine in 2 Species of Tortoises (*Chelonoidis carbonaria* and *Geochelone platynota*)", Journal of Exotic Pet Medicine (2014); 23(4): 380-383.
Erkola, et al., "Comparison of intramuscular dexmedetomidine and midazolam premedication for elective abdominal hysterectomy", Anesthesia & Analgesia (1994); 79(4): 646-653.
EudraCT Clinical Trial No. 2016-001567-37, Efficacy of single dose intranasal dexmedetomidine for conscious sedation in dental practice in dentophobic uncooperative patients with intellectual disability. University Medical Center Groningen, Date of record first entered Jul. 20, 2016, https://www.clinicaltrialsregister.eu/ctr-search/trial/2016-001567-37/NL, downloaded May 6, 2018, 5 pages.
Extended European Search Report for Application No. 20866739.4, mailed on Aug. 25, 2023, 8 pages.
Extended European Search Report for European Patent Application No. 15850725.1, dated May 24, 2018, 11 pages.
Extended European Search Report for European Patent Application No. 17885750.4, dated Jul. 16, 2020, 7 pages.
Extended European Search Report for European Patent Application No. 19824839.5, dated Feb. 28, 2022, 14 pages.
Extended European Search Report for European Patent Application No. 19826778.3, dated May 10, 2022, 6 pages.
Extended European Search Report for European Patent Application No. 20844019.8, dated Mar. 31, 2023, 19 pages.
Ezz, "Preoperative intranasal dexmedetomidine versus intranasal ketamine for prevention of emergence agitation after sevoflurane in myringotomy patients: A randomized clinical trial", Egyptian Journal of Anaesthesia (2017); 33(2): 141-146.
Farag, et al., "Using Dexmedetomidine to Manage Patients with Cocaine and Opioid Withdrawal, Who Are Undergoing Cerebral Angioplasty for Cerebral Vasospasm", Anesthesia & Analgesia (Dec. 2006); 103(6): 1618-1620.
Ferguson, et al., "Intranasal dexmedetomidine: Procedural sedation in palliative care: A case report", Palliative Medicine (2021); 35(8): 1625-1628.
Finkel, et al., "The use of dexmedetomidine to facilitate acute discontinuation of opioids after cardiac transplantation in children", Critical Care Medicine (2005); 33(9): 2110-2112.
Finkel, et al., "The Use of Dexmedetomidine to Facilitate Opioid and Benzodiazepine Detoxification in an Infant", Anesthesia & Analgesia (2004); 98: 1658-1659.
Flaquer, et al., "Mitochondrial genetic variants identified to be associated with posttraumatic stress disorder", Translational Psychiatry (2015); 5(e524); 7 pages.
Frommeyer, et al., "Dexmedetomidine reduces ventricular arrhythmias in a model of drug-induced QT-prolongation", European Heart Journal (2020); 41(Supplement_2): p. 398.
Fu, et al., "Practical Manual for the Diagnosis and Treatment of Psychological Abnormalities", Shanghai Education Publishing House, 1st Edition (Sep. 2015); p. 92; 2 pages with English translation of relevant portion.
Gagnon, et al., "Transition from Dexmedetomidine to Enteral Clonidine for ICU Sedation: An Observational Pilot Study", Pharmacotherapy (2015); 35(3): 251-259.
Garg, et al., "Efficacy of dexmedetomidine for prevention of emergence agitation in patients posted for nasal surgery under desflurane anaesthesia: A prospective double-blinded randomised controlled trial", Indian Journal of Anaesthesia (2018); 62: 524-530.
Garg, et al., "Use of dexmedetomidine with Propofol in modified electroconvulsive therapy: stable hemodynamics, optimum seizure duration and early recovery", Anaesthesia and Anaesthetics (2018); 2(1): 1-5.
Garrity, et al., "Dexmedetomidine-Induced Sedation Does Not Mimic the Neurobehavioral Phenotypes of Sleep in Sprague Dawley Rat", Sleep (2015); 38(1): 73-84.
Gaudio, et al., "Alfaxalone anaesthesia in Lemur catta following dexmedetomidine-butorphanol-midazolam sedation", Veterinary Anaesthesia and Analgesia (2018); 45(3): 351-356.
Gerlach, et al., "Dexmedetomidine-associated bradycardia progressing to pulseless electrical activity: case report and review of the literature", Pharmacotherapy: The Journal of Human Pharmacology and Drug Therapy (2009); 29: 392e-398e.
Gertler, et al., "Dexmedetomidine: a novel sedative-analgesic agent", BUMC Proceedings (2001); 14: 13-21.
Ghai, et al., "Effect of Low Dose Dexmedetomidine on Emergence Delirium and Recovery Profile following Sevoflurane Induction in Pediatric Cataract Surgeries", Journal of Anesthesiology (2015); 2015(617074); 7 pages.
Ghali, et al., "Preanesthetic medication in children: A comparison of intranasal dexmedetomidine versus oral midazolam", Saudi Journal of Anaesthesia (2011); 5(4): 387-391.
Gilsbach, et al., "Are the pharmacology and physiology of 2adrenoceptors determined by 2heteroreceptors and autoreceptors respectively?", British Journal of Pharmacology (2012); 165: 90-102.
Gioeni, et al., "Evaluation of an oral transmucosal administration of dexmedetomidine-butorphanol and dexmedetomidine-methadone in dogs", International Journal of Health and Animal Science Food Safety (2013); 4(1); Proceeding of Veterinary and Animal Science Days (2017, Jun. 6-8); Milan, Italy, 2 pages.
Gioeni, et al., "Oral transmucosal or intramuscular administration of dexmedetomidine-methadone combination in dogs: Sedative and physiological effects", Animals (2020); 10(2057): 1-11.
Giovannitti, et al., "Alpha-2 Adrenergic Receptor Agonists: A Review of Current Clinical Applications", Anesthesia Progress (2015); 62: 31-38.
Glue, et al., "Influence of CYP2D6 activity on the pharmacokinetics and pharmacodynamics of a single 20 mg dose of ibogaine in healthy volunteers", The Journal of Clinical Pharmacology (2015); 20 pages.
Gossop, "The development of a short opiate withdrawal scale (SOWS)", Addictive Behaviors (1990); 15(5): 487-490.
Granholm, et al., "Evaluation of the clinical efficacy and safety of intramuscular and intravenous doses of dexmedetomidine and medetomidine in dogs and their reversal with atipamezole", Veterinary Anaesthesia and Analgesia (2006); 33(4): 214-223.
Gray, et al., "Psychometric properties of the life events checklist", Assessment (2004); 11(4): 330-341.
Grubb, et al., "Cardiovascular and respiratory effects, and quality of anesthesia produced by alfaxalone administered intramuscularly to cats sedated with dexmedetomidine and hydromorphone", Journal of Feline Medicine and Surgery (2013); 15(10): 858-865.
Gu, et al., "ED50 of Intranasal Dexmedetomidine Sedation for Transthoracic Echocardiography in Children with or without a History of Cardiac Surgery for Cyanotic Congenital Heart Disease", Hindawi BioMed Research International (2020); 2020(1349432); 7 pages.

(56) References Cited

OTHER PUBLICATIONS

Guler, et al., "Single-dose dexmedetomidine reduces agitation and provides smooth extubation after pediatric adenotonsillectomy", Pediatric Anesthesia (2005); 15(9): 762-766.
Gumus, et al., "Comparison of Effects of Different Dexmedetomidine and Chloral Hydrate Doses Used in Sedation on Electroencephalography in Pediatric Patients", Journal of Child Neurology (2015); 30(8): 983-988.
Gupta, et al., "Comparison between intranasal dexmedetomidine and intranasal midazolam as premedication for brain magnetic resonance imaging in pediatric patients: A prospective randomized double blind trial", Journal of Anaesthesiology, Clinical Pharmacology (2017); 33(2): 236-240.
Guthrie, et al., "Pharmacologic interventions for the treatment of opioid dependence and withdrawal", DICP, The Annals of Pharmacotherapy (Jul./Aug. 1990); 24: 721-734.
Gutirrez, "Clinical case of rapid opiate detoxification under anesthesia", Anestesia Pediatrica e Neonatale (2011); 9(1); 10 pages.
Gyanesh, et al., "Comparison between intranasal dexmedetomidine and intranasal ketamine as premedication for procedural sedation in children undergoing MRI: a double-blind, randomized, placebo-controlled trial", Journal of Anesthesia (2014); 28(1): 12-18.
Haenecour, et al., "Prolonged dexmedetomidine infusion and drug withdrawal in critically ill children", Journal of Pediatric Pharmacology and Therapeutics (2017); 22(6): 453-460.
Hamilton, "A rating scale for depression", Journal of Neurology, Neurosurgery, and Psychiatry (1960); 23(1): 56-62.
Han, et al., "A randomized study of intranasal vs. intravenous infusion of dexmedetomidine in gastroscopy", International Journal of Clinical Pharmacology and Therapeutics (2014); 52(9): 756-761.
Handley, et al., "Effects of alpha-adrenoceptor agonists and antagonists in a maze-exploration model of 'fear'-motivated behaviour", Naunyn-Schmiedeberg's Archives of Pharmacology (1984); 327: 1-5.
Hassan, et al., "A comparison of the effect of paroxetine and amitriptyline on the tyramine pressor response test", British Journal of Clinical Pharmacology (1985); 19(5): 705-706.
Hauber, et al., "Dexmedetomidine as a Rapid Bolus for Treatment and Prophylactic Prevention of Emergence Agitation in Anesthetized Children", Anesthesia & Analgesia (2015); 121(5): 1308-1315.
Hitt, et al., "An Evaluation of Intranasal Sufentanil and Dexmedetomidine for Pediatric Dental Sedation", Pharmaceutics (2014); 6(1): 175-184.
Honey, et al., "2-Receptor Agonists for Treatment and Prevention of Iatrogenic Opioid Abstinence Syndrome in Critically Ill Patients", Annals of Pharmacotherapy (Sep. 2009); 43: 1506-1511.
Hong, et al., "Dexmedetomidine alleviates smoke-induced bronchial and alveolar epithelial cell injury", General Physiology and Biophysics (2020); 39(3): 293-300.
Hong, et al., "Dexmedetomidine preconditioning ameliorates lung injury induced by pulmonary ischemia/reperfusion by upregulating promoter histone H3K4me3 modification of KGF-2", Experimental Cell Research (2021); 406(112762); 11 pages.
Hospira, "Safety Data Sheet, Product Name: Precedex (dexmedetomidine hydrochloride) Injection, Solution", MSDS Coordinator: Hospira GEHS, Date Revised: Jun. 2, 2014; 7 pages.
Hossein, et al., "Comparing the effect of premedication with intra-nasal dexmedetomidine and intra-nasal midazolam on sedation and anxiety level in children undergoing elective surgery", Journal of Anaesthesiology and Pain (2016); 6(3): 1-10; English abstract only; 1 page.
Howland, et al., "Caffeinated alcoholic beverages: An emerging public health problem", American Journal of Preventive Medicine (2011); 40(2): 268-271.
Hrishi, et al., "A Novel Use of a Novel Drug: Preoperative Nasal Preparation with Dexmedetomidine for Transnasal Transsphenoidal Neurosurgery Approach in Skull Base Neurosurgery", Indian Journal of Neurosurgery (2017); 6 pages.
Hsiao, "Sublingual dexmedetomidine as a potential new treatment for agitation", JAMA (Feb. 22, 2022); 327(8): 723-725.
Hsu, et al., "Selection of medications for pediatric procedural sedation outside of the operating room", Up To Date (Last Updated: Oct. 10, 2017) [online] https://www.uptodate.com/contents/selectionof-medications-for-pediatric-procedural-sedation-outside-of-the-operating-room (Access date: Mar. 29, 2019); 15 pages.
Huang, et al., "Dexmedetomidine Directly Increases Tau Phosphorylation", Journal of Alzheimer's Disease (2015); 44: 839-850.
Ibacache, et al., "Single-Dose Dexmedetomidine Reduces Agitation After Sevoflurane Anesthesia in Children", Anesthesia & Analgesia (2004); 98(1): 60-63.
Ibrahim, "A prospective, randomized, double blinded comparison of intranasal dexmedetomidine vs intranasal ketamine in combination with intravenous midazolam for procedural sedation in school aged children undergoing MRI", Anesthesia Essays and Researches (2014); 8(2): 179-186.
Igalmi (dexmedetomidine) sublingual film, for sublingual or buccal use, Sublingual film: 120 mcg and 180 mcg, Highlights of Prescribing Information, Revised Apr. 2022 (Apr. 2022), Initial U.S. Approval: 1999, Reference ID: 4964494, Distributed by: BioXcel Therapeutics, Inc. 555 Long Wharf Drive 12th Floor New Haven, CT 06511; 21 pages.
Igalmi (dexmedetomidine) sublingual film, for sublingual or buccal use, Sublingual film: 120 mcg and 180 mcg, Highlights of Prescribing Information, Revised Jul. 2022 (Jul. 2022), Initial U.S. Approval: 1999, Distributed by: BioXcel Therapeutics, Inc. 555 Long Wharf Drive 12th Floor New Haven, CT 06511; 21 pages.
Iirola, et al., "Bioavailability of dexmedetomidine after intranasal administration", European Journal of Clinical Pharmacology (2011); 67(8): 825-831.
Iirola, et al., "Population pharmacokinetics of dexmedetomidine during long-term sedation in intensive care patients", British Journal of Anaesthesia (2012); 108(3): 460-468.
International Preliminary Report on Patentability for International Application No. PCT/US2020/051256 dated Mar. 31, 2022, 16 pages.
International Preliminary Report on Patentability for International Application No. PCT/US2022/011130, mailed Jul. 13, 2023, 8 pages.
International Preliminary Report on Patentability for International Application No. PCT/US2022/017963 dated Sep. 7, 2023, 10 pages.
International Preliminary Report on Patentability for International Application No. PCT/US2022/035919 dated Jan. 11, 2024, 8 pages.
International Preliminary Report on Patentability in International Application No. PCT/US2015/055828 dated Apr. 18, 2017, 8 pages.
International Preliminary Report on Patentability in International Application No. PCT/US2017/069030, mailed Jul. 11, 2019, 7 pages.
International Preliminary Report on Patentability in International Application No. PCT/US2019/039268, mailed Jan. 7, 2021, 18 pages.
International Preliminary Report on Patentability in International Application No. PCT/US2019/039308, mailed Jan. 7, 2021, 12 pages.
International Preliminary Report on Patentability in International Application No. PCT/US2020/042618 dated Feb. 3, 2022, 19 pages.
International Preliminary Report on Patentability in International Application No. PCT/US2021/017857, mailed Aug. 25, 2022, 8 pages.
International Preliminary Report on Patentability in International Application No. PCT/US2021/054171, mailed Apr. 20, 2023, 13 pages.
International Search Report and Written Opinion, for International Application No. PCT/US2017/069030, mailed Feb. 28, 2018, 8 pages.
International Search Report and Written Opinion for International Application No. PCT/US2021/017857 dated Apr. 26, 2021, 9 pages.
International Search Report and Written Opinion for International Application No. PCT/US2022/011130 dated Mar. 16, 2022, 10 pages.

(56) References Cited

OTHER PUBLICATIONS

International Search Report and Written Opinion for International Application No. PCT/US2022/017963 dated May 23, 2022, 15 pages.
International Search Report and Written Opinion for International Application No. PCT/US2022/035919, mailed on Oct. 5, 2022, 10 pages.
International Search Report and Written Opinion for International Application No. PCT/US2023/073874 dated Jan. 26, 2024, 9 pages.
International Search Report and Written Opinion of the International Searching Authority for International Application No. PCT/US2019/039268, mailed Sep. 13, 2019, 20 pages.
International Search Report and Written Opinion of the International Searching Authority for International Application No. PCT/US2019/039308, mailed Sep. 13, 2019, 15 pages.
International Search Report and Written Opinion of the International Searching Authority for International Application No. PCT/US2020/042618, mailed Mar. 1, 2021, 22 pages.
International Search Report and Written Opinion of the International Searching Authority for International Application No. PCT/US2020/051256, mailed Dec. 10, 2020, 18 pages.
International Search Report and Written Opinion of the International Searching Authority for International Application No. PCT/US2021/054171, mailed Feb. 15, 2022, 18 pages.
International Search Report for International Application No. PCT/US2015/055828, mailed Mar. 1, 2016; 4 pages.
Invitation to Pay Additional Fees in International Application No. PCT/US2015/055828 dated Dec. 9, 2015, 2 pages.
Invitation to Pay Additional Fees in International Application No. PCT/US2020/042618 dated Dec. 22, 2020, 2 pages.
Invitation to Pay Additional Fees in International Application No. PCT/US2021/054171 dated Dec. 15, 2021, 2 pages.
IRCT Registration No. IRCT2015103011398N9, Effect of intranasal administration of dexmedetomidine in providing moderate sedation for patients undergoing ERCP ; a randomized control trial. Iran University of Medical Sciences, Registration date Nov. 4, 2015, http://en.irct.ir/trial/11663 , downloaded May 5, 2018, 12 pages.
Isik, et al., "Dexmedetomidine decreases emergence agitation in pediatric patients after sevoflurane anesthesia without surgery", Pediatric Anesthesia (2006); 16(7): 748-753.
Jaakola, et al., "Intramuscular dexmedetomidine premedication—an alternative to midazolam-fentanyl-combination in elective hysterectomy?", Acta Anaesthesiologica Scandinavica (1994); 38(3): 238-243.
Jayaram, et al., "A comparative study to evaluate the effect of intranasal dexmedetomidine versus oral alprazolam as a premedication agent in morbidly obese patients undergoing bariatric surgery", Journal of Anaesthesiology Clinical Pharmacology (Apr.-Jun. 2013); 29(2): 179-182.
Jiří, "Intramuscular Dexmedetomidine In Burns Victims—Preliminary Results", Anaesthesiology and Intensive Care Medicine (2008); 2: 82-86 (with English Abstract).
Jia, et al., "A randomised study of intranasal dexmedetomidine and oral ketamine for premedication in children", Anaesthesia (2013); 68(9): 944-949.
Jia et al., "Application of intranasal dexmedetomidine hydrochloride combined sevoflurane inhalation anesthesia in pediatric lingual frenoplasty", Journal of Xinxiang Medical University (2015); 32(8): 732-734; English Abstract only.
Johnson, et al., "The Combine Saftee: a structured instrument for collecting adverse events adapted for clinical studies in the alcoholism field", Journal of Studies on Alcohol (2005); Supplement 15: 157-167.
Jun, et al., "The effects of intranasal dexmedetomidine premedication in children: a systematic review and meta-analysis", Canadian Journal of Anesthesia/Journal Canadien D'anesthésie (2017); 64: 947-961.
Jung, et al., "1877: Dexmedetomidine for Treatment of Refractory Opioid Withdrawal", Critical Care Medicine (2016); 44(12 Suppl.); 1 page.
Jung, et al., "Dexmedetomidine for Treatment of Refractory Heroin Withdrawal", Journal of Emergency Nursing (Mar. 2017); 43(2): 182-184.
Jung, et al., "Effect of dexmedetomidine on emergence agitation in male patients undergoing closed reduction of a nasal bone fracture", Rawal Medical Journal (Apr.-Jun. 2015); 40(2): 191-196.
Kambow, et al., "Randomized Double Blind Clinical Trial Of Intramuscular Dexmedetomidine V/S Midazolam As Premedication In Paediatric Surgical Patients", Journal of Evolution of Medical and Dental Sciences (2016); 5(42): 2566-2570.
Kang, et al., "The correlation of heart rate between natural sleep and dexmedetomidine sedation", Korean Journal of Anesthesiology (2019); 72(2): 164-168.
Karaaslan, et al., "Comparison of buccal and intramuscular dexmedetomidine premedication for arthroscopic knee surgery", Journal of Clinical Anesthesia (2006); 18(8): 589-593.
Kawaai, et al., "Dexmedetomidine decreases the oral mucosal blood flow", British Journal of Oral and Maxillofacial Surgery (2013); 51: 928-931.
Kaya, et al., "The Effects of Intramuscular Dexmedetomidine Premedication on Hemodynamics, Plasma Norepinephrine, Cortisol and Glucose Concentrations", O.M.Ü. T>p Dergisi (2006); 23(1): 9-16.
Keating, "Dexmedetomidine: A Review of Its Use for Sedation in the Intensive Care Setting", Drugs (2015); 75: 1119-1130.
Keck Jr, "The management of acute mania", BMJ (2003); 327(7422): 1002-1003.
Keles, et al., "The Effect of Oral Dexmedetomidine Premedication on Preoperative Cooperation and Emergence Delirium in Children Undergoing Dental Procedures", Hindawi BioMed Research International (2017); 2017(6742183); 7 pages.
Kelley, et al., "Intramuscular Dexmedetomidine & Midazolam for Preoperative Sedation: A Case Series", Pediatric Anasthesia, University of Pittsburgh, Poster Board (Winter 2013) [online] http://www2.pedsanesthesia.org/meetings/2013winter/posters/uploads/373--NM-293.pdf; 1 page.
Kerfoot, et al., "Effects of family history of alcohol dependence on the subjective response to alcohol using the intravenous alcohol clamp", Alcoholism: Clinical and Experimental Research (2013); 37(12): 2011-2018.
Khenissi, et al., "Comparison of intramuscular alfaxalone and ketamine combined with dexmedetomidine and butorphanol for castration in cats", Journal of Feline Medicine and Surgery (2016); 19(8): 791-797.
Kim, et al., "Appropriate dose of dexmedetomidine for the prevention of emergence agitation after desflurane anesthesia for tonsillectomy or adenoidectomy in children: up and down sequential allocation", BMC Anesthesiology (2015); 15(79); 6 pages.
Kim, et al., "Dexmedetomidine for sedation in pediatric patients who received more than 20 sessions of radiation therapy-two cases report", Korean Journal of Anesthesiology (2016); 69 (6): 627-631.
Kim, et al., "Risk Factors of Emergence Agitation in Adults Undergoing General Anesthesia for Nasal Surgery", Clinical and Experimental Otorhinolaryngology (Mar. 2015); 8(1): 46-51.
Kiresuk, et al., "Goal attainment scaling: A general method for evaluating comprehensive community mental health programs", Community Mental Health Journal (1968); 4: 443-453.
Kobayashi, et al., "Efficacy of Dexmedetomidine for Controlling Delirium in Intensive Care Unit Patients", Japanese Journal of Anesthesiology [Masui] (2007); 56(10): 1155-1160.
Kobayashi, et al., "Mechanism of the Inhibitory Effect of Surfactants on Intramuscular Absorption of Drugs", Chemical and Pharmaceutical Bulletin (1977); 25(7): 1547-1554.
Konia, "Oral dexmedetomidine for preoperative sedation in an adult uncooperative autistic patient", Journal of Clinical Anesthesia (2016); 34: 29-31.
Korpivaara, et al., "Dexmedetomidine oromucosal gel for noise-associated acute anxiety and fear in dogsa randomised, double-blind, placebo-controlled clinical study", Veterinary Record (2017); 7 pages.

(56) References Cited

OTHER PUBLICATIONS

Korpivaara, et al., "Effect of dexmedetomidine oromucosal gel for alleviation of canine acute fear and anxiety associated with noise at sub-sedative doses—A pilot study", Poster presented at the BSAVA Congress 2014; 1 page.
Kostoglou, et al., "Effect of β-carotene on health status and performance of sows and their litters", Journal of Animal Physiology and Animal Nutrition (2000); 83(3): 150-157.
Kranzler, et al., "Naltrexone vs. nefazodone for treatment of alcohol dependence: A placebo-controlled trial", Neuropsychopharmacology (2000); 22(5): 493-503.
Krimins, et al., "Hemodynamic effects in dogs after intramuscular administration of a combination of dexmedetomidine-butorphanol-tiletamine-zolazepam or dexmedetomidine-butorphanol-ketamine", American Journal of Veterinary Research (2012); 73(9): 1363-1370.
Kästner, et al., "Clinical comparison of preanaesthetic intramuscular medetomidine and dexmedetomidine in domestic sheep", DTW. Deutsche Tierarztliche Wochenschrift (2001); 108(10): 409-413.
Kumar, et al., Efficacy of intranasal dexmedetomidine versus oral midazolam for paediatric premedication, Indian Journal of Anaesthesia (Feb. 2017); 61(2): 125-130.
Kumar, et al., "Role of dexmedetomidine for sedation in a patient with schizophrenia for strabismus surgery", Indian Journal of Anaesthesia (2016); 60(11): 856-857.
Kumari, et al., "Clinico-anesthetic and Hemodynamic Effects of Midazolam and Dexmedetomidine-Midazolam with Propofol in Dogs During Ovariohysterectomy", The Philippine Journal of Veterinary Medicine (2017); 54(1): 46-53; English abstract only; 1 page.
Kundra, et al., "Oral ketamine and dexmedetomidine in adults' burns wound dressing—A randomized double blind cross over study", Burns (2013); 39: 1150-1156.
Kurlansky, et al., "Role of the carrier solution in cyclosporine pharmacokinetics in the baboon", The Journal of Heart Transplantation (1986); 5(4): 312-316.
Lalumiere, et al., "Post-Training Intra-Basolateral Amygdala Infusions of Norepinephrine Enhance Consolidation of Memory for Contextual Fear Conditioning", The Journal of Neuroscience (Jul. 30, 2003); 23(17): 6754-6758.
Lami, et al., "Transmucosal dexmedetomidine for computed tomography sedation", Paediatric Anaesthesia (2008); 18: 349-350.
Lang, et al., "Emotional imagery: Conceptual structure and pattern of somato-visceral response", Psychophysiology (1980); 17(2): 179-192.
Lang, et al., "Fear behavior, fear imagery, and the psychophysiology of emotion: the problem of affective response integration", Journal of Abnormal Psychology (1983); 92(3): 276-306.
Lassen, "Potent and long-lasting potentiation of two 5-hydroxytryptophan-induced effects in mice by three selective 5-HT uptake inhibitors", European Journal of Pharmacology (1978); 47(3): 351-358.
Laursen, et al., "Paroxetine in the treatment of depression-a randomized comparison with amitriptyline", Acta Psychiatrica Scandinavica (1985); 71(3): 249-255.
Lee, et al., "Antioxidant approaches for the treatment of Alzheimer's disease", Expert Review of Neurotherapeutics (2010); 10(7): 1201-1208.
Lehman, et al., "Practice Guideline for the Treatment of Patients With Schizophrenia", American Psychiatric Association Practice Guidelines, Second Edition (2010); 184 pages.
Lei, et al., "Incidence and risk factors of bradycardia in pediatric patients undergoing intranasal dexmedetomidine sedation", Acta Anaesthesiologica Scandinavica (2020); 64: 464-471.
Levänen, et al., "Dexmedetomidine Premedication Attenuates Ketamine-induced Cardiostimulatory Effects and Postanesthetic Delirium", Anesthesiology (1995); 82: 1117-1125.
Li, et al., "A comparison of intranasal dexmedetomidine for sedation in children administered either by atomiser or by drops", Anaesthesia (2016); 71: 522-528.
Li, et al., "Dexmedetomidine inhibits inflammation in microglia cells under stimulation of LPS and ATP by c-Fos/NLRP3/caspase-1 cascades", EXCLI Journal (2018); 17: 302-311.
Li, et al., "Impact of dexmedetomidine on the incidence of delirium in elderly patients after cardiac surgery: A randomized controlled trial", PLoS ONE (Feb. 9, 2017); 12(2): e0170757; 15 pages.
Li, et al., "Intranasal dexmedetomidine for sedation in children undergoing transthoracic echocardiography study a prospective observational study", Pediatric Anesthesia (2015); 25: 891-896.
Li, et al., "Intranasal dexmedetomidine with and without buccal midazolam for procedural sedation in autistic children: a double-blind randomised controlled trial", The Lancet (2017); p. 26; English abstract only; 1 page.
Li, et al., "The 95% effective dose of intranasal dexmedetomidine sedation for pulmonary function testing in children aged 1-3 years: A biased coin design up-and-down sequential method", Journal of Clinical Anesthesia (2020); 63(109746); 5 pages.
Lieberman, et al., "Separate and concomitant use of lamotrigine, lithium, and divalproex in bipolar disorders", Current Psychiatry Reports (2004); 6(6): 459-465.
Lili, et al., "The application of dexmedetomidine in children undergoing vitreoretinal surgery", Journal of Anesthesia (2012); 26(4): 556-561.
Lin, et al., "Efficacy of premedication with intranasal dexmedetomidine on inhalational induction and postoperative emergence agitation in pediatric undergoing cataract surgery with sevoflurane", Journal of Clinical Anesthesia (2016); 33: 289-295.
Liu, et al., "Safety and sedative effect of intranasal dexmedetomidine in mandibular third molar surgery: a systematic review and meta-analysis", Drug Design, Development and Therapy (2019); 13: 1301-1310.
Liu, et al., "Comparison of sedative effects of two methods of intranasal dexmedetomidine in cardiac ultrasonography in infants with congenital heart disease", Practical Medicine and Clinic (2015); 18(12): 1452-1454; English abstract only; 2 pages.
Liu, et al., "Determination of the 90% effective dose of intranasal dexmedetomidine for sedation during electroencephalography in children", Acta Anaesthesiologica Scandinavica (2019); 63: 847-852.
Liu, et al., "Dexmedetomidine Versus Propofol Sedation Improves Sublingual Microcirculation After Cardiac Surgery: A Randomized Controlled Trial", Journal of Cardiothoracic and Vascular Anesthesia (Dec. 2016); 30(6): 1509-1515.
Liu, et al., "Effects of preoperative intranasal Dexmedetomidine for the bispectral index and median effective concentration of Sevoflurane in children with abdominal surgery by inhalation anesthesia of Sevoflurane", China Medical Herald (2017); 14(34): 66-69, 73; 5 pages with English Abstract.
Liyan, et al., "Effect of dexmedetomidine on minimum alveolar concentration of sevoflurane in children undergoing inhalation anesthesia", Beijing Medical Journal (2017); 39(6): 581-584; English abstract only; 1 page.
Li, et al., "Comparison of preoperative application of different doses of dexmedetomidine intranasal in children undergoing outpatient surgery", Sichuan Medicine (2015); 36(09): 1209-1211; English abstract only; 2 pages.
Li, et al., "Pharmacokinetic and pharmacodynamic study of intranasal and intravenous dexmedetomidine", British Journal of Anaesthesia (2018); 120(5): 960-968.
Louis, et al., "Effects of dexmedetomidine on delirium duration of non-intubated ICU patients (4D trial): study protocol for a randomized trial", Trials (2018); 19(307); 11 pages.
Lu, et al., "Intranasal Dexmedetomidine as a Sedative Premedication for Patients Undergoing Suspension Laryngoscopy: A Randomized Double-Blind Study", PLoS ONE (2016); 11(5): e0154192; 12 pages.
Lu, "Modern Traditional Chinese Medicine Formulation Technology", Hubei Science and Technology Press (Sep. 30, 2001); 460-463.
Maccioli, et al., "Dexmedetomidine to Facilitate Drug Withdrawal", Anesthesiology (Feb. 2003); 98(2): 575-577.

(56) References Cited

OTHER PUBLICATIONS

Machida, "Nenmaku tekiyou seizai [mucous membrane applying pharmaceutical formulation or mucous membrane application product]", New Drug Delivery System, 1st impression (Jan. 31, 2000); pp. 77-85.

Maclaren, et al., "A randomized, double-blind pilot study of dexmedetomidine versus midazolam for intensive care unit sedation: patient recall of their experiences and short-term psychological outcomes", Journal of Intensive Care Medicine (2015); 30(3): 167-175.

Madhav, et al., "Orotransmucosal drug delivery systems: A review", Journal of Controlled Release (2009); 140: 2-11.

Mahmoud, et al., "Dexmedetomidine: review, update, and future considerations of paediatric perioperative and periprocedural applications and limitations", British Journal of Anaesthesia (2015); 171-182.

Malhotra, et al., "Comparative evaluation of dexmedetomidine and midazolam-ketamine combination as sedative agents in pediatric dentistry: A double-blinded randomized controlled trial", Contemporary Clinical Dentistry (2016); 7: 186-192.

Manaa, et al., "Fentanyl versus dexmedetomidine effect on agitation after sevoflurane anaesthesia", Saudi Journal of Anaesthesia (2007); 1: 57-61.

Martin, et al., "Development and validation of the biphasic alcohol effects scale", Alcoholism: Clinical and Experimental Research (1993); 17(1): 140-146.

Martin, et al., "The Role of the 2-Adrenoceptor Agonist Dexmedetomidine in Postsurgical Sedation in the Intensive Care Unit", Journal of Intensive Care Medicine (2003); 18: 29-41.

Mason, et al., "10AP3-7 Intramuscular dexmedetomidine for pediatric electroencephalogram (EEG) sedation", European Journal of Anaesthesiology (EJA) (2012); p. 161.

Mason, et al., "Intramuscular dexmedetomidine: an effective route of sedation preserves background activity for pediatric electroencephalograms", The Journal of Pediatrics (2012); 161(5): 927-932.

Mason, et al., "Intramuscular Dexmedetomidine Sedation for Pediatric MRI and CT", American Journal of Roentgenology (Sep. 2011); 197: 720-725.

Mazy, et al., "Spinal anesthesia for lengthy lower limb orthopedic surgeries: dexmedetomidine plus fentanyl versus dexmedetomidine", Ain-Shams Journal of Anesthesiology (2019); 11(10); 8 pages.

Mello, et al., "Buprenorphine effects on human heroin self-administration: an operant analysis", Journal of Pharmacology and Experimental Therapeutics (1982); 223(1): 30-39.

Micieli, et al., "Sedative and cardiovascular effects of intranasal or intramuscular dexmedetomidine in healthy dogs", Veterinary Anaesthesia and Analgesia (2017); 44(4): 703-709.

Miller, et al., "Comparison of Intranasal Dexmedetomidine and Oral Pentobarbital Sedation for Transthoracic Echocardiography in Infants and Toddlers: A Prospective, Randomized, Double-Blind Trial", Anesthesia & Analgesia (Jun. 2018); 126(6): 2009-2016.

Miller, et al., "Current Understanding of the Neurobiology of Agitation", Western Journal of Emergency Medicine (Jul. 2020); 21(4): 841-848.

Miller, et al., "Does intranasal dexmedetomidine provide adequate plasma concentrations for sedation in children: a pharmacokinetic study", British Journal of Anaesthesia (2018); 120(5): 1056-1065.

Miller, et al., "Dosing and efficacy of intranasal dexmedetomidine sedation for pediatric transthoracic echocardiography: a retrospective study", Canadian Journal of Anesthesia (2016); 63(7): 834-841.

Misra, et al., "Effect of preoperative dexmedetomidine nebulization on the hemodynamic response to laryngoscopy and intubation: a randomized control trial", Korean Journal of Anesthesiology (2021); 74(2): 150-157.

Mizrak, et al., "Dexmedetomidine Use during Strabismus Surgery in Agitated Children", Medical Principles and Practice (2011); 20(5): 427-432.

Mizrak, et al., "Premedication with dexmedetomidine and midazolam attenuates agitation after electroconvulsive therapy", Journal of Anesthetics (2009); 23(1): 6-10.

Mohite, et al., "Role of dexmedetomidine in pediatric dental sedation", Journal of Dental Anesthesia and Pain Medicine (2019 ); 19(2): 83-90.

Mohr, et al., "Treatment of acute agitation in psychotic disorders", Neuroendocrinology Letters (2005); 26(4): 327-335.

Montoya, et al., "Validation of the Excited Component of the Positive and Negative Syndrome Scale (PANSS-EC) in a naturalistic sample of 278 patients with acute psychosis and agitation in a psychiatric emergency room", Health and Quality of Life Outcomes (2011); 9(18); 11 pages.

Morean, et al., "The drug effects questionnaire: psychometric support across three drug types", Psychopharmacology (2013); 227: 177-192.

Moret, et al., "Biochemical profile of midalcipran (F 2207), 1-phenyl-1-diethyl-aminocarbonyl-2-aminomethyl-cyclopropane (Z) hydrochloride, a potential fourth generation antidepressant drug", Neuropharmacology (1985); 24(12): 1211-1219.

Moshiri, et al., "Premedication effect of dexmedetomidine and alfentanil on seizure time, recovery duration, and hemodynamic responses in electroconvulsive therapy", Annals of Cardiac Anaesthesia (2016); 19(2): 263-268.

Mostafa, et al., "Effect of Different Doses of Dexmedetomidine on Stress Response and Emergence Agitation after Laparoscopic Cholecystectomy: Randomized Controlled Double-Blind Study", Journal of Anesthesia & Clinical Research (2017); 8(2): 1000707; 6 pages.

Mountain, et al., "Dexmedetomidine as a Pediatric Anesthetic Premedication to Reduce Anxiety and to Deter Emergence Delirium", AANA Journal (Jun. 2011); 79(3): 219-224.

Mukherjee, et al., "Emergence agitation prevention in paediatric ambulatory surgery: A comparison between intranasal Dexmedetomidine and Clonidine", Journal of Pharmacy Practice and Research (2015); 4(1): 24-30.

Multz, "Prolonged Dexmedetomidine Infusion as an Adjunct in Treating Sedation-Induced Withdrawal", Anesthesia & Analgesia (2003); 96: 1054-1055.

Muszkat, et al., "Alpha2-Adrenergic Receptor-Induced Vascular Constriction in Blacks and Whites", Hypertension (2004); 43: 31-35.

Na, et al., "Randomized controlled trial on influence of nasal administration of dexmedetomidine after induction of anesthesia on agitation of children in ophthalmologic surgery", Adverse Drug Reactions Journal (2016); 18(2): 95-98, English abstract only; 1 page.

Naples, et al., "Comparison of the Anesthetic Effects of Oral Transmucosal Versus Injectable Medetomidine in Combination with Tiletamine-Zolazepam for Immobilization of Chimpanzees (*Pan troglodytes*)", Journal of Zoo and Wildlife Medicine (2010); 41(1): 50-62.

Nasr, et al., "Ultra-rapid opiate detoxification using dexmedetomidine under general anesthesia", Journal of Opioid Management (Sep./Oct. 2011); 7(5): 337-344.

Nawrat, "Triple combo: calming Alzheimer's agitation with AI, wearables and a novel drug", Medical Device Network (Jan. 28, 2020) [online] https://www.medicaldevice-network.com/analysis/wearable-ai-device-for-agitation/#:~:text= (Access Date: Aug. 1, 2022); 4 pages.

Neville, et al., "Double-blind Randomized Controlled Trial of Intranasal Dexmedetomidine Versus Intranasal Midazolam as Anxiolysis Prior to Pediatric Laceration Repair in the Emergency Department", Academic Emergency Medicine (Aug. 2016); 23(8): 910-917.

Ni, et al., "Effect of Dexmedetomidine on Preventing Postoperative Agitation in Children: A Meta-Analysis", PLoS ONE (2015); 10(5): e0128450; 13 pages.

Nitturi, et al., " A Comparative Evaluation of Intranasal Dexmedetomidine and Intranasal Midazolam for Premedication in Pediatric Surgery", IAIM (2018); 5(1): 82-94.

Niyogi, et al., "Attenuation of haemodynamic responses to laryngoscopy and endotracheal intubation with dexmedetomidine: A comparison between intravenous and intranasal route", Indian Journal of Anaesthesia (2019); 63: 915-923.

(56) References Cited

OTHER PUBLICATIONS

Nizari, et al., "Non-amyloidogenic effects of 2 adrenergic agonists: implications for brimonidine-mediated neuroprotection", Cell Death & Disease (2016); 7(e2514);13 pages.

Nooh, et al., "Intranasal atomized dexmedetomidine for sedation during third molar extraction", International Journal of Oral and Maxillofacial Surgery (2013); 42: 857-862.

Nuamah et al., "The past, present and future of opioid withdrawal assessment: a scoping review of scales and technologies", BMC Medical Informatics and Decision Making (2019); 19(113); 11 pages.

O'Brien, et al., "Dexmedetomidine and the successful management of electroconvulsive therapy postictal agitation: a case report", The Journal of ECT (2010); 26(2): 131-133.

Ohmori, et al., "Post-operative cardiac arrest induced by co-administration of amiodarone and dexmedetomidine: a case report", Journal of Intensive Care (2015); 3(43): 1-5.

Oschman, et al., "Dexmedetomidine for opioid and benzodiazepine withdrawal in pediatric patients", American Journal of Health-System Pharmacy (Jul. 1, 2011); 68: 1233-1238.

Ouchi, et al., "Dexmedetomidine Dose Dependently Enhances the Local Anesthetic Action of Lidocaine in Inferior Alveolar Nerve Block A Randomized Double-Blind Study", Regional Anesthesia & Pain Medicine (May-Jun. 2016); 41(3): 348-355.

Pant, et al., "Comparison of Sublingual Midazolam and Dexmedetomidine for Premedication in Children", Minerva Anestesiologica (2014); 80(2): 167-175.

Parikh, et al., "Single Dose Pharmacokinetics of Fentanyl Sublingual Spray and Oral Transmucosal Fentanyl Citrate in Healthy Volunteers: A Randomized Crossover Study", Clinical Therapeutics (2013); 35(3): 236-243.

Park, et al., "Dexmedetomidine Oral Mucosa Patch for Sedation Suppresses Apoptosis in Hippocampus of Normal Rats", International Neurourology Journal (2017); 21(Suppl 1):S39-S47.

Parmar, et al., "A Review On Sublingual Spray: Novel Drug Delivery System", IJPSR (2017); 8(11): 4533-4539.

Pasin, et al., "Dexmedetomidine vs Midazolam as Preanesthetic Medication in Children: a Meta-Analysis of Randomized Controlled Trials", Pediatric Anesthesia (2015); 9 pages.

Patel, et al., "Vasovagal syncope and severe bradycardia following intranasal dexmedetomidine for pediatric procedural sedation", Paediatric Anaesthesia (2014); 24: 446-448.

Pavithra, et al., "Comparison of two doses of intranasal dexmedetomidine as premedication in children", Pediatric Anesthesia and Critical Care Journal (2017); 5(2): 86-94.

Peker, et al., "A-600 Buccal versus intramuscular dexmedetomidine premedication for arthroscopic knee surgery under spinal anesthesia", European Journal of Anaesthesiology (EJA) (2006); p. 156.

Peng, et al., "Premedication with dexmedetomidine in pediatric patients: a systematic review and meta-analysis", Clinics (2014); 69(11): 777-786.

Penttilä, et al., "Cardiovascular and parasympathetic effects of dexmedetomidine in healthy subjects", Canadian Journal of Physiology and Pharmacology (2004); 82(5): 359-362.

Pestieau, et al., "The effect of dexmedetomidine during myringotomy and pressure equalizing tube placement in children", Pediatric Anesthesia (2011); 21(11): 1128-1135.

Phan, et al., "Clinical Uses of Dexmedetomidine in Pediatric Patients", Pediatric Drugs (2008); 10(1): 49-69.

Picard, et al., "Psychological Stress and Mitochondria: A Systematic Review", Psychosomatic Medicine (Feb./Mar. 2018); 80(2): 141-153.

Pinelas, et al., "Effects of different doses of dexmedetomidine on anaesthetic induction with alfaxalone—a clinical trial", Veterinary Anaesthesia and Analgesia (2013); 41(4): 378-385.

Pons, et al., "Effects of dexmedetomidine administered at acupuncture point GV20 compared to intramuscular route in dogs", Journal of Small Animal Practice (2016); 6 pages.

Porters, et al., "Sedative and antinociceptive effects of dexmedetomidine and buprenorphine after oral transmucosal or intramuscular administration in cats", Veterinary Anaesthesia and Analgesia (2014); 41(1): 90-96.

Porters, et al., "Pharmacokinetics of oral transmucosal and intramuscular dexmedetomidine combined with buprenorphine in cats", Journal of Veterinary Pharmacology and Therapeutics (2014); 38(2): 203-208.

Posner, "Measuring Alertness", Annals of the New York Academy of Sciences (2008); 1129: 193-199.

Prabhu, et al., "Comparison of oral dexmedetomidine versus oral midazolam as premedication to prevent emergence agitation after sevoflurane anaesthesia in paediatric patients", Indian Journal of Anaesthesia (2017); 61(2): 131-136.

PRECEDEX (dexmedetomidine hydrochloride) Injection, Highlights of Prescribing Information, Revised Jun. 2013 (Jun. 2013), Initial U.S. Approval: 1999, Reference ID: 3326669, Manufactured and Distributed by: Hospira, Inc. Lake Forest, IL 60045 USA; 24 pages.

PRECEDEX (dexmedetomidine hydrochloride) Injection, Highlights of Prescribing Information, Revised Mar. 2016 (Mar. 2016), Initial U.S. Approval: 1999, Reference ID: 3915582, Manufactured and Distributed by: Hospira, Inc. Lake Forest, IL 60045 USA; 23 pages.

Preskorn, et al., "Double-Blind, Placebo-Controlled, Single Ascending Dose, Study to Determine the Efficacy, Safety, and Pharmacokinetics of a BXCL 501 (Sublingual Dexmedetomidine) in Agitation Associated With Schizophrenia or Related Disorders", Neuropsychopharmacology, (Oct. 2019); 44: 78-229; ACNP 58th Annual Meeting: Poster Session 1-M72; 1 page.

Preskorn, et al., "Effect of Sublingual Dexmedetomidine vs Placebo on Acute Agitation Associated With Bipolar Disorder A Randomized Clinical Trial", JAMA (2022); 327(8): 727-736.

Preskorn, "How an Understanding of the Function of the Locus Coeruleus Led to Use of Dexmedetomidine to Treat Agitation in Bipolar Disorder: Example of Rational Development of Psychiatric Medications", Journal of Psychiatric Practice (May 2022); 28(3): 227-233.

Proctor, et al., "Oral Dexmedetomidine Attenuates Hemodynamic Responses during Emergence from General Anesthesia in Chronically Instrumented Dogs", Anesthesiology (1991); 74: 108-114.

Proctor, et al., "Premedication with Oral Dexmedetomidine Alters Hemodynamic Actions of Intravenous Anesthetic Agents in Chronically Instrumented Dogs", Anesthesiology (1992); 77: 554-562.

Purushotham, et al., "Intranasal Dexmedetomidine Versus Oral Midazolam As Premedication In Anaesthesia In Children", Research Journal of Pharmaceutical, Biological and Chemical Sciences (Jul.-Aug. 2017); 8(4): 1219-1241.

Qi, et al., "The observation of the sedation effects of intranasal methods of dexmedetomidine for magnetic resonance imaging in children", BIO Web of Conferences (2017); 8(01043); 4 pages.

Qiao, et al., "Intranasal atomised dexmedetomidine optimises surgical field visualisation with decreased blood loss during endoscopic sinus surgery: a randomized study", Rhinology (2016); 54: 38-44.

Qiao, et al., "Pediatric premedication: a double-blind randomized trial of dexmedetomidine or ketamine alone versus a combination of dexmedetomidine and ketamine", BMC Anesthesiology (2017); 17(158); 7 pages.

Qiu, et al., "Sedative effects of different doses of intranasal dexmedetomidine in different age groups of children", Journal of Medical Postgraduates (2014); (4): 394-397; English abstract only; 1 page.

Rahman, et al., "The use of dexmedetomidine for refractory agitation in substance abuse patient", Crit Care & Shock (2010); 13: 59-60.

Rajalakshmi, et al., "A Comparative Study Between Intranasal Dexmedetomidine and Intranasal Ketamine As A Premedication in Paediatric Surgeries", Indian Journal of Applied Research (2014); 4(12): 379-381.

(56) References Cited

OTHER PUBLICATIONS

Ralevski, et al., "Preliminary findings on the interactive effects of IV ethanol and IV nicotine on human behavior and cognition: a laboratory study", Nicotine & Tobacco Research (2012); 14(5): 596-606.
Raszplewicz, et al., "Comparison of sedation scores and propofol induction doses in dogs after intramuscular premedication with butorphanol and either dexmedetomidine or medetomidine", Veterinary Anaesthesia and Analgesia (2013); 40(6): 584-589.
Rathbone, et al., "Mechanisms, barriers and pathways of oral mucosal drug permeation", Advanced Drug Delivery Reviews (1993); 12: 41-60.
Ravipati, et al., "Dexmedetomidine decreases the requirement of ketamine and propofol during burns debridement and dressings", Clinical Investigation (2014); 58(2): 138-142.
Ray, et al., "Acute alcohol effects on repetition priming and word recognition memory with equivalent memory cues", Brain and Cognition (2006); 60(2): 118-127.
Ray, et al., "Dexmedetomidine for sedation during electroencephalographic analysis in children with autism, pervasive developmental disorders, and seizure disorders", Journal of Clinical Anesthesia (2008); 20: 364-368.
Reade et al., "Sedation and delirium in the intensive care unit", New England Journal of Medicine (Jan. 30, 2014); 370(5): 444-454.
Reynolds, et al., "Measuring state changes in human delay discounting: an experiential discounting task", Behavioural Processes (2004); 67(3): 343-356.
Riker, et al., "Dexmedetomidine vs Midazolam for Sedation of Critically Ill Patients A Randomized Trial", JAMA (Feb. 4, 2009); 301(5): 489-499.
Risinger, et al., "M72 double-blind, placebo-controlled, single ascending dose study to determine the efficacy, safety, and pharmacokinetics of BXCL501 (Sublingual Dexmedetomidine) in agitation associated with Schizophrenia or related disorders", BioXcel Therapeutics, ACNP Clinical Poster (2019); 2 pages.
Roberts, et al., "Characterizing the experience of agitation in patients with bipolar disorder and schizophrenia", BMC Psychiatry (2018); 18(104); 8 pages.
Robertson, et al., "The absolute configurations and pharmacological activities of the optical isomers of fluoxetine, a selective serotonin-uptake inhibitor", Journal of Medicinal Chemistry (1988); 31(7): 1412-1417.
Rojas-Gomez, et al., "Sedation and Physiological Response to Intranasal Dexmedetomidine (IN-DEX) in Patients with Severe Chronic Obstructive Pulmonary Disease (COPD)", American Journal of Respiratory and Critical Care Medicine (2016); 193(Abstract A3548); 1 page.
Roosens, et al., "The use of dexmedetomidine in extreme agitation", Tijdschrift Voor Psychiatrie (2017); 59(9); 554-558, with English abstract.
Rosen, et al., "Neuropsychological correlates of suboptimal adherence to metformin", Journal of Behavioral Medicine (2003); 26: 349-360.
Rosen, et al., "The Pittsburgh Agitation Scale", American Journal of Geriatric Psychiatry (1994); p. 549.
Rossi, et al., "Management of agitation in Huntington's disease: A review of the literature", Cureus (2020); 12(8): e9748; 5 pages.
Rothbaum, et al., "Early intervention may prevent the development of posttraumatic stress disorder: a randomized pilot civilian study with modified prolonged exposure", Biological Psychiatry (2012); 72: 957-963.
Ryu, et al., "Sedation Protocol Using Dexmedetomidine for Third Molar Extraction", Journal of Oral and Maxillofacial Surgery (2016); 74: 926.e1-926.e7; 7 pages.
Saad, et al., "Intranasal dexmedetomidine versus intranasal midazolam as pre-anesthetic medication in pediatric age group undergoing adenotonsillectomy", Ain-Shams Journal of Anesthesiology (2020); 12(40); 10 pages.
Saito, et al., "Usefulness of dexmedetomidine to prevent emergence agitation in a patient with Krabbe disease: a case report", JA Clinical Reports (2018); 4(34); 4 pages.
Sakr, et al., "Support vector machines to define and detect agitation transition", IEEE Transactions on Affective Computing (Jul.-Dec. 2010); 1(2): 98-108.
Sakurai, et al., "Buccal administration of dexmedetomidine as a preanesthetic in children", Journal of Anesthesia (2010); 24: 49-53.
Santana, et al., "Retrospective study of intranasal dexmedetomidine as a prophylactic against emergence delirium in pediatric patients undergoing ear tube surgery", International Journal of Pediatric Otorhinolaryngology (2017); 100: 39-43.
Santangelo, et al., "Transnasal administration of a combination of dexmedetomidine, midazolam and butorphanol produces deep sedation in New Zealand White rabbits", Veterinary Anaesthesia and Analgesia (2016); 43(2): 209-214.
Santos, et al., "Sedative and cardiorespiratory effects of dexmedetomidine and buprenorphine administered to cats via oral transmucosal or intramuscular routes", Veterinary Anaesthesia and Analgesia (2010); 37(5): 417-424.
Santos, et al., "Effects of intramuscular dexmedetomidine in combination with ketamine or alfaxalone in swine", Veterinary Anaesthesia and Analgesia (2016); 43(1): 81-85.
Sato, et al., "Effect of single-dose dexmedetomidine on emergence agitation and recovery profiles after sevoflurane anesthesia in pediatric ambulatory surgery", Journal of Anesthesia (2010); 24(5): 675-682.
Savla, et al., "Effect of intranasal dexmedetomidine or oral midazolam premedication on sevoflurane EC50 for successful laryngeal mask airway placement in children: a randomized, double-blind, placebo-controlled trial", Pediatric Research (2014); 24(4): 433-439.
Sazuka, et al., "Dexmedetomidine dose dependently decreases oral tissue blood flow during sevoflurane and propofol anesthesia in rabbits", Journal of Oral and Maxillofacial Surgery (2012); 70(8): 1808-1814; 31 pages.
Scheinin, et al., "Intramuscular Dexmedetomidine as Premedication for General Anesthesia: A Comparative Multicenter Study", Anesthesiology (1993); 78: 1065-1075.
Scheinin, et al., "Pharmacodynamics and pharmacokinetics of intramuscular dexmedetomidine", Clinical Pharmacology & Therapeutics (1992); 52(5): 537-546.
Schmidt, et al., "Effects of preanesthetic administration of midazolam, clonidine, or dexmedetomidine on postoperative pain and anxiety in children", Pediatric Anesthesia (2007); 17(7): 667-674.
Schnellbacher, et al., "The Efficacy of Intranasal Administration of Dexmedetomidine and Ketamine to Yellow-Bellied Sliders (*Trachemys scripta scripta*)", Journal of Herpetological Medicine and Surgery (2012); 22(3-4): 91-98.
Schweizer, et al., "Neuropsychological profile of acute alcohol intoxication during ascending and descending blood alcohol concentrations", Neuropsychopharmacology (2006); 31(6): 1301-1309.
Segovia, et al., "Pre-anaesthetic medication with intranasal dexmedetomidine and oral midazolam as an anxiolytic. A clinical trial", Analesdepediatria (2013); 81(4): 226-231.
Sessler, et al., "The Richmond Agitation-Sedation Scale: validity and reliability in adult intensive care unit patients", American Journal of Respiratory and Critical Care Medicine (2002); 166(10): 1338-1344.
Sethi, et al., "Conscious sedation in a psychiatric patient: A challenge", Journal of Anaesthesiology Clinical Pharmacology (2017); 33(3): 416-417.
Shah, et al., "Physiologic and biochemical effects of electroacupuncture combined with intramuscular administration of dexmedetomidine to provide analgesia in goats", American Journal of Veterinary Research (2016); 77(3): 252-259; English abstract only; 1 page.
Shaikh, et al., "Mucoadhesive drug delivery systems", Journal of Pharmacy and Bioallied Sciences (Jan.-Mar. 2011); 3(1): 89-100.
Shams, et al., "Ketofol-Dexmedetomidine combination in ECT: A punch for depression and agitation", Indian Journal of Anaesthesia (2014); 58(3): 275-280.
Sharan, et al., "A comparison of dexmedetomidine with propofol versus esmolol with propofol to attenuate the hemodynamic stress

(56) References Cited

OTHER PUBLICATIONS responses after electroconvulsive therapy", Indian Journal of Psychiatry (Jul.-Sep. 2017); 59(3): 366-369.
Sheehan, et al., "The Mini-International Neuropsychiatric Interview (MINI): the development and validation of a structured diagnostic psychiatric interview for DSM-IV and ICD-10", Journal of Clinical Psychiatry (1998); 59(20): 22-33.
Shehabi, et al., "The effect of dexmedetomidine on agitation during weaning of mechanical ventilation in critically ill patients", Anaesthesia and Intensive Care (2010); 38(1): 82-90.
Sheta, et al., "Intranasal dexmedetomidine vs midazolam for premedication in children undergoing complete dental rehabilitation: a double-blinded randomized controlled trial", Pediatric Anesthesia (2014); 24(2): 181-189.
Shetty, et al., "Efficacy of Intranasal Dexmedetomidine for Conscious Sedation in Patients Undergoing Surgical Removal of Impacted Third Molar: A Double-Blind Split Mouth Study", Journal of Maxillofacial and Oral Surgery (2016); 15(4): 512-516.
Shi, et al., "Intranasal Dexmedetomidine in Termination of First Trimester Pregnancy of Suction Evacuation", Journal of Anesthesia and Clinical Research (2017); 8(11): 1000781; 7 pages.
Singh, et al., " A comparative evaluation of analgo-sedative effects of oral dexmedetomidine and ketamine: a triple-blind, randomized study", Anesthesia (2014); 24: 1252-1259.
Singla, et al., "Comparison of dexmedetomidine versus midazolam for intranasal premedication in children posted for elective surgery: a double-blind, randomised study", Southern African Journal of Anaesthesia and Analgesia (2015); 21(6):154-157.
Sinha, "How does stress increase risk of drug abuse and relapse?", Psychopharmacology (2001); 158: 343-359.
Sivrikaya, et al., "Intranasal Dexmedetomidine Versus Midazolam Premedication in Paediatric Patients: A Prospective Study", Ecronicon Anaesthesia (2015); 2(3): 139-147.
Slingsby, et al., "Thermal antinociception after dexmedetomidine administration in cats: a comparison between intramuscular and oral transmucosal administration", Journal of Feline Medicine and Surgery (2009); 11(10): 829-834.
Sobel, et al., "Intramuscular administration of human tissue-type plasminogen activator in rabbits and dogs and its implications for coronary thrombolysis", Circulation (1987); 75(6): 1261-1272.
Sobell, et al., "Timeline follow-back: A technique for assessing self-reported alcohol consumption", Measuring Alcohol Consumption: Psychosocial and Biochemical Methods (1992): 41-72.
Sofuoglu, et al., "Riluzole and d-amphetamine interactions in humans", Progress in Neuro-Psychopharmacology and Biological Psychiatry (2008); 32(1): 16-22.
Song, et al., "Dexmedetomidine Injection during Strabismus Surgery Reduces Emergence Agitation without Increasing the Oculocardiac Reflex in Children: A Randomized Controlled Trial", PLoS ONE (2016); 11(9): e0162785, 12 pages.
Spalink, et al., "Intranasal dexmedetomidine for adrenergic crisis in familial dysautonomia", Clinical Autonomic Research (2017); 4 pages.
Sperl, et al., "Alpha-2 Adrenoreceptor Antagonist Yohimbine Potentiates Consolidation of Conditioned Fear", The International Journal of Neuropsychopharmacology (2022); 25(9): 759-773.
Srinivasa, et al., "Study of Dexmedetomidine as intramuscular premedication in outpatient cataract surgery: A placebo-controlled study", IAIM (2016); 3(2): 60-68.
Staines, "BioXcel to trial Apple Watch-drug combination to prevent Alzheimer's agitation episodes", PharmaPhorum (Sep. 19, 2019) [online] https://pharmaphorum.com/news/bioxcel-to-trial-apple-watch-drug-combination-to-prevent-alzheimers-agitation-episodes/ (Access Date: Aug. 1, 2022); 2 pages.
Su, et al., "Dexmedetomidine for prevention of delirium in elderly patients after non-cardiac surgery: a randomised, double-blind, placebo-controlled trial", Lancet (2016); 388: 1893-1902.
Subramanian, et al., "A three-stage alcohol clamp procedure in human subjects", Alcoholism: Clinical and Experimental Research (2002); 26(10): 1479-1483.
Sulton, et al., "The Use of Intranasal Dexmedetomidine and Midazolam for Sedated Magnetic Resonance Imaging in Children: A Report From the Pediatric Sedation Research Consortium", Pediatric Emergency Care (2017); 36(3): 138-142.
Sun, et al., "Dexmedetomidine inhibits astrocyte pyroptosis and subsequently protects the brain in in vitro and in vivo models of sepsis", Cell Death and Disease (2019); 10(167); 13 pages.
Sun, et al., "Low-Dose Intramuscular Dexmedetomidine as Premedication: A Randomized Controlled Trial", Medical Science Monitor (2014); 20: 2714-2719.
Sundaram, et al., "A Comparative Evaluation of Intranasal Dexmedetomidine and Intranasal Midazolam for Premedication in Children: A Double Blind Randomised Controlled Trial", JIDA (Jul. 2011); 5(7): 777-781.
Surendar, et al., "A comparative evaluation of intranasal dexmedetomidine, midazolam and ketamine for their sedative and analgesic properties: a triple blind randomized study", The Journal of Clinical Pediatric Dentistry (2014); 38(3): 255-261.
Sutcliffe, et al., "Efficacy of Selective PDE4D Negative Allosteric Modulators in the Object Retrieval Task in Female Cynomolgus Monkeys (*Macaca fascicularis*)", PLoS ONE (2014); 9(7): e102449; 16 pages.
Swift, et al., "Naltrexone-induced alterations in human ethanol intoxication", The American Journal of Psychiatry (1994); 151(10): 1463-1467.
Talon, et al., "Intranasal Dexmedetomidine Premedication is Comparable With Midazolam in Burn Children Undergoing Reconstructive Surgery", Journal of Burn Care & Research (2009); 30(4): 599-605.
Tammam, "Comparison of the efficacy of dexmedetomidine, ketamine, and a mixture of both for pediatric MRI sedation", Egyptian Journal of Anaesthesia (2013); 29(3): 241-246.
Tammam, et al., "Quality of MRI pediatric sedation: Comparison between intramuscular and intravenous dexmedetomidine", Egyptian Journal of Anaesthesia (2013); 29: 47-52.
Tang, et al., "Dexmedetomidine Controls Agitation and Facilitates Reliable, Serial Neurological Examinations in a Non-Intubated Patient with Traumatic Brain Injury", Neurocritical Care (Mar. 3, 2010); 7 pages.
Tang, et al., "Intranasal Dexmedetomidine on Stress Hormones, Inflammatory Markers, and Postoperative Analgesia after Functional Endoscopic Sinus Surgery", Mediators of Inflammation (2015); 2015(939431); 9 pages.
Tang, et al., "The effect of intranasal administration of dexmedetomidine to assist local anesthesia in patients with endoscopic nasal surgery", Chinese Journal of Anesthesiology (2016); 36(2); English abstract only; 4 pages.
Tayari, et al., "Methadone and Dexmedetomidine Combination as Premedicant Agents for Ovariectomy in Cats", American Journal of Animal and Veterinary Sciences (2015); 10(2): 101-111.
Tazeroualti, et al., "Oral clonidine vs midazolam in the prevention of sevoflurane-induced agitation in children. A prospective, randomized, controlled trial", British Journal of Anaesthesia (2007); 98(5): 667-671.
Tetef, "Effectiveness of Transmucosal Sedation for Special Needs Populations in the Ambulatory Care Setting", AORN Journal (Dec. 2014); 100(6): 651-669.
Tobi et al., "Emergence Delirium in a Schizophrenic Patient who Underwent Craniotomy for Elevation of Depressed Skull Fracture under General Anaesthesia: A Case Report", International Journal for Case Reports (2018); 2(2:8); 3 pages.
Tobias, "Dexmedetomidine to Control Agitation and Delirium from Toxic Ingestions in Adolescents", The Journal of Pediatric Pharmacology and Therapeutics (2010); 15(1): 43-48.
Tobias, "Dexmedetomidine to treat opioid withdrawal in infants following prolonged sedation in the pediatric ICU", Journal of Opioid Management (Jul./Aug. 2006); 2(4): 201-205.
Tobias, "Subcutaneous dexmedetomidine infusions to treat or prevent drug withdrawal in infants and children", Journal of Opioid Management (Jul./Aug. 2008); 4(4): 187-191.
Tomita, et al., "The Effect of Dexmedetomidine on Oral Mucosal Blood Flow and the Absorption of Lidocaine", Anesthesia Progress (2018); 65: 168-176.

(56) References Cited

OTHER PUBLICATIONS

Trevisan et al., "Intranasal dexmedetomidine and intravenous ketamine for procedural sedation in a child with alpha-mannosidosis: a magic bullet?", Italian Journal of Pediatrics (2019); 45(119); 6 pages.

Tug, et al., "Comparison of Two Different Intranasal Doses of Dexmedetomidine in Children for Magnetic Resonance Imaging Sedation", Pediatric Drugs (2015); 7 pages.

UK Competent Authority, Chemicals Regulation Directorate, Health and Safety Executive, United Kingdom "CLH report, Proposal for Harmonised Classification and Labelling Based on Regulation (EC) No. 1272/2008 (CLP Regulation), Annex VI, Part 2, Substance Name: Medetomidine", CLH Report for Medetomidine, Version No. 1 (Oct. 2014); 64 pages.

UMIN-CTR Clinical Trial Identifier: UMIN000020446, "Intranasal Premedication with Dexmedetomidine and midazolam in ophthalmic surgery for pediatrics, are they really equally effective?", Mansoura Faculty of Medicine, Mansoura University (Date of disclosure of study information: Feb. 1, 2016, Last modified: Jan. 5, 2016) [online] https://upload.umin.ac.jp/cgi-open-bin/ctr_e/ctr_view.cgi?recptno=R000023623 (Access Date: May 5, 2018); 5 pages.

Upadhyay, et al., "Dexmedetomidine Infusion to Facilitate Opioid Detoxification and Withdrawal in a Patient with Chronic Opioid Abuse", Indian Journal of Palliative Care (Sep.-Dec. 2011); 17(3): 251-254.

Upadhyay et al., "Prolonged dexmedetomidine infusion to facilitate drug detoxification and withdrawal in patients with multiple drugs addiction", Critical Care and Shock (2011); 14: 84-88.

Upthegrove, et al., "Depression and schizophrenia: cause, consequence, or trans-diagnostic issue?", Schizophrenia Bulletin (2017); 5 pages.

U.S. Appl. No. 16/474,882: Declaration of Dr. Sheldon Preskorn, M.D. with Appendix A and B, signed Jul. 30, 2023; 58 pages.

U.S. Appl. No. 16/474,882: Declaration of Dr. W. Douglas Weaver, M.D. with Appendix A, B, C and D, signed May 9, 2023; 120 pages.

U.S. Appl. No. 17/496,470: Declaration of Dr. Sheldon Preskorn, M.D. with Appendix A and B, signed Jul. 29, 2023; 57 pages.

U.S. Appl. No. 17/993,422: Declaration of Dr. W. Douglas Weaver, M.D. with Appendix A, signed May 8, 2023; 212 pages.

Uusalo, et al., "Feasibility of Intranasal Dexmedetomidine in Treatment of Postoperative Restlessness, Agitation, and Pain in Geriatric Orthopedic Patients", Drugs & Aging (2021); 38: 441-450.

Uusalo, et al., "Pharmacokinetics and Sedative Effects of Intranasal Dexmedetomidine in Ambulatory Pediatric Patients", Anesthesia & Analgesia (Apr. 2020); 130(4): 949-957.

Vandael, et al., "Risk factors for QTc-prolongation: systematic review of the evidence", International Journal of Clinical Pharmacy (2017); 39(1): 16-25.

Vega, et al., "Prevention of Opioid Withdrawal Syndrome After Pediatric Heart Transplantation: Usefulness of Dexmedetomidine", Scientific Letters/ Revista Española de Cardiología (2013); 66(7): 593-595.

Virkkilä, et al., "Dexmedetomidine as intramuscular premedication for day-case cataract surgery", Anaesthesia (1994); 49(10): 853-858.

Virkkilä, et al., "Dexmedetomidine as intramuscular premedication in outpatient cataract surgery", Anaesthesia (1993); 48(6): 482-487.

Walsh, et al., "Use of intranasal dexmedetomidine for preoperative sedation in the pediatric population: a case series", Anesthesiology (Oct. 21, 2008); 109(A1378); 1 page.

Wang, et al., "Comparison of Intranasal Dexmedetomidine and Oral Midazolam for Premedication in Pediatric Dental Patients under General Anesthesia: A Randomised Clinical Trial", BioMed Research International (2020); 2020(5142913), 7 pages.

Wang, et al., "Effects of dexmedetomidine nasal spray on preoperative sedation and analgesia and postoperative agitation in children with ventricular septal defect closure", Chinese Journal of Experimental Surgery (2016); 33(3); 3 pages; English abstract only.

Wang, et al., "Pharmacokinetics of Intranasally Administered Dexmedetomidine in Chinese Children", Frontiers in Pharmacology (Jul. 2019); 10(756); 9 pages.

Wang, et al., "The sedative effects and the attenuation of cardiovascular and arousal responses during anesthesia induction and intubation in pediatric patients: a randomized comparison between two different doses of preoperative intranasal dexmedetomidine", Pediatric Anesthesia (2014); 24(3): 275-281.

Ward, et al., "The treatment of acute agitation associated with schizophrenia or bipolar disorder: investigational drugs in early stages of their clinical development, and their clinical context and potential place in therapy", Expert Opinion on Investigational Drugs (Mar. 2020); 29(3): 245-257.

Weafer, et al., "Alcohol-related stimuli reduce inhibitory control of behavior in drinkers", Psychopharmacology (2012); 222: 489-498.

Weerink, et al., "Clinical Pharmacokinetics and Pharmacodynamics of Dexmedetomidine", Clinical Pharmacokinetics (2017); 56(8): 893-913.

Wesson, et al., "The clinical opiate withdrawal scale (COWS)", Journal of Psychoactive Drugs (2003); 35(2): 253-259.

Whittington, et al., "Dexmedetomidine increases tau phosphorylation under normothermic conditions in vivo and in vitro", Neurobiology of Aging (2015); 36: 2414-2428.

Whittington, et al., "Dexmedetomidine induces tau hyperphosphorylation in the mouse hippocampus", Alzheimer's & Dementia (Jul. 2012); 8(4): P461-P462.

Wikipedia, "Bipolar I disorder" Mar. 30, 2018 [online] https://en.wikipedia.org/w/index.php?title=Bipolar_I_disorder&oldid=833316388 (Access Date: Nov. 18, 2020); 5 pages.

Wikipedia, "Young Mania Rating Scale" Dec. 28, 2019 [online] https://en.wikipedia.org/w/index.php?title=Young_Mania_Rating_Scale&oldid=932847993 (Access Date: Apr. 27, 2023); 2 pages.

Willner, "Validity, reliability and utility of the chronic mild stress model of depression: a 10-year review and evaluation", Psychopharmacology (1997); 134: 319-329.

Wilson, et al., "The Psychopharmacology of Agitation: Consensus Statement of the American Association for Emergency Psychiatry Project BETA Psychopharmacology Workgroup", The Western Journal of Emergency Medicine (2012); 13(1): 26-34.

Winstock, et al., "'Should I stay or should I go?' Coming off methadone and buprenorphine treatment", International Journal of Drug Policy (2011); 22: 77-81.

Wong, et al., "Cutaneous allergic reaction to intramuscular vitamin K1", Australian Journal of Dermatology (1999); 40(3): 147-152.

Written Opinion of the International Searching Authority for International application No. PCT/US2015/055828 mailed Mar. 1, 2016; 7 pages.

Wu, et al., Annual Prevalence of Diagnosed Schizophrenia in the USA: A Claims Data Analysis Approach, Psychological Medicine (2006); 36(11): 1535-1540.

Wu, et al., "Efficacy and safety of intravenous dexmedetomidine in adjuvant general anesthesia", Chinese Journal of Anesthesiology (2007); 9: 773-776; English abstract only; 4 pages.

Wu, et al., "Intranasally Administered Adjunctive Dexmedetomidine Reduces Perioperative Anesthetic Requirements in General Anesthesia", Yonsei Medical Journal (2016); 57(4): 998-1005.

Wu, et al., "Neuroprotective effect of dexmedetomidine in a murine model of traumatic brain injury", Scientific Reports (2018); 8(4935); 10 pages.

Xu, "Assessment of the Effects of Dexmedetomidine on Outcomes of Traumatic Brain Injury Using Propensity Score Analysis", BMC Anesthesiology (2022); 22(280); 8 pages.

Xu, et al., "ED50 of dexmedetomidine nasal drip in induction of hypnosis in children during computed tomography", Zhonghua Yi Xue Za Zhi (Jun. 2014); 94(24): 1886-1888; English abstract only.

Xu, et al., "Effects of dexmedetomidine on the recovery profiles from general anesthesia in patients undergoing endoscopic sinus surgery", International Journal of Clinical and Experimental Medicine (2016); 9(5): 8405-8410.

Xu, et al., "Effects of Two Intranasal Dexmedetomidine Doses as Premedication on Sevoflurane EC 50 for Successful Laryngeal Mask Airway Placement in Children", Zhongguo Yi Xue Ke Xue Yuan Xue Bao (Dec. 2016); 38(6): 627-631; English abstract only.

Xu, et al., "Efficacy and Safety of Intranasal Dexmedetomidine During Recovery From Sevoflurane Anesthesia in Children: A

(56) References Cited

OTHER PUBLICATIONS

Systematic Review and Meta-analysis", Clinical Neuropharmacology (Sep./Oct. 2021); 44(5): 157-168.

Yamane, et al., "Effect of Dexmedetomidine Injected Into the Oral Mucosa in Combination With Lidocaine on Local Anesthetic Potency in Humans: A Crossover Double-Blind Study", Journal of Oral and Maxillofacial Surgery (2015); 73: 616-621.

Yang, et al., " Effect of dexmedetomidine on postoperative cognitive dysfunction and inflammation in patients after general anaesthesia, A PRISMA-compliant systematic review and meta-analysis", Medicine (2019); 98:18(e15383); 10 pages.

Yang, et al., " Fifty Percent Effective Dose of Intranasal Dexmedetomidine Sedation for Transthoracic Echocardiography in Children With Cyanotic and Acyanotic Congenital Heart Disease", Journal of Cardiothoracic and Vascular Anesthesia (2020); 34: 966-971.

Yang, et al., "Analysis of 17 948 pediatric patients undergoing procedural sedation with a combination of intranasal dexmedetomidine and ketamine", Pediatric Anesthesia (2019); 29(1): 85-91.

Yao, et al., "Intranasal dexmedetomidine premedication reduces minimum alveolar concentration of sevoflurane for laryngeal mask airway insertion and emergence delirium in children: a prospective, randomized, doubleblind, placebocontrolled trial", Pediatric Anesthesia (2015); 25(5): 492-498.

Yi, et al., "New sedative and analgesic drug—dexmedetomidine", Chinese Journal of New Drugs and Clinical Remedies (2011); 30(5): 5-10; with English abstract.

Yuen, et al., "A Comparison of Intranasal Dexmedetomidine and Oral Midazolam for Premedication in Pediatric Anesthesia: A Double-Blinded Randomized Controlled Trial", Anesthesia & Analgesia (2008); 106(6): 1715-1721.

Yuen, et al., "A Double-Blind, Crossover Assessment of the Sedative and Analgesic Effects of Intranasal Dexmedetomidine", Anesthesia & Analgesia (2007); 105(2): 374-380.

Yuen, et al., "A randomised comparison of two intranasal dexmedetomidine doses for premedication in children", Anaesthesia (2012); 67(11): 1210-1216.

Yuen, et al., "Optimal timing for the administration of intranasal dexmedetomidine for premedication in children", Anaesthesia (2010); 65(9): 922-939.

Yun, et al., "Effects of intranasal dexmedetomidine for children undergoing cleft lip and palate repair surgery", International Journal of Somatology (2016); 43(4): 401-405 (with English Abstract).

Özcengiz et al., "Oral melatonin, dexmedetomidine, and midazolam for prevention of postoperative agitation in children", Journal of Anesthesia (2011); 25: 184-188.

Zeller, et al., "Managing Agitation Associated with Schizophrenia and Bipolar Disorder in the Emergency Setting", Western Journal of Emergency Medicine (Mar. 2016); 17(2): 165-172.

Zhang, et al., "Dimebon (Latrepirdine) Enhances Mitochondrial Function and Protects Neuronal Cells from Death", Journal of Alzheimer's Disease (2010); 21(2): 389-402.

Zhang, et al., "Median Effective Dose of Intranasal Dexmedetomidine for Rescue Sedation in Pediatric Patients Undergoing Magnetic Resonance Imaging", Anesthesiology (2016); 125(6): 1130-1135.

Zhang, et al., "The Effect of Dexmedetomidine on Cognitive Function and Protein Expression of A, p-Tau, and PSD95 after Extracorporeal Circulation Operation in Aged Rats", Hindawi BioMed Research International (2018); 2018(4014021); 8 pages.

Zhang et al., "The Safety and Efficacy of Intranasal Dexmedetomidine During Electrochemotherapy for Facial Vascular Malformation: A Double-Blind, Randomized Clinical Trial", Journal of Oral and Maxillofacial Surgery (2013); 71(11): 1835-1842.

Zheng, et al., " Administration of Dexmedetomidine inhibited NLRP3 inflammasome and microglial cell activities in hippocampus of traumatic brain injury rats", Bioscience Reports (2018); 38(5): BSR20180892; 11 pages.

Zimmermann, et al., "Modeling alcohol self-administration in the human laboratory", Behavioral Neurobiology of Alcohol Addiction (2013): 315-353.

Zornow, et al., "Dexmedetomidine Decreases Cerebral Blood Flow Velocity in Humans", Journal of Cerebral Blood Flow & Metabolism (1993); 13(2): 350-353.

Zub, et al., "Preliminary experience with oral dexmedetomidine for procedural and anesthetic premedication", Pediatric Anesthesia (2005); 15: 932-938.

NON-SEDATING DEXMEDETOMIDINE TREATMENT REGIMENS

CROSS REFERENCE TO RELATED APPLICATIONS

This application is a continuation application of U.S. patent application Ser. No. 18/216,890, filed Jun. 30, 2023, which is a continuation application of U.S. patent application Ser. No. 17/993,422, filed Nov. 23, 2022, now U.S. Pat. No. 11,890,272, which is a continuation application of U.S. patent application Ser. No. 17/628,021, filed Jan. 18, 2022, which is a U.S. national stage of International Patent Application No. PCT/US2020/042618, filed Jul. 17, 2020, which claims the benefit of priority under 35 U.S.C. 119 (e) to U.S. Provisional Patent Application No. 62/876,371 filed Jul. 19, 2019; U.S. Provisional Patent Application No. 62/877,056 filed Jul. 22, 2019; U.S. Provisional Patent Application No. 62/963,769 filed Jan. 21, 2020; U.S. Provisional Patent Application No. 62/970,411 filed Feb. 5, 2020; U.S. Provisional Patent Application No. 62/977,554 filed Feb. 17, 2020; U.S. Provisional Patent Application No. 63/037,759 filed Jun. 11, 2020; and U.S. Provisional Patent Application No. 62/943,022 filed Dec. 3, 2019; the disclosures of each of which are incorporated herein by reference in their entireties.

FIELD

Disclosed herein are methods of treating a human subject having a condition (e.g. agitation) which can be improved using an alpha-2 adrenergic receptor agonist. The methods comprise administering dexmedetomidine or a pharmaceutically acceptable salt thereof at a suitable dose, and via an appropriate route of administration, to achieve a plasma concentration profile that provides a rapid improvement to the subject's condition without also inducing significant sedation. The administration regimens are also selected to provide maximum therapeutic benefit to the subject, without incurring any significant side effects, such as undesirable cardiovascular events. Suitable routes of administration include sublingual, buccal, oral, intranasal and parenteral. The disclosed methods are particularly suitable for the treatment of agitation or signs of agitation, especially when associated with neurodegenerative and/or neuropsychiatric diseases such as schizophrenia, a bipolar illness such as bipolar disorder or mania, dementia, depression and delirium.

BACKGROUND

On Dec. 17, 1999, the U.S. Food and Drug Administration approved a dexmedetomidine product, PRECEDEX®, formulated as an intravenous solution for continuous infusion, and indicated as a sedative agent for initially intubated and mechanically ventilated patients during treatment in an intensive care setting. PRECEDEX® was later approved as a sedative agent for non-intubated patients prior to and/or during surgical and other procedures.

Dexmedetomidine has also been administered intravenously and via other routes to treat a range of conditions, often peri- or post-surgery, including the treatment of pain, anxiety, delirium, withdrawal symptoms, sleep disorders and agitation. However, administration of dexmedetomidine in an appropriate dosage form to provide effective, rapid, relief for the subject without also causing significant sedation is a challenging task. The utilization of dexmedetomidine has also been limited in clinical practice due to its common side effects, such as hypotension and bradycardia. For example, significant cardiovascular side-effects have occurred at therapeutic doses following administration of dexmedetomidine hydrochloride via a sublingual spray or tablets, or intravenously. Thus, a continuing, unmet need exists for an effective dexmedetomidine product which does not cause significant sedation, and desirably is effective without also producing significant adverse effects, such as cardiovascular events. The unmet need is particularly acute for non-addictive medicines that can effectively treat agitation or signs of agitation without also producing the aforementioned adverse effects and sedation.

The inventors of the present application have surprisingly found that relatively high doses of dexmedetomidine hydrochloride can be well-tolerated by human subjects without inducing accompanying significant sedation, when administered via particular treatment regimens. For example, a dose of at least 180 μg of dexmedetomidine hydrochloride, administered sublingually, is shown herein, according to the present disclosure, to be effective to treat agitation without inducing significant sedation, while being safe and well tolerated. Surprisingly, doses of 120 μg and 180 μg of dexmedetomidine hydrochloride, administered sublingually, such as via a film, have also been found to produce pharmacokinetic profiles that are superior to PRECEDEX®, leading to fewer cardiovascular adverse events. Further, the inventors have found that subjects respond well when dexmedetomidine hydrochloride is administered at doses of at least 180 μg, and show a significant improvement in agitation as early as 45 minutes following administration, with the calming effect maintained for a prolonged period of time, e.g. up to at least 24 hours.

SUMMARY

In some embodiments, the present disclosure provides methods of treating agitation or signs of agitation in a human subject with schizophrenia or bipolar disorder (e.g. bipolar I disorder), without also inducing significant sedation, comprising administering dexmedetomidine or a pharmaceutically acceptable salt thereof at a dose resulting in a mean total exposure of dexmedetomidine, as measured by plasma AUC from T0 to T∞, of about 3800 ng*h/L.

In some embodiments, the present disclosure provides methods of treating agitation or signs of agitation in a human subject with schizophrenia or bipolar disorder, without also inducing significant sedation, comprising administering dexmedetomidine or a pharmaceutically acceptable salt thereof at a dose resulting in a mean total exposure of dexmedetomidine, as measured by plasma AUC from T0 to T∞, of about 1800 ng*h/L.

In some embodiments, the present disclosure provides methods of treating agitation or signs of agitation in a human subject with schizophrenia or bipolar disorder, without also inducing significant sedation, comprising administering dexmedetomidine or a pharmaceutically acceptable salt thereof at a dose resulting in a total exposure of dexmedetomidine, as measured by plasma AUC from T0 to T∞, from about 600 ng*h/L to about 12600 ng*h/L.

In some embodiments, the present disclosure provides methods of treating agitation or signs of agitation in a human subject with schizophrenia or bipolar disorder, without also inducing significant sedation, comprising administering dexmedetomidine or a pharmaceutically acceptable salt thereof at a dose resulting in a total exposure of dexmedetomidine, as measured by plasma AUC from T0 to T∞, from about 590 ng*h/L to about 8750 ng*h/L.

The present disclosure also provides methods of treating agitation or signs of agitation in a human subject with schizophrenia or bipolar disorder, without also inducing significant sedation, comprising administering about 180 μg of dexmedetomidine or a pharmaceutically acceptable salt thereof as a single dose. In another embodiment, an additional dose of 90 μg or 60 μg may be taken after 2 hours of first dose.

The present disclosure further provides methods of treating agitation or signs of agitation in a human subject with schizophrenia or bipolar disorder, without also inducing significant sedation, comprising administering about 120 μg of dexmedetomidine or a pharmaceutically acceptable salt thereof as a single dose. In another embodiment, an additional dose of 90 μg or 60 μg may be taken after 2 hours of first dose.

In some embodiments, the present disclosure provides administering about 180 μg of dexmedetomidine hydrochloride sublingually as a single dose to a human subject, wherein said administration results in substantially lower systemic exposure levels of dexmedetomidine than administration of PRECEDEX® at its highest approved dose, as measured by comparative Cmax and AUC values.

In some embodiments, the present disclosure provides administering about 120 μg of dexmedetomidine hydrochloride sublingually as a single dose to a human subject, wherein said administration results in substantially lower systemic exposure levels of dexmedetomidine than administration of PRECEDEX® at its highest approved dose, as measured by comparative Cmax and AUC values.

The lower systemic exposure reduces the risk of reduced blood pressure and/or respiratory depression commonly encountered when administrating effective amounts of PRECEDEX®.

In some embodiments, the administration of about 180 μg of dexmedetomidine hydrochloride sublingually as a single dose provides about a three-fold reduction in the Cmax value compared to administration of PRECEDEX®. In some embodiments, the aforementioned sublingual administration provides about a 7.5-fold reduction in the AUC value compared to administration of PRECEDEX®. In one particular embodiment, administering a sublingual film to a human subject comprising about 180 μg of dexmedetomidine hydrochloride provides about a three-fold reduction in the Cmax value and about a 7.5-fold reduction in the AUC value compared to administration of PRECEDEX®.

In some embodiments, the present disclosure provides the administration of about 180 μg of dexmedetomidine or a pharmaceutically acceptable salt thereof sublingually or buccally to a human subject, wherein said administration results in mean plasma absorption levels of dexmedetomidine from about 80% to about 125% of the following values: Cmax of about 400 ng/L and AUC from T0 to T∞ of about 2900 ng*h/L.

In some embodiments, the present disclosure provides the administration of about 120 μg of dexmedetomidine or a pharmaceutically acceptable salt thereof sublingually or buccally to a human subject, wherein said administration results in mean plasma absorption levels of dexmedetomidine from about 80% to about 125% of the following values: Cmax of about 220 ng/L and AUC from T0 to T∞ of about 1420 ng*h/L.

In some embodiments, the present disclosure provides the administration of about 180 μg of dexmedetomidine or a pharmaceutically acceptable salt thereof sublingually or buccally to a human subject, wherein said administration results in plasma absorption levels of dexmedetomidine from about 80% to about 125% of the following values: Cmax from about 100 ng/L to about 800 ng/L and AUC from T0 to T∞ of about 600 hr*ng/L about 9500 hr*ng/L.

In some embodiments, the present disclosure provides the administration of about 120 μg of dexmedetomidine or a pharmaceutically acceptable salt thereof sublingually or buccally to a human subject, wherein said administration results in plasma absorption levels of dexmedetomidine from about 80% to about 125% of the following values: Cmax from about 110 ng/L to about 400 ng/L and AUC from T0 to T∞ of about 590 hr*ng/L about 4400 hr*ng/L.

The present disclosure also provides methods of treating agitation or signs of agitation in a human subject with dementia, without also inducing significant sedation, comprising administering about 30 μg to about 180 μg of dexmedetomidine or a pharmaceutically acceptable salt thereof. In some embodiments, the disclosure provides methods of treating agitation or signs of agitation in a human subject with dementia, without also inducing significant sedation, comprising administering 30 μg, 60 μg or 90 μg of dexmedetomidine or a pharmaceutically acceptable salt thereof as a single dose in a day. In some embodiments, the disclosure provides methods of treating agitation or signs of agitation in a human subject with dementia, without also inducing significant sedation, comprising oromucosally administering an unit dose containing about 30 μg to about 90 μg of dexmedetomidine or a pharmaceutically acceptable salt thereof one to six times a day at an interval of at least 2 hours (e.g. 2, 4, 6, 8, or 12 hours) in the event of persistent or recurrent agitation. In some embodiments, dexmedetomidine or a pharmaceutically acceptable salt thereof (e.g. hydrochloride) is administered oromucosally (e,g. sublingually or buccally) as a film.

The present disclosure provides a method of reducing a period of opioid withdrawal in a human subject in need thereof, comprising administering to said subject dexmedetomidine or a pharmaceutically acceptable salt thereof twice daily, wherein the period of withdrawal is up to 14 days. In some embodiments, the period of withdrawal may be 13 days, 12 days, 11 days, 10 days, 9 days, 8 days, 7 days, 6 days, 5 days, 4 days, or 3 days. In another embodiment, the human subject is an adult (at least 18 years old). In some embodiments, dexmedetomidine or a pharmaceutically acceptable salt is administered oromucosally (i.e. sublingually, buccally), orally, intranasally or parenterally. In some embodiments, dexmedetomidine or a pharmaceutically acceptable salt (e.g. hydrochloride) is administered sublingually as a film. In some embodiments, dexmedetomidine or a pharmaceutically acceptable salt thereof is oromucosally administered at a dose range of about 30 μg to about 200 μg. In specific embodiment, dexmedetomidine or a pharmaceutically acceptable salt thereof is oromucosally administered at a unit dose containing about 30 μg, about 60 μg, about 90 μg, 120 μg or 180 μg twice daily. In some embodiments, the opioid may be selected from the group consisting of, but are not limited to fentanyl, morphine, codeine, heroin, oxycodone, hydrocodone, alfentanil carfentanil, tramadol, hydromorphone, buprenorphine, naloxone, naltrexone, remifentanil butorphanol, meperidine, methadone, dextropropoxyphene (propoxyphene) thebaine, sufentanil or pentazocine.

The present disclosure also provides methods of managing or treating agitation in delirium in subjects, without also inducing significant sedation, comprising administering about 20 μg to about 240 μg of dexmedetomidine or a pharmaceutically acceptable salt thereof. In some embodiments, the subject is hospitalized. In some embodiments, the subject is hospitalized in the intensive care unit. In some embodiments, dexmedetomidine or a pharmaceutically acceptable salt thereof is oromucosally administered at a unit dose containing about 20 μg or 60 μg as a single dose. In some embodiments, each dosage unit may be administered one to four times at an appropriate dosing interval (for e.g. of at least 0.5 hours) to produce a desired effect; for example, 20 μg unit is administered four times at a dosing interval of 0.5 hours within 6 hours of first dose to produce the effect of a 80 μg dose or 60 μg unit is administered four times at a dosing interval of 0.5 hours within 6 hours of first dose to produce the effect of 240 μg dose. In some embodiments, dexmedetomidine or a pharmaceutically acceptable salt thereof is administered oromucosally (e,g. sublingually or buccally) as a film.

The present disclosure also provides a method of treating agitation associated with schizophrenia or bipolar disorder, comprising administering a unit dose composition comprising about 120 μg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

In some embodiments, the present disclosure provides a method of treating agitation associated with schizophrenia or bipolar disorder, comprising administering a unit dose composition comprising about 180 μg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

The present disclosure also provides a method of treating agitation associated with schizophrenia or bipolar disorder, comprising administering a unit dose composition comprising about 120 to about 180 μg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

The present disclosure also provides methods of treating or ameliorating opioid withdrawal symptoms, comprising administering a composition comprising dexmedetomidine or a pharmaceutically acceptable salt thereof (e.g. dexmedetomidine hydrochloride) to a human patient in need thereof, wherein the patient is at least 18 years and wherein the period of withdrawal is up to 14 days. "Opioid withdrawal" refers to a variety of signs and complaints appearing with the abrupt removal of, or a rapid decrease in the regular dosage of opioids. Physical manifestations may include sweating, nausea, yawning, chills, diarrhea, papillary dilation, piloerection, tachycardia, increased blood pressure, hypersensitivity to pain, stomach cramps, and muscle cramps. Psychological manifestations of opioid withdrawal observed may include agitation, dysphoria, restlessness, irritability, anxiety, and depression. In some embodiments, the opioid withdrawal symptom is agitation. Onset often begins within 6-24 hours from last opioid use. In some embodiments, treating or ameliorating opioid withdrawal refers to the treatment or lessening of one or more of the aforementioned symptoms. The treating or ameliorating may be measured by a variety of well-known means in the art, including but not limited to, the Clinical Opiate Withdrawal Scale (COWS) and/or Short Opiate Withdrawal Scale of Gossop (SOWS-Gossop) score.

The present disclosure also provides a pharmaceutical composition comprising from about 20 μg to about 240 μg dexmedetomidine or a pharmaceutically acceptable salt thereof (e.g. dexmedetomidine hydrochloride). In some embodiments, the dose of dexmedetomidine is about 120 μg. In some embodiments, the dose of dexmedetomidine is about 180 μg.

The present disclosure also provides methods of achieving a ≥40% reduction in agitation, within 2 hours of administering a composition comprising dexmedetomidine or a pharmaceutically acceptable salt thereof, as measured by the PEC scale. In some embodiments, the agitation is reduced within about 20 minutes to about 1 hour; for example, within about 20 minutes, about 30 minutes, or about 40 minutes. In some embodiments, the reduction in agitation ≥40%, ≥50%, ≥60%, ≥70%, ≥80%, ≥90%, or ≥100%. In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the composition comprises about 120 μg of dexmedetomidine. In some embodiments, the composition comprises about 180 μg of dexmedetomidine. In some embodiments, the patient has schizophrenia. In some embodiments, the patient has bipolar disorder.

The present disclosure also provides a method of achieving a PEC score reduction in agitation for a sustained period of time in a subject with bipolar disorder or schizophrenia comprising administering to the subject a pharmaceutical composition comprising dexmedetomidine or a pharmaceutically acceptable salt thereof at a dose of about 120 mcg to about 180 mcg wherein the PEC score reduction is about −8 to about −10 and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 mcg. In some embodiments, dexmedetomidine or a pharmaceutically acceptable salt thereof is administered at a dose of about 180 mcg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the PEC score reduction is about −8, about −9, or about −10.

The present disclosure also provides a method of achieving an ACES score improvement for a sustained period of time in a subject with bipolar disorder or schizophrenia comprising administering to the subject a pharmaceutical composition comprising dexmedetomidine or a pharmaceutically acceptable salt thereof at a dose of about 120 mcg to about 180 mcg wherein the ACES score is improved to about 3 to about 4 and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 mcg. In some embodiments, dexmedetomidine or a pharmaceutically acceptable salt thereof is administered at a dose of about 180 mcg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the ACES score is about 4.

The present disclosure also provides a method of achieving an CGI-I score improvement for a sustained period of time in a subject with bipolar disorder or schizophrenia comprising administering to the subject a pharmaceutical composition comprising dexmedetomidine or a pharmaceutically acceptable salt thereof at a dose of about 120 mcg to about 180 mcg wherein the CGI-I score is improved to about 1 (very much improved) or about a 2 (much improved) and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 mcg. In some embodiments, dexmedetomidine or a pharmaceutically acceptable salt thereof is administered at a dose of about 180 mcg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the CGI-I score is about 1.

DETAILED DESCRIPTION

Figure 1:
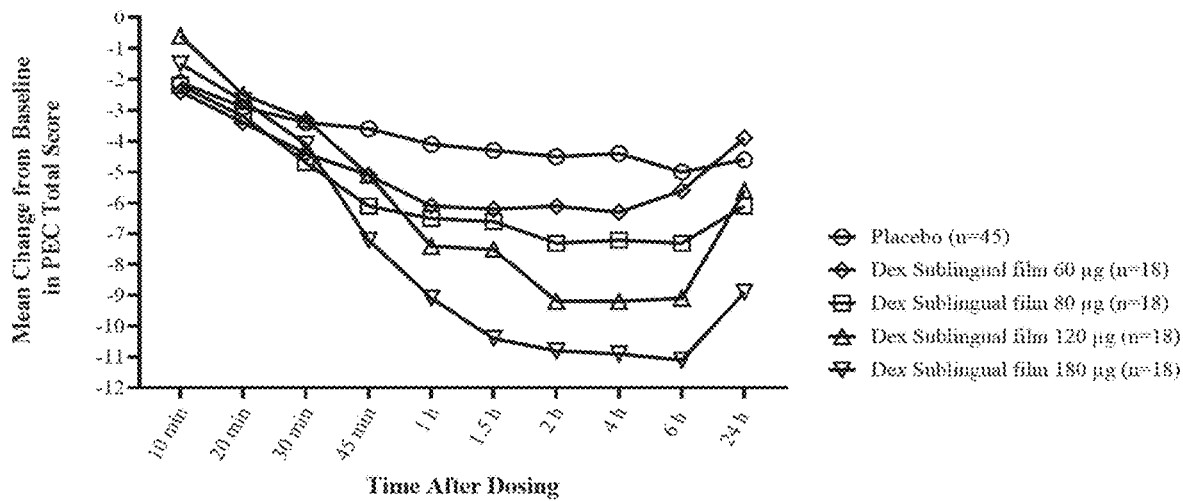
FIG. 1: depicts the mean change from baseline in PEC total score in schizophrenic patients (Intent to treat Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.

Abbreviations:
ACES: Agitation-Calmness Evaluation Scale;
AD: Alzheimer disease;
AE: Adverse event;
AUC: Area under the curve;
AUClast: area under the curve, calculated to the last observable time point;
AUC0-Inf: Area under the plasma concentration-time curve from time of administration to infinity
BID: twice a day;
BMI: Body mass index;
CGI-I: Clinical Global Impression-Improvement
CGI-S: Clinical Global Impression-Severity
Cmax: maximum plasma concentration;
COWS: Clinical Opiate Withdrawal Scale;
CMAI: Cohen Mansfield Agitation Inventory
CMC: Carboxy methylcellulose
C-SSRS: Columbia Suicide Severity Rating Scale
CT: Computed tomography;
CTCAE: Common Terminology Criteria for Adverse Events;
DBP: Diastolic Blood Pressure
Dex or DEX: Dexmedetomidine
DLB: Dementia with Lewy bodies;
DLT: Dose Limiting Toxicity;
DSM: Diagnostic and Statistical Manual of Mental Disorders;
DT: Disintegration time,
ECG: Electrocardiogram;
FTD: Fronto temporal disease;
HPC: Hydroxypropyl cellulose;
HPMC: Hydroxyl propyl methyl cellulose
HR: Heart rate
ICH: International Conference on Harmonisation;
ICU— Intensive care unit;
IUD: intrauterine device
IPD: In-patient Departments;
ITT: Intent to treat Population
LAR: Legally authorized representative;
LSM: Least square mean
LS: Least square;
MedDRA: Medical Dictionary for Regulatory Activities;
MMRM: Mixed model repeated measures;
MMSE: Mini-Mental State Examination;
MRI: Magnetic resonance imaging;
MW: Molecular weight;
mm: Millimeter;
mcg: microgram,
mg: Milligrams;
μg: microgram;
ml: milliliter;
mmHG: millimeters of mercury;
msec: millisecond;
ng: nanogram;
OPD: Out-Patient Department;
PANSS: Positive and Negative Syndrome Scale;
PAS: Pittsburgh Agitation Scale;
PCRS: Placebo-Control Reminder Script;
PEC: PANSS Excitement Component;
PEO: Polyethylene oxide;
PD: Pharmacodynamic;
PK: Pharmacokinetics
PVA: Polyvinyl alcohol;
QTcF: QT interval corrected for heart rate using Fridericia's formula;
QID: Quater in die
RASS: Richmond Agitation Sedation Scale;
SAE: Serious adverse event; SOWS-Gossop: Short Opiate Withdrawal Scale of Gossop;
SAP: Statistical Analysis Plan;
SBP: Systolic Blood Pressure
SD=standard deviation;
SE=standard error
SL: Sublingual;
$T_{1/2}$: Elimination half-life;
TEAE: treatment emergent adverse event;
Tmax: Time of maximum plasma concentration;
Wt %: Weight percentage
ULN: upper limit of normal
VAS: Visual Analog Scale;
YMRS: Young Mania Rating Scale Definitions:

As used herein, "about" means plus or minus 10% of the indicated numerical value.

The terms "formulation" and "composition" are used interchangeably, except where otherwise clearly intended to have different meanings.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity. As such, the terms "a" (or "an"), "one or more" and "at least one" are used interchangeably herein. In addition, reference to w,g, "an agent" by the indefinite article "a" or "an" does not exclude the possibility that more than one of the agents are present, unless the context clearly requires that there is one and only one of the agents.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

The term "pharmaceutically acceptable carrier" refers to a pharmacologically inert substance to be used as a carrier. As used herein, the phrase "carrier" and "excipients" are used interchangeably, except where otherwise clearly intended to have different meanings.

The term "agitation", as used herein, means irritability, emotional outburst, impaired thinking, or excess motor and verbal activity that may occur due to either dysfunction of specific brain regions such as frontal lobes or due to dysfunction of neurotransmitter systems such as dopamine and nor-epinephrine. In the present invention, agitation also includes aggression and hyper-arousal in post-traumatic stress disorder. The agitation may be acute or chronic.

The term "the signs of agitation" includes excessive motor activity (examples include: pacing, rocking, gesturing, pointing fingers, restlessness, performing repetitious mannerisms), verbal aggression (e.g. yelling, speaking in an excessively loud voice, using profanity, screaming, shouting, threatening other people), physical aggression (e.g. grabbing, shoving, pushing, clenching hands into fists, resisting, hitting others, kicking objects or people, scratching, biting, throwing objects, hitting self, slamming doors, tearing things), and destroying property.

The term "without significant sedation" and the like means that the patient experiences a level of sedation not greater than Level 3 on the Ramsay Sedation Scale. Level 3 means sedated but responds to commands. In some embodiments, the dexmedetomidine may be dosed to achieve a Richmond Agitation Sedation Scale (RASS) of −1 ("light sedation").

The term "dissolvable" means the films herein are readily disintegrated, e.g. at least within about 20 minutes, following administration to the oral mucosa. Disintegration is achieved by saliva and/or other aqueous materials on the mucosal surface.

The term "neuropsychiatric conditions" includes, but is not limited to, schizophrenia, bipolar illness (bipolar disorder, bipolar mania), depression, delirium or other related neuropsychiatric conditions.

The term "an effective amount" is interchangeable with "therapeutically effective dose," or "therapeutically effective amount," and refers to an amount sufficient to produce the desired effect. An effective amount is sufficient to cause an improvement in a condition (e.g. agitation) of the subject.

The terms "treating," and "treatment," as used herein refer to curative therapy, prophylactic therapy, and/or preventative therapy and can be used interchangeably.

The term "significantly reduced" refers to a reduction level by at least 10% or higher, preferably 20% or higher, more preferably 40% or higher, even more preferably 60% or higher, still more preferably 80% or higher, and 90% or higher, as compared to a control. For example, in the context of agitation, the a skilled artisan will readily understand that the reduction can be measured in terms of well-known agitation scales, such as PEC score and CGI-I (described in more detail in the examples). As an example, when agitation is significantly reduced in a patient, the reduction may be interpreted as those who achieve at least a 10%, 20%, 30%, 40%, 50%, 60%, 70%, 80%, 90%, or 100% or greater reduction in PEC total score from baseline (e.g. measured at 2 hours post-dose). In some embodiments, significantly reduced agitation refers to at least a 40% reduction in PEC total score from baseline. Similarly, a significant reduction in agitation may be measured on the CGI-I scale and may refer to a patient that has a score of 1 or 2 on the CGI-I scale (e.g. measured at 1, 2, or 4 hours post-dose) or the Agitation-Calmness Evaluation Scale (ACES) scale and may refer to a patient that has a score of e.g. 3 or higher.

The term "pharmaceutically acceptable salt" refers to a salt known to be non-toxic and commonly used in the pharmaceutical literature. Typical inorganic acids used to form such salt include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyl alkandioic acids, aromatic acids, aliphatic and aromatic sulfonic acids may also be used. A preferred salt is the hydrochloride salt.

The term "film" herein includes thin films, sheets and wafers, in any shape, including rectangular, square, or other desired shape. The film may be of any desired thickness and size, such that it can be conveniently placed sub-lingually in the patient. For example, the film may be a relatively thin film having a thickness of from about 20 micrometers to about 200 micrometers or may be a somewhat thicker film having a thickness of from about 20 micrometers to about 1000 micrometers. In certain embodiments, the film may be even thicker, e.g., having a thickness greater than about 30 millimeters.

As used herein, the phrase "water-soluble polymer" refers to (i) a polymer that is at least partially soluble in water, and desirably fully or predominantly soluble in water, and/or (ii) a polymer that absorbs water. Polymers that absorb water are referred to herein as water-swellable polymers.

The term "self-supporting" means the films herein maintain structural integrity upon handling without the need for a backing layer. Some flexibility in the film is contemplated and may be desirable.

As used herein, the phrase "disposed within a polymer matrix" means that dexmedetomidine or a pharmaceutically acceptable salt thereof is incorporated directly into the polymer solution prior to the formation of the solid polymer matrix film composition.

As used herein, the phrase "deposited on the surface of a polymer matrix" means that dexmedetomidine or a pharmaceutically acceptable salt thereof is formulated as liquid composition separate from the preparation of the solid polymer matrix, and deposited onto the solid polymer, e.g. as one or more micro-deposits, where it dries. The dried product is sometimes referred to herein as the "micro-deposited matrix film". The drug liquid formulation may be in any form, including as a solution, emulsion, suspension, or dispersion.

The term "intranasal administration" means administration by the nasal route, whereby a drug is insufflated through the nose. The administration can be either topical or systemic, meaning the locally delivered drug can go on to exhibit either purely local or systemic effects.

The term "parenteral" refers to administration of a drug by injection under one or more layer of skin or mucous membrane, and can include, for example, subcutaneous, intravenous, intraperitoneal or intramuscular injection.

The term "proportion of treatment responders" is defined as those subjects exhibiting about a 40% drop in PEC score at 2 hours.

The term"clinically significant cardiovascular effects" means herein a lowering in blood pressure (hypotension) and/or heart rate (bradycardia) to the extent that medical intervention is required to address the cardiovascular side effects, where the term "medical intervention" means an intervention that more serious than administering fluids, such as an energy drink.

I. Active Agent

Dexmedetomidine has the IUPAC name (+) 4-(S)-[1-(2,3-dimethylphenyl)ethyl]-1H-imidazole. As the monohydrochloride salt, it is predominantly used as a medication for the sedation of patients during treatment in an intensive care setting or to sedate patients prior to and/or during surgical and other procedures. Such medication is currently sold under the registered trade name "PRECEDEX".

Pharmaceutically acceptable salts of dexmedetomidine that may be used herein include generally any suitable salt that has been or may be approved by the US FDA or other appropriate foreign or domestic agency for administration to a human. Non-limiting examples of suitable pharmaceutically acceptable salts include salts of inorganic acids such as hydrochloric, hydrobromic, nitric, carbonic, monohydrocarbonic, phosphoric, monohydrogen phosphoric, dihydrogen phosphoric, sulfuric, hydrogen sulfuric, and hydroiodic acid. Other examples include salts derived from non-toxic organic acids, including acetic, propionic, isobutyric, maleic, malonic, benzoic, succinic, suberic, fumaric, lactic, mandelic, phthalic, benzenesulfonic, p-toluenesulfonic, citric, tartaric, and methanesulfonic acids, or combinations of these acid salts. Exemplary salts include dexmedetomidine hydrochloride, dexmedetomidine hydrobromide, dexmedetomidine sulfate, dexmedetomidine sulfonate, dexmedetomidine phosphate, dexmedetomidine nitrate, dexmedetomidine formate, dexmedetomidine citrate, dexmedetomidine tartrate, dexmedetomidine malate, dexmedetomidine benzoate, dexmedetomidine salicylate, dexmedetomidine ascorbate or the like. In other embodiments, deuterated forms of dexmedetomidine or a pharmaceutically acceptable salt thereof may be included.

II. Dosage

In some embodiments, the dosage of dexmedetomidine or a pharmaceutically acceptable salt thereof administered may conveniently be in the range of between about 0.5 μg to about 1200 μg, depending on the route of administration etc. Examples of suitable dosages include: about 0.5 μg to about 1200 μg, about 0.5 μg to about 500 μg, about 0.5 μg to about 450 μg, about 0.5 μg to about 405 μg, about 0.5 μg to about 360 μg, about 0.5 μg to about 270 μg, about 0.5 μg to about 180 μg, and about 0.5 μg to about 120 μg. The dose may be administered one or more times a day including twice, three times, four times, five times or six times per day.

In some embodiments, dexmedetomidine or a pharmaceutically acceptable salt thereof may be administered at a dose of about 10 μg to about 300 μg, e.g. about 10 μg to 270 μg, about 20 μg to about 240 μg, about 30 μg to about 180 μg, about 40 μg to about 140 μg, about 60 μg to about 120 μg, about 70 μg to about 100 μg, about 80 μg to about 100 μg of unit dose total weight of pharmaceutical composition. These doses can be provided via one or more units to deliver the total dose. Examples of suitable doses include (in μg): about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245 and about 250.

In one embodiment, dexmedetomidine or a pharmaceutically acceptable salt thereof may be administered oromucosally (e.g. sublingually or buccally) at a dose of about 10 μg to about 300 μg, e.g. about 10 μg to 270 μg, about 20 μg to about 240 μg, about 30 μg to about 180 μg, about 40 μg to about 140 μg, about 50 μg to about 120 μg, about 60 μg to about 120 μg, about 70 μg to about 100 μg, about 80 μg to about 100 μg of unit dose total weight of sublingual film composition. These doses can be provided via one or more units to deliver the total dose. Examples of suitable doses include (in μg): about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245 and about 250.

In some embodiments, dexmedetomidine or a pharmaceutically acceptable salt thereof may be administered at a dose of about 120 μg to about 405 μg, e.g. about 120 μg to about 270 μg, including about 120 μg and about 180 μg of unit dose total weight of pharmaceutical composition. These doses can be provided via one or more units to deliver the total dose. Examples of suitable doses include (in μg): about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400 and about 405.

In another embodiment, dexmedetomidine or a pharmaceutically acceptable salt thereof may be administered oromucosally (e.g. sublingually or buccally) at a dose of about 120 μg to about 405 μg, e.g. about 120 μg to about 270 μg, including about 120 μg and about 180 μg of unit dose total weight of sublingual film composition. These doses can be provided via one or more units to deliver the total dose. Examples of suitable doses include (in μg): about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, about 400 and about 405.

In some embodiments, dexmedetomidine or a pharmaceutically acceptable salt thereof may be administered orally at a dose of about 500 μg to about 1500 μg, e.g. about 900 μg to about 1200 μg, based on total weight of oral composition. These doses can be provided via one or more units to deliver the total dose. Examples of suitable doses include (in μg): about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1010, about 1020, about 1030, about 1040, about 1050, about 1060, about 1070, about 1080, about 1090, about 1100, about 1110, about 1120, about 1130, about 1140, about 1150, about 1160, about 1170, about 1180, about 1190, about 1200, about 1210, about 1220, about 1230, about 1240, about 1250, about 1260, about 1270, about 1280, about 1290, about 1300, about 1310, about 1320, about 1330, about 1340, about 1350, about 1360, about 1370, about 1380, about 1390, about 1400, about 1410, about 1420, about 1430, about 1440, about 1450, about 1460, about 1470, about 1480, about 1490 and about 1500.

In some embodiments, dexmedetomidine or a pharmaceutically acceptable salt thereof may be administered intramuscularly at a dose of about 100 μg to about 200 μg, e.g. about 120 μg to about 190 μg, based on total weight of intramuscular injection. Examples of suitable doses include (in μg): about 100, about 105, about 110, about 115, about 120, about 125, about 130, about 135, about 140, about 145, about 150, about 155, about 160, about 165, about 170, about 175, about 180, about 185, about 190, about 195 and about 200.

The exemplary dosage of dexmedetomidine or a pharmaceutically acceptable salt thereof to be administered to a particular patient, will depend on the type and extent of the condition, the overall health status of the particular patient, the particular form of dexmedetomidine or a pharmaceutically acceptable salt thereof being administered, and the particular formulation used to treat the patient.

III. Pharmaceutical Compositions

According to the present disclosure, dexmedetomidine or a pharmaceutically acceptable salt thereof can be administered to the human subject through various routes, including oromucosal (e.g. sublingual, buccal), oral, parenteral and the like. Formulations suitable for use according to the present disclosure are outlined below. Additional formulations suitable for use according to the present disclosure are described in US 2020/0000717, which is hereby incorporated by reference in its entirety for all purposes.

Oromucosal Formulations (Sublingual and or Buccal Formulations)

Dexmedetomidine or a pharmaceutically acceptable salt thereof can be formulated, according to the present disclosure, into dosage forms suitable for sublingual or buccal administration. Such dosage forms include tablets, powders, pills, films, capsules, liquids, gels, syrups, slurries, suspensions, and the like. In one embodiment, dexmedetomidine or a pharmaceutically acceptable salt thereof is formulated as a film product.

Carriers suitable for inclusion in sublingual or buccal formulations include, but are not limited to, sugars, starches, cellulose and its derivatives, malt, gelatin, talc, calcium sulphate, vegetable oils, synthetic oils, polyols, alginic acid, phosphate buffered solutions, emulsifiers, isotonic saline, pyrogen—free water and combinations thereof. Carriers which readily dissolve in saliva may be preferred.

Sublingual or buccal formulations may also include other pharmaceutically acceptable carriers and/or excipients such as binders, lubricants, diluents, coatings, disintegrants, barrier layer components, glidants, colouring agents, solubility enhancers, gelling agents, fillers, proteins, co-factors, emulsifiers, solubilising agents, suspending agents and mixtures thereof. Particular excipients, which may be used according to this disclosure, are known in the art, for example as described in Handbook of Pharmaceutical Excipients, fifth edition, 2005 edited by Rowe et al., Mcgraw Hill.

Films

Suitable films for sublingual or buccal administration (i.e. oromucosal administration) according to the present disclosure comprise dexmedetomidine or a pharmaceutically acceptable salt thereof either (i) disposed within a polymer matrix or (ii) deposited on the surface of a polymer matrix, e.g., on the surface of a "placebo" film.

Polymer Component of Film

The polymer component consists of one or more water-soluble polymers within the film matrix and/or as part of the drug-containing deposit (e.g. one or more droplets) on the surface of the polymer. In some embodiments of the disclosure, the polymer component consists of a single water-soluble polymer. In some embodiments, the polymer component consists of two or more water-soluble polymers, including two or more of the same water-soluble polymers having different molecular weights.

The polymer component in the film matrix is of a suitable composition and present in a sufficient amount to ensure rapid disintegration of the film matrix in the oral mucosa. For example, the presence of the polymer component may allow the film matrix to disintegrate completely oromucosally in about 15 seconds to about 180 seconds, for example, about 30 seconds to about 180 seconds, including about 120 seconds. The polymer component in the film matrix also provides the film with sufficient strength (i.e. the film is self-supporting).

When present in one or more droplets of the dexmedetomidine composition deposited onto the surface of the polymer matrix/substrate, the polymer component may, for example, consist of the water-soluble polymer hydroxypropyl cellulose, although different water-soluble polymers are also contemplated as described hereinafter under the definition "first water-soluble polymer" and "second water soluble polymer". For example, the polymer component may consist of one, two or three hydroxypropyl celluloses having different molecular weights. The molecular weights of the different hydroxypropyl celluloses may conveniently range from (i) less than about 60,000 daltons (e.g. about 5,000 daltons to about 49,000 daltons) (ii) about 90,000 daltons to about 200,000 daltons and (iii) about 200,000 daltons to about 500,000 daltons. The two or more hydroxypropyl celluloses may be mixed in any suitable ratio to achieve the desired droplet viscosity. The viscosity of the dexmedetomidine composition solution or suspension can be measured using a Brookfield viscometer with a small sample adapter at a temperature of 25° C. and may range from about 5 cps to about 3700 cps. For example, it may range from about 5 cps to about 500 cps, about 6 cps to about 200 cps, about 6 cps to about 100 cps or about 6 cps to about 50 cps. In some embodiments of the present disclosure, the viscosity of the dexmedetomidine composition solution or suspension is from about 6 cps to about 20 cps at 25° C. and a shear rate of about 7 (l/s).

When present in a monolithic (i.e. placebo or drug-containing) film, the polymer component may, for example, consist of one water soluble polymer or two different water-soluble polymers. When two different water-soluble polymers are present, one of the water-soluble polymers may include the same polymer but present in the polymer component as a combination of different molecular weights. For example, the polymer component may consist of one, two or three hydroxypropyl celluloses having different molecular weights, although different water-soluble polymers are also contemplated as described hereinafter under the definition "first water-soluble polymer" and "second water soluble polymer" such as polyethylene oxide. The molecular weights of the different hydroxypropyl celluloses may conveniently range from (i) less than about 60,000 daltons (e.g. about 5000 daltons to about 49000 daltons) (ii) about 90000 daltons to about 200000 daltons and (iii) about 200,000 daltons to about 500,000 daltons (e.g. about 300000 daltons to about 450000 daltons). The two or more hydroxypropyl celluloses (e.g. low and high molecular weight hydroxypropyl celluloses) may be mixed in any suitable ratio to achieve the desired film properties. When present in a monolithic (i.e. placebo or drug-containing) film or micro-deposited film matrix composition, the polymer component may conveniently consist of one or more water-soluble polymers having a molecular weight less than about 60,000 daltons (e.g. about 5,000 daltons to about 49,000 daltons), and/or from about 90000 daltons to about 200,000 daltons and/or about 200,000 daltons to about 500,000 daltons (e.g. about 300000 daltons to about 450000 daltons). When a structurally different water-soluble polymer is also present, it may conveniently have a higher molecular weight, for example a molecular weight greater than about 500,000 daltons.

In some embodiments, the disclosure provides pharmaceutical film compositions, comprising: (i) dexmedetomidine or a pharmaceutically acceptable salt thereof; (ii) a polymer component consisting of a first water-soluble polymer having a molecular weight less than about 60,000 daltons (e.g. about 5,000 daltons to about 49,000 daltons), and one or more second-water soluble polymers having a molecular weight greater than about 60,000 daltons; and, optionally, (iii) one or more pharmaceutically acceptable carriers.

In some embodiments, the disclosure provides pharmaceutical film compositions consisting essentially of: (i) dexmedetomidine or a pharmaceutically acceptable salt thereof; (ii) a polymer component consisting of a first water-soluble polymer having a molecular weight less than about 60,000 daltons (e.g. about 5,000 daltons to about 49,000 daltons), and one or more second-water soluble polymers having a molecular weight greater than about 60,000 daltons; and, optionally, (iii) one or more pharmaceutically acceptable carriers.

In some embodiments, the disclosure provides pharmaceutical film compositions consisting of: (i) dexmedetomidine or a pharmaceutically acceptable salt thereof; (ii) a polymer component consisting of a first water-soluble polymer having a molecular weight less than about 60,000 daltons (e.g. about 5,000 daltons to about 49,000 daltons), and one or more second water-soluble polymers having a molecular weight greater than about 60,000 daltons; and, optionally, (iii) one or more pharmaceutically acceptable carriers.

Examples of one or more first water-soluble polymers are selected from the group consisting of hydroxypropyl cellulose (HPC), hydroxyethyl cellulose, hydroxypropyl methylcellulose (HPMC), carboxymethyl cellulose, methyl cellulose and mixtures thereof, including mixtures of the same polymer having different molecular weights.

Examples of one or more second water-soluble polymers are selected from the group consisting of hydroxypropyl cellulose, hydroxypropyl methylcellulose, hydroxyethyl cellulose, carboxy methylcellulose, methylcellulose and mixtures thereof, including mixtures of the same polymer having different molecular weights. Polyethylene oxide (PEO) may also be present herein as a second water-soluble polymer or may be described separately hereinafter in the pharmaceutical film compositions as an example of a pharmaceutically acceptable carrier, or more particularly, as a mucoadhesive agent.

In one embodiment, the weight ratio of said first water-soluble polymer to said second water-soluble polymer(s) (including PEO when present in the film) in the entire film composition is from about 2:1 to about 1:50, for example about 1:1 to about 1:40, including about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, about 1:25, about 1:26, about 1:27, about 1:28, about 1:29, about 1:30, about 1:31, about 1:32, about 1:33, about 1:34, about 1:35, about 1:36, about 1:37, about 1:38, about 1:39, about 1:40.

In a further embodiment, the weight ratio of said first water-soluble polymer to said second water-soluble polymer(s) (including PEO when present in the film) in the entire film composition is from about 1:10 to about 1:30, about 1:15 to about 1:25 or about 1:15 to about 1:20. In some embodiments, a ratio of about 1:15 to about 1:20 provides beneficial functional effects.

Examples of other water-soluble polymers which may be included in the film with the first water-soluble polymer/second water-soluble polymer or replace such polymer(s) include povidone (polyvinylpyrrolidone), copovidone (co-polymers of N-vinyl-2-pyrrolidone and vinyl acetate), polyvinyl alcohol, polyethylene glycol, polyacrylic acid, methylmethacrylate copolymer, carboxyvinyl copolymers, polydextrose, pullulan, carboxymethyl cellulose, sodium alginate, chitosan, xanthan gum, tragacanth gum, guar gum, acacia gum, arabic gum, starch, carrageenan, gelatin and mixtures thereof. The water-soluble polymer component, including water-soluble polymer carriers when present, may conveniently comprise about 40% to about 99.8%, about 50% to about 99.7%, about 60% to about 99.6% of the film composition, based on the weight of the film on a dry weight basis.

In some embodiments, the polymer component for the film composition comprises a first water-soluble polymer present in an amount of from about 2% to about 15% on a dry weight basis of the polymer component (e.g. at about 3% to about 8% w/w of the total film weight). This water-soluble polymer may conveniently have a molecular weight from about 5,000 daltons to about 49,000 daltons. Examples of suitable such water-soluble polymers include those selected from the group consisting of hydroxypropyl cellulose, hydroxyethyl cellulose, hydroxypropyl methylcellulose, carboxymethyl cellulose, methyl cellulose, and mixtures thereof.

In some embodiments, low molecular weight hydroxypropyl cellulose may be present in the film at about 3% to about 8% w/w of the total film weight.

In some embodiments, the one or more second water-soluble polymers (including water-soluble polymer carriers such as polyethylene oxide) may, for example, be present in an amount of from about 50 to about 98 weight percent on dry weight basis of the polymer component. The one or more second water-soluble polymers each has a molecular weight greater than 60,000 daltons; for example, from about 90,000 daltons to about 1,500,000 daltons, especially when the polymer is selected from the group consisting of polyethylene oxide, hydroxypropyl cellulose, hydroxypropyl methylcellulose, hydroxyethyl cellulose, carboxy methylcellulose, methylcellulose, and mixtures thereof.

In some embodiments, the one or more second water-soluble polymers may together be present in the film at about 25% to about 40% w/w of the total film weight when the one or more second water-soluble polymers each has a molecular weight from about 90,000 daltons to about 200,000 daltons and/or from about 200,000 daltons to about 500,000 daltons, and the polymer is selected from the group consisting of hydroxypropyl cellulose, hydroxypropyl methylcellulose, hydroxyethyl cellulose, carboxy methylcellulose, methylcellulose, and mixtures thereof.

In some embodiments, a polyethylene oxide may be present in the film at about 50% to about 60% w/w of the total film weight.

In one embodiment, the polymer component for the film composition consists of a low molecular weight, water-soluble polymer (e.g., having a molecular weight less than about 60,000 daltons) and one or more high molecular weight polymers (e.g., having a molecular weight greater about 60,000, up to about 1,500,000 daltons when a polyethylene oxide is included in the polymer mixture or up to about 500,000 daltons when a polyethylene oxide is not included in the polymer mixture). This polymer combination, especially when the polymers are a combination of hydroxypropyl cellulose and polyethylene oxide, lends certain advantages to the tensile strength and pharmacokinetics of the film composition.

In some embodiments, the present disclosure provides a film composition comprising (e.g. consisting essentially of):
  (i) a therapeutically effective amount of dexmedetomidine or a pharmaceutically acceptable salt thereof;
  (ii) a polymer component consisting of one or more water-soluble polymers: and
  (iii) one or more pharmaceutically acceptable carriers.

In one embodiment, the present disclosure provides a film composition comprising (e.g. consisting essentially of):
  (i) therapeutically effective amount of dexmedetomidine or a pharmaceutically acceptable salt thereof;
  (ii) a polymer component consisting of: (a) one or more first water-soluble polymer (e.g. hydroxypropyl cellulose, hydroxypropyl methylcellulose, hydroxyethyl cellulose, carboxy methylcellulose, methylcellulose, and mixtures thereof) having a molecular weight from about 5,000 daltons to about 49,000 daltons, for example, in about 2 to about 15 weight percent on dry weight basis of the total polymer component: and (b) one or more second water-soluble polymers (e.g. polyethylene oxide, hydroxypropyl cellulose, hydroxypropyl methylcellulose, hydroxyethyl cellulose, carboxy methylcellulose, methylcellulose, and mixtures thereof) having a molecular weight greater than 60,000 daltons, such as greater than 100000 daltons, for example in about 50 to about 98 weight percent on dry weight basis of the total polymer component; and
  (iii) one or more pharmaceutically acceptable carriers.

The molecular weight of hydroxypropyl cellulose, when present in the film of the present disclosure, may be varied, and may be present as both a low molecular weight, water-soluble polymer and as one or more high molecular weight, water-soluble polymers. In some embodiments, the molecular weight may be less than about 60,000 daltons (e.g. about 5,000 daltons to about 49,000 daltons). In other embodiments the molecular weight may be in the range from about 90,000 daltons to about 200,000 daltons. In yet other embodiments, the molecular weight may be in the range from about 200,000 daltons to about 500,000 daltons.

Hydroxypropyl cellulose, when part of the film composition including polyethylene oxide, may conveniently be present in the range from about 10% to about 90% by weight on a dry weight basis of the polymer component, e.g. about 20% to about 80% by weight on dry weight basis of the polymer component, e.g. about 20% to about 50% by weight on dry weight basis of the polymer component, e.g. about 25% to about 45% by weight on dry weight basis of the polymer component.

The molecular weight of polyethylene oxide, when present in the film of the present disclosure, may also be varied. In some embodiments, a water-soluble, high molecular weight polyethylene oxide may be used, for example, to increase muco-adhesivity of the film. In certain embodiments, the molecular weight may range from about 100,000 daltons to about 1,500,000 daltons, including about 100,000, 200,000, 300,000, 600,000, 900,000 or 1,000,000 daltons. In some embodiments, it may be desirable to use a combination of polyethylene oxide having a molecular weight of about 600,000 daltons to about 900,000 daltons with polyethylene oxide having a molecular weight of about 100,000 daltons to about 300,000 daltons in the polymer component.

Polyethylene oxide, when part of the film composition, may conveniently be present range from about 30% to about 90% by weight on a dry weight basis of the total polymer component, e.g. about 40% to about 85% by weight on a dry weight basis of the polymer component, e.g. about 55% to about 80% by weight on a dry weight basis of the polymer component.

Such film compositions may contain the drug dispersed within the film, or micro-deposited onto a surface of the film. When micro-deposited on the surface of a "placebo" film, the drug may conveniently be added as part of a dexmedetomidine composition as one or more droplets in a liquid carrier, such as a solvent (e.g. an alcohol such as ethanol), optionally together with one or more (e.g. two) water-soluble polymers and/or pharmaceutically acceptable carriers. Suitable water-soluble polymers include (1) a low molecular weight, water-soluble polymer, for example a low molecular weight, water-soluble polymer having a molecular weight of less than about 60,000 daltons (e.g. a molecular weight of about 5,000 daltons to about 49,000 daltons and optionally (2) one or more (e.g. one or two) high molecular weight, water-soluble polymers, for example a high molecular weight, water-soluble polymer having a molecular weight of greater than about 60,000 daltons (e.g. a molecular weight of from about 60,000 daltons to about 150,000 daltons such as hydroxypropyl cellulose (77,000 MW), hydroxypropyl cellulose (80,000 MW), hydroxypropyl cellulose (90,000 MW), or hydroxypropyl cellulose (140,000 MW)) and/or a high molecular weight, water-soluble polymer having a molecular weight of greater than about 60,000 daltons (e.g. a molecular weight of from about 200,000 daltons to about 900,000 daltons such as hydroxypropyl cellulose (340,000 MW), hydroxypropyl cellulose (370,000 MW), polyethylene oxide (200,000 MW) or polyethylene oxide (600,000 MW)). Each water-soluble polymer may independently be selected from the group consisting of hydroxypropyl cellulose, hydroxypropyl methylcellulose, hydroxyethyl cellulose, carboxymethyl cellulose, polyethylene oxide and methyl cellulose, e.g. hydroxypropyl cellulose and/or polyethylene oxide.

In some embodiments, the dexmedetomidine composition comprises dexmedetomidine hydrochloride, a low molecular weight polymer which is hydroxypropyl cellulose and one or two high molecular weight polymers which are each hydroxypropyl cellulose in an ethanol solvent.

In one embodiment, the dexmedetomidine composition comprises dexmedetomidine or a pharmaceutically acceptable salt thereof (e.g. dexmedetomidine hydrochloride), hydroxypropyl cellulose (40,000 MW) and one or both of hydroxypropyl cellulose (140,000 MW) and hydroxypropyl cellulose (370,000 MW).

In another embodiment, the dexmedetomidine composition comprises dexmedetomidine or a pharmaceutically acceptable salt thereof (e.g. dexmedetomidine hydrochloride), and only two hydroxypropyl celluloses, namely hydroxypropyl cellulose (40,000 MW) and hydroxypropyl cellulose (140,000 MW).

In some embodiments, the deposition composition may be in any form, including as a solution, emulsion, suspension or dispersion. For example, the dexmedetomidine composition may be added as one or more droplets in an ethanol-based solution, optionally containing a pH-neutralizing agent such as sodium hydroxide. In some embodiments, the film substrate surface contains two or more micro-deposited spots of dexmedetomidine hydrochloride (e.g. two microdeposited spots) in a polymer matrix. The viscosity of deposition solution/suspension may range from about 6 cps to about 3700 cps as measured at 25° C. using a Brookfield viscometer with a small sample adapter. As an example, it may range from about 5 cps to about 500 cps, about 6 cps to about 200 cps, about 6 cps to about 100 cps or about 6 cps to about 50 cps.

In some embodiments of the present disclosure, the viscosity of the dexmedetomidine composition is from about 6 cps to about 20 cps at 25° C. and a shear rate of about 7 (1/s).

Following drying to remove the solvent, the film comprises a film substrate (e.g. a placebo) with the dexmedetomidine composition as previously described but absent the solvent deposited (e.g. micro-deposited) on the surface of the film substrate. The dried composition containing dexmedetomidine or a pharmaceutically acceptable salt thereof (e.g. dexmedetomidine hydrochloride) may cover the whole of the film substrate surface or only part of the film substrate surface.

In some embodiments, the dried dexmedetomidine composition appears as one or more discrete drug-containing droplets on the film substrate surface. Alternatively, stenciling may be used to achieve a one or more defined and discrete regions of drug-containing composition on the surface of the film substrate.

In some embodiments, the disclosure provides a dry film product comprising a film substrate with one or more discrete drug-containing droplets on the film substrate surface, wherein each such drug-containing droplet comprises dexmedetomidine or a pharmaceutically acceptable salt thereof, and hydroxypropyl cellulose of two molecular weights: hydroxypropyl cellulose (40,000 MW) available as HPC-SSL, and hydroxypropyl cellulose (140,000 MW) marketed under the tradename of Klucel™ Type JF NF, and wherein the film substrate comprises hydroxypropyl cellulose of three molecular weights: hydroxypropyl cellulose (40,000 MW), hydroxypropyl cellulose (140,000 MW), and hydroxypropyl cellulose (370,000 MW) marketed under the tradename of Klucel™ Type GF NF. In some embodiments, the film substrate also comprises polyethylene oxide (600,000 MW) available under the name of Sentry Polyox WSR 205 LEO NF.

In some embodiments, the dry film product comprises a deposition composition (also referred to herein as a "dexmedetomidine composition") comprising: (i) dexmedetomidine hydrochloride, present at about 9% to about 50% w/w of the deposition composition, e.g. about 15% to about 25% w/w of the deposition composition; (ii) hydroxypropyl cellulose (40,000 MW), present at about 5% to about 85% w/w of the deposition composition; (iii) hydroxypropyl cellulose (140,000 MW) present at about 5% to 85% w/w of the deposition composition; and (iv) hydroxypropyl cellulose (370,000 MW) present at about 0% to about 65% w/w of the deposition composition. The film also comprises a polymer matrix, wherein the polymer matrix comprises: (i) hydroxypropyl cellulose (40,000 MW) present at about 3% to about 40% w/w of the polymer matrix; (ii) hydroxypropyl cellulose (140,000 MW) present at about 3% to about 40% w/w of the polymer matrix; (iii) hydroxypropyl cellulose (370,000 MW) present at about 0% to about 30% w/w of the polymer matrix, and (iv) polyethylene oxide (600,000 MW) present at about 55% to about 75% w/w of the polymer matrix.

In some embodiments, the dry film product (e.g. a microdeposited film product) comprises (i) dexmedetomidine hydrochloride, present at about 1% to about 50% w/w of the total film weight; (ii) hydroxypropyl cellulose (40,000 MW), present at about 2% to about 30% w/w of the total film weight; (iii) hydroxypropyl cellulose (140,000 MW) present at about 2% to about 30% w/w of the total film weight; (iv) hydroxypropyl cellulose (370,000 MW) present at about 10% to about 50% w/w of the total film weight, (v) polyethylene oxide (600,000 MW) present at about 40% to about 75% w/w of the total film weight and (vi) optionally other pharmaceutically acceptable carriers.

In some embodiments, the films disclosed herein combine several types of hydroxypropyl cellulose (HPC) to provide a film with advantageous properties. For example, the film composition may contain two or three of hydroxypropyl cellulose (40,000 MW), hydroxypropyl cellulose (140,000 MW) and hydroxypropyl cellulose (370,000 MW) in combination. In certain embodiments, polyethylene oxide (600,000 MW) is included with these types of HPC when part of a monolithic film.

In certain film compositions of the present disclosure, a low molecular weight hydroxypropyl cellulose (e.g. 40,000 MW) is present at about 3% to about 8% (e.g. about 5%) w/w of the total film weight, a high molecular weight hydroxypropyl cellulose (e.g. 140,000 MW) is present at about 3% to about 8% (e.g. about 5%) w/w of the total film weight, a high molecular weight hydroxypropyl cellulose (e.g. 370,000 MW) is present at about 20% to about 40% w/w of the total film weight, and a polyethylene oxide (e.g. 600,000 MW) is present at about 40% to about 70%, (e.g. about 50% to about 60%) w/w of the total film weight. In some embodiments, the two high molecular weight, water-soluble polymers are together present at about 25% to about 40% w/w of the total film weight.

The selection and ratio of water-soluble polymers can be made to effect complete dissolution of the film composition in oral mucosal fluids within seconds to minutes, e.g. in about 0.25 minutes to about 15 minutes, thus ensuring delivery of a therapeutically effective amount of dexmedetomidine or a pharmaceutically acceptable salt thereof via the oral mucosa. For example, the film compositions may reside in the sublingual or buccal region of the mouth up to about 15 minutes, up to about 10 minutes, or up to about 5 minutes, including for a period of from about 30 seconds to about 15 minutes, about 1 minute to about 10 minutes, or about 1 minute to about 5 minutes.

The standard basket or paddle apparatus described in any pharmacopoeia can be used for in vitro dissolution testing. The selection of dissolution medium will essentially depend as per the sink conditions and highest dose of drug. The temperature of dissolution medium should be maintained at 37±0.5° C. and rpm at 50 (see Bala et al., in Int J Pharm Investigation, vol. 3(2), pages 67-76).

Films disclosed herein have several functional advantages to promote rapid onset of drug effect. In some embodiments, thin films compositions of the disclosure have a disintegration time (DT) of about 15 seconds to about 180 seconds, about 15 seconds to about 160 seconds, about 25 seconds to about 150 seconds, about 15 seconds to about 140 seconds, about 15 seconds to about 120 seconds, about 40 seconds to about 120 seconds, about 50 seconds to about 120 seconds, for example about 120 seconds, when applied sublingually or buccally. A disintegration time in this time-frame provides optimal onset of drug effects.

In some embodiments, thin film compositions of the invention have mucoadhesion properties that provide practical benefits of localizing the film to the sublingual location and reducing, or preventing, effective removal prior to dissolution. This quality is particularly advantageous in a clinical setting with an agitated subject. Thus, in some embodiments, thin film compositions have a mucoadhesion force (the mucoadhesion strength or shear strength) of about 50 g or above, about 100 g or above, about 200 g or above, about 300 g or above, about 400 g or above, about 500 g or above, about 600 g or above, about 700 g or above, about 800 g or above, about 900 g or above, about 1000 g or above. In some embodiments, the mucoadhesion force is in a range of about 300 g to about 4000 g, about 500 g to about 3000 g, or about 1000 g to about 2000 g.

Burst strength of the film also contributes to drug delivery. Certain thin film compositions of the invention have a burst strength at or above 50 g, 100 g, 200 g, 300 g, 400 g, 500 g, 600 g, 700 g, 800 g, 900 g, 1000 g, 1100 g, 1200 g, 1300 g, 1400 g, 1500 g, 1600 g, 1700 g, 1800 g, 1900 g, 2,000 g, 2,500 g, 3,000 g, 3,500 g, 4,000 g, 4,500 g, 5,000 g, 5,500 g, 6,000 g, 6,500 g, 7,000 g, 7,500 g, 8,000 g, 8,500 g, 9,000 g, 9,500 g, 10,000 g or 15,000 g. For example, the burst strength may be in a range of about 200 g to about 15000 g, about 300 g to about 10,000 g, or 400 g to about 5,000 g.

Pharmaceutically Acceptable Carriers

The film compositions may further comprise one or more pharmaceutically acceptable carriers that includes, but is not limited to, liquid carriers, flavours, sweeteners, refreshing agents, antioxidants, pH adjusting agents, permeation enhancers, mucoadhesive agents, plasticizers, bulking agents, surfactants/non-ionic solubilizers, stabilizers, antifoam agents, colors or the like. In certain embodiments, the film compositions are substantially free of acidic buffer or other acidic agents.

Liquid Carriers

According to some embodiments, the pharmaceutically acceptable carrier includes a liquid carrier. The liquid carrier comprises one or more solvents useful in the preparation of the polymer matrix (drug containing or placebo) and deposition composition on the polymer matrix. In some embodiments, the solvent may be water. In some embodiments, the solvent may a polar organic solvent including, but are not limited to, ethanol, isopropanol, acetone, butanol, benzyl alcohol and mixtures thereof. In some embodiments, the solvent may be a non-polar organic solvent, such as methylene chloride, toluene, ethyl acetate and mixtures thereof. Certain solvents are alcohols, especially ethanol, water and mixtures thereof. Desirably, the solvent content in the wet polymer matrix is at least about 30% by weight of the total wet weight of the total film composition prior to drying. The subsequent dried film composition will desirably contain less than about 10% by weight of solvent, more desirably less than about 8% by weight of solvent, even more desirably less than about 6% by weight of solvent and most desirably less than about 2% by weight of solvent.

Flavors/Sweeteners/Refreshing Agents

It may be beneficial to add a sweetener, flavoring agent, refreshing agent, taste-masking agent or a combination thereof to the film compositions to improve the film composition taste. Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. In one embodiment, the flavor is a peppermint oil flavour available as peppermint oil, NF.

The amount may be varied in order to obtain the result desired in the final product. Such variations are within the capabilities of those skilled in the art without the need for undue experimentation. In general, amounts of about 0.1% to about 30 wt % may be used in the films to supply flavoring. Suitable sweeteners include both natural and artificial sweeteners. Non-limiting examples of suitable sweeteners include, e.g.: water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts and water-soluble sweeteners derived from naturally occurring water-soluble sweeteners, such as a chlorinated derivatives of ordinary sugar (sucrose), known, for example, as sucralose. In one embodiment, the sweetener is sucralose.

Flavoring agents, sweeteners and refreshing agents can be added in conventional quantities, generally up to a total amount of about 0.01% to about 10% of the weight of the film on a dry weight basis, e.g. from about 0.1% to about 7% of the weight of the film on a dry weight basis, e.g. about 0.1% to about 5% based on the weight of the film on a dry weight basis.

Other taste-masking agents include, for example polymers, oils, or waxes. In one embodiment, dexmedetomidine or a pharmaceutically acceptable salt thereof is coated with a taste-masking agent prior to formulation of the film compositions. In some embodiments, if a taste-masking agent is used to coat the active ingredient, it may be present in an amount of from about 5% to about 80% by weight of the particle or granule containing the active ingredient. In another embodiment, the taste-masking agent is present in an amount from about 25% to about 35% by weight of the particle or granule containing the active ingredient.

Antioxidants

Examples of oxygen scavengers or antioxidants that substantially improve long-term stability of the film composition against oxidative degradation include sulfite salts, such as sodium sulfite, sodium bisulfite, sodium metabisulfite and analogous salts of potassium and calcium. A suitable amount of the sulfite salt (e.g., sodium sulfite) is up to about 5%, e.g. about 0.001% to about 2% based on the weight of the film composition on a dry weight basis.

pH-Adjusting Agents/pH-Neutralizing Agents

The absorption of dexmedetomidine or a pharmaceutical acceptable salt thereof through the oral mucosa may increase in an alkaline microenvironment. As an example, this may be achieved when the film compositions are maintained at a pH of above 6, from about 6 to about 9, or about 6.5 to about 8. In some embodiments, the film may include an alkaline substance that increases the pH of the film product. Non-limiting examples of pH-adjusting/pH-neutralizing agents include bicarbonates (e.g., sodium bicarbonate), citrates (e.g., potassium citrate), carbonates (e.g., calcium carbonate), lactates (e.g., sodium lactate), acetates (e.g., calcium acetate), alkaline buffer (e.g. glycine), sodium hydroxide, sodium chloride or the like. An alkaline buffer, such as glycine, is one example of a pH-neutralizing agent. A suitable amount of pH-adjusting/pH-neutralizing agent present in the film composition includes, for example, up to about 10%, e.g. about 1% to about 5% based on the weight of the film composition on a dry weight basis Permeation Enhancer Agents Certain effective penetration enhancers that promote absorption of dexmedetomidine or a pharmaceutically acceptable salt thereof across the oral mucosa include alcohols. An alcohol penetration enhancer, such as butanol, can conveniently be added to the film composition in an amount of up to about 10%, e.g. about 0.1% to about 5%, e.g. about 1% to about 3% based on the weight of the film composition on a dry weight basis.

Mucoadhesive Agents

Examples of mucoadhesive agents that can be added to the film composition include, but are not limited to, sodium alginate, sodium carboxymethyl cellulose, guar gum, polyethylene oxide, hydroxyethyl cellulose, hydroxypropyl cellulose, hydroxypropylmethyl cellulose, karaya gum, methylcellulose, retene, tragacanth and the like. One mucoadhesive agent is polyethylene oxide, which may conveniently be added to the film composition in an amount of from about 20% to about 90%, e.g. about 40% to about 70% based on the total weight of the film composition on a dry weight basis.

Plasticizers

Plasticizers that can be effectively employed herein include polyethylene glycol, propylene glycol, tributyl citrate, triethyl citrate and glycerol. Depending on the selected film-forming polymer(s) and other components of the film formulation, a suitable amount of plasticizer included in the film composition may typically be up to about 10%, e.g. about 0.1% to about 5%, e.g. about 0.5% to about 5% based on the weight of the film on a dry weight basis. For certain applications, higher molecular weight polyethylene glycols may be utilized, including polyethylene oxide Fillers:

Suitable fillers that can be added to a film composition of include starch, calcium salts, such as calcium carbonate, and sugars, such as lactose, glucose, sucrose, mannose, sorbitol, mannitol, galactitol, sucralose, trehalose and combinations thereof. The amount of filler that can conveniently be added to the film formulation is typically up to about 25%, e.g. about 0.5% to about 20%, e.g. about 1% to about 15%, e.g. about 2% to about 10%, based on the weight of the film composition on a dry weight basis.

Surfactants/Non-Ionic Solubilizers

The film typically incorporates at least one surfactant/non-ionic solubilizer including, for example, but are not limited to, a poloxamer, polyoxyl hydrogenated castor oil, glyceryl polyethylene glycol oxystearates, fatty acid glyceryl polyglyceryl esters, polyglyceryl esters, and combinations thereof. The amount of surfactant(s) that can be added to the film composition is typically up to about 5%, e.g. about 0.5% to about 3%, e.g. about 1% to about 3% based on the weight of the film composition on a dry weight basis.

Anti-Foaming Components

Simethicone is an example of a useful anti-foaming and/or de-foaming agent, although other anti-foaming and/or de-foaming agents may suitable be used. An anti-foaming and/or de-foaming agent such as simethicone may be added to the film composition in an amount from about 0.01% to about 5.0%, more desirably from about 0.05% to about 2.5%, and most desirably from about 0.1% to about 1.0% based on the weight of the film composition on a dry weight basis.

Colorants

Color additives that may be included in a film composition include food, drug and cosmetic colors (FD&C), drug and cosmetic colors (D&C), or external drug and cosmetic colors (Ext. D&C). These colors are dyes, their corresponding lakes, and certain natural and derived colorants. Certain examples of color additives are inorganic pigments, such as oxides of iron or titanium, added in concentrations ranging from about 0.001% to about 10%, e.g. about 0.01% to about 3%, based on the weight of the film composition on a dry weigh basis. In one embodiment, the color used for the dexmedetomidine composition (i.e. the deposit composition) is different from the color used for the film substrate (e.g. the placebo film). One color of the monolithic film and the film substrate of the micro-deposited film is emerald green, and available as Fast Emerald Green Shade (06507). One color of the dexmedetomidine composition (i.e. the deposit composition) is a different color from the color of the film substrate, e.g. blue (available as FD&C Blue No. 1). In some embodiments of the film embodiments of the present invention, for example, as described in aspects and embodiments hereinabove, is a film comprising about 180 μg of dexmedetomidine or a pharmaceutically acceptable salt thereof containing two blue color microdeposited spots of dexmedetomidine hydrochloride on the green color film substrate.

In some embodiments of the film embodiments of the present invention, for example, as described in aspects and embodiments hereinabove, is a film comprising about 120 μg of dexmedetomidine or a pharmaceutically acceptable salt thereof.

In one embodiment (A), there is provided a self-supporting, dissolvable, film, comprising:
  (i) about 180 μg of dexmedetomidine or a pharmaceutically acceptable salt thereof (e.g. the hydrochloride salt);
  (ii) one or more water-soluble polymers;
  (iii) a polyethylene oxide and, optionally,
  (iv) one or more pharmaceutically acceptable carriers.

In another embodiment (B), there is provided a self-supporting, dissolvable, film, comprising:
  (i) about 120 μg of dexmedetomidine or a pharmaceutically acceptable salt thereof (e.g. the hydrochloride salt);
  (ii) one or more water-soluble polymers;
  (iii) a polyethylene oxide and, optionally,
  (iv) one or more pharmaceutically acceptable carriers.

In a particular embodiment, the just-mentioned one or more water-soluble polymers (ii) of embodiment (A) or (B) above comprises a low molecular weight, water-soluble polymer and two high molecular weight, water-soluble polymers, for example wherein the low molecular weight, water-soluble polymer has a molecular weight from about 5,000 daltons to about 49,000 daltons (e.g. about 40,000 daltons), and each high molecular weight, water-soluble polymer has a molecular weight of greater than about 60,000 daltons (e.g. where one of the two high molecular weight, water-soluble polymers has a molecular weight of about 140,000 daltons, and the other high molecular weight, water-soluble polymer has a molecular weight of about 370,000 daltons). Each water-soluble polymer is, in some embodiments, hydroxypropyl cellulose. The polyethylene oxide, in some embodiments, has a molecular weight of about 600,000 daltons.

In certain embodiments, there is provided a pharmaceutical film composition comprising or consisting essentially of therapeutically effective amount of dexmedetomidine or pharmaceutically acceptable salt thereof and one or more excipients selected from polyethylene oxide, hydroxypropyl cellulose, sucralose, peppermint oil, Emerald green colorant, and FD&C blue colorant.

In another embodiment (C), there is provided a self-supporting, dissolvable, film, comprising:
(i) about 180 μg of dexmedetomidine or a pharmaceutically acceptable salt thereof (e.g. the hydrochloride salt);
(ii) a low molecular weight, water-soluble polymer having a molecular weight of about 40,000 daltons;
(iii) a high molecular weight, water-soluble polymer having a molecular weight from about 140,000 daltons;
(iv) a high molecular weight, water-soluble polymer having a molecular weight from about 370,000 daltons; and
(v) a water-soluble polyethylene oxide having a molecular weight of about 600,000 daltons.

In another embodiment (D), there is provided a self-supporting, dissolvable, film, comprising:
(i) about 120 μg of dexmedetomidine or a pharmaceutically acceptable salt thereof (e.g. the hydrochloride salt);
(ii) a low molecular weight, water-soluble polymer having a molecular weight of about 40,000 daltons;
(iii) a high molecular weight, water-soluble polymer having a molecular weight from about 140,000 daltons;
(iv) a high molecular weight, water-soluble polymer having a molecular weight from about 370,000 daltons; and
(v) a water-soluble polyethylene oxide having a molecular weight of about 600,000 daltons.

In a particular embodiment of the just-mentioned films of embodiments (C) and (D), the film components excluding dexmedetomidine or a pharmaceutically acceptable salt thereof form a single layer film substrate, and dexmedetomidine or a pharmaceutically acceptable salt thereof is present on the surface of the film substrate (e.g. within a composition comprising dexmedetomidine or a pharmaceutically acceptable salt thereof, a low molecular weight, water-soluble polymer having a molecular weight of about 40,000 daltons, and a high molecular weight, water-soluble polymer having a molecular weight of about 140,000 daltons). Each water-soluble polymer is, in some embodiments, hydroxypropyl cellulose.

In another embodiment (E), there is provided a self-supporting, dissolvable, film, comprising:
(a) a composition consisting essentially of:
(i) about 180 μg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b).

In another embodiment (F), there is provided a self-supporting, dissolvable, film, comprising:
(a) a composition consisting essentially of:
(i) about 120 μg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b).

In a particular embodiment of the just-mentioned films of embodiments (E) and (F), dexmedetomidine hydrochloride is present at about 0.1% to about 2% w/w of the total film weight, hydroxypropyl cellulose (40,000 MW) is present at about 4% to about 8% w/w of the total film weight, hydroxypropyl cellulose (140,000 MW) is present at about 4% to about 8% w/w of the total film weight, hydroxypropyl cellulose (370,000 MW) is present at about 25% to about 30% w/w of the total film weight, and polyethylene oxide (600,000 MW) is present at about 50% to about 60% w/w of the total film weight.

In some embodiments, the pharmaceutical composition of the present disclosure provides detectable $C_{max}$ of dexmedetomidine in human plasma concentration after single dose administration and multiple dose administrations of the pharmaceutical composition of the present disclosure. In some embodiments, the pharmaceutical composition of the present disclosure provides a $T_{max}$ of dexmedetomidine in human plasma concentration after a single dose administration or multiple dose administrations of the pharmaceutical composition of the present disclosure. In some embodiments, pharmaceutical compositions of the present disclosure provides detectable Area Under the Curve (AUC) of dexmedetomidine and its metabolites in human plasma concentration after single dose administration or multiple dose administrations. In some embodiments, the AUC of dexmedetomidine (or its metabolites) is measured from time 0 (the time of administration) to 12 hours from the time 0 and is expressed as $AUC_{0-12\,h}$. In some embodiments, the AUC of dexmedetomidine (or its metabolites) is measured from time 0 (the time of administration) to 24 hours from the time 0 and is expressed as $AUC_{0-24\,h}$. In some embodiments, the AUC of dexmedetomidine (or its metabolites) is measured from time 0 to the last measurable concentration and is expressed as $AUC_{0-last}$. In some embodiments, the AUC of dexmedetomidine (or its metabolites) is measured from time 0 (the time of administration) to time extrapolated to infinity and is expressed as $AUC_{0-Inf}$. In some embodiments, the ranges and values for $AUC_{0-last}$ and $AUC_{0-Inf}$ for dexmedetomidine (or its metabolites) are similar to the ranges and values for $AUC_{0-6\,h}$ for dexmedetomidine (or its metabolites). Thus, in some embodiments, the ranges and values for $AUC_{0-6\,h}$ disclosed herein can also serve as the ranges and values for $AUC_{0-last}$ and $AUC_{0-inf}$.

In some embodiments, administration of film (E) oromucosally (e.g. sublingually or buccally) to subjects with schizophrenia at about 180 μg of dexmedetomidine hydrochloride resulted in pharmacokinetic parameters from about 80% to about 125% of the following values: $C_{max}$ from about 100 ng/L to about 800 ng/L, $T_{max}$ from about 1 hours to about 8 hours and $AUC_{last}$ from about 500 hr*ng/L to about 8900 hr*ng/L. In some embodiments, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 525 ng/L, about 550 ng/L, about 575 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L. In some embodiment, the $T_{max}$ is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, or about 10 h. In some embodiments, the $AUC_{last}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, about 5500 hr*ng/L, about 5750 hr*ng/L, about 6000 hr*ng/L, about 6250 hr*ng/L, about 6500 hr*ng/L, about 6750 hr*ng/L, about 7000 hr*ng/L, about 7250 hr*ng/L, about 7500 hr*ng/L, about 7750 hr*ng/L, about 8000 hr*ng/L, about 8250 hr*ng/L, about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, or about 11875 hr*ng/L. In some embodiments, the film is administered sublingually.

In some embodiments, administration of film (F) oromucosally (e.g. sublingually or buccally) to subjects with schizophrenia at about 120 µg of dexmedetomidine hydrochloride resulted in pharmacokinetic parameters from about 80% to about 125% of the following values: $C_{max}$ from about 110 ng/L to about 400 ng/L, $T_{max}$ from about 1 hours to about 4 hours and $AUC_{last}$ from about 500 hr*ng/L to about 4200 hr*ng/L. In some embodiments, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, or about 500 ng/L. In some embodiments, the $T_{max}$ is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h. In some embodiments, the $AUC_{last}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, or about 5500 hr*ng/L. In specific embodiment, the film is administered sublingually.

In some embodiments, the present disclosure provides pharmaceutical buccal film compositions comprising or consisting essentially of therapeutically effective amount of dexmedetomidine or pharmaceutically acceptable salt thereof, one or more mucoadhesive polymers and optional excipients selected from one or more of plasticizers, penetration enhancers, coloring agents, sweetening agents, flavoring agents, taste-making agents or salivary stimulants. Mucoadhesive polymers may be selected from hydrophilic polymers and hydrogels. Examples of hydrophilic polymers include polyvinyl alcohol [PVA], sodium carboxy methylcellulose [NaCMC], hydroxyl propyl methyl cellulose [HPMC], hydroxyl ethyl cellulose and hydroxypropyl cellulose [HPC]. Examples of hydrogels include anionic polymers like carbopol, polyacrylates, cationic polymers like chitosan and non-ionic polymers like Eudragit analogues.

Sprays, Drops or Gels

In some embodiments, the present disclosure provides pharmaceutical spray compositions or drop compositions suitable for sublingual or buccal administration comprising or consisting essentially of a therapeutically effective amount of dexmedetomidine or pharmaceutically acceptable salt thereof and one or more pharmaceutically acceptable liquids (from about 1% to about 99.995% by weight). Such liquids may be solvents, co-solvents, or non-solvents for dexmedetomidine or a pharmaceutically acceptable salt thereof. Examples of pharmaceutically acceptable liquids include water, ethanol, dimethyl sulfoxide, propylene glycol, polyethylene glycol, propylene carbonate, glycerine, N-methylpyrrolidone, pharmaceutically acceptable oils (e.g., soybean, sunflower, peanut, etc.) or the like. The pharmaceutically acceptable liquid is selected either to dissolve dexmedetomidine or pharmaceutically acceptable salt thereof, to produce a stable, homogenous suspension of it, or to form any combination of a suspension or solution. In addition to these ingredients, spray or drop formulations of dexmedetomidine or pharmaceutically acceptable salt thereof may include one or more excipients such as viscosity modulating materials (e.g. polymers, sugars, sugar alcohols, gums, clays, silicas, and the like, such as polyvinylpyrrolidone (PVP)); preservatives (e.g., ethanol, benzyl alcohol, propylparaben and methylparaben); flavoring agents (e.g. peppermint oil), sweeteners (e.g., sugars such as sucrose, glucose, dextrose, maltose, fructose, etc.), artificial sweeteners (e.g. saccharin, aspartame, acesulfame, sucralose), or sugar alcohols (e.g. mannitol, xylitol, lactitol, maltitol syrup); buffers and pH-adjusting agent (e.g., sodium hydroxide, citrate, and citric acid); coloring agents; fragrances, chelating agents (e.g., EDTA); UV absorbers and antifoam agents (e.g., low molecular weight alcohols, dimethicone). In addition to one or more of the aforementioned ingredients suitable for sublingual or buccal sprays or drops, gel formulations of dexmedetomidine or pharmaceutically acceptable salt thereof may include one or more excipients such as viscosity modulating materials (e.g. water soluble or water swellable polymers such as carbopol, hydroxypropyl cellulose, hydroxypropyl methyl cellulose, carboxymethyl cellulose).

Sprays, drops, and gels may be made by mixing appropriate quantities of the foregoing ingredients in accordance with standard good manufacturing practices. Such excipients may be included in the formulation to improve patient or subject acceptance or taste, to improve bioavailability, to increase shelf-life, to reduce manufacturing and packaging costs, to comply with requirements of governmental regulatory agencies, and for other purposes. The relative amounts of each ingredient should not interfere with the desirable pharmacological and pharmacokinetic properties of the resulting formulation.

In some embodiments, there is provided an oromucosal spray composition comprising or consisting essentially of therapeutically effective amount of dexmedetomidine or pharmaceutically acceptable salt thereof and one or more pharmaceutically acceptable carrier or excipients.

A patient may, in one embodiment, be treated by administering sublingually or buccally 1 to 2 actuations from a spray pump. An advantage of spray delivery is the ability to easily titrate patients by 1 or 2 doses as required by a single actuation.

Pump action sprays are characterized in requiring the application of external pressure for actuation, for example, external manual, mechanical or electrically initiated pressure. This is in contrast to pressurized systems, e.g., propellant-driven aerosol sprays, where actuation is typically achieved by controlled release of pressure e.g., by controlled opening of a valve.

Various sublingual spray formulations comprising dexmedetomidine hydrochloride at doses of 20 μg, 30 μg, 60 μg, 90 μg, 120 μg and 180 μg and excipients as described in table 1.

TABLE 1

Sublingual spray formulation embodiments according to the disclosure

| Ingredients | Sublingual Spray Formulation Embodiment No. | | | |
|---|---|---|---|---|
| | 1 | 2 | 3 | 4 |
| N-methylpyrrolidone | ✓ | | | |
| Propylene Glycol | | ✓ | | |
| Polyethylene Glycol | | | ✓ | |
| Glycerine | | | | ✓ |
| Ethanol | ✓ | ✓ | ✓ | ✓ |
| Sucralose | ✓ | ✓ | ✓ | ✓ |
| Peppermint Oil | ✓ | ✓ | ✓ | ✓ |
| Purified water | ✓ | ✓ | ✓ | ✓ |
| Optionally other pharmaceutically acceptable excipients | ✓ | ✓ | ✓ | ✓ |

Various sublingual drop compositions comprising dexmedetomidine hydrochloride at doses of 20 μg, 30 μg, 60 μg, 90 μg, 120 μg and 180 μg and excipients as described in table 2.

TABLE 2

Sublingual drop formulations embodiments according to the disclosure

| Ingredients | Sublingual Drop Formulation Embodiment No. | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Povidone | ✓ | ✓ | ✓ | ✓ | ✓ | | | | | | | | | |
| N-methylpyrrolidone | ✓ | | | | | | ✓ | | | | ✓ | | | |
| Hydroxypropyl methylcellulose | | | | | | | | ✓ | ✓ | ✓ | ✓ | | | |
| Carbopol | | | | | | | | | | | | ✓ | ✓ | ✓ |
| Polyethylene glycol | | | | ✓ | | | | | | | | | ✓ | |
| Propylene glycol | | ✓ | | | | | ✓ | | | | ✓ | | | |
| Glycerine | | | ✓ | | | | | | ✓ | | | | ✓ | |
| Ethanol | | | | | ✓ | | | ✓ | | | | | | ✓ |
| Sucralose | ✓ | ✓ | ✓ | ✓ | ✓ | ✓ | ✓ | ✓ | ✓ | ✓ | ✓ | ✓ | ✓ | ✓ |
| Peppermint Oil | ✓ | ✓ | ✓ | ✓ | ✓ | ✓ | ✓ | ✓ | ✓ | ✓ | ✓ | ✓ | ✓ | ✓ |
| Purified water | ✓ | ✓ | ✓ | ✓ | ✓ | ✓ | ✓ | ✓ | ✓ | ✓ | ✓ | ✓ | ✓ | ✓ |
| Optionally other pharmaceutically acceptable excipients | ✓ | ✓ | ✓ | ✓ | ✓ | ✓ | ✓ | ✓ | ✓ | ✓ | ✓ | ✓ | ✓ | ✓ |

Various sublingual gel compositions comprising dexmedetomidine hydrochloride at doses of 20 μg, 30 μg, 60 μg, 90 μg, 120 μg and 180 μg and excipients as described in table 3.

TABLE 3

Sublingual gel formulations embodiments according to the disclosure.

| Ingredients | Sublingual Gel Formulation Embodiment Nos. | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Carbopol | ✓ | | | ✓ | | | ✓ | ✓ | | | | | ✓ | | |
| Hydroxypropyl methylcellulose | | ✓ | | | ✓ | | | ✓ | | | ✓ | | | ✓ | |
| Hydroxypropyl cellulose | | | | | | | | | | | | | | | |
| Carboxymethyl cellulose | | | ✓ | | | ✓ | | | | ✓ | | ✓ | | | ✓ |
| N-Methylpyrrolidone | | | | | ✓ | ✓ | ✓ | | | | | | | | |
| Propylene glycol | | | | | | | | ✓ | ✓ | | ✓ | | | | |
| Polyethylene glycol | | | | | | | | | | | | ✓ | | ✓ | ✓ |

TABLE 3-continued

Sublingual gel formulations embodiments according to the disclosure.

Sublingual Gel Formulation Embodiment Nos.

| Ingredients | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Glycerine | | | | | | | | | | | | | ✓ | ✓ | ✓ |
| Ethanol | ✓ | ✓ | ✓ | | | | | | | | | | | | |
| Sucralose | ✓ | ✓ | ✓ | ✓ | ✓ | ✓ | ✓ | ✓ | ✓ | ✓ | ✓ | | ✓ | ✓ | ✓ |
| Peppermint oil | | ✓ | ✓ | ✓ | ✓ | ✓ | ✓ | ✓ | ✓ | ✓ | ✓ | | ✓ | ✓ | ✓ |
| Purified water | ✓ | ✓ | ✓ | ✓ | ✓ | ✓ | ✓ | ✓ | ✓ | ✓ | ✓ | ✓ | ✓ | ✓ | ✓ |
| Optionally other pharmaceutically acceptable excipients | ✓ | ✓ | ✓ | ✓ | ✓ | ✓ | ✓ | ✓ | ✓ | ✓ | ✓ | ✓ | ✓ | ✓ | ✓ |

Tablets

In some embodiments, the present disclosure provides tablet formulations suitable for oromucosal administration (e.g. sublingual or buccal administration) comprising or consisting essentially of therapeutically effective amount of dexmedetomidine or pharmaceutically acceptable salt thereof and one or more pharmaceutically acceptable carrier (from about 1% to about 99.995% by weight). Such carriers may be taste masking agents, diluents, disintegrants, binders, lubricants, glidants, flavouring agents or liquid solvents. Examples of pharmaceutically acceptable liquids include water, ethanol, dimethyl sulfoxide, propylene glycol, polyethylene glycol, propylene carbonate, glycerine, N-methylpyrrolidone, pharmaceutically acceptable oils (e.g., soybean, sunflower, peanut, etc.) or the like. Taste masking agents include, for example, amberlite, Opadry® AMB TAN, polymethacrylates (especially Eudragit® L100), sodium starch glycolate (Primojel), carbopol polymers, PEG-5M, sodium acetate, ethylcellulose, betacyclodextrin. Flavouring agents may be, for example, mint powder, menthol, vanillin, aspartame, acesulfame potassium, saccharin. Disintegrants include, for example, sodium starch glycolate, low-substituted hydroxy propyl cellulose, alginic acid, carbon dioxide, carboxymethylcellulose calcium, carboxymethylcellulose sodium, croscarmellose sodium, guar gum, methylcellulose, polacrilin potassium, poloxamer, sodium alginate. Diluents may be, for example, microcrystalline cellulose, dextrates, dextrose, fructose, mannitol, sucralose, sorbitol, starch, pregelatinized starch, sucrose, xylitol, maltose, maltodextrin, maltitol. Binders may be, for example, alginic acid, carbomer, ethyl cellulose, gelatine, liquid glucose, guar gum, hydroxyethyl cellulose, methylcellulose, polydextrose, polyethylene oxide, hydroxypropyl methylcellulose, hydroxypropyl cellulose, sodium alginate. At least one lubricant may conveniently be incorporated into the formulation to prevent the powder from adhering to tablet punches during the compression procedure. Lubricants may be, for example, talc, magnesium stearate, calcium stearate, glyceryl behenate, hydrogenated castor oil, stearic acid, sodium lauryl sulphate. Glidants are used to promote powder flow by reducing interparticle friction and cohesion. These are used in combination with lubricants as they have no ability to reduce die wall friction. Glidants, may be, for example, colloidal silicon dioxide, calcium silicate, calcium phosphate tribasic.

Various buccal tablet formulations comprising dexmedetomidine hydrochloride at doses of 20 μg, 30 μg, 60 μg, 90 μg, 120 μg and 180 μg and excipients as described in table 4.

TABLE 4

Buccal tablet formulation embodiments according to the disclosure.

Buccal Tablet Formulation Embodiment No.

| Ingredients | 1 | 2 | 3 | 4 | 5 |
|---|---|---|---|---|---|
| Lactose monohydrate | ✓ | ✓ | ✓ | ✓ | ✓ |
| Polyethylene oxide | ✓ | | | | |
| Hydroxypropyl cellulose | | ✓ | | | |
| Hydroxypropyl methylcellulose | | | | | ✓ |
| Sodium alginate | | | | ✓ | |
| Xanthan gum | | | ✓ | | |
| Sucralose | ✓ | ✓ | ✓ | ✓ | ✓ |
| Magnesium stearate | ✓ | ✓ | ✓ | ✓ | ✓ |
| Talc | | ✓ | ✓ | ✓ | ✓ |
| Optionally other pharmaceutically acceptable excipients | ✓ | ✓ | ✓ | ✓ | ✓ |

Various sublingual tablet compositions comprising dexmedetomidine hydrochloride at doses of 20 μg, 30 μg, 60 μg, 90 μg, 120 μg and 180 μg and excipients as described in table 5.

TABLE 5

Sublingual tablet formulation embodiments according to the disclosure.

Sublingual Tablet Formulation Embodiment No.

| Ingredients | 1 | 2 | 3 | 4 | 5 | 6 | 7 | 8 | 9 | 10 |
|---|---|---|---|---|---|---|---|---|---|---|
| Lactose Monohydrate | ✓ | ✓ | ✓ | ✓ | ✓ | ✓ | ✓ | ✓ | ✓ | ✓ |
| Hydroxypropyl methylcellulose | ✓ | ✓ | | | | | | | | |
| Hydroxypropyl cellulose | | | ✓ | ✓ | | | | | | |
| Croscarmellose Sodium | ✓ | | ✓ | | ✓ | | ✓ | | ✓ | |
| Sodium starch glycolate | | ✓ | | ✓ | | ✓ | | ✓ | | ✓ |
| Polyethylene oxide | | | | | ✓ | ✓ | | | | |
| Xanthan gum | | | | | | | ✓ | ✓ | | |
| Sodium alginate | | | | | | | | | ✓ | ✓ |
| Sucralose | ✓ | ✓ | ✓ | ✓ | ✓ | ✓ | ✓ | ✓ | ✓ | ✓ |
| Magnesium stearate | ✓ | ✓ | ✓ | ✓ | ✓ | ✓ | ✓ | ✓ | ✓ | ✓ |

TABLE 5-continued

Sublingual tablet formulation embodiments according to the disclosure.

| Ingredients | Sublingual Tablet Formulation Embodiment No. | | | | | | | | | |
|---|---|---|---|---|---|---|---|---|---|---|
|  | 1 | 2 | 3 | 4 | 5 | 6 | 7 | 8 | 9 | 10 |
| Optionally other pharmaceutically acceptable excipients | ✓ | ✓ | ✓ | ✓ | ✓ | ✓ | ✓ | ✓ | ✓ | ✓ |

Intranasal Formulations

The compositions of the disclosure may be administered to the nasal cavity in any suitable form. For example, the composition may be administered to the nasal cavity in the form of a spray emulsion, suspension or solution, as drops or as a powder.

A powder blend according to the present disclosure may be prepared by mixing dexmedetomidine or a pharmaceutically acceptable salt thereof with inert ingredients that are standard in the art. Such inert ingredients include, but are not limited to diluents such as calcium phosphate, lactose, sugars such as dextrose and sucrose, polyols such as mannitol and sorbitol, and microcrystalline cellulose, glidants such as colloidal silica and lubricants such as magnesium stearate and hydrogenated vegetable oil and surfactants such as polysorbates; and polyethylene glycol. For preparing a uniform powder blend on a small scale, a pestle and mortar and/or sieve may be appropriate whereas mechanical mixers are required for larger scale manufacture. There are numerous types of mixers available and these are widely described in the literature, for example Chapter 37, Remington: The Science and Practice of Pharmacy, 20 Edition, Lipincott, Williams and Wilkins, Baltimore, 2000.

If the powder composition of the disclosure comprises granules, these granules may be produced by techniques well known to those skilled in the art such as wet granulation, dry granulation (slugging), extrusion/spheronisation, fluid bed granulation and spray congealing. Further details on granulation processes may be found in the literature, for example Chapter 6, Pharmaceutical Principles of Solid Dosage Forms, J. T. Carstensen, Technomic, Lancaster, P A, 1993.

In addition to dexmedetomidine or a pharmaceutically acceptable salt thereof, other ingredients may be incorporated into the granules. Such other ingredients include, but are not limited to diluents such as calcium phosphate, lactose, dextrose, mannitol and microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, and lubricants such as magnesium stearate and hydrogenated vegetable oil. Methods for preparation of microspheres are well known to those skilled in the art and include, but are not limited to, spray drying, interfacial polymerisation, coarcervation/phase separation and solvent evaporation. Methods for producing microspheres are described in, for example, Physicochemical Principles of Pharmacy, 3rd Edition, pages 357 to 360, A T Florence and D Attwood, Macmillan, London, 1998 and Physical Pharmacy, 4th Edition, pages 516 to 519, A Martin, Wilkins and Wilkins, Baltimore, 1993. The microspheres may alternatively be produced using the methods described in WO98/30207 and the documents cited therein.

The powder compositions of the present disclosure may be administered to the subject in aerosolised form whereby energy from patient inhalation (sniffing) is used to aerosolise the powder into the nasal cavity or where the device itself provides the aerosolisation energy, such as via compressed air. An example of the former device is manufactured by Pfeiffer and an example of the latter is the "Monopowder" manufactured by Valois. The present invention also provides a nasal drug delivery device or a dose cartridge for use in a nasal delivery device loaded with a composition as defined above.

In one embodiment, the compositions of the disclosure also disclose the process for preparing the solutions of the disclosure comprises mixing the components in a suitable solvent such as water, ethanol, propylene glycol, polyethylene glycol, glycofurol, benzyl benzoate and polyoxyethylene castor oil derivatives. The compositions may be prepared using methods known in the art.

The solutions of the present disclosure may also contain other pharmaceutically acceptable ingredients well known in the art. Such ingredients include, but are not limited to, thickening, adhesive or gelling agents, such as, but are not limited to, celluloses (e.g. hydroxypropyl methylcellulose, methylcellulose, hydroxypropyl cellulose and microcrystalline cellulose), carbomers, polyethylene oxide, poloxamers or polyethylene glycols, antioxidants (for example sodium metabisulphite), chelating agents (such as edetic acid or one of its salts), preservatives (such as potassium sorbate, parabens, phenylethyl alcohol or benzalkonium chloride), flavours, sweeteners, thickening, adhesive or gelling agents, including, but are not limited to, celluloses such as hydroxypropyl methylcellulose, methylcellulose, hydroxypropyl cellulose, sodium carboxyl cellulose and microcrystalline cellulose, poloxamers, polyethylene glycols, carbomers or polyethylene oxide.

The solutions of the disclosure may contain a preservative and/or are sterile. If preservatives are omitted from the compositions, microorganisms may be removed using any suitable method known in the art, for example by making the compositions aseptically or by terminally sterilising them. In some embodiments, the compositions of the invention are non-pyrogenic.

In one embodiment, intranasal compositions of the present disclosure comprise aqueous suspension, solution, or emulsion containing materials in addition to the active ingredient, such as suitable dispersant and/or wetting agent, for example propylene glycol or polyethylene glycol, emulsifier, suspending agent, surfactant, solubilizer, vehicle etc.

The pharmaceutical composition may also be formulated as liposomes, microcapsules or centrosomes, with one or more suitable pharmaceutically acceptable carrier.

In addition to dexmedetomidine or a pharmaceutically acceptable salt thereof, microspheres used in the present disclosure may include ingredients that are known in the art to be suitable to be included in microspheres such as, but are not limited to, starches, dextrans, gelatin, albumin, collagen, hyaluronic acid, chitosan, lactose, sucrose, dextrose, mannitol, methacrylate copolymers such as the Eudragit® polymers (Degussa, Germany), celluloses such as methylcellulose, and polyesters such as poly(lactide-co-glycolide).

Any device that is suitable for intranasal administration can be used. In some embodiments, the device is a metered dose device. The metered dose device can deliver a specific dosage amount of the composition. The metered dose device can be a unit-dose, bi-dose, or a multi-dose device. The pharmaceutically effective amount that can be administered using a metered dose device can be a unit dose device. The metered dose can, in some embodiments, be a device that can deliver a pharmaceutical composition intranasally.

Examples of metered dose devices include, but are not limited to, devices that are pump devices, mechanical devices, pressurized devices, and/or electromechanical devices. Examples of a metered dose device include, but are not limited to, a spray pump, a pre-compression nasal spray pump, a metered valve device, an actuated spray device, a side actuated spray device, a syringe nasal spray device (e.g. a syringe that has an atomizer to deliver a spray to the nasal cavity), a mucosal atomization device, an electromechanical pump device (with and without a counter), and the like. Examples of metered dose devices also include, but are not limited to, devices manufactured by Aptar Pharma (Congers, NY) and are commercially available. Examples of metered dose devices also include, but are not limited to, UDS (Aptar Pharma), BDS (Aptar Pharma), eDevices (Aptar Pharma), Equadel (Aptar Pharma), Latitude (Aptar Pharma), DF30 (Aptar Pharma), VP7 (Aptar Pharma), Classic Nasal Device (Aptar Pharma), MAD Nasal Drug Device (Wolf Tory Medical, Inc.), BD Accuspray SCF™ (Becton Dickinson), and the like. Another example includes, but is not limited to, an Aptar Unitdose Intranasal System.

Parenteral Formulations:

Liquid pharmaceutical compositions for parenteral administration may be formulated for administration by injection or continuous infusion. Routes of administration by injection or infusion can include, but are not limited to, intravenous, intraperitoneal, intramuscular, intrathecal, and subcutaneous. In some embodiments, parenteral formulations can include prefilled syringes, vials, powder for infusion for reconstitution, concentrate for infusion to be diluted before delivery (ready to dilute) or solutions (ready to use).

Injectable pharmaceutical compositions can be aqueous isotonic solutions or suspensions, and suppositories can be prepared from fatty emulsions or suspensions.

The pharmaceutical compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

In certain embodiments, the pharmaceutical compositions of the present disclosure include biodegradable subcutaneous implant, osmotically controlled device, subcutaneous implant, subcutaneous sustained release injection, lipid nanoparticles, liposomes, and the like. Liquid preparations can include, but are not limited to, solutions, suspensions and emulsions. Such preparations are exemplified by water or water/propylene glycol solutions for parenteral injection. Liquid preparations may also include solutions for intranasal administration.

For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled to render the preparation isotonic.

The liquid vehicle used for the preparation of the intramuscular injection may be, for example, water, a saline solution, another aqueous liquid (aqueous solvent) or non-aqueous liquid (non-aqueous solvent). Non-aqueous solvents may include organic solvents such as ethanol, isopropyl alcohol, diethylene glycol monoethyl ether or other alkyl derivative, polyol (e.g., glycerol, propylene glycol, and liquid polyethylene glycol, and the like) or oily vehicles such as castor oil, arachis oil, sesame oil, or other solvents such as carboxymethylcellulose, polysorbate and mixtures thereof. These aqueous and non-aqueous solvents can also act as a co-solvent to increase the solubility of drugs or to reduce the viscosity of oily vehicles.

The formulation may contain an excipient. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrrolidones; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. As used herein, the term "stabilizer" refers to a compound optionally used in the pharmaceutical compositions of the present invention in order to avoid the need for sulphite salts and increase storage life. Non-limiting examples of stabilizers include antioxidants. Buffer systems for use with the formulations include citrate; acetate; bicarbonate; and phosphate buffers.

The formulation also may contain a non-ionic detergent. Examples of non-ionic detergents include but are not limited to Polysorbate 20, Polysorbate 80, Triton X-100, Triton X-114, Nonidet P-40, Octyl α-glucoside, Octyl β-glucoside, Brij 35, Pluronic, and Tween 20.

The parenteral formulations of the present disclosure can be sterilized. Non-limiting examples of sterilization techniques include filtration through a bacterial-retaining filter, terminal sterilization, incorporation of sterilizing agents, irradiation, and heating.

Administration of the above-described parenteral formulations may be by periodic injections of a bolus of the preparation, or may be administered by intravenous or intraperitoneal administration from a reservoir which is external (e.g., an intravenous bag) or internal (e.g., a bioerodable implant, a bioartificial or organ). See, e.g., U.S. Pat. Nos. 4,407,957 and 5,798,113, each incorporated herein by reference in their entireties. Intrapulmonary delivery methods and apparatus are described, for example, in U.S. Pat. Nos. 5,654,007, 5,780,014, and 5,814,607, each incorporated herein by reference in their entireties. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated herein by reference in their entireties. Any of the formulations described herein can be administered in these methods. Further injectable formulations of dexmedetomidine are disclosed in U.S. Pat. Nos. 8,242,158, 9,649,296, JP. Patent No. 5,921, 928, JP. Pat. Appl. No. 2016154598, CN Pat. Appl. No. 103284945, CN Pat. Appl. No. 104161760, CN Pat. Appl. No. 105168122, CN Pat. Appl. No. 105534891, CN Pat. Appl. No. 106038538, U.S. Pat. Appl. No. 20170128421, CN Pat. Appl. No. 107028880, CN Pat. Appl. No. 107412152, CN Pat. Appl. No. 108498469, EP Patent. No. 2252290, JP. Pat. Appl. No. 2019048091 and U.S. Pat. Appl. No. 20190183729.

In certain non-limiting embodiments, the dexmedetomidine intramuscular composition of the present disclosure comprises dexmedetomidine, or a pharmaceutically acceptable salt thereof, at a concentration of between about 0.05 µg/mL and about 15 µg/mL, sodium chloride at a concentration of between about 0.01 and about 2.0 weight percent and pH in the range of about 1 to about 10.

Oral Formulations:

The present disclosure includes oral formulations that can be used for delivering dexmedetomidine. Examples of oral formulations includes tablets, orally disintegrating tablets, mouth dissolving tablets, wafers, solution, suspension, emulsions, and capsules.

The disclosure encompasses oral disintegrating tablets comprising dexmedetomidine or a pharmaceutically acceptable salt thereof and at least one orally disintegrating carrier, wherein the oral disintegrating tablet disintegrates in about 0.5 to about 120 seconds and/or a therapeutically effective amount of the dexmedetomidine is absorbed into the bloodstream within about 1 to about 5 minutes. In some embodiments, a therapeutically effective amount of the dexmedetomidine is absorbed into the bloodstream within about 3 minutes.

In some embodiments, the at least one orally disintegrating carrier is selected from the group consisting of water-soluble sugars or sugar alcohol, crospovidone, (low-substituted) hydroxypropyl cellulose, croscarmellose sodium, microcrystalline cellulose, lactose, pregelatinized starch, sodium starch glycolate, sodium lauryl sulphate, crystalline cellulose and the combination thereof. The water-soluble sugars or sugar alcohol is selected from the group consisting of sucrose, sorbitol, mannitol, xylitol, erythritol, isomalt and fructose. In some embodiments, the orally disintegrating carriers together constitute at least 50 wt. %, for example at least 80 wt. % or at least 85 wt. % of the orally disintegrating carriers. The aforementioned carriers are in the form of particles typically have a volume weighted mean particle size of 50-300 micrometers, for example of 70-200 micrometers. F-Melt® (Fuji Chemical Industry Co.) is an example of a commercially available particulate material that contains a disintegrating agent dispersed in a matrix containing C4-C6 sugar alcohol (mannitol and xylitol). Ludiflash® (BASF) is another example of a commercially available particulate material that contains a disintegrating agent dispersed in a matrix of C4-C6 sugar alcohol (mannitol).

The orally disintegrating tablet as used herein may be prepared by mixing the dexmedetomidine with water-soluble diluents and compressed in a tablet. A suspension comprising dexmedetomidine may be prepared with appropriate excipients and the dexmedetomidine suspension may be dispensed into blister packs and freeze-dried. An exemplary freeze-dried preparation platform that could be used for the dexmedetomidine ODT is the ZYDIS® (Catalent, Somerset, NJ, USA) formulation. In particular, the excipients, including water, are blended and the dexmedetomidine is separately milled to size and mixed with the excipients. The suspension then undergoes lyophilization by flash freezing and freeze drying. Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993.674; 8,048,449; 8,127,516; 8,158,152; 8,221,480; 8,256,233; and 8,313,768, each of which is incorporated herein by reference in its entirety.

A liquid pharmaceutical suspension of the present disclosure for oral administration contains at least one particulate drug as active ingredient wherein active ingredient is dexmedetomidine or a pharmaceutically acceptable salt thereof. The particulate dexmedetomidine may be partially dissolved in the liquid phase, but preferably more than about 50 percent should be particulates. The suspension of the present disclosure contains at least one suspending polymer exhibiting plastic flow that imparts a yield value of about 0.2 to about 15 Pa, preferably from about 0.5 to about 10 Pa Polymers exhibiting Bingham plastic and shear-thinning plastic flow are preferred. Polymers exhibiting thixotropic plastic flow can be used only if the lag time to recover 50% of the yield value is fast, less than about an hour, preferably less than about five minutes, most preferably less than about a minute. The polymer exhibiting plastic flow may be selected from but are not limited to xanthan gum, carbomer, microcrystalline cellulose, carboxymethylcellulose, sodium carboxymethylcellulose, and combinations thereof. The final yield value of the suspension must be less than about 15 Pa, preferably less than about 10 Pa to ensure that the product is pourable without shaking.

In addition to a yield value, the rheology of the final suspension should have an apparent viscosity of at least about 50 cps, preferably at least about 100 cps, most preferably at least about 200 cps, at a shear rate of 100 sec-1 to retard particle motion when the shear rate exceeds the yield value such as when shaking or pouring. For thixotropic plastic fluid, the high viscosity retards particle motion while the yield value is recovering after application of shear. When the suspending polymer(s) added to impart the yield value is not adequate to achieve the desired apparent viscosity of at least about 50 cps at a shear rate of 100 sec-1, viscosity-building agents with no yield value can be added. These viscosity-building agents may be selected from but are not limited to hydroxypropyl cellulose, hydroxypropyl methylcellulose, povidone, guar gum, locust bean gum, and combinations thereof.

The liquid suspension of the present disclosure may contain additional ingredients used in the drug industry, herein referred to as additives. Additives include well-known components, but are not limited to sweetening agents, flavors, colorants, antioxidants, chelating agents, surfactants, wetting agents, antifoaming agents, pH modifiers, acidifiers, preservatives, cosolvents, and mixtures thereof.

The present disclosure concerns also a homogeneous and stable pharmaceutical solution of dexmedetomidine suitable for oral administration to a mammal.

The oral liquid pharmaceutical solution of this disclosure comprises dexmedetomidine or a pharmaceutically acceptable salt thereof and one or more pharmaceutically acceptable excipient which is selected from the group comprising co-solvents, solvents, antioxidants, microbial preservatives, buffering agents, aromatic agents, sweeteners and diluents.

Co-solvents and solvents may include but are not limited to glycerine, alcohols, propylene glycol, polyethylene glycol, benzyl alcohol, water, ethanol, isopropyl alcohol or their mixtures thereof.

Suitable antioxidants may include but are not limited to butylated hydroxyanisole (BHA), butylated hydroxytoluene (BHT), ascorbic acid, beta-carotene, alpha-tocopherol, propyl gallate, gentisic acid sodium ascorbate, sodium bisulfite, sodium metabisulfite, monothioglycero, cysteine, thioglycolate sodium, acetone sodium bisulfite, ascorbate (sodium/acid), bisulfite sodium, cystein/cysteinate HCl, dithionite sodium (Na hydrosulfite, Na sulfoxylate), gentisic acid, gentisic acid ethanolamine, glutamate monosodium, formaldehyde sulfoxylate sodium, metabisulfite potassium, metabisulfite sodium, monothioglycerol (thioglycerol), propyl gallate, sulfite sodium, tocopherol alpha, thioglycolate sodium, EDTA in calcium and sodium compounds or the mixtures thereof.

Buffering agents may include but are not limited to ascorbic acid, acetic acid, tartaric acid, citric acid monohydrate, trisodium citrate dehydrate, sodium citrate, potassium citrate, sodium phosphate, tricalcium phosphate, calcium carbonate, sodium bicarbonate, calcium phosphate, carbonated calcium phosphate, magnesium hydroxide, hydrochloric acid, sodium hydroxide or their mixtures thereof.

Diluents may include but are not limited to maltitol solution, glucose syrup, glycerin, sorbitol and mannitol solutions, sucrose, sorbitol, xylitol, dextrose, fructose, sugar potassium, aspartame, saccharine, saccharine sodium, spray dried or anhydrase lactose, mannitol, starch or their mixtures thereof.

Sweeteners may include but are not limited to sucralose, aspartame, acesulfame-K, thaumatin, mogroside, saccharin and salts thereof, sodium cyclamate, glucose, sucrose, lactose, fructose, mannitol, sorbitol, lactitol, xylitol, erythritol, glycyrrhizin, monosodium glycyrrhizinate, monoammonium glycyrrhizinate, isomalt, glycerine, dextrose or their mixtures thereof.

Aromatic agents may include but are not limited to fruit aromas such as orange, banana, strawberry, cherry, wild cherry, lemon and the like, and other aromas such as cardamom, anis, mint, menthol, vanillin or their mixtures thereof.

Microbial preservatives may include but are not limited to sodium benzoate, benzoic acid, boric acid, sorbic acid and their salts thereof, benzyl alcohol, benzalkonium chloride, parahydroxybenzoic acids and their alkyl esters, methyl and propyl parabens or their mixtures thereof.

In one embodiment, the present disclosure relates to an oral solid pharmaceutical composition, e.g. in form of a tablet, comprising pharmacologically effective amounts of dexmedetomidine or a pharmaceutically acceptable salt thereof and at least one pharmaceutically acceptable excipient. The compositions of the disclosure comprise additives conventional in the dosage form in question. Tabletting aids, commonly used in tablet formulation can be used and reference is made to the extensive literature on the subject, see in particular Fiedler's "Lexikon der Hilfsstoffe", 4th Edition, ECV Aulendorf, 1996, which is incorporated herein by reference. These include but are not limited to disintegrants, binders, lubricants, glidants, stabilising agents, fillers or diluents, surfactants and the like.

As disintegrants suitable for compositions of this disclosure, one can particularly mention crosslinked PVP, crospovidone, guar gum, alginic acid, sodium alginate, crosslinked CMC and Ac-Di-Sol®. In some embodiments, the disintegrant is crospovidone.

As binders suitable for compositions of this disclosure, one can particularly mention starches, e.g. potato starch, wheat starch, corn starch, celluloses such as microcrystalline cellulose, e.g. products known under the registered trademarks Avicel®, Filtrak®, Heweten® or Pharmacel®, hydroxypropyl cellulose, hydroxyethyl cellulose, and hydroxypropylmethyl cellulose, e.g. hydroxypropyl cellulose having a hydroxypropyl content of 5 to 16% by weight and a molecular weight of from 80 000 to 1 150 000, more particularly 140 000 to 850 000.

As glidants suitable for compositions of this disclosure, one can mention in particular colloidal silica, e.g. Aerosil®, magnesium trisilicate, powdered cellulose, starch, talc, and tribasic calcium phosphate.

As fillers or diluents suitable for compositions of this invention, one can mention confectioner's sugar, compressible sugar, dextrates, dextrin, dextrose, lactose, mannitol, sorbitol, sucrose, microcrystalline cellulose, in particular having a density of about 0.45 g/cm3, e.g. Avicel®, or powdered cellulose, and talc.

A preferred filler may be Avicel®.

As lubricants suitable for compositions of this disclosure, one can mention in particular magnesium-, aluminium-, or calcium-stearate, polyethylene glycol (PEG) having a molecular weight of 4,000 to 8,000, and talc.

One or more of these additives may be selected and used by the skilled artisan having regard to the particular desired properties of the solid oral dosage form by routine experimentation and without any undue burden. The amount of each type of additive employed, e.g. glidant, binder, disintegrant, filler or diluent and lubricant may vary within ranges conventional in the art. For example, the amount of glidant may vary within a range of from 0.1 to 10% by weight, in particular 0.1 to 5% by weight, e.g. 0.1 to 0.5% by weight; the amount of binder may vary within a range of from about 10 to 65.3% by weight, e.g. 10 to 45%, e.g. 20 to 30% by weight; the amount of disintegrant may vary within a range of 5 to 60% by weight, e.g. 13 to 50%, e.g. 15 to 40%, e.g. 20 to 30%, e.g. 25%; the amount of filler or diluent may vary within a range of from 15 to 65% by weight e.g. 20 to 50%, e.g. 25 to 40%, e.g. 30%, whereas the amount of lubricant may vary within a range of from 0.1 to 5.0% by weight.

IV. Methods and Administration

In some embodiments (A), the present disclosure provides a method of treating a condition (e.g. agitation) in a human subject, comprising administering dexmedetomidine or a pharmaceutically acceptable salt thereof as a single dose of at least about 120 µg to said subject. In some embodiments, the treatment is effective without causing significant sedation. In some embodiments, the condition is agitation or signs of agitation. In some embodiments, the agitation or signs of agitation are associated with schizophrenia. In some embodiments, the agitation or signs of agitation are associated with a bipolar illness such as bipolar I disorder. In some embodiments, the treatment is effective without causing clinically significant cardiovascular effects.

In some embodiments, dexmedetomidine or a pharmaceutically acceptable salt thereof is administered at a dose of about 120 µg to about 405 µg, such as about 120 µg to about 270 µg, or at a dose of about 180 µg to about 405 µg, such as about 180 µg to about 270 µg, including administering doses of about 120 µg or about 180 µg.

In some embodiments, dexmedetomidine or a pharmaceutically acceptable salt thereof is administered at a dose of about 120 µg to about 405 µg, such as about 120 µg to about 270 µg, or at a dose of about 180 µg to about 405 µg, such as about 180 µg to about 270 µg, including administering doses of about 120 µg or about 180 µg, to treat agitation or signs of agitation in a human subject.

In some embodiments, dexmedetomidine or a pharmaceutically acceptable salt thereof is administered at a dose of about 120 µg to about 405 µg, such as about 120 µg to about 270 µg, or at a dose of about 180 µg to about 405 µg, such as about 180 µg to about 270 µg, including administering doses of about 120 µg or about 180 µg, to treat agitation or signs of agitation in a human subject with schizophrenia or bipolar disorder, without also inducing significant sedation.

In some embodiments, dexmedetomidine or a pharmaceutically acceptable salt thereof is administered at a dose of about 120 µg to about 405 µg, such as about 120 µg to about 270 µg, or at a dose of about 180 µg to about 405 µg, such as about 180 µg to about 270 µg, including administering doses of about 120 µg or about 180 µg, to treat agitation or signs of agitation in a human subject with schizophrenia or bipolar disorder, without also inducing significant sedation or causing clinically significant cardiovascular effects.

In some embodiments (B), the present disclosure provides a method of treating agitation or signs of agitation in a human subject with schizophrenia or bipolar disorder, without also inducing significant sedation, comprising administering dexmedetomidine or a pharmaceutically acceptable salt thereof (e.g. the hydrochloride salt) as a single dose of about 120 µg or about 180 µg. In some embodiments, the treatment is effective without causing clinically significant cardiovascular effects.

In some embodiments, the present disclosure provides a method of treating acute agitation associated with schizophrenia and bipolar disorder (e.g. bipolar I disorder) in a human subject, comprising oromucosally administering a film composition comprising dexmedetomidine or a pharmaceutically acceptable salt thereof (e.g. hydrochloride salt) as a single dose of 120 µg or 180 µg. In some embodiments, an additional dose (e.g. 90 µg or 60 µg) may be taken after a suitable period of time (e.g. 2-hours) in the event of persistent or recurrent agitation (e.g. by cutting a 180 µg or 120 µg film in half).

In some embodiments, the present disclosure provides a method of treating acute agitation associated with schizophrenia and bipolar disorder (e.g. bipolar I disorder) in a human subject, comprising oromucosally administering a film composition comprising dexmedetomidine or a pharmaceutically acceptable salt thereof (e.g. hydrochloride salt), wherein the subject is co-treated with an anti-psychotic agent. Suitable anti-psychotic agents contemplated within the scope of the present disclosure include but are not limited to aripiprazole, benperidol, flupentixol, amisulpride, chlorpromazine, asenapine, risperidone, ziprasidone, lurasidone, clozapine, cariprazine, olanzapine and quetiapine. In some embodiments, the anti-psychotic agent is aripiprazole.

In a particular embodiment (C), the present disclosure provides methods of treating agitation or signs of agitation in a human subject with dementia, without also inducing significant sedation, comprising administering from about 30 µg to about 180 µg of dexmedetomidine or a pharmaceutically acceptable salt thereof. In some embodiments, 30 µg, 60 µg or 90 µg of dexmedetomidine or a pharmaceutically acceptable salt thereof are administered as a single dose in a day. In some embodiments, an additional dose (e.g. 30 µg) may be taken after a suitable period of time (e.g. 2, 4, 6, 8, or 12 hours) in the event of persistent or recurrent agitation. In some embodiments, dexmedetomidine or a pharmaceutically acceptable salt thereof is oromucosally administered as a unit dose containing about 30 µg to about 90 µg between 1 and 6 times in a day. For example, dexmedetomidine or a pharmaceutically acceptable salt thereof is oromucosally administered 1, 2, 3, 4, 5, or 6 times every 2 hours, every 4 hours, every 6 hours, every 8 hours, every 10 hours, or every 12 hours. In some embodiments, each unit dose containing about 30 µg to 60 µg of dexmedetomidine or a pharmaceutically acceptable salt thereof may be taken one to six times in a day at an interval of 2 hours with the provision of maximum of three doses within 12 hours of first dose. In some embodiments, each unit dose containing about 90 µg of dexmedetomidine or a pharmaceutically acceptable salt thereof may be taken one to four times in a day at an interval of 2 hours with the provision of maximum of two doses within 12 hours of first dose. In some embodiments, dexmedetomidine or a pharmaceutically acceptable salt thereof is administered oromucosally (e.g. sublingually or buccally) as a film. In some embodiments, the dosing may be achieved by cutting a film in half to deliver a half-dose (e.g. a 60 µg dose may be administered with a half of a second 60 µg dose (30 µg) to make a 90 µg dose.).

In a particular embodiment (D), the present disclosure also provides methods of managing or treating agitation in delirium in subjects, without also inducing significant sedation, comprising administering about 20 µg to about 240 µg of dexmedetomidine or a pharmaceutically acceptable salt thereof. In some embodiments, the subject is hospitalized. In some embodiments, the subject is hospitalized in the intensive care unit. In some embodiments, dexmedetomidine or a pharmaceutically acceptable salt thereof (e.g. the hydrochloride salt) is oromucosally administered at a unit dose containing about 20 µg or about 60 µg as a single dose. In some embodiments, each unit dose may be administered one to four times at an appropriate dosing interval (e.g. every 0.5 hour, 1 hour, 2 hours, or 3 hours) within 6 hours of first dose to produce a desired effect; for example, 20 µg unit is administered four times at a dosing interval of 0.5 hours within 6 hours of first dose to produce the effect of a 80 µg dose or 60 µg unit is administered four times at a dosing interval of 0.5 hours within 6 hours of first dose to produce the effect of 240 µg dose. In some embodiments, the treatment is effective without causing clinically significant cardiovascular effects. In some embodiments, dexmedetomidine or a pharmaceutically acceptable salt thereof is administered oromucosally (e.g. sublingually or buccally) as a film described herein.

In a particular embodiment (E), the present disclosure provides a method of reducing a period of opioid withdrawal in a human subject in need thereof, comprising administering to said subject dexmedetomidine or a pharmaceutically acceptable salt thereof twice daily, wherein the period of withdrawal is up to 14 days. In some embodiments, the period of withdrawal may be 13 days, 12 days, 11 days, 10 days, 9 days, 8 days, 7 days, 6 days, 5 days, 4 days, or 3 days. In some embodiments, the human subject is an adult (i.e. at least 18 years old) and suffering with opioid use disorder who is physically dependent on opioids. In some embodiments, dexmedetomidine or a pharmaceutically acceptable salt is administered sublingually, buccally, orally, intranasally or parenterally. In some embodiments, dexmedetomidine or a pharmaceutically acceptable salt (e.g. hydrochloride) is administered sublingually as a film. In some embodiments, dexmedetomidine or a pharmaceutically acceptable salt thereof is oromucosally administered at a dose range of about 30 µg to about 200 µg as a single dose. In some embodiments, dexmedetomidine is administered as a dose of about 30 µg, about 60 µg, or about 90 µg, about 120 µg or about 180 µg, twice daily approximately 12 hours apart for a period of at least 3 days (e.g. 3 days, 4 days, 5 days, 6 days, 7 days, 8 days, 9 days, 10 days, 11 days, 12 days or 13 days). In further embodiments, each unit may be administered at an appropriate dosing interval (e.g. about 12 hours between doses) or can be administered concurrently, for example two units of 30 µg can be administered concurrently to produce the effect of a 60 µg dose or three units of 60 µg can be administered concurrently to produce the effect of a 180 µg dose. In an embodiment, the withdrawal symptoms following the treatment are assessed using the Clinical Opiate Withdrawal Scale and/or the Short Opiate Withdrawal Scale of Gossop (e.g. over a 10-day period). In some embodiments, the opioid may be selected from the group consisting of, but are not limited to fentanyl, morphine, codeine, heroin, oxycodone, hydrocodone, alfentanil carfentanil, tramadol, hydromorphone, buprenorphine, naloxone, naltrexone, remifentanil butorphanol, meperidine, methadone, dextropropoxyphene (propoxyphene) thebaine, sufentanil or pentazocine. In some embodiments, the opioid had been administered for the amount of time longer than neonate treatment prior to withdrawal. It was unexpectedly discovered that dexmedetomidine is effective at reducing the period of opioid withdrawal in an adult subject. This is surprising because opioids (e.g. fentanyl) become localized in body fat over time and are released intermittently and have unpredictable effects on patients during the withdrawal process. Due to the high degree of variability and intermittent release of opioids, a clinician would not expect repeated administration of dexmedetomidine to be an effective therapy.

In some embodiments, the present disclosure provides a method of promoting non-rapid eye movement (non-REM) stage 3 sleep in a human subject, comprising administering sublingually an effective amount of dexmedetomidine or a pharmaceutically acceptable salt thereof as a single dose. In some embodiments, the human subject is hospitalized in ICU with hyperactive delirium.

In some embodiments, the present disclosure provides a method of treating cocaine toxicity and/or symptoms associated with cocaine toxicity comprising administering oromucosally an effective amount of dexmedetomidine or a pharmaceutically acceptable salt thereof. In some embodiments. In some embodiments, dexmedetomidine or a pharmaceutically acceptable salt thereof is administered as an oromucosal film at a dose range of about 30 μg to about 200 μg as a single dose or as a multi-dose therapy.

In another embodiment (F), the present disclosure provides a method of treating agitation or signs of agitation in a human subject with schizophrenia or bipolar disorder, without also inducing significant sedation, comprising administering an appropriate amount of dexmedetomidine or a pharmaceutically acceptable salt thereof (e.g. the hydrochloride salt) resulting in a mean total exposure of dexmedetomidine, as measured by plasma AUC from T0 to T∞, of about 3800 ng*h/L. In some embodiments, the treatment is effective without causing clinically significant cardiovascular effects. In some embodiments, the dexmedetomidine is administered as a single dose. In some embodiments, the mean total exposure of dexmedetomidine, as measured by plasma AUC from T0 to T∞, is from about 80% to about 125% of 3800 ng*h/L. For example, the AUC is about 3024 ng*h/L, about 3100 ng*h/L, about 3200 ng*h/L, about 3300 ng*h/L, about 3400 ng*h/L, about 3500 ng*h/L, about 3600 ng*h/L, about 3700 ng*h/L, about 3800 ng*h/L, about 3900 ng*h/L, about 4000 ng*h/L, about 4100 ng*h/L, about 4200 ng*h/L, about 4300 ng*h/L, about 4400 ng*h/L, about 4500 ng*h/L, about 4600 ng*h/L, or about 4725 ng*h/L.

In another embodiment (G), the present disclosure provides a method of treating agitation or signs of agitation in a human subject with schizophrenia or bipolar disorder, without also inducing significant sedation, comprising administering an appropriate amount of dexmedetomidine or a pharmaceutically acceptable salt thereof (e.g. the hydrochloride salt) resulting in a mean total exposure of dexmedetomidine, as measured by plasma AUC from T0 to T∞, of about 1800 ng*h/L. In some embodiments, the treatment is effective without causing clinically significant cardiovascular effects. In some embodiments, the dexmedetomidine is administered as a single dose. In some embodiments, the mean total exposure of dexmedetomidine, as measured by plasma AUC from $T_0$ to T0, is from about 80% to about 125% of 1800 ng*h/L. For example, the AUC is about 1440 ng*h/L, 1500 ng*h/L, about 1600 ng*h/L, about 1700 ng*h/L, about 1800 ng*h/L, about 1900 ng*h/L, about 2000 ng*h/L, about 2100 ng*h/L, about 2200 ng*h/L, or about 2250 ng*h/L.

In a further embodiment (H), the present disclosure provides a method of treating agitation or signs of agitation in a human subject with schizophrenia or bipolar disorder, without also inducing significant sedation, comprising administering an appropriate amount of dexmedetomidine or a pharmaceutically acceptable salt thereof resulting in a total exposure of dexmedetomidine, as measured by plasma AUC from T0 to T∞, from about 600 to about 9500 ng*h/L. In some embodiments, the treatment is effective without causing clinically significant cardiovascular effects. In some embodiments, the dexmedetomidine is administered as a single dose. In some embodiments, the mean total exposure of dexmedetomidine, as measured by plasma AUC from T0 to T∞, is from about 80% to about 125% of about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, or about 11875 hr*ng/L.

In a further embodiment (I), the present disclosure provides a method of treating agitation or signs of agitation in a human subject with schizophrenia or bipolar disorder, without also inducing significant sedation, comprising administering an appropriate amount of dexmedetomidine or a pharmaceutically acceptable salt thereof resulting in a total exposure of dexmedetomidine, as measured by plasma AUC from T0 to T∞, from about 590. to about 4400 ng*h/L. In some embodiments, the treatment is effective without causing clinically significant cardiovascular effects. In some embodiments, the dexmedetomidine is administered as a single dose. In some embodiments, the mean total exposure of dexmedetomidine, as measured by plasma AUC from T0 to T∞, is from about 80% to about 125% of about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, or about 5500 hr*ng/L.

In some embodiments of each of embodiments (A) to (I), dexmedetomidine or a pharmaceutically acceptable salt thereof may be administered orally, oromucosally (e.g. sublingually, buccally), intravenously, intramuscularly, subcutaneously, topically, transdermally, intratracheally, intraperitoneally, intraorbitally, by implantation, by inhalation, intrathecally, intraventricularly or intranasally.

In some embodiments of each of embodiments (A) to (I), dexmedetomidine or a pharmaceutically acceptable salt thereof is administered to the subject by the sublingual, buccal, oral, intranasal or parenteral route. In some embodiments, dexmedetomidine or a pharmaceutically acceptable salt thereof is administered by the sublingual or buccal route. In some embodiments, dexmedetomidine or a pharmaceutically acceptable salt thereof is administered sublingually in the form of a tablet, film, spray, gel or drops, particularly a film. In some embodiments, the film is placed under the tongue, close to the base of the tongue, on the left or right side. In some embodiments, dexmedetomidine or a pharmaceutically acceptable salt thereof is administered buccally in the form of a film, patch or tablet, particularly a film. In some embodiments, the film is placed against the inner lip or check, close to the jaw line. In some embodiments, dexmedetomidine or a pharmaceutically acceptable salt thereof is administered parenterally to the subject in the form of an intramuscular injection. In some embodiments, dexmedetomidine or a pharmaceutically acceptable salt thereof is administered to the subject by oral route. In some embodiments, dexmedetomidine or a pharmaceutically acceptable salt thereof is administered orally in the form of tablets, orally disintegrating tablets (ODTs), effervescent tablets, capsules, pellets, pills, lozenges or troches, powders, dispersible granules, catchets, aqueous solutions, syrups, emulsions, suspensions, solutions, soft gels, dispersions and the like. In some embodiments, dexmedetomidine or a pharmaceutically acceptable salt thereof is administered orally to the subject in the form of an orally disintegrating tablet.

In some embodiments, dexmedetomidine or a pharmaceutically acceptable salt thereof is administered sublingually to the subject as a single dose containing about 180 µg dexmedetomidine or a pharmaceutically acceptable salt thereof, wherein agitation or signs of agitation are treated without also inducing clinically significant cardiovascular effects. In some embodiments, agitation or signs of agitation is treated without diastolic blood pressure falling below about 60 mmHg and/or without heart rate falling below about 50 beats per minute.

In some embodiments, dexmedetomidine or a pharmaceutically acceptable salt thereof is administered sublingually to the subject as a single dose containing about 120 µg dexmedetomidine or a pharmaceutically acceptable salt thereof, wherein agitation or signs of agitation is treated without also inducing clinically significant cardiovascular effects. In some embodiments, agitation or signs of agitation is treated without systolic blood pressure falling below about 80 mmHg and or/without diastolic blood pressure falling below about 60 mmHg and/or without heart rate falling below about 50 beats per minute.

In certain embodiments, there is provided a method of treating agitation or signs of agitation in a human subject with schizophrenia or bipolar disorder, without also inducing significant sedation, comprising sublingually administering a dose of about 180 µg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Tmax is about 1 to about 8 hours. In some embodiments, the dexmedetomidine is administered as a single dose. In some embodiments, the total exposure of dexmedetomidine, as measured by plasma AUC from T0 to T∞, is from about 80% to about 125% of about 600 to about 9500 ng*h/L. For example, about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, or about 11875 hr*ng/L. In some embodiments, the plasma Tmax from T0 to $T_{max}$ is from about 80% to about 125% of about 1 to about 8 hours. For example, about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, or about 10 h.

In certain embodiments, there is provided a method of treating agitation or signs of agitation in a human subject with schizophrenia or bipolar disorder, without also inducing significant sedation, comprising sublingually administering a dose of about 120 µg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma $T_{max}$ is about 1 to about 4 hours. In some embodiments, the dexmedetomidine is administered as a single dose. In some embodiments, the total exposure of dexmedetomidine, as measured by plasma AUC from $T_0$ to T∞, is from about 80% to about 125% of about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, or about 5500 hr*ng/L. In some embodiments, the plasma $T_{max}$ from $T_0$ to T∞, is from about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, or about 5.0 h.

In some embodiments, there is provided a method of treating a condition (e.g. agitation) in a human subject, comprising administering to said subject about 180 µg of dexmedetomidine or a pharmaceutically acceptable salt thereof sublingually to said subject, resulting in mean plasma absorption levels of dexmedetomidine from about 80% to about 125% of the following values: Cmax from about 300 ng/L to about 500 ng/L (e.g. about 400 ng/L) and AUC from T0 to T∞ of from about 2300 ng*h/L to about 3600 ng*h/L (e.g. about 2900 ng*h/L). For example, the Cmax is about 240 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, or about 625 ng/L and the AUC0-inf is about 1840 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, or about 4500 hr*ng/L.

In some embodiments, there is provided a method of treating a condition (e.g. agitation) in a human subject, comprising administering to said subject about 120 μg of dexmedetomidine or a pharmaceutically acceptable salt thereof sublingually to said subject, resulting in mean plasma absorption levels of dexmedetomidine from about 80% to about 125% of the following values: Cmax from about 150 ng/L to about 350.ng/L (e.g. about 220 ng/L) and AUC from T0 to T∞ of from about 1100. ng*h/L to about 1800 ng*h/L (e.g. about 1410 ng*h/L). For example, the Cmax is about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, and the AUC0-inf is about 900 hr*ng/L, about 1000 hr*ng/L, about 1250 hr*ng/L, about 1500 hr*ng/L, about 1750 hr*ng/L, about 2000 hr*ng/L, or about 2250 hr*ng/L.

In some embodiments, there is provided a method of treating agitation or signs of agitation in a human subject with schizophrenia or bipolar disorder, without also inducing significant sedation, comprising sublingually administering a dose of about 180 μg of dexmedetomidine or a pharmaceutically acceptable salt thereof to said subject, resulting in a mean total exposure of dexmedetomidine, as measured by plasma AUC from T0 to T∞ of about 3800 ng*h/L, wherein the mean plasma Cmax is about 400 ng/L. In some embodiments, the plasma AUC from T0 to T∞ is from 80% to about 125% of about 3800 ng*h/L, wherein the mean plasma Cmax is from about 80% to about 125% of about 400 ng/L.

In some embodiments, there is provided a method of treating agitation or signs of agitation in a human subject with schizophrenia or bipolar disorder, without also inducing significant sedation, comprising sublingually administering a dose of about 120 μg of dexmedetomidine or a pharmaceutically acceptable salt thereof to said subject, resulting in a mean total exposure of dexmedetomidine, as measured by plasma AUC from T0 to T∞ of about 1800 ng*h/L, wherein the mean plasma Cmax is about 200 ng/L. In some embodiments, the plasma AUC from T0 to T∞ is from 80% to about 125% of about 1800 ng*h/L, wherein the mean plasma Cmax is from about 80% to about 125% of about 200 ng/L.

In some embodiments, there is provided a method of treating agitation or signs of agitation in a human subject with schizophrenia or bipolar disorder, without also inducing significant sedation, comprising sublingually administering a dose of about 180 μg of dexmedetomidine or a pharmaceutically acceptable salt thereof to said subject, resulting in a mean total exposure of dexmedetomidine, as measured by plasma AUC from T0 to T∞ of about 3800 ng*h/L, wherein the median plasma Tmax is about 2 hours. In some embodiments, the plasma AUC from T0 to T∞ is from 80% to about 125% of about 3800 ng*h/L, wherein the median plasma Tmax is from about 80% to about 125% of about 2 hours.

In some embodiments, there is provided a method of treating agitation or signs of agitation in a human subject with schizophrenia or bipolar disorder, without also inducing significant sedation, comprising sublingually administering a dose of about 120 μg of dexmedetomidine or a pharmaceutically acceptable salt thereof to said subject, resulting in a mean total exposure of dexmedetomidine, as measured by plasma AUC from T0 to T∞ of about 1800 ng*h/L, wherein the median plasma Tmax is about 2 hours. In some embodiments, the plasma AUC from T0 to T∞ is from 80% to about 125% of about 1800 ng*h/L, wherein the median plasma Tmax is from about 80% to about 125% of about 2 hours.

In some embodiments, there is provided a method of treating agitation or signs of agitation in a human subject with schizophrenia or bipolar disorder, without also inducing significant sedation, comprising sublingually administering a dose of about 180 μg of dexmedetomidine or a pharmaceutically acceptable salt thereof to said subject resulting in a mean total exposure of dexmedetomidine, as measured by plasma AUC from T0 to T∞ of about 3800 ng*h/L, wherein the mean plasma Cmax is about 400 ng/L and the median plasma Tmax is about 2 hours. In some embodiments, the plasma AUC from T0 to T∞ is from 80% to about 125% of about 3800 ng*h/L, the mean plasma Cmax is from about 80% to about 125% of about 400 ng/L, and the median plasma Tmax is from about 80% to about 125% of about 2 hours.

In some embodiments, there is provided a method of treating agitation or signs of agitation in a human subject with schizophrenia or bipolar disorder, without also inducing significant sedation, comprising sublingually administering a dose of about 120 μg of dexmedetomidine or a pharmaceutically acceptable salt thereof to said subject resulting in a mean total exposure of dexmedetomidine, as measured by plasma AUC from T0 to T∞ of about 1800 ng*h/L, wherein the mean plasma Cmax is about 200 ng/L and the median plasma Tmax is about 2 hours. In some embodiments, the plasma AUC from T0 to T∞ is from 80% to about 125% of about 1800 ng*h/L, the mean plasma Cmax is from about 80% to about 125% of about 200 ng/L, and the median plasma Tmax is from about 80% to about 125% of about 2 hours.

In some embodiments, there is provided a method of treating agitation or signs of agitation in a human subject with schizophrenia or bipolar disorder, without also inducing significant sedation, comprising sublingually administering a dose of about 180 μg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Cmax is about 100 ng/L to about 800 ng/L. In some embodiments, the plasma AUC from T0 to T∞ is from 80% to about 125% of about 600 ng*h/L to about 9500 ng*h/L and the mean plasma Cmax is from about 80% to about 125% of about 100 ng/L to about 800 ng/L.

In some embodiments, there is provided a method of treating agitation or signs of agitation in a human subject with schizophrenia or bipolar disorder, without also inducing significant sedation, comprising sublingually administering a dose of about 120 μg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma Cmax is about 110 ng/L to about 400 ng/L. In some embodiments, the plasma AUC from T0 to T∞ is from 80% to about 125% of about 590 ng*h/L to about 4400 ng*h/L and the mean plasma Cmax is from about 80% to about 125% of about 110 ng/L to about 400 ng/L.

In certain embodiments, there is provided a method of treating agitation or signs of agitation in a human subject with schizophrenia or bipolar disorder, without also inducing significant sedation, comprising sublingually administering a dose of 180 μg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Tmax is about 1 to about 8 hours. In some embodiments, the plasma AUC from T0 to T∞ is from 80% to about 125% of about 600 ng*h/L to about 9500 ng*h/L and the plasma Tmax is from about 80% to about 125% of about 1 to about 8 hours.

In certain embodiments, there is provided a method of treating agitation or signs of agitation in a human subject with schizophrenia or bipolar disorder, without also inducing significant sedation, comprising sublingually administering a dose of 120 μg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma Tmax is about 1 to about 4. hours. In some embodiments, the plasma AUC from T0 to T∞ is from 80% to about 125% of about 5900 ng*h/L to about 4400 ng*h/L and the plasma Tmax is from about 80% to about 125% of about 1 to about 4 hours.

In some embodiments, there is provided a method of treating a condition (e.g. agitation) in a human subject, comprising administering to said subject about 180 μg of dexmedetomidine or a pharmaceutically acceptable salt thereof sublingually to said subject, resulting in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/L.

In some embodiments, there is provided a method of treating a condition (e.g. agitation) in a human subject, comprising administering to said subject about 120 μg of dexmedetomidine or a pharmaceutically acceptable salt thereof sublingually to said subject, resulting in plasma absorption levels of dexmedetomidine from about 80% to about 125% of the following values: Cmax from about 110 ng/L to about 400 ng/L and AUC from T0 to $T_{max}$ of about 590 hr*ng/L to about 4400.hr*ng/L.

In certain embodiments, there is provided a method of treating a condition (e.g. agitation) in a human subject in need thereof, without also inducing significant sedation, comprising administering an unit dose of 180 μg or 120 μg dexmedetomidine or a pharmaceutically acceptable salt thereof to said subject, resulting in rapid absorption with maximum concentration achieved on average within about 2.5 hours after administration.

In some embodiments, there is provided a method of treating a condition (e.g. agitation) in a human subject, comprising administering about 180 μg of dexmedetomidine or a pharmaceutically acceptable salt thereof sublingually to said subject, resulting in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/L. In some embodiments, the plasma Tmax is about 1 hour to about 8 hours.

In some embodiments, there is provided a method of treating a condition (e.g. agitation) in a human subject, comprising administering about 120 μg of dexmedetomidine or a pharmaceutically acceptable salt thereof sublingually to said subject, resulting in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L. In some embodiments, the plasma Tmax is about 1 hour to about 4 hours.

In some embodiments, there is provided a method of treating a condition (e.g. agitation) in a human subject, comprising administering to said subject about 180 μg of dexmedetomidine or a pharmaceutically acceptable salt thereof sublingually to said subject, resulting in mean plasma absorption levels of dexmedetomidine from about 80% to about 125% of the following values: Cmax of from about 300 ng/L to about 500 ng/L (e.g. about 400 ng/L) and AUC from T0 to T∞ of from about 2300 ng*h/L. to about 3600 ng*h/L (e.g. about 2900 ng*h/L), In some embodiments, the plasma Tmax is about 2 hours.

In some embodiments, there is provided a method of treating a condition (e.g. agitation) in a human subject, comprising administering to said subject about 120 μg of dexmedetomidine or a pharmaceutically acceptable salt thereof sublingually to said subject, resulting in mean plasma absorption levels of dexmedetomidine from about 80% to about 125% of the following values: Cmax of from about 150 ng/L to about 300 ng/L (e.g. about 220 ng/L) and AUC from T0 to T∞ of from about 1100 ng*h/L to about 1800 ng*h/L (e.g. about 1400 ng*h/L). In some embodiments, the plasma Tmax is about 2 hours.

In certain embodiments, there is provided a method of treating agitation or signs of agitation in a human subject with schizophrenia or bipolar disorder, without also inducing significant sedation, comprising buccally administering a dose of 180 Mg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Tmax is about 1 to about 8 hours.

In certain embodiments, there is provided a method of treating agitation or signs of agitation in a human subject with schizophrenia or bipolar disorder, without also inducing significant sedation, comprising buccally administering a dose of 120 μg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma Tmax is about 1 to about 4 hours.

In some embodiments, there is provided a method of treating a condition (e.g. agitation) in a human subject, comprising administering to said subject about 180 μg of dexmedetomidine or a pharmaceutically acceptable salt thereof buccally to said subject, resulting in mean plasma absorption levels of dexmedetomidine from about 80% to about 125% of the following values: Cmax from about 300 ng/L to about 500 ng/L (e.g. about 400 ng/L) and AUC from T0 to T∞ of from about 2300 ng*h/L to about 3600 ng*h/L (e.g. about 2900 ng*h/L).

In some embodiments, there is provided a method of treating a condition (e.g. agitation) in a human subject, comprising administering to said subject about 120 μg of dexmedetomidine or a pharmaceutically acceptable salt thereof buccally to said subject, resulting in mean plasma absorption levels of dexmedetomidine from about 80% to about 125% of the following values: Cmax from about 150 ng/L to about 300 ng/L (e.g. about 220.ng/L) and AUC from T0 to T∞ of from about 1100 ng*h/L to about 1800 ng*h/L (e.g. about 1400 ng*h/L).

In some embodiments, there is provided a method of treating agitation or signs of agitation in a human subject with schizophrenia or bipolar disorder, without also inducing significant sedation, comprising buccally administering a dose of about 180 μg of dexmedetomidine or a pharmaceutically acceptable salt thereof to said subject, resulting in a mean total exposure of dexmedetomidine, as measured by plasma AUC from T0 to T∞ of about 3800 ng*h/L, wherein the mean plasma Cmax is about 400 ng/L.

In some embodiments, there is provided a method of treating agitation or signs of agitation in a human subject with schizophrenia or bipolar disorder, without also inducing significant sedation, comprising buccally administering a dose of about 120 μg of dexmedetomidine or a pharmaceutically acceptable salt thereof to said subject, resulting in a mean total exposure of dexmedetomidine, as measured by plasma AUC from T0 to T∞ of about 1800 ng*h/L, wherein the mean plasma Cmax is about 200 ng/L.

In some embodiments, there is provided a method of treating agitation or signs of agitation in a human subject with schizophrenia or bipolar disorder, without also inducing significant sedation, comprising buccally administering a dose of about 180 μg of dexmedetomidine or a pharmaceutically acceptable salt thereof to said subject, resulting in a mean total exposure of dexmedetomidine, as measured by plasma AUC from T0 to T∞ of about 3780 ng*h/L, wherein the median plasma Tmax is about 2 hours.

In some embodiments, there is provided a method of treating agitation or signs of agitation in a human subject with schizophrenia or bipolar disorder, without also inducing significant sedation, comprising buccally administering a dose of about 120 μg of dexmedetomidine or a pharmaceutically acceptable salt thereof to said subject, resulting in a mean total exposure of dexmedetomidine, as measured by plasma AUC from T0 to T∞ of about 1800 ng*h/L, wherein the median plasma Tmax is about 2 hours.

In some embodiments, there is provided a method of treating agitation or signs of agitation in a human subject with schizophrenia or bipolar disorder, without also inducing significant sedation, comprising buccally administering a dose of about 180 μg of dexmedetomidine or a pharmaceutically acceptable salt thereof to said subject resulting in a mean total exposure of dexmedetomidine, as measured by plasma AUC from T0 to T∞ of about 3800 ng*h/L, wherein the mean plasma Cmax is about 400 ng/L and the median plasma Tmax is about 2 hours.

In some embodiments, there is provided a method of treating agitation or signs of agitation in a human subject with schizophrenia or bipolar disorder, without also inducing significant sedation, comprising buccally administering a dose of about 120 μg of dexmedetomidine or a pharmaceutically acceptable salt thereof to said subject resulting in a mean total exposure of dexmedetomidine, as measured by plasma AUC from T0 to T∞ of about 1800 ng*h/L, wherein the mean plasma Cmax is about 200 ng/L and the median plasma Tmax is about 2 hours.

In some embodiments, there is provided a method of treating agitation or signs of agitation in a human subject with schizophrenia or bipolar disorder, without also inducing significant sedation, comprising buccally administering a dose of about 180 μg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Cmax is about 100 ng/L to about 800 ng/L.

In some embodiments, there is provided a method of treating agitation or signs of agitation in a human subject with schizophrenia or bipolar disorder, without also inducing significant sedation, comprising buccally administering a dose of about 120 μg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma Cmax is about 110 ng/L to about 400 ng/L.

In certain embodiments, there is provided a method of treating agitation or signs of agitation in a human subject with schizophrenia or bipolar disorder, without also inducing significant sedation, comprising buccally administering a dose of about 180 μg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Tmax is about 1 to about 8 hours.

In certain embodiments, there is provided a method of treating agitation or signs of agitation in a human subject with schizophrenia or bipolar disorder, without also inducing significant sedation, comprising buccally administering a dose of about 120 μg of dexmedetomidine or a pharmaceutically acceptable salt thereof resulting in a total exposure of dexmedetomidine, as measured by plasma AUC from T0 to T∞, from about 590 to about 4400 ng*h/L, wherein the plasma Tmax is about 1 to about 4 hours.

In some embodiments, there is provided a method of treating a condition (e.g. agitation) in a human subject, comprising administering to said subject about 180 μg of dexmedetomidine or a pharmaceutically acceptable salt thereof buccally to said subject, resulting in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/L.

In some embodiments, there is provided a method of treating a condition in a human subject, comprising administering to said subject about 120 μg of dexmedetomidine or a pharmaceutically acceptable salt thereof buccally to said subject, resulting in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L.

In some embodiments, there is provided a method of treating a condition (e.g. agitation) in a human subject, comprising administering about 180 μg of dexmedetomidine or a pharmaceutically acceptable salt thereof buccally to said subject, resulting in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/, wherein the plasma Tmax is about 1 hour to about 8 hours.

In some embodiments, there is provided a method of treating a condition (e.g. agitation) in a human subject, comprising administering about 120 μg of dexmedetomidine or a pharmaceutically acceptable salt thereof buccally to said subject, resulting in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L, wherein the plasma Tmax is about 1 hour to about 4 hours.

In some embodiments, there is provided a method of treating a condition (e.g. agitation) in a human subject, comprising administering to said subject about 180 µg of dexmedetomidine or a pharmaceutically acceptable salt thereof buccally to said subject, resulting in mean plasma absorption levels of dexmedetomidine from about 80% to about 125% of the following values: Cmax of from about 300 ng/L to about 500 ng/L (e.g. about 400 ng/L) and AUC from T0 to T∞ of from about 2300 ng*h/L to about 3600 ng*h/L (e.g. about 2900 ng*h/L), wherein the median plasma Tmax is about 2 hours.

In some embodiments, there is provided a method of treating a condition (e.g. agitation) in a human subject, comprising administering to said subject about 120 µg of dexmedetomidine or a pharmaceutically acceptable salt thereof buccally to said subject, resulting in mean plasma absorption levels of dexmedetomidine from about 80% to about 125% of the following values: Cmax of from about 150 ng/L to about 300 ng/L (e.g. about 200 ng/L) and AUC from T0 to T∞ of from about 1100 ng*h/L to about 1800 ng*h/L (e.g. about 1400 ng*h/L), wherein the median plasma Tmax is about 2 hours.

In certain embodiments, dexmedetomidine or a pharmaceutically acceptable salt thereof is administered parenterally to the subject in the form of an intramuscular injection, wherein dexmedetomidine or a pharmaceutically acceptable salt thereof is administered at a dose of about 140 µg to about 190 µg.

In some embodiments, there is provided a method of treating agitation or signs of agitation in a human subject with schizophrenia or bipolar disorder, without also inducing significant sedation, comprising intramuscularly administering a dose of about 120 µg to about 190 µg of dexmedetomidine or a pharmaceutically acceptable salt thereof resulting in a total exposure of dexmedetomidine, as measured by plasma AUC from T0 to T∞, from about 600 to about 9500 ng*h/L, wherein the plasma Tmax is about 5 minutes to about 4 hours.

In some embodiments, there is provided a method of treating agitation or signs of agitation in a human subject with schizophrenia or bipolar disorder, without also inducing significant sedation, comprising intramuscularly administering a dose of about 120 µg to about 190 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the plasma Tmax is about 5 minutes to about 4 hours.

In some embodiments, there is provided a method of treating agitation or signs of agitation in a human subject with schizophrenia or bipolar disorder, without also inducing significant sedation, comprising intramuscularly administering a dose of about 120 µg to about 190 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the plasma Cmax is about 200 to about 800 ng/L.

In some embodiments, there is provided a method of treating agitation or signs of agitation in a human subject with schizophrenia or bipolar disorder, without also inducing significant sedation, comprising intramuscularly administering a dose of about 120 µg to about 190 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the median Tmax is about 2 hours.

In some embodiments, there is provided a method of treating agitation or signs of agitation in a human subject with schizophrenia or bipolar disorder, without also inducing significant sedation, comprising intravenously administering a dose of about 120 µg to about 190 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the plasma Tmax is about 5 minutes to about 15 minutes.

In some embodiments, dexmedetomidine or a pharmaceutically acceptable salt thereof is administered orally to the subject, wherein dexmedetomidine or a pharmaceutically acceptable salt thereof is administered at a dose of about 900 µg to about 1200 µg.

In certain embodiments, there is provided a method of treating agitation or signs of agitation in a human subject with schizophrenia or bipolar disorder, without also inducing significant sedation, comprising orally administering a dose of about 900 µg to about 1200 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the plasma Tmax is about 1 hour to about 8 hours.

In certain embodiments, there is provided a method of treating agitation or signs of agitation in a human subject with schizophrenia or bipolar disorder, without also inducing significant sedation, comprising orally administering a dose of about 900 µg to about 1200 µg of dexmedetomidine or a pharmaceutically acceptable salt thereof resulting in a total exposure of dexmedetomidine, as measured by plasma AUC from T0 to T∞, from about 600 to about 12600 ng*h/L, wherein the median Tmax is about 2 hours.

In some embodiments, dexmedetomidine or a pharmaceutically acceptable salt thereof is administered as a single dose (e.g. as a single unit dose or multiple unit doses administered simultaneously).

Another embodiment of the present disclosure provides a self-supporting, dissolvable, film comprising about 180 µg of dexmedetomidine hydrochloride, wherein application of said film sublingually to a subject with schizophrenia or bipolar disorder results in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/L.

Another embodiment of the present disclosure provides a self-supporting, dissolvable, film comprising about 120 µg of dexmedetomidine hydrochloride, wherein application of said film sublingually to a subject with schizophrenia or bipolar disorder results in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L.

Another embodiment of the present disclosure provides a self-supporting, dissolvable, film comprising about 180 µg of dexmedetomidine hydrochloride, wherein application of said film sublingually to a subject with schizophrenia or bipolar disorder results in plasma absorption levels of dexmedetomidine from about 80% to about 125% of the following values: Cmax from about 300 ng/L to about 500 ng/L (e.g. about 400 ng/L) and AUC from T0 to T∞ of about 2300 ng*h/L to about 3600 ng*h/L (e.g. about 2900 ng*h/L), wherein the median plasma Tmax is about 2 hours.

Another embodiment of the present disclosure provides a self-supporting, dissolvable, film comprising about 120 µg of dexmedetomidine hydrochloride, wherein application of said film sublingually to a subject with schizophrenia or bipolar disorder results in plasma absorption levels of dexmedetomidine from about 80% to about 125% of the following values: Cmax from about 150 ng/L to about 300. ng/L (e.g. about 200 ng/L) and AUC from T0 to T∞ of about 1100 ng*h/L. to about 1800 ng*h/L (e.g. about 1400 ng*h/L), wherein the median plasma Tmax is about 2 hours.

Another embodiment of the present disclosure provides a self-supporting, dissolvable, film comprising about 180 µg to about 240 µg of dexmedetomidine hydrochloride, wherein application of said film sublingually to a subject with schizophrenia or bipolar disorder results in a total exposure of dexmedetomidine, as measured by plasma AUC from T0 to T∞, from about 600 to about 12600 ng*h/L, wherein the plasma Tmax is about 1 to about 8 hours.

Another embodiment of the present disclosure provides a self-supporting, dissolvable, film comprising:
(a) a composition consisting essentially of:
(i) about 180 µg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in plasma absorption levels of dexmedetomidine from about 80% to about 125% of the following values: Cmax from about 100 ng/L to about 800 ng/L and AUC from $T_0$ to T∞ of about 600 hr*ng/L to about 9500 hr*ng/L. For example, the Cmax is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 525 ng/L, about 550 ng/L, about 575 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, to about 1000 ng/L, and the $AUC_{0\text{-}inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, about 7500 hr*ng/L, about 7750 hr*ng/L, about 8000 hr*ng/L, about 8250 hr*ng/L, about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L. In some embodiments, the Tmax is from about 1 to about 8 hours. For example, the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h.

Another embodiment of the present disclosure provides a self-supporting, dissolvable, film comprising:
(a) a composition consisting essentially of:
(i) about 120 µg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L. For example, the Cmax is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, to about 500 ng/L, and the $AUC_{0\text{-}inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L. In some embodiments, the Tmax is from about 1 to about 4 hours. For example, the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h.

Another embodiment of the present disclosure provides a self-supporting, dissolvable, film comprising:
(a) a composition consisting essentially of:
(i) about 180 µg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in plasma absorption levels of dexmedetomidine from about 80% to about 125% of the following values: Cmax from about 100 ng/L to about 800 ng/L and AUC from $T_0$ to $T\infty$ of about 600 hr*ng/L to about 9500 hr*ng/L, wherein the plasma Tmax is about 1 hour to about 8 hours. For example, the Cmax is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, to about 1000 ng/L, and the $AUC_{0-inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, and the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h.

Another embodiment of the present disclosure provides a self-supporting, dissolvable, film comprising:
(a) a composition consisting essentially of:
(i) about 120 μg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in plasma absorption levels of dexmedetomidine from about 80% to about 125% of the following values: Cmax from about 110 ng/L to about 400 ng/L and AUC from T0 to T∞ of about 590 hr*ng/L to about 4400 hr*n/L, wherein the plasma Tmax is about 1 hour to about 4 hours. For example, the Cmax is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, to about 500 ng/L, and the $AUC_{0-inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, and the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h.

Another embodiment of the present disclosure provides a self-supporting, dissolvable, film comprising:
(a) a composition consisting essentially of:
(i) about 180 μg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in mean plasma absorption levels of dexmedetomidine from about 80% to about 125% of the following values: Cmax of about 300 ng/L to about 474 ng/L (e.g. about 400 ng/L) and AUC from $T_0$ to $T\infty$ of about 2300 ng*h/L. to about 3600 ng*h/L (e.g. about 2900 ng*h/L), wherein the median plasma Tmax is about 2 hours. For example, the Cmax is about 300 ng/L, about 325 ng/L, about 350 ng/L, about 375 ng/L, about 400 ng/L, about 425 ng/L, about 450 ng/L, to about 475 ng/L, and the AUC0-inf is about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L. In some embodiments, the Tmax is from about 1 to about 4 hours. For example, the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h.

Another embodiment of the present disclosure provides a self-supporting, dissolvable, film comprising:
(a) a composition consisting essentially of:
(i) about 120 μg of dexmedetomidine hydrochloride;
(ii) hydroxypropyl cellulose (40,000 MW); and
(iii) hydroxypropyl cellulose (140,000 MW); and
(b) a film substrate consisting essentially of:
(i) hydroxypropyl cellulose (40,000 MW);
(ii) hydroxypropyl cellulose (140,000 MW);
(iii) hydroxypropyl cellulose (370,000 MW); and
(iv) polyethylene oxide (600,000 MW);
wherein the composition of part (a) is present on the surface of the film substrate (b), and wherein application of said film sublingually to a subject with schizophrenia or bipolar disorder results in mean plasma absorption levels of dexmedetomidine from about 80% to about 125% of the following values: Cmax of about 150 ng/L to about 300 ng/L (e.g. about 200 ng/L) and AUC from $T_0$ to $T\infty$ of about 1100 ng*h/L. to about 1800 ng*h/L (e.g. about 1400 ng*h/L), wherein the median plasma Tmax is about 2 hours. For example, the Cmax is about 150 ng/L, about 175 ng/L, about 200 ng/L, about 225 ng/L, about 250 ng/L, about 275 ng/L, or about 300 ng/L, and the $AUC_{0-inf}$ is about 1100 hr*ng/L, about 1250 hr*ng/L, about 1500 hr*ng/L, about 1750 hr*ng/L, to about 1800 hr*ng/L. In some embodiments, the Tmax is from about 1 to about 4 hours. For example, the Tmax is about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h Another embodiment of the present disclosure provides a self-supporting, dissolvable, film comprising:
(a) a composition consisting essentially of:
  (i) about 180 μg of dexmedetomidine hydrochloride;
  (ii) hydroxypropyl cellulose (40,000 MW); and
  (iii) hydroxypropyl cellulose (140,000 MW); and
(b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b), and wherein application of said film sublingually to a subject with schizophrenia or bipolar disorder results in a total exposure of dexmedetomidine, as measured by plasma AUC from $T_0$ to $T\infty$, from about 600 to about 12600 ng*h/L, wherein the plasma Tmax is about 1 to about 8 hours. For example, the $AUC_{0-inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, about 11750 hr*ng/L, about 12000 hr*ng/L, about 12250 hr*ng/L, or about 12600 hr*ng/L, and the Tmax is about 1 h, about 2 h, about 3 h, about 4 h, about 5 h, about 6 h, about 7 h, or about 8 h.

Another embodiment of the present disclosure provides a self-supporting, dissolvable, film comprising:
(a) a composition consisting essentially of:
  (i) about 120 μg of dexmedetomidine hydrochloride;
  (ii) hydroxypropyl cellulose (40,000 MW); and
  (iii) hydroxypropyl cellulose (140,000 MW): and
(b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b), and wherein application of said film sublingually to a subject with schizophrenia or bipolar disorder results in a total exposure of dexmedetomidine, as measured by plasma AUC from $T_0$ to $T\infty$, from about 590 to about 8750 ng*h/L, wherein the plasma Tmax is about 1 to about 4 hours. For example, the $AUC_{0-inf}$ is about 590 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, about 8500 hr*ng/L, or about 8750 hr*ng/L, and the Tmax is about 1 h, about 2 h, about 3 h, or about 4 h.

In some embodiments, agitation or signs of agitation are significantly reduced within 60 minutes in a patient with schizophrenia or bipolar disorder following administration of a single dose of 120 μg or 180 μg of dexmedetomidine or a pharmaceutically acceptable salt thereof (e.g. dexmedetomidine hydrochloride, as measured by the relative PEC scores just prior to and 60 minutes after administering dexmedetomidine or a pharmaceutically acceptable salt thereof.

In some embodiments, the relative PEC scores are different by at least six points. In another embodiment, the relative PEC scores are different by at least eight points. In yet another embodiment, the difference in relative PEC scores is maintained for at least six hours. In a particular embodiment, a difference of at least eight points is maintained for up to about 24 hours when administering a single dose of 180 μg of dexmedetomidine or a pharmaceutically acceptable salt thereof (e.g. dexmedetomidine hydrochloride).

In some embodiments, the decrease in PEC score at 2 hours, as measured by change from baseline total PEC score post-administration of 180 μg of dexmedetomidine hydrochloride is −10.8 compared to placebo (4.5). In some embodiments, the decrease in PEC score at 2 hours post-administration of 180 μg of dexmedetomidine hydrochloride is greater (−10.8) as compared to administering 120 μg (−9.2) or 80 μg (−7.3) dexmedetomidine hydrochloride. In some embodiments, dexmedetomidine or a pharmaceutically acceptable salt thereof is administered immediately prior to or immediately following the appearance of agitation or signs of agitation in the human subject.

In some embodiments, dexmedetomidine or a pharmaceutically acceptable salt thereof is administered within 10 minutes following the appearance of agitation or signs of agitation in the human subject. In some embodiments, an additional dose of 90 μg or 60 μg may be taken after a suitable period of time (e.g. two hours) of first dosing.

In some embodiments, following administering a unit dose of about 30 μg, about 60 μg, about 90 μg, about 120 μg, or about 180 μg of dexmedetomidine or a pharmaceutically acceptable thereof in a human subject experiencing opioid withdrawal symptoms (e.g. agitation or signs of agitation), the withdrawal symptoms are significantly reduced as measured by the relative COWS and/or the SOWS-Gossop scores just prior to and 2 hour post administration of dexmedetomidine or a pharmaceutically acceptable salt thereof. In a particular embodiment, each unit may be administered twice daily over an appropriate period of withdrawal (e.g. for at least 3, 4, 5, 6, 7, 8, 9, 10, 11, 12, 13, or 14 days).

In certain embodiments, following administering of about 20 μg to about 240 μg of dexmedetomidine or a pharmaceutically acceptable salt thereof (e.g. dexmedetomidine hydrochloride) to an agitated human subject with delirium hospitalized (e.g. in an ICU), the agitation or signs of agitation and delirium severity are significantly reduced as measured by the RASS and DRS-R-98 respectively. For example, the agitation or signs of agitation and delirium severity are significantly reduced as measured by the RASS and DRS-R-98 just prior to and after every 30 minutes, 1 hour, 2 hours, 3, hours, 4 hours, 5 hours, or 6 hours post-administration of dexmedetomidine. In some embodiments, dexmedetomidine is oromucosally (e.g. sublingually or buccally) administered one to four times a day at an appropriate dosing interval (e.g. after every 30 minutes) within 6 hours of first dose to produce a desired effect; for example, a 20 µg unit dose is administered four times at a dosing interval of 30 minutes within 6 hours of first dose to produce the effect of a 80 µg dose or a 60 µg unit dose is administered four times at a dosing interval of 30 minutes within 6 hours of first dose to produce the effect of a 240 µg.

In some embodiments, following administration of about 30 µg to about 90 µg of dexmedetomidine or a pharmaceutically acceptable salt thereof (e.g. dexmedetomidine hydrochloride) to an agitated human subject with dementia, the agitation or signs of agitation are significantly reduced as measured by the PAS and PEC. For example, the agitation or signs of agitation are significantly reduced as measured by the PAS and PEC just prior to and after every 2 hours up to at least 24 hours post administration of dexmedetomidine or a pharmaceutically acceptable salt thereof. In one embodiment, dexmedetomidine is oromucosally (e.g. sublingually or buccally) administered. In some embodiments, each unit dose comprises about 30 µg to 60 µg of dexmedetomidine or a pharmaceutically acceptable salt thereof. In some embodiments, a dose of dexmedetomidine may be taken 1, 2, 3, 4, 5, or 6 times in a day every 2 hours with the provision of maximum of three doses within 12 hours of first dose. In some embodiments, each unit dose containing about 90 µg of dexmedetomidine or a pharmaceutically acceptable salt thereof may be taken 1, 2, 3, or 4 times in a day at every 2 hours with the provision of maximum of two doses within 12 hours of first dose.

In some embodiments, dexmedetomidine or a pharmaceutically acceptable salt thereof is administered oromucosally (e.g. sublingually or buccally) as a film. In some embodiments, the dosing may be achieved by cutting the film into half to deliver a half-dose (for e.g. 60 µg dose may be administered with a half of a 60 µg dose (30 µg) to make a 90 µg dose.).

In some embodiments, the present disclosure provides a method of treating agitation associated with schizophrenia or bipolar disorder, comprising administering a unit dose composition comprising about 120 µg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

In accordance with some embodiments of the methods of treating agitation comprising administering a unit dose composition comprising about 120 µg of dexmedetomidine, the composition may be administered a variety of means. For example, in some embodiments, the composition comprising dexmedetomidine (e.g. dexmedetomidine hydrochloride) or a pharmaceutically acceptable salt is administered sublingually, buccally, orally, intranasally or parenterally. In some embodiments, the composition is administered sublingually or buccally. In some embodiments, the composition is administered sublingually in the form of a tablet, film, spray, gel or drops. In some embodiments, the composition is administered buccally in the form of a film, patch or tablet.

In accordance with some embodiments of the methods of treating agitation comprising administering a unit dose composition comprising about 120 µg of dexmedetomidine, the method may further comprises administering a second dose of dexmedetomidine after a period of time ranging from about 30 minutes to about 12 hours. For example, the period of time may be about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, or about 23 hours. In some embodiments, the second dose is administered after a period of about 2 hours. In some embodiments, the second dose ranges from about 10 µg to about 180 µg. For example, the additional dose may be about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170, or about 180 µg. In some embodiments, the additional dose is about 60 µg or 90 µg.

In accordance with some embodiments of the methods of treating agitation comprising administering a unit dose composition comprising about 120 µg of dexmedetomidine, the unit dose composition may be administered to a patient in the fasted state. In some embodiments, the unit dose composition has been administered in the fed state.

In accordance with some embodiments of the methods of treating agitation comprising administering a unit dose composition comprising about 120 µg of dexmedetomidine, agitation is significantly reduced within about 2 hours of administering the composition, as measured by a mean change in Positive and Negative Syndrome Scale Excited Component (PEC) scores relative to baseline. In some embodiments, the agitation is significantly reduced within about 45 minutes to about 1 hour. In some embodiments, the agitation is significantly reduced in less than 45 minutes (e.g. about 15 minutes, about 20 minutes, about 25 minutes, about 30 minutes). In some embodiments, the patient experiences ≥40% decrease from baseline in PEC score. For example, the patient may experience greater than or equal to about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, or about 150% from baseline. Treatment efficacy may also be compared by comparing PEC score to placebo. In some embodiments, the PEC score is ≥30% lower than placebo (e.g. the placebo group has mean change from baseline in PEC total score of −3 and the dexmedetomidine-containing composition has a score of −3.9). For example, compared to placebo, the patient's PEC score may be lower by greater than or equal to about 30,%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In some embodiments, the patient experiences a mean change in PEC score of greater than about −4 (i.e. a decrease of 4 or more points)

relative to baseline within 2 hours of administering the composition. For example, at the 2 hour time point, the patient may experience a mean change in PEC score of greater than about −4, about −5, about −6, about −7, about −8, about −9, about −10, about −11, or about −12. In some embodiments, the decrease in PEC score (e.g. of greater than about −4) is maintained for at least six hours following administration of the composition. For example, if a patient experiences a mean change from baseline in PEC total score of e.g. −6 at 2 hours, then at 6 hours patient's mean change in PEC score will be about −6 or lower (e.g. −7, −8, etc.). In some embodiments, the decrease in PEC score (e.g. of greater than about −4) is substantially maintained for at least six hours following administration of the composition. For example, if a patient experiences a mean change from baseline in PEC total score of e.g. −6 at 2 hours, then at 6 hours patient's mean change in PEC score will be about −4, about −5, or about −6 or lower (e.g. −7, −8, etc.). In some embodiments, the mean change in PEC score is greater than or equal to −8 and is maintained from 2 hours post administration up to at least about 6 hours following administration of the composition.

In accordance with some embodiments of the methods of treating agitation comprising administering a unit dose composition comprising about 120 μg of dexmedetomidine, the subject is treated without experiencing significant sedation. In some embodiments, the subject is treated without experiencing clinically significant cardiovascular effects.

In accordance with some embodiments of the methods of treating agitation comprising administering a unit dose composition comprising about 120 μg of dexmedetomidine, administration of a single dose provides a mean $C_{max}$ within the range of about 80% to about 125% of about 110 ng/L to about 400 ng/L. For example, a single dose provides a mean Cm of about 88 ng/L, about 100 ng/L, about 125 ng/L, about 150 ng/L about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, about 475 ng/L, or about 500 ng/L, including all integers and ranges therebetween. In some embodiments, the mean $C_{max}$ is between about 100 ng/L to about 500 ng/L, about 150 ng/L to about 450 ng/L, about 150 ng/L to about 400 ng/L, about 200 ng/L to about 350 ng/L, about 200 ng/L to about 300 ng/L, about 200 ng/L to about 250 mg/L, or about 210 ng/L to about 240 ng/L. In some embodiments, the mean $C_{max}$ is within the range of about 80% to about 125% of about 238 ng/L. the mean $C_{max}$ is within the range of about 80% to about 125% of about 238 ng/L. In some embodiments, the mean $C_{max}$ is about 238 ng/L.

In accordance with some embodiments of the methods of treating agitation comprising administering a unit dose composition comprising about 120 μg of dexmedetomidine, administration of a single dose provides a mean $AUC_{0-inf}$ within the range of about 80% to about 125% of about 590 hr*ng/L to about 4400 hr*ng/L. For example, a single dose provides a mean $AUC_{0-inf}$ of about 475 hr*ng/L, about 500 hr*ng/L, about 1000 hr*ng/L, about 1500 hr*ng/L, about 2000 hr*ng/L, about 2500 hr*ng/L, about 3000 hr*ng/L, about 3500 hr*ng/L, about 4000 hr*ng/L, about 4500 hr*ng/L, about 5000 hr*ng/L, or about 5500 hr*ng/L, including all integers and ranges therebetween. In some embodiments, the mean AUC0-r is between about 500 hr*ng/L to about 5000 hr*ng/L, about 500 hr*ng/L to about 4000 hr*ng/L, about 500 hr*ng/L to about 3000 hr*ng/L, about 1000 hr*ng/L to about 3000 hr*ng/L, about 1000 hr*ng/L to about 2500 hr*ng/L, about 1000 hr*ng/L to about 2000 hr*ng/L, about 1000 hr*ng/L to about 1500 hr*ng/L, or about 1500 hr*ng/L to about 2000 hr*ng/L. In some embodiments, the mean $AUC_{0-inf}$ is within the range of about 80% to about 125% of about 1800 ng*h/L. In some embodiments, the mean AUC0-t is about 1800 ng*h/L.

In accordance with some embodiments of the methods of treating agitation comprising administering a unit dose composition comprising about 120 μg of dexmedetomidine, administration of a single dose provides a mean $T_{max}$ within the range of about 80% to about 125% of about 1 hour to about 4 hours. For example, a single dose provides a mean $T_{max}$ of about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h. In some embodiments, the $T_{max}$ is between about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In accordance with some embodiments of the methods of treating agitation comprising administering a unit dose composition comprising about 120 μg of dexmedetomidine, administration of a single dose provides a geometric mean $C_{max}$ within the range of about 80% to about 125% of about 110 ng/L to about 400 ng/L. For example, a single dose provides a geometric mean $C_{max}$ of about 88 ng/L, about 100 ng/L, about 125 ng/L, about 150 ng/L about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, about 475 ng/L, or about 500 ng/L, including all integers and ranges therebetween. In some embodiments, the geometric mean $C_{max}$ is between about 100 ng/L to about 500 ng/L, about 150 ng/L to about 450 ng/L, about 150 ng/L to about 400 ng/L, about 200 ng/L to about 350 ng/L, about 200 ng/L to about 300 ng/L, about 200 ng/L to about 250 mg/L, or about 210 ng/L to about 240 ng/L. In some embodiments, the geometric mean $C_{max}$ is within the range of about 80% to about 125% of about 220 ng/L. In some embodiments, the geometric mean $C_{max}$ is about 220 ng/L. In some embodiments, the median $C_{max}$ is about 238 ng/L.

In accordance with some embodiments of the methods of treating agitation comprising administering a unit dose composition comprising about 120 μg of dexmedetomidine, administration of a single dose provides a geometric mean $AUC_{0-inf}$ within the range of about 80% to about 125% of about 590 hr*ng/L to about 4400 hr*ng/L. For example, a single dose provides a geometric mean $AUC_{0-inf}$ of about 475 hr*ng/L, about 500 hr*ng/L, about 1000 hr*ng/L, about 1500 hr*ng/L, about 2000 hr*ng/L, about 2500 hr*ng/L, about 3000 hr*ng/L, about 3500 hr*ng/L, about 4000 hr*ng/L, about 4500 hr*ng/L, about 5000 hr*ng/L, or about 5500 hr*ng/L, including all integers and ranges therebetween. In some embodiments, the geometric mean $AUC_{0-inf}$ is between about 500 hr*ng/L to about 5000 hr*ng/L, about 500 hr*ng/L to about 4000 hr*ng/L, about 500 hr*ng/L to about 3000 hr*ng/L, about 1000 hr*ng/L to about 3000 hr*ng/L, about 1000 hr*ng/L to about 2500 hr*ng/L, about 1000 hr*ng/L to about 2000 hr*ng/L, about 1000 hr*ng/L to about 1500 hr*ng/L, about 1500 hr*ng/L to about 2000 hr*ng/L, about 1200 hr*ng/L to about 1500 hr*ng/L, about 1300 hr*ng/L to about 1500 hr*ng/L, or about 1350 hr*ng/L to about 1450 hr*ng/L. In some embodiments, the geometric mean $AUC_{0-inf}$ is within the range of about 80% to about 125% of about 1410 ng*h/L. In some embodiments, the geometric mean $AUC_{0-inf}$ is about 1410 ng*h/L.

In accordance with some embodiments of the methods of treating agitation comprising administering a unit dose composition comprising about 120 µg of dexmedetomidine, administration of a single dose provides a geometric mean $T_{max}$ within the range of about 80% to about 125% of about 1 hour to about 4 hours. For example, a single dose provides a geometric mean $T_{max}$ of about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h. In some embodiments, the geometric mean $T_{max}$ is between about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In accordance with some embodiments of the methods of treating agitation comprising administering a unit dose composition comprising about 120 µg of dexmedetomidine, administration of a single dose provides a median $C_{max}$ within the range of about 80% to about 125% of about 110 ng/L to about 400 ng/L. For example, a single dose provides a median $C_{max}$ of about 88 ng/L, about 100 ng/L, about 125 ng/L, about 150 ng/L about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, about 475 ng/L, or about 500 ng/L, including all integers and ranges therebetween. In some embodiments, the mean median $C_{max}$ is between about 100 ng/L to about 500 ng/L, about 150 ng/L to about 450 ng/L, about 150 ng/L to about 400 ng/L, about 200 ng/L to about 350 ng/L, about 200 ng/L to about 300 ng/L, about 200 ng/L to about 250 mg/L, or about 210 ng/L to about 240 ng/L. In some embodiments, the median $C_{max}$ is within the range of about 80% to about 125% of about 230 ng/L. In some embodiments, the median $C_{max}$ is about 230 ng/L.

In accordance with some embodiments of the methods of treating agitation comprising administering a unit dose composition comprising about 120 µg of dexmedetomidine, administration of a single dose provides a median $AUC_{0-inf}$ within the range of about 80% to about 125% of about 590 hr*ng/L to about 4400 hr*ng/L. For example, a single dose provides a median $AUC_{0-inf}$ of about 475 hr*ng/L, about 500 hr*ng/L, about 1000 hr*ng/L, about 1500 hr*ng/L, about 2000 hr*ng/L, about 2500 hr*ng/L, about 3000 hr*ng/L, about 3500 hr*ng/L, about 4000 hr*ng/L, about 4500 hr*ng/L, about 5000 hr*ng/L, or about 5500 hr*ng/L, including all integers and ranges therebetween. In some embodiments, the median $AUC_{0-inf}$ is between about 500 hr*ng/L to about 5000 hr*ng/L, about 500 hr*ng/L to about 4000 hr*ng/L, about 500 hr*ng/L to about 3000 hr*ng/L, about 1000 hr*ng/L to about 3000 hr*ng/L, about 1000 hr*ng/L to about 2500 hr*ng/L, about 1000 hr*ng/L to about 2000 hr*ng/L, about 1000 hr*ng/L to about 1500 hr*ng/L, about 1500 hr*ng/L to about 2000 hr*ng/L, about 1000 hr*ng/L to about 1250 hr*ng/L, about 1000 hr*ng/L to about 1200 hr*ng/L, about 1100 hr*ng/L to about 1200 hr*ng/L, or about 1150 hr*ng/L to about 1250 hr*ng/L. In some embodiments, the median $AUC_{0-inf}$ is within the range of about 80% to about 125% of about 1180 ng*h/L. In some embodiments, the median $AUC_{0-inf}$ is about 1180 ng*h/L.

In accordance with some embodiments of the methods of treating agitation comprising administering a unit dose composition comprising about 120 µg of dexmedetomidine, administration of a single dose provides a median $T_{max}$ within the range of about 80% to about 125% of about 1 hour to about 4 hours. For example, a single dose provides a median $T_{max}$ of about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, to about 5.0 h. In some embodiments, the median $T_{max}$ is between about 1 h to about 4 h, about 1 h to about 3 h, about 1.5 h to about 3 h, about 1.75 h to about 2.5 h, about 1.75 h to about 2.25 h. In some embodiments, the median $T_{max}$ is within the range of about 80% to about 125% of about 2 hours. In some embodiments, the median $T_{max}$ is about 2 hours.

In accordance with some embodiments of the methods of treating agitation comprising administering a unit dose composition comprising about 120 µg of dexmedetomidine, the aforementioned pharmacokinetic parameters are non-steady state.

In some embodiments, the present disclosure provides a method of treating agitation associated with schizophrenia or bipolar disorder, comprising administering a unit dose composition comprising about 180 µg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

In accordance with some embodiments of the methods of treating agitation comprising administering a unit dose composition comprising about 180 µg of dexmedetomidine, the composition may be administered a variety of means. For example, in some embodiments, the composition comprising dexmedetomidine (e.g. dexmedetomidine hydrochloride) or a pharmaceutically acceptable salt is administered sublingually, buccally, orally, intranasally or parenterally. In some embodiments, the composition is administered sublingually or buccally. In some embodiments, the composition is administered sublingually in the form of a tablet, film, spray, gel or drops. In some embodiments, the composition is administered buccally in the form of a film, patch or tablet.

In accordance with some embodiments of the methods of treating agitation comprising administering a unit dose composition comprising about 180 µg of dexmedetomidine, the method may further comprises administering a second dose of dexmedetomidine after a period of time ranging from about 30 minutes to about 12 hours. For example, the period of time may be about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, or about 23 hours. In some embodiments, the second dose is administered after a period of about 2 hours. In some embodiments, the second dose ranges from about 10 µg to about 180 µg. For example, the additional dose may be about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg. about 160 µg, about 170, or about 180 µg. In some embodiments, the additional dose is about 60 µg or 90 µg.

In accordance with some embodiments of the methods of treating agitation comprising administering a unit dose composition comprising about 180 μg of dexmedetomidine, the unit dose composition may be administered to a patient in the fasted state. In some embodiments, the unit dose composition has been administered in the fed state.

In accordance with some embodiments of the methods of treating agitation comprising administering a unit dose composition comprising about 180 μg of dexmedetomidine, agitation is significantly reduced within about 2 hours of administering the composition, as measured by a mean change in Positive and Negative Syndrome Scale Excited Component (PEC) scores relative to baseline. In some embodiments, the agitation is significantly reduced within about 45 minutes to about 1 hour. In some embodiments, the agitation is significantly reduced in less than 45 minutes (e.g. about 15 minutes, about 20 minutes, about 25 minutes, about 30 minutes). In some embodiments, the patient experiences ≥40% decrease from baseline in PEC score. For example, the patient may experience greater than or equal to about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, or about 150% from baseline. Treatment efficacy may also be compared by comparing PEC score to placebo. In some embodiments, the PEC score is ≥30% lower than placebo (e.g. the placebo group has mean change from baseline in PEC total score of −3 and the dexmedetomidine-containing composition has a score of −3.9). For example, compared to placebo, the patient's PEC score may be lower by greater than or equal to about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In some embodiments, the patient experiences a mean change in PEC score of greater than about −4 (i.e. a decrease of 4 or more points) relative to baseline within 2 hours of administering the composition. For example, at the 2 hour time point, the patient may experience a mean change in PEC score of greater than about −4, about −5, about −6, about −7, about −8, about −9, about −10, about −11, or about −12. In some embodiments, the decrease in PEC score (e.g. of greater than about −4) is maintained for at least six hours following administration of the composition. For example, if a patient experiences a mean change from baseline in PEC total score of e.g. −6 at 2 hours, then at 6 hours patient's mean change in PEC score will be about −6 or lower (e.g. −7, −8, etc.). In some embodiments, the decrease in PEC score (e.g. of greater than about −4) is substantially maintained for at least six hours following administration of the composition. For example, if a patient experiences a mean change from baseline in PEC total score of e.g. −6 at 2 hours, then at 6 hours patient's mean change in PEC score will be about −4, about −5, or about −6 or lower (e.g. −7, −8, etc.). In some embodiments, the mean change in PEC score is greater than or equal to −8 and is maintained from 2 hours post administration up to at least about 24 hours following administration of the composition.

In accordance with some embodiments of the methods of treating agitation comprising administering a unit dose composition comprising about 180 μg of dexmedetomidine, the subject is treated without experiencing significant sedation. In some embodiments, the subject is treated without experiencing clinically significant cardiovascular effects.

In accordance with some embodiments of the methods of treating agitation comprising administering a unit dose composition comprising about 180 μg of dexmedetomidine, administration of a single dose provides a mean $C_{max}$ within the range of about 80% to about 125% of about 100 ng/L to about 800 ng/L. For example, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L, including all integers and ranges therebetween. In some embodiments, the mean $C_{max}$ is between about 100 ng/L to about 1000 ng/L, about 100 ng/L to about 800 ng/L, about 200 ng/L to about 600 ng/L, about 300 ng/L to about 600 ng/L, about 300 ng/L to about 500 ng/L, about 350 ng/L to about 500 ng/L, about 300 ng/L to about 450 ng/L, about 400 ng/L to about 500 ng/L, or about 400 ng/L to about 450 ng/L. In some embodiments, the mean $C_{max}$ is within the range of about 80% to about 125% of about 440 ng/L. In some embodiments, the mean $C_{max}$ is about 440 ng/L In accordance with some embodiments of the methods of treating agitation comprising administering a unit dose composition comprising about 180 μg of dexmedetomidine, administration of a single dose provides a mean $AUC_{0-inf}$ within the range of about 80% to about 125% of about 600 hr*ng/L to about 9500 hr*ng/L. For example, the $AUC_{0-inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, including all integers and ranges therebetween. In some embodiments, the $AUC_{0-inf}$ is between about 500 hr*ng/L to about 10000 hr*ng/L, about 1000 hr*ng/L to about 7500 hr*ng/L, about 1000 hr*ng/L to about 6000 hr*ng/L, to about 1500 hr*ng/L to about 5000 hr*ng/L, about 2000 hr*ng/L to about 5000 hr*ng/L, about 2000 hr*ng/L to about 4000 hr*ng/L, about 2000 hr*ng/L to about 3000 hr*ng/L, about 2500 hr*ng/L to about 4000 hr*ng/L, about 3000 hr*ng/L to about 4000 hr*ng/L, about 3500 hr*ng/L to about 4000 hr*ng/L, or about 2500 hr*ng/L to about 3000 hr*ng/L. In some embodiments, the mean $AUC_{0-inf}$ is within the range of about 80% to about 125% of about 3800 ng*h/L. In some embodiments, the mean $AUC_{0-inf}$ is about 3800 ng*h/L.

In accordance with some embodiments of the methods of treating agitation comprising administering a unit dose composition comprising about 180 μg of dexmedetomidine, administration of a single dose provides a mean $T_{max}$ within the range of about 80% to about 125% of about 1 hour to about 8 hours. For example, a single dose provides a mean $T_{max}$ of About 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h. In some embodiments, the $T_{max}$ is between about 1 h to about 8 h, about 1 h to about 6 h, about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In accordance with some embodiments of the methods of treating agitation comprising administering a unit dose composition comprising about 180 μg of dexmedetomidine, administration of a single dose provides a geometric mean $C_{max}$ within the range of about 80% to about 125% of about 100 ng/L to about 800 ng/L. For example, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L, including all integers and ranges therebetween. In some embodiments, the geometric mean $C_{max}$ is between about 100 ng/L to about 1000 ng/L, about 100 ng/L to about 800 ng/L, about 200 ng/L to about 600 ng/L, about 300 ng/L to about 600 ng/L, about 300 ng/L to about 500 ng/L, about 350 ng/L to about 500 ng/L, about 300 ng/L to about 450 ng/L, about 400 ng/L to about 500 ng/L, about 400 ng/L to about 450 ng/L, about 350 ng/L to about 450 ng/L, or about 350 ng/L to about 400 ng/L. In some embodiments, the geometric mean $C_{max}$ is within the range of about 80% to about 125% of about 380 ng/L. In some embodiments, the geometric mean $C_{max}$ is about 380 ng/L.

In accordance with some embodiments of the methods of treating agitation comprising administering a unit dose composition comprising about 180 μg of dexmedetomidine, administration of a single dose provides a geometric mean $AUC_{0\text{-}inf}$ within the range of about 80% to about 125% of about 600 hr*ng/L to about 9500 hr*ng/L. For example, the AUC0-win is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, including all integers and ranges therebetween. In some embodiments, the $AUC_{0\text{-}inf}$ is between about 500 hr*ng/L to about 10000 hr*ng/L, about 1000 hr*ng/L to about 7500 hr*ng/L, about 1000 hr*ng/L to about 6000 hr*ng/L, to about 1500 hr*ng/L to about 5000 hr*ng/L, about 2000 hr*ng/L to about 5000 hr*ng/L, about 2000 hr*ng/L to about 4000 hr*ng/L, about 2000 hr*ng/L to about 3000 hr*ng/L, about 2500 hr*ng/L to about 4000 hr*ng/L, about 3000 hr*ng/L to about 4000 hr*ng/L, about 3500 hr*ng/L to about 4000 hr*ng/L, or about 2500 hr*ng/L to about 3000 hr*ng/L. In some embodiments, the geometric mean $AUC_{0\text{-}inf}$ is within the range of about 80% to about 125% of about 2880 ng*h/L. In some embodiments, the geometric mean AUC0-t is about 2880 ng*h/L.

In accordance with some embodiments of the methods of treating agitation comprising administering a unit dose composition comprising about 180 μg of dexmedetomidine, administration of a single dose provides a geometric mean $T_{max}$ within the range of about 80% to about 125% of about 1 hour to about 8 hours. For example, a single dose provides a geometric mean $T_{max}$ of about 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h. In some embodiments, the $T_{max}$ is between about 1 h to about 8 h, about 1 h to about 6 h, about 1 h to about 4 h, about 1 h to about 3 h, about 1.5 h to about 3 h, about 1.75 h to about 2.5 h, about 1.75 h to about 2.25 h. In some embodiments, the geometric mean $T_{max}$ is within the range of about 80% to about 125% of about 2 hours. In some embodiments, the geometric mean $T_{max}$ is about 2 hours.

In accordance with some embodiments of the methods of treating agitation comprising administering a unit dose composition comprising about 180 μg of dexmedetomidine, administration of a single dose provides a median $C_{max}$ within the range of about 80% to about 125% of about 100 ng/L to about 800 ng/L. For example, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L, including all integers and ranges therebetween. In some embodiments, the median $C_{max}$ is between about 100 ng/L to about 1000 ng/L, about 100 ng/L to about 800 ng/L, about 200 ng/L to about 600 ng/L, about 300 ng/L to about 600 ng/L, about 300 ng/L to about 500 ng/L, about 350 ng/L to about 500 ng/L, about 300 ng/L to about 450 ng/L, about 400 ng/L to about 500 ng/L, about 400 ng/L to about 450 ng/L, about 450 ng/L to about 500 ng/L, about 470 ng/L to about 490 ng/L. In some embodiments, the median $C_{max}$ is within the range of about 80% to about 125% of about 485 ng/L. In some embodiments, the median $C_{max}$ is about 485 ng/L In accordance with some embodiments of the methods of treating agitation comprising administering a unit dose composition comprising about 180 µg of dexmedetomidine, administration of a single dose provides a median AUC0-r within the range of about 80% to about 125% of about 600 hr*ng/L to about 9500 hr*ng/L. For example, the $AUC_{0\text{-}inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, including all integers and ranges therebetween. In some embodiments, the $AUC_{0\text{-}inf}$ is between about 500 hr*ng/L to about 10000 hr*ng/L, about 1000 hr*ng/L to about 7500 hr*ng/L, about 1000 hr*ng/L to about 6000 hr*ng/L, to about 1500 hr*ng/L to about 5000 hr*ng/L, about 2000 hr*ng/L to about 5000 hr*ng/L, about 2000 hr*ng/L to about 4000 hr*ng/L, about 2000 hr*ng/L to about 3000 hr*ng/L, about 2500 hr*ng/L to about 4000 hr*ng/L, about 3000 hr*ng/L to about 4000 hr*ng/L, about 3500 hr*ng/L to about 4000 hr*ng/L, or about 2500 hr*ng/L to about 3000 hr*ng/L. In some embodiments, the median $AUC_{0\text{-}inf}$ is within the range of about 80% to about 125% of about 2900 ng*h/L. In some embodiments, the median $AUC_{0\text{-}inf}$ is about 2900 ng*h/L.

In accordance with some embodiments of the methods of treating agitation comprising administering a unit dose composition comprising about 180 µg of dexmedetomidine, administration of a single dose provides a median $T_{max}$ within the range of about 80% to about 125% of about 1 hour to about 8 hours. For example, a single dose provides a median $T_{max}$ of About 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h. In some embodiments, the $T_{max}$ is between about 1 h to about 8 h, about 1 h to about 6 h, about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In accordance with some embodiments of the methods of treating agitation comprising administering a unit dose composition comprising about 180 µg of dexmedetomidine, the aforementioned pharmacokinetic parameters are non-steady state.

In some embodiments, the present disclosure provides a method of treating agitation associated with schizophrenia or bipolar disorder, comprising administering a unit dose composition comprising about 120 to about 180 µg of dexmedetomidine (e.g. dexmedetomidine hydrochloride) or a pharmaceutically acceptable salt thereof to a human patient. For example, in some embodiments, the patient has schizophrenia, in some embodiments, the patient has bipolar disorder (E.g. bipolar I disorder, and in some embodiments, the patient has both schizophrenia and bipolar disorder (e.g. bipolar I disorder).

In accordance with some embodiments of the methods of treating agitation comprising administering a unit dose composition comprising about 120 µg to about 180 µg of dexmedetomidine, the composition may be administered a variety of means. For example, in some embodiments, the composition comprising dexmedetomidine (e.g. dexmedetomidine hydrochloride) or a pharmaceutically acceptable salt is administered sublingually, buccally, orally, intranasally or parenterally. In some embodiments, the composition is administered sublingually or buccally. In some embodiments, the composition is administered sublingually in the form of a tablet, film, spray, gel or drops. In some embodiments, the composition is administered buccally in the form of a film, patch or tablet.

In accordance with some embodiments of the methods of treating agitation comprising administering a unit dose composition comprising about 120 µg to about 180 µg of dexmedetomidine, the method may further comprises administering a second dose of dexmedetomidine after a period of time ranging from about 30 minutes to about 12 hours. For example, the period of time may be about 30 minutes, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, or about 23 hours. In some embodiments, the second dose is administered after a period of about 2 hours. In some embodiments, the second dose ranges from about 10 µg to about 180 µg. For example, the additional dose may be about 10 µg, about 20 µg, about 30 µg, about 40 µg, about 50 µg, about 60 µg, about 70 µg, about 80 µg, about 90 µg, about 100 µg, about 110 µg, about 120 µg, about 130 µg, about 140 µg, about 150 µg, about 160 µg, about 170, or about 180 µg. In some embodiments, the additional dose is about 60 µg or 90 µg.

In accordance with some embodiments of the methods of treating agitation comprising administering a unit dose composition comprising about 120 µg to about 180 µg of dexmedetomidine, the unit dose composition may be administered to a patient in the fasted state. In some embodiments, the unit dose composition has been administered in the fed state.

In accordance with some embodiments of the methods of treating agitation comprising administering a unit dose composition comprising about 120 µg to about 180 µg of dexmedetomidine, agitation is significantly reduced within about 2 hours of administering the composition, as measured by a mean change in Positive and Negative Syndrome Scale Excited Component (PEC) scores relative to baseline. In some embodiments, the agitation is significantly reduced within about 45 minutes to about 1 hour. In some embodiments, the agitation is significantly reduced in less than 45 minutes (e.g. about 15 minutes, about 20 minutes, about 25 minutes, about 30 minutes). In some embodiments, the patient experiences ≥40% decrease from baseline in PEC score. For example, the patient may experience greater than or equal to about 40%, about 45%, about 50%, about 55%, about 60%, about 65%, about 70/6, about 75%, about 80%, about 85%, about 90%, about 95%, about 100%, about 105%, about 110%, about 115%, about 120%, about 125%, about 130%, about 135%, about 140%, about 145%, or about 150% from baseline. Treatment efficacy may also be compared by comparing PEC score to placebo. In some embodiments, the PEC score is ≥30% lower than placebo (e.g. the placebo group has mean change from baseline in PEC total score of −3 and the dexmedetomidine-containing composition has a score of −3.9). For example, compared to placebo, the patient's PEC score may be lower by greater than or equal to about 30,%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In some embodiments, the patient experiences a mean change in PEC score of greater than about −4 (i.e. a decrease of 4 or more points) relative to baseline within 2 hours of administering the composition. For example, at the 2 hour time point, the patient may experience a mean change in PEC score of greater than about −4, about −5, about −6, about −7, about −8, about −9, about −10, about −11, or about −12. In some embodiments, the decrease in PEC score (e.g. of greater than about −4) is maintained for at least six hours following administration of the composition. For example, if a patient experiences a mean change from baseline in PEC total score of e.g. −6 at 2 hours, then at 6 hours patient's mean change in PEC score will be about −6 or lower (e.g. −7, −8, etc.). In some embodiments, the decrease in PEC score (e.g. of greater than about −4) is substantially maintained for at least six hours following administration of the composition. For example, if a patient experiences a mean change from baseline in PEC total score of e.g. −6 at 2 hours, then at 6 hours patient's mean change in PEC score will be about −4, about −5, or about −6 or lower (e.g. −7, −8, etc.). In some embodiments, the mean change in PEC score is greater than or equal to −8 and is maintained from 2 hours post administration up to at least about 24 hours following administration of the composition.

In accordance with some embodiments of the methods of treating agitation comprising administering a unit dose composition comprising about 120 μg to about 180 μg of dexmedetomidine, the subject is treated without experiencing significant sedation. In some embodiments, the subject is treated without experiencing clinically significant cardiovascular effects.

In accordance with some embodiments of the methods of treating agitation comprising administering a unit dose composition comprising about 120 μg to about 180 μg of dexmedetomidine, administration of a single dose provides a mean $C_{max}$ within the range of about 80% to about 125% of about 100 ng/L to about 800 ng/L. For example, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L, including all integers and ranges therebetween. In some embodiments, the mean $C_{max}$ is between about 100 ng/L to about 1000 ng/L, about 100 ng/L to about 800 ng/L, about 200 ng/L to about 600 ng/L, about 300 ng/L to about 600 ng/L, about 300 ng/L to about 500 ng/L, about 350 ng/L to about 500 ng/L, about 300 ng/L to about 450 ng/L, about 400 ng/L to about 500 ng/L, or about 400 ng/L to about 450 ng/L, about 100 ng/L to about 500 ng/L, about 150 ng/L to about 450 ng/L, about 150 ng/L to about 400 ng/L, about 200 ng/L to about 350 ng/L, about 200 ng/L to about 300 ng/L, about 200 ng/L to about 250 mg/L, or about 210 ng/L to about 240 ng/L. In some embodiments, the mean $C_{max}$ is within the range of about 80% to about 125% of 200 ng/L to about 500 ng/L. In some embodiments, the mean $C_{max}$ is about 230 ng/L to about 440 ng/L.

In accordance with some embodiments of the methods of treating agitation comprising administering a unit dose composition comprising about 120 μg to about 180 μg of dexmedetomidine, administration of a single dose provides a mean $AUC_{0-inf}$ within the range of about 80% to about 125% of about 600 hr*ng/L to about 9500 hr*ng/L. For example, the $AUC_{0-inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, including all integers and ranges therebetween. In some embodiments, the $AUC_{0-inf}$ is between about 500 hr*ng/L to about 10000 hr*ng/L, about 1000 hr*ng/L to about 7500 hr*ng/L, about 1000 hr*ng/L to about 6000 hr*ng/L, to about 1500 hr*ng/L to about 5000 hr*ng/L, about 2000 hr*ng/L to about 5000 hr*ng/L, about 2000 hr*ng/L to about 4000 hr*ng/L, about 2000 hr*ng/L to about 3000 hr*ng/L, about 2500 hr*ng/L to about 4000 hr*ng/L, about 3000 hr*ng/L to about 4000 hr*ng/L, about 500 hr*ng/L to about 5000 hr*ng/L, about 500 hr*ng/L to about 4000 hr*ng/L, about 500 hr*ng/L to about 3000 hr*ng/L, about 1000 hr*ng/L to about 3000 hr*ng/L, about 1000 hr*ng/L to about 2500 hr*ng/L, about 1000 hr*ng/L to about 2000 hr*ng/L, about 1000 hr*ng/L to about 1500 hr*ng/L, or about 1500 hr*ng/L to about 2000 hr*ng/L, about 3500 hr*ng/L to about 4000 hr*ng/L, or about 2500 hr*ng/L to about 3000 hr*ng/L. In some embodiments, the mean $AUC_{0-inf}$ is within the range of about 80% to about 125% of 1400 ng*h/L to about 4000 hr*ng/L. In some embodiments, the mean $AUC_{0-inf}$ is about 3800 ng*h/L. In some embodiments, the mean $AUC_{0-inf}$ is within the range of about 80% to about 125% of 1800 ng*h/L to about 3800 ng*h/L.

In accordance with some embodiments of the methods of treating agitation comprising administering a unit dose composition comprising about 120 µg to about 180 µg of dexmedetomidine, administration of a single dose provides a mean $T_{max}$ within the range of about 80% to about 125% of about 1 hour to about 8 hours. For example, a single dose provides a mean $T_{max}$ of About 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h. In some embodiments, the $T_{max}$ is between about 1 h to about 8 h, about 1 h to about 6 h, about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In accordance with some embodiments of the methods of treating agitation comprising administering a unit dose composition comprising about 120 µg to about 180 µg of dexmedetomidine, the aforementioned pharmacokinetic parameters are non-steady state.

In some embodiments, the present disclosure provides methods of treating or ameliorating opioid withdrawal symptoms, comprising administering a composition comprising dexmedetomidine or a pharmaceutically acceptable salt thereof (e.g. dexmedetomidine hydrochloride) to a human patient in need thereof, wherein the patient is at least 18 years and wherein the period of withdrawal is up to 14 days. "Opioid withdrawal" refers to a variety of signs and complaints appearing with the abrupt removal of, or a rapid decrease in the regular dosage of opioids. Physical manifestations may include sweating, nausea, yawning, chills, diarrhea, papillary dilation, piloerection, tachycardia, increased blood pressure, hypersensitivity to pain, stomach cramps, and muscle cramps. Psychological manifestations of opioid withdrawal observed may include agitation, dysphoria, restlessness, irritability, anxiety, and depression. In some embodiments, the opioid withdrawal symptom is agitation. Onset often begins within 6-24 hours from last opioid use. In some embodiments, treating or ameliorating opioid withdrawal refers to the treatment or lessening of one or more of the aforementioned symptoms. The treating or ameliorating may be measured by a variety of well-known means in the art, including but not limited to, the Clinical Opiate Withdrawal Scale (COWS) and/or Short Opiate Withdrawal Scale of Gossop (SOWS-Gossop) score.

Thus, in some embodiments, the present disclosure provides methods of treating or ameliorating agitation associated with opioid withdrawal symptoms. In some embodiments, the treatment or amelioration comprises reducing the period of opioid withdrawal. For example, a patient treated in accordance with the embodiments of the present disclosure, may experience an opioid withdrawal period of about 3, about 4, about 5, about 6, about 7, about 8, about 9, about 10, about 11, about 12, about 13, or about 14 days, where a similar patient that was not treated in accordance with the embodiments of the present disclosure will have a longer opioid withdrawal treatment.

In some embodiments, the composition is administered twice daily. In some embodiments, the composition comprises a dose range of dexmedetomidine or a pharmaceutically acceptable salt thereof of between about 30 µg and about 200 µg. For example, the composition comprises a unit dose of about 30 µg, about 60 µg, about 90 µg, about 120 µg, or 180 µg of dexmedetomidine or a pharmaceutically acceptable salt thereof. In some embodiments, a single dose of a composition comprising about 180 µg dexmedetomidine or a pharmaceutically acceptable salt thereof is effective for up to at least about 24 hours. In some embodiments, the composition is administered twice daily for 7 days.

In some embodiments, the patient is suffering from opioid withdrawal, wherein the opioid is one or more of fentanyl, morphine, codeine, heroin, oxycodone, hydrocodone, alfentanil carfentanil, tramadol, hydromorphone, buprenorphine, naloxone, naltrexone, remifentanil butorphanol, meperidine, methadone, dextropropoxyphene (propoxyphene) thebaine, sufentanil and pentazocine. In some embodiments, the opioid is fentanyl. In some embodiments, the opioid had been administered for amount of time longer than neonate treatment prior to withdrawal.

In some embodiments, the composition is administered sublingually, buccally, orally, intranasally or parenterally. In some embodiments, the composition is administered sublingually in the form of a tablet, film, spray, gel or drops. In some embodiments, the composition is administered sublingually in the form of a film. In some embodiments, the composition is administered buccally in the form of a film, patch or tablet. In some embodiments, the composition is administered buccally in the form of a film. In some embodiments, the patient is treated without also inducing clinically significant cardiovascular effects.

In some embodiments, the present disclosure provides a pharmaceutical composition comprising from about 20 µg to about 240 µg dexmedetomidine or a pharmaceutically acceptable salt thereof (e.g. dexmedetomidine hydrochloride). In some embodiments, the dose of dexmedetomidine is about 120 µg. In some embodiments, the dose of dexmedetomidine is about 180 µg.

In some embodiments, the composition is formulated for sublingual or buccal administration. In some embodiments, the composition is formulated for sublingual administration in the form of a tablet, film, spray, gel or drops. In some embodiments, the composition is formulated for buccal administration in the form of a film, patch or tablet.

In some embodiments, the pharmaceutical composition comprising from about 20 µg to about 240 µg dexmedetomidine is administered to a patient having agitation associated with schizophrenia or bipolar disorder, the agitation is significantly reduced within about 2 hours of administering the composition as measured by a mean change in Positive and Negative Syndrome Scale Excited Component (PEC) scores relative to baseline. For example, the agitation is significantly reduced with 30 minutes, 45 minutes, 1 hour, 90 minutes, or about 2 hours. In some embodiments, the patient experiences ≥40% decrease from baseline in PEC score. For example, the patient may experience greater than or equal to about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, or about 150% from baseline. Treatment efficacy may also be compared by comparing PEC score to placebo. In some embodiments, the PEC score is ≥30% lower than placebo (e.g. the placebo group has mean change from baseline in PEC total score of −3 and the dexmedetomidine-containing composition has a score of −3.9). For example, compared to placebo, the patient's PEC score may be lower by greater than or equal to about 30,%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, or about 200%. In some embodiments, the patient experiences a mean change in PEC score of greater than about −4 (i.e. a decrease of 4 or more points) relative to baseline within 2 hours of administering the composition. For example, at the 2 hour time point, the patient may experience a mean change in PEC score of greater than about −4, about −5, about −6, about −7, about −8, about −9, about −10, about −11, or about −12. In some embodiments, the decrease in PEC score (e.g. of greater than about −4) is maintained for at least six hours following administration of the composition. For example, if a patient experiences a mean change from baseline in PEC total score of e.g. −6 at 2 hours, then at 6 hours patient's mean change in PEC score will be about −6 or lower (e.g. −7, −8, etc.). In some embodiments, the mean change in PEC score is greater than or equal to −8 and is maintained from 2 hours post administration up to at least about 24 hours following administration of the composition.

In accordance with some embodiments of the pharmaceutical composition comprising from about 20 μg to about 240 μg dexmedetomidine, the subject is treated without experiencing significant sedation. In some embodiments, the subject is treated without experiencing clinically significant cardiovascular effects.

Administration of a single dose of the pharmaceutical composition comprising from about 20 μg to about 240 μg dexmedetomidine provides a mean $C_{max}$ within the range of about 80% to about 125% of about 100 ng/L to about 800 ng/L. For example, the $C_{max}$ is about 80 ng/L, about 100 ng/L, about 125 ng/L, about 150 ng/L, about 175 ng/L, about 200 ng/L, about 225 ng/L, about 250 ng/L, about 275 ng/L, about 300 ng/L, about 325 ng/L, about 350 ng/L, about 375 ng/L, about 400 ng/L, about 425 ng/L, about 450 ng/L, and 475 ng/L, about 500 ng/L, about 600 ng/L, about 625 ng/L, about 650 ng/L, about 675 ng/L, about 700 ng/L, about 725 ng/L, about 750 ng/L, about 775 ng/L, about 800 ng/L, about 825 ng/L, about 850 ng/L, about 875 ng/L, about 900 ng/L, about 925 ng/L, about 950 ng/L, about 975 ng/L, or about 1000 ng/L, including all integers and ranges therebetween. In some embodiments, the mean $C_{max}$ is between about 100 ng/L to about 1000 ng/L, about 100 ng/L to about 800 ng/L, about 200 ng/L to about 600 ng/L, about 300 ng/L to about 600 ng/L, about 300 ng/L to about 500 ng/L, about 350 ng/L to about 500 ng/L, about 300 ng/L to about 450 ng/L, about 400 ng/L to about 500 ng/L, or about 400 ng/L to about 450 ng/L, about 100 ng/L to about 500 ng/L, about 150 ng/L to about 450 ng/L, about 150 ng/L to about 400 ng/L, about 200 ng/L to about 350 ng/L, about 200 ng/L to about 300 ng/L, about 200 ng/L to about 250 mg/L, or about 210 ng/L to about 240 ng/L. In some embodiments, the mean $C_{max}$ is within the range of about 80% to about 125% of 200 ng/L to about 500 ng/L. In some embodiments, the mean $C_{max}$ is about 230 ng/L to about 440 ng/L.

Administration of a single dose of the pharmaceutical composition comprising from about 20 μg to about 240 μg dexmedetomidine provides a mean $AUC_{0\text{-}inf}$ within the range of about 80% to about 125% of about 600 hr*ng/L to about 9500 hr*ng/L. For example, the $AUC_{0\text{-}inf}$ is about 470 hr*ng/L, about 500 hr*ng/L, about 600 hr*ng/L, about 700 hr*ng/L, about 800 hr*ng/L, about 900 hr*ng/L, about 1000 hr*ng/L, about 1250 hr*ng/L, about 1500 hr*ng/L, about 1750 hr*ng/L, about 2000 hr*ng/L, about 2250 hr*ng/L, about 2500 hr*ng/L, about 2750 hr*ng/L, about 3000 hr*ng/L, about 3250 hr*ng/L, about 3500 hr*ng/L, about 3750 hr*ng/L, about 4000 hr*ng/L, about 4250 hr*ng/L, about 4500 hr*ng/L, about 4750 hr*ng/L, about 5000 hr*ng/L, about 5250 hr*ng/L, to about 5500 hr*ng/L, about 5750 hr*ng/L, about 6000 hr*ng/L, about 6250 hr*ng/L, to about 6500 hr*ng/L, about 6750 hr*ng/L, about 7000 hr*ng/L, about 7250 hr*ng/L, to about 7500 hr*ng/L, about 7750 hr*ng/L, about 8000 hr*ng/L, about 8250 hr*ng/L, to about 8500 hr*ng/L, about 8750 hr*ng/L, about 9000 hr*ng/L, about 9250 hr*ng/L, about 9500 hr*ng/L, about 9750 hr*ng/L, about 10000 hr*ng/L, about 10250 hr*ng/L, about 10500 hr*ng/L, about 10750 hr*ng/L, about 11000 hr*ng/L, about 11250 hr*ng/L, about 11500 hr*ng/L, to about 11875 hr*ng/L, including all integers and ranges therebetween. In some embodiments, the $AUC_{0\text{-}inf}$ is between about 500 hr*ng/L to about 10000 hr*ng/L, about 1000 hr*ng/L to about 7500 hr*ng/L, about 1000 hr*ng/L to about 6000 hr*ng/L, to about 1500 hr*ng/L to about 5000 hr*ng/L, about 2000 hr*ng/L to about 5000 hr*ng/L, about 2000 hr*ng/L to about 4000 hr*ng/L, about 2000 hr*ng/L to about 3000 hr*ng/L, about 2500 hr*ng/L to about 4000 hr*ng/L, about 3000 hr*ng/L to about 4000 hr*ng/L, about 500 hr*ng/L to about 5000 hr*ng/L, about 500 hr*ng/L to about 4000 hr*ng/L, about 500 hr*ng/L to about 3000 hr*ng/L, about 1000 hr*ng/L to about 3000 hr*ng/L, about 1000 hr*ng/L to about 2500 hr*ng/L, about 1000 hr*ng/L to about 2000 hr*ng/L, about 1000 hr*ng/L to about 1500 hr*ng/L, or about 1500 hr*ng/L to about 2000 hr*ng/L, about 3500 hr*ng/L to about 4000 hr*ng/L, or about 2500 hr*ng/L to about 3000 hr*ng/L. In some embodiments, the mean AUC0-f is within the range of about 80% to about 125% of 1400 ng*h/L to about 4000 hr*ng/L. In some embodiments, the mean AUC0-w is about 3800 ng*h/L. In some embodiments, the mean $AUC_{0\text{-}inf}$ is within the range of about 80% to about 125% of 1800 ng*h/L to about 3800 ng*h/L.

Administration of a single dose of the pharmaceutical composition comprising from about 20 μg to about 240 μg dexmedetomidine provides a mean $T_{max}$ within the range of about 80% to about 125% of about 1 hour to about 8 hours. For example, a single dose provides a mean $T_{max}$ of About 0.8 h, about 0.9 h, about 1 h, about 1.25 h, about 1.5 h, about 1.75 h, about 2.0 h, about 2.25 h, about 2.5 h, about 2.75 h, about 3.0 h, about 3.25 h, about 3.5 h, about 3.75 h, about 4.0 h, about 4.25 h, about 4.5 h, about 4.75 h, about 5.0 h, about 5.25 h, about 5.5 h, about 5.75 h, about 6.0 h, about 6.25 h, about 6.5 h, about 6.75 h, about 7.0 h, about 7.25 h, about 7.5 h, about 7.75 h, about 8.0 h, about 8.25 h, about 8.5 h, about 8.75 h, about 9.0 h, about 9.25 h, about 9.5 h, about 9.75 h, to about 10 h. In some embodiments, the $T_{max}$ is between about 1 h to about 8 h, about 1 h to about 6 h, about 1 h to about 4 h, about 1 h to about 3 h, about 1.5 h to about 3 h, about 1.75 h to about 2.5 h, about 1.75 h to about 2.25 h. In some embodiments, the $T_{max}$ is within the range of about 80% to about 125% of about 2 hours. In some embodiments, the $T_{max}$ is about 2 hours.

In some embodiments, the aforementioned pharmacokinetic parameters are non-steady state.

In some embodiments, the present disclosure provides methods of reducing agitation to a 1 (very much improved) or 2 (much improved) within 2 hours of administering a composition comprising dexmedetomidine or a pharmaceutically acceptable salt thereof (e.g. dexmedetomidine hydrochloride), as measured by the Clinical Global Impression-Improvement Scale. In some embodiments, the agitation is reduced within about 30 minutes to about 1 hour. In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23, or about 24 hours. In some embodiments, the composition comprises about 120 µg of dexmedetomidine. In some embodiments, the composition comprises about 180 µg of dexmedetomidine. In some embodiments, the patient has schizophrenia. In some embodiments, the patient has bipolar disorder.

In some embodiments, the present disclosure provides methods of reducing agitation to a 3 (mild agitation) or 4 (normal behavior) within 2 hours of administering a composition comprising dexmedetomidine or a pharmaceutically acceptable salt thereof, as measured by the Agitation-Calmness Evaluation Scale (ACES). In some embodiments, the agitation is reduced within about 30 minutes to about 1 hour. In some embodiments, the reduction in agitation is reduced to a 4 (normal behavior). In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the composition comprises about 120 µg of dexmedetomidine. In some embodiments, the composition comprises about 180 µg of dexmedetomidine. In some embodiments, the patient has schizophrenia. In some embodiments, the patient has bipolar disorder.

In some embodiments, the present disclosure provides methods of achieving a ≥40% reduction in agitation, within 2 hours of administering a composition comprising dexmedetomidine or a pharmaceutically acceptable salt thereof, as measured by the PEC scale. In some embodiments, the agitation is reduced within about 30 minutes to about 1 hour. In some embodiments, the reduction in agitation ≥40%, ≥50%, ≥60%, ≥70%, ≥80%, ≥90%, or ≥100%. In some embodiments, the reduction in agitation is maintained for greater than about 2 hours. For example, the reduction in agitation is maintained for about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the composition comprises about 120 µg of dexmedetomidine. In some embodiments, the composition comprises about 180 µg of dexmedetomidine. In some embodiments, the patient has schizophrenia. In some embodiments, the patient has bipolar disorder.

In some embodiments, the present disclosure provides a method of achieving a PEC score reduction in agitation for a sustained period of time in a subject with bipolar or schizophrenic subject comprising administering to the subject a pharmaceutical composition comprising dexmedetomidine or a pharmaceutically acceptable salt thereof at a dose of about 120 µg to about 180 µg wherein the PEC score reduction is about −8 to about −10 and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 µg. In some embodiments, dexmedetomidine or a pharmaceutically acceptable salt thereof is administered at a dose of about 180 µg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the PEC score reduction is about −8, about −9, or about −10.

In some embodiments, the present disclosure provides a method of achieving an ACES score improvement for a sustained period of time in a subject with bipolar or schizophrenic subject comprising administering to the subject a pharmaceutical composition comprising dexmedetomidine or a pharmaceutically acceptable salt thereof at a dose of about 120 µg to about 180 µg wherein the ACES score is improved to about 3 to about 4 and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 mcg. In some embodiments, dexmedetomidine or a pharmaceutically acceptable salt thereof is administered at a dose of about 180 mcg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the ACES score is about 4.

In some embodiments, the present disclosure provides a method of achieving an CGI-I score improvement for a sustained period of time in a subject with bipolar or schizophrenic subject comprising administering to the subject a pharmaceutical composition comprising dexmedetomidine or a pharmaceutically acceptable salt thereof at a dose of about 120 µg to about 180 µg wherein the CGI-I score is improved to about a 1 (very much improved) or about a 2 (much improved) and wherein the sustained period is about 2 hours to about 6 hours. In some embodiments, the composition comprises dexmedetomidine hydrochloride. In some embodiments, dexmedetomidine or a pharmaceutically acceptable salt thereof is administered at a dose of about 120 µg. In some embodiments, dexmedetomidine or a pharmaceutically acceptable salt thereof is administered at a dose of about 180 µg. In some embodiments, the sustained period is about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In some embodiments, the CGI-I score is about 1.

SPECIFIC EMBODIMENTS

Embodiment 1. A method of treating agitation or signs of agitation in a human subject with schizophrenia or bipolar disorder, without also inducing significant sedation, comprising administering dexmedetomidine or a pharmaceutically acceptable salt thereof at a dose resulting in a mean total exposure of dexmedetomidine, as measured by plasma AUC from T0 to T∞, of about 3800 ng*h/L.

Embodiment 2. A method of treating agitation or signs of agitation in a human subject with schizophrenia or bipolar disorder, without also inducing significant sedation, comprising administering dexmedetomidine or a pharmaceutically acceptable salt thereof at a dose resulting in a total exposure of dexmedetomidine, as measured by plasma AUC from T0 to T∞, from about 600 to about 12600 ng*h/L.

Embodiment 3. A methods of treating agitation or signs of agitation in a human subject with schizophrenia or bipolar disorder, without also inducing significant sedation, comprising administering dexmedetomidine or a pharmaceutically acceptable salt thereof at a dose resulting in a mean total exposure of dexmedetomidine, as measured by plasma AUC from T0 to T∞, of about 1800 ng*h/L.

Embodiment 4. A method of treating agitation or signs of agitation in a human subject with schizophrenia or bipolar disorder, without also inducing significant sedation, comprising administering dexmedetomidine or a pharmaceutically acceptable salt thereof at a dose resulting in a total exposure of dexmedetomidine, as measured by plasma AUC from T0 to T∞, from about 590 ng*h/L to about 8750 ng*h/L.

Embodiment 5. The method of embodiments 1 to 4, wherein said agitation or signs of agitation is associated with schizophrenia.

Embodiment 6 The method of embodiments 1 to 4, wherein dexmedetomidine or a pharmaceutically acceptable salt thereof is administered sublingually, buccally, orally, intranasally or parenterally.

Embodiment 7. The method of embodiment 6, wherein dexmedetomidine or a pharmaceutically acceptable salt thereof is administered sublingually or buccally.

Embodiment 8. The method of embodiment 6, wherein dexmedetomidine or a pharmaceutically acceptable salt thereof is administered sublingually.

Embodiment 9. The method of embodiment 6, wherein dexmedetomidine or a pharmaceutically acceptable salt thereof is administered sublingually in the form of a tablet, film, spray, gel or drops.

Embodiment 10. The method of embodiment 6, wherein dexmedetomidine or a pharmaceutically acceptable salt thereof is administered sublingually in the form of a film.

Embodiment 11. The method of embodiment 6, wherein dexmedetomidine or a pharmaceutically acceptable salt thereof is administered buccally.

Embodiment 12. The method of embodiment 6, wherein dexmedetomidine or a pharmaceutically acceptable salt thereof is administered buccally in the form of a film, patch or tablet.

Embodiment 13. The method of embodiment 6, wherein dexmedetomidine or a pharmaceutically acceptable salt thereof is administered parenterally.

Embodiment 14. The method of embodiment 13, wherein dexmedetomidine or a pharmaceutically acceptable salt thereof is administered parenterally in the form of an intramuscular injection.

Embodiment 15. The method of embodiment 6, wherein dexmedetomidine or a pharmaceutically acceptable salt thereof is administered orally.

Embodiment 16. The method of any one of embodiments 1 to 15, wherein dexmedetomidine or a pharmaceutically acceptable salt thereof is administered as a single dose.

Embodiment 17. The method of any one of embodiments 1 to 15, wherein dexmedetomidine or a pharmaceutically acceptable salt thereof is administered as a single dose containing about 180 µg dexmedetomidine or a pharmaceutically acceptable salt thereof.

Embodiment 18. The method of any one of embodiments 1 to 15, wherein dexmedetomidine or a pharmaceutically acceptable salt thereof is administered as a single dose containing about 120 µg dexmedetomidine or a pharmaceutically acceptable salt thereof.

Embodiment 19. The method of embodiment 14, wherein dexmedetomidine or a pharmaceutically acceptable salt thereof is administered at a dose of about 140 to 190 µg.

Embodiment 20 The method of embodiment 15, wherein dexmedetomidine or a pharmaceutically acceptable salt thereof is administered at a dose of about 900 to 1200 µg.

Embodiment 21. The method of any one of embodiments 1 to 20, wherein agitation or signs of agitation is treated without also inducing clinically significant cardiovascular effects.

Embodiment 22. The method of any one of embodiments 1 to 21, wherein agitation or signs of agitation are significantly reduced within 60 minutes of administering dexmedetomidine or a pharmaceutically acceptable salt thereof.

Embodiment 23. The method of any one of embodiments 1 to 21, wherein agitation or signs of agitation are significantly reduced within 60 minutes of administering dexmedetomidine or a pharmaceutically acceptable salt thereof, as measured by a significant relative change in PEC scores just prior to and 60 minutes after administering dexmedetomidine or a pharmaceutically acceptable salt thereof.

Embodiment 24. The method of embodiment 23, wherein the said relative PEC scores are different by at least six points.

Embodiment 25. The method of embodiment 23, wherein the said relative PEC scores are different by at least eight points.

Embodiment 26. The method of embodiment 24 or 25, wherein the difference in relative PEC scores is maintained for at least six hours following administration of dexmedetomidine or a pharmaceutically acceptable salt thereof.

Embodiment 27. The method of embodiment 23, wherein the said relative PEC scores are different by at least eight points, and wherein this difference of at least eight points is maintained for up to at least about 24 hours following administration of dexmedetomidine or a pharmaceutically acceptable salt thereof.

Embodiment 28. The method of any one of embodiments 1 to 27, wherein the mean plasma Cmax is about 400 ng/L.

Embodiment 29. The method of any one of embodiments 1 to 28, wherein the median plasma Tmax is about 2.0 hours.

Embodiment 30. The method of any one of embodiments 1 to 29, wherein the mean plasma Cmax is about 400 ng/L and the median plasma Tmax is about 2.0 hours.

Embodiment 31. The method of any one of embodiments 28 to 30, wherein dexmedetomidine or a pharmaceutically acceptable salt thereof is administered sublingually.

Embodiment 32. The method of any one of embodiments 28 to 30, wherein dexmedetomidine or a pharmaceutically acceptable salt thereof is administered sublingually in the form of a film.

Embodiment 33. The method of any one of embodiments 1 to 27, wherein the plasma Cmax is about 100 to about 1100 ng/L.

Embodiment 34. The method of any one of embodiments 1 to 27, wherein the plasma Cmax is about 200 to about 800 ng/L.

Embodiment 35. The method of any one of embodiments 1 to 27, wherein the plasma Cmax is about 3000 to about 5000 ng/L.

Embodiment 36. The method of any one of embodiments 33 to 35, wherein the plasma Tmax is about 1 to about 8 hours.

Embodiment 37. The method of any one of embodiments 33 to 35, wherein the plasma Tmax is about 5 minutes to about 4 hours.

Embodiment 38. The method of any one of embodiments 33 to 35, wherein the plasma Tmax is about 5 to about 15 minutes.

Embodiment 39. A method of treating a condition (e.g. agitation) in a human subject, comprising administering to said subject about 180 µg of dexmedetomidine or a pharmaceutically acceptable salt thereof sublingually or buccally to said subject, resulting in mean plasma absorption levels of dexmedetomidine from about 80% to about 125% of the following values: Cmax of from about 300 ng/L to about 500.ng/L (e.g. about 400 ng/L) and AUC from T0 to Tao of from about 2300 ng*h/L to about 3600 ng*h/L (e.g. about 2900 ng*h/L).

Embodiment 40. A method of treating a condition (e.g. agitation) in a human subject, comprising administering to said subject about 180 µg of dexmedetomidine or a pharmaceutically acceptable salt thereof sublingually or buccally to said subject, resulting in plasma absorption levels of dexmedetomidine from about 80% to about 125% of the following values: Cmax from about 100 ng/L to about 800 ng/L and AUC from T0 to T∞ of about 600 hr*ng/L to about 9500 hr*ng/L.

Embodiment 41. A method of treating a condition (e.g. agitation) in a human subject, comprising administering to said subject about 120 µg of dexmedetomidine or a pharmaceutically acceptable salt thereof sublingually or buccally to said subject, resulting in mean plasma absorption levels of dexmedetomidine from about 80% to about 125% of the following values Cmax from about 150 ng/L to about 300 ng/L (e.g. about 220.ng/L) and AUC from T0 to T∞ of from about 1100 ng*h/L to about 1800 ng*h/L (e.g. about 1420 ng*h/L).

Embodiment 42. A method of treating a condition (e.g. agitation) in a human subject, comprising administering to said subject about 120 µg of dexmedetomidine or a pharmaceutically acceptable salt thereof sublingually or buccally to said subject, resulting in plasma absorption levels of dexmedetomidine from about 80% to about 125% of the following values: Cmax from about 110 ng/L to about 400 ng/L and AUC from T0 to T∞ of about 590 hr*ng/L to about 4400 hr*ng/L.

Embodiment 43. The method of embodiments 39 to 42, wherein the condition is agitation or signs of agitation.

Embodiment 44. The method of embodiment 39 to 43, wherein said agitation or signs of agitation is associated with schizophrenia or bipolar disorder.

Embodiment 45. The method of any one of embodiments 39 to 44 wherein dexmedetomidine or a pharmaceutically acceptable salt thereof is administered oromucosally (e.g. sublingually or buccally).

Embodiment 46. The method of embodiments 45, wherein dexmedetomidine or a pharmaceutically acceptable salt thereof is administered sublingually in the form of a tablet, film, spray, gel or drops.

Embodiment 47. The method of embodiment 46, wherein dexmedetomidine or a pharmaceutically acceptable salt thereof is administered in the form of a film.

Embodiment 48. The method of embodiment 45, wherein dexmedetomidine or a pharmaceutically acceptable salt thereof is administered buccally.

Embodiment 49. The method of embodiment 48, wherein dexmedetomidine or a pharmaceutically acceptable salt thereof is administered buccally in the form of a film, patch or tablet.

Embodiment 50. The method of embodiment 49, wherein dexmedetomidine or a pharmaceutically acceptable salt thereof is administered in the form of a film.

Embodiment 51. The method of any one of embodiments 39 to 50, wherein dexmedetomidine or a pharmaceutically acceptable salt thereof is administered as a single dose.

Embodiment 52. The method of any one of embodiments 39 to 51, wherein the subject is treated without also inducing significant sedation.

Embodiment 53. The method of any one of embodiments 39 to 52, wherein the subject is treated without also inducing clinically significant cardiovascular effects.

Embodiment 54. The method of any one of embodiments 43 to 53, wherein agitation or signs of agitation are significantly reduced within 60 minutes of administering dexmedetomidine or a pharmaceutically acceptable salt thereof.

Embodiment 55. The method of any one of embodiments 43 to 54, wherein agitation or signs of agitation are significantly reduced within 60 minutes of administering dexmedetomidine or a pharmaceutically acceptable salt thereof, as measured by the relative PEC scores just prior to and 60 minutes after administering dexmedetomidine or a pharmaceutically acceptable salt thereof.

Embodiment 56. The method of embodiment 55, wherein the said relative PEC scores are different by at least six points.

Embodiment 57. The method of embodiment 55, wherein the said relative PEC scores are different by at least eight points.

Embodiment 58. The method of embodiment 56 or 57 wherein the difference in relative PEC scores is maintained for at least six hours following administration of dexmedetomidine or a pharmaceutically acceptable salt thereof.

Embodiment 59. The method of embodiment 55, wherein the said relative PEC scores are different by at least eight points, and wherein this difference of at least eight points is maintained for up to at least about 24 hours following administration of dexmedetomidine or a pharmaceutically acceptable salt thereof.

Embodiment 60. The method of any one of embodiments 39 to 59, wherein the median plasma Tmax is about 2 hours.

Embodiment 61. The method of any one of embodiments 39 to 59, wherein the plasma Tmax is about 1 to about 8 hours.

Embodiment 62. A method of treating agitation or signs of agitation in a human subject with schizophrenia or bipolar disorder, without also inducing significant sedation, comprising administering 180 µg dexmedetomidine or a pharmaceutically acceptable salt thereof as a single dose.

Embodiment 63. A method of treating agitation or signs of agitation in a human subject with schizophrenia or bipolar disorder, without also inducing significant sedation, comprising administering 120 µg dexmedetomidine or a pharmaceutically acceptable salt thereof as a single dose.

Embodiment 64. A method of mitigation or preventing the occurrence of a further agitation event in a human subject with schizophrenia or bipolar disorder within about 24 hours of an earlier agitation event, comprising administering about 180 µg dexmedetomidine or a pharmaceutically acceptable salt thereof as a single dose immediately following said earlier agitation event.

Embodiment 65. A method of mitigation or preventing the occurrence of a further agitation event in a human subject with schizophrenia or bipolar disorder within about 24 hours of an earlier agitation event, comprising administering about 120 µg dexmedetomidine or a pharmaceutically acceptable salt thereof as a single dose immediately following said earlier agitation event.

Embodiment 66. The method of embodiment 62 or 63, wherein said agitation or signs of agitation is associated with schizophrenia.

Embodiment 67. A method of treating agitation or signs of agitation in a human subject with dementia, without also inducing significant sedation, comprising oromucosally administering about 30 µg of dexmedetomidine or a pharmaceutically acceptable salt thereof one to six times a day at a dosing interval of at least 2 hours.

Embodiment 68. A method of treating agitation or signs of agitation in a human subject with dementia, without also inducing significant sedation, comprising oromucosally administering about 60 µg of dexmedetomidine or a pharmaceutically acceptable salt thereof one to six times a day at a dosing interval of at least 2 hours.

Embodiment 69. A method of treating agitation or signs of agitation in a human subject with dementia, without also inducing significant sedation, comprising oromucosally administering about 90 µg of dexmedetomidine or a pharmaceutically acceptable salt thereof one to four times a day at a dosing interval of at least 2 hours.

Embodiment 70. A method of treating agitation or signs of agitation in a human subject with delirium hospitalized in ICU, without also inducing significant sedation, comprising oromucosally administering about 20 µg of dexmedetomidine or a pharmaceutically acceptable salt one to four times within 6 hours of first dose at a dosing interval of at least 30 minutes thereof.

Embodiment 71. A method of treating agitation or signs of agitation in a human subject with delirium hospitalized in ICU, without also inducing significant sedation, comprising oromucosally administering about 60 µg of dexmedetomidine or a pharmaceutically acceptable salt thereof one to four times within 6 hours of first dose at a dosing interval of at least 30 minutes Embodiment 72. A method of reducing a period of opioid withdrawal by administering to a human subject of at least 18 years in need thereof dexmedetomidine twice daily for the period of withdrawal, wherein the period of withdrawal is up to 14 days.

Embodiment 73. The method of embodiment 72, wherein the dexmedetomidine is administered at a dose range between 30 µg to about 200 µg.

Embodiment 74. The method of embodiment 73, wherein the dexmedetomidine is administered at a unit dose of about 30 µg, 60 µg, 90 µg, 120 µg and 180 µg. Embodiment 75. The method of embodiment 72, wherein the period of withdrawal is up to: 13 days, 12 days, 11 days, 10 days, 9 days, 8 days, 7 days, 6 days, 5 days, 4 days, or 3 days.

Embodiment 76. The method of embodiment 72, wherein the opioid is selected from the group comprising of fentanyl, morphine, codeine, heroin, oxycodone, hydrocodone, alfentanil carfentanil, tramadol, hydromorphone, buprenorphine, naloxone, naltrexone, remifentanil butorphanol, meperidine, methadone, dextropropoxyphene (propoxyphene) thebaine, sufentanil or pentazocine.

Embodiment 77. The method of embodiment 72, wherein the opioid had been administered for amount of time longer than neonate treatment prior to withdrawal.

Embodiment 78. A method of treating agitation or signs of agitation in a human subject with schizophrenia or bipolar disorder, without also inducing significant sedation, comprising administering an oromucosal film comprising about 120 µg or about 180 µg dexmedetomidine or a pharmaceutically acceptable salt thereof as a single dose.

Embodiment 79. The method of embodiment 78, wherein the subject has been previously administered a liquid formulation of dexmedetomidine or a pharmaceutically acceptable salt thereof via a parenteral route (intravenous, intramuscular, subcutaneous injection or intravenous infusion).

Embodiment 80. The method of any of embodiments 78 and 79, wherein the oromucosal administration is followed within 3 to 5 hours of previous administration of liquid formulation of dexmedetomidine via a parenteral route.

Embodiment 81. The method of embodiment 78, wherein the parenteral administration is followed within 3 to 5 hours of previous administration of oromucosal film.

Embodiment 82. The method of embodiment 79, wherein the liquid formulation is prefilled in disposable syringes for self-administration by patients with an auto-injector.

Embodiment 83. The method of embodiment 78, wherein the subject is currently is co-treated with an anti-psychotic.

Embodiment 84. The method of embodiments 83, wherein the anti-psychotic is selected from but are not limited to aripiprazole, benperidol. flupentixol, amisulpride, chlorpromazine, asenapine, risperidone, ziprasidone, lurasidone, clozapine, cariprazine, olanzapine and quetiapine. In a preferred embodiment, the anti-psychotic is aripiprazole.

Embodiments 85. The method of embodiment 72, wherein improvement in the subject is assessed using a Clinical Opiate Withdrawal Scale and/or the Short Opiate Withdrawal Scale of Gossop (e.g. over a 10-day period) after following the treatment.

Embodiment 86. The method of embodiment 70 or 71, wherein changes in severity of delirium are measured using DRS-R-98 scale.

Embodiment 87. The method of embodiment 70 or 71, wherein changes in agitation are monitored using RASS scale.

Embodiment 88. The method of any one of the embodiments 62, 63, 64, 65, wherein dexmedetomidine or a pharmaceutically acceptable salt thereof is administered oromucosally (e.g. sublingually, buccally), orally, intranasally or parenterally.

Embodiment 89. The method of any one of the embodiments 67, 68, 69, 70, 71 and 72, wherein dexmedetomidine or a pharmaceutically acceptable salt thereof is administered oromucosally (e.g. sublingually or buccally) in the form of a tablet, film, spray, gel or drops.

Embodiment 90. The method of embodiment 89, wherein dexmedetomidine or a pharmaceutically acceptable salt thereof is administered sublingually in the form of a tablet, film, spray, gel or drops.

Embodiment 91. The method of embodiment 90, wherein dexmedetomidine or a pharmaceutically acceptable salt thereof is administered sublingually in the form of a film.

Embodiment 92. The method of embodiment 89, wherein dexmedetomidine or a pharmaceutically acceptable salt thereof is administered buccally in the form of a film, patch or tablet.

Embodiment 93. The method of embodiment 92, wherein dexmedetomidine or a pharmaceutically acceptable salt thereof is administered buccally in the form of a film.

Embodiment 94. The method of embodiments 62 to 65, wherein dexmedetomidine or a pharmaceutically acceptable salt thereof is administered parenterally in the form of an intravenous or intramuscular injection or an intravenous infusion.

Embodiment 95. The method of embodiments 62 to 65, wherein dexmedetomidine or a pharmaceutically acceptable salt thereof is administered by intramuscular injection.

Embodiment 96. The method of embodiments 62 to 65, wherein dexmedetomidine or a pharmaceutically acceptable salt thereof is administered once a day.

Embodiment 97. The method of claim 62 to 65, 67, 68, 69, 70, 71 and 72, wherein agitation or signs of agitation is treated without also inducing clinically significant cardiovascular effects.

Embodiment 98. The method of claim 62 or claim 64, wherein a single dose of about 180 μg dexmedetomidine or a pharmaceutically acceptable salt thereof is effective for up to at least about 24 hours.

Embodiment 99. The method of embodiments 62 to 65, wherein agitation or signs of agitation are significantly reduced within 60 minutes of administering dexmedetomidine or a pharmaceutically acceptable salt thereof, as measured by a significant relative change in PEC scores just prior to and 60 minutes after administering dexmedetomidine or a pharmaceutically acceptable salt thereof.

Embodiment 100. The method of embodiment 99, wherein the said relative PEC scores are different by at least six points or eight points.

Embodiment 101. The method of embodiment 99 or embodiment 100, wherein the difference in relative PEC scores is maintained for at least six hours following administration of dexmedetomidine or a pharmaceutically acceptable salt thereof.

Embodiment 102. The method of embodiment 99 or embodiment 100, wherein the said relative PEC scores are different by at least eight points, and wherein this difference of at least eight points is maintained for up to at least about 24 hours following administration of dexmedetomidine or a pharmaceutically acceptable salt thereof.

Embodiment 103. The method of any of relevant preceding embodiments, where dexmedetomidine or a pharmaceutically acceptable salt thereof is administered as a film, wherein said film is a self-supporting, dissolvable, film, comprising:
(i) dexmedetomidine or a pharmaceutically acceptable salt thereof;
(ii) one or more water-soluble polymers; and, optionally,
(iii) one or more pharmaceutically acceptable carriers.

Embodiment 104. The method of embodiment 103, wherein (ii) comprises a low molecular weight, water-soluble polymer and two high molecular weight, water-soluble polymers.

Embodiment 105. The method of embodiment 104, wherein the low molecular weight, water-soluble polymer has a molecular weight from about 5,000 daltons to about 49,000 daltons, and each high molecular weight, water-soluble polymer has a molecular weight of greater than about 60,000 daltons.

Embodiment 106. The method of embodiment 104, wherein the low molecular weight, water-soluble polymer has a molecular weight of about 40,000 daltons, one of the two high molecular weight, water-soluble polymers has a molecular weight of about 140,000 daltons, and the other high molecular weight, water-soluble polymer has a molecular weight of about 370,000 daltons.

Embodiment 107. The method of any one of embodiments 103 to 106, wherein each water-soluble polymer is hydroxypropyl cellulose.

Embodiment 108. The method of any one of embodiments 103 to 106, wherein the film also comprises a polyethylene oxide.

Embodiment 109. The method of embodiment 108, wherein the polyethylene oxide has a molecular weight of about 600,000 daltons.

Embodiment 110. The method of any of relevant preceding embodiments, where dexmedetomidine or a pharmaceutically acceptable salt thereof is administered as a film, wherein said film is a self-supporting, dissolvable, film, comprising:
(i) dexmedetomidine or a pharmaceutically acceptable salt thereof;
(ii) a low molecular weight, water-soluble polymer having a molecular weight of about 40,000 daltons;
(iii) a high molecular weight, water-soluble polymer having a molecular weight from about 140,000 daltons;
(iv) a high molecular weight, water-soluble polymer having a molecular weight from about 370,000 daltons; and
(v) a water-soluble polyethylene oxide having a molecular weight of about 600,000 daltons.

Embodiment 111. The method of embodiment 110, wherein the film components excluding dexmedetomidine or a pharmaceutically acceptable salt thereof form a single layer film substrate, and dexmedetomidine or a pharmaceutically acceptable salt thereof is present on the surface of the film substrate.

Embodiment 112. The method of embodiment 111, wherein dexmedetomidine or a pharmaceutically acceptable salt thereof is present on the surface of the film substrate within a composition comprising dexmedetomidine or a pharmaceutically acceptable salt thereof, a low molecular weight, water-soluble polymer having a molecular weight of about 40,000 daltons, and a high molecular weight, water-soluble polymer having a molecular weight of about 140,000 daltons.

Embodiment 113. A method of treating agitation associated with schizophrenia or bipolar disorder, comprising administering a unit dose composition comprising about 120 μg of dexmedetomidine or a pharmaceutically acceptable salt thereof to a human patient.

Embodiment 114. The method of embodiment 113, wherein the patient has schizophrenia.

Embodiment 115. The method of embodiment 113 or embodiment 114, wherein the patient has bipolar I disorder.

Embodiment 116. The method of any one of embodiments 113-115, wherein the composition comprises dexmedetomidine hydrochloride.

Embodiment 117. The method of any one of embodiments 113-116, wherein the composition is administered sublingually or buccally.

Embodiment 118. The method of embodiment 117, wherein the composition is administered sublingually in the form of a tablet, film, spray, gel or drops.

Embodiment 119. The method of embodiment 117, wherein the composition is administered buccally in the form of a film, patch or tablet.

Embodiment 120. The method of any one of embodiments 113-119, further comprising administering a second dose after a period of time ranging from about 30 minutes to about 12 hours.

Embodiment 121. The method of embodiment 120, wherein the additional dose is about 60 μg or 90 μg.

Embodiment 122. The method of embodiment 120 or embodiment 121, wherein the second dose is administered after a period of about 2 hours.

Embodiment 123. The method of any one of embodiments 113-122, wherein the patient is in a fed state.

Embodiment 124. The method of any one of embodiments 113-122, wherein the patient is in a fasted state.

Embodiment 125. The method of any one of embodiments 113-124, wherein agitation is significantly reduced within about 2 hours of administering the composition, as measured by a mean change in Positive and Negative Syndrome Scale Excited Component (PEC) scores relative to baseline.

Embodiment 126. The method of embodiment 125, wherein the agitation is significantly reduced within about 30 minutes to about 1 hour.

Embodiment 127. The method of embodiment 125 or embodiment 126, wherein the patient experiences ≥40% decrease from baseline in PEC score.

Embodiment 128. The method of embodiment 127, wherein the patient experiences ≥60% decrease from baseline in PEC score.

Embodiment 129. The method of any one of embodiments 125-128, wherein the PEC score is 30% lower than placebo.

Embodiment 130. The method of embodiment 129, wherein the PEC score is ≥60% lower than placebo.

Embodiment 131. The method of any one of embodiments 125-130, wherein the mean change in PEC score is greater than −4 (i.e. a decrease of 4 or more points) relative to baseline within 2 hours of administering the composition.

Embodiment 132. The method of embodiment 131, wherein mean change in PEC score is greater than −6 relative to baseline within 2 hours of administering the composition.

Embodiment 133. The method of embodiment 131, wherein mean change in PEC score is greater than −8 relative to baseline within 2 hours of administering the composition.

Embodiment 134. The method of any one of embodiments 125-133, wherein the decrease in PEC score is maintained for at least six hours following administration of the composition.

Embodiment 135. The method of any one of embodiments 125-134, wherein the mean change in PEC score is greater than or equal to −8 and is maintained from 2 hours post administration up to at least about 6 hours following administration of the composition.

Embodiment 136. The method of any one of embodiments 113-135, wherein the subject is treated without experiencing significant sedation.

Embodiment 137. The method of any one of embodiments 113-136, wherein the subject is treated without experiencing clinically significant cardiovascular effects.

Embodiment 138. The method of any one of embodiments 113-137, wherein administration of a single dose provides a mean $C_{max}$ within the range of about 80% to about 125% of about 110 ng/L to about 400 ng/L.

Embodiment 139. The method of embodiment 138, wherein the mean $C_{max}$ is within the range of about 80% to about 125% of about 238 ng/L.

Embodiment 140. The method of embodiment 138, wherein the mean $C_{max}$ is about 238 ng/L Embodiment 141. The method of any one of embodiments 113-140, wherein administration of a single dose provides a mean $AUC_{0\text{-}inf}$ within the range of about 80% to about 125% of about 590 hr*ng/L to about 4400 hr*ng/L.

Embodiment 142. The method of embodiment 141, the mean $AUC_{0\text{-}inf}$ is within the range of about 80% to about 125% of about 1810 ng*h/L.

Embodiment 143. The method of embodiment 141, wherein the mean $AUC_{0\text{-}inf}$ is about 1810 ng*h/L.

Embodiment 144. The method of any one of embodiments 113-143 wherein administration of a single dose provides a mean $T_{max}$ within the range of about 80% to about 125% of about 1 hour to about 4 hours.

Embodiment 145. The method of embodiment 144, wherein the mean $T_{max}$ is within the range of about 80% to about 125% of about 2 hours.

Embodiment 146. The method of embodiment 144, wherein the mean $T_{max}$ is about 2 hours.

Embodiment 147. The method of any one of embodiments 113-146, wherein administration of a single dose provides a geometric mean $C_{max}$ within the range of about 80% to about 125% of about 110 ng/L to about 400 ng/L.

Embodiment 148. The method of embodiment 147, wherein the geometric mean $C_{max}$ is within the range of about 80% to about 125% of about 220 ng/L.

Embodiment 149. The method of embodiment 147, wherein the geometric mean $C_{max}$ is about 220 ng/L Embodiment 150. The method of any one of embodiments 113-149, wherein administration of a single dose provides a geometric mean $AUC_{0\text{-}inf}$ within the range of about 80% to about 125% of about 590 hr*ng/L to about 4400 hr*ng/L.

Embodiment 151. The method of embodiment 150, the geometric mean $AUC_{0\text{-}inf}$ is within the range of about 80% to about 125% of about 1410 ng*h/L.

Embodiment 152. The method of embodiment 150, wherein the geometric mean $AUC_{0\text{-}inf}$ is about 1410 ng*h/L.

Embodiment 153. The method of any one of embodiments 113-152 wherein administration of a single dose provides a geometric mean $T_{max}$ within the range of about 80% to about 125% of about 1 hour to about 4 hours.

Embodiment 154. The method of embodiment 153, wherein the geometric mean $T_{max}$ is within the range of about 80% to about 125% of about 2 hours.

Embodiment 155. The method of embodiment 153, wherein the geometric mean $T_{max}$ is about 2 hours.

Embodiment 156. The method of any one of embodiments 113-155, wherein administration of a single dose provides a median $C_{max}$ within the range of about 80% to about 125% of about 110 ng/L to about 400 ng/L.

Embodiment 157. The method of embodiment 156, wherein the median $C_{max}$ is within the range of about 80% to about 125% of about 230 ng/L.

Embodiment 158. The method of embodiment 156, wherein the median $C_{max}$ is about 230 ng/L.

Embodiment 159. The method of any one of embodiments 113-158, wherein administration of a single dose provides a median $AUC_{0\text{-}inf}$ within the range of about 80% to about 125% of about 590 hr*ng/L to about 4400 hr*ng/L.

Embodiment 160. The method of embodiment 159, the median $AUC_{0\text{-}inf}$ is within the range of about 80% to about 125% of about 1180 ng*h/L.

Embodiment 161. The method of embodiment 141, wherein the median $AUC_{0\text{-}inf}$ is about 1810 ng*h/L.

Embodiment 162. The method of any one of embodiments 113-161 wherein administration of a single dose provides a median $T_{max}$ within the range of about 80% to about 125% of about 1 hour to about 4 hours.

Embodiment 163. The method of embodiment 162, wherein the median $T_{max}$ is within the range of about 80% to about 125% of about 2 hours.

Embodiment 164. The method of embodiment 162, wherein the median $T_{max}$ is about 2 hours.

Embodiment 165. The method of any one of embodiments 138-164, wherein the pharmacokinetic parameters are non-steady state.

Embodiment 166. A method of treating agitation associated with schizophrenia or bipolar disorder, comprising administering a unit dose composition comprising about 180 µg of dexmedetomidine or a pharmaceutically acceptable salt thereof to a human patient.

Embodiment 167. The method of embodiment 166, wherein the patient has schizophrenia.

Embodiment 168. The method of embodiment 166 or embodiment 167, wherein the patient has bipolar I disorder.

Embodiment 169. The method of any one of embodiments 166-168, wherein the composition comprises dexmedetomidine hydrochloride.

Embodiment 170. The method of any one of embodiments 166-169, wherein the composition is administered sublingually or buccally.

Embodiment 171. The method of embodiment 170, wherein the composition is administered sublingually in the form of a tablet, film, spray, gel or drops.

Embodiment 172. The method of embodiment 170, wherein the composition is administered buccally in the form of a film, patch or tablet.

Embodiment 173. The method of any one of embodiments 166-172, further comprising administering a second dose after a period of time ranging from about 30 minutes to about 12 hours.

Embodiment 174. The method of embodiment 173, wherein the additional dose is about 60 µg or 90 µg.

Embodiment 175. The method of embodiment 8 or embodiment 174, wherein the second dose is administered after a period of about 2 hours.

Embodiment 176. The method of any one of embodiments 166-175, wherein the patient is in a fed state.

Embodiment 177. The method of any one of embodiments 166-175, wherein the patient is in a fasted state.

Embodiment 178. The method of any one of embodiments 166-177, wherein agitation is significantly reduced within about 2 hours of administering the composition, as measured by a mean change in Positive and Negative Syndrome Scale Excited Component (PEC) scores relative to baseline.

Embodiment 179. The method of embodiment 178, wherein the agitation is significantly reduced within about 30 minutes to about 1 hour.

Embodiment 180. The method of embodiment 178 or embodiment 179, wherein the patient experiences ≥40% decrease from baseline in PEC score.

Embodiment 181. The method of embodiment 180, wherein the patient experiences ≥60% decrease from baseline in PEC score.

Embodiment 182. The method of any one of embodiments 178-181, wherein the PEC score is 30% lower than placebo.

Embodiment 183. The method of embodiment 182, wherein the PEC score is ≥60% lower than placebo.

Embodiment 184. The method of any one of embodiments 178-183, wherein the mean change in PEC score is greater than −4 (i.e. a decrease of 4 or more points) relative to baseline within 2 hours of administering the composition.

Embodiment 185. The method of embodiment 184, wherein mean change in PEC score is greater than −6 relative to baseline within 2 hours of administering the composition.

Embodiment 186. The method of embodiment 184, wherein mean change in PEC score is greater than −8 relative to baseline within 2 hours of administering the composition.

Embodiment 187. The method of any one of embodiments 178-186, wherein the decrease in PEC score is maintained for at least six hours following administration of the composition.

Embodiment 188. The method of any one of embodiments 178-187, wherein the mean change in PEC score is greater than or equal to −8 and is maintained from 2 hours post administration up to at least about 24 hours following administration of the composition.

Embodiment 189. The method of any one of embodiments 166-188, wherein the subject is treated without experiencing significant sedation.

Embodiment 190. The method of any one of embodiments 166-189, wherein the subject is treated without experiencing clinically significant cardiovascular effects.

Embodiment 191. The method of any one of embodiments 166-190, wherein administration of a single dose provides a mean $C_{max}$ within the range of about 80% to about 125% of about 100 ng/L to about 800 ng/L.

Embodiment 192. The method of embodiment 191, wherein the mean $C_{max}$ is within the range of about 80% to about 125% of about 440 ng/L Embodiment 193. The method of embodiment 191, wherein the mean $C_{max}$ is about 440 ng/L Embodiment 194. The method of any one of embodiments 166-193, wherein administration of a single dose provides a mean $AUC_{0-inf}$ within the range of about 80% to about 125% of about 600 hr*ng/L to about 9500 hr*ng/L.

Embodiment 195. The method of embodiment 194, the mean $AUC_{0-inf}$ is within the range of about 80% to about 125% of about 3800 ng*h/L.

Embodiment 196. The method of embodiment 194, the mean $AUC_{0-inf}$ is about 3800 ng*h/L.

Embodiment 197. The method of any one of embodiments 166-196, herein administration of a single dose provides a mean $T_{max}$ within the range of about 80% to about 125% of about 1 hour to about 8 hours.

Embodiment 198. The method of embodiment 197, wherein the mean $T_{max}$ is within the range of about 80% to about 125% of about 2 hours.

Embodiment 199. The method of embodiment 197, wherein the mean $T_{max}$ is about 2 hours.

Embodiment 200. The method of any one of embodiments 166-199, wherein administration of a single dose provides a geometric mean $C_{max}$ within the range of about 80% to about 125% of about 100 ng/L to about 800 ng/L.

Embodiment 201. The method of embodiment 200, wherein the geometric mean $C_{max}$ is within the range of about 80% to about 125% of about 380 ng/L.

Embodiment 202. The method of embodiment 200, wherein the geometric mean $C_{max}$ is about 380 ng/L.

Embodiment 203. The method of any one of embodiments 166-202, wherein administration of a single dose provides a geometric mean $AUC_{0-inf}$ within the range of about 80% to about 125% of about 600 hr*ng/L to about 9500 hr*ng/L.

Embodiment 204. The method of embodiment 203, the geometric mean AUC0-w is within the range of about 80% to about 125% of about 2880 ng*h/L.

Embodiment 205. The method of embodiment 203, wherein the geometric mean $AUC_{0-inf}$ is about 2880 ng*h/L.

Embodiment 206. The method of any one of embodiments 166-205 wherein administration of a single dose provides a geometric mean $T_{max}$ within the range of about 80% to about 125% of about 1 hour to about 8 hours.

Embodiment 207. The method of embodiment 206, wherein the geometric mean $T_{max}$ is within the range of about 80% to about 125% of about 2 hours.

Embodiment 208. The method of embodiment 206, wherein the geometric mean $T_{max}$ is about 2 hours.

Embodiment 209. The method of any one of embodiments 166-208, wherein administration of a single dose provides a median $C_{max}$ within the range of about 80% to about 125% of about 110 ng/L to about 800 ng/L.

Embodiment 210. The method of embodiment 209, wherein the median $C_{max}$ is within the range of about 80% to about 125% of about 485 ng/L.

Embodiment 211. The method of embodiment 209, wherein the median $C_{max}$ is about 485 ng/L.

Embodiment 212. The method of any one of embodiments 166-211, wherein administration of a single dose provides a median $AUC_{0-inf}$ within the range of about 80% to about 125% of about 600 hr*ng/L to about 9500 hr*ng/L.

Embodiment 213. The method of embodiment 212, the median $AUC_{0-inf}$ is within the range of about 80% to about 125% of about 2900 ng*h/L.

Embodiment 214. The method of embodiment 194, wherein the median $AUC_{0-inf}$ is about 2900 ng*h/L.

Embodiment 215. The method of any one of embodiments 166-214 wherein administration of a single dose provides a median $T_{max}$ within the range of about 80% to about 125% of about 1 hour to about 8 hours.

Embodiment 216. The method of embodiment 215, wherein the median $T_{max}$ is within the range of about 80% to about 125% of about 2 hours.

Embodiment 217. The method of embodiment 215, wherein the median $T_{max}$ is about 2 hours.

Embodiment 218. The method of any one of embodiments 191-217, wherein the pharmacokinetic parameters are non-steady state.

Embodiment 219. A method of treating agitation associated with schizophrenia or bipolar disorder, comprising administering a unit dose composition comprising about 120 µg to about 180 µg of dexmedetomidine or a pharmaceutically acceptable salt thereof to a human patient.

Embodiment 220. The method of embodiment 219, wherein the patient has schizophrenia.

Embodiment 221. The method of embodiment 219 or embodiment 220, wherein the patient has bipolar I disorder.

Embodiment 222. The method of any one of embodiments 219-221, wherein the composition comprises dexmedetomidine hydrochloride.

Embodiment 223. The method of any one of embodiments 219-222, wherein the unit dose of dexmedetomidine is about 120 µg.

Embodiment 224. The method of any one of embodiments 219-222, wherein the unit dose of dexmedetomidine is about 180 µg.

Embodiment 225. The method of any one of embodiments 219-224, wherein the composition is administered sublingually or buccally.

Embodiment 226. The method of embodiment 225, wherein the composition is administered sublingually in the form of a tablet, film, spray, gel or drops.

Embodiment 227. The method of embodiment 225, wherein the composition is administered buccally in the form of a film, patch or tablet.

Embodiment 228. The method of any one of embodiments 219-227, further comprising administering a second dose after a period of time ranging from about 30 minutes to about 12 hours.

Embodiment 229. The method of embodiment 228, wherein the additional dose is about 60 µg or 90 µg.

Embodiment 230. The method of embodiment 228 or embodiment 229, wherein the second dose is administered after a period of about 2 hours.

Embodiment 231. The method of any one of embodiments 219-230, wherein agitation is significantly reduced within about 2 hours of administering the composition, as measured by a mean change in Positive and Negative Syndrome Scale Excited Component (PEC) scores relative to baseline.

Embodiment 232. The method of embodiment 231, wherein the agitation is significantly reduced within about 30 minutes to about 1 hour.

Embodiment 233. The method of embodiment 231 or embodiment 232, wherein the patient experiences ≥40% decrease from baseline in PEC score.

234. The method of embodiment 233, wherein the patient experiences ≥60% decrease from baseline in PEC score.

Embodiment 235. The method of any one of embodiments 231-234, wherein the PEC score is 30% lower than placebo.

Embodiment 236. The method of embodiment 235, wherein the PEC score is ≥60% lower than placebo.

Embodiment 237. The method of any one of embodiments 231-236, wherein the mean change in PEC score is greater than −4 (i.e. a decrease of 4 or more points) relative to baseline within 2 hours of administering dexmedetomidine.

Embodiment 238. The method of embodiment 237, wherein mean change in PEC score is greater than −6 relative to baseline within 2 hours of administering the composition.

Embodiment 239. The method of embodiment 237, wherein mean change in PEC score is greater than −8 relative to baseline within 2 hours of administering the composition.

Embodiment 240. The method of any one of embodiments 231-239, wherein the decrease in PEC score is maintained for at least six hours following administration of the composition.

Embodiment 241. The method of any one of embodiments 231-240, wherein the mean change in PEC score is greater than or equal to −8 and is maintained from 2 hours post administration up to at least about 24 hours following administration of the composition.

Embodiment 242. The method of any one of embodiments 219-241, wherein the subject is treated without experiencing significant sedation.

Embodiment 243. The method of any one of embodiments 219-242, wherein the subject is treated without experiencing clinically significant cardiovascular effects.

Embodiment 244. The method of any one of embodiments 219-243, wherein administration of a single dose provides a mean peak plasma concentration ($C_{max}$) within the range of about 80% to about 125% of about 100 ng/L to about 800 ng/L.

Embodiment 245. The method of embodiment 244, wherein the mean $C_{max}$ is within the range of about 80% to about 125% of about 200 ng/L to about 500 ng/L.

Embodiment 246. The method of embodiment 244, wherein the mean $C_{max}$ is within the range of about 80/6 to about 125% of 230 ng/L to about 440 ng/L.

Embodiment 247. The method of any one of embodiments 219-246, wherein administration of a single dose provides a mean area under the curve $(AUC)_{0\text{-}inf}$ within the range of about 80% to about 125% of about 590 hr*ng/L to about 9500 hr*ng/L.

Embodiment 248. The method of embodiment 247, wherein the mean $AUC_{0\text{-}inf}$ is within the range of about 80% to about 125% of 1400 ng*h/L to about 4000 hr*ng/L.

Embodiment 249. The method of embodiment 247, wherein the mean $AUC_{0\text{-}inf}$ is within the range of about 80% to about 125% of 1800 ng*h/L to about 3800 ng*h/L.

Embodiment 250. The method of any one of embodiments 219-249 wherein administration of a single dose provides a mean time to peak plasma concentration $(T_{max})$ within the range of about 80% to about 125% of about 1 hour to about 8 hours.

Embodiment 251. The method of embodiment 250, wherein the mean $T_{max}$ is within the range of about 80% to about 125% of about hours.

Embodiment 252. The method of embodiment 250, wherein the mean $T_{max}$ is about 2 hours.

Embodiment 253. The method of any one of embodiments 244-252, wherein the pharmacokinetic parameters are non-steady state.

Embodiment 254. The method of any one of embodiments 219-253, wherein the patient is in a fed state.

Embodiment 255. The method of any one of embodiments 219-253, wherein the patient is in a fasted state.

Embodiment 256. A method of treating or ameliorating opioid withdrawal symptoms, comprising administering a composition comprising dexmedetomidine or a pharmaceutically acceptable salt thereof to a human patient in need thereof, wherein the patient is at least 18 years and wherein the period of withdrawal is up to 14 days.

Embodiment 257. The method of embodiment 256, wherein the treatment comprises reducing the period of opioid withdrawal.

Embodiment 258. The method of embodiment 256 or embodiment 257, wherein the treating or ameliorating is measured by the Clinical Opiate Withdrawal Scale (COWS) and/or Short Opiate Withdrawal Scale of Gossop (SOWS-Gossop) score.

Embodiment 259. The method of any one of embodiments 256-258, wherein the composition is administered twice daily.

Embodiment 260. The method of any one of embodiments 256-259, wherein the composition comprises a dose range of dexmedetomidine or a pharmaceutically acceptable salt thereof of between about 30 μg and about 200 μg.

Embodiment 261. The method of any one of embodiments 256-260, wherein the composition comprises a unit dose of about 30 μg, about 60 μg, about 90 μg, about 120 μg, or 180 μg of dexmedetomidine or a pharmaceutically acceptable salt thereof.

Embodiment 262. The method of any one of embodiments 256-261, wherein the period of withdrawal is up to 13 days, 12 days, 11 days, 10 days, 9 days, 8 days, 7 days, 6 days, 5 days, 4 days, or 3 days.

Embodiment 263. The method of any one of embodiments 256-262, wherein the opioid is selected from the group comprising of fentanyl, morphine, codeine, heroin, oxycodone, hydrocodone, alfentanil carfentanil, tramadol, hydromorphone, buprenorphine, naloxone, naltrexone, remifentanil butorphanol, meperidine, methadone, dextropropoxyphene (propoxyphene) thebaine, sufentanil and pentazocine.

Embodiment 264. The method of embodiment 263, wherein the opioid is selected from the group comprising of fentanyl.

Embodiment 265. The method of any one of embodiments 256-262, wherein the opioid had been administered for amount of time longer than neonate treatment prior to withdrawal.

Embodiment 266. The method of any one of embodiments 256-265, wherein the composition is administered sublingually, buccally, orally, intranasally or parenterally.

Embodiment 267. The method of embodiments any one of embodiments 256-266, wherein the composition is administered sublingually in the form of a tablet, film, spray, gel or drops.

Embodiment 268. The method of embodiment 267, wherein the composition is administered sublingually in the form of a film.

Embodiment 269. The method of any one of embodiments 256-266, wherein the composition is administered buccally in the form of a film, patch or tablet.

Embodiment 270. The method of embodiment 269, wherein the composition is administered buccally in the form of a film.

Embodiment 271. The method of any one of embodiments 256-270, wherein the patient is treated without also inducing clinically significant cardiovascular effects.

Embodiment 272. The method of any one of embodiments 256-271 wherein a single dose of a composition comprising about 180 μg dexmedetomidine or a pharmaceutically acceptable salt thereof is effective for up to at least about 24 hours.

Embodiment 273. The method of any one of embodiments 256-272, wherein the composition comprises dexmedetomidine hydrochloride.

Embodiment 274. The method of any one of embodiments 256-273, wherein the opioid withdrawal symptom is agitation.

Embodiment 275. The method of any one of embodiments 256-274, wherein the composition is administered twice daily for 7 days.

Embodiment 276. A pharmaceutical composition comprising from about 20 μg to about 240 μg dexmedetomidine or a pharmaceutically acceptable salt thereof.

Embodiment 277. The composition of embodiment 276, wherein dexmedetomidine is present as dexmedetomidine hydrochloride.

Embodiment 278. The composition of embodiment 276 or embodiment 277, wherein the dose of dexmedetomidine is about 120 μg.

Embodiment 279. The composition of any one of embodiments 276-278, wherein the dose of dexmedetomidine is about 180 μg.

Embodiment 280. The composition of any one of embodiments 276-279, wherein the composition is formulated for sublingual or buccal administration.

Embodiment 281. The composition of embodiment 280, wherein the composition is formulated for sublingual administration in the form of a tablet, film, spray, gel or drops.

Embodiment 282. The composition of embodiment 280, wherein the composition is formulated for buccal administration in the form of a film, patch or tablet.

Embodiment 283. The composition of any one of embodiments 276-282, wherein if administered to a patient having agitation associated with schizophrenia or bipolar disorder, the agitation is significantly reduced within about 2 hours of administering the composition as measured by a mean change in Positive and Negative Syndrome Scale Excited Component (PEC) scores relative to baseline.

Embodiment 284. The composition of embodiment 283, wherein the agitation is significantly reduced within about 30 minutes to about 1 hour.

Embodiment 285. The composition of embodiment 283 or embodiment 284, wherein the patient experiences ≥40% decrease from baseline in PEC score.

Embodiment 286. The composition of embodiment 285, wherein the patient experiences ≥60% decrease from baseline in PEC score.

Embodiment 287. The composition of any one of embodiments 283-286, wherein the PEC score is ≥30% lower than placebo.

Embodiment 288. The composition of embodiment 287, wherein the PEC score is ≥60% lower than placebo.

Embodiment 289. The composition of any one of embodiments 283-288, wherein the mean change in PEC score is greater than −4 (i.e. a decrease of 4 or more points) relative to baseline within 2 hours of administering the composition.

Embodiment 290. The composition of embodiment 289, wherein mean change in PEC score is greater than −6 relative to baseline within 2 hours of administering the composition.

Embodiment 291. The composition of embodiment 289, wherein mean change in PEC score is greater than −8 relative to baseline within 2 hours of administering the composition.

Embodiment 292. The composition of any one of embodiments 283-291, wherein the decrease in PEC score is maintained for at least six hours following administration of the composition.

Embodiment 293. The composition of any one of embodiments 283-292, wherein the mean change in PEC score is greater than or equal to −8 and is maintained from 2 hours post administration up to at least about 24 hours following administration of the composition.

Embodiment 294. The composition of any one of embodiments 283-293, wherein the subject is treated without experiencing significant sedation.

Embodiment 295. The composition of any one of embodiments 283-294, wherein the subject is treated without experiencing clinically significant cardiovascular effects.

Embodiment 296. The composition of any one of embodiments 276-295, wherein if administered to a patient having schizophrenia or bipolar disorder, a single dose provides a mean $C_{max}$ within the range of about 80% to about 125% of about 100 ng/L to about 800 ng/L.

Embodiment 297. The composition of embodiment 296, wherein the geometric mean $C_{max}$ is from about 200 ng/L to about 400 ng/L.

Embodiment 298. The composition of embodiment 296, wherein the mean $C_{max}$ is within the range of about 80% to about 125% of 230 ng/L to about 440 ng/L.

Embodiment 299. The composition of any one of embodiments 276-298, wherein if administered to a patient having schizophrenia or bipolar disorder, a single dose provides a mean $aAUC_{0-inf}$ within the range of about 80% to about 125% of about 590 hr*ng/L to about 9500 hr*ng/L.

Embodiment 300. The composition of embodiment 299, wherein the mean $AUC_{0-inf}$ is within the range of about 80% to about 125% of 1400 ng*h/L to about 4000 hr*ng/L.

Embodiment 301. The composition of embodiment 299, wherein the mean $AUC_{0-inf}$ is within the range of about 80% to about 125% of 1800 ng*h/L to about 3800 ng*h/L.

Embodiment 302. The composition of any one of embodiments 276-301, wherein if administered to a patient having schizophrenia or bipolar disorder, a single dose provides a mean time to peak plasma concentration ($T_{max}$) within the range of about 80% to about 125% of about 1 hour to about 8 hours.

Embodiment 303. The composition of embodiment 302, wherein the mean $T_{max}$ is within the range of about 80% to about 125% of about hours.

Embodiment 304. The composition of embodiment 302, wherein the mean $T_{max}$ is about 2 hours.

Embodiment 305. The composition of any one of embodiments 296-304, wherein the pharmacokinetic parameters are non-steady state.

Embodiment 306. The composition of any one of embodiments 283-305, wherein the patient is in a fed state.

Embodiment 307. The composition of any one of embodiments 283-305, wherein the patient is in a fasted state.

Embodiment 308. A method of treating agitation associated with schizophrenia or bipolar disorder, comprising administering a unit dose composition comprising dexmedetomidine or a pharmaceutically acceptable salt thereof to a human patient, wherein the dose provides one or more of the following pharmacokinetic parameters:
(1) a mean Cm within the range of about 80% to about 125% of about 110 ng/L to about 400 ng/L; and/or
(2) a mean AUC0-w within the range of about 80% to about 125% of about 590 hr*ng/L to about 4400 hr*ng/L; and/or
(3) a mean $T_{max}$ within the range of about 80% to about 125% of about 1 hour to about 4 hours.

Embodiment 309. The method of embodiment 308, wherein the patient has schizophrenia.

Embodiment 310. The method of embodiment 308 or embodiment 309, wherein the patient has bipolar I disorder.

Embodiment 311. The method of any one of embodiments 308-310, wherein the composition comprises dexmedetomidine hydrochloride.

Embodiment 312. The method of any one of embodiments 308-311, wherein the composition is administered sublingually or buccally.

Embodiment 313. The method of embodiment 312, wherein the composition is administered sublingually in the form of a tablet, film, spray, gel or drops.

Embodiment 314. The method of embodiment 312, wherein the composition is administered buccally in the form of a film, patch or tablet.

Embodiment 315. The method of any one of embodiments 308-314, further comprising administering a second dose after a period of time ranging from about 30 minutes to about 12 hours.

Embodiment 316. The method of embodiment 315, wherein the additional dose is about 60 µg or 90 µg.

Embodiment 317. The method of embodiment 315 or embodiment 316, wherein the second dose is administered after a period of about 2 hours.

Embodiment 318. The method of any one of embodiments 308-317, wherein the patient is in a fed state.

Embodiment 319. The method of any one of embodiments 308-317, wherein the patient is in a fasted state.

Embodiment 320. The method of any one of embodiments 308-319, wherein agitation is significantly reduced within about 2 hours of administering the composition, as measured by a mean change in Positive and Negative Syndrome Scale Excited Component (PEC) scores relative to baseline.

Embodiment 321. The method of embodiment 320, wherein the agitation is significantly reduced within about 30 minutes to about 1 hour.

Embodiment 322. The method of embodiment 320 or embodiment 321, wherein the patient experiences ≥40% decrease from baseline in PEC score.

Embodiment 323. The method of embodiment 322, wherein the patient experiences ≥60% decrease from baseline in PEC score.

Embodiment 324. The method of any one of embodiments 320-323, wherein the PEC score is 30% lower than placebo.

Embodiment 325. The method of embodiment 324, wherein the PEC score is 60% lower than placebo.

Embodiment 326. The method of any one of embodiments 320-325, wherein the mean change in PEC score is greater than −4 (i.e. a decrease of 4 or more points) relative to baseline within 2 hours of administering the composition.

Embodiment 327. The method of embodiment 326, wherein mean change in PEC score is greater than −6 relative to baseline within 2 hours of administering the composition.

Embodiment 328. The method of embodiment 326, wherein mean change in PEC score is greater than −8 relative to baseline within 2 hours of administering the composition.

Embodiment 329. The method of any one of embodiments 320-328, wherein the decrease in PEC score is maintained for at least six hours following administration of the composition.

Embodiment 330. The method of any one of embodiments 320-329, wherein the mean change in PEC score is greater than or equal to −8 and is maintained from 2 hours post administration up to at least about 6 hours following administration of the composition.

Embodiment 331. The method of any one of embodiments 308-330, wherein the subject is treated without experiencing significant sedation.

Embodiment 332. The method of any one of embodiments 308-331, wherein the subject is treated without experiencing clinically significant cardiovascular effects.

Embodiment 333. The method of any one of embodiments 308-332 wherein two or more of the pharmacokinetic parameters are present.

Embodiment 334. The method of any one of embodiments 308-333, wherein all three of the pharmacokinetic parameters are present.

Embodiment 335. The method of any one of embodiments 308-334, wherein the mean $C_{max}$ is within the range of about 80% to about 125% of about 238 ng/L.

Embodiment 336. The method of embodiment 335, wherein the mean $C_{max}$ is about 238 ng/L Embodiment 337. The method of any one of embodiments 308-336, wherein administration of a single dose provides a mean $AUC_{0-inf}$ within the range of about 80% to about 125% of about 1810 ng*h/L.

Embodiment 338. The method of embodiment 337, wherein the mean about 1810 ng*h/L.

Embodiment 339. The method of any one of embodiments 308-338 wherein administration of a single dose provides a mean $T_{max}$ within the range of about 80% to about 125% of about 2 hours.

Embodiment 340. The method of embodiment 339, wherein the mean $T_{max}$ is about 2 hours.

Embodiment 341. The method of any one of embodiments 308-340, wherein the pharmacokinetic parameters are non-steady state.

Embodiment 342. A method of treating agitation associated with schizophrenia or bipolar disorder, comprising administering a unit dose composition comprising dexmedetomidine or a pharmaceutically acceptable salt thereof to a human patient, wherein the dose provides one or more of the following pharmacokinetic parameters:

(1) a mean $C_{max}$ within the range of about 80% to about 125% of about 100 ng/L to about 800 ng/L; and/or (2) a mean $AUC_{0-inf}$ within the range of about 80% to about 125% of about 600 hr*ng/L to about 9500 hr*ng/L; and/or (3) a mean $T_{max}$ within the range of about 80% to about 125% of about 1 hour to about 8 hours.

Embodiment 343. The method of embodiment 342, wherein the patient has schizophrenia.

Embodiment 344. The method of embodiment 342 or embodiment 343, wherein the patient has bipolar I disorder.

Embodiment 345. The method of any one of embodiments 342-344, wherein the composition comprises dexmedetomidine hydrochloride.

Embodiment 346. The method of any one of embodiments 342-345, wherein the composition is administered sublingually or buccally.

Embodiment 347. The method of embodiment 346, wherein the composition is administered sublingually in the form of a tablet, film, spray, gel or drops.

Embodiment 348. The method of embodiment 346, wherein the composition is administered buccally in the form of a film, patch or tablet.

Embodiment 349. The method of any one of embodiments 342-348, further comprising administering a second dose after a period of time ranging from about 30 minutes to about 12 hours.

Embodiment 350. The method of embodiment 349, wherein the additional dose is about 60 μg or 90 μg.

Embodiment 351. The method of embodiment 349 or embodiment 350, wherein the second dose is administered after a period of about 2 hours.

Embodiment 352. The method of any one of embodiments 342-351, wherein the patient is in a fed state.

Embodiment 353. The method of any one of embodiments 342-351, wherein the patient is in a fasted state.

Embodiment 354. The method of any one of embodiments 342-353, wherein agitation is significantly reduced within about 2 hours of administering the composition, as measured by a mean change in Positive and Negative Syndrome Scale Excited Component (PEC) scores relative to baseline.

Embodiment 355. The method of embodiment 354, wherein the agitation is significantly reduced within about 30 minutes to about 1 hour.

Embodiment 356. The method of embodiment 354 or embodiment 355, wherein the patient experiences ≥40% decrease from baseline in PEC score.

Embodiment 357. The method of embodiment 356, wherein the patient experiences ≥60% decrease from baseline in PEC score.

Embodiment 358. The method of any one of embodiments 354-357, wherein the PEC score is ≥30% lower than placebo.

Embodiment 359. The method of embodiment 358, wherein the PEC score is 60% lower than placebo.

Embodiment 360. The method of any one of embodiments 354-359, wherein the mean change in PEC score is greater than −4 (i.e. a decrease of 4 or more points) relative to baseline within 2 hours of administering the composition.

Embodiment 361. The method of embodiment 360, wherein mean change in PEC score is greater than −6 relative to baseline within 2 hours of administering the composition.

Embodiment 362. The method of embodiment 360, wherein mean change in PEC score is greater than −8 relative to baseline within 2 hours of administering the composition.

Embodiment 363. The method of any one of embodiments 354-362, wherein the decrease in PEC score is maintained for at least six hours following administration of the composition.

Embodiment 364. The method of any one of embodiments 354-363, wherein the mean change in PEC score is greater than or equal to −8 and is maintained from 2 hours post administration up to at least about 6 hours following administration of the composition.

Embodiment 365. The method of any one of embodiments 342-364, wherein the subject is treated without experiencing significant sedation.

Embodiment 366. The method of any one of embodiments 342-365, wherein the subject is treated without experiencing clinically significant cardiovascular effects.

Embodiment 367. The method of any one of embodiments 342-366 wherein two or more of the pharmacokinetic parameters are present.

Embodiment 368. The method of any one of embodiments 342-367, wherein all three of the pharmacokinetic parameters are present.

Embodiment 369. The method of any one of embodiments 342-368, wherein the mean $C_{max}$ is within the range of about 80% to about 125% of about 440 ng/L.

Embodiment 370. The method of embodiment 369, wherein the mean $C_{max}$ is about 440 ng/L Embodiment 371. The method of any one of embodiments 342-370, wherein administration of a single dose provides a mean $AUC_{0-inf}$ within the range of about 80% to about 125% of about 3800 ng*h/L.

Embodiment 372. The method of embodiment 371, wherein the mean about 3800 ng*h/L.

Embodiment 373. The method of any one of embodiments 342-372 wherein administration of a single dose provides a mean $T_{max}$ within the range of about 80% to about 125% of about 2 hours.

Embodiment 374. The method of embodiment 373, wherein the mean $T_{max}$ is about 2 hours.

Embodiment 375. The method of any one of embodiments 342-374, wherein the pharmacokinetic parameters are non-steady state.

Embodiment 376. The method of any of the preceding embodiments, wherein agitation is reduced to a 1 (very much improved) or 2 (much improved) within 2 hours of administering the composition, as measured by the Clinical Global Impression-Improvement Scale.

Embodiment 377. The method of embodiment 376, wherein the agitation is reduced within about 30 minutes to about 1 hour.

Embodiment 378. The method of embodiment 377, wherein the agitation is reduced within about 30 minutes.

Embodiment 379. The method of any one of embodiments 376-378, wherein the reduction in agitation is reduced to a 1 (very much improved).

Embodiment 380. The method of embodiment any one of embodiments 376-379, wherein the reduction in agitation is maintained for greater than about 2 hours.

Embodiment 381. The method of any one of embodiments 376-380, wherein the reduction in agitation is maintained for greater than about 4 hours.

Embodiment 382. The method of any one of embodiments 376-381, wherein the reduction in agitation is maintained for greater than about 6 hours.

Embodiment 383. The method of any one of embodiments 376-382, wherein the reduction in agitation is maintained for greater than about 8 hours.

Embodiment 384. The method of any one of embodiments 376-383, wherein the composition comprises 120 μg of dexmedetomidine.

Embodiment 385. The method of any one of embodiments 376-383, wherein the composition comprises 180 μg of dexmedetomidine.

Embodiment 386. The method of any one of embodiments 376-385, wherein the patient has schizophrenia.

Embodiment 387. The method of any one of embodiments 376-386, wherein the patient has bipolar disorder.

Embodiment 388. The method of any of the preceding embodiments, wherein agitation is reduced to a 3 (mild agitation) or 4 (normal behavior) within 2 hours of administering the composition, as measured by the Agitation-Calmness Evaluation Scale (ACES).

Embodiment 389. The method of embodiment 388, wherein the agitation is reduced within about 30 minutes to about 1 hour.

Embodiment 390. The method of embodiment 388 or embodiment 389, wherein the reduction in agitation is reduced to a 4 (normal behavior).

Embodiment 391. The method of any one of embodiments 388-390, wherein the reduction in agitation is maintained for greater than about 2 hours.

Embodiment 392. The method of any one of embodiments 388-391, wherein the reduction in agitation is maintained for greater than about 4 hours.

Embodiment 393. The method of any one of embodiments 388-392, wherein the reduction in agitation is maintained for greater than about 6 hours.

Embodiment 394. The method of any one of embodiments 388-393, wherein the reduction in agitation is maintained for greater than about 8 hours.

Embodiment 395. The method of any one of embodiments 388-394, wherein the composition comprises 120 μg of dexmedetomidine.

Embodiment 396. The method of any one of embodiments 388-394, wherein the composition comprises 180 μg of dexmedetomidine.

Embodiment 397. The method of any one of embodiments 388-396, wherein the patient has schizophrenia.

Embodiment 398. The method of any one of embodiments 388-397, wherein the patient has bipolar disorder.

Embodiment 399. The method of any of the preceding embodiments, wherein the patient experiences a ≥40 reduction in agitation, as measured by the PEC Scale.

Embodiment 400. The method of embodiment 399, wherein the agitation is reduced within about 30 minutes to about 1 hour.

Embodiment 401. The method of embodiment 399 or embodiment 400, wherein the patient experiences a ≥60 reduction in agitation.

Embodiment 402. The method any one of embodiments 399-401, wherein the patient experiences a ≥80 reduction in agitation.

Embodiment 403. The method of any one of embodiments 399-402, wherein the reduction in agitation is maintained for greater than about 2 hours.

Embodiment 404. The method of any one of embodiments 399-403, wherein the reduction in agitation is maintained for greater than about 4 hours.

Embodiment 405. The method of any one of embodiments 399-404, wherein the reduction in agitation is maintained for greater than about 6 hours.

Embodiment 406. The method of any one of embodiments 399-405, wherein the reduction in agitation is maintained for greater than about 8 hours.

Embodiment 407. The method of any one of embodiments 399-406, wherein the composition comprises 120 µg of dexmedetomidine.

Embodiment 408. The method of any one of embodiments 399-406, wherein the composition comprises 180 µg of dexmedetomidine.

Embodiment 409. The method of any one of embodiments 399-408, wherein the patient has schizophrenia.

Embodiment 410. The method of any one of embodiments 399-409, wherein the patient has bipolar disorder.

Embodiment 411. A method of achieving a PEC score reduction in agitation for a sustained period of time in a subject with bipolar or schizophrenic subject comprising administering to the subject a pharmaceutical composition comprising dexmedetomidine or a pharmaceutically acceptable salt thereof at a dose of about 120 mcg to about 180 mcg wherein the PEC score reduction is about −8 to about −10 and wherein the sustained period is about 2 hours to about 6 hours.

Embodiment 412. The method of embodiment 411, wherein the composition comprises dexmedetomidine hydrochloride.

Embodiment 413. The method of embodiment 411 or 412, comprising dexmedetomidine or a pharmaceutically acceptable salt thereof at a dose of about 120 mcg.

Embodiment 414. The method of embodiment 411 or 412, comprising dexmedetomidine or a pharmaceutically acceptable salt thereof at a dose of about 180 mcg.

Embodiment 415. The method according to any one of embodiments 411 to 414, wherein the sustained period is about 4 hours.

Embodiment 416. The method according to embodiment 415, wherein the sustained period is about 6 hours.

Embodiment 417. The method according to any one of embodiments 411-416, wherein the PEC score reduction is about −10.

Embodiment 418. A method of achieving an ACES score improvement for a sustained period of time in a subject with bipolar or schizophrenic subject comprising administering to the subject a pharmaceutical composition comprising dexmedetomidine or a pharmaceutically acceptable salt thereof at a dose of about 120 mcg to about 180 mcg wherein the ACES score is improved to about 3 to about 4 and wherein the sustained period is about 2 hours to about 6 hours.

Embodiment 419. The method of embodiment 418, wherein the composition comprises dexmedetomidine hydrochloride.

Embodiment 420. The method of embodiment 418 or 419, comprising dexmedetomidine or a pharmaceutically acceptable salt thereof at a dose of about 120 mcg.

Embodiment 421. The method of embodiment 418 or 419, comprising dexmedetomidine or a pharmaceutically acceptable salt thereof at a dose of about 180 mcg.

Embodiment 422. The method according to any one of embodiments 418 to 421, wherein the sustained period is about 4 hours.

Embodiment 423. The method according to embodiment 422, wherein the sustained period is about 6 hours.

Embodiment 424. The method according to any one of embodiments 418-423, wherein the ACES score is about 4.

Embodiment 425. A method of achieving an CGI-I score improvement for a sustained period of time in a subject with bipolar or schizophrenic subject comprising administering to the subject a pharmaceutical composition comprising dexmedetomidine or a pharmaceutically acceptable salt thereof at a dose of about 120 mcg to about 180 mcg wherein the CGI-I score is improved to about a 1 (very much improved) or about a 2 (much improved) and wherein the sustained period is about 2 hours to about 6 hours.

Embodiment 426. The method of embodiment 425, wherein the composition comprises dexmedetomidine hydrochloride.

Embodiment 427. The method of embodiment 425 or 426, comprising dexmedetomidine or a pharmaceutically acceptable salt thereof at a dose of about 120 mcg.

Embodiment 428. The method of embodiment 425 or 426, comprising dexmedetomidine or a pharmaceutically acceptable salt thereof at a dose of about 180 mcg.

Embodiment 429. The method according to any one of embodiments 425 to 428, wherein the sustained period is about 4 hours.

Embodiment 430. The method according to embodiment 425, wherein the sustained period is about 6 hours.

Embodiment 431 The method according to any one of embodiments 425-430, wherein the CGI-I score is about 1.

Embodiment 432. The method of any one of embodiments 110 to 112, wherein each water-soluble polymer is hydroxypropyl cellulose.

Embodiment 433. The method of any one of embodiments 103 to 113, wherein the dexmedetomidine or a pharmaceutically acceptable salt thereof is dexmedetomidine hydrochloride.

Embodiment 434. The method of any relevant preceding embodiments, wherein dexmedetomidine hydrochloride is administered as a film, wherein said film is a self-supporting, dissolvable, film, comprising:
(a) a composition comprising:
  (i) dexmedetomidine hydrochloride;
  (ii) hydroxypropyl cellulose (40,000 MW); and
  (iii) hydroxypropyl cellulose (140,000 MW); and
(b) a film substrate comprising:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
    wherein the composition of part (a) is present on the surface of the film substrate (b).

Embodiment 435. The method of any relevant preceding embodiment, wherein dexmedetomidine hydrochloride thereof is administered as a film, wherein said film is a self-supporting, dissolvable, film, comprising:
(a) a composition consisting essentially of:
  (i) dexmedetomidine hydrochloride;
  (ii) hydroxypropyl cellulose (40,000 MW); and
  (iii) hydroxypropyl cellulose (140,000 MW); and
(b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b).

Embodiment 436. The method of embodiment 434 or embodiment 435, wherein dexmedetomidine hydrochloride is present at about 0.1% to about 0.2% w/w of the total film weight, hydroxypropyl cellulose (40,000 MW) is present at about 4% to about 6% w/w of the total film weight, hydroxypropyl cellulose (140,000 MW) is present at about 4% to about 6% w/w of the total film weight, hydroxypropyl cellulose (370,000 MW) is present at about 27% to about 30% w/w of the total film weight, and polyethylene oxide (600,000 MW) is present at about 55% to about 60% w/w of the total film weight.

Embodiment 437. A self-supporting, dissolvable, film, comprising:

(a) a composition consisting essentially of:
  (i) about 180 μg of dexmedetomidine hydrochloride;
  (ii) hydroxypropyl cellulose (40,000 MW); and
  (iii) hydroxypropyl cellulose (140,000 MW); and (b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
    wherein the composition of part (a) is present on the surface of the film substrate (b).

Embodiment 438. The film of embodiment 437 wherein dexmedetomidine hydrochloride is present at about 0.1% to about 0.2% w/w of the total film weight, hydroxypropyl cellulose (40,000 MW) is present at about 4% to about 6% w/w of the total film weight, hydroxypropyl cellulose (140,000 MW) is present at about 4% to about 6% w/w of the total film weight, hydroxypropyl cellulose (370,000 MW) is present at about 27% to about 30% w/w of the total film weight, and polyethylene oxide (600,000 MW) is present at about 55% to about 60% w/w of the total film weight.

Embodiment 439. A self-supporting, dissolvable, film, comprising:

(a) a composition consisting essentially of:
  (i) about 120 μg of dexmedetomidine hydrochloride;
  (ii) hydroxypropyl cellulose (40,000 MW); and
  (iii) hydroxypropyl cellulose (140,000 MW); and (b) a film substrate consisting essentially of:
  (i) hydroxypropyl cellulose (40,000 MW);
  (ii) hydroxypropyl cellulose (140,000 MW);
  (iii) hydroxypropyl cellulose (370,000 MW); and
  (iv) polyethylene oxide (600,000 MW);
wherein the composition of part (a) is present on the surface of the film substrate (b).

Embodiment 440. The film of embodiment 439 wherein dexmedetomidine hydrochloride is present at about 0.1% to about 0.2% w/w of the total film weight, hydroxypropyl cellulose (40,000 MW) is present at about 4% to about 6% w/w of the total film weight, hydroxypropyl cellulose (140,000 MW) is present at about 4% to about 6% w/w of the total film weight hydroxypropyl cellulose (370,000 MW) is present at about 27% to about 30 w/w of the total film weight, and polyethylene oxide (600,000 MW) is present at about 55% to about 60% w/w of the total film weight.

Embodiment 441. The method of any of relevant preceding embodiments, where dexmedetomidine or a pharmaceutically acceptable salt thereof is administered as a sublingual spray, sublingual drop, sublingual gel, buccal tablet or sublingual tablet as embodied in table 1, table 2, table 3, table 4 or table 5 respectively.

Example 1: Dexmedetomidine Sublingual Film Formulation

TABLE 6

Dexmedetomidine deposited on the surface of a polymer matrix film composition

| Ingredients | Concentration g/100 g (10 μg film) | Concentration g/100 g (20 μg film) | Function |
| --- | --- | --- | --- |
| Drug-containing composition | | | |
| Dexmedetomidine hydrochloride | 0.136 | 0.267 | Active agent |
| Hydroxypropyl cellulose, HPC-SSL (MW = 40,000) | 0.301 | 0.593 | Film former |
| Hydroxypropyl cellulose (MW = 140,000) | 0.301 | 0.593 | Film former |
| FD&C Blue #1 Granular | 0.002 | 0.004 | Color |
| Ethyl Alcohol as a solvent | qs | qs | Solvent |
| Polymer matrix composition | | | |
| Hydroxypropyl cellulose (MW = 140,000) | 4.803 | 4.768 | Film former |
| Hydroxypropyl cellulose, HPC-SSL (MW = 40,000) | 4.803 | 4.768 | Film former |
| Hydroxypropyl cellulose (MW = 370,000) | 28.809 | 28.601 | Film former |
| Fast Emerald Green Shade (NO. 06507) | 0.129 | 0.128 | Color |
| Sucralose, USP-NF Grade | 0.993 | 0.985 | Sweetener |
| Peppermint Oil, NF | 2.104 | 2.089 | Flavor |
| Polyethylene oxide (Sentry Polyox WSR 205 LEO NF) (MW = 600,000) | 57.618 | 57.202 | Film former & Mucoadhesive |
| Water as a solvent | qs | qs | Solvent |

(A) Process for the Preparation of Polymer Matrix:

Polymer mixture: Polyethylene oxide and fast emerald green shade were mixed in water for at least 180 minutes at about 1400 rpm to about 2000 rpm. Sucralose, hydroxypropyl cellulose (molecular weight 140K), hydroxypropyl cellulose, HPC-SSL (molecular weight 40K) and hydroxypropyl cellulose (molecular weight 370K) were added and mixed for at least 120 minutes at about 1600 rpm to 2000 rpm. Peppermint Oil was added to water and the resultant dispersion was then added to the polymer mixture and mixed for at least 30 minutes. The resultant mixture was further mixed under vacuum (248 torr) for at least for 30 minutes at a speed of 350 rpm and at temperature of 22.9° C.

Coating station: A roll was placed on an unwind stand and the leading edge was thread through guide bars and coating bars. The silicone-coated side of the liner was placed faced up. A gap of 40 millimeters was maintained between the coating bars. The oven set point was adjusted to 70° C. and the final drying temperature was adjusted to 85° C.

Coating/drying process: The polymer mixture was poured onto the liner between the guide bars and the coating bars. The liner was pulled slowly through the coating bar at a constant speed by hand until no liquid was remained on the coating bars. The liner was cut to approximately 12-inch length hand sheets using a safety knife. Each hand sheet was placed on a drying board and was tapped on the corners to prevent curl during drying. The hand sheets were dried in the oven until the moisture content was less than 5% (approximately 30 minutes) and then removed from the drying board.

The coating weights were checked against the acceptance criteria, and if met, the hand sheets were then stacked and placed in a 34 inch×40 inch foil bag that was lined with PET release liner.

(B) Process for the Preparation of Deposition Solution:

FDC blue was dissolved in ethyl alcohol for at least 180 minutes. Dexmedetomidine hydrochloride was added to the ethyl alcohol solution with continuous stirring for 10 minutes at about 400 rpm to about 800 rpm. Hydroxypropyl cellulose (40K) and hydroxypropyl cellulose (140K) were added to the mixture, and stirred for at least 30 minutes until all the materials were dissolved.

(C) Process for the Preparation of Micro-Deposited Matrix:

The deposition solution obtained in Step (B) above was filled into a pipette to the required volume (determined according to the specific drug product strength of the final product). An appropriate amount (1.5 microliters= approximately 5 μg) of the deposition solution were deposited (e.g. as droplets) onto the polymer matrix obtained in Step (A), and repeated to a total of 10 times (i.e. 10 deposits/droplets) with space between each deposit to prevent merging of the deposits/droplets and allow subsequent cutting of the film into individual drug-containing units. The film was initially die cut in individual units with dimensions of 22 mm×8.8 mm containing a single deposit of the drug-containing composition. The die cut micro-deposited matrixes were then dried in an oven for 70° C. for 10 minutes and further die cut into 10 units with each unit containing a single deposit of the drug-containing composition.

(D) Packaging:

Each defect-free unit was sealed individually into a foil pouch, which was then heat sealed. If the heat seal was acceptable the package was considered as an acceptable unit for commercial use.

Other unit strengths (e.g. 40 μg and 60 μg films) were similarly prepared by varying the concentrations of drug, polymers and colorant within the drug-containing composition. For example, the 40 μg and 60 μg, films were prepared from drug-containing compositions containing, respectively, approximately 2× and 3×, the amounts of drug, polymers and colorant that appear in the 20 μg drug-containing composition described in table 6 above.

Example 2

TABLE 7

Dexmedetomidine deposited on the surface of a polymer matrix film composition

| Ingredients | Concentration mg/unit (80 μg film) | Concentration mg/unit (120 μg film) | Concentration mg/unit (180 μg film) | Function |
| --- | --- | --- | --- | --- |
| Drug-containing composition | | | | |
| Dexmedetomidine hydrochloride | 0.0945 | 0.142 | 0.213 | Active agent |
| Hydroxypropyl cellulose, HPC-SSL (MW = 40,000) | 0.0812 | 0.122 | 0.183 | Film former |
| Hydroxypropyl cellulose (MW = 140,000) | 0.0812 | 0.122 | 0.183 | Film former |
| FD&C Blue #1 Granular | 0.0008 | 0.001 | 0.002 | Color |
| Ethyl Alcohol as a solvent | q.s | q.s. | q.s. | Solvent |
| Polymer matrix composition | | | | |
| Hydroxypropyl cellulose (MW = 140,000) | 0.627 | 0.627 | 0.627 | Film former |
| Hydroxypropyl cellulose, HPC-SSL (MW = 40,000) | 0.627 | 0.627 | 0.627 | Film former |
| Hydroxypropyl cellulose (MW = 370,000) | 3.763 | 3.763 | 3.763 | Film former |
| Fast Emerald Green Shade (NO. 06507) | 0.017 | 0.017 | 0.017 | Color |
| Sucralose, USP-NF Grade | 0.130 | 0.130 | 0.130 | Sweetener |
| Peppermint Oil, NF | 0.275 | 0.275 | 0.275 | Flavor |
| Polyethylene oxide (Sentry Polyox WSR 205 LEO NF) (MW = 600,000) | 7.526 | 7.526 | 7.526 | Film former & Mucoadhesive |
| Water as a solvent | qs | qs | qs | Solvent |

The formulations (80 μg, 120 μg and 180 jpg) in table 7 were prepared using the same manufacturing process as described above in Example 1.

Example 3: A Phase Ib Multicenter, Randomized, Double-Blind, Placebo-Controlled, Multiple Ascending Dose Study to Determine Efficacy, Pharmacokinetics and Safety of Dexmedetomidine Hydrochloride Sublingual Film in Treating Agitation Associated with Schizophrenia Primary Objective:

To determine the doses of dexmedetomidine hydrochloride sublingual film needed to effectively reduce symptoms of acute agitation associated with schizophrenia, schizoaffective disorder or schizophreniform disorder assessed using the Positive and Negative Syndrome Scale-Excited Component (PEC) change from baseline after drug treatment.

Secondary Objective:

Determine PK, safety and tolerability of the various film strengths of dexmedetomidine hydrochloride sublingual film in patients with acute agitation associated with schizophrenia, schizoaffective disorder or schizophreniform disorder.

1. Describe overall clinical improvement after drug administration by Clinical Global Impression-Improvement scale (CGI-I).
2. Describe the duration of calming effect as measured by PEC and ACES.
3. Determine the safety profile of dexmedetomidine hydrochloride sublingual film as measured by vital signs and reports of adverse events.
4. Describe the overall tolerability in terms of adverse event reports and local site (oral/sublingual) tolerability of the sublingual film.
5. Describe the pharmacokinetics of dexmedetomidine hydrochloride sublingual film in the patient population.
6. Visual Analog Scales (VAS) to capture subject's opinion on taste and acceptability as well as questions regarding likability of study medication.

Methodology: This was a two-stage adaptive Phase Ib trial design. It was a randomized, double-blind, placebo-controlled, multiple ascending dose study assessing efficacy, pharmacokinetics, safety and tolerability of dexmedetomidine hydrochloride sublingual film dosing in adult (18-65 years old) males and females with acute agitation associated with schizophrenia, schizoaffective disorder, or schizophreniform disorder.

The first stage was designed to characterize a safe and tolerable dose range which produced a calming effect as measured using the PEC total score. The second stage was designed to enroll a total of 40 subjects per dose group in a three-arm placebo-controlled design to better characterize the broader range of safety and tolerability as well as better estimate variability (effect size).

Adaptive evaluation of escalating dose regimens of 20 µg, 60 µg and 120 µg were performed for the first stage, with an option to test a different dose should a safety or tolerability signal be observed. Male and female adults with acute agitation associated with schizophrenia, schizoaffective disorder, or schizophreniform disorder were enrolled in each cohort. Investigators were permitted to repeat dosing 1 hour after administration if there was a lack of significant efficacy (PEC change from baseline ≤40%) (maximum number of doses per subject was 2) and in the absence of safety concerns.

Blinded periodic safety data reviews were undertaken after completion of dosing each cohort to review all safety data as it became available. Dose escalation was allowed unless a safety or tolerability issue became evident upon periodic regular safety reviews. Based upon blinded analyses of the safety and tolerability of all subject cohorts, additional doses were selected.

Eligible subjects (acutely agitated subjects with schizophrenia, schizoaffective, or schizophreniform disorder) were identified in outpatient clinics, mental health, psychiatric or medical emergency services including medical/psychiatric observation units, or as newly admitted to a hospital setting for acute agitation or already in hospital for chronic underlying conditions. Subjects were domiciled in a clinical research setting or hospitalized to remain under medical supervision while undergoing screening procedures to assess eligibility.

Upon confirmation of eligibility, subjects were randomized to dexmedetomidine hydrochloride sublingual film or placebo film. At the beginning of each study session, a single dose of dexmedetomidine hydrochloride sublingual film was self-administered sublingually, after training with a placebo film and under the supervision of an unblinded staff who did not participate in evaluation of safety or efficacy. The drug film was retained in the sublingual (SL) cavity until dissolved. Participants were also evaluated for local irritation around the area where the film was placed. Efficacy and safety assessments were conducted periodically before and after dosing. If reduction in PEC was less than or equal to 40% one hour after the first administration, the investigator could administer a second dose of dexmedetomidine hydrochloride sublingual film (of the same randomized dose) with an additional PEC assessment completed at 1.5 hr post-dose. All efforts were made to have the patient perform all assessments as per protocol. However, should the patient's situation warrant it, standard of care treatment was initiated, preferably after the 4 hr assessments were completed. In Stage 1 each cohort included 27 subjects randomized 2:1 to dexmedetomidine hydrochloride sublingual film or placebo film (i.e. 18 received dexmedetomidine hydrochloride sublingual film and 9 received placebo film). Three doses were initially planned (total of 81 subjects). Per protocol, different or additional doses could be tested based on ongoing safety reviews, and two additional dose levels were tested: 80 µg and 180 µg (Table 8).

Efficacy Assessments:

The efficacy of dexmedetomidine hydrochloride sublingual film on reducing acute agitation was assessed using the Positive and Negative Syndrome Scale-Excited Component (PEC) scale which was performed at screening, baseline (i.e. also referred to as pre-dose) and at 10, 20, 30, 45 min; 1, 1.5, 2, 4, 6 and 24 hours post the first dose.

Overall agitation and sedation were evaluated with the Agitation-Calmness Evaluation Scale (ACES), which was performed at baseline (pre-dose) and at 2 and 4 hours post-first dose.

The change in agitation in response to treatment was also measured by the Clinical Global Impressions-Improvement (CGI-I), performed at 1, 2 and 4 hours post the first dose.

Safety and Tolerability Assessments:

AEs, clinical laboratory tests, electrocardiogram (ECG) with rhythm strip, and vital signs were monitored for tolerability assessment. All observed and volunteered AEs were recorded. The relationship of AEs to the study drugs was graded as not related, unlikely/remotely related, possibly related, probably related or definitely related by the investigators.

Resting vital signs including systolic blood pressure (SBP), diastolic blood pressure (DBP), and heart rate, as well as ECG were measured at prior to the PK assessments. Resting vital signs (SBP, DBP and HR) were taken at screening, baseline (pre-dose) and at 30 min, 1, 2, 4 and 8 hours post-first dose. Orthostatic measurements which included (SBP, DBP, HR, respiratory rate and temperature) were taken at screening, pre-dose, 2, 4 and 24 hours post-first dose. ECGs were conducted at screening, baseline (pre-dose), 2 and 24 hours post-first dose. The application site of the SL preparation (buccal mucosa) were also inspected for any signs of local irritation.

Safety and tolerability assessments were continued until the morning of Day 3 (day of discharge) and were repeated on Day 7(+2). AEs evaluation were conducted at screening, baseline (pre-dose), 2 hours, Day 3 and Day 7(+2) post-the first dose. Safety Labs including chemistry, hematology, urinalysis, UDS, alcohol breathalyzer, and urine pregnancy were performed at screening, Day 3 and Day 7(+2).

Any abnormal vital sign measurement, clinical laboratory test, physical examination finding, or ECG parameter deemed clinically significant by the investigator was repeated, including test results obtained on the final study day or upon early termination. For any test abnormality deemed clinically significant, repeat analysis was performed during the follow-up period and until the value returned to baseline (or within normal limits) or the investigator deemed the abnormality to be stable and no longer of clinical concern.

Three analysis populations were defined for the study.

Safety Population: All subjects who receive study drug

Intent to treat (ITT) Population: All subjects in the Safety Population who have a PEC Score Per Protocol (PP) Population: All subjects in the ITT Population with no major protocol deviations Subjects were on a range of typically prescribed antipsychotics.

TABLE 8

Arms and Interventions

| Arms | Intervention |
|---|---|
| Placebo Comparator: Placebo Sublingual Film with no active drug; single administration | Drug: Placebo film Placebo film for dexmedetomidine hydrochloride |
| Experimental: 20 µg Sublingual Film containing 20 µg dexmedetomidine; single administration with repeat dose after 1 hour | Drug: Sublingual film containing dexmedetomidine hydrochloride Administration: Sublingual film containing dexmedetomidine for the treatment of agitation associated with Schizophrenia |

TABLE 8-continued

Arms and Interventions

| Arms | Intervention |
|---|---|
| Experimental: 60 µg Sublingual Film containing 60 µg dexmedetomidine; single administration | Drug: Sublingual film containing dexmedetomidine hydrochloride. Administration: Sublingual film containing dexmedetomidine for the treatment of agitation associated with Schizophrenia |
| Experimental: 80 µg Sublingual Film containing 80 µg dexmedetomidine; single administration | Drug: Sublingual film containing dexmedetomidine hydrochloride. Administration: Sublingual film containing dexmedetomidine for the treatment of agitation associated with Schizophrenia |
| Experimental: 120 µg 2 Sublingual Films, each containing 60 µg dexmedetomidine; single administration of 2 films | Drug: Sublingual film containing dexmedetomidine hydrochloride. Administration: Sublingual film containing dexmedetomidine for the treatment of agitation associated with Schizophrenia |
| Experimental: 180 µg 3 Sublingual Films, each containing 60 µg dexmedetomidine; single administration of 3 films | Drug: Sublingual film containing dexmedetomidine hydrochloride. Administration: Sublingual film containing dexmedetomidine for the treatment of agitation associated with Schizophrenia |

Number of Subjects (Planned and Analyzed):

An estimated 81 subjects in Stage 1 were planned in 3 cohorts (27 per cohort), however including the 2 additional cohorts (80 µg and 180 µg dexmedetomidine hydrochloride sublingual films), a total of 135 subjects were enrolled in 5 cohorts and analyzed.

Diagnosis and Main Criteria for Eligibility:

Inclusion Criteria:
1. Male and female patients between the ages of 18 to 65 years, inclusive.
2. Patients who had met Diagnostic and Statistical Manual of Mental Disorders, Fifth Edition (DSM-5) criteria for schizophrenia, schizoaffective, or schizophreniform disorder.
3. Patients who were judged to be clinically agitated at screening and baseline (pre-dose with a total score of ≥14 on the 5 items (poor impulse control, tension, hostility, uncooperativeness, and excitement) comprising the PANSS Excited Component (PEC).
4. Patients who have a score of ≥4 on at least 1 of the 5 items on the PEC at baseline (pre-dose).
5. Patients who read, understood and provide written informed consent.
6. Patients who were in good general health prior to study participation as determined by a detailed medical history, physical examination, 12-lead ECG with rhythm strip, blood chemistry profile, hematology, urinalysis and in the opinion of the Principal Investigator.
7. Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that could be used by the participant and/or his/her partner include abstinence, birth control pills or patches, diaphragm with spermicide, intrauterine device (IUD), condom with foam or spermicide, vaginal spermicidal suppository, surgical sterilization and progestin implant or injection. Prohibited methods include: the rhythm method, withdrawal, condoms alone, or diaphragm alone.

Exclusion Criteria:
1. Patients with agitation caused by acute intoxication, including positive identification of alcohol by breathalyzer or drugs of abuse or non-prescription drugs (with the exception of tetrahydrocannabinol (THC)) during urine screening.
2. Patients treated within 4 hours prior to study drug administration with benzodiazepines, other hypnotics or oral or short-acting intramuscular antipsychotics.
3. Treatment with alpha-1 noradrenergic blockers (terazosin, doxazosin, tamsulosin, and alfuzosin, and prazocin) or other prohibited medications.
4. Patients with significant risk of suicide or homicide per the investigator's assessment, or any suicidal behaviour in last 6 months prior to screening.
5. Female patients who had a positive pregnancy test at screening or were breastfeeding.
6. Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
7. History of syncope or other syncopal attacks, current evidence of hypovolemia, orthostatic hypotension, a screening heart rate of <55 beats per minutes (bpm) or systolic blood pressure (SBP)<110 mmHg or diastolic blood pressure (DBP)<70 mmHg.
8. Patients with laboratory or ECG abnormalities considered clinically significant by the investigator or qualified designee [Advanced heart block (second-degree or above atrioventricular block without pacemaker), diagnosis of Sick sinus syndrome] that would have clinical implications for the patient's participation in the study.
9. Patients with serious or unstable medical illnesses. These include current hepatic (moderate severe hepatic impairment), renal, gastroenterologic, respiratory, cardiovascular (including ischemic heart disease, congestive heart failure), endocrinologic, or hematologic disease.
10. Patients who had received an investigational drug within 30 days prior to the current agitation episode.
11. Patients who were unable to use the sublingual film or considered by the investigator, for any reason, to be an unsuitable candidate for receiving dexmedetomidine; e.g. patients with a history of allergic reactions to dexmedetomidine.

Test Product, Dose and Mode of Administration:

Dexmedetomidine sublingual film (formulation of Examples 1 and 2 above) was tested in a small, solid-dose film formulations with dimensions of approximately 193.6 mm2 in area and 0.7 mm thick designed to completely dissolve in the SL space within 2-3 minutes. Reference therapy, Dose and Mode of Administration:

Matching placebo films to be taken sublingually as described above.

Duration of Treatment: 1 day

Criteria for Evaluation: The primary endpoints in this study pertained to the efficacy, pharmacokinetics, safety, and tolerability of each dose level.

Efficacy: The efficacy of dexmedetomidine hydrochloride sublingual film on acute agitation was assessed using the Positive and Negative Syndrome Scale-Excited Component (PEC) scale. PEC comprised 5 items associated with agitation: poor impulse control, tension, hostility, uncooperativeness, and excitement; each scored 1 (minimum) to 7 (maximum). The PEC, the sum of these 5 subscales, thus ranging from 5 to 35.

Overall agitation and sedation were evaluated with the Agitation-Calmness Evaluation Scale (ACES), where 1 indicates marked agitation; 2—moderate agitation; 3—mild agitation; 4—normal behavior; 5—mild calmness; 6—moderate calmness, 7—marked calmness; 8—deep sleep; and 9—unarousable.

The change in agitation in response to treatment was also measured by the Clinical Global Impressions-Improvement (CGI-I). CGI-I scores range from 1 to 7: 0=not assessed (missing), 1=very much improved, 2=much improved, 3=minimally improved, 4=no change, 5=minimally worse, 6=much worse, 7=very much worse.

Pharmacokinetics:

Pharmacokinetic analysis was performed using dexmedetomidine plasma concentrations after administration of dexmedetomidine hydrochloride sublingual films. A dose proportionality analysis was conducted.

Safety and tolerability: AEs, clinical laboratory tests, ECG with rhythm strip, vital signs and signs of local irritation (buccal) were monitored for safety and tolerability.

Additional Assessments:
  Demographic Data
  Medical History
  Prior and Concomitant Medication
  Physical Examination and
  Pregnancy testing Statistical Analysis:

Efficacy Analyses: The primary efficacy endpoint of the study was the absolute change from baseline in PEC score at 120 mins (2 hours). The intent to treat population (ITT) was analyzed and consisted of all patients who took any study medication and who had both baseline and at least 1 efficacy assessment after dosing. Analyses were conducted using a restricted maximum likelihood repeated measures mixed model on change from baseline values with baseline as a covariate and timepoint, and its interaction with treatment groups as repeated measures using an unstructured covariance structure. Responder comparisons were made via Fisher's exact test.

Pharmacokinetic Analyses:

Pharmacokinetic analysis was conducted using a validated install of Phoenix® WinNonlin® version 8.1. Non-compartmental analysis was also conducted on the final audited data which consisted of a total of 135 participants in 5 cohorts receiving 20, 60, 80 (1×20 µg films and 1×60 µg films), 120 (2×60 µg films) and 180 µg (3×60 µg films) of dexmedetomidine sublingual films. All areas under the concentration-time curve (AUCs) were calculated using the linear trapezoidal method. Dose proportionality was assessed using a power model for PK parameters. Mean and individual concentration (sorted by dose level) versus time plots were generated.

Safety and Tolerability Analyses:

Safety data analysis was conducted on all subjects receiving at least 1 dose of study drug. The number and percentage of subjects experiencing 1 or more AEs were summarized by treatment, relationship to study drug, and severity. AEs were coded using Medical Dictionary for Regulatory Activities (Med DRA) terminology. Listings of subjects who experience withdrawal due to an AE, serious AEs and/or death were presented. Laboratory parameters were summarized by treatment using descriptive statistics and data listings of clinically significant abnormalities. Vital signs and ECG data were summarized by changes from baseline values at each dose level using descriptive statistics.

Sample Size Determination: The sample size is based on clinical experience and judgment relative to the study design and objectives in Stage 1. A sample size of at least 18 subjects on active drug in each dosing cohort should provide adequate clinical information to meet the objectives of the study.

All efficacy, safety, and tolerability measurements were conducted at regularly scheduled intervals as described in table 9.

TABLE 9

Schedule of Events

| | | | Treatment Evaluation Day 1 | | | | | | | | | |
|---|---|---|---|---|---|---|---|---|---|---|---|---|
| | Screening | Pre-Dose[1] | Post Dose Time[1] | | | | | | | | | |
| Activity Time point | Pre-treatment | −1 hr to time 0 | 10 min | 20 min | 30 min | 45 min | 1 hr | 1.5 hr | 2 hr | 4 hr | 6 hr | 8 hr |
| Informed Consent | X | | | | | | | | | | | |
| Medical History | X | | | | | | | | | | | |
| Demographics | X | | | | | | | | | | | |
| Weight | X | | | | | | | | | | | |
| Height | X | | | | | | | | | | | |
| BMI | X | | | | | | | | | | | |
| MINI | X | | | | | | | | | | | |
| PANSS[10] | | X | | | | | | | | | | X |
| Physical Exam | X | | | | | | | | | | | |
| Safety Labs[5] | X | | | | | | | | | | | |
| ECG with rhythm strip [9] | X | X | | | | | | X | | | | |
| Resting vital signs[2] | X | X | | | X | | X | | X | X | X | X |
| Orthostatic vital signs[2] | X | X | | | | | | | X | X | | X |
| Admit to Unit | X | | | | | | | | | | | |
| Training/Review of study drug administration | | X | | | | | | | | | | |
| Inclusion/Exclusion criteria | X | X | | | | | | | | | | |
| Randomization | | X | | | | | | | | | | |
| Study drug administration[8] | | X | | | | | | | | | | |
| PCRS[11] | X | X | | | | | | X | | | | |
| PEC[3] | X | X | X | X | X | X | X | X | X | X | X | X |
| ACES | | X | | | | | | | | X | X | |
| CGI-Severity[4] | X | X | | | | | | | | | | |
| CGI-Improvement[4] | | | | | | | X | | X | X | X | |
| C-SSRS | X | | | | | | | | | | | |

TABLE 9-continued

| Activity Time point | | | | | | | | | | | | | |
|---|---|---|---|---|---|---|---|---|---|---|---|---|---|
| Buccal (SL) assessment for local irritation[7] | | | | | | | X | | X | X | | | |
| Visual Analog Scales | | | | | X | | | | | | | | |
| Likability Question | | | | | X | | | | | | | | |
| PK Sampling[6] | | X | | | | | | X | X | X* | X | X | X |
| Concomitant Medications | X | X | | | | | | | | | | | |
| Adverse Events | X | X | X | X | X | X | X | X | X | X | X | X | |

Schedule of Events

Treatment Evaluation Day 2, 3 and 7

| Activity Time point | Screening Pre-treatment | Day 2 Follow-Up (+1) 24 hr (−9/+12 hr) | Day 3 Discharge | Day 7 (+2) End of Study |
|---|---|---|---|---|
| Informed Consent | X | | | |
| Medical History | X | | | |
| Demographics | X | | | |
| Weight | X | X | | |
| Height | X | | | |
| BMI | X | | | |
| MINI | X | | | |
| PANSS[10] | | X | | |
| Physical Exam | X | X | | |
| Safety Labs[5] | X | | X | X |
| ECG with rhythm strip [9] | X | X | | |
| Resting vital signs[2] | X | X | | |
| Orthostatic vital signs[2] | X | X | | |
| Admit to Unit | X | | | |
| Training/Review of study drug administration | | | | |
| Inclusion/Exclusion criteria | X | | | |
| Randomization | | | | |
| Study drug administration[8] | | | | |
| PCRS[11] | X | X | | |
| PEC[3] | X | X | | |
| ACES | | | | |
| CGI-Severity[4] | X | | | |
| CGI-Improvement[4] | | | | |
| C-SSRS | X | X | | |
| Buccal (SL) assessment for local irritation[7] | | X | | |
| Visual Analog Scales | | | | |
| Likability Question | | | | |
| PK Sampling[6] | | X | | |
| Concomitant Medications | X | X | X | X |
| Adverse Events | X | X | X | X |

Abbreviations: ACES = Agitation-Calmness Evaluation Scale; BMI = body mass index; CLIA = Clinical Laboratory Improvement Amendments; CGI-I = Clinical Global Impression-Improvement; CGI-S = Clinical Global Impression-Severity; C-SSRS = Columbia-Suicide Severity Rating Scale; DBP = diastolic blood pressure; ECG = electrocardiogram; MINI = Mini International Neuropsychiatric Interview; PANSS = Positive and Negative Syndrome Scale; PCRS = Placebo Control Reminder Script; PEC = Positive and Negative Syndrome Scale—Excited Component; PK = pharmacokinetic; SBP = systolic blood pressure; SL = sublingual; UDS = urine drug screen Notes to the Schedule of Events:

[1] Pre-dose assessments had a window of 60 minutes prior to first dose. Timing of all subsequent assessments was relative to the first dose. All post-dose assessments had a window of ±3 minutes until 2 hours and ±10 minutes until 8 hours.

[2] Resting vital signs (SBP, DBP and HR) will be taken at Screening, Pre-dose and at 30 min, 1, 2, 4 and 8 hours post first dose. Triplicate measurements were performed in case of Systolic BP <90 mmHg, Diastolic BP <60 mmHg or Pulse <60 bpm. Orthostatic measurements (SBP, DBP, HR, respiratory rate and temperature) were taken at Screening, Pre-dose, 2, 4 and 24 hours post first dose. Vital signs were done prior to each PK sample.

[3] PEC was performed at Screening, Pre-dose and at 10, 20, 30, 45 min; 1, 1.5, 2, 4, 6 and 24 hours post first dose.

[4] CGI-Severity was performed at Screening and pre-dose. CGI-Improvement was performed at 1, 2 and 4 hours post first dose. The PEC (preceded by the Placebo Control Reminder Script [PCRS], when required) was done prior to any other assessments.

[5] Safety Labs included chemistry, hematology, urinalysis, UDS (local lab)(only conducted at screening), alcohol breathalyzer (only conducted at screening), and urine pregnancy (only conducted at screening). Screening/enrollment labs: local labs drawn within 7 days prior to screening may suffice with the exception of urine drug screen. If results not available on the same day, a 'desktop' or non-CLIA test might be performed; to confirmed, results from a CLIA-certified laboratory should be recorded once available.

[6] PK blood samples were collected Predose (up to 15 min prior to first and, if applicable, second dose), 1, 1.5, 2, 4, 6, 8-10 hrs (collect one sample between 8 and 10 hours) and 24 hr after first dose. A sample may not be collected if the Physician indicates in source documents that the patient is in a mental state that was not conducive to PK sample collection. Non-compliance or refusal of all or any PK draw were exclusionary nor result in ET. All PK collections had a window of ±3 minutes with the exception of the 24 hour post-dose collection which had a window of ±1 hour.
*For re-dosed subjects only: PK blood sample was collected at 2.5 hrs post first dose in addition to the other times.

[7] Buccal exam (at 30 min ±15, and other times ±30 min) for local irritation performed by blinded staff. Day 2 follow up with +1 day window.

[8] In the investigator's clinical judgement the same randomized dose might be repeated at 1 hr if there was no clinical effect (PEC change from baseline ≤40%) and in the absence of safety concerns.

[9] ECG for pre-dose was not repeated if screening ECG was conducted on the day of dosing. ECGs collected following treatment were performed prior to PK assessments

[10] PANSS had administered at any time on the day of dosing prior to dosing and post-dose. Full PANSS was to be conducted in addition to stand alone PEC.

[11] PCRS was performed immediately prior to the PEC

Results Summary:

1. Data Sets Analyzed

The number of subjects in each dataset were the same for all 3 populations (ie, Safety. ITT and PP) (Table 10). Additionally, the number of subjects in each dataset were the same for the pharmacokinetic population, as all subjects provided blood samples for analysis.

TABLE 10

Summary of Datasets Analyzed

| Dataset | Placebo (N = 45) | Dexmedetomidine sublingual film | | | | | Overall (N = 135) |
|---|---|---|---|---|---|---|---|
| | | 20 μg (N = 18) | 60 μg (N = 18) | 80 μg (N = 18) | 120 μg (N = 18) | 180 μg (N = 18) | |
| Safety Population | 45 (100.0) | 18 (100.0) | 18 (100.0) | 18 (100.0) | 18 (100.0) | 18 (100.0) | 135 (100.0) |
| Intent-to-Treat Population | 45 (100.0) | 18 (100.0) | 18 (100.0) | 18 (100.0) | 18 (100.0) | 18 (100.0) | 135 (100.0) |
| Per-Protocol Population | 45 (100.0) | 18 (100.0) | 18 (100.0) | 18 (100.0) | 18 (100.0) | 18 (100.0) | 135 (100.0) |

Disposition:

A total of 135 subjects were enrolled and received study drug and comprised the Safety Population. Of the 135 subjects, all subjects completed the inpatient study drug treatment period: 127 subjects completed the end of the study period (i.e. study Day 7). Of the 8 subjects who did not complete the study, 7 subjects were lost to follow-up after discharge from the inpatient facility on study Day 3 and 1 subject withdrew from the study on study Day 3.

2. Demographics and Baseline Characteristics:

For subjects in the Safety Population (N=135), mean age was 47.6 years, the majority of subjects were male (65.9/6 [89/135]), and mean BMI was 30.58 kg/m2. Subjects were predominantly Black or African American (74.8% [101/135]) and not Hispanic or Latino (90.4% [122/135]). The majority of subjects in all treatment groups had a diagnosis of schizophrenia (assessed by the Mini-International Neuropsychiatric Interview [MINI-Plus] instrument). The proportion of subjects with schizophrenia ranged from 72.2% to 83.3% in the Dexmedetomidine sublingual film treatment groups. Based on MINI-Plus results, all subjects in the study met the inclusion criteria of having a diagnosis of schizophrenia, schizoaffective, or schizophreniform disorder (Table 11).

TABLE 11

Demographics and Baseline Characteristics

| Variable | Placebo (N = 45) | Dexmedetomidine sublingual film | | | | | Overall (N = 135) |
|---|---|---|---|---|---|---|---|
| | | 20 μg (N = 18) | 60 μg (N = 18) | 80 μg (N = 18) | 120 μg (N = 18) | 180 μg (N = 18) | |
| Age (years) | | | | | | | |
| Mean (SD) | 48.4 (10.88) | 50.1 (7.37) | 45.8 (10.87) | 50.2 (9.72) | 40.5 (8.40) | 49.1 (10.61) | 47.6 (10.26) |
| Median | 52.0 | 50.0 | 47.0 | 52.0 | 40.0 | 48.0 | 50.0 |
| Min-Max | 21, 63 | 29, 59 | 26, 63 | 26, 63 | 25, 54 | 26, 64 | 21, 64 |
| Gender, n % | | | | | | | |
| Male | 27 (60.0) | 9 (50.0) | 15 (83.3) | 13 (72.2) | 13 (72.2) | 12 (66.7) | 89 (65.9) |
| Female | 18 (40.0) | 9 (50.0) | 3 (16.7) | 5 (27.8) | 5 (27.8) | 6 (33.3) | 46 (34.1) |
| Race, n % | | | | | | | |
| Black or African American | 37 (82.2) | 13 (72.2) | 11 (61.1) | 12 (66.7) | 15 (83.3) | 13 (72.2) | 101 (74.8) |
| White | 7 (15.6) | 5 (27.8) | 7 (38.9) | 6 (33.3) | 2 (11.1) | 4 (22.2) | 31 (23.0) |
| Asian | 0 | 0 | 0 | 0 | 0 | 1 (5.6) | 1 (0.7) |
| Multiple | 1 (2.2) | 0 | 0 | 0 | 0 | 0 | 1 (0.7) |
| Unknown | 0 | 0 | 0 | 0 | 1 (5.6) | 0 | 1 (0.7) |
| Ethnicity, n % | | | | | | | |
| Not Hispanic or Latino | 44 (97.8) | 16 (88.9) | 15 (83.3) | 15 (83.3) | 16 (88.9) | 16 (88.9) | 122 (90.4) |
| Hispanic or Latino | 1 (2.2) | 2 (11.1) | 3 (16.7) | 3 (16.7) | 2 (11.1) | 2 (11.1) | 13 (9.6) |
| Height (cm) | | | | | | | |
| Mean (SD) | 171.15 (10.25) | 169.29 (10.63) | 174.08 (11.12) | 174.90 (10.66) | 175.33 (13.81) | 174.87 (8.95) | 172.85 (10.87) |
| Median | 169.00 | 170.30 | 174.05 | 175.90 | 175.70 | 175.25 | 173.00 |
| Min-Max | 149.9, 198.1 | 149.9, 188.0 | 150.5, 195.0 | 157.0, 198.1 | 137.0, 205.0 | 160.0, 188.4 | 137.0, 205.0 |

TABLE 11-continued

Demographics and Baseline Characteristics

| | | Dexmedetomidine sublingual film | | | | | |
|---|---|---|---|---|---|---|---|
| Variable | Placebo (N = 45) | 20 μg (N = 18) | 60 μg (N = 18) | 80 μg (N = 18) | 120 μg (N = 18) | 180 μg (N = 18) | Overall (N = 135) |
| Weight (kg) | | | | | | | |
| Mean (SD) | 86.86 (16.62) | 86.92 (18.83) | 94.89 (15.53) | 92.84 (19.77) | 90.54 (18.04) | 100.53 (19.10) | 91.05 (18.06) |
| Median | 84.10 | 82.50 | 97.10 | 91.95 | 90.80 | 100.45 | 91.00 |
| Min-Max | 56.8, 121.2 | 58.9, 119.6 | 64.9, 127.7 | 65.3, 133.6 | 57.2, 135.4 | 68.4, 143.2 | 56.8, 143.2 |
| Body Mass Index (kg/m$^2$) | | | | | | | |
| Mean (SD) | 29.74 (5.61) | 30.23 (5.37) | 31.45 (5.47) | 30.56 (7.02) | 29.81 (6.96) | 32.97 (6.47) | 30.58 (6.06) |
| Median | 29.27 | 29.58 | 31.09 | 30.03 | 29.08 | 32.56 | 29.40 |
| Min-Max | 17.9, 41.5 | 20.9, 40.3 | 22.5, 42.8 | 20.9, 44.5 | 18.3, 45.4 | 24.8, 45.4 | 17.9, 45.4 |

Abbreviations: cm = centimeter; kg = kilogram; max = maximum; min = minimum; SD = standard deviation; Percentages are based on the number of Safety Population subjects in each treatment arm.

3. Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 5 dose cohorts (20 μg, 60 μg, 80 μg, 120 μg and 180 μg) with 18 active patients (total of 90 patients) and 9 placebo patients (total of 45 patients) in each cohort. Active patients in each of the 5 dose cohorts were compared to placebo patients from all 5 cohorts (pooled placebo group). The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

The efficacy of dexmedetomidine hydrochloride sublingual film as measured by PEC reduction is dose-responsive and robust. The decrease from baseline in PEC score in the 180 μg dose group showed significant response with a −10.8 mean change from baseline (CFB) total PEC score at 2 hours post dosing compared to placebo (Table 12 and FIG. 1). Mean changes from baseline were −9.2 and −7.3 points, respectively for the 120 μg and 80 μg treatment groups, compared to placebo (−4.5 Mean change). LSM mean differences from placebo were −2.9 (P=0.0210), −4.6 (P=0.0003), and −6.3 (P<0.0001) for the 80 μg, 120 μg, and 180 μg treatment groups (table 11) Mean changes from baseline at 2 hours post dosing in the 20 μg and 60 μg groups were not significantly different than placebo. Additionally, as early onset of action is an important attribute for therapy in reducing agitation, the 180 μg group showed a statistically significant separation from placebo as early as 45 minutes post dosing (LS mean difference of −3.5 [P<0.0049]).

TABLE 12

Summary of Change from Baseline at all Timepoints in PANSS-PEC Total Score by Treatment Group (Intent to treat population)

| | | Dexmedetomidine Sublingual film | | | | |
|---|---|---|---|---|---|---|
| Time Point Statistics | Placebo (N = 45) | 20 μg (N = 18) | 60 μg (N = 18) | 80 μg (N = 18) | 120 μg (N = 18) | 180 μg (N = 18) |
| Baseline, n | | | | | | |
| Mean (SD) | 18.1 (2.37) | 17.5 (2.33) | 17.5 (2.07) | 17.4 (1.42) | 18.3 (1.64) | 18.3 (2.95) |
| 10 minutes post-dose | | | | | | |
| Mean (SD) | 16.0 (4.33) | 16.2 (2.86) | 15.1 (3.92) | 15.2 (3.26) | 17.8 (3.19) | 16.8 (4.26) |
| Change from baseline, mean (SD) | −2.1 (3.60) | −1.3 (1.67) | −2.4 (3.45) | −2.2 (3.01) | −0.6 (2.31) | −1.5 (2.68) |
| Change from baseline, LS mean (SE) | −2.1 (0.5) | −1.4 (0.7) | −2.5 (0.7) | −2.3 (0.7) | −0.5 (0.7) | −1.4 (0.7) |
| LSM difference (SE)[a] | | 0.7 (0.9) | −0.4 (0.9) | −0.2 (0.9) | 1.6 (0.9) | 0.7 (0.9) |
| 20 minutes post-dose | | | | | | |
| Mean (SD) | 15.2 (4.41) | 15.1 (2.88) | 14.1 (4.64) | 14.2 (3.81) | 15.8 (3.47) | 15.6 (4.12) |
| Change from baseline, mean (SD) | −2.9 (3.60) | −2.4 (2.33) | −3.4 (4.29) | −3.2 (3.89) | −2.5 (3.03) | −2.7 (2.72) |
| Change from baseline, LS mean (SE) | −2.9 (0.5) | −2.5 (0.8) | −3.5 (0.8) | −3.3 (0.8) | −2.4 (0.8) | −2.6 (0.8) |
| LSM difference (SE)[a] | | 0.4 (1.0) | −0.6 (1.0) | −0.4 (1.0) | 0.5 (1.0) | 0.2 (1.0) |
| 30 minutes post-dose | | | | | | |
| Mean (SD) | 14.8 (4.94) | 14.2 (2.79) | 13.1 (4.97) | 12.7 (3.82) | 15.0 (3.74) | 14.2 (4.48) |
| Change from baseline, mean (SD) | −3.3 (4.46) | −3.3 (3.07) | −4.4 (4.67) | 4.7 (3.82) | −3.3 (3.56) | −4.1 (3.26) |

TABLE 12-continued

Summary of Change from Baseline at all Timepoints in PANSS-PEC Total Score by Treatment Group (Intent to treat population)

| | | Dexmedetomidine Sublingual film | | | | |
|---|---|---|---|---|---|---|
| Time Point Statistics | Placebo (N = 45) | 20 µg (N = 18) | 60 µg (N = 18) | 80 µg (N = 18) | 120 µg (N = 18) | 180 µg (N = 18) |
| Change from baseline, LS mean (SE) | −3.2 (0.6) | 3.4 (0.9) | −4.5 (0.9) | −4.8 (0.9) | −3.2(0.9) | −4.0(0.9) |
| LSM difference (SE)[a] | | −0.2 (1.1) | −1.2 (1.1) | −1.5 (1.1) | 0.0 (1.1) | −0.7 (1.1) |
| 45 minutes post-dose | | | | | | |
| Mean (SD) | 14.5 (4.88) | 13.8 (3.15) | 12.4 (5.41) | 11.3 (4.80) | 13.3 (4.66) | 11.1 (5.08) |
| Change from baseline, mean (SD) | −3.6 (4.14) | −3.7 (2.83) | −5.1 (5.11) | −6.1 (5.13) | −5.1 (4.92) | −7.2 (4.73) |
| Change from baseline, LS mean (SE) | −3.6 (0.7) | −3.8 (1.0) | −5.2 (1.0) | −6.2 (1.0) | −5.0 (1.0) | −7.1 (1.0) |
| LSM difference (SE)[a] | | −0.2 (1.2) | −1.6 (1.2) | −2.6 (1.2) | −1.4 (1.2) | −3.5 (1.2) |
| 1 hour post-dose | | | | | | |
| Mean (SD) | 14.0 (4.65) | 13.0 (4.33) | 11.4 (5.40) | 10.9 (5.03) | 10.9 (5.29) | 9.2 (4.08) |
| Change from baseline, mean (SD) | −4.1 (4.29) | −4.5 (3.67) | −6.1 (5.49) | −6.5 (5.28) | −7.4 (5.48) | −9.1 (4.58) |
| Change from baseline, LS mean (SE) | −4.0, 0.7 | −4.6 (1.1) | −6.2 (1.1) | −6.6(1.1) | −7.3 (1.1) | −9.0 (1.1) |
| LSM difference (SE)[a] | | −0.6 (1.3) | −2.2 (1.3) | −2.6 (1.3) | −3.3 (1.3) | −5.0 (1.3) |
| P-value[b] | | 0.6647 | 0.0968 | 0.0488 | 0.0130 | 0.0002 |
| 1.5 hours post-dose | | | | | | |
| Mean (SD) | 13.8 (4.62) | 12.1 (4.13) | 11.3 (5.26) | 10.8 (5.81) | 10.8 (5.52) | 7.8 (3.05) |
| Change from baseline, mean (SD) | −4.3 (4.43) | −5.4 (3.96) | −6.2 (5.24) | −6.6 (6.05) | −7.5 (5.57) | −10.4 (4.38) |
| Change from baseline, LS mean (SE) | −4.3 (0.7) | −5.5 (1.1) | −6.3 (1.1) | −6.7 (1.1) | −7.4 (1.1) | 10.4 (1.1) |
| LSM difference (SE)[a] | | −1.2 (1.3) | −2.0 (1.3) | −2.4 (1.3) | −3.1 (1.3) | −6.1 (1.3) |
| P-value[b] | | 0.3661 | 0.1279 | 0.0743 | 0.0199 | <0.0001 |
| 2 hours post-dose | | | | | | |
| Mean (SD) | 13.6 (4.56) | 11.0 (3.87) | 11.4 (5.07) | 10.1 (5.45) | 9.1 (4.20) | 7.4 (2.68) |
| Change from baseline, mean (SD) | −4.5 (4.58) | −6.5 (3.91) | −6.1 (5.09) | −7.3 (5.70) | −9.2 (4.47) | −10.8 (3.15) |
| Change from baseline, LS mean (SE) | −4.5 (0.7) | −6.6 (1.0) | −6.1 (1.0) | −7.4 (1.0) | −9.1 (1.0) | −10.8 (1.0) |
| LSM difference (SE)[a] | | −2.1 (1.2) | −1.7 (1.2) | −2.9 (1.2) | −4.6 (1.2) | −6.3 (1.2) |
| P-value[b] | | 0.0933 | 0.1850 | 0.0210 | 0.0003 | <0.0001 |
| 4 hours post-dose | | | | | | |
| Mean (SD) | 13.7 (4.13) | 9.4 (3.90) | 11.2 (5.11) | 10.2 (5.12) | 9.1 (3.69) | 7.3 (2.54) |
| Change from baseline, mean (SD) | −4.4 (4.44) | −8.1 (4.32) | −6.3 (5.22) | −7.2 (5.48) | −9.2 (4.02) | −10.9 (3.61) |
| Change from baseline, LS mean (SE) | −4.3 (0.7) | −8.1(1.0) | −6.4(1.0) | −7.3 (1.0) | −9.1 (1.0) | −10.9 (1.0) |
| LSM difference (SE)[a] | | −3.8 (1.2) | −2.1 (1.2) | −2.9 (1.2) | −4.8 (1.2) | −6.5 (1.2) |
| P-value[b] | | 0.0022 | 0.0895 | 0.0172 | 0.0001 | <0.0001 |
| 6 hours post-dose | | | | | | |
| Mean (SD) | 13.1 (4.22) | 10.0 (4.00) | 11.9 (5.21) | 10.1 (4.90) | 9.3 (4.23) | 7.2 (2.51) |
| Change from baseline, mean (SD) | −5.0 (4.79) | −7.5 (4.03) | −5.6 (5.19) | −7.3 (5.30) | −9.1 (5.00) | −11.1 (3.47) |
| Change from baseline, LS mean (SE) | −4.9 (0.7) | −7.6 (1.1) | −5.6 (1.1) | −7.4 (1.1) | −9.0 (1.1) | −11.0 (1.1) |
| LSM difference (SE)[a] | | −2.7 (1.3) | −0.7 (1.3) | −2.5 (1.3) | −4.0 (1.3) | −6.0 (1.3) |
| P-value[b] | | 0.0375 | 0.5752 | 0.0490 | 0.0018 | <0.0001 |
| 24 hours post-dose | | | | | | |
| Mean (SD) | 13.5 (3.91) | 11.4 (3.58) | 13.6 (4.10) | 11.3 (4.18) | 12.8 (3.59) | 9.4 (4.82) |
| Change from baseline, mean (SD) | 4.6 (4.03) | −6.1 (4.23) | −3.9 (4.34) | −6.1 (4.50) | −5.6 (3.29) | −8.9 (3.53) |
| Change from baseline, LS mean (SE) | −4.6 (0.6) | −6.2 (0.9) | −4.0 (0.9) | −6.2 (0.9) | −5.5 (0.9) | −8.8 (0.9) |
| LSM difference (SE)[a] | | −1.6(1.1) | 0.6 (1.1) | −1.6 (1.1) | −0.9 (1.1) | −4.2 (1.1) |
| P-value[b] | | 0.1464 | 0.5697 | 0.1407 | 0.4310 | 0.0002 |

Figure 2:
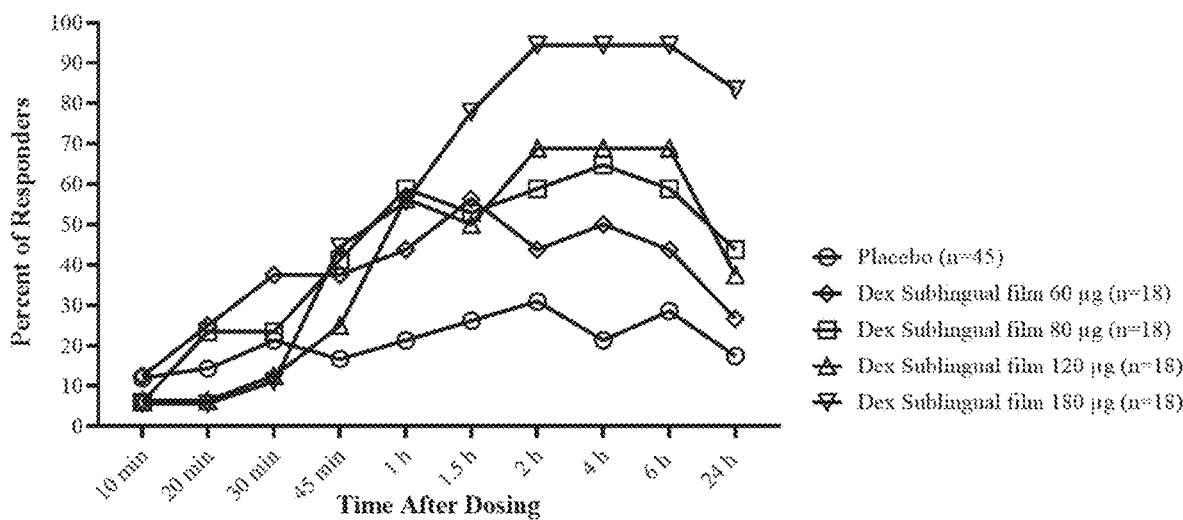
FIG. 2: depicts the percent of responders in PEC total score over time in schizophrenic patients (Intent to treat Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.

Note:
subjects counts for all timepoints were 18 subjects for each dexmedetomidine sublingual film treatment group and 45 subjects for the placebo group
[a]Treatment effect between dexmedetomidine sublingual film and placebo
[b]p value comparing dexmedetomidine sublingual film and placebo PEC Responder Analyses: The proportion of treatment responders, defined as those with a 40% decrease from baseline in PEC total score at 2 hours post dose, was greatest in the 180 µg group (94.4% [P<0.0001] for 180 µg, 68.8% [P=0.0158] for 120 µg, 58.8% for 80 µg [P=0.0759]) and significantly greater than placebo (31% responders) (Table 13 and FIG. 2). Response rates with 180 µg were significantly higher than placebo starting at 45 minutes post dose (44.4% versus 16.7%, respectively), continued to increase after 2 hours (to 94.4% at 4 and 6 hours) and sustained until at least 24 hours post-dose (83.3% versus 17.5%, respectively). Finally, the durability of calming effects of the 180 µg dose was remarkably prolonged with a sustained statistically significant reduction in PEC evident after 24 hrs. After a single dose in the 180 µg group, 83.3% of subjects maintained response after 24 hours with a mean PEC decrease of −8.9 (Mean CFB) compared to 37.5% in the 120 µg group (−5.6 Mean CFB) and 43.8% in the 80 µg group (−6.1 Mean CFB. Response rates over time for the 80 µg and 120 µg groups were high and similar between the 2 groups (Table 13 and FIG. 2).

TABLE 13

Percent of Responders in the PEC Score (Intent to treat Population)

| Time Point Statistics | Placebo (N = 45) | Dexmedetomidine Sublingual Film | | | | |
|---|---|---|---|---|---|---|
| | | 20 μg (N = 18) | 60 μg (N = 18) | 80 μg (N = 18) | 120 μg (N = 18) | 180 μg (N = 18) |
| 10 minutes post-dose | | | | | | |
| Percent responders | 11.9% | 0% | 12.5% | 5.9% | 6.3% | 5.6% |
| 20 minutes post-dose | | | | | | |
| Percent responders | 14.3% | 0% | 25.0% | 23.5% | 6.3% | 5.6% |
| 30 minutes post-dose | | | | | | |
| Percent responders | 21.4% | 11.8% | 37.5% | 23.5% | 12.5% | 11.1% |
| 45 minutes post-dose | | | | | | |
| Percent responders | 16.7% | 17.6% | 37.5% | 41.2% | 25.0% | 44.4% |
| 1 hour post-dose | | | | | | |
| Percent responders | 21.4% | 29.4% | 43.8% | 58.8% | 56.3% | 55.6% |
| P-value[a] | | 0.5178 | 0.1091 | 0.0120 | 0.0236 | 0.0150 |
| 1.5 hours post-dose | | | | | | |
| Percent responders | 26.2% | 41.2% | 56.3% | 52.9% | 50.0% | 77.8% |
| P-value[a] | | 0.3505 | 0.0612 | 0.0699 | 0.1190 | 0.0004 |
| 2 hours post-dose | | | | | | |
| Percent responders | 31.0% | 58.8% | 43.8% | 58.8% | 68.8% | 94.4% |
| P-value[a] | | 0.0759 | 0.3735 | 0.0759 | 0.0158 | <0.0001 |
| 4 hours post-dose | | | | | | |
| Percent responders | 21.4% | 64.7% | 50.0% | 64.7% | 68.8% | 94.4% |
| P-value[a] | | 0.0024 | 0.0519 | 0.0024 | 0.0015 | <0.0001 |
| 6 hours post-dose | | | | | | |
| Percent responders | 28.6% | 64.7% | 43.8% | 58.8% | 68.8% | 94.4% |
| P-value[a] | | 0.0173 | 0.3510 | 0.0399 | 0.0075 | <0.0001 |
| 24 hours post-dose | | | | | | |
| Percent responders | 17.5% | 43.8% | 26.7% | 43.8% | 37.5% | 83.3% |
| P-value[a] | | 0.0838 | 0.4676 | 0.0838 | 0.1610 | <0.0001 |

A responder is defined as a subject who achieved a ≥40% decrease from baseline in PEC score after dosing.
The number of subjects with non-missing data in the dexmedetomidine sublingual film treatment groups were: 18 (180 μg), 17 (20 μg and 80 μg), and 16 (60 μg and 120 μg); 42 subjects in the placebo group had non-missing data.
[a]P-value based on a comparison of dexmedetomidine sublingual film versus placebo via a Fisher's exact test PANSS-EC (5 Items Subscale Scores): The PEC 5 subscale scores associated with agitation (ie, poor impulse control, tension, hostility, uncooperativeness, and excitement) were summarized in table 14, at 2 hours post dosing, significant improvements (ie, decreases) from baseline in all 5 PEC subscale scores were observed in the 80 μg, 120 μg and 180 μg groups compared to placebo; with the exception of "excitement" in the 80 μg group.

TABLE 14

Change from Baseline in PANSS-EC subscale scores at 2 hours post dosing in schizophrenia patients (Intent to treat Population)

| PANNS-EC Subscale Statistics | Placebo (N = 45) | Dexmedetomidine Sublingual Film | | | | |
|---|---|---|---|---|---|---|
| | | 20 μg (N = 18) | 60 μg (N = 18) | 80 μg (N = 18) | 120 μg (N = 18) | 180 μg (N = 18) |
| Poor Impulse Control | | | | | | |
| Baseline, Mean (SD) | 3.5 (0.63) | 3.5 (0.62) | 3.5 (0.62) | 3.3 (0.49) | 3.4 (0.50) | 3.4 (0.70) |
| 2 hours post-dose | | | | | | |
| Mean (SD) | 2.7 (0.87) | 2.1 (1.13) | 2.2 (1.11) | 1.9 (1.06) | 1.7 (0.75) | 1.4 (0.70) |
| Change from baseline, mean (SD) | 0.8 (0.89) | −1.4 (1.14) | −1.3 (1.13) | −1.4 (1.04) | −1.7 (1.03) | −2.0 (0.91) |
| Change from baseline, LS mean (SE) | −0.8 (0.1) | −1.4 (0.2) | −1.3 (0.2) | 1.4 (0.2) | 1.7 (0.2) | −2.0 (0.2) |
| LSM difference (SE)[a] | | −0.6 (0.3) | −0.5 (0.3) | −0.6 (0.3) | −0.9 (0.3) | −1.2 (0.3) |
| p value | | 0.0307 | 0.0810 | 0.0178 | 0.0009 | <0.0001 |
| Tension | | | | | | |
| Baseline, Mean (SD) | 4.0 (0.64) | 3.8 (0.65) | 3.6 (0.92) | 3.8 (0.71) | 4.1 (0.47) | 4.1 (0.87) |
| 2 hours post-dose | | | | | | |
| Mean (SD) | 3.0 (1.13) | 2.4 (1.15) | 2.3 (1.32) | 2.1 (1.23) | 1.9 (1.06) | 1.5 (0.71) |
| Change from baseline, mean (SD) | −1.0 (1.24) | −1.3 (1.14) | 1.3 (1.19) | 1.7 (1.45) | −2.2 (0.92) | −2.6 (1.04) |
| Change from baseline, LS mean (SE) | 0.9 (0.2) | 0.5 (0.3) | −0.5 (0.3) | −0.8 (0.3) | −1.2 (0.3) | −1.6 (0.3) |
| LSM difference (SE)a | | −0.5 (0.3) | −0.5 (0.3) | −0.8 (0.3) | −1.2 (0.3) | −1.6 (0.3) |
| p value | | 0.1397 | 0.0947 | 0.0085 | 0.0002 | <0.0001 |
| Hostility | | | | | | |
| Baseline, Mean (SD) | 3.5 (0.73) | 3.5 (0.62) | 3.6 (0.70) | 3.3 (0.77) | 3.6 (0.62) | 3.6 (0.61) |
| 2 hours post-dose | | | | | | |
| Mean (SD) | 2.6 (1.12) | 2.2 (0.71) | 2.4 (1.04) | 1.9 (1.11) | 1.8 (0.79) | 1.4 (0.51) |
| Change from baseline, mean (SD) | −0.9 (1.11) | −1.3 (0.84) | 1.2 (1.15) | −1.4 (1.14) | −1.7 (1.18) | 2.2 (0.71) |
| Change from baseline, LS mean (SE) | −0.9 (0.1) | −1.3 (0.2) | −1.1 (0.2) | −1.5 (0.2) | −1.7 (0.2) | −2.1 (0.2) |

TABLE 14-continued

Change from Baseline in PANSS-EC subscale scores at 2 hours post dosing in schizophrenia patients (Intent to treat Population)

|  |  | Dexmedetomidine Sublingual Film | | | | |
| --- | --- | --- | --- | --- | --- | --- |
| PANNS-EC Subscale Statistics | Placebo (N = 45) | 20 μg (N = 18) | 60 μg (N = 18) | 80 μg (N = 18) | 120 μg (N = 18) | 180 μg (N = 18) |
| LSM difference (SE)a |  | −0.4 (0.3) | −0.2 (0.3) | −0.6 (0.3) | −0.8 (0.3) | −1.2 (0.3) |
| p value |  | 0.0973 | 0.3609 | 0.0272 | 0.0029 | <0.0001 |
| Uncooperativeness | | | | | | |
| Baseline, Mean (SD) | 3.3 (0.72) | 3.2 (0.81) | 3.3 (0.83) | 3.4 (0.92) | 3.4 (0.70) | 3.2 (0.81) |
| 2 hours post-dose | | | | | | |
| Mean (SD) | 2.5 (0.97) | 2.0 (0.84) | 2.2 (0.94) | 2.0 (1.24) | 1.7 (0.91) | 1.4 (0.62) |
| Change from baseline, mean (SD) | −0.8 (0.98) | −1.2 (1.06) | −1.1 (1.11) | −1.4 (1.33) | −1.8 (1.06) | −1.8 (0.81) |
| Change from baseline, LS mean (SE) | −0.8 (0.1) | −1.3 (0.2) | −1.1 (0.2) | −1.4 (0.2) | −1.7 (0.2) | −1.8 (0.2) |
| LSM difference (SE)a |  | −0.5 (0.3) | −0.3 (0.3) | −0.6 (0.3) | −1.0 (0.3) | −1.0 (0.3) |
| p value |  | 0.0669 | 0.2607 | 0.0268 | 0.0004 | 0.0001 |
| Excitement | | | | | | |
| Baseline, Mean (SD) | 3.8 (0.64) | 3.5 (0.62) | 3.6 (0.70) | 3.5 (0.62) | 3.8 (0.71) | 3.9 (0.64) |
| 2 hours post-dose | | | | | | |
| Mean (SD) | 2.7 (1.07) | 2.3 (0.83) | 2.3 (1.24) | 2.1 (1.37) | 1.9 (1.06) | 1.6 (0.70) |
| Change from baseline, mean (SD) | 1.1 (1.11) | 1.2 (0.88) | −1.2 (1.22) | −1.4 (1.46) | −1.9 (1.02) | −2.3 (0.77) |
| Change from baseline, LS mean (SE) | −1.1 (0.2) | −1.3 (0.2) | −1.3 (0.2) | −1.5 (0.2) | 1.8 (0.2) | −2.2 (0.2) |
| LSM difference (SE)a |  | −0.2 (0.3) | −0.2 (0.3) | −0.4 (0.3) | −0.8 (0.3) | −1.2 (0.3) |
| p value |  | 0.3967 | 0.4394 | 0.1577 | 0.0081 | <0.0001 |

Secondary Efficacy Endpoints:

Changes in secondary efficacy measures (i.e., ACES and CGI-I scores) at 2 hours post-dose were consistent with the results for PEC total scores and were indicative of improvement in symptoms of agitation after treatment with dexmedetomidine sublingual film.

Figure 3:
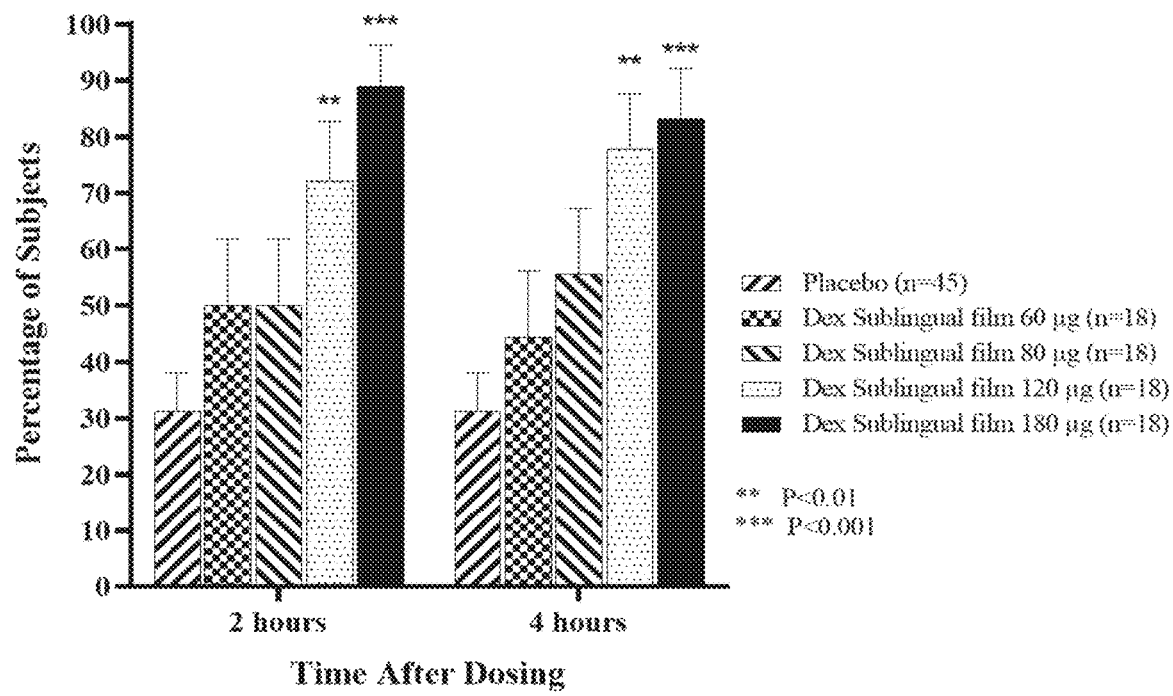
FIG. 3: depicts resolution of agitation as measured by achieving an ACES Score of at least 4 over time in schizophrenic patients (Intent to treat Population) treated with a sublingual film containing dexmedetomidine hydrochloride (60 μg, 80 μg, 120 μg and 180 μg) versus a placebo group. The error bars in the figure represent "standard error". The preparation of dexmedetomidine hydrochloride sublingual films (60 μg) is exemplified in Example 1 and dexmedetomidine hydrochloride sublingual films (80 μg, 120 μg and 180 μg) are exemplified in Example 2.

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in the three highest doses evaluated (80 μg; p=0.0150), (120 μg; p=0.0003) and (180 μg; p<0.0001). At 2 hours after dosing, subjects in the 80 μg, 120 μg, and 180 μg treatment groups showed significantly greater improvements relative to placebo in ACES scores (+2.3 [P=0.0150], +3.1 [P=0.0003], and +4.2 [P=<0.0001], respectively, compared to placebo of +1.2). The improvements at 4 hours post-dose were similar (+2.1 [P=0.0252], +3.2 [P=<0.0001], and +4.1 [P=<0.0001], placebo was +1.1). (Table 15 and FIG. 3). In terms of calming effect (as measured by ACES scores), mean scores in 120 μg and 180 μg groups increased from a baseline of approximately 2 "moderate agitation" to 5.1 "mild calmness" and 6.2 "moderate calmness", respectively at 2 hours post-dose, compared with a score of 3.4 "mild agitation" in the placebo group. The improvements in calmness in the groups were statistically significant with P values of 0.0003 and <0.0001, respectively, compared with placebo (Table 15).

Time to resolution of agitation: The percentage of subjects achieving an ACES score of at least 4 (normal)) at 2 and 4 hours post dosing is displayed in FIG. 3. At 2 and 4 hours after dosing, the percentage of subjects who achieved a ACES score of at least 4, which indicated resolution of agitation, was significantly greater in the 120 μg group (72.2% [P=0.0045] and 77.8% [P=0.0016], respectively) and the 180 μg group (88.9% [P<0.0001] and 83.3% [P=0.0002], respectively) compared with the placebo group (31.1% at both 2 and 4 hours post-dose). In terms of sedation (as measured by ACES scores) the results indicated that a total of 9 subjects in the treatment groups had scores of 8 "deep sleep" at 2 hours and/or 4 hours post-dose, however, no subject in any of the treatment groups had a score of 9 "unarousable." (Table 16). Calming effect was durable lasting at least 6 hours as evidenced by separation from placebo for 80 μg, 120 μg and 180 μg dose groups.

TABLE 15

Change from Baseline in ACES Score at 2 and 4 hours post dosing (Intent to treat population)

|  |  | Dexmedetomidine Sublingual Film | | | | |
| --- | --- | --- | --- | --- | --- | --- |
| Time Post dose | Placebo (N = 45) | 20 μg (N = 18) | 60 μg (N = 18) | 80 μg (N = 18) | 120 μg (N = 18) | 180 μg (N = 18) |
| Baseline, n | | | | | | |
| Mean (SD) | 2.1 (0.55) | 2.3 (0.49) | 2.2 (0.55) | 2.2 (0.55) | 2.0 (0.34) | 1.9 (0.54) |
| 2 hours post-dose | | | | | | |
| Mean (SD) | 3.4 (1.55) | 3.8 (1.11) | 4.2 (1.70) | 4.6 (2.25) | 5.1 (2.05) | 6.2 (1.58) |
| Change from baseline, mean (SD)a | 1.2 (1.46) | 1.4 (1.29) | 2.0 (1.71) | 2.3 (2.43) | 3.1 (2.03) | 4.2 (1.83) |

TABLE 15-continued

Change from Baseline in ACES Score at 2 and 4 hours post dosing (Intent to treat population)

| | | Dexmedetomidine Sublingual Film | | | | |
|---|---|---|---|---|---|---|
| Time Post dose | Placebo (N = 45) | 20 μg (N = 18) | 60 μg (N = 18) | 80 μg (N = 18) | 120 μg (N = 18) | 180 μg (N = 18) |
| Change from baseline, LS mean (SE)[b] | 1.2 (0.3) | 1.6 (0.4) | 2.1 (0.4) | 2.4 (0.4) | 3.0 (0.4) | 4.1 (0.4) |
| LSM difference (SE)[c] | | 0.4 (0.5) | 0.8 (0.5) | 1.2 (0.5) | 1.8 (0.5) | 2.9 (0.5) |
| P-value[d] | | 0.4371 | 0.0795 | 0.0150 | 0.0003 | <0.0001 |
| | | 4 hours post-dose | | | | |
| Mean (SD) | 3.2 (1.42) | 4.4 (1.54) | 3.9 (1.76) | 4.3 (2.22) | 5.2 (1.72) | 6.0 (1.75) |
| Change from baseline, mean (SD)[a] | 1.1 (1.40) | 2.1 (1.53) | 1.7 (1.81) | 2.1 (2.19) | 3.2 (1.69) | 4.1 (2.04) |
| Change from baseline, LS mean (SE)[b] | 1.1 (0.3) | 2.3 (0.4) | 1.8 (0.4) | 2.2 (0.4) | 3.1 (0.4) | 3.9 (0.4) |
| LSM difference (SE)[c] | | 1.2 (0.5) | 0.7 (0.5) | 1.1 (0.5) | 2.0 (0.5) | 2.8 (0.5) |
| P-value[d] | | 0.0164 | 0.1524 | 0.0252 | <0.0001 | <0.0001 |

[a]Change from baseline (pre-dose) ACES score, with positive values in favor of improvement.
[b]Least square mean and standard error per treatment group.
[c]Treatment Effect: Least square mean difference, standard error, and 95% confidence intervals between Dexmedetomidine sublingual film and Placebo.
[d]p value comparing Dexmedetomidine sublingual film and Placebo

TABLE 16

Subjects Rates with an ACES Scores of 8 (Deep Sleep) or 9 (Unarousable Sleep) for all dose groups

| ACES Score | Dose Group | Number of Subjects at Baseline | Number of Subjects at 2 hr | Number of Subjects at 4 hr |
|---|---|---|---|---|
| Deep Sleep ACES Score = 8 | Placebo | 0 | 0 | 0 |
| | 20 μg | 0 | 0 | 1 |
| | 60 μg | 0 | 0 | 0 |
| | 80 μg | 0 | 1 | 1 |
| | 120 μg | 0 | 2 | 0 |
| | 180 μg | 0 | 2 | 3 |
| Unarousable Sleep ACES Score = 9 | Placebo | 0 | 0 | 0 |
| | 20 μg | 0 | 0 | 0 |
| | 60 μg | 0 | 0 | 0 |
| | 80 μg | 0 | 0 | 0 |
| | 120 μg | 0 | 0 | 0 |
| | 180 μg | 0 | 0 | 0 |

Figure 4:
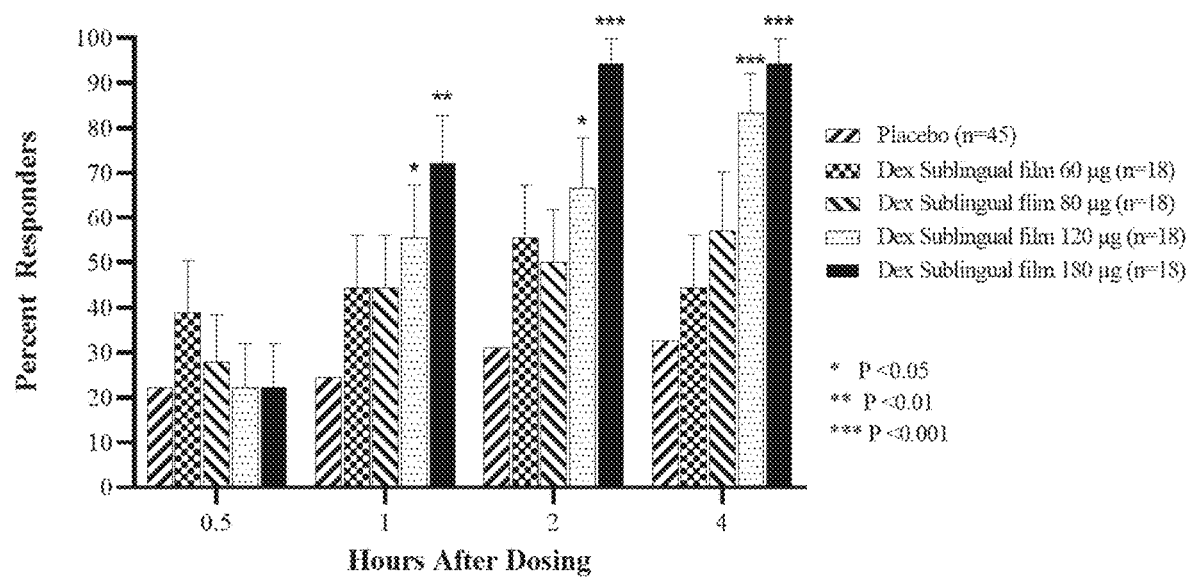
FIG. 4: depicts percent of responders in CGI-I Score over time in schizophrenic patients (Intent to treat Population) treated with a sublingual film containing dexmedetomidine hydrochloride (60 μg, 80 μg, 120 μg and 180 μg) versus a placebo group. The error bars in the figure represent "standard error". The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.

CGI-I scores: Mean baseline CGI-S scores were comparable across all treatment groups (range: 3.9 to 4.3). The CGI-S scores indicated that the subjects were clinically agitated (ie, moderately ill) prior to dosing (Table 17). Significant improvements in agitation (ie, lower CGI-I scores) from baseline were observed at 1 hour after dosing in the dexmedetomidine sublingual film 120 μg and 180 μg groups. Mean (SD) scores were 2.3 (1.13) and 2.1 (0.87), respectively, compared with 3.0 (0.98) in the placebo group (Table 18). LSM differences from placebo were −0.7 (P=0.0167) and −0.9 (P=0.0019) in the 120 μg and 180 μg groups, respectively. Significant improvements in agitation (i.e. lower mean CGI-I scores) from baseline were observed at 2 hours post-dose in the 120 μg group (1.9 [P=0.0007]) and in the 180 μg group (0.4 [P<0.0001]), compared with a mean score of 3 in the placebo group (Table 18). LSM differences from placebo were −1.1 (P=0.0007) and −1.6 (P<0.0001). Significant improvements were also observed at 4 hours post-dose in the dexmedetomidine sublingual film 120 μg and 180 μg groups The percentage of subjects achieving CGI-I scores of 1 or 2 ('very much improved' or 'much improved') at 2 hours post-dose was significantly higher in the 120 μg group (66.7 [P=0.0125]) and in the 180 μg dose group (94.4% [P<0.0001]), compared with placebo (31.0%). Significant improvements were also observed at 1 hour and at 4 hours after dosing for both treatment groups (Table 19 and FIG. 4).

TABLE 17

CGI-S Mean Scores at Baseline (Intent to treat Population)

| | | Dexmedetomidine Sublingual Film | | | | |
|---|---|---|---|---|---|---|
| Time Point Statistics | Placebo (N = 45) | 20 μg (N = 18) | 60 μg (N = 18) | 80 μg (N = 18) | 120 μg (N = 18) | 180 μg (N = 18) |
| Number of subjects | 45 | 18 | 18 | 18 | 18 | 18 |
| | | Baseline (pre-dose) | | | | |
| Mean (SD) | 4.2 (0.44) | 3.9 (0.47) | 4.1 (0.68) | 4.1 (0.32) | 4.3 (0.57) | 4.3 (0.46) |
| Minimum-Maximum | 3.0-5.0 | 3.0-5.0 | 3.0-5.0 | 4.0-5.0 | 3.0-5.0 | 4.0-5.0 |

TABLE 18

Summary of Change from Baseline for CGI-I Score (Intent to treat Population)

| Time Point Statistics | Placebo (N = 45) | Dexmedetomidine Sublingual Film | | | | |
|---|---|---|---|---|---|---|
| | | 20 μg (N = 18) | 60 μg (N = 18) | 80 μg (N = 18) | 120 μg (N = 18) | 180 μg (N = 18) |
| Number of subjects | 45 | 18 | 18 | 18 | 18 | 18 |
| *30 minutes post-dose* | | | | | | |
| Mean (SD) | 3.1 (1.04) | 3.1 (0.76) | 2.8 (1.15) | 3.2 (1.15) | 3.1 (0.76) | 3.1 (0.76) |
| LS mean (SE) [a] | 3.2 (0.1) | 3.1 (0.2) | 2.8 (0.2) | 3.2 (0.2) | 3.1 (0.2) | 3.1 (0.2) |
| LSM difference (SE)[b] | | −0.1 (0.3) | −0.4 (0.3) | −0.0 (0.3) | −0.1 (0.3) | −0.1 (0.3) |
| P-value[c] | | 0.7431 | 0.1778 | 0.9022 | 0.7431 | 0.7431 |
| *1 hour post-dose* | | | | | | |
| Mean (SD) | 3.0 (0.98) | 2.9 (0.83) | 2.4 (1.20) | 2.8 (1.42) | 2.3 (1.13) | 2.1 (0.87) |
| LS mean (SE)[a] | 3.0 (0.2) | 2.9 (0.3) | 2.4 (0.3) | 2.8 (0.3) | 2.3 (0.3) | 2.1 (0.3) |
| LSM difference (SE)[b] | | −0.1 (0.3) | −0.6 (0.3) | −0.2 (0.3) | −0.7 (0.3) | −0.9 (0.3) |
| P-value[c] | | 0.7098 | 0.0645 | 0.5769 | 0.0167 | 0.0019 |
| *2 hours post-dose* | | | | | | |
| Mean (SD) | 3.0 (1.09) | 2.4 (0.98) | 2.3 (1.13) | 2.6 (1.54) | 1.9 (1.00) | 1.4 (0.61) |
| LS mean (SE) [a] | 3.0 (0.2) | 2.4 (0.3) | 2.3 (0.3) | 2.6 (0.3) | 1.9 (0.3) | 1.4 (0.3) |
| LSM difference (SE)[b] | | −0.6 (0.3) | −0.7 (0.3) | −0.4 (0.3) | −1.1 (0.3) | −1.6 (0.3) |
| P-value[c] | | 0.0701 | 0.0190 | 0.2034 | 0.0007 | <0.0001 |
| *4 hours post-dose* | | | | | | |
| Mean (SD) | 3.0 (1.08) | 2.4 (0.92) | 2.8 (1.22) | 2.6 (1.60) | 1.8 (0.73) | 1.4 (0.62) |
| LS mean (SE) [a] | 3.0 (0.2) | 2.4 (0.3) | 2.8 (0.3) | 2.7 (0.3) | 1.8 (0.3) | 1.4 (0.3) |
| LSM difference (SE)[b] | | −0.6 (0.3) | −0.2 (0.3) | −0.3 (0.3) | −1.2 (0.3) | −1.5 (0.3) |
| P-value[c] | | 0.0516 | 0.5071 | 0.4139 | 0.0001 | <0.0001 |

Clinical Global Impression-Improvement scores range from 1 (Very much improved) to 7 (Very much worse). Test statistics and estimates are from a restricted maximum likelihood repeated measures mixed model on observed values with timepoint and its interaction with treatment group as repeated measures using an unstructured covariance structure.
[a] Least square mean and standard error per treatment group. The corresponding estimates for the placebo group are not included as they vary with the dexmedetomidine sublingual film dosing group being compared.
[b] Treatment Effect: Least square mean difference, standard error, and 95% confidence intervals between dexmedetomidine sublingual film and Placebo
[c] P value comparing dexmedetomidine sublingual film and Placebo

TABLE 19

Percent of Responders in the CGI-I Scale over Time (Intent-to-Treat Population)

| Time Point Statistics | Placebo (N = 45) | Dexmedetomidine sublingual film | | | | |
|---|---|---|---|---|---|---|
| | | 20 μg (N = 18) | 60 μg (N = 18) | 80 μg (N = 18) | 120 μg (N = 18) | 180 μg (N = 18) |
| *30 minutes post-dose* | | | | | | |
| Percent responders | 22.2% | 22.2% | 38.9% | 27.8% | 22.2% | 22.2% |
| P-value[a] | | 1.000 | 0.2158 | 0.7457 | 1.000 | 1.000 |
| *1 hour post-dose* | | | | | | |
| Percent responders | 24.4% | 38.9% | 44.4% | 44.4% | 55.6% | 72.2% |
| P-value[a] | | 0.3549 | 0.1383 | 0.1383 | 0.0361 | 0.0011 |
| *2 hours post-dose* | | | | | | |
| Percent responders | 31.1% | 55.6% | 55.6% | 50.0% | 66.7% | 94.4% |
| P-value[a] | | 0.0896 | 0.0896 | 0.2462 | 0.0125 | <0.0001 |
| *4 hours post-dose* | | | | | | |
| Percent responders | 32.6% | 55.6% | 44.4% | 57.1% | 83.3% | 94.4% |
| P-value[a] | | 0.1499 | 0.3968 | 0.1231 | 0.0005 | <0.0001 |

Figure 5A:
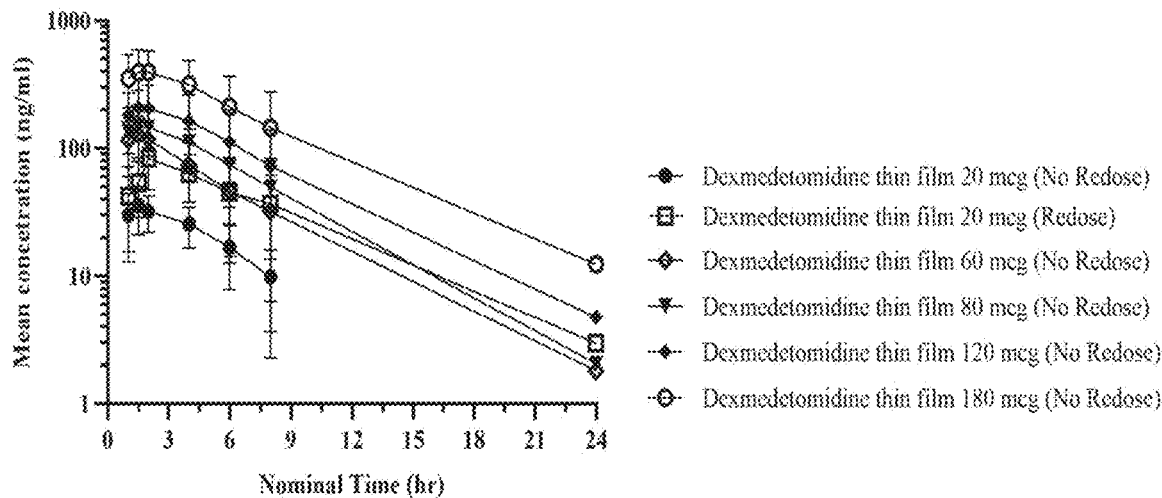
FIG. 5A: depicts mean dexmedetomidine plasma concentration vs. nominal time sorted by dose and redose (Semilog Scale) in schizophrenic patients (Pharmacokinetic Population) treated with a sublingual film containing dexmedetomidine hydrochloride (20 μg, 20 μg (redose), 60 μg, 80 μg, 120 μg and 180 μg) versus a placebo group. The preparation of dexmedetomidine hydrochloride sublingual films (20 μg and 60 μg) are exemplified in Example 1 and dexmedetomidine hydrochloride sublingual films (80 μg, 120 μg and 180 μg) are exemplified in Example 2.
Figure 5B:
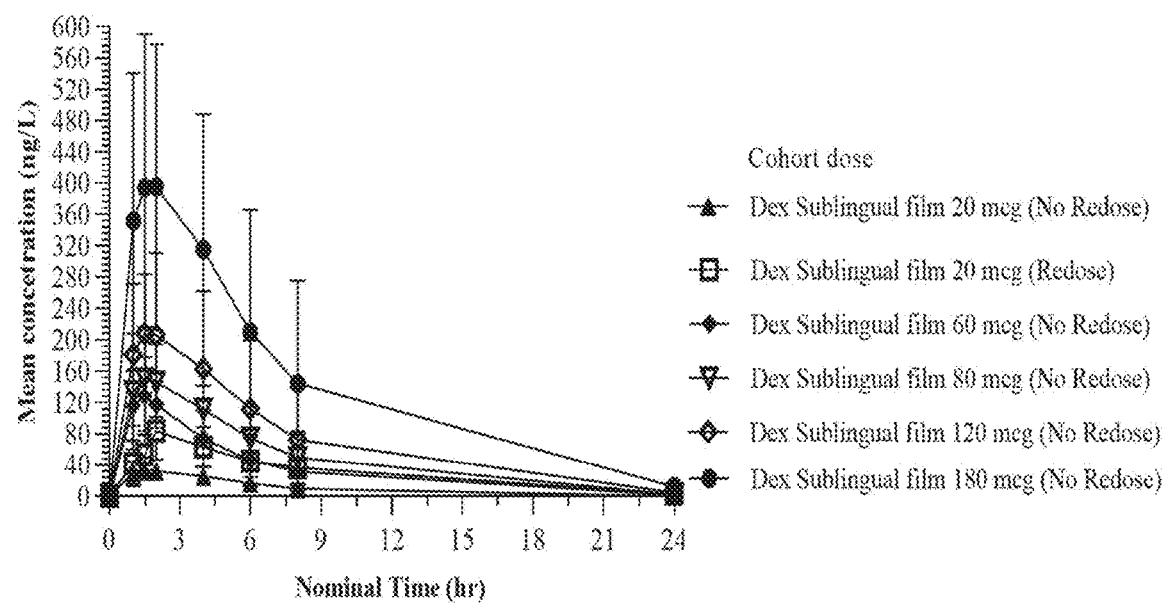
FIG. 5B: depicts mean dexmedetomidine plasma concentration vs. nominal time sorted by dose and redose (Linear Scale) in schizophrenic patients (Pharmacokinetic Population) treated with a sublingual film containing dexmedetomidine hydrochloride (20 μg, 20 μg (redose), 60 μg, 80 μg, 120 μg and 180 μg) versus a placebo group. The preparation of dexmedetomidine hydrochloride sublingual films (20 μg and 60 μg) are exemplified in Example 1 and dexmedetomidine hydrochloride sublingual films (80 μg, 120 μg and 180 μg) are exemplified in Example 2.

[a] P-value based on a comparison of dexmedetomidine sublingual film versus placebo via a Fisher's exact test Pharmacokinetic Results:

Pharmacokinetic analysis was conducted using a validated install of Phoenix® WinNonlin® version 8.1. Non-compartmental analysis was also conducted on the final audited data which consisted of a total of 135 participants in 5 cohorts receiving 20, 60, 80 (1×20 μg films and 1×60 μg films), 120 (2×60 μg films) and 180 μg (3×60 μg films) of dexmedetomidine sublingual film. Measurable concentrations of dexmedetomidine were observed at the first collected post dose plasma sample (1 hr) for all dose levels and tabulated in table 20. There were no measurable concentrations at pre-dose (0 hr) at any dose level. Measurable concentrations of dexmedetomidine were observable until 8 hr for all dose levels with measurable concentrations at 24 hr in some subjects at each dose level (Table 20; FIGS. 5A and 5B). Dexmedetomidine sublingual film is absorbed rapidly with maximum concentration achieved on average within about 2.5 hours after administration. The median $T_{max}$ ranged from 1.50-2.31 hr while the median t1/2 ranged from 2.36-3.06 hr across the 5 dose levels. The exposure ($C_{max}$ and AUC) increased in an approximately dose proportional manner within the dose range (20 μg-180 μg) studied after single administration. The median $C_{max}$ ranged from about 40 ng/L to about 500 ng/L. After absorption, it was eliminated with about a 3-hour half-life which was consistent across dose groups. In 20 μg dose group, 8 of 18 subjects were given a second dose of dexmedetomidine sublingual film, the exposure ($C_{max}$ and AUC) was about 2-fold higher than in the group which was not redosed Observed exposures following a single dose of 180 μg (Mean Cmax: 379 ng/L; Mean AUC 2881 ng/L) (Table 20) are significantly below the mean exposures (IV PRECEDEX® at approved dose is estimated): Cmax: 1339 ng/L; AUC: 31713 ng·h/L (PKPD18-1054) with the highest approved dose of dexmedetomidine.

TABLE 20

Individual and summary statistics of PK parameter estimates of dexmedetomidine in plasma after administration of dexmedetomidine sublingual film in schizophrenia patients.

| Cohort | Dose (ug) | Re-dose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| 1 | 20 | No | 01-001 | 35.54 | 1.50 | 224.01 | NC | NC |
| | | | 01-002 | 38.55 | 1.50 | 186.08 | NC | 3.79 |
| | | | 01-010 | 59.82 | 1.00 | 104.40 | NC | 2.12 |
| | | | 01-026 | 14.07 | 4.02 | 57.43 | NC | NC |
| | | | 07-015 | 33.41 | 1.53 | 177.60 | NC | 5.36 |
| | | | 07-030 | 34.31 | 2.00 | 176.11 | 203.81 | 2.29 |
| | | | 10-027 | 35.38 | 2.00 | 184.37 | NC | 3.64 |
| | | | 23-016 | 69.05 | 1.48 | 264.45 | NC | 2.95 |
| | | | 23-018 | 40.37 | 1.97 | 154.62 | 186.40 | 3.17 |
| | | | 23-020 | 38.49 | 1.95 | 190.81 | 226.26 | 2.51 |
| | | | N | 10 | 10 | 10 | 3 | 8 |
| | | | Mean | 39.90 | 1.89 | 171.99 | 205.49 | 3.23 |
| | | | SD | 15.02 | 0.81 | 57.74 | 19.98 | 1.05 |
| | | | CV % | 37.6 | 42.89 | 33.57 | 9.72 | 32.61 |
| | | | Min | 14.07 | 1.00 | 57.43 | 186.40 | 2.12 |
| | | | Median | 37.02 | 1.74 | 180.99 | 203.81 | 3.06 |
| | | | Max | 69.05 | 4.02 | 264.45 | 226.26 | 5.36 |
| | | | Geometric Mean | 37.16 | 1.78 | 160.36 | 204.85 | 3.09 |
| | | | Geometric CV % | 43.89 | 36.99 | 45.49 | 9.72 | 31.23 |
| 1 | 20 | Yes | 01-009 | 130.44 | 2.00 | 662.46 | NC | 3.94 |
| | | | 01-013 | 122.23 | 2.00 | 486.82 | 563.33 | 2.73 |
| | | | 05-007 | 49.87 | 2.50 | 230.06 | NC | 4.02 |
| | | | 05-008 | 66.64 | 2.12 | 272.47 | 304.52 | 2.00 |
| | | | 05-021 | 86.86 | 2.50 | 410.74 | NC | 3.10 |
| | | | 05-023 | 52.29 | 2.50 | 236.04 | NC | NC |
| | | | 05-024* | 138.69 | 8.03 | 1912.52 | NC | NC |
| | | | 07-028 | 125.70 | 2.00 | 476.62 | 519.25 | 1.81 |
| | | | N | 8 | 8 | 8 | 3 | 6 |
| | | | Mean | 96.59 | 2.96 | 585.96 | 462.37 | 2.93 |
| | | | SD | 36.95 | 2.06 | 556.20 | 138.47 | 0.94 |
| | | | CV % | 38.26 | 69.85 | 94.92 | 29.95 | 31.98 |
| | | | Min | 49.87 | 2.00 | 230.06 | 304.52 | 1.81 |
| | | | Median | 104.54 | 2.31 | 443.68 | 519.25 | 2.91 |
| | | | Max | 138.69 | 8.03 | 1912.52 | 563.33 | 4.02 |
| | | | Geometric Mean | 89.71 | 2.61 | 453.42 | 446.60 | 2.80 |
| | | | Geometric CV % | 44.50 | 49.35 | 78.77 | 34.37 | 34.49 |
| 2 | 60 | No | 01-044 | 93.67 | 1.00 | 442.23 | NC | 3.10 |
| | | | 01-047 | 73.42 | 1.00 | 265.85 | 293.67 | 2.23 |
| | | | 01-055 | 113.35 | 1.50 | 474.46 | 562.60 | 2.87 |
| | | | 01-056 | 154.79 | 1.50 | 413.53 | 428.64 | 1.48 |
| | | | 03-036 | 83.52 | 1.55 | 347.11 | 369.07 | 1.62 |
| | | | 05-050 | 121.52 | 1.00 | 355.87 | 381.27 | 1.84 |
| | | | 05-052 | 105.84 | 1.50 | 330.30 | 369.14 | 2.36 |
| | | | 06-033 | 253.14 | 1.45 | 737.87 | 834.44 | 2.27 |
| | | | 06-034 | 206.42 | 1.53 | 887.27 | 1007.71 | 2.35 |
| | | | 06-041 | 144.27 | 2.07 | 1714.29 | 1882.10 | 6.98 |
| | | | 06-043 | 186.40 | 1.02 | 748.96 | 877.63 | 2.53 |
| | | | 07-048 | 201.12 | 0.98 | 874.85 | 1030.25 | 2.81 |
| | | | 08-046* | 93.22 | 2.00 | 346.61 | NC | NC |
| | | | 09-042 | 146.17 | 3.95 | 2072.02 | 2195.38 | 5.43 |
| | | | 10-032 | 136.25 | 1.50 | 650.22 | NC | NC |
| | | | 10-035 | 127.27 | 1.50 | 519.54 | 616.68 | 2.78 |
| | | | 10-039 | 144.93 | 1.00 | 603.55 | 691.00 | 2.27 |
| | | | 10-045 | 127.30 | 1.50 | 495.69 | 548.50 | 2.30 |
| | | | N | 18 | 18 | 18 | 15 | 16 |
| | | | Mean | 139.59 | 1.53 | 680.71 | 805.85 | 2.83 |
| | | | SD | 47.22 | 0.69 | 481.66 | 555.95 | 1.42 |
| | | | CV % | 33.83 | 45.0 | 70.76 | 68.89 | 50.15 |
| | | | Min | 73.42 | 0.98 | 265.85 | 293.67 | 1.48 |
| | | | Median | 131.78 | 1.50 | 507.61 | 616.68 | 2.36 |
| | | | Max | 253.14 | 3.95 | 2072.02 | 2195.38 | 6.98 |
| | | | Geometric Mean | 132.56 | 1.43 | 575.95 | 674.14 | 2.60 |
| | | | Geometric CV % | 33.88 | 36.02 | 59.93 | 65.01 | 40.94 |
| 3 | 120 | No | 01-059 | 128.89 | 2.00 | 1143.72 | 1192.51 | 5.28 |
| | | | 01-062 | 380.78 | 2.00 | 2927.15 | 2958.80 | 3.64 |
| | | | 01-065 | 393.58 | 4.00 | 3935.47 | 4063.95 | 4.62 |
| | | | 01-080 | 316.57 | 1.00 | 1536.77 | 1538.84 | 2.60 |
| | | | 01-082 | 315.51 | 4.00 | 4156.65 | 4371.55 | 5.32 |

TABLE 20-continued

Individual and summary statistics of PK parameter estimates of dexmedetomidine in plasma after administration of dexmedetomidine sublingual film in schizophrenia patients.

| Cohort | Dose (ug) | Re-dose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| | | | 01-086 | 201.58 | 1.00 | 915.85 | 918.48 | 2.56 |
| | | | 03-068 | 308.19 | 1.02 | 1039.39 | 1039.79 | 2.02 |
| | | | 06-077 | 108.84 | 3.82 | 585.94 | 586.93 | 2.59 |
| | | | 06-078 | 228.53 | 1.47 | NC | NC | NC |
| | | | 06-083 | 154.65 | 1.47 | 592.96 | 593.28 | 2.01 |
| | | | 06-084 | 160.33 | 1.47 | 682.91 | 683.47 | 2.59 |
| | | | 07-066 | 366.09 | 2.00 | 3920.86 | 4012.15 | 4.35 |
| | | | 10-063 | 184.22 | 2.00 | NC | NC | 3.50 |
| | | | 10-076 | 149.11 | 2.00 | 990.19 | 989.76 | 2.81 |
| | | | 23-069 | 286.88 | 2.00 | 1230.19 | 1230.90 | 1.98 |
| | | | 23-070 | 243.63 | 1.52 | NC | NC | 3.21 |
| | | | 23-073* | 125.62 | 4.00 | NC | NC | NC |
| | | | 23-074 | 233.12 | 1.55 | 1162.59 | 1166.09 | 2.83 |
| | | | N | 18 | 18 | 18 | 14 | 16 |
| | | | Mean | 238.12 | 2.13 | 1513.91 | 1810.47 | 3.25 |
| | | | SD | 92.98 | 1.06 | 1264.13 | 1395.65 | 1.1 |
| | | | CV % | 39.05 | 50.03 | 83.50 | 77.09 | 34.27 |
| | | | Min | 108.84 | 1.00 | 499.50 | 586.93 | 1.98 |
| | | | Median | 230.83 | 2.00 | 970.38 | 1179.30 | 2.82 |
| | | | Max | 393.58 | 4.00 | 4158.05 | 4371.55 | 5.32 |
| | | | Geometric Mean | 220.53 | 1.91 | 1169.33 | 1411.79 | 3.08 |
| | | | Geometric CV % | 42.89 | 49.10 | 78.73 | 81.15 | 33.71 |
| 4 | 180 | No | 01-089 | 490.60 | 1.00 | 5498.99 | 5592.92 | 3.92 |
| | | | 01-097 | 636.45 | 1.50 | 2508.31 | 2676.44 | 1.76 |
| | | | 01-105 | 685.45 | 1.00 | 2628.09 | 3126.77 | 2.73 |
| | | | 01-111* | 88.10 | 8.00 | 1311.33 | NC | NC |
| | | | 05-088 | 127.77 | 1.02 | 520.53 | 569.19 | 2.03 |
| | | | 05-098 | 563.94 | 1.47 | 2435.38 | 2644.08 | 1.86 |
| | | | 05-100 | 487.88 | 1.47 | 4630.43 | 4705.04 | 3.90 |
| | | | 06-091 | 592.99 | 3.98 | 6835.79 | 7310.47 | 5.92 |
| | | | 06-093 | 406.57 | 2.07 | 2173.00 | NC | 3.22 |
| | | | 07-095* | 443.70 | 2.00 | 1911.81 | NC | NC |
| | | | 10-090 | 546.65 | 2.00 | 3808.10 | NC | 5.19 |
| | | | 10-123 | 797.37 | 1.50 | 8928.20 | 9468.70 | 5.80 |
| | | | 10-127 | 640.01 | 2.00 | 2444.45 | 2746.20 | 2.30 |
| | | | 10-129 | 483.07 | 2.00 | 3578.09 | 4340.66 | 9.65 |
| | | | 23-103 | 225.12 | 1.98 | 1034.07 | 1140.28 | 1.90 |
| | | | 23-104 | 227.51 | 1.97 | 1086.53 | NC | 2.94 |
| | | | 23-125 | 237.95 | 1.98 | 943.23 | 1049.33 | 2.10 |
| | | | 23-126 | 224.88 | 1.98 | 1243.11 | NC | 2.84 |
| | | | N | 18 | 18 | 18 | 12 | 16 |
| | | | Mean | 439.22 | 2.16 | 2973.31 | 3780.85 | 3.63 |
| | | | SD | 206.41 | 1.60 | 2255.10 | 2663.22 | 2.12 |
| | | | CV % | 46.99 | 73.99 | 75.84 | 70.44 | 58.29 |
| | | | Min | 88.10 | 1.00 | 520.53 | 569.19 | 1.76 |
| | | | Median | 485.48 | 1.98 | 2439.91 | 2936.49 | 2.89 |
| | | | Max | 797.37 | 8.00 | 8928.20 | 9468.70 | 9.65 |
| | | | Geometric Mean | 379.13 | 1.87 | 2294.38 | 2881.18 | 3.20 |
| | | | Geometric CV % | 68.19 | 52.19 | 87.67 | 100.34 | 53.08 |
| 5 | 80 | No | 01-144 | 160.18 | 2.00 | 784.24 | 917.99 | 2.49 |
| | | | 02-133 | 142.99 | 2.03 | 747.42 | 886.35 | 2.41 |
| | | | 02-142 | 222.79 | 2.00 | 2480.66 | 2594.62 | 5.37 |
| | | | 03-112 | 68.41 | 1.55 | 416.50 | NC | NC |
| | | | 03-114 | 70.46 | 1.03 | 244.38 | NC | NC |
| | | | 03-120 | 107.00 | 1.53 | 450.79 | 531.82 | 2.67 |
| | | | 03-134 | 135.30 | 1.55 | 759.89 | 894.79 | 2.57 |
| | | | 08-092 | 167.57 | 1.88 | 938.26 | NC | NC |
| | | | 08-094 | 199.63 | 1.45 | 684.60 | 737.33 | 1.88 |
| | | | 08-109 | 102.29 | 1.50 | 561.56 | NC | 3.12 |
| | | | 09-137 | 151.89 | 2.25 | 635.19 | 767.51 | 3.07 |
| | | | 20-115 | 224.70 | 1.22 | 1114.91 | 1366.03 | 2.72 |
| | | | 20-138 | 175.94 | 4.32 | 2218.17 | 2334.99 | 5.33 |
| | | | 20-140 | 182.32 | 1.58 | 659.20 | 702.28 | 1.78 |
| | | | 20-141 | 253.29 | 1.20 | 888.38 | NC | 4.75 |
| | | | 22-131 | 184.62 | 2.12 | 1020.28 | NC | 2.96 |
| | | | 24-116 | 315.11 | 1.53 | 1145.23 | 1305.66 | 2.53 |
| | | | 24-130 | 139.94 | 4.03 | 1325.85 | 1375.38 | 4.93 |
| | | | N | 18 | 18 | 18 | 12 | 15 |
| | | | Mean | 166.91 | 1.93 | 948.64 | 1201.23 | 3.24 |
| | | | SD | 62.75 | 0.88 | 579.45 | 651.50 | 1.22 |

TABLE 20-continued

Individual and summary statistics of PK parameter estimates of dexmedetomidine in plasma after administration of dexmedetomidine sublingual film in schizophrenia patients.

| Cohort | Dose (ug) | Re-dose | Subject ID | Cmax (ng/L) | Tmax (hr) | AUClast (hr*ng/L) | AUCinf_obs (hr*ng/L) | t1/2 (hr) |
|---|---|---|---|---|---|---|---|---|
| | | | CV % | 37.59 | 45.71 | 61.08 | 54.24 | 37.76 |
| | | | Min | 68.41 | 1.03 | 244.38 | 531.82 | 1.78 |
| | | | Median | 163.88 | 1.57 | 772.07 | 906.39 | 2.72 |
| | | | Max | 315.11 | 4.32 | 2480.66 | 2594.62 | 5.37 |
| | | | Geometric Mean | 155.27 | 1.79 | 816.58 | 1071.37 | 3.05 |
| | | | Geometric CV % | 42.27 | 38.50 | 60.56 | 51.21 | 36.76 |

3. Safety and Tolerability:

Dexmedetomidine sublingual film (formulations of Example 1 and 2) was well tolerated and had a favourable safety profile in the treatment of subjects with agitation. An overview of subjects who experienced at least 1 treatment emergent adverse event (TEAE) by treatment group for the safety population is given in Tables 21 and 22. Overall, a total of 55 subjects (40.7% [55/135]) experienced a least 1 TEAE. The proportion of subjects who experienced TEAEs was similar in the 80 µg, 120 µg, and 180 µg dose groups (55.6%, 66.7%, and 66.7%, respectively). In comparison, the proportion of subjects with TEAEs was lower in the 20 µg and 60 µg dose groups (27.8% and 33.3%, respectively) and the placebo group (22.2%). Most (81.1%) of the TEAEs in all treatment groups were mild in severity. Almost all (90.9%) of the TEAEs were considered to be related to study drug in all treatment groups. None of the subjects experienced a TEAE that was considered to be severe in intensity. There were no deaths, SAEs, or discontinuations due to an AE reported in this study (Tables 21 and 22).

The TEAEs reported in this study were consistent with known common side effects of dexmedetomidine, namely, dry mouth, bradycardia, hypotension, and somnolence (Table 21).

The most frequently reported TEAE was somnolence with 26 subjects experiencing the event of which 20 events were mild in severity and 4 events were moderate in severity. Incidences for somnolence in the groups were 16.7% (20 µg and 60 µg), 22.2% (120 µg), 33.3% (80 µg), and 44.4% (180 µg): incidence in the placebo group was 4.4%. The second most frequently reported TEAE was dry mouth which was reported by 5.6%, 16.7%, 16.7%, and 11.1% of subjects in the 20 µg, 80 µg, 120 µg, and 180 µg groups, respectively, compared with 13.3% of subjects in the placebo group. No subject in the 60 µg dose group reported an event of dry mouth. All cases of dry mouth were mild in severity.

In the dexmedetomidine hydrochloride treatment groups, TEAEs associated with vital signs were: hypotension in 6 subjects (n=2 [120 µg], n=4 [180 µg]), orthostatic hypotension (n=1 [80 µg], n=1 [120 µg], and n=1 [180 µg]), and bradycardia (n=1 [20 µg]). All subjects recovered from the events.

Three laboratory related adverse events (3× upper limit of normal for T Bili, 3+ Glucose in urine, and 4+ Protein in urine) were being followed-up at each respective clinical site and remained unresolved at this time. Otherwise there were no clinically significant changes in laboratory parameters and ECG assessments. No physical examination finding was considered clinically significant by the investigators. None of the subjects had a negative reaction (i.e. local irritation) to study drug as determined by buccal examination.

Also, the dose dependent decreases in SBP and DBP were observed with maximum changes at 2 hours post-dose:

- SBP: −4.6 (9.63), −5.6 (10.85), −8.2 (11.50), −12.1 (20.50), and −14.7 (12.09) mmHg in the 20 µg, 60 µg, 80 µg, 120 µg, and 180 µg groups, respectively, and +1.2 (9.23) mmHg in the placebo group.
- DBP: 0.3 (10.39), −5.3 (7.86), −6.4. (8.05), −7.8 (9.40), and −6.6 (6.41) mmHg in the 20 µg, 60 µg, 80 µg, 120 µg, and 180 µg groups, respectively, and +0.2 (7.82) mmHg in the placebo group.
- HR: −0.1 (6.24), −3.9 (9.13), −0.8 (8.39), −2.2 (13.03), and −10.7 (12.97) bpm in the 20 µg, 60 µg, 80 µg, 120 µg, and 180 µg groups, respectively, and −0.8 (8.29) bpm in the placebo group.

Further, the orthostatic measurements of SBP, DBP, and HR were performed after the subject had been standing for a total of 5 minutes.

Figure 6A:
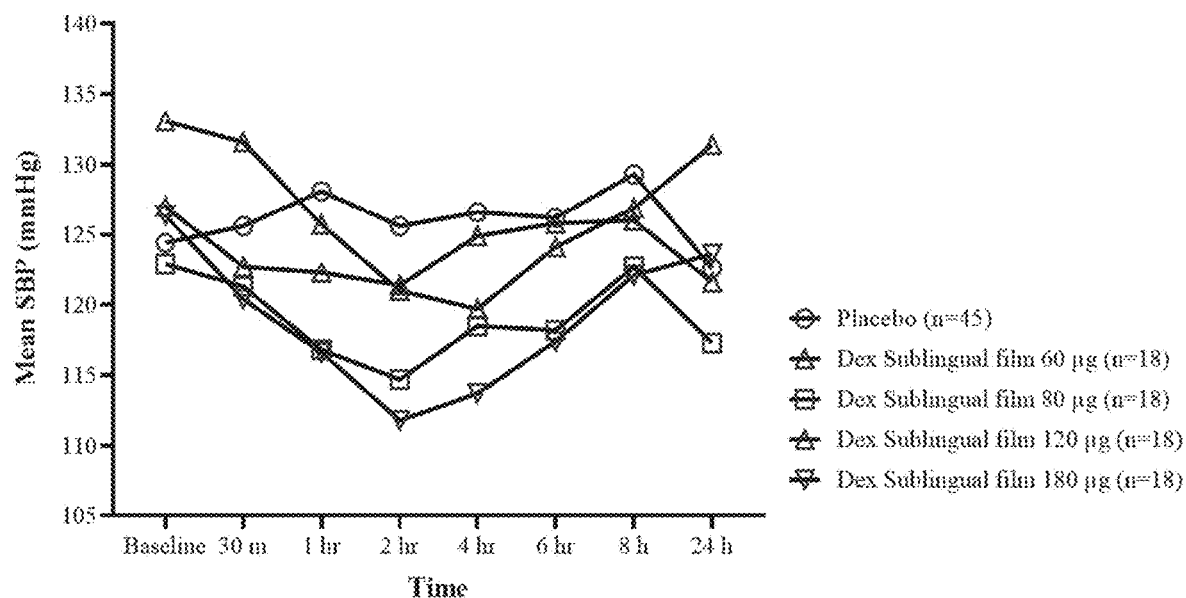
FIG. 6A: depicts mean values for resting systolic blood pressure (SBP) over time in schizophrenic patients (Safety Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.
Figure 6B:
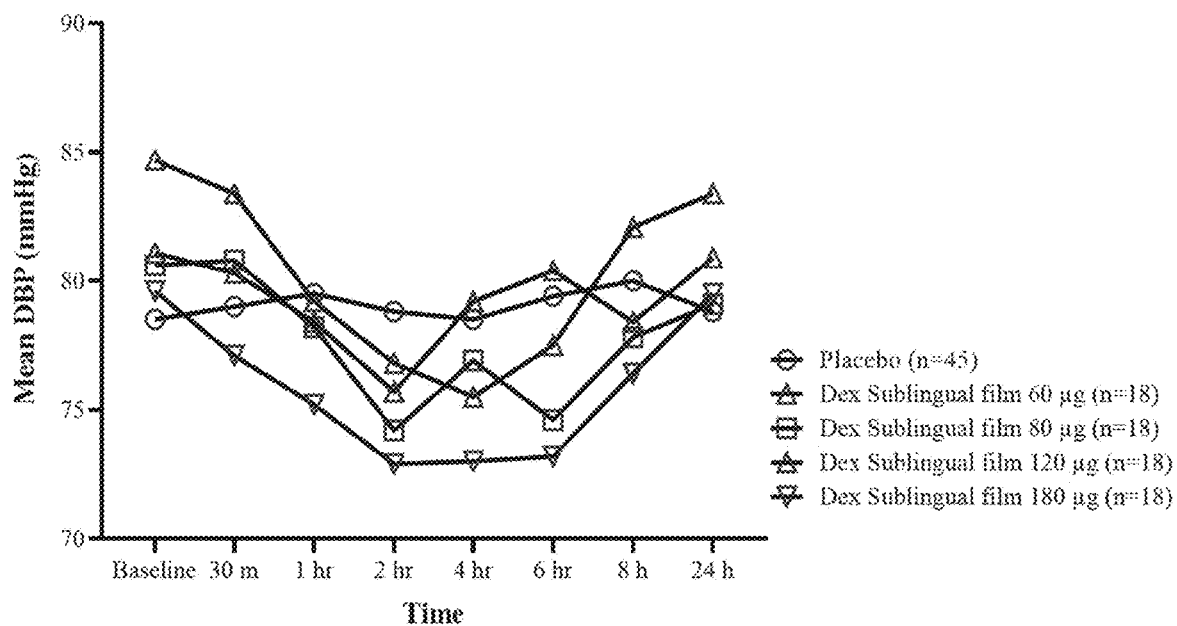
FIG. 6B: depicts mean values for resting diastolic blood pressure (DBP) over time in schizophrenic patients (Safety Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.
Figure 6C:
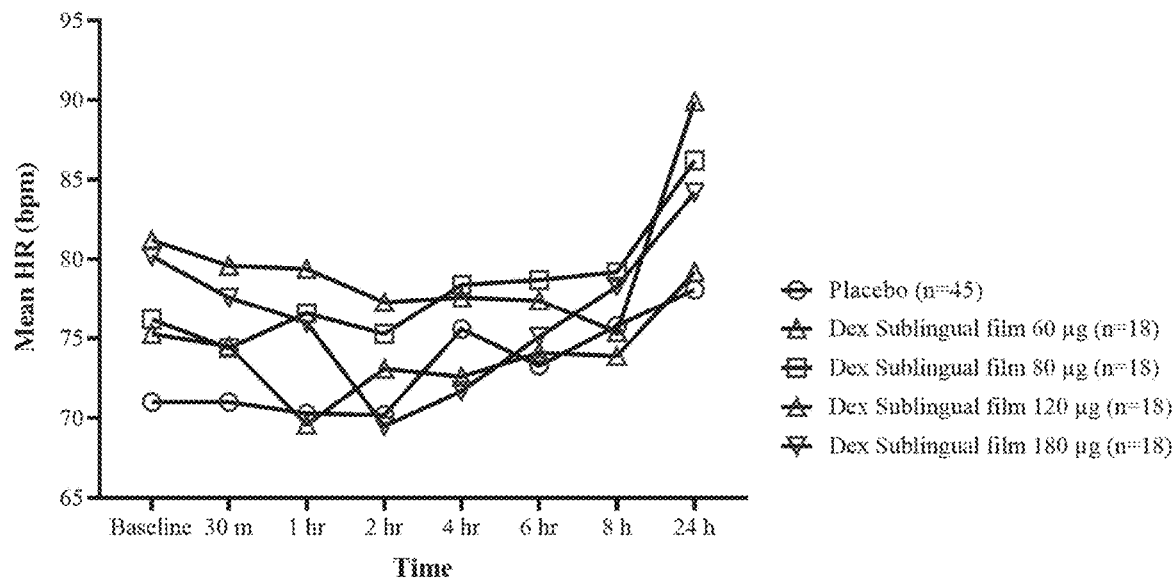
FIG. 6C: depicts mean values for resting heart rate (HR) over time in schizophrenic patients (Safety Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.
Figure 7A:
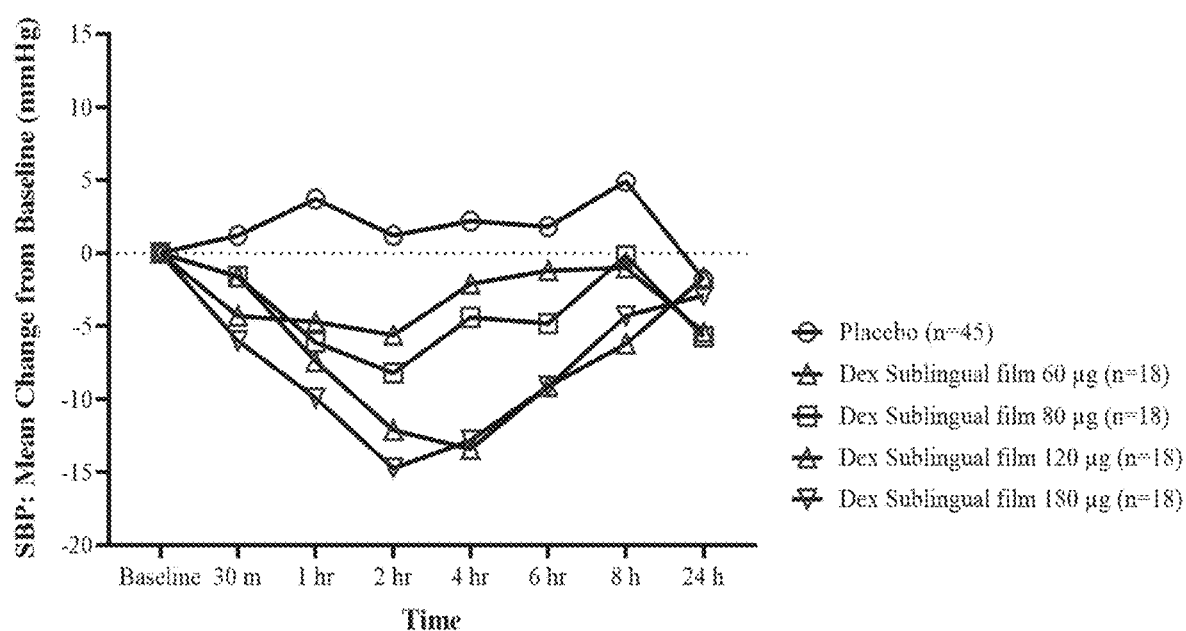
FIG. 7A: depicts mean change from baseline for resting systolic blood pressure (SBP) over time in schizophrenic patients (Safety Population) treated with a sublingual film containing dexmedetomidine hydrochloride (60 μg, 80 μg, 120 μg and 180 μg) versus a placebo group. The preparation of dexmedetomidine hydrochloride sublingual film (60 μg) is exemplified in Example 1 and dexmedetomidine hydrochloride sublingual films (80 μg, 120 μg and 180 μg) are exemplified in Example 2.
Figure 7B:
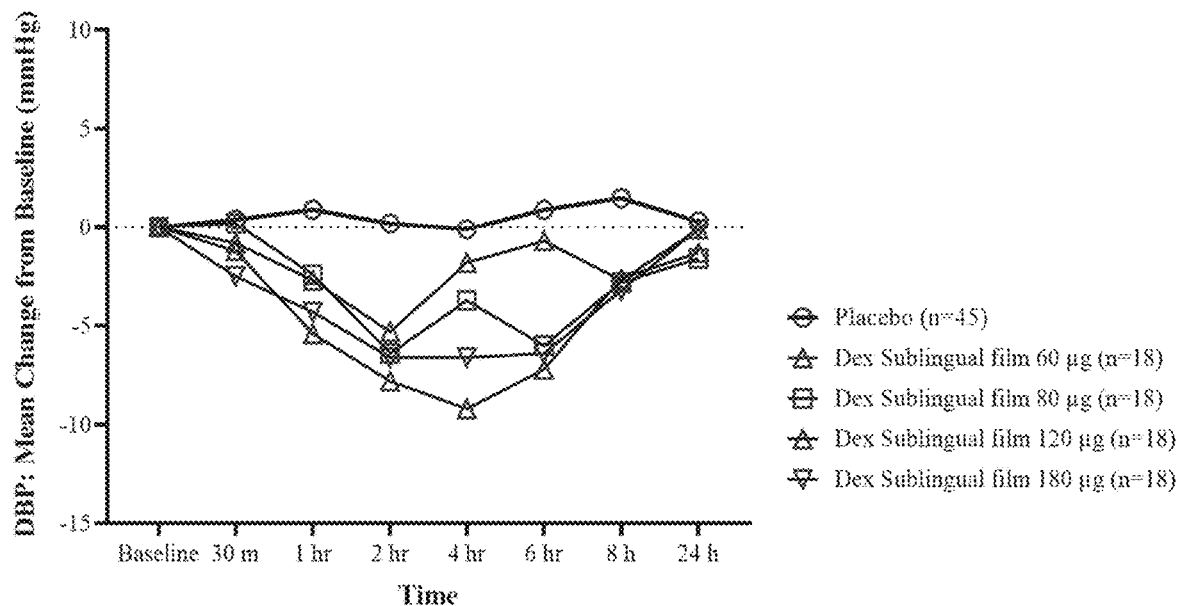
FIG. 7B: depicts mean change from baseline for resting diastolic blood pressure (DBP) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.
Figure 7C:
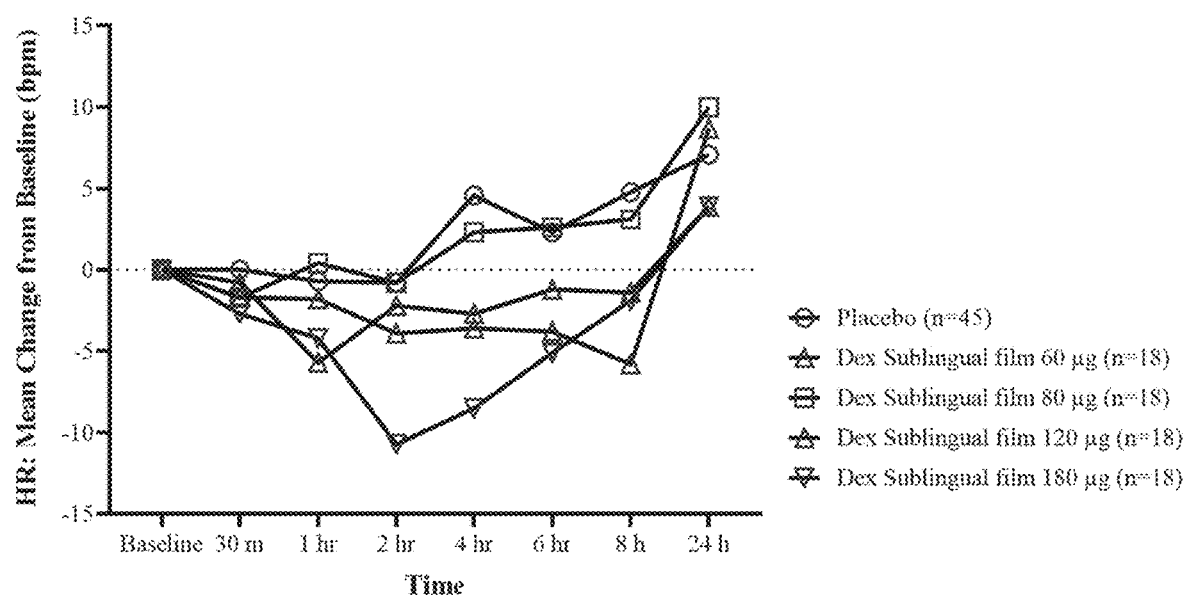
FIG. 7C: depicts mean change from baseline for resting heart rate (HR) over time in schizophrenic patients (Safety Population) treated with a sublingual film containing dexmedetomidine hydrochloride (60 µg, 80 µg, 120 µg and 180 µg) versus a placebo group. The preparation of dexmedetomidine hydrochloride sublingual film (60 µg) is exemplified in Example 1 and dexmedetomidine hydrochloride sublingual films (80 µg, 120 µg and 180 µg) are exemplified in Example 2.

Mean changes from baseline at hours 2 postdosing for standing SBP, DBP, and HR are provided below (FIGS. 7A, 7B and 7C). These changes are similar to the changes from baseline values for resting measurements for SBP, DP, and HR (FIGS. 6A, 6B and 6C). Total of 3 subjects (1 in each dose groups 80 µg, 120 µg, and 180 µg) experienced TEAEs of orthostatic hypotension.

Mean (±SD) changes from baseline at 2 hours postdosing for standing SBP, DBP, and HR were:

- SBP: −3.1 (8.34), −4.6 (9.04), −12.6 (12.83), −11.9 (16.43) and −15.0 (11.3) mmHg in the 20 µg, 60 µg, 80 µg, 120 µg, and 180 µg dose groups, respectively, and +0.5 (8.35) mmHg in the placebo group.
- DBP: −1.4 (6.97), −4.2 (4.78), −6.7 (8.49), −6.9 (7.86), and −7.1 (8.51) mmHg in the 20 µg, 60 µg, 80 µg, 120 µg, and 180 µg dose groups, respectively, and −1.3 (7.36) mmHg in the placebo group.
- HR. 0.6 (7.92), −4.3 (11.87), −1.1 (10.47), −1.7 (13.98), and −10.4 (10.08) bpm in the 20 µg, 60 µg, 80 µg, 120 µg, and 180 µg dose groups, respectively, and −0.3 (9.88) bpm in the placebo group.

TABLE 21

Treatment Emergent Adverse Events by System Organ Class and Preferred Term During the Treatment Period (Safety Population)

| System Organ Class Preferred Term | Placebo (N = 45) | Dexmedetomidine sublingual film | | | | |
|---|---|---|---|---|---|---|
| | | 20 µg (N = 18) | 60 µg (N = 18) | 80 µg (N = 18) | 120 µg (N = 18) | 180 µg (N = 18) |
| Any AEs | 10 (22.2) | 5 (27.8) | 6 (33.3) | 10 (55.6) | 12 (66.7) | 12 (66.7) |
| Nervous system disorders | 6 (13.3) | 4 (22.2) | 4 (22.2) | 8 (44.4) | 9 (50.0) | 9 (50.0) |
| Somnolence | 2 (4.4) | 3 (16.7) | 3 (16.7) | 6 (33.3) | 4 (22.2) | 8 (44.4) |
| Headache | 2 (4.4) | 1 (5.6) | 0 | 1 (5.6) | 3 (16.7) | 0 |
| Dizziness | 2 (4.4) | 0 | 2 (11.1) | 1 (5.6) | 1 (5.6) | 0 |
| Paraesthesia | 0 | 0 | 0 | 1 (5.6) | 1 (5.6) | 0 |
| Hypoaesthesia | 0 | 0 | 1 (5.6) | 0 | 0 | 0 |
| Sedation | 0 | 0 | 0 | 0 | 0 | 1 (5.6) |
| Gastrointestinal disorders | 7 (15.6) | 2 (11.1) | 1 (5.6) | 4 (22.2) | 4 (22.2) | 2 (11.1) |
| Dry mouth | 6 (13.3) | 1 (5.6) | 0 | 3 (16.7) | 3 (16.7) | 2 (11.1) |
| Constipation | 0 | 0 | 1 (5.6) | 1 (5.6) | 0 | 0 |
| Diarrhoea | 0 | 0 | 0 | 0 | 1 (5.6) | 0 |
| Dyspepsia | 0 | 1 (5.6) | 0 | 0 | 0 | 0 |
| Nausea | 1 (2.2) | 0 | 0 | 0 | 0 | 0 |
| Toothache | 1 (2.2) | 0 | 0 | 0 | 0 | 0 |
| Vascular disorders | 0 | 0 | 0 | 1 (5.6) | 3 (16.7) | 5 (27.8) |
| Hypotension | 0 | 0 | 0 | 0 | 2 (11.1) | 4 (22.2) |
| Orthostatic hypotension | 0 | 0 | 0 | 1 (5.6) | 1 (5.6) | 1 (5.6) |
| Investigations | 3 (6.7) | 0 | 1 (5.6) | 0 | 1 (5.6) | 1 (5.6) |
| Alanine aminotransferase increased | 1 (2.2) | 0 | 0 | 0 | 0 | 0 |
| Aspartate aminotransferase increased | 1 (2.2) | 0 | 0 | 0 | 0 | 0 |
| Blood bilirubin increased | 0 | 0 | 1 (5.6) | 0 | 0 | 0 |
| Glucose urine present | 0 | 0 | 0 | 0 | 1 (5.6) | 0 |
| Heart rate increased | 1 (2.2) | 0 | 0 | 0 | 0 | 0 |
| Liver function test increased | 1 (2.2) | 0 | 0 | 0 | 0 | 0 |
| Protein urine present | 0 | 0 | 0 | 0 | 0 | 1 (5.6) |
| Infections and infestations | 1 (2.2) | 0 | 1 (5.6) | 0 | 1 (5.6) | 0 |
| Cellulitis | 0 | 0 | 0 | 0 | 1 (5.6) | 0 |
| Nasopharyngitis | 1 (2.2) | 0 | 0 | 0 | 0 | 0 |
| Urinary tract infection | 0 | 0 | 1 (5.6) | 0 | 0 | 0 |
| Cardiac disorders | 0 | 0 | 0 | 0 | 1 (5.6) | 0 |
| Bradycardia | 0 | 0 | 0 | 0 | 1 (5.6) | 0 |
| Musculoskeletal and connective tissue disorders | 0 | 0 | 0 | 1 (5.6) | 0 | 0 |
| Pain in extremity | 0 | 0 | 0 | 1 (5.6) | 0 | 0 |

TABLE 22

Summary of Adverse Events (Safety Population)

| Category, n (%) | Placebo (N = 45) | Dose groups | | | | |
|---|---|---|---|---|---|---|
| | | 20 µg (N = 18) | 60 µg (N = 18) | 80 µg (N = 18) | 120 µg (N = 18) | 180 µg (N = 18) |
| Any TEAE | 10 (22.2) | 5 (27.8) | 6 (33.3) | 10 (55.6) | 12 (66.7) | 12 (66.7) |
| Any treatment related TEAE | 10 (22.2) | 4 (22.2) | 5 (27.8) | 10 (55.6) | 10 (55.6) | 11 (61.1) |
| TEAE severity | | | | | | |
| Mild | 8 (17.8) | 5 (27.8) | 5 (27.8) | 9 (50.0) | 11 (61.1) | 7 (38.9) |
| Moderate | 2 (4.4) | 0 | 1 (5.6) | 1 (5.6) | 1 (5.6) | 5 (27.8) |
| Severe | 0 | 0 | 0 | 0 | 0 | 0 |
| Any SAE | 0 | 0 | 0 | 0 | 0 | 0 |
| Any AE leading to discontinuation | 0 | 0 | 0 | 0 | 0 | 0 |

Abbreviations: AE = adverse events; TEAE = treatment-emergent adverse event; SAE = serious adverse event Percentages are based on the number of Safety Population subjects in each treatment arm. If a subject experienced more than one adverse event in a category, the subject is counted only once in that category.

Conclusion: Dexmedetomidine sublingual film treatment significantly improved the severity of agitation from baseline as measured by PEC, CGI-I, and ACES scales in schizophrenia patients. The primary efficacy endpoint was met in 80 µg, 120 µg, and 180 µg treatment groups as there was significant improvements in PEC total scores from baseline at 2 hours post-dose with mean changes of −7.3, −9.2, and −10.8 points, respectively, versus −4.5 for placebo. LSM differences from placebo were −2.9 (P=0.0210), −4.6 (P=0.0003), and −6.3 (P<0.0001) for the 80 µg, 120 µg, and 180 µg groups, compared with placebo The proportion of responders (ie, a ≥40% decrease in PEC total score) at 2 hours post-dose was significantly higher in the 120 µg and 180 µg dose groups (68.8% [P=0.0158]) and 94.4% [P<0.0001], respectively) compared with placebo (31.0%). Further, changes in secondary efficacy measures (ie, CGI-I and ACES scores) at 2 hours post-dose were consistent with the results for PEC total scores and were indicative of improvement in symptoms of agitation after treatment with Dexmedetomidine sublingual film.

Example 4: A Phase Ib/II, Multicenter, Randomized, Double Blind, Placebo Controlled, Ascending Dose Finding, Efficacy, Pharmacokinetic and Safety Study of Dexmedetomidine Hydrochloride Sublingual Film in Agitation Associated with Dementia Primary Objective:
Describe the safety and tolerability of single doses of dexmedetomidine hydrochloride that are efficacious in treatment of acute agitation associated with dementia.
Secondary Objective:
1. Describe the onset and magnitude of calming effects of different doses of Dexmedetomidine hydrochloride on symptoms of acute agitation associated with dementia compared to placebo.
2. Describe the duration of calming as measured by PEC and ACES.
3. Describe the tolerability and safety profile of Dexmedetomidine hydrochloride, as determined by adverse events and vital signs versus placebo.
4. Describe clinical effects as measured by the Clinician Global Impression of Severity of agitation scale (CGI-S) and then Improvement (CGI-I) after drug administration.
5. Describe the frequency of agitation using the Cohen Mansfield Agitation Inventory (CMAI) at baseline, 1 hour and 2 hours post dose.
6. Determine the approximate dissolution time of Dexmedetomidine hydrochloride films in the sublingual space.
7. Assess the local tolerability via buccal examination after dosing Dexmedetomidine hydrochloride film.
8. Describe the pharmacokinetics and exposure of dexmedetomidine as delivered by sublingual Dexmedetomidine hydrochloride dosing.

Methodology: This is an adaptive Phase Ib trial design. It is a randomized, double-blind, placebo-controlled, multiple ascending dose study assessing efficacy, pharmacokinetics, safety and tolerability of Dexmedetomidine hydrochloride dosing in adult (65 years and older) males and females with acute agitation associated with dementia.

The study will attempt to characterize a safe and tolerable dose range in at least 30 subjects, (4:1 randomization to active: placebo) per dose level, at each of the three dose levels, that results in a calming effect as measured using the Pittsburgh Agitation Scale (PAS) (Table 23).

Evaluation of three doses of 30 µg, 60 µg and 90 µg are planned, with an option to test different doses based on tolerability and safety. This is an adaptive design as doses selected for testing may be different from these, based upon safety reviews. Doses lower or higher may be chosen to test, and repeated, up to 180 µg within each cohort. Dexmedetomidine hydrochloride films may be divided in half if needed to deliver half-dose strengths. Except for the first dose cohort (30 µg), each subsequent dose level will be authorized after a safety review of the previous dosing cohort. Dosing may be repeated in the case of persistent or recurrent agitation, if there is no significant improvement (CGI-I of 1 or 2 as 'very much' or 'much improved') and no safety events evident. Dosing may be repeated up to a total of two repeat doses (at the same randomization group Active: Placebo) for all cohorts except for 90 µg dose which can only be repeated once (total 180 µg) if necessary, at 2 hours post first dose but only after the 2-hour assessments are conducted and only within 12 hours post first dose. Patients can only be re-dosed if they are hemodynamically stable, not hypotensive (must be greater than 90/60 diastolic/systolic) and not bradycardic (must be greater than 60 bpm). Patients also cannot be re-dosed if they are orthostatic (a drop of 20 points in either SBP or DBP) or if they are experiencing an AE. Not only does this determine individual response to a single dose but determines if a given subject is responsive to a second dose, and may respond to a greater dose, or could be categorized as a non-responder to dexmedetomidine hydrochloride despite being exposed to a greater total dose.

Periodic safety data reviews will be undertaken on an ongoing basis to review all subjects assigned and dosed, as data and analyses become available. Dose escalation will be allowed unless a safety or tolerability issue becomes evident upon periodic regular safety review.

Patients enrolling at a site are sequentially assigned to the lowest dose cohort (including placebo) followed by enrollment assignment to increasing dose cohorts. This sequential escalating adaptive enrollment ensures subject safety; the lowest dose cohort completes accrual first, higher dose cohorts complete last. In addition, those subjects assessed as requiring a second dose for efficacy provide early evidence of safety/tolerability of higher doses as they are effectively exposed to doses that approximate the next dose cohort. The majority of patients will be enrolled and evaluated in lower dose cohorts before a higher dose cohort is initiated. Further, if evidence of intolerability arises from analyses integrating PK, exposure and safety/tolerability of all subjects and doses, the dose regimen may be altered, or a different dose may be selected to test the hypothesis that a (typically lower) dose regimen is better tolerated. Eligible patients (those with any type of dementia) may be identified in SNIFFs, mental health, psychiatric or medical emergency services, including medical/psychiatric observation units, or as newly admitted to a hospital setting for acute agitation or already in hospital for chronic underlying conditions. Subjects will likely remain in their facility while undergoing screening procedures to assess eligibility. Upon confirmation of eligibility, subjects will be randomized to Dexmedetomidine hydrochloride or placebo film. At the beginning of each study session, a single dose of Dexmedetomidine hydrochloride film will be administered sublingually by the patient if able with instructions from an unblinded staff member who will not participate in evaluation of safety or efficacy. The drug film will be retained in the sublingual cavity until dissolved. Participants will also be evaluated for local irritation around the area where the film is placed. Efficacy and safety assessments will be conducted periodically before and after dosing. The next cohort will be dosed after completing accrual of most prior panels, in accord with regular ongoing periodic safety and PK review as eligible subjects are assigned, dosed, and data becomes available.

Vital signs and ECGs will be conducted at the time points indicated in the schedule of events. Participants will be allowed water as desired 15 minutes after completion of dosing. Safety and tolerability assessments will be continued until the morning of Day 3 (day of discharge) and will be repeated on Day 7+2. Smoking will be permitted according to the site's policies. After the 4 hr assessments are completed, at the discretion of the PI, rescue therapy may be initiated using standard of care treatment which may include lorazepam 0.5-5 mg po/IM or an antipsychotic medication po/IM.

Any abnormal vital sign measurement, clinical laboratory test, physical examination finding, or ECG parameter deemed clinically significant by the investigator will be repeated, including test results obtained on the final study day or upon early termination. For any test abnormality deemed clinically significant, repeat analysis will be performed during the follow-up period and until the value returns to baseline (or within normal limits) or the investigator deems the abnormality to be of no clinical significance. Subjects presenting with a clinically significant Urinary Tract Infection (UTI) as determined by clinical laboratory tests will be excluded from the study.

Efficacy Assessments:

Efficacy measurements will be taken up to and including 24 hours post first dose. The effects of Dexmedetomidine hydrochloride on acute agitation will be assessed by the following scales: Pittsburgh Agitation Scale (PAS), the PANSS-EC (PEC), CMAI, CGI-Severity for Agitation and CGI-Improvement for Agitation. If there is no significant improvement in CGI (CGI-I of 1 or 2 as "very much" or "much improved") and there are no evident safety concerns, a second film (of same assignment active vs. placebo) may be given.

Safety and Tolerability Assessments:

AEs, clinical laboratory tests, ECG, and vital signs will be monitored, and all observed and volunteered AEs will be recorded. Blood pressure, heart rate and ECG will be completed per schedule of assessments. Any abnormal clinically significant (investigator determined) vital sign measurement, clinical laboratory test, physical examination finding, or ECG parameter will be repeated, until the value returns to baseline (or within normal limits) or the investigator deems the abnormality to be of no clinical significance. Orthostatic assessments will follow the CDC guidelines for the elderly (e.g. blood pressure upon standing for 1 and 3 minutes). Safety and tolerability assessments will be continued until the morning of Day 2 and Day 3 and will be repeated on Day 7+2.

TABLE 23

Arms and Interventions

| Arms | Intervention |
|---|---|
| Active Comparator: Cohort 1: 30 µg Cohort 1 consists of 10 patients out of whom 8 patients receive 30 µg film and the remaining 2 patients receive a placebo | Drug: Sublingual film containing dexmedetomidine hydrochloride for the treatment of agitation associated with Dementia Drug: Placebo Film Placebo film for dexmedetomidine hydrochloride |
| Active Comparator: Cohort 2: 60 g Cohort 2 consists of 10 patients out of whom 8 patients receive 60 µg film and the remaining 2 patients receive a placebo | Drug: Sublingual film containing dexmedetomidine hydrochloride for the treatment of agitation associated with Dementia Drug: Placebo Film Placebo film for dexmedetomidine hydrochloride |
| Active Comparator: Cohort 3: 90 µg Cohort 3 consists of 10 patients out of whom 8 patients receive 90 µg film and the remaining 2 patients receive a placebo | Drug: Sublingual film containing dexmedetomidine hydrochloride for treatment of agitation associated with Dementia Drug: Placebo Film Placebo film for dexmedetomidine hydrochloride |

Number of Subjects (Planned)

At least 30 subjects (10 per cohort) will be enrolled at up to 3 study sites in the United States. However, it is possible that the sponsor may opt to expand the number of sites and subjects per dose cohort (up to 80 total patients) as the study progresses.

Subjects:

Eligible individuals with any form of dementia who have a history of recent agitation (6 months or less) or their legally authorized representative (LAR) will sign an informed consent. Upon confirmation of eligibility, subjects will be randomized to either dexmedetomidine hydrochloride sublingual film or placebo film. Ten (10) subjects who exhibit acute agitation associated with dementia in each cohort will be enrolled (4:1 randomization; e.g.: eight dexmedetomidine hydrochloride sublingual film, two placebo films). Once subjects become agitated, they will proceed with Day 1 assessments.

TABLE 24

Schedule of Events

| Activity Time point | Pre-Screening[8] Pre-treatment | Screening Pre-treatment | Pre-Dose −1 hr to time 0 | Treatment Evaluation Day 1 | | | | | | | | |
|---|---|---|---|---|---|---|---|---|---|---|---|---|
| | | | | 5 min | 10 min | 15 min | 30 min | 1 hr | 2 hr | 4 hr | 6 hr | 8 hr |
| Informed Consent | X | | | | | | | | | | | |
| Medical History | X | X | | | | | | | | | | |
| Demographics | X | X | | | | | | | | | | |
| Weight | X | | | | | | | | | | | |
| Height | X | | | | | | | | | | | |
| Mini-Mental State exam | X | | | | | | | | | | | |
| Clinical Dementia Rating Score | X | | | | | | | | | | | |
| Physical Exam | X | X | | | | | | | | | | |
| Safety Labs[3] | X | | | | | | | | | | | |
| UTI and pregnancy | | X | | | | | | | | | | |
| ECG with rhythm trip[7] | X | | X | | | | X | | | | | |
| Pulse oximetry | | | X | | | | X | X | X | X | X | X |
| Resting vital signs[2] | X | X | X | | | | X | X | X | X | X | X |
| Orthostatic vital signs[2] | X | X | X | | | | X | X | X | X | | X |
| Inclusion/Exclusion criteria | X | X | X | | | | | | | | | |

TABLE 24-continued

| Activity Time point | | | | | | | | | | | | |
|---|---|---|---|---|---|---|---|---|---|---|---|---|
| Randomization | | | X | | | | | | | | | |
| CMAI | | | X | | | | X | X | | | | X |
| Study drug administration[6] | | | | | | | | | | | | |
| PAS | X | X | X | | | | X | X | X | X | | X |
| PEC | X | | X | | | | X | X | X | X | | X |
| ACES | | | X | | | | X | X | X | | | X |
| CGI-Severity Agitation | | | X | | | | | X | | | | |
| CGI-Improvement/ change in Agitation | | | | | | | X | X | X | X | | X |
| C-SSRS | X | X | | | | | | | | | | |
| Buccal (SL) assessment[5] | | | | X | X | X | X | | X | X | | |
| PK Sampling[4] | | | | | | | X | X | X* | X | | X |
| Concomitant Meds | X | X | X | X | X | X | X | X | X | X | X | X |
| Adverse Events | X | X | X | X | X | X | X | X | X | X | X | X |

Schedule of Events

| Activity Time point | Day 2 Follow-Up (+1) 24 hr (−9/+12 hr) | Day 3 Discharge | Day 7 (+2) End of Study |
|---|---|---|---|
| Informed Consent | | | |
| Medical History | | | |
| Demographics | | | |
| Weight | X | | |
| Height | | | |
| Mini-Mental State exam | X | | |
| Clinical Dementia Rating Score | X | | |
| Physical Exam | X | | |
| Safety Labs[3] | | X | X |
| UTI and pregnancy | | | |
| ECG with rhythm strip[7] | X | | |
| Pulse oximetry | X | | |
| Resting vital signs[2] | X | | |
| Orthostatic vital signs[2] | X | | |
| Inclusion/Exclusion criteria | | | |
| Randomization | | | |
| CMAI | X | X | X |
| Study drug administration[6] | | | |
| PAS | X | X | X |
| PEC | X | X | X |
| ACES | | | |
| CGI-Severity Agitation | X | | |
| CGI-Improvement/ change in Agitation | | | |
| C-SSRS | X | | |
| Buccal (SL) assessment[5] | X | | |
| PK Sampling[4] | X | | |
| Concomitant Meds | X | X | X |
| Adverse Events | X | X | X |

Notes to the Schedule of Events:

[1]Pre-dose assessments will have a window of 60 minutes prior to first dose. If possible, Pre-dose CMAI should be performed within 45 min prior to dosing and PAS, PEC and CGI-S should be performed within 15 min prior to dosing. Timing of all subsequent assessments is relative to the first dose. All post-dose assessments will have a window of −10/+20 minutes until 2 hours and ±30 minutes until 8 hours. All post-dose efficacy assessments should be conducted prior to any other assessments at each time point.

[2]Resting vital signs (SBP, DBP and HR) will be taken upon having the subject recumbent for 5 min at Pre Screening, Screening, Pre-dose and at 30 min, 1, 2, 46, 8 and 24 hours post first dose. Triplicate measurements to be performed in case of Systolic BP <90 mmHg, Diastolic BP <60 mmHg or Pulse < 60 bpm. Orthostatic measurements (SBP, DBP, HR, respiratory rate and temperature) will be taken upon having the subject stand, with measurements taken upon standing for 1 and 3 minutes, per CDC guidelines for elderly) at Pre Screening, Screening, Pre-dose, 30 min, 1, 2, 4, 8 and 24 hours post first dose. Vital signs are to be done prior to PK samples.

[3]Safety Labs will include chemistry, hematology, urinalysis, and UDS (local lab, only conducted at Pre Screening). Labs drawn within 28 days prior to dosing may suffice with the exception of urine drug screen.

[4]PK blood samples will be collected at 30 min, 1, 2, 4, 8-10 hours (collect one sample between 8 and 10 hours) and 24 hr after first dose. A sample may not be collected if the Physician indicates in source documents that the patient is in a mental state that is not conducive to PK sample collection. Non-compliance or refusal of all or any PK draw will not be exclusionary nor result in Early termination (ET). All PK collections will have a window of ±10 minutes except for the 24-hour post-dose collection which will have a window of ±1 hour.
*For re-dosed subjects only: PK blood sample will be collected at 2.5 hrs. post first dose in addition to the other times.

[5]Buccal exam for local irritation and drug dissolution time will be performed by unblinded staff at 5, 10, 15, 30 min, 2 h, 4 h and 24 hours post first dose.

[6]In the investigator's clinical judgement, the same randomized dose and or a lower dose may be repeated after 2 hr post first dose assessments are complete, if there is persistent or recurrent agitation as measured by (improvement on the CGI-I) and in the absence of safety concerns. Doses can be repeated twice in a span of 12 hours, except for the 90 µg cohort, which can only be repeated once. If necessary, placement of study drug may be performed by unblinded research staff member. Antihypertensives or other medications can be held on the day of study drug administration at the discretion of the PI.

[7]ECG for pre-dose needs to be collected but if unable to be assessed it will not constitute a protocol deviation. ECGs collected following treatment are to be performed prior to PK assessments.

[8]Day 1 to be performed within 28 days from Pre-Screening Assessments. If subject does not become agitated within the 28-day window, they are considered a pre-screen failure. However, the subject can be rescreened once at the discretion of the investigator.

Diagnosis and Main Criteria for Eligibility:
Inclusion Criteria
1. Male and female patients 65 years and older.
2. Patients who have met DSM-5 criteria for neurocognitive disorder, or dementia who have history of instances of acute agitation.
3. History of agitation to the point that it impairs social activities, requires staffing or medical intervention (kick, bite, flailing, etc.), or impairs ability for functional activities of daily living.
4. Patients who meet IPA diagnostic criterion for agitation.
5. Patients who are judged to be clinically agitated at Pre-dose with a total score of ≥8 on the 4 items (aberrant vocalization, motor agitation, aggressiveness, and resisting care) comprising the Pittsburgh Agitation Scale (PAS).
6. Patients who have a score of ≥2 on at least 1 of the 4 items on the Pittsburgh Agitation Scale (PAS).
7. Patients who read, understand and provide written informed consent, or who have a Legally Authorized Representative (LAR).
8. Patients who are in good general health prior to study participation as determined by a detailed medical history, physical examination, 12-lead ECG, blood chemistry profile, hematology, urinalysis and in the opinion of the Principal Investigator.
9. Female participants, if of child-bearing potential and sexually active, and male participants, if sexually active with a partner of child-bearing potential, who agree to use a medically acceptable and effective birth control method throughout the study and for one week following the end of the study. Medically acceptable methods of contraception that may be used by the participant and/or his/her partner include abstinence, birth control pills or patches, diaphragm with spermicide, intrauterine device (IUD), condom with foam or spermicide, vaginal spermicidal suppository, surgical sterilization and progestin implant or injection. Prohibited methods include: the rhythm method, withdrawal, condoms alone, or diaphragm alone.

Exclusion Criteria
1. Patients with agitation caused by acute intoxication must be excluded. Positive identification of non-prescription drugs during urine screening excludes the subject.
2. Patients treated within 4 hours prior to study drug administration with benzodiazepines, other sedatives, hypnotics or oral or short-acting intramuscular antipsychotics must be excluded.
3. Treatment with alpha-1 noradrenergic blockers, alpha adrenergic antagonists within 8 hours prior to dosing.
4. No new chronic medications initiated in the past 14 days prior to screening excluding over-the-counter products taken sporadically.
5. Patients with significant risk of suicide or homicide per the investigator's assessment, or any patient with an answer of "yes" to item 4 or 5 on the CSSRS.
6. Patients who have hydrocephalus, seizure disorder, or history of significant head trauma, subarachnoid bleeding, brain tumor, encephalopathy, meningitis, or focal neurological findings, with a recent large (non-microvascular) stroke, who may be considered medically unstable or in recovery must be excluded. Patients with a remote history of stroke may be included, regardless of size/location.
7. History of clinically significant syncope or other syncopal attacks, orthostatic hypotension within the past two years, current evidence of hypovolemia, orthostatic hypotension (≥20 mmHg drop in systolic BP following 1 and 3 minutes of standing) and bradycardia, a baseline (Pre-dose) heart rate of <60 beats per minutes or systolic blood pressure <110 mmHg or diastolic BP<70 mmHg must be excluded.
8. Patients with laboratory or ECG abnormalities considered clinically significant by the investigator or qualified designee [Advanced heart block (second-degree or above atrioventricular block without pacemaker), diagnosis of Sick sinus syndrome] that would have clinical implications for the patient's participation in the study must be excluded.
9. Patients with serious or unstable or uncontrolled medical illnesses must be excluded. These include current hepatic (moderate-severe hepatic impairment), renal, gastro-enterologic, respiratory, cardiovascular (including ischemic heart disease, congestive heart failure), endocrinologic, or hematologic disease.
10. Patients who have received an investigational drug within 30 days prior to the current agitation episode must be excluded.
11. Patients who are considered by the investigator, for any reason, to be an unsuitable candidate for receiving dexmedetomidine, or unable to use the sublingual film, must be excluded; e.g. patients with a history of allergic reactions to dexmedetomidine must be excluded.
12. Patients experiencing clinically significant pain, per Investigator.

Method of Assigning Subjects to Treatment Groups

Upon confirmation of eligibility, subjects will be randomized to Dexmedetomidine hydrochloride or placebo film. In each of the three-dose cohorts, 10 participants (8 drug treated, 2 placebo) will be randomized 4:1 Dexmedetomidine hydrochloride film: Placebo. Study randomization will be computer generated.

Treatment Administration

Dosing may be achieved by cutting of a film, widthwise, directly in the middle, to make a half dose. Dosing may also be achieved by administration of 1 to 3 films [e.g. a 60 μg dose may be administered with a half of a 60 μg dose (30 μg) to make a 90 μg dose]. At the beginning of each study session, patients will be instructed on how to self-administer the investigational product. If the patient can self-administer, he/she will self-administer the dose of Dexmedetomidine hydrochloride or placebo film sublingually under supervision of an unblinded staff member who will not participate in evaluation of safety or efficacy. The investigational product will be retained in the sublingual cavity until dissolved. If sublingual administration is not possible, the film may be placed inside the lower lip. The location of the placement of the film should be noted in the subject's chart. Objective buccal mucosal examination and time of film dissolution by unblinded study staff per Table 24 will be conducted.

Study Procedures

Subjects or their LAR will provide written informed consent, and assent as applicable, before any study-related procedures are initiated, including the cessation of prohibited concomitant therapy. The schedule of events to be performed during the study is provided in Table 24.

Study Assessments

Efficacy: The effect of study drug will be evaluated using several validated instruments as given below.

PANSS-Excited Component (PEC)

Agitation-Calmness Evaluation Scale (ACES)

Cohen Mansfield Agitation Inventory (CMAI):

Assessment of drug effect on frequency of acute agitation will be also done using the CMAI. The CMAI is a rating questionnaire consisting of 29 behaviors each rated on a 7-point scale of frequency. It is possible that all 29 behaviors will not be relevant to a specific patient. Only behaviors manifested by the subject at baseline will be assessed throughout the study resulting in a modified CMAI. Behaviors which are present immediately pre-dose will be rated throughout the post-dose time-points. At each time-point after pre-dose, the rater will note items (behaviors) which were not manifested prior to dosing have not emerged since last CMAI assessment. Should they emerge, these items shall be included in ratings.

Pittsburgh Agitation Scale (PAS):

The Pittsburgh Agitation Scale (PAS) is an instrument based on direct observations of the patient that is developed to monitor the severity of agitation associated with dementia. There are four Behavior Groups observed (using a 0 to 4-point scale) in the patient, Aberrant Vocalization, Motor Agitation, Aggressiveness, Resting Care.

CGI-S and CGI-I for Agitation:

Both CGI-I and CGI-S will be focused on the severity of agitation rather than the severity of the overall illness of dementia.

Clinical Global Impression of Severity (CGI-S) will be rated based upon the severity of agitation at screening and pre-dose (immediately prior to start of dosing).

Severity of agitation will be assessed based on following scale:
- 0=Not assessed
- 1=Normal not at all symptomatic
- 2=Minimally symptomatic—few or mild symptoms—little interference with patients functioning
- 3=Mildly symptomatic—low level of symptoms—little interference in social functioning
- 4=Moderately symptomatic—some prominent symptoms—some interference in functioning
- 5=Markedly symptomatic—significant symptoms with very substantial interference in functioning
- 6=Severely symptomatic—very marked symptoms make it difficult for patients to engage with others
- 7=Among the most extremely symptomatic subjects—extreme symptoms—patient is incapacitated or highly dangerous to self or others requires extra care and supervision Drug response on agitation will be evaluated by the Clinical Global Impressions-Improvement (CGI-I) which is performed after dosing and evaluated relative to pre-dose baseline agitation. The CGI-I scores range from 1 to 7:
- 0=not assessed (missing),
- 1=very much improved,
- 2=much improved,
- 3=minimally improved,
- 4=no change,
- 5=minimally worse,
- 6=much worse,
- 7=very much worse Clinical Diagnosis and Description of Dementia:

The subtype of dementia will be determined and recorded based upon clinical neurologic and psychiatric evaluation to include review of all available medical information, medical records, documentation of prior evaluations, family/caretaker interviews, records, laboratory, genetics or other biomarkers, and results of neuroimaging (if available). The following scales will characterize subject's dementia (DSM-5 Major Neurocognitive disorder) in terms of cognitive and functional impairment:

MMSE

The Folstein Mini-Mental State Examination (MMSE) is an examination that tests an elderly person's cognitive ability. Domains measured by the MMSE include orientation to time and place, registration, attention and calculation, recall, naming, repetition, comprehension, reading, writing, and drawing. Total points on this test is 30. Any score of 24 or more (out of 30) indicates a normal cognition. Below this, scores can indicate severe ($\leq 9$ points), moderate (10-18 points) or mild (19-23 points) cognitive impairment.

CDR®

The CDR® (Alzheimer's Disease Research Center, Washington University, St Louis) is a 5-point scale used to characterize six domains of cognitive and functional performance applicable to Alzheimer Disease and related dementias: memory, orientation, judgment & problem solving, community affairs, home & hobbies, and personal care. A score of 0 connotes no cognitive impairment, and then the remaining four points are for various stages of dementia where:
- CDR-0=normal
- CDR-0.5=very mild dementia
- CDR-1=mild
- CDR-2=moderate
- CDR-3=severe Safety Safety will be assessed during the study by the monitoring and recording of AEs, clinical laboratory test results (hematology, biochemistry, and urinalysis), vital sign measurements (systolic and diastolic blood pressures, heart rate measured as pulse, respiratory rate, and temperature), ECG, and physical examination findings.

Adverse events (AEs) will be characterized by type, severity, seriousness, and relationship to treatment. Adverse events will be coded by preferred term and system organ class using MedDRA version 20.0.

Pharmacokinetics

Blood samples (4 ml) will be collected at 0.5, 1, 2, 4, 8- and 24-hours post-dose per Schedule of Events (Table 24).

For each subject, up to 6 blood samples (24 mL of blood) will be collected during the study for PK analysis. In addition, approximately 15 mL of blood will be collected at screening, approximately 15 mL of blood will be collected at Day 3 Discharge, and approximately 15 mL of blood will be collected at Day 7(+2) for clinical laboratory testing. The total volume of blood collected during the study is expected to be approximately 69 mL.

For re-dosed subjects only: an extra PK blood sample (4 ml) will be collected at 2.5 hours post first dose in addition to the other times, totaling approximately 73 ml. All PK sampling will occur only after the all other assessments at that time point are conducted.

Pharmacokinetic Analyses

All pharmacokinetic parameters will be calculated using non-compartmental analysis using WinNonlin. Actual sampling times will be used in all pharmacokinetic analyses. Per protocol times will be used to calculate mean plasma concentrations for graphical displays. Other PK analyses may be performed as appropriate.

Example 5: A Phase Ib/II, Multicenter, Randomized, Double Blind, Placebo Controlled, Ascending Dose Finding, Efficacy, Pharmacokinetic and Safety Study of Dexmedetomidine Hydrochloride Sublingual Film to Treat Symptoms of Acute Opioid Withdrawal in Patients with Opioid Use Disorder Who are Physically Dependent on Opioids Primary Objective:

Establish the safety and tolerability of ascending doses of dexmedetomidine hydrochloride sublingual film relative to placebo in subjects with opioid use disorder who are physically dependent on opioids and maintained on oral morphine.

Secondary Objectives:

Establish the efficacy of dexmedetomidine hydrochloride sublingual film relative to placebo in improving the following:
1. Opioid withdrawal symptoms:
    Short Opiate Withdrawal Scale of Gossop (SOWS-GOSSOP) and
    Clinical Opiate Withdrawal Scale (COWS)
2. Time to dropout after opioid discontinuation
3. Percentage of subjects dropping out after opioid discontinuation
4. Assessment of safety reflected by scores on the Agitation and Calmness Evaluation Scale (ACES) assessment Exploratory Objective:

Evaluation of pharmacokinetics in subjects undergoing opiate withdrawal.

Study Design: This inpatient Phase Ib study will assess the safety, pharmacokinetics, and early signs of efficacy of escalating doses of dexmedetomidine hydrochloride sublingual film versus placebo following discontinuation of morphine maintenance. The opioid maintenance phase will be occurring during Study Days 1-5; the randomized dexmedetomidine hydrochloride sublingual film/placebo phase will occur on Study Days 6-12. This will be followed by 2 days of placebo sublingual film (for dexmedetomidine) and morphine-placebo treatment for all remaining subjects on days 13-14.

After a 30-day screening period, eligible male and female adult subjects with OUD who are physically dependent on opioids will be admitted to an inpatient unit. At the start of the opioid maintenance phase (Study Days 1-5), subjects (n=125 enrollers) will receive oral morphine (30 mg) four times a day (QID) approximately every 6 hours or up to 5 times per day as needed. The total dose of morphine during the first two days of stabilization (Study Days 1-2) can vary at the discretion of the investigator, between 120 mg and 150 mg per day depending on patients abuse history and need for higher dose to stabilize withdrawal symptoms. During the next three days (Study Days 3-5), all subjects will receive a standard dose of morphine (30 mg QID) totaling 120 mg in a day. In addition, all subjects will receive placebo films, approximately 12 hours apart during this opioid maintenance phase (i.e., Days 1-5) to simulate and thus blind treatment with dexmedetomidine sublingual film during Days 6-12.

Starting on the morning of Day 6, blinded abrupt discontinuation of active morphine will begin by replacing active morphine with placebo morphine. Placebo morphine capsules will be identical in appearance to the morphine capsules taken during the opioid maintenance period. On this day (Study Day 6), subjects will be randomized (within each cohort, 20 subjects will receive active dexmedetomidine sublingual film and 5 subjects will receive placebo) to receive either placebo or dexmedetomidine hydrochloride films administered twice a day (BID), approximately 12 hours apart at approximately 8 am and 8 pm. Placebo sublingual film or dexmedetomidine sublingual film will be administered on Days 6-12. On days 13 and 14, all remaining subjects will receive placebo morphine capsules (QID) and placebo sublingual films (BID).

It is anticipated that a total of 5 cohorts will be tested (n=25 per cohort) with potential to add cohorts or select different doses/schedule of dosing based on ongoing safety review and medical monitoring. The following doses will be administered: 30 µg (Cohort 1), 60 µg (Cohort 2), 90 µg (Cohort 3), 120 µg (Cohort 4), and 180 µg (Cohort 5). Safety and tolerability will be monitored continuously and summarized upon completion of each cohort by medical safety review. Studies of opioid withdrawal with placebo arms are likely to have high dropout rates, thus, the dropouts prior to Day 6 may be replaced to ensure enough sample size entering the treatment phase. The study is intended to be flexible and adaptable and as such, the dosing frequency, the doses and the number of cohorts of dexmedetomidine hydrochloride sublingual film may be changed as a result of review of safety, tolerability and efficacy data.

Opioid withdrawal symptoms (SOWS-Gossop and COWS) will be measured throughout the inpatient period at Predose, 2 hours post dose, pre 2nd dose and 2 hours post second dose. Additional/SOWS-Gossop/COWS may be administered at investigator discretion. Transition to treatment for opioid use disorder will be offered prior to patients leaving the unit.

Vital Signs, SOWS-Gossop, COWS, pulse oximetry and electrocardiogram (ECG) with rhythm strip will be measured as per the schedule of assessments (Table 25. Dexmedetomidine sublingual film or placebo will be self-administered sublingually under staff observation and subjects will be allowed fluids as desired 15 minutes after completion of dosing. Safety and tolerability assessments will be continued until the morning of Day 14 (day of discharge).

Any abnormal vital sign measurement, clinical laboratory test, physical examination finding, or ECG parameter deemed clinically significant by the investigator will be repeated, including test results obtained on the final study day or upon early termination. For any test abnormality deemed clinically significant, repeat analysis will be performed during the follow-up period and until the value returns to baseline (or within normal limits) or the investigator deems the abnormality to be stable and no longer of clinical concern.

Diagnosis and Main Criteria for Eligibility:

Inclusion Criteria
1. Male and female subjects who are 18 years of age to less than 65 years of age.
2. Meets criteria for moderate to severe opioid use disorder as per Diagnostic and Statistical Manual of Mental Disorders, Fifth Edition (DSM-5) criteria and confirmed by the Mini-International Neuropsychiatric Interview (MINI) with physiological dependence as evidenced by a Clinical Opiate Withdrawal (COWS) score of >5 or a positive naloxone challenge upon admission on Day 1.
3. Subjects who can read, understand and provide written informed consent.

4. Women of childbearing potential must have a negative pregnancy test and agree to be abstinent or use an acceptable method of contraception for the duration of the study.

Exclusion Criteria
1. Positive urine pregnancy test at screening or when tested or currently breast feeding.
2. Clinically significant history of cardiac disease, screening and baseline heart rate of <55 beats per minutes or systolic blood pressure <110 mmHg or diastolic blood pressure <70 mmHg.
3. History or presence of a significant medical disease or disorder which, in the opinion of the investigator, increases the risk or may confound the interpretation of study measures, as confirmed by screening laboratory results.
4. Hepatic dysfunction (marked by ascites, or bilirubin >10% above the upper limit of normal [ULN] or liver function tests >3×ULN) at the screening visit.
5. Acute active Hepatitis B or C as evidenced by positive serology and aspartate aminotransferase (AST)/alanine aminotransferase (ALT)>2×ULN.
6. Clinically significant abnormal ECG findings such as second or third degree heart block, uncontrolled arrhythmia, or QTc interval >450 msec for males, and >470 msec for females at screening or prior to dosing.
7. Any psychiatric disorder that would compromise ability to complete study requirements.
8. Currently meets DSM-5 criteria for substance abuse disorder, moderate or severe for any substance other than opioids, caffeine, or nicotine.
9. History of suicidal behavior within the last 1 year prior to screening.
10. Participation in a clinical trial of a non-FDA-approved pharmacological agent within 30 days prior to screening.
11. Use of any excluded medication at screening or anticipated/required use during the study period.
12. Subjects with a history of intolerance to morphine.
13. Any finding that, in the view of the principal investigator, would compromise the subject's ability to fulfill the protocol visit schedule or visit requirements.

Study Treatments

Test Product, Dose, and Mode of Administration:

Dexmedetomidine hydrochloride sublingual film 30 μg, 60 μg, 90 μg, 120 μg and 180 μg doses as a thin film formulation of Dexmedetomidine for sublingual (SL) administration. The product is a small, solid-dose film formulation designed to completely dissolve in the SL space within 1-3 minutes.

Reference Therapy, Dosage and Mode of Administration:

Matching placebo films to be taken sublingually as described above.

Duration of Treatment:

30 mg QID or 5×/day Morphine and placebo sublingual film (of dexmedetomidine): 5 days; BID dexmedetomidine hydrochloride sublingual film or placebo sublingual film and morphine placebo: 7 days, placebo sublingual film (of dexmedetomidine) and morphine placebo: 2 days.

Study Procedures

Subjects will provide written informed consent before any study-related procedures are initiated, including the cessation of prohibited concomitant therapy.

TABLE 25

Schedule of Visits and Assessments

| | | Inpatient Admission (14 days) | | | | |
| --- | --- | --- | --- | --- | --- | --- |
| | | | Detoxification | | | |
| | Screening[1] | Morphine maintenance | Randomization & first day of treatment | Treatment Phase | Post Treatment phase or ET | One-week Follow-up |
| Day | −2 to −1 | Days 1-5 | Day 6 | Days 7-12 | Days 13-14 | Day 21 (±3 days) |
| Naloxone Administration[2] | | X | | | | |
| Informed Consent | X | | | | | |
| Inclusion/Exclusion Criteria[3] | X | | X | | | |
| Mini International Neuropsychiatric Inventory (MINI) | X | | | | | |
| Columbia Suicide Severity Rating Scale (C-SSRS) | X | | | | | |
| Randomization (Day 6) | | | X | | | |
| Demographics | X | | | | | |
| Medical and Psychiatric History | X | | | | | |
| Concomitant Medications | X | X | X | X | X | X |
| Physical Exam and 12-Lead ECG[4] | X | X | X | X | X | |
| Safety labs | X | | X | | | X |
| Vital Signs Measurements[5] | X | X | X | X | X | X |
| Buccal SL assessment[6] | | X | X | X | X | |
| Rapid Urine Pregnancy Testing[7] | X | X | | | | |
| AE Monitoring | X | X | X | X | X | X |
| Urine Toxicology/BAL[8] | X | X | X | X | | X |
| Timeline Followback | X | | | | | X |
| Pharmacokinetics[9] | | | X | X[10] | | |
| SOWS & COWS[11] | X | X | X | X | X | |
| Administration of Morphine | | X | | | | |

TABLE 25-continued

Schedule of Visits and Assessments

| | | Inpatient Admission (14 days) | | | |
| | | | Detoxification | | |
| | Screening[1] | Morphine maintenance | Randomization & first day of treatment | Treatment Phase | Post Treatment phase or ET | One-week Follow-up |
|---|---|---|---|---|---|---|
| Administration of Dexmedetomidine sublingual film or Placebo[12] | | | X | X | | |
| Administration of Morphine Placebo[13] | | | X | X | | |
| Administration of sublingual film placebo (for dex) and morphine placebo | | | | | X | |
| Agitation and Calmness Evaluation Scale (ACES)[14] | | X | X | X | | |

Notes:
[1]All procedures must be completed prior to subject randomization and within 30 days of signing informed consent.
[2]Subjects have the option of naloxone challenge on admission if not displaying signs/symptoms of withdrawal. If naloxone is administered, subjects may receive morphine to alleviate the opioid withdrawal symptoms that may be present at the end of the challenge test.
[3]Inclusion/Exclusion criteria evaluated at Screening and pre dose on Randomization Day 6.
[4]ECG will be done on Screening, pre-morning dose of sublingual film -placebo (of dex) on Day 1-5, pre-dose on Day 6, and on Days 13-14.
[5]Vital sign measurements will include orthostatic blood pressure, pulse, and measurement of oxygen saturation. Vitals will be taken on days 1-5 once daily, and pre each dose on days 6-12, and once daily on days 13 and 14.
[6]Buccal exam at 30 min post first dose for signs of local irritation on Days 1, 6, & 12. Buccal exam will be done prior to discharge on Day 14. Additional buccal exam may be done at investigator's discretion or in case of a relevant adverse event.
[7]During screening, a rapid urine pregnancy test will be performed. As part of inpatient admission, a rapid urine pregnancy test will be performed on Study Day 1.
[8]Urine drug testing will include opioids (fentanyl), buprenorphine, methadone, , benzodiazepines, cocaine (benzoylecgonine), amphetamines, and other drugs. Breath alcohol levels (BAL) will be assessed at screening, Day 1 and follow-up.
[9]Blood samples for pharmacokinetic analyses will only take place on inpatient Study Days 6 and 12 at 0, 2, , 6, and 12 hr after the first dose of Dexmedetomidine sublingual film of the day. The 12 hr. sample will be taken just before the administration of the next dose of Dexmedetomidine sublingual film or placebo sublingual film (for dexmedetomidine). A window of +/−5 mins per PK sample will be allowed without deviation.
[10]PK samples will be collected on Day 12 only at the scheduled times.
[11]COWS and SOWS-Gossop assessments will be performed Pre-dose, 2 hour post-dose, pre-$2^{nd}$ dose, and 2 hour post $2^{nd}$ dose. Additional assessments can be done at investigator's discretion.
[12]Administration of Dexmedetomidine sublingual film or Placebo will be given BID (approximately 8 am and 8 pm [+/−30 minutes]). On Days 1-5, subjects will receive placebo sublingual films (of dex) approximately 12 hours apart, besides their morphine treatments.
[13]Morphine placebo will be administered at approximate same time as Day 1-5.
[14]Administration of the Agitation and Calmness Evaluation Scale (ACES) will occur at approximately two hours after (−5/+15 mins) Dexmedetomidine sublingual film or placebo dosing (approximately 10 am and 10 pm).

Criteria for Evaluation:

Efficacy assessment: Determine the preliminary efficacy of sublingual dosing of dexmedetomidine hydrochloride sublingual film in the target population compared to placebo, as measured by improved peak SOWS-Gossop scores.

The effect of study drug will be evaluated using several validated instruments as described below.

Short Opiate Withdrawal Scale of Gossop (Also-Gossop)

The SOWS-Gossop is a 10-item patient reported measure designed to measure the symptoms of withdrawal in subjects who are dependent on opioids (Gossop, 1990). Each of the 10 items represents a symptom: "Feeling Sick," "Stomach Cramps," "Muscle Spasms/Twitching," "Feeling of Coldness," "Heart Pounding," "Muscular Tension," "Aches and Pains," "Yawning," "Runny Eyes," and "Insomnia/Problems Sleeping." Subjects evaluate the severity of each symptom over the last 24 hours by selecting either as "None," "Mild," "Moderate," or "Severe."

The SOWS-Gossop total score range from 0 to 30, with higher scores indicating greater severity of withdrawal symptoms.

Clinical Opiate Withdrawal Scale

The COWS is an 11-item questionnaire designed to measure a patient's level of opiate withdrawal (Wesson and Ling, 2003). Symptoms evaluated include resting pulse rate, sweating, restlessness, pupil size, bone or joint aches, runny nose or tearing, gastrointestinal upset, tremor, yawning, anxiety or irritability, and gooseflesh. COWS total scores range from 0 to 48: scores 5 to 12 are mild, 13 to 24 are moderate, 25 to 36 are moderately severe, and over 36 are severe withdrawal Safety and Tolerability Assessments:

COWS, SOWS-Gossop, adverse events (AEs), clinical laboratory tests, ECG with rhythm strip, pulse oximetry and vital signs will be monitored for tolerability assessment. The ACES assessment will also be administered as a safety measure. All observed and volunteered AEs will be recorded. The relationship of AEs to the study drugs will be graded as not related, unlikely/remotely related, possibly related, probably related or definitely related by the investigators. Vital signs including systolic blood pressure (SBP), diastolic blood pressure (DBP), orthostatic blood pressure, heart rate, and oxygen saturation will be measured daily throughout the study. The application site of the SL preparation (buccal mucosa) will be inspected for any signs of local irritation.

Additional Assessments:
  Demographic Data
  Medical and Psychiatric History
  Prior and Concomitant Medication
  Physical Examination
  Suicidality
  Pregnancy
Pharmacokinetics Blood samples (4 ml) will be collected at 0, 2, 6, and 12 hours after the first dose of dexmedetomidine hydrochloride sublingual film on Study Days 6 and 12. The 12 hr. sample will be taken just before the administration of the next dose of dexmedetomidine sublingual film or placebo.

Statistical Analysis:

Primary Outcome: Safety and tolerability of ascending doses of dexmedetomidine hydrochloride sublingual film in subjects with OUD who are physically dependent on opioids.

Secondary Outcomes:
1) Peak SOWS-Gossop score during Days 6-14.
2) Peak COWS score during Days 6-14
3) Average COWS scores per day for Days 6-14 (an average will be calculated for each day in order to assess time course of withdrawal symptoms).
4) Average SOWS-Gossop scores per day on Days 6-14.
5) Time to dropout after discontinuation of morphine maintenance (Days 6-14).
6) Percentage of subjects dropping out after discontinuation of opioid maintenance within each treatment group between Days 6-14
7) Overall agitation and sedation will be evaluated with the ACES.

Efficacy Analyses

Primary: After the morphine maintenance phase, treatment differences between dexmedetomidine hydrochloride sublingual film and placebo on peak SOWS-Gossop scores on Days 6-14 will be analyzed using linear regression or Mixed Model Repeated Measures [MMRM]. Treatment differences between dexmedetomidine sublingual film and placebo on peak SOWS scores on Day 7 (two days after opiate discontinuation) as well as peak SOWS on Days 6 14 will be analyzed. The intent-to-treat population will be analyzed and consist of all patients who take any study medication and who had both baseline and at least 1 efficacy assessment after dosing.

Secondary: Peak COWS scores during Days 6-14 will each be compared between the dexmedetomidine hydrochloride sublingual film and placebo groups using linear regression or MMRM. Time to dropout after discontinuation of morphine maintenance will be analyzed using a Cox proportional-hazards model. Kaplan-Meier estimates will also be used to generate survival curves over time in each treatment group. Logistic regression model will be used to compare the dexmedetomidine hydrochloride sublingual film and placebo groups on the numbers of subjects dropping out after opioid discontinuation. Listings of subjects who withdraw from the study due to an AE, serious AEs and/or death or lack of treatment effect will be presented. Laboratory parameters will be summarized by treatment using descriptive statistics and data listings of clinically significant abnormalities. Vital signs and ECG data will be summarized by changes from baseline values using descriptive statistics. Chi-square (or Fisher's exact) tests will be used to compare the frequencies of AEs or serious AEs on blood pressure, heart rate, or respiratory drive between dexmedetomidine hydrochloride sublingual film and placebo, at the beginning of Day 6 and then daily during the remainder of this study.

Pharmacokinetic Analyses

A separate SAP for the PK analyses will be prepared for the study and will be finalized prior to database lock. Data from subjects who participated in the study will be included in the pharmacokinetic analysis. Subjects with missing sample concentrations will be included in the pharmacokinetic analyses provided their pharmacokinetic parameters can be adequately characterized based upon the remaining data.

Safety Analyses

Safety data analyses will be conducted on all subjects receiving at least 1 dose of study drug. The number and percentage of subjects experiencing 1 or more AEs will be summarized by treatment, relationship to study drug, and severity. AEs will be coded using Medical Dictionary for Regulatory Activities (MedDRA) terminology.

Example 6: A Phase Ib/II Randomized, Double Blind, Placebo Controlled, Dose Finding, Efficacy and Safety Study of Dexmedetomidine Hydrochloride Sublingual Film to Treat Patients Hospitalized in the ICU with Delirium and Agitation Key Objectives:
1. To assess the impact of dexmedetomidine sublingual film on cardiovascular parameters, including blood pressure, heart rate, and QTc interval, in hospitalized patients with hyperactive delirium.
2. To assess the incidence of other side effects following the administration of dexmedetomidine sublingual film in the same patient group.
3. To explore the impact of dexmedetomidine sublingual film on agitation and delirium severity
4. To identify the optimal dose of dexmedetomidine that is effective at reducing agitation and delirium severity without causing significant side effects.

Inclusion/Exclusion Criteria

Inclusion Criteria:
1. Adults hospitalized on a medical or surgical intensive care unit at MGH
2. Diagnosis of delirium, assessed according to DSM-5 criteria (DSM-5) by a licensed psychiatrist
3. Body mass index (BMI) between 18 and 30 kg/m$^2$, inclusive, at screening
4. Weight at least 60 kg (132 pounds), at screening
5. Sufficiently physically healthy in the opinion of the study and clinical teams to receive dexmedetomidine sublingual film Exclusion Criteria:
1. Per medical record or team report, diagnoses of:
   Dementia
   Significant traumatic brain injury
   History of stroke, with persistent neurologic deficits
2. Presence of any of the following cardiovascular comorbidities
   Sick sinus syndrome
   A resting heart rate of <55 beats per minutes or systolic blood pressure <100 mmHg or >160 mmHg or diastolic BP<70 mmHg or >95 mmHg at enrollment and prior to dosing.
   Evidence of cardiac ischemia on a 12-lead electrocardiogram (ECG)
   Corrected QT interval of >450 msec
   Presence of a permanent pacemaker device
3. Per medical record (notes, current medications, flowsheets):
   Second degree (or greater) AV block without a pacemaker
   Known allergy or adverse reaction to dexmedetomidine
   Current use of dexmedetomidine
4. Inability to take sublingual dexmedetomidine due to severe agitation, neurological impairment, NPO status, or other cause.
5. Hepatic impairment (liver function tests >3 times the upper limit of normal)

6. Severe renal impairment (GFR<30 ml/min or on dialysis)
7. Weight <60 kg
8. Pregnancy (in women; tested with serum or urine hCG)
9. Non-fluency in English
10. Prior enrollment in the study, with receipt of study medication, during the current or a previous hospitalization Assessment for Inclusion Criteria:

Inclusion and exclusion criteria will be assessed in a stepwise fashion. Prior to approaching participants/surrogates, study staff will review the electronic medical record to assess for exclusionary conditions and will discuss with clinical teams if the presence or absence of such conditions is unclear. Only those patients who do not clearly meet exclusion criteria will be evaluated further for inclusion and exclusion criteria by the study psychiatrist.

Specifically, the study psychiatrist will confirm a diagnosis of delirium through review of the medical record, evaluation of the potential participant, and discussion with the inpatient team if any questions about diagnosis remain following the evaluation. Delirium will be diagnosed using DSM-5 criteria:

1.) There is a disturbance in attention and awareness.
2.) The disturbance develops over a short period of time, represents an acute change from baseline, and tends to fluctuate over the course of the day.
3.) There is an additional disturbance in cognition.
4.) The disturbances are not better explained by an underlying neurocognitive disorder (e.g., dementia).
5.) The disturbances do not occur in the context of a severely reduced level of arousal (e.g., coma).
6.) There is evidence that the disturbance is a direct physiological consequence of another medical condition, substance intoxication or withdrawal, or exposure to a toxin, or is due to multiple etiologies.

This clinical diagnosis will be made in the context of a psychiatric and cognitive evaluation, including bedside tests of orientation, attention, and memory.

If a patient meets criteria for delirium, the study psychiatrist will then review the patient's medical record further and speak with the inpatient team to determine if any exclusion criteria are present. To ensure the clinical team feels that the participant is medically able to tolerate dexmedetomidine, they will be asked whether they would consider the participant to be suitable to receive dexmedetomidine intravenously if he/she were to become agitated. If participants meet diagnostic criteria for delirium and do not meet any exclusion criteria, they will be considered eligible for inclusion in the study.

Following enrollment in the study, laboratory testing and obtainment of an ECG will be performed to confirm clinical stability prior to medication administration. If a participant is experiencing agitation immediately following enrollment and confirmation of clinical stability, the participant will be eligible to be randomized to receive the study medication. If the participant does not have evidence of agitation, the participant will be monitored on a daily basis for the development of agitation (RASS≥1) and will be randomized only if/once agitation has developed. While patients with or without agitation will be eligible for enrollment in the study, only those participants who become agitated will receive dexmedetomidine film.

Study Procedures

A. Data Collection and Monitoring

Initial screening and data collection. As noted, prior to enrollment, study psychiatrists will assess the patient for inclusion and exclusion criteria via brief medical record review, discussion with primary treatment team, diagnostic evaluation (DSM-5 criteria), and assessment for decision-making capacity. For enrolled subjects, chart reviews will be performed to gather baseline characteristics (Table 26—schedule of events).

Further screening for eligibility to receive study medication. Following enrollment, laboratory studies, including comprehensive metabolic panel (glucose, sodium, potassium, chloride, bicarbonate, calcium, carbon dioxide, magnesium, blood urea nitrogen, creatinine, uric acid, inorganic phosphorus) and liver function tests (alkaline phosphatase, aspartate aminotransferase [AST], alanine aminotransferase [ALT], gamma-glutamyl transferase, total bilirubin) will be performed.

Additionally, serum human chorionic gonadotropin (HCG; female participants only) will be obtained. If these laboratory studies were already drawn during this admission, new samples will not be drawn unless a change in clinical status that might affect them has occurred. Finally, a standard, 12-lead ECG will be obtained. The ECG parameters assessed will include heart rate and PR, QRS, QT, and QTc using Bazett's (QTcB) and Fridericia's (QTcF) correction methods. The QTcF will be considered the standard QTc interval to evaluate any changes in QTc in response to the study medication. The ECGs will be interpreted by the investigator, and if needed in the medical opinion of the principal investigator or designee, the findings will be confirmed by a cardiologist, critical care physician, or anesthesiologist. Study medication administration will not occur until all necessary laboratory studies have resulted and the participant's eligibility for medication administration has been confirmed.

Monitoring for the development of agitation: On a daily basis during the work week, the participant will be evaluated by a study team member using the Richmond Agitation Sedation Scale (RASS). If/when a participant is found to have significant agitation (defined as a RASS score ≥1), the participant will undergo baseline monitoring procedures and will be randomized to one of the two treatment conditions.

Randomization: Participants will be randomized to receive either 20 μg or 60 μg of dexmedetomidine sublingually. As dexmedetomidine is available in 10 and 60 μg films, those receiving 20 μg will receive two 10 μg films, while those receiving 60 μg will receive a 60 μg film and a placebo film to ensure blinding of staff and participants. Participants will receive repeat dosing every 30 minutes for up to three additional doses, leading to maximum doses of 80 μg and 240 μg, respectively. Both investigators and clinicians will be blind to the participant's group, with only the study pharmacist aware of the dose of medication on the films.

Baseline monitoring. Following enrollment, the study team will record baseline measures of heart rate, blood pressure, and oxygen saturation. An ECG will be performed and QTcF measured. Next, the physician will evaluate the patient using the RASS and DRS-R-98 to measure baseline agitation and delirium severity, respectively.

Medication administration. Dexmedetomidine sublingual film will be administered by the study physician or study nurse as per the manufacturer's instructions. Specifically, the film will be placed into the participant's mouth. The participants will be instructed to keep the film in their mouth until it dissolves. If the participant is unable to hold the medication in their mouth (e.g., they spit it out), the participant will not be re-dosed. Dexmedetomidine administration will be repeated every 30 minutes if the participant continues to have agitation (RASS≥1) and does not meet any cardiovascular stopping criteria. Dosing times and maximum medication doses are as follows in table 27:

4) There is a decrease in heart rate of 20 beats per minute or a drop below 55 beats per minute.
5) ECG reveals QTc>500 msec.
6) Attainment of a RASS of −1.

TABLE 26

Schedule of study events.

| Measure | Pre-enrollment | Baseline | Med Admin. | 30 min | 1 h | 1.5 h | 2 h | 2.5 h | 3 h | 3.5 h | 4 h | 4.5 h | 6 h |
|---|---|---|---|---|---|---|---|---|---|---|---|---|---|
| Delirium Screening (CAM-ICU) | X | | | | | | | | | | | | |
| Delirium Diagnosis (DSM-5) | X | | | | | | | | | | | | |
| Agitation (RASS) | X | X | X | X | X | X | X | X | X | X | X | X | X |
| Delirium Severity (DSR-R-98) | | X | | | | X | | X | | X | | X | X |
| Heart Rate | | X | X | X | X | X | X | X | X | X | X | X | X |
| Blood Pressure | | X | X | X | X | X | X | X | X | X | X | X | X |
| Oxygen Saturation | | X | X | X | X | X | X | X | X | X | X | X | X |
| Electrocardiogram | | X | | | | X | | | X | | | X | X |
| Other side effects | | | | | | | | | | | | | X |

TABLE 27

Dosing times and maximum medication doses

| Group | Administration Time (minutes) | | | | Total Dose |
|---|---|---|---|---|---|
| | 0 | 30 | 60 | 90 | |
| 20 μg | 20 μg | 20 μg | 20 μg | 20 μg | 80 μg |
| 60 μg | 60 μg | 60 μg | 60 μg | 60 μg | 240 μg |

Monitoring for side effects. Heart rate, blood pressure, oxygen saturation, use of supplemental oxygen, and use of pressors will be monitored continuously and recorded every 30 minutes from the participant's Epic flowsheet or using the telemetry monitor/automated blood pressure cuff for the 6 hours following the initial medication administration (baseline; Time 0). An ECG will be performed at 1.5, 3, 4.5, and 6 hours, and QTc will be calculated using the Fridericia formula, as described above. Study staff will also monitor the participant and speak with nursing staff at 6 hours to assess for any other side effects/complaints the patient may have had during the time since medication administration. These will be assessed formally using a list of side effects reported for dexmedetomidine in post-marketing surveillance.

Monitoring of agitation and delirium severity. The RASS will be performed every 30 minutes (up to 6 hours post-baseline) by study staff (research coordinator, nurse, or study psychiatrist) to monitor for agitation. The DRS-R-98 will be performed by the study physician at 1, 2, 3, 4, and 6 hours post-baseline to assess for changes in delirium severity. If patients require additional treatments to manage agitation following medication administration within the 6-hour monitoring period, all efficacy and safety assessments from that point forward will continue, but those time points for those patients will not be analyzed in the primary data analysis.

Dosing will be stopped at any time if any of the following occurs:
1) There is >30 mm Hg decrease in systolic or diastolic blood pressure.
2) There is an isolated drop in Systolic BP<95 mmHg.
3) There is an isolated drop Diastolic BP<55 mmHg.

Study Drugs:
In this study, we will administer the medication in sublingual film formulation (absorbed sublingually) at a dose of 20 or 60 μg (with repeated administration, participants may receive a total of up to 80 μg or 240 μg, respectively).

Data Collection
Baseline data. Prior to administration of dexmedetomidine, the study physician will perform the RASS and DRS-R-98 to assess level of agitation and delirium severity. Heart rate, blood pressure, and oxygen saturation will be recorded from the participant's telemetry monitor and using an automated blood pressure cuff. Finally, an ECG will be performed, and the study physician will calculate a QTc interval.

Cardiovascular parameters and side effects. Following administration of dexmedetomidine, heart rate, blood pressure and oxygen saturation will be recorded every 30 minutes from the telemetry monitor or Epic flowsheet. Consistent with prior research, we will monitor for the following side effects:
(a) Bradycardia—heart rate <55 beats per minute (or ≥20% reduction in heart rate from baseline if baseline heart rate is <70 beats per minute)
(b) Hypotension—systolic blood pressure <95 mmHg (or ≥20% decrease in systolic blood pressure from baseline if baseline systolic blood pressure is <120 mm Hg), or the addition or increase of vasopressors
(c) Tachycardia—heart rate >100 beats per minute (or ≥20% increase in heart rate from baseline if baseline heart rate is >83 beats per minute)
(d) Hypertension—systolic blood pressure >160 mmHg (or ≥20% increase in systolic blood pressure from baseline if baseline systolic blood pressure is >133 mm Hg)
(e) Hypoxia—oxygen saturation <90% (or ≥5% decrease in absolute value of oxygen saturation if baseline oxygen saturation is less than 95%), or increase in the amount of supplemental oxygen required to maintain oxygen saturation >90%
(f) ECG changes (including QTc prolongation)—The ECG parameters will include heart rate, PR interval, QRS interval, QT interval, and QTc interval (rate correction using QTcB and QTcF methods). Summaries of ECG results and the change from baseline will be presented. The numbers and percentages of participants with a QTc increase from baseline to 90-minute ECG time point will be summarized using the following change categories:

a. QTc interval increase from baseline >30 to ≤60 msec b. QTc interval increase from baseline >60 msec In addition, QTc values will be summarized by gender as normal to prolonged in accordance with Committee for Proprietary Medicinal Products (CPMP) Points to Consider regarding the assessment of the potential for QT interval prolongation shown in the Table 28:

TABLE 28

QTcF Intervals: Upper and Lower Limits of Normal, Borderline, and Prolonged Intervals

|  | Males | Females |
| --- | --- | --- |
| Normal | ≤430 msec | ≤450 msec |
| Borderline | >430 to ≤450 msec | >450 to ≤470 msec |
| Prolonged | >450 msec | >470 msec |

Note:
In accordance with CPMP guidelines.

Similarly, the numbers and percentages of participants with absolute QTc interval values above certain thresholds will be summarized by gender using the following limits in accordance with International Conference on Harmonisation (ICH) E14 guidance:

QTc interval >450 to ≤480 msec

QTc interval >480 msec

QTc interval ≥500 msec

A listing of participants with QTc change from baseline between 30 to 60 msec and ≥60 msec will be provided. A listing of participants with abnormal QTc interval values (>450 msec to <500 msec and ≥500 msec) will be provided to the Sponsor as well.

Non-cardiovascular side effects. During the final assessment (6 hours after the initial dose of the medication), participants will be asked the following question: "Have you noticed any new physical problems or side effects since receiving the study medication?" In addition, the participant's primary nurse will be asked whether the patient had signs or symptoms of new medical conditions or side effects (e.g., muscle stiffness, tremor, rash) since the administration of the medication, using a checklist of side effects reported in post-marketing surveillance.

Impact on Agitation and Delirium Severity.

(a) Agitation: Agitation will be measured using the RASS, a 10-point scale to quantify levels of consciousness and agitation. This validated measure can be administered in less than one minute and has clear definitions for levels of arousal/agitation. The RASS will be administered at baseline and every 30 minutes (up to 6 hours post-baseline) by a research coordinator, study nurse, or study psychiatrist.

(b) Delirium severity: The DRS-R-98 will be used as a measure of delirium severity. This 16-item scale can be used to screen for/diagnose delirium, but it also includes 13 items to assess delirium severity. It is reliable and has been validated in patients with delirium. This scale will be administered by a study physician at baseline, then 1, 2, 3, 4, and 6 hours after the initial dexmedetomidine administration.

Example 7: Phase 1, Randomized, Single-Blind, Placebo-Controlled, Single Ascending Dose Study of the Pharmacokinetics, Safety & Tolerability of Dexmedetomidine Sublingual Film (Example 1 Formulation) in Healthy Adult Volunteers This was a randomized, single-blind, placebo-controlled, single ascending dose pharmacokinetics, safety and tolerability study with 4 dosing groups in healthy adult (18-65 years-old) males and females. The study protocol was reviewed and approved by an institutional review board of site(s). This study was conducted in accordance with the Declaration of Helsinki and ICH—Good Clinical Practices (GCP).

Primary Objective: Determine the PK, safety and tolerability of the various film strengths of dexmedetomidine sublingual film for identification of appropriate film dosage strengths to be carried forward into subsequent clinical trials.

Secondary Objectives:
1. Determine the PD effects of the various film strengths of dexmedetomidine sublingual film.
2. Determine the relationship between PD effects and plasma concentrations of the dexmedetomidine.
3. Determine the time to onset of drowsiness after dexmedetomidine sublingual film administration.
4. Determine the length of sedative effect after dexmedetomidine sublingual film administration.
5. Determine the approximate dissolution time of dexmedetomidine sublingual films in the SL space.
6. Determine local irritation that may be caused by dexmedetomidine sublingual film.

Endpoints
Primary
Pharmacokinetics
1. Area under the curve (AUC0-12, AUC0-24, AUC0-inf) for 0 to 12 hours and 0 to 24 hours post dosing for dexmedetomidine plasma concentration.
2. Determine peak plasma dexmedetomidine concentration ($C_{max}$).
3. Determine time corresponding to peak dexmedetomidine concentration level ($T_{max}$).
4. Determine terminal half-life (t1/2) of dexmedetomidine from the central compartment.
5. Determine the volume of distribution (Vz) of dexmedetomidine.
6. Determine the clearance of dexmedetomidine (CL) from the central compartment.

Safety and Tolerability
1. Determine electrocardiogram (ECG) and vital sign abnormalities including adverse effects on blood pressure (BP), heart rate, or respirations with various film strengths of dexmedetomidine sublingual film.
2. Determine abnormal laboratory values following administration of dexmedetomidine sublingual film.
3. Determine changes in physical examination following administration of dexmedetomidine sublingual film
4. Number of subjects experiencing an AE up to Day 14 following dexmedetomidine sublingual film administration.
5. Number of subjects who discontinued study treatment or removed SL films due to an AE or other reason.
6. The degree to which AEs can be tolerated by assessing the number of subjects requiring:
Hemodynamic interventions for maintaining BP;
Cardiac interventions for maintaining heart rate;
Respiratory interventions for maintaining oxygen saturation.

Secondary
1. The sedative effect assessed by RASS and Visual analogue scales/sedation (VAS/S) on day of dexmedetomidine sublingual film dosing.
2. Time in minutes and seconds from administration of dexmedetomidine sublingual film until RASS of −1 on day of dexmedetomidine sublingual film dosing.
3. Time in minutes and seconds from RASS of −1 till resolution of drowsiness on day of dexmedetomidine sublingual film dosing.
4. Time in minutes and seconds from SL administration of dexmedetomidine sublingual film till its complete dissolution or up to 30 minutes.

Study design: It was a randomized, single-blind, placebo controlled, single ascending dose PK, safety and tolerability study conducted in healthy adult (18-65-year-old) males and females. The study evaluated increasing doses of dexmedetomidine sublingual film in 4 cohorts of healthy adult participants.

Four (4) doses were evaluated derived from three film strengths of 10 µg, 40 µg, and 60 µg: 10 µg, 20 µg (2×10 µg film), 40 µg, and 60 µg in Cohort 1, 2, 3 and 4 respectively. During the review of the safety and tolerability data from Cohort 3 dosing (40 µg), it was observed that 6 symptomatic subjects had reported dizziness upon standing, four of whom had concomitant intermittent hypotension or bradycardia (SBP/DBP/heart rate with >30 mmHg decrease from baseline, SBP<90 or DBP<60 or heart rate <50). While the results remained blinded, it was decided to decrease the planned dose for Cohort 4 to 40 µg. The actual doses administered to subjects in this study included 10 µg (cohort 1), 20 µg (cohort 2) and 40 µg (cohorts 3 and 4).

All eligible participants, who have been previously screened, arrived at the clinical research unit (CRU) a day before for admission and baseline assessment. They were domiciled in the CRU for 4 days (Day −1, 1, 2 and 3) and discharged on Day 4, and were under medical supervision during this time. The pre-dose evaluation of all the participants was done approximately between 07:00 and 09:00 hours, after an overnight fast of at least 8 hours. The participants were given free access to drinking water until at least one hour before dosing. A venous catheter was inserted for allowing sampling for PK. At the beginning of each study session, a single dose of dexmedetomidine sublingual film (Example 1) was administered sublingually by an unblinded staff. The dexmedetomidine sublingual film was retained in the sublingual cavity until dissolved. Evaluations were done every 5 minutes for the first 15 minutes and then every 15 minutes to determine the time to dissolution of the film. Subjects were also evaluated for local irritation around the area where the film was placed. The subjects were not allowed to sit or stand up during the first 2 hours after dexmedetomidine sublingual film dosing, except when performing standing BP measurements. After 2 hours, the subjects were allowed to sit in their beds, however, during sampling, they had to rest in supine or semi-recumbent position. The ECG, BP and oxygen saturation were monitored as per the schedule (Table 29). Subjects were allowed water as desired at least 1 hour after drug administration. Standard meals were offered at approximately 4, 8, and 12 hours after dexmedetomidine sublingual film dosing. However, no food or drinks were permitted until an investigator confirms that each subject was capable of oral intake, based on the degree of sedation and ability to control urination. Lavatory visits were also allowed, but along with an attendant. Day 2 and 3 had no dietary restriction, but there was complete restriction on smoking and alcohol intake during the length of CRU stay. After plasma sampling for 24 hours following dosing of dexmedetomidine sublingual film, the safety and tolerability assessments were continued until the morning of Day 4 (day of discharge), and were repeated on Day 5, Day 7±1 and Day 14±2.

Number of Subjects:
The study evaluated increasing doses of dexmedetomidine sublingual film (example 1—formulation) in 4 cohorts of healthy adult subjects. In the first two cohorts (Cohort 1 and Cohort 2), twelve (12) new subjects were enrolled per cohort, randomized in a ratio of 2:1, i.e. 8 receiving dexmedetomidine sublingual film and 4 receiving Placebo film.

Subjects receiving active drug in Cohort 1/Cohort 2 were to be escalated to receive high dose of active drug in Cohort 3/Cohort 4 and subjects receiving Placebo in Cohort 1/Cohort 2 were to receive Placebo in Cohort 3/Cohort 4 respectively. Six new subjects were to be randomized to receive the active drug in Cohort 3/Cohort 4. Dose-proportionality and dose-exposure response were to be evaluated in the subjects that crossed over to Cohort 3/Cohort 4. The effect of dexmedetomidine sublingual film on BP, heart rate, RASS score, other AEs and PK parameters were to be evaluated in new subjects who were not previously exposed to dexmedetomidine sublingual films. In case of placebo dropouts, while escalating from Cohort 1 to Cohort 3 or Cohort 2 to Cohort 4, additional new subjects were to be randomized to make up the total subjects to 4 subjects in Placebo arm of Cohort 3 and Cohort 4.

TABLE 29

Schedule of Assessments

| Activity | Screen | Day −1 (Admission; Visit 1) | Day 1 (Study drug dosing)[1] | Day 2 & 3 (Observation in CRU) | Day 4 (At time of discharge) | Day 5 (Visit 2)[4] | Day 7 ± 1 (Visit 3)[4] | Day 14 ± 2 (Visit 4, EOS)[4] |
|---|---|---|---|---|---|---|---|---|
| Informed Consent Form | X | | | | | | | |
| Demographics | X | | | | | | | |
| Medical History | X | X | | | | | | |
| Weight/Body Mass Index | X | X | | | X | X | X | X |
| Height | X | | | | | | | |
| Inclusion/Exclusion criteria | X | X | X | | | | | |
| Randomization | | X | | | | | | |
| Safety Labs (Chemistry, hematology, U/A, UDS[2] were done by the unit's local lab) | X | X | | | X | | | |
| Pregnancy test (Blood HCG) | X | | | | | | | |
| Pregnancy test (Urine HCG) | | X | | | | | | |
| Coagulation (PT/INR) | X | | | | | | | |

TABLE 29-continued

Schedule of Assessments

| Activity | Screen | Day −1 (Admission; Visit 1) | Day 1 (Study drug dosing)[1] | Day 2 & 3 (Observation in CRU) | Day 4 (At time of discharge) | Day 5 (Visit 2)[4] | Day 7 ± 1 (Visit 3)[4] | Day 14 ± 2 (Visit 4, EOS)[4] |
|---|---|---|---|---|---|---|---|---|
| Physical Exam | X | X | | X | X | X | X | X |
| Complete Neurological Exam | X | | | | | | X | |
| Brief Neurological Exam | | X | X (at resolution of drowsiness after drug administration) | | | | | |
| Vital signs (systolic and diastolic blood pressure, pulse rate, respiration and oxygen saturation) | X | X | 0 (predose), 10, 20 and 30 min, then every 15 min till 6 hours. Thereafter prior to PK samples (if any) (±15 min) or hourly until time of sleep and again with last sample at 24-hour (±15 min). | X | X | X | X | X |
| Standing blood pressure | | X (at night) | X (−2 hours predose, 2, 4, 6 hours postdose) | X | X | | | |
| ECG | X | X | Every 3 hours (from 0 until 6 hours postdose (±15 min). | X | X | X | X | X |
| Admit to Unit | | X | | | | | | |
| Study Drug Preparation (unblinded pharmacist) | | | X | | | | | |
| Venous Catheter Placement | | | X | | | | | |
| Study drug Sublingually Film buccal dissolution | | | X (Section Error! Reference source not found.) | | | | | |
| Buccal/Sublingual Exam for local irritation | X | X | X (at every hour starting from predose until time of sleep and again with last sample at 24-hour (±15 min). | X | X | X | X | X |
| RASS[3] | | | X 0 min, every 5 min until drowsiness is achieved (RASS of −1); then every 15 min until resolution of drowsiness Prior to PK sample collection, till resolution of drowsiness | | | | | |
| VAS/S | | | 0 min, every 30 min until resolution of drowsiness Prior to PK sample collection (±5 min) | | | | | |
| Training | | X | | | | | | |
| PK Sampling | | | As per sampling schedule (Section Error! Reference source not found. ) | | | | | |
| Discharge | | | | | X | | | |
| Concomitant Meds | X | X | X | X | X | X | X | X |
| Adverse Events | X | X (Section Error! Reference source not found.) | X | X | X | X | X | X |

ECG: electrocardiogram; hCG: human chorionic gonadotropin; PK: pharmacokinetic; PT/INR: prothrombin time/international normalized ratio; RASS: Richmond Agitation Sedation Scale; U/A: Urine Analysis; UDS: Urinary Drug Screen; VAS/S: visual analogue scales/sedation
[1]Predose assessments had a window of 60 min prior to drug administration.
[2]UDS was not done at the discharge day
[3]If a subject did not achieve drowsiness (RASS of −1) on or before the 90 minute postdose timepoint, the procedure was to be performed at 5 minute increments until 90 minutes postdose, then at 15-minute increments until 120 minutes postdose. RASS had a 3 minute window period.
[4]Any abnormal vital sign measurement, clinical laboratory test, physical examination finding, or ECG parameter deemed clinically significant by the investigator was to be repeated, including test results obtained on the final single-blind study day or upon early termination. For any test abnormality deemed clinically significant, repeat analysis was to be performed during the follow-up period and until the value returned to baseline (or within normal limits) or the investigator deemed the abnormality to be of no clinical significance.

Inclusion Criteria:
1. Healthy males and non-pregnant/non-breast-feeding females between 18 and 65 years of age, both inclusive.
2. Subjects who were capable of giving written informed consent for the study
3. Subjects that had body weight ≥50 kg with body mass index (BMI) in the range of 19-30 kg/m2, both inclusive
4. Subjects having physical examination and vital signs judged to be within normal limits by the PI or designee.
5. Subjects whose clinical laboratory tests (complete blood count, blood chemistry, and urinalysis) were within normal limits or are clinically acceptable to the PI or designee.
6. Subjects who were sufficiently physically healthy to receive a SL dose strength of dexmedetomidine sublingual film, and tolerate drowsiness, in the opinion of the PI or designee.
7. Subjects who were fluent in English and have ability to understand written and verbal protocol-related requirements in English.
8. Subjects who were willing and able to be confined to the CRU for approximately 4-5 days per dosing cohort and comply with the study schedule and study requirements.
9. Subjects that had reliable intravascular access from which to draw blood samples.
10. Male subjects, if non-vasectomized, must agree to use a condom with spermicide or abstain from sexual intercourse, during the trial and for 3 months after stopping the medication.
11. Male subject must not donate sperm starting at screening and throughout the study period, and for 90 days after the final study drug administration.
12. For female subjects of child-bearing potential, the subject must be willing to practice a clinically accepted method of birth control from at least 30 days prior to the first administration of the study medication, during the study, and for at least 30 days after the last dose of the study medication.
13. For female of non-childbearing potential, the subject was surgically sterile (i.e. has undergone hysterectomy, bilateral oophorectomy, or tubal ligation) or in a menopausal state (at least 1 year without menses), as confirmed by Follicle stimulating hormone (FSH) levels.

Exclusion Criteria:
1. The subjects with a history of allergic reaction or intolerance to the study drug or related compounds and additives.
2. The subjects with a history of major surgery within 4 weeks of screening.
3. The subjects with a history of significant traumatic brain injury.
4. The subjects with a history of alcohol or drug dependence by Diagnostic and Statistical Manual of Mental Disorders IV criteria during the 6-month period prior to study entry.
5. The subjects with a history of or presence of clinically significant psychiatric illnesses mental retardation, borderline personality disorder, anxiety disorder, or organic brain syndrome.
6. The subjects with a history of orthostatic hypotension (i.e., a sustained reduction of systolic BP (SBP) of at least 20 mmHg or diastolic BP (DBP) of 10 mmHg, or both, within 3 min of standing or head-up tilt to at least 60° on a tilt table) and high vagal tone.
7. The subjects who regularly consume large amounts of xanthine-containing substances (i.e., more than 5 cups of coffee or equivalent amounts of xanthine-containing substances per day).
8. The subjects who were on maintenance medications that could inhibit or induce the CYP2A6 enzyme.
9. The subjects who had received dexmedetomidine or other alpha-2-agonists within 1 week of the study date.
10. The subjects who had clinically significant sleep apnea or chronic obstructive pulmonary disease or history of asthma.
11. The subjects with suicidal tendency in the judgement of the PI or designee.
12. The subjects with clinical laboratory abnormalities (including positivity for Hep B, Hep C, HIV) unless treated to remission status.
13. The subjects with abnormal vital signs measurement in the judgement of the PI or designee, unless treated to remission status.
14. The subjects those were enrolled in another clinical study (e.g., laboratory or clinical evaluation) or have received an investigational drug in the past 30 days (or within 5 half-lives of the investigational drug, if >30 days).
15. The subjects that had a resting heart rate of <65 beats per minute or SBP<110 mmHg or >140 mmHg or DBP<70 mmHg or >100 mmHg at screening and pre-dosing. Have evidence of a clinically significant 12 lead ECG abnormality. Subjects that previously failed eligibility criteria at the Screening visit or Day 1 predose due to Exclusion 15 for a resting heart rate <70 beats per minute but not <65 beats per minute may be rescreened.
16. The subjects with an aberrant oral/buccal anatomy, inflammation or pathology which in the opinion of the PI, may affect SL drug administration and absorption.
17. The subjects with hepatic impairment or who have hepatic dysfunction defined as a history of hepatic dysfunction and an Alanine Aminotransferase (ALT) and Aspartate Aminotransferase (AST) values greater than 2 times normal in the past 6 months prior to study drug administration.
18. The subjects who had donated blood within 30 days prior to screening or plasma donation within 7 days prior to screening.
19. The subject who was part of the study staff personnel or family members of the study staff personnel.

Study duration: 39-42 days.

Treatments Administered

The following treatments were administered on Day 1:

Active: Dexmedetomidine hydrochloride SL film at dose levels of 10 μg (1×10 μg film), 20 μg (2×10 jig films) and 40 μg (1×40 μg film)

Placebo: Placebo SL film

Cohort 1 and Cohort 2 were given 10 μg and 20 μg (2×10 μg films), respectively, Cohort 3 and Cohort 4 received 40 μg of dexmedetomidine sublingual film. All Cohorts were given accompanying Placebo. Except for the first dose cohort (10 μg dose), each subsequent dose level was authorized after safety review of the previous dosing cohort. Dexmedetomidine hydrochloride sublingual film (having dot) was different from Placebo in appearance.

Results:
Data Sets Analyzed
Safety Population

The safety population includes all randomized subjects who received at least 1 dose of single-blind study drug (n=42).

Pharmacokinetic Population

The PK population includes 28 subjects receiving dexmedetomidine sublingual film. Fourteen subjects who received placebo were not included in the PK analysis. For the subjects receiving placebo only visual analogue scale/sedation (VAS/S), Richmond Agitation-Sedation Scale (RASS), and vital signs (diastolic blood pressure, systolic blood pressure, pulse rate, respiratory rate, and oxygen saturation) versus time plots were provided.

Pharmacodynamic Population

The PD population includes all randomized subjects who received at least 1 dose of single-blind study drug and had post-baseline PD assessments performed (n=42).

Demographic and Other Baseline Characteristics

Overall, the majority of healthy subjects participating in the study (59.5%) were white (non-Hispanic or Latino), a smaller proportion (31.8%) were black (African American). There was 1 (2.4%) Hispanic or Latino subject and 1 (2.4%) Asian subject in the study.

Overall, the number of male and female subjects in the study was comparable: 22 (52.4%) of all subjects were male and 20 (47.6%) were female. The mean age was 44.8 years; the subjects ranged in age from 20 to 65 years; 22 (52.4%) subjects were between 20 and 49 years and 20 (47.6%) subjects were between >49 and 65 years.

The majority of the subjects in the Placebo group were male (64.3%). Among the subjects administered dexmedetomidine sublingual film, the proportion of male (46.4%) and female (53.6%) subjects was comparable.

The physical measurements in the placebo and dexmedetomidine sublingual film group were comparable as well: a mean body mass index (BMI) was 25.50 kg/m² in the subjects administered dexmedetomidine sublingual film and 25.83 kg/m² in the Placebo group.

Figure 8:
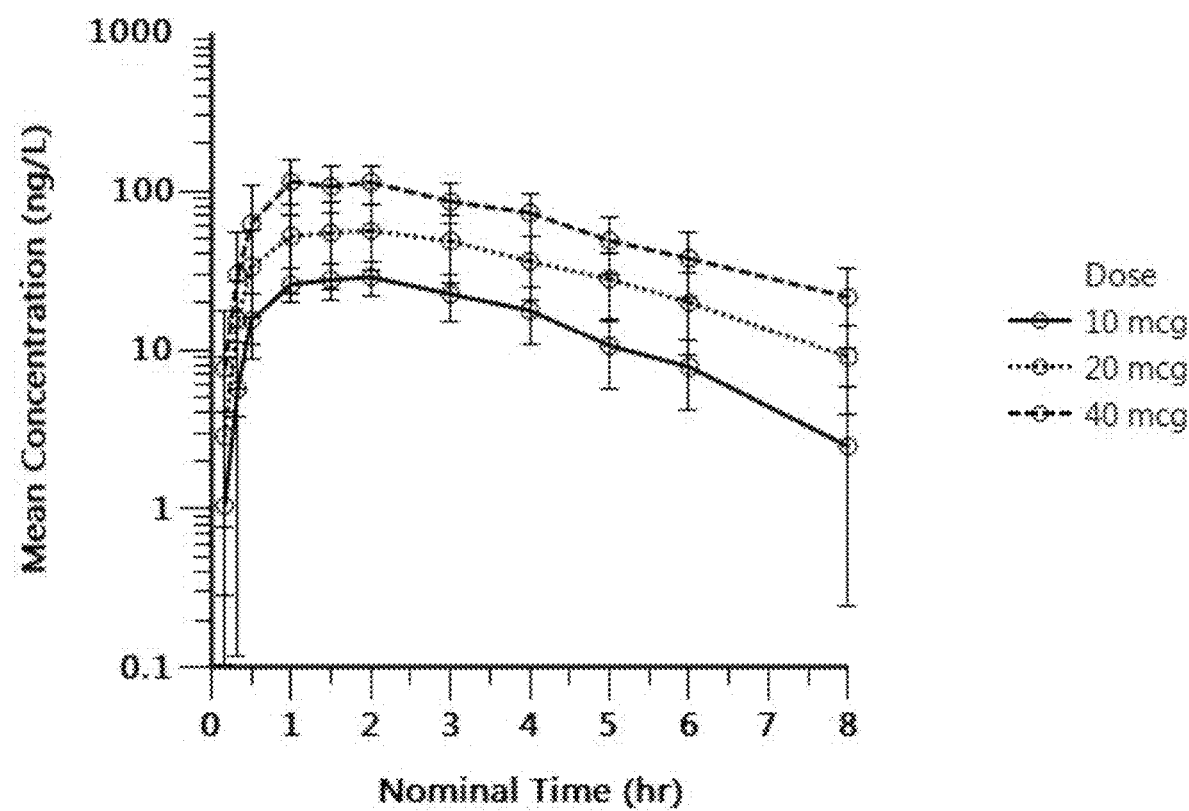
FIG. 8: shows the mean dexmedetomidine plasma log concentration vs. time for dose levels 10 µg, 20 µg and 40 µg of dexmedetomidine sublingual film (Semi-log scale). Error bars represent 1 standard deviation.
Figure 9A:
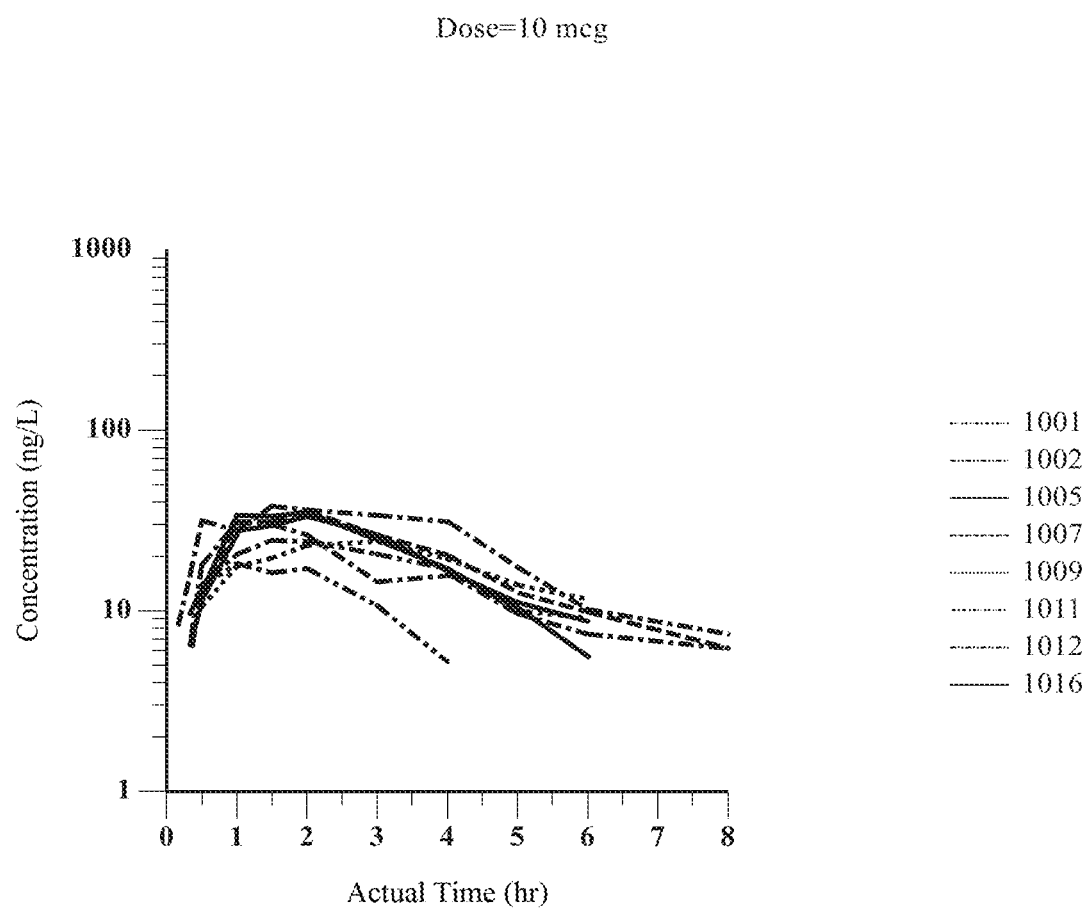
FIG. 9A: depicts individual dexmedetomidine concentration-time profiles for all subjects by dose after administration of dexmedetomidine sublingual film (10 µg) Semi-log Scale. Dexmedetomidine sublingual film is exemplified in Example 1.
Figure 9B:
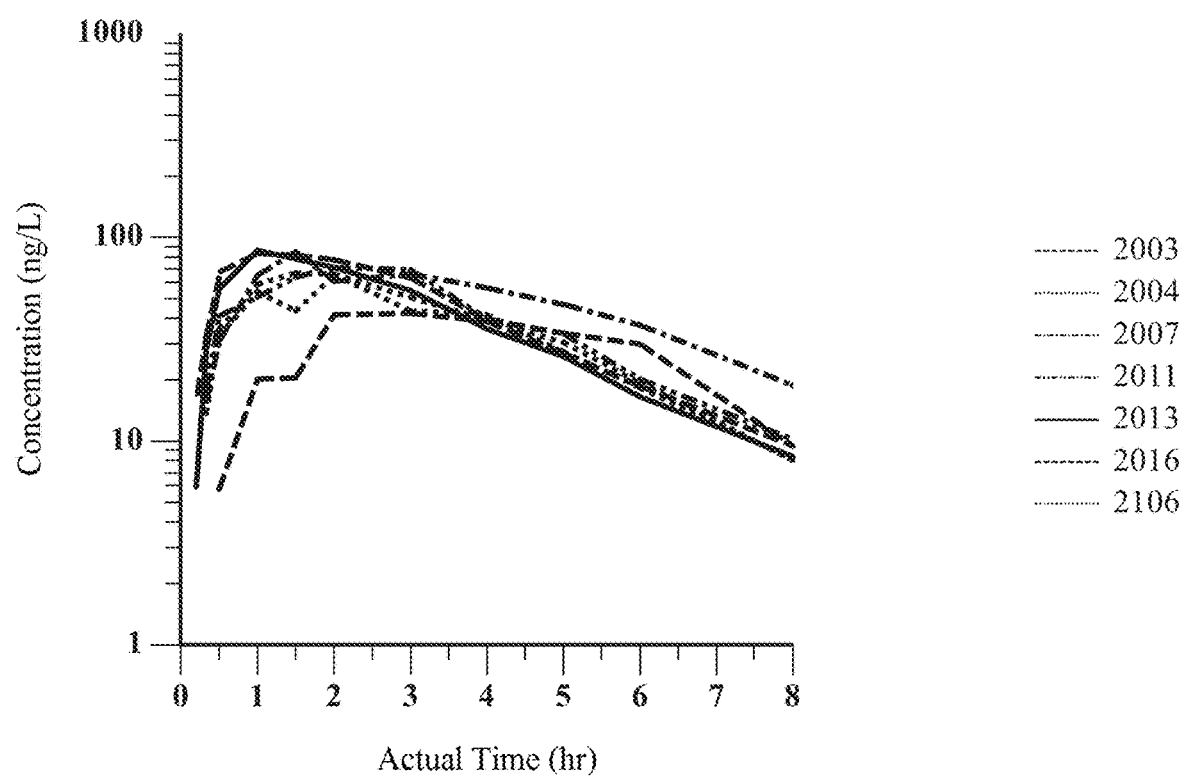
FIG. 9B: depicts individual dexmedetomidine concentration-time profiles for all subjects by dose after administration of dexmedetomidine sublingual film (20 µg) Semi-log Scale. Dexmedetomidine sublingual film is exemplified in Example 1.
Figure 9C:
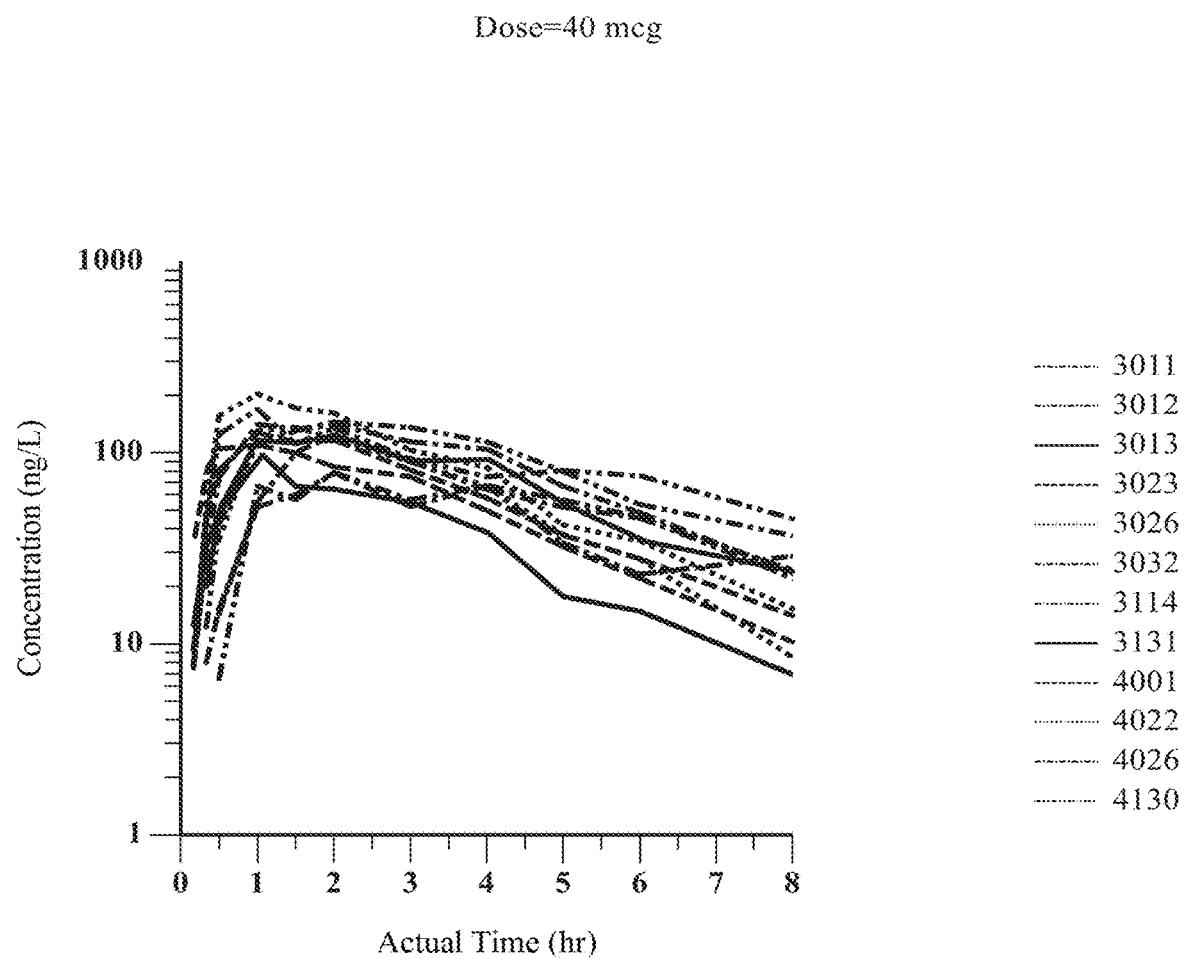
FIG. 9C: depicts individual dexmedetomidine concentration-time profiles for all subjects by dose after administration of dexmedetomidine sublingual film (40 µg) Semi-log Scale. The preparation of Dexmedetomidine sublingual film is exemplified in Example 1.

Pharmacokinetic results: Dexmedetomidine was rapidly absorbed with measurable concentrations observed at 10 minutes for all dose levels and until 8 hours postdose for the 10 μg dose levels and until 10 and 12 hours postdose for 20 μg and 40 μg dose levels, respectively, with a short mean $t_{1/2}$ that ranged between 1.82-2.16 h. Mean±SD DEX plasma concentrations-time profiles at each dose (semi-log scale) plotted against sampling time until 8 hrs postdose are presented in FIG. 8. Dose proportionality assessment indicated that $C_{max}$ and AUCs increased in a dose-proportional manner with mean $C_{max}$ ranged between 29.21 and 122.84 ng/L and mean $AUC_{0\text{-}inf}$ ranged between 130.62 and 561.57 hr·ng/L. Similar trends were seen with $AUC_{last}$ and AUC0-24 (Tables 30 to 32; FIGS. 9A to 9C)).

TABLE 30 summarizes pharmacokinetics parameters of 10 micrograms dexmedetomidine sublingual film in healthy volunteers
10 μg dexmedetomidine sublingual film

| Subject ID | Cmax (ng/L) | Tmax (hr) | t½ (hr) | AUClast (hr*ng/L) | AUC0-INF (hr*ng/L) |
|---|---|---|---|---|---|
| 1001 | 37.94 | 1.5 | 2.06 | 179.19 | 201.32 |
| 1002 | 18.27 | 1.00 | 1.17 | 49.45 | 58.27 |
| 1005 | 33.28 | 2.00 | 1.86 | 116.63 | 140.07 |
| 1007 | 35.74 | 2.00 | 2.95 | 142.22 | 168.59 |

TABLE 30-continued summarizes pharmacokinetics parameters of 10 micrograms dexmedetomidine sublingual film in healthy volunteers
10 μg dexmedetomidine sublingual film

| Subject ID | Cmax (ng/L) | Tmax (hr) | t½ (hr) | AUClast (hr*ng/L) | AUC0-INF (hr*ng/L) |
|---|---|---|---|---|---|
| 1009 | 24.15 | 3.02 | 2.70 | 102.76 | |
| 1011 | 30.87 | 1.00 | 2.75 | 114.35 | 138.82 |
| 1012 | 24.53 | 1.50 | 2.58 | 98.28 | |
| 1016 | 35.19 | 2.00 | 1.24 | 119.28 | 129.17 |
| N | 8 | 8 | 8 | 8 | 6 |
| Mean | 30 | 1.752 | 2.163 | 115.271 | 139.37 |
| SD | 6.930 | 0.66 | 0.693 | 37.05 | 47.69 |
| CV % | 23.1 | 37.62 | 32.0 | 32.1 | 34.22 |
| Min | 18.27 | 1.00 | 1.17 | 49.45 | 58.27 |
| Median | 32.08 | 1.75 | 2.32 | 115.49 | 139.45 |
| Max | 37.94 | 3.02 | 2.95 | 179.19 | 201.32 |
| Geometric Mean | 29.214 | 1.65 | 2.051 | 109.22 | 130.62 |
| Geometric CV % | 25.79 | 39.08 | 37.61 | 38.59 | 44.75 |

TABLE 31 summarizes pharmacokinetics parameters of 20 micrograms dexmedetomidine sublingual film in healthy volunteers
20 μg dexmedetomidine sublingual film

| Subject ID | Cmax (ng/L) | Tmax (hr) | t½ (hr) | AUClast (hr*ng/L) | AUC0-INF (hr*ng/L) |
|---|---|---|---|---|---|
| 2001 | 0.00 | | | 0.00 | 0.00 |
| 2003 | 83.08 | 1.00 | 2.2 | 359.59 | 389.48 |
| 2004 | 65.17 | 2.00 | 1.72 | 259.50 | 279.49 |
| 2007 | 84.90 | 1.50 | 1.60 | 401.79 | 416.92 |
| 2011 | 70.76 | 2.00 | 1.85 | 309.75 | 337.01 |
| 2013 | 85.92 | 1.00 | 1.85 | 307.97 | 330.48 |
| 2016 | 42.34 | 3.00 | 1.97 | 198.79 | 225.81 |
| 2106 | 66.75 | 1.50 | 1.57 | 283.34 | 301.60 |
| N | 8 | 7 | 7 | 8 | 8 |
| Mean | 62.37 | 1.71 | 1.824 | 265.092 | 285.10 |
| SD | 28.982 | 0.70 | 0.221 | 123.337 | 129.91 |
| CV % | 46.47 | 40.75 | 12.1 | 46.5 | 45.57 |
| Min | 0.00 | 1.00 | 1.57 | 0.00 | 0.00 |
| Median | 68.76 | 1.50 | 1.85 | 295.66 | 316.04 |
| Max | 85.92 | 3.00 | 2.20 | 401.79 | 416.92 |
| Geometric Mean | — | 1.601 | 1.813 | — | — |
| Geometric CV % | — | 41.30 | 11.95 | — | — |

TABLE 32 summarizes pharmacokinetics parameters of 40 μg dexmedetomidine sublingual film in healthy volunteers
40 μg dexmedetomidine sublingual film

| Subject ID | Cmax (ng/L) | Tmax (hr) | t½ | AUClast (hr*ng/L) | AUC0-INF (hr*ng/L) |
|---|---|---|---|---|---|
| 3011 | 140.25 | 1.00 | 1.78 | 685.15 | 709.61 |
| 3012 | 78.69 | 2.00 | 2.00 | 427.97 | 461.18 |
| 3013 | 97.01 | 1.07 | 1.76 | 292.84 | 310.29 |
| 3023 | 126.60 | 1.00 | 1.86 | 493.89 | 508.98 |
| 3026 | 135.02 | 1.50 | 1.38 | 482.44 | 499.41 |
| 3032 | 78.06 | 2.00 | | 378.67 | |
| 3114 | 167.99 | 1.00 | 2.05 | 777.66 | 806.08 |
| 3131 | 123.52 | 2.02 | 2.42 | 600.88 | 627.60 |
| 4001 | 109.62 | 1.00 | 1.82 | 419.51 | 446.40 |
| 4022 | 204.03 | 1.00 | 1.82 | 664.47 | 704.50 |
| 4026 | 123.68 | 2.00 | 1.83 | 507.83 | 534.00 |
| 4130 | 143.95 | 2.00 | 1.97 | 772.97 | 798.78 |
| N | 12 | 12 | 11 | 12 | 11 |
| Mean | 127.37 | 1.47 | 1.88 | 542.02 | 582.24 |

TABLE 32-continued summarizes pharmacokinetics parameters of 40 μg
dexmedetomidine sublingual film in healthy volunteers 40 μg dexmedetomidine sublingual film

| Subject ID | Cmax (ng/L) | Tmax (hr) | t½ | AUClast (hr*ng/L) | AUC0-INF (hr*ng/L) |
|---|---|---|---|---|---|
| SD | 35.79 | 0.49 | 0.25 | 157.144 | 158.70 |
| CV % | 28.10 | 33.75 | 13.44 | 28.99 | 27.25 |
| Min | 78.06 | 1.00 | 1.38 | 292.84 | 310.29 |
| Median | 125.14 | 1.28 | 1.83 | 500.86 | 534.00 |
| Max | 204.03 | 2.02 | 2.42 | 777.66 | 806.08 |
| Geometric Mean | 122.84 | 1.39 | 1.87 | 520.58 | 561.57 |
| Geometric CV % | 28.87 | 35.22 | 13.7 | 30.84 | 29.65 |

Pharmacodynamic Results:

The sedative effect of dexmedetomidine sublingual film was assessed by RASS and Visual analogue scales/sedation (VAS/S) on day of dexmedetomidine sublingual film dosing. The assessment included:

Time in minutes and seconds from administration of dexmedetomidine sublingual film until RASS of −1;

Time in minutes and seconds from RASS of −1 till resolution of drowsiness;

Time in minutes and seconds from SL administration of dexmedetomidine sublingual film till its complete dissolution or 30 minutes.

Richmond Agitation Sedation Scale

All RASS scores assessed during the study ranged between −2 (Light Sedation) and 0 (Alert and Calm). The baseline score for all subjects was 0 (Alert and Calm). Overall, a total of 14 subjects achieved drowsiness (RASS of −1) across all treatments. Of these, 2 received 10 μg dose group, 4 received 20 μg dose group, 5 received 40 μg dose group, and 3 received Placebo. Two subjects also achieved light sedation (RASS of −2), 1 received 10 μg dose group and the other one received Placebo.

The mean times to achieve drowsiness from baseline for subjects administered dexmedetomidine sublingual film and placebo is summarized in Table 33. Overall, the time to achieve drowsiness was variable across all treatment groups and ranged from 19 minutes to 85 minutes in dexmedetomidine sublingual film groups and from 19 minutes 17 seconds to 107 minutes 29 seconds in placebo group. No statistically significant between-group differences were observed for either 10 μg or 40 μg treatment groups.

The duration from onset of drowsiness (RASS of −1) until resolution for subjects administered dexmedetomidine sublingual film and Placebo is summarized in Table 34. Overall, the duration from onset of drowsiness (RASS of −1) until resolution was variable across all treatment groups and ranged from 05 minutes 05 seconds to 91 minutes. Mean duration in subjects administered dexmedetomidine sublingual film was 48 minutes 24 seconds, and subjects administered placebo presented a mean duration of 37 minutes 25 seconds.

TABLE 33

Achievement of Drowsiness (in minutes:seconds) from Baseline Assessed by RASS of −1

| | Dexmedetomidine sublingual film | | | | | | | |
|---|---|---|---|---|---|---|---|---|
| | Cohort 1 (10 μg) | | Cohort 2 (20 μg) | Cohort 3 (40 μg) | | Cohort 4 (40 μg) | Cohort 3 + 4 (40 μg) | |
| Statistics | Active (N = 8) | Placebo (N = 4) | Active (N = 8) | Active (N = 8) | Placebo (N = 4) | Active (N = 4) | Active (N = 12) | Placebo (N = 6) |
| n | 2 | 2 | 4 | 3 | 1 | 2 | 5 | 1 |
| Mean (SD) | 31:30 (3:32) | 65:47 (58:58) | 59:16 (18:16) | 47:30 (10:27) | 19:17 | 24:00 (7:40) | 38:60 (15:15) | 19:17 |
| Median | 31:30 | 65:47 | 54:20 | 44:20 | 19:17 | 24:00 | 39:00 | 19:17 |
| Min, Max | 29:00, 34:00 | 24:50, 107:29 | 44:00, 85:00 | 39:00, 59:10 | 19:17, 19:17 | 19:00, 29:00 | 19:00, 59:10 | 19:17, 19:17 |
| P-value vs Placebo[a] | 1.000 | | | 0.5000 | | | 0.6667 | |

[a]P-value is based on a non-parametric two-sided (exact) Wilcoxon test.
n—number of subjects who have reached at least RASS of −1 at any time in the first 2 hours

TABLE 34

Duration from RASS of −1 till Resolution of Drowsiness (in minutes:seconds)

| | Dexmedetomidine sublingual film | | | | | | | |
|---|---|---|---|---|---|---|---|---|
| Statistics | Cohort 1 10 μg (N = 8) | Cohort 2 20 μg (N = 8) | Cohort 3 40 μg (N = 8) | Cohort 4 40 μg (N = 4) | Cohort 3 and 4 40 μg (N = 12) | Overall Active[a] (N = 28) | Pooled Placebo[a] (N = 14) | Overall[a] (N = 42) |
| n | 2 | 4 | 3 | 2 | 5 | 11 | 2 | 13 |
| Mean | 84:30 | 53:49 | 28:00 | 32:03 | 29:37 | 48:24 | 37:25 | 46:43 |
| (SD) | (9:12) | (10:56) | (30:29) | (38:07) | (28:52) | (28:45) | (10:38) | (26:44) |
| Median | 84:30 | 52:39 | 15:01 | 32:03 | 15:01 | 59:00 | 37:25 | 45:12 |
| Min, Max | 78:00, 91:00 | 44:00, 66:00 | 6:10, 62:50 | 5:05, 59:00 | 5:05, 62:50 | 5:05, 91:00 | 29:54, 44:56 | 5:05, 91:00 |

Figure 10A:
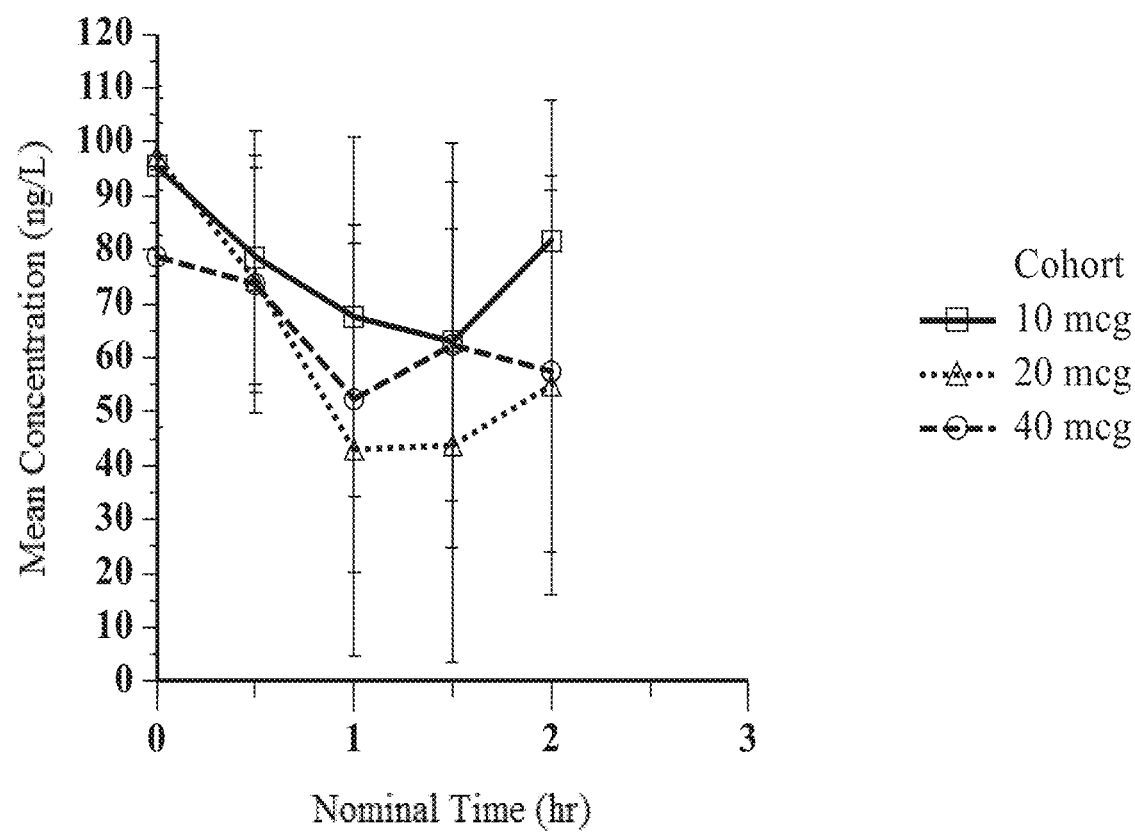
FIGS. 10A-10B: depict mean VAS/S score vs. nominal time after administration of dexmedetomidine sublingual film (10 µg, 20 µg, 40 µg) and placebo. Dexmedetomidine sublingual film (10 µg and 20 µg) and the preparation of dexmedetomidine sublingual film (40 µg) are exemplified in Example 1.
Figure 10B:
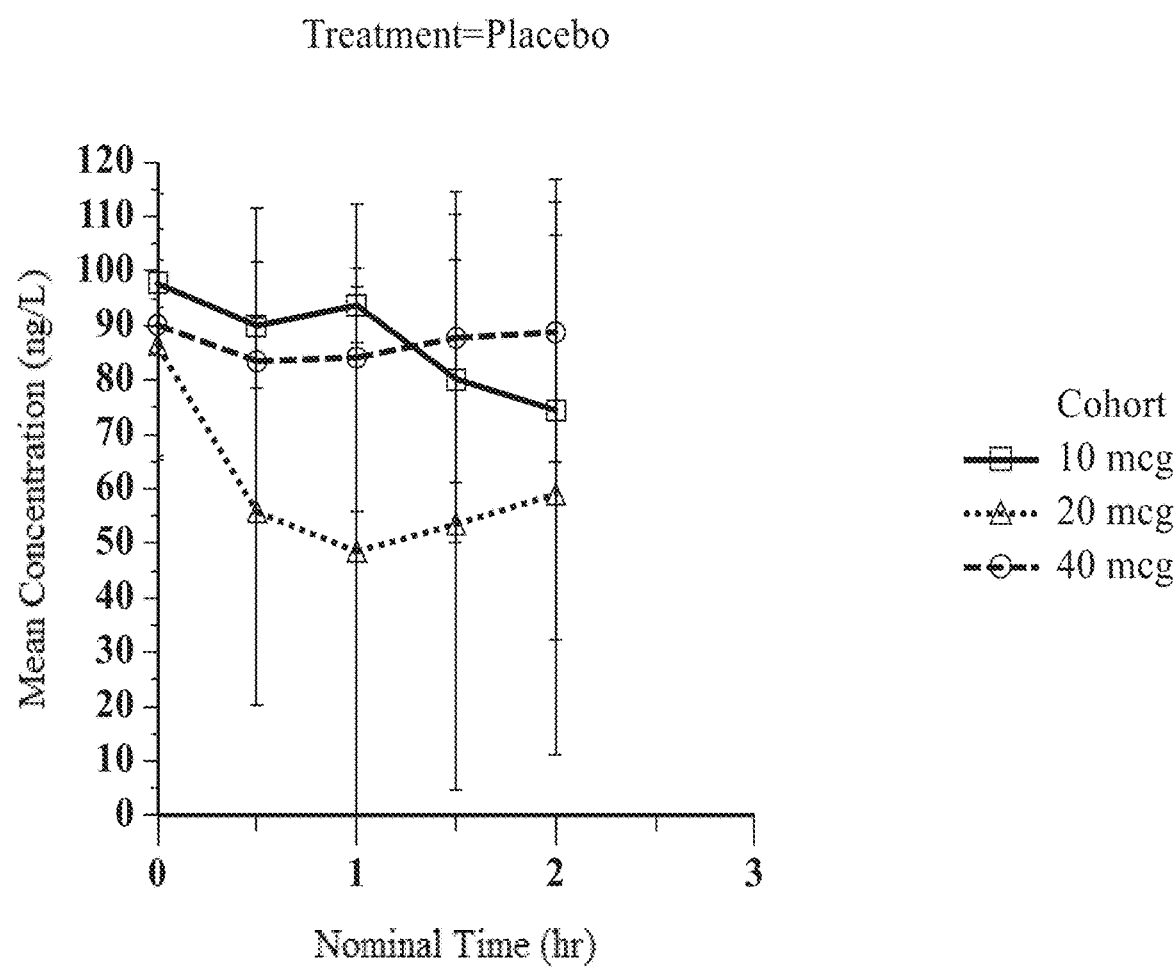
Figure 11A:
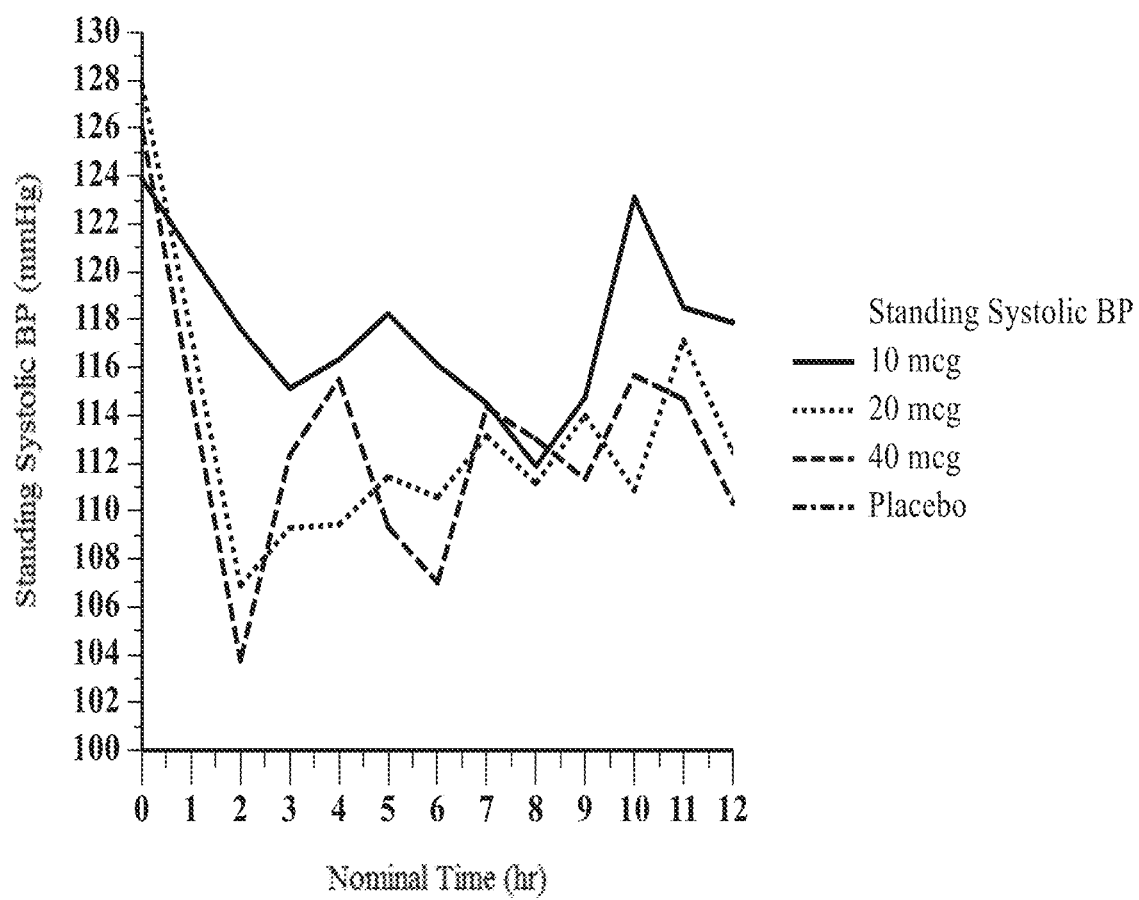
FIGS. 11A-11B: depict standing systolic BP vs nominal time after administration of dexmedetomidine sublingual film (10 µg, 20 µg, 40 µg) and placebo. Dexmedetomidine sublingual film (10 µg and 20 µg) and the preparation of dexmedetomidine sublingual film (40 µg) are exemplified in Example 1.
Figure 11B:
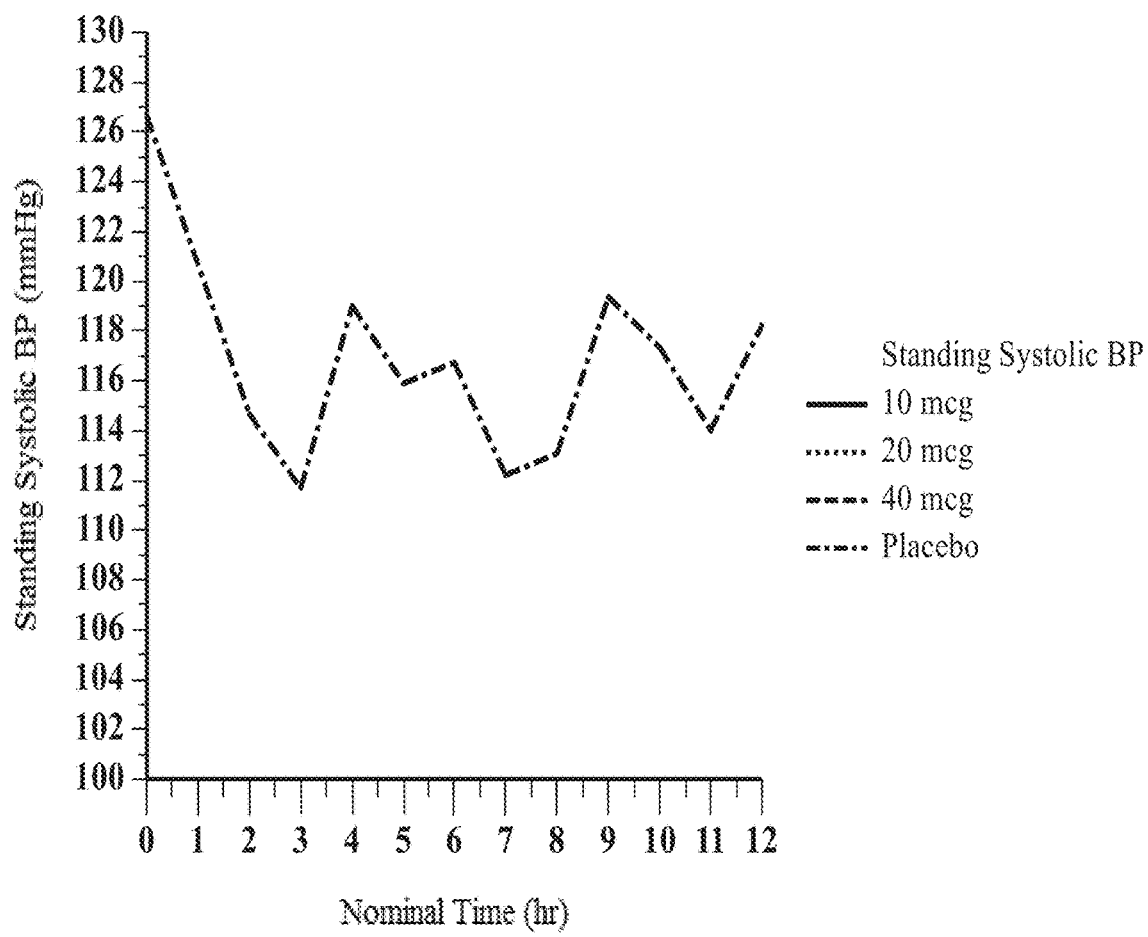
Figure 12A:
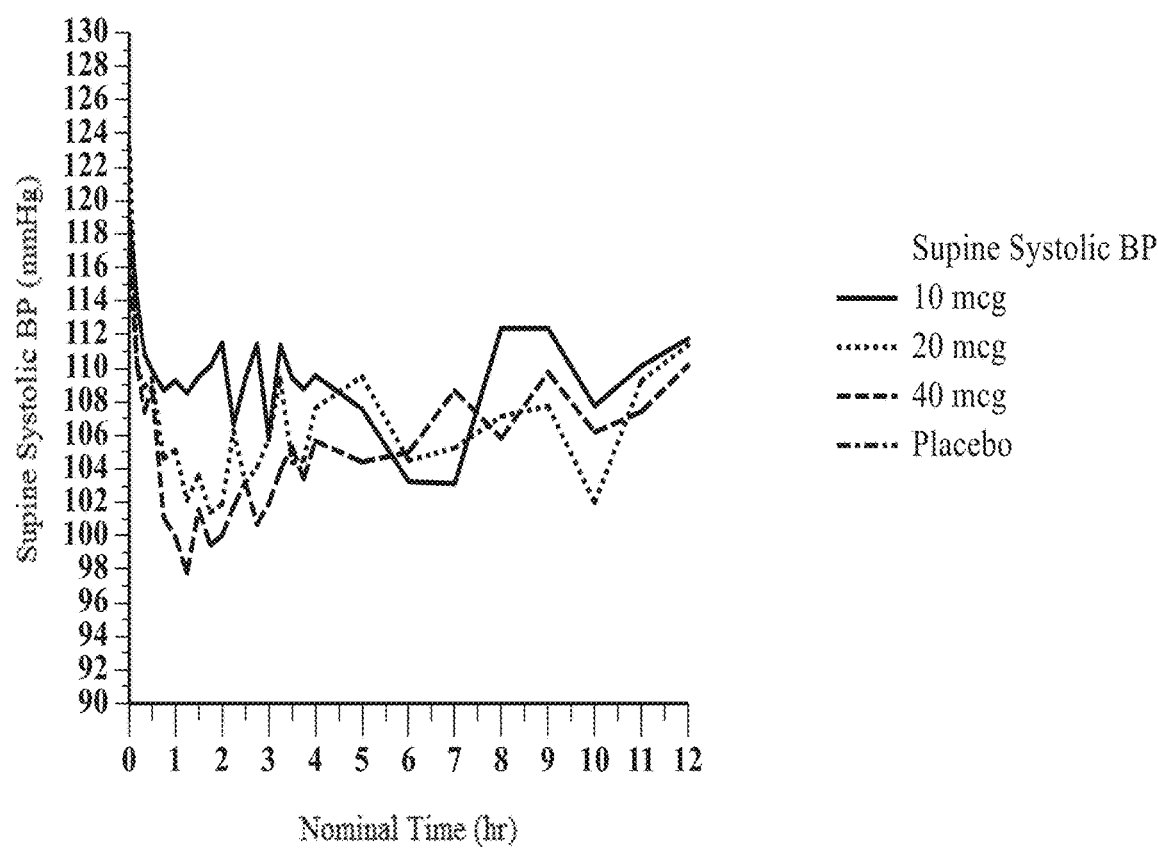
FIGS. 12A-12B: depict supine systolic BP. vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.
Figure 12B:
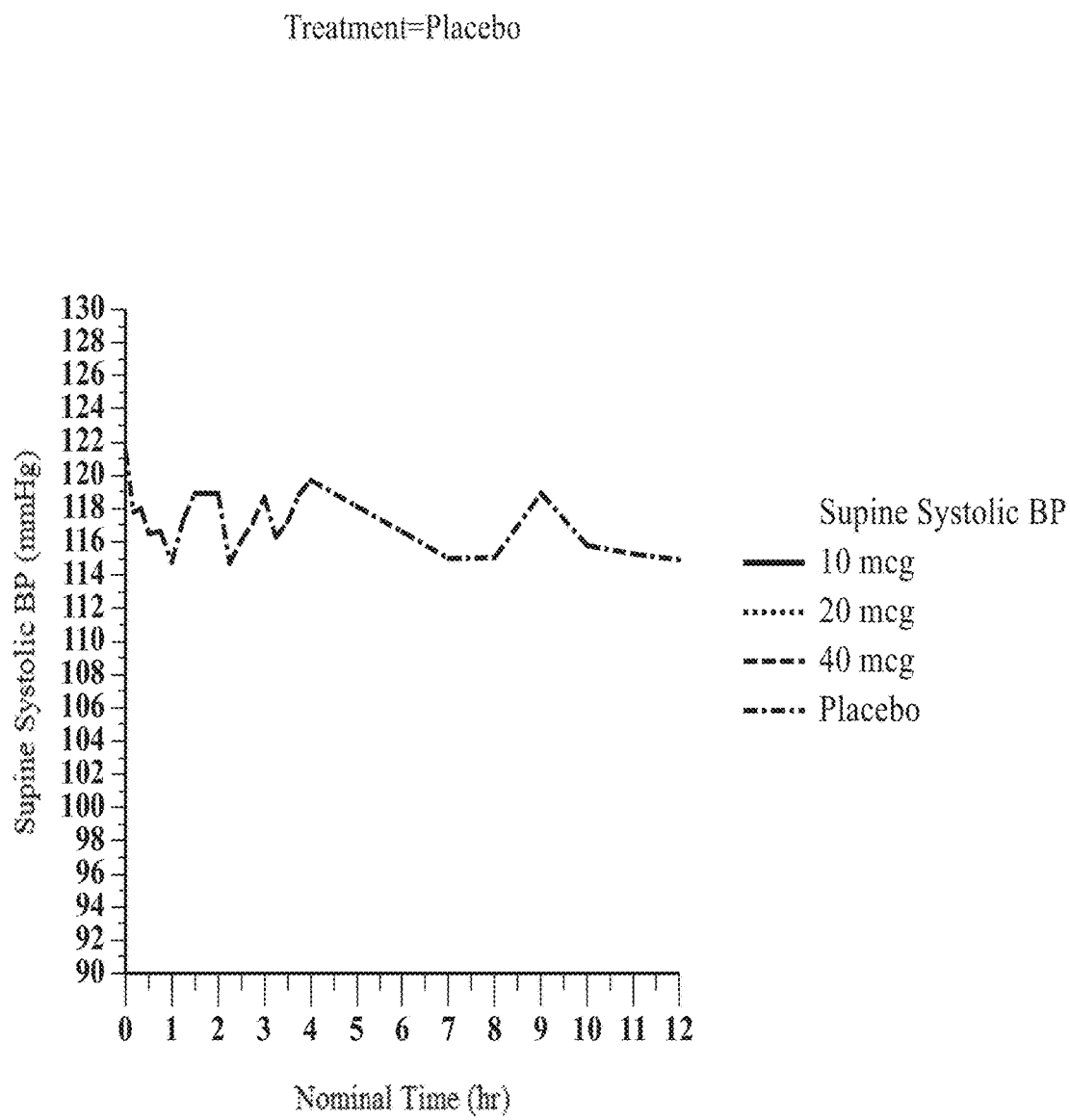
Figure 13A:
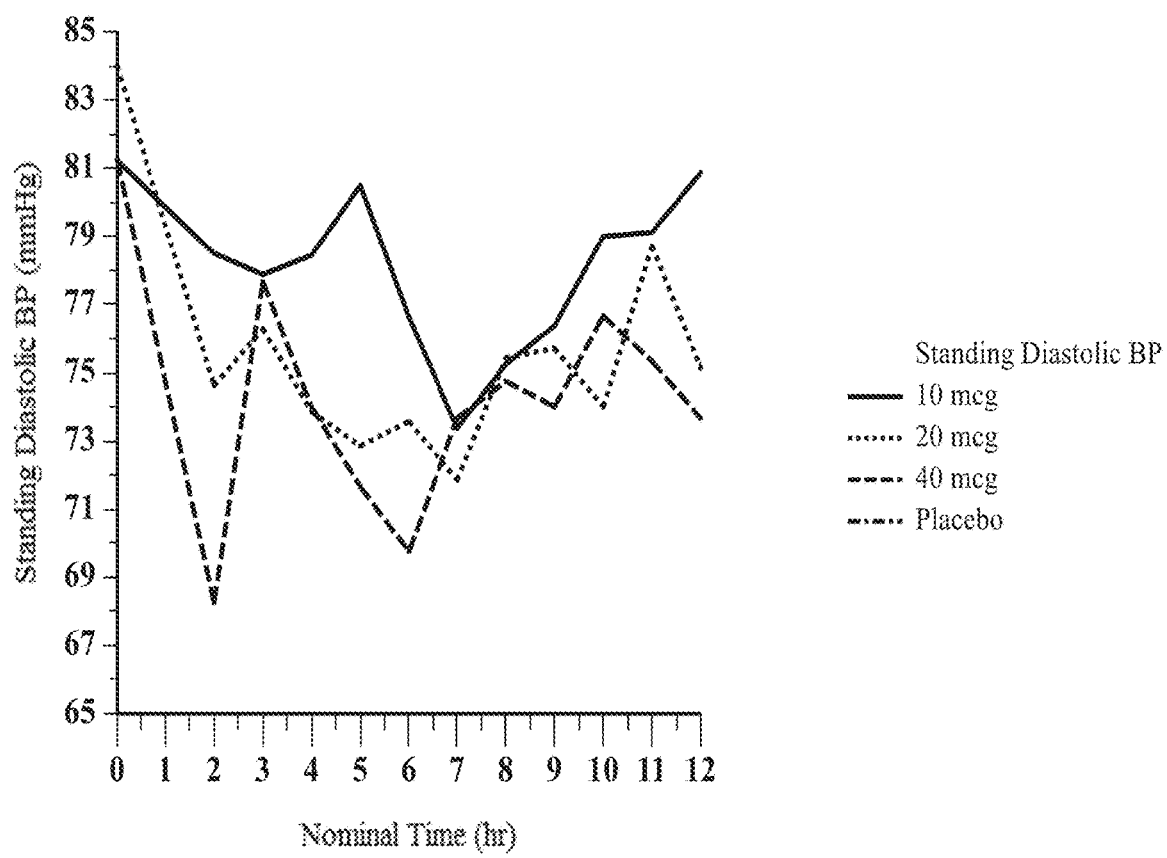
FIGS. 13A-13B: depict standing diastolic BP vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.
Figure 13B:
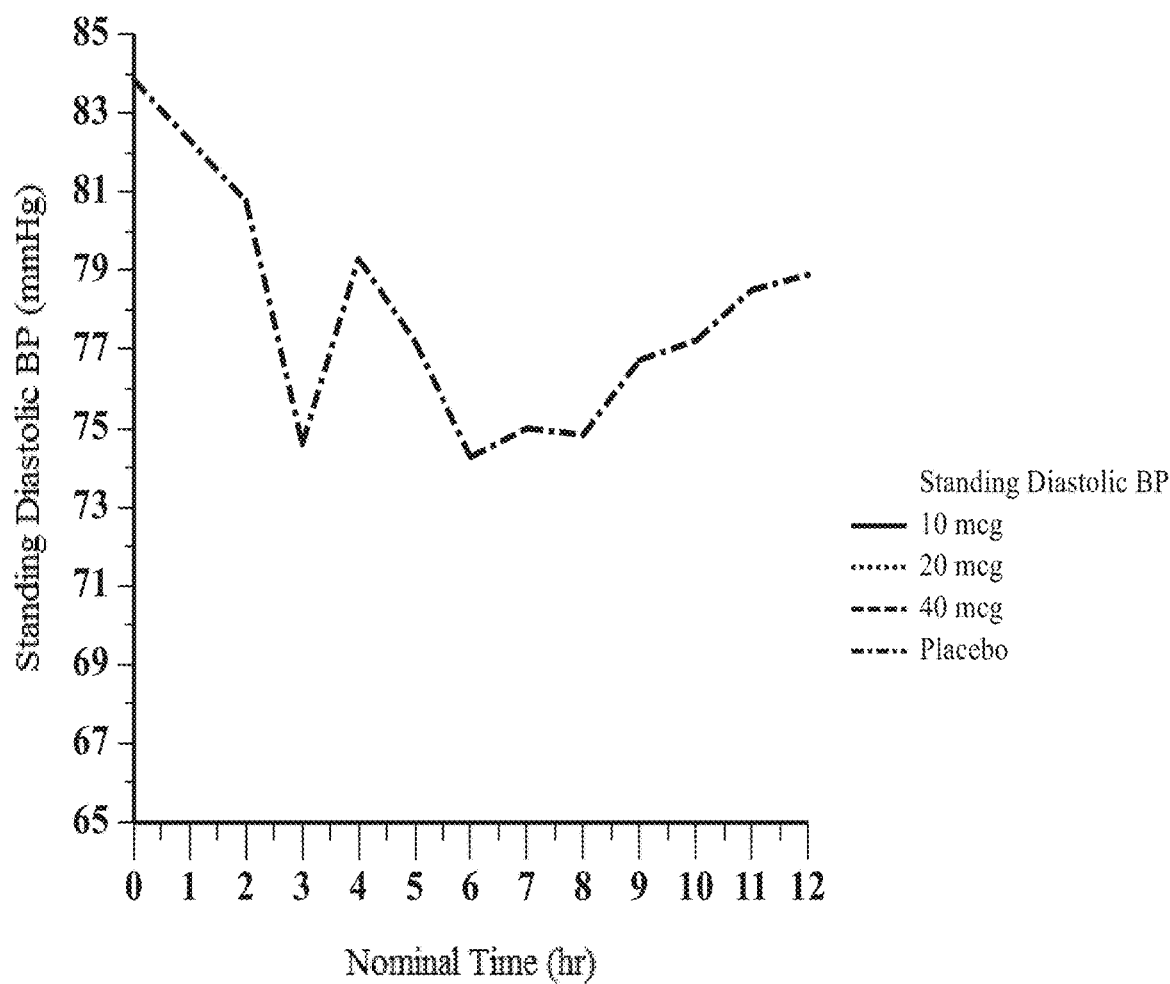
Figure 14A:
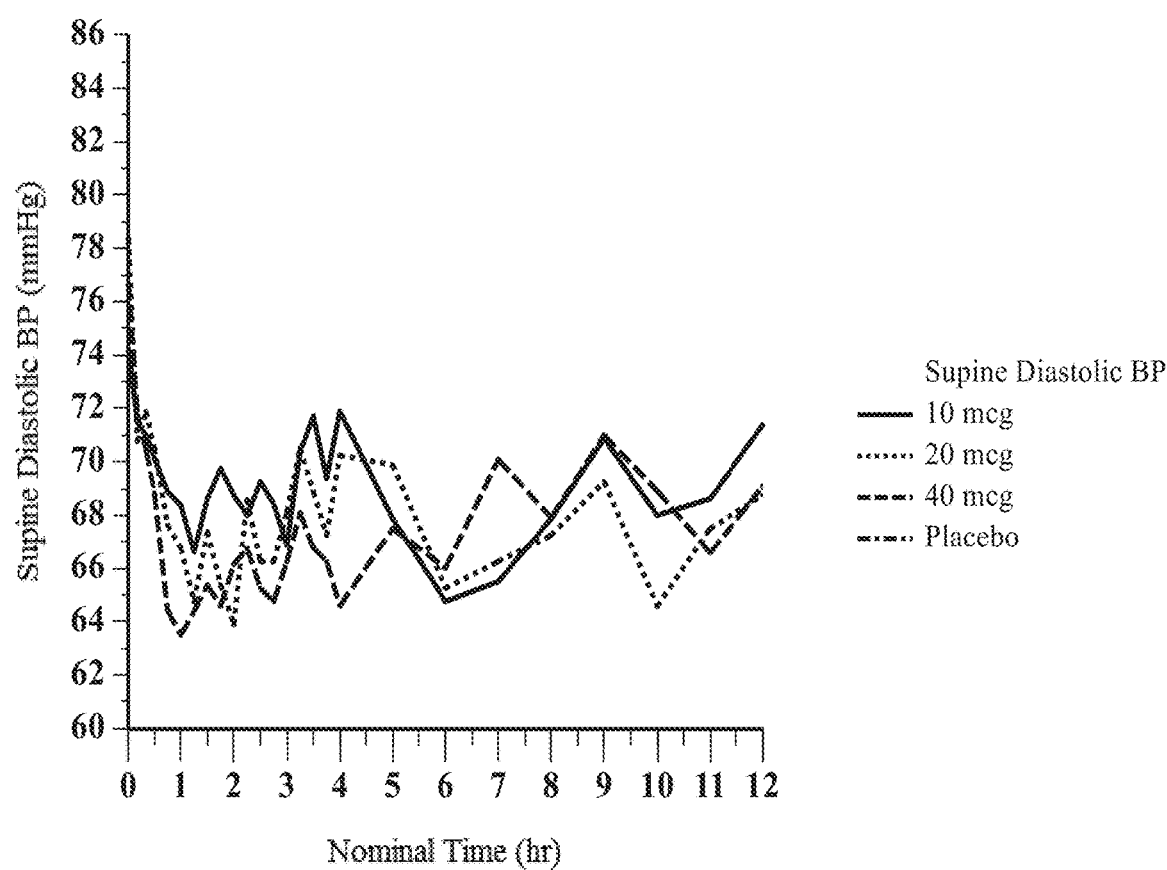
FIGS. 14A-14B: depict supine diastolic BP vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.
Figure 14B:
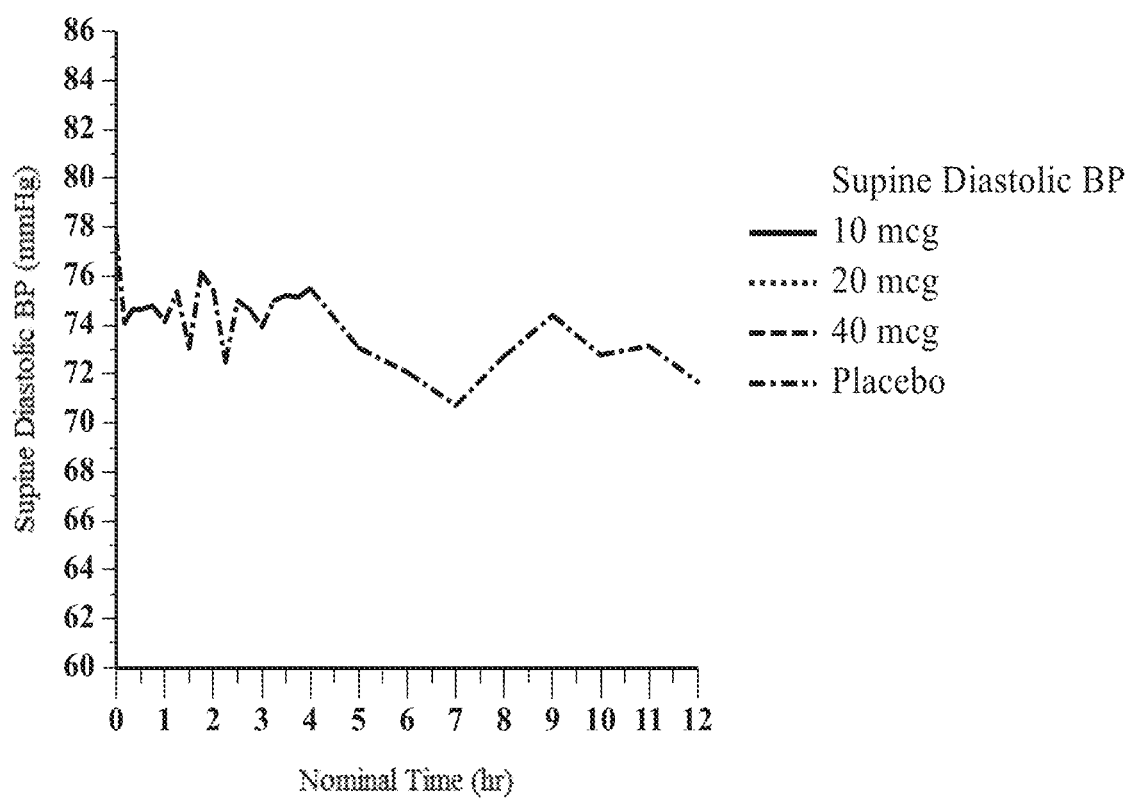
Figure 15A:
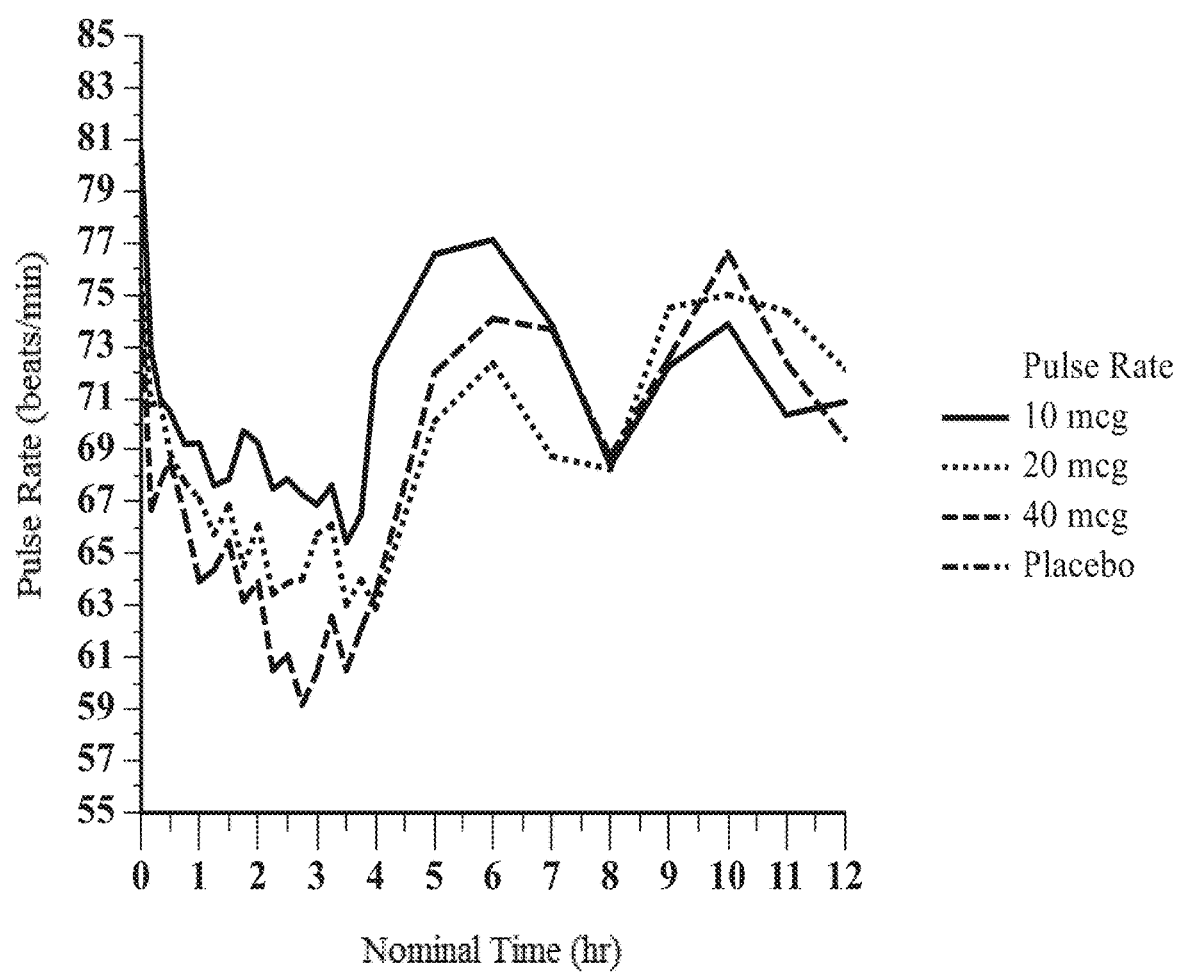
FIGS. 15A-15B: depict pulse rate vs nominal time after administration of dexmedetomidine sublingual film 10 µg, 20 µg and 40 µg and placebo. Dexmedetomidine sublingual film (10 µg and 20 µg) and the preparation of dexmedetomidine sublingual film (40 µg) are exemplified in Example 1.
Figure 15B:
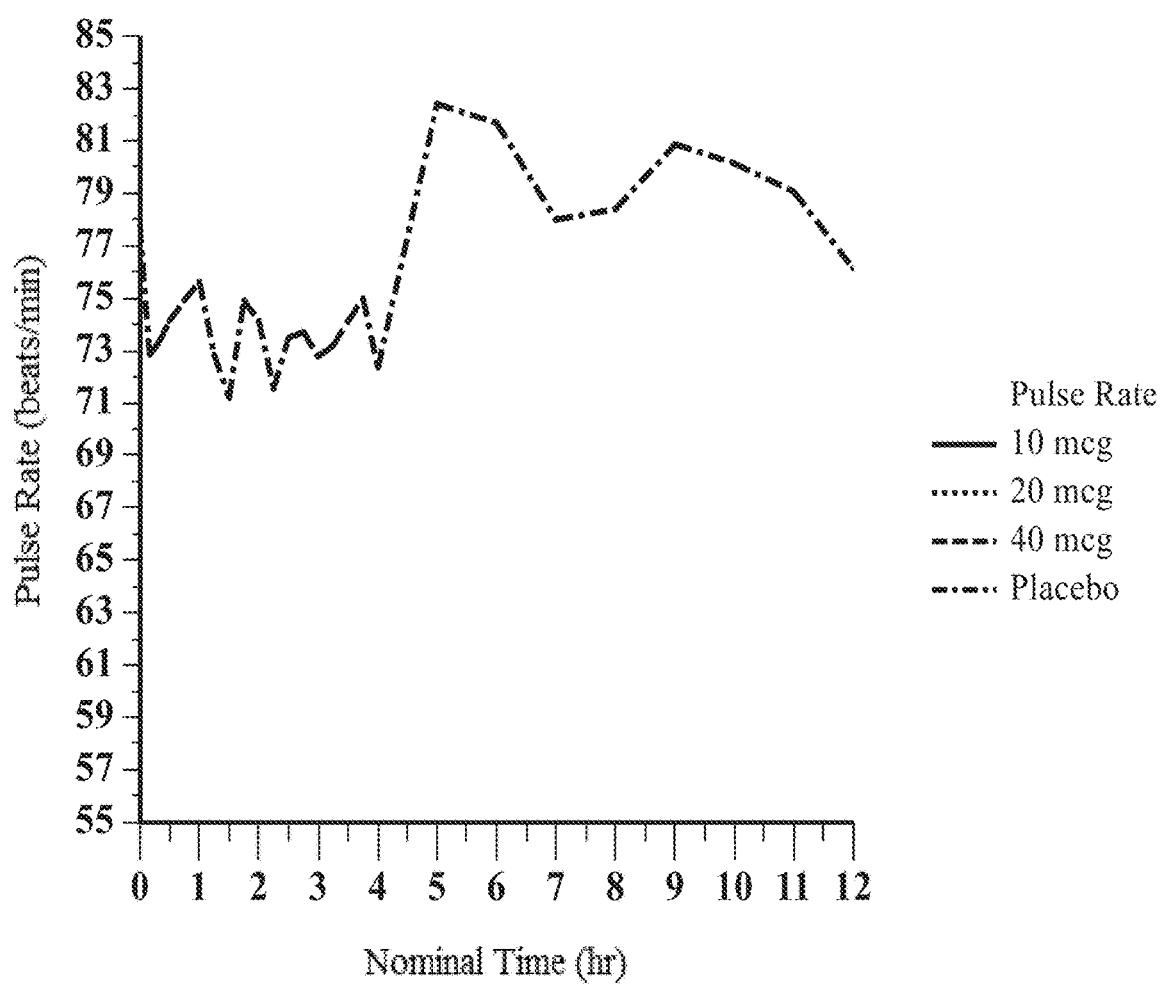

[a]Overall Active, Pooled Placebo and Overall columns include assessment counts not subject level counts.
n—number of subjects who have reached at least RASS of −1 at any time in the first 2 hours Visual Analogue Scales/Sedation:

The subjective sedative effect of dexmedetomidine was assessed by means of VAS. Subjects were asked to score their feeling on a 100-mm horizontal scale, with 0 indicating very sleepy and 100 indicating very alert. Overall, VAS scores were variable with the lowest scores being generally observed at the 1.0 and 1.5-hour timepoints for subjects dosed with dexmedetomidine sublingual film. Mean scores observed at pre-dose 0.5, 1, 1.5- and 2-hours following treatment with dexmedetomidine sublingual film or placebo and P-values are presented in Table 35 and FIGS. 10A-10B. There were no statistically significant between-group differences (Active vs. Placebo) observed in Cohorts 1 (10 µg), Cohort 2 (20 µg) and Cohorts 3 and 4 combined (40 µg dose). Statistically significant differences were only seen in Cohort 3 (40 jig). However, the statistical significance in this cohort was also reported for the pre-dose assessment (P<0.05; Table 35) indicating that the study environments and score variability may have affected the outcome.

Dexmedetomidine Sublingual Film Dissolution Time:

A single dose of dexmedetomidine sublingual film was administered sublingually. For 20 µg dose cohort, two (2) 10 µg films were administered simultaneously. The drug film was retained in the sublingual cavity until it had dissolved. There was an evaluation every 5 minutes for the first 15 minutes, and then every 15 minutes to determine the time to dissolution of the film. Mean, median, and min and max dissolution time for each treatment group in minutes:seconds are presented in Table 36. Overall, duration from the SL administration of dexmedetomidine sublingual film or Placebo film until its complete dissolution was variable and ranged from 3 minutes to 44 minutes 11 second. Mean (SD) and median dissolution times were similar for dexmedetomidine sublingual film (14:09 (11:33); 11:11, minutes: seconds) and Placebo (13:32 (12:49); 8:28, minutes: seconds) films. No subject presented aberrant oral/buccal anatomy or inflammation during the buccal mucosal irritation examination.

Safety Evaluation:

Based on the results in this study, the following safety conclusions can be made:

There were no deaths or serious TEAEs reported in the study. One subject administered dexmedetomidine sublingual film 10-µg had a decrease in heart rate >30 beats per minute (withdrawal criterion) therefore had become ineligible to participate in Cohort 3. An overall summary of AEs is provided in Table 37.

A total of 52 TEAEs were reported by 25 of the 28 subjects (89%) administered dexmedetomidine sublingual film and 20 TEAEs were reported by 10 of the 14 subjects (71%) administered placebo. All TEAEs were recovered by the end of the study.

Subjects administered dexmedetomidine sublingual film reported TEAEs with an incidence of 75% for 10 µg dose group, 88% for 20 µg dose group and 100% for 40 µg dose group. Drug-related TEAEs were reported with an incidence of 75% following administration of 10 µg dose group, 88% following administration of 20 µg dose group, 92% following administration of 40 µg dose group and 64% following administration of placebo.

The most experienced TEAE during the study was somnolence, which was reported with a slightly higher frequency at doses of 20 µg and 40 µg (75% each) compared to the 10 µg dose and placebo (50% each) (Table 38).

The majority of TEAEs were mild in severity in all treatment groups with only few moderate TEAEs reported. Moderate TEAEs were experienced following administration of 10 µg dose (1/12; 8%), 40 µg dose (2/30; 7%) and administration of placebo (4/20; 20%). No severe TEAEs were reported in this study.

No subject dosed in this study required hemodynamic/medical interventions for maintaining BP, cardiac interventions for maintaining heart rate or respiratory interventions for maintaining oxygen saturation. No subject was withdrawn due to a TEAE. The data is further depicted in FIGS. 11 to 15.

Two subjects presented symptomatic changes in vital signs that were considered clinically significant and reported as vital signs related TEAEs. One subject administered placebo had a decrease in DBP and SBP that were recorded as drug-related TEAEs of moderate and mild intensity, respectively and 1 subject administered 40 µg dose group had decreases in heart rate that were recorded as 2 drug-related TEAEs of mild intensity. All TEAEs were resolved within 1 day from onset.

There were no clinically significant changes in laboratory parameters and ECG assessments. No physical examination finding was considered clinically significant by the investigator. All neurological examinations performed during the study were normal and no subject presented aberrant oral/buccal anatomy or inflammation during the buccal mucosal irritation examination.

TABLE 35

(cont'd) Summary of Visual Analogue Scales/Sedation

| Timepoint | Statistics | Cohort 1 (10 µg) | | Cohort 2 (20 µg) | | Cohort 3 (40 µg) | |
|---|---|---|---|---|---|---|---|
| | | Active (N = 8) | Placebo (N = 4) | Active (N = 8) | Placebo (N = 4) | Active (N = 8) | Placebo (N = 4) |
| Pre-dose | n | 8 | 4 | 8 | 4 | 8 | 4 |
| | Mean | 95.5 | 97.8 | 97.4 | 86.5 | 74.8 | 100 |
| | (SD) | (12.73) | (4.50) | (6.25) | (21.30) | (35.29) | (0.00) |
| | P-value | 1 | | 0.2384 | | 0.0485* | |
| 0.5 Hour | n | 8 | 4 | 8 | 4 | 8 | 4 |
| | Mean | 78.8 | 90.0 | 74.4 | 55.8 | 73.0 | 93.0 |
| | (SD) | (23.50) | (11.52) | (20.87) | (35.61) | (25.72) | (12.68) |
| | P-value | 0.4788 | | 0.2788 | | 0.0465* | |
| 1.0 Hour | n | 5 | 4 | 8 | 4 | 8 | 4 |
| | Mean | 67.6 | 93.8 | 43.0 | 48.5 | 42.8 | 94.3 |
| | (SD) | (33.30) | (6.65) | (38.26) | (48.50) | (32.98) | (10.18) |
| | P-value | 0.3175 | | 0.9737 | | 0.0121* | |

TABLE 35-continued (cont'd) Summary of Visual Analogue Scales/Sedation

| Timepoint | Statistics | Cohort 1 (10 µg) | | Cohort 2 (20 µg) | | Cohort 3 (40 µg) | |
|---|---|---|---|---|---|---|---|
| | | Active (N = 8) | Placebo (N = 4) | Active (N = 8) | Placebo (N = 4) | Active (N = 8) | Placebo (N = 4) |
| 1.5 Hour | n | 8 | 4 | 8 | 4 | 7 | 3 |
| | Mean | 63.0 | 80.3 | 43.8 | 53.5 | 53.0 | 99.7 |
| | (SD) | (29.69) | (30.18) | (40.02) | (48.64) | (41.68) | (0.58) |
| | P-value | 0.4586 | | 0.4869 | | 0.0167* | |
| 2.0 Hour | n | 8 | 4 | 8 | 4 | 7 | 3 |
| | Mean | 81.8 | 74.5 | 54.9 | 59.0 | 50.9 | 99.7 |
| | (SD) | (25.97) | (42.19) | (38.92) | (47.79) | (36.22) | (0.58) |
| | P-value | 0.9253 | | 0.8848 | | 0.0167* | |

TABLE 35

Summary of Visual Analogue Scales/Sedation

| Timepoint | Statistics | Cohort 4 (40 µg) | | Cohort 3 + 4 (40 µg) | | Overall |
|---|---|---|---|---|---|---|
| | | Active (N = 4) | Placebo (N = 2) | Active (N = 12) | Placebo (N = 6) | (N = 42) |
| Pre-dose | n | 4 | 2 | 12 | 6 | 60 |
| | Mean (SD) | 86.8 (25.84) | 70.5 (41.72) | 78.8 (31.78) | 90.2 (24.09) | 87.5 (24.18) |
| | P-value | 0.8 | | 0.139 | | |
| 0.5 Hour | n | 4 | 2 | 12 | 6 | 60 |
| | Mean (SD) | 75.0 (22.67) | 64.5 (48.79) | 73.7 (23.71) | 83.5 (28.09) | 76.3 (24.24) |
| | P-value | 0.8 | | 0.2203 | | |
| 1.0 Hour | n | 4 | 2 | 12 | 6 | 57 |
| | Mean (SD) | 71.5 (22.61) | 64.0 (49.50) | 52.3 (32.13) | 84.2 (28.22) | 61.7 (34.97) |
| | P-value | 0.8 | | 0.0691 | | |
| 1.5 Hour | n | 4 | 2 | 11 | 5 | 56 |
| | Mean (SD) | 78.8 (25.59) | 70.0 (42.43) | 62.4 (37.52) | 87.8 (26.72) | 65.0 (36.06) |
| | P-value | 0.9333 | | 0.0627 | | |
| 2.0 Hour | n | 3 | 2 | 10 | 5 | 54 |
| | Mean (SD) | 73.0 (24.88) | 72.5 (37.48) | 57.5 (33.56) | 88.8 (23.93) | 67.9 (34.28) |
| | P-value | 0.8 | | 0.0513 | | |

P-values are calculated for Active vs Placebo for each cohort. P-value based on non-parametric two-sided (exact) Wilcoxon test.
*Statistically significant between-group difference (Active vs Placebo)

TABLE 36

Duration from SL Administration (in minutes:seconds) of Dexmedetomidine sublingual film till its Complete Dissolution (PD Population)

| | Dexmedetomidine sublingual film | | | | | | | |
|---|---|---|---|---|---|---|---|---|
| Statistics | Cohort 1 10 µg (N = 8) | Cohort 2 20 µg (N = 8) | Cohort 3 40 µg (N = 8) | Cohort 4 40 µg (N = 4) | Cohort 3 and Cohort 4 40 µg (N = 12) | Overall Active* (N = 28) | Pooled Placebo* (N = 14) | Overall* (N = 42) |
| n | 8 | 8 | 8 | 4 | 12 | 28 | 13 | 41 |
| Mean (SD) | 9:03 (7:52) | 23:49 (12:36) | 14:26 (10:04) | 4:26 (2:24) | 11:06 (9:30) | 14:09 (11:33) | 13:32 (12:49) | 13:58 (11:49) |
| Median | 5:11 | 29:01 | 14:05 | 3:23 | 8:09 | 11:11 | 8:28 | 8:28 |
| Min, Max | 3:00, 24:30 | 8:00, 44:01 | 3:18, 29:01 | 3:00, 8:00 | 3:00, 29:01 | 3:00, 44:01 | 3:00, 44:11 | 3:00, 44:11 |

*Overall Active, Pooled Placebo and Overall columns include assessment counts not subject level counts

TABLE 37

Summary of Adverse Events

| | Dexmedetomidine sublingual film | | | | | | Placebo (N = 14) n (%) | Overall (N = 42) n (%) |
|---|---|---|---|---|---|---|---|---|
| | Cohort 1 10 µg (N = 8) n (%) | Cohort 2 20 µg (N = 8) n (%) | Cohort 3 40 µg (N = 8) n (%) | Cohort 4 40 µg (N = 4) n (%) | Cohort 3 and Cohort 4 40 µg (N = 12) n (%) | Overall (N = 28) n (%) | | |
| AEs reported | | | | | | | | 75 |
| TEAEs reported | 12 | 10 | 24 | 6 | 30 | 52 | 20 | 72 |
| Subjects with at least one TEAE[a] | 6 (75.0) | 7 (87.5) | 8 (100.0) | 4 (100.0) | 12 (100.0) | 25 (89.3) | 10 (71.4) | 35 (83.3) |
| Subjects with at least one drug-related TEAE[a] | 6 (75.0) | 7 (87.5) | 8 (100.0) | 3 (75.0) | 11 (91.7) | 24 (85.7) | 9 (64.3) | 33 (78.6) |
| TEAEs relationship[b] | | | | | | | | |
| Possibly related | 4 (33.3) | 2 (20.0) | 5 (20.8) | 0 | 5 (16.7) | 11 (21.2) | 4 (20.0) | 15 (20.8) |
| Probably related | 2 (16.7) | 0 | 7 (29.2) | 1 (16.7) | 8 (26.7) | 10 (19.2) | 3 (15.0) | 13 (18.1) |
| Definitely related | 3 (25.0) | 8 (80.0) | 12 (50.0) | 3 (50.0) | 15 (50.0) | 26 (50.0) | 10 (50.0) | 36 (50.0) |
| Related | 0 | 0 | 0 | 0 | 0 | 0 | 1 (5.0) | 1 (1.4) |
| Unrelated/unlikely | 3 (25.0) | 0 | 0 | 2 (33.3) | 2 (6.7) | 5 (9.6) | 2 (10.0) | 7 (9.7) |
| TEAEs severity[b] | | | | | | | | |
| Mild | 11 (91.7) | 10 (100.0) | 22 (91.7) | 6 (100.0) | 28 (93.3) | 49 (94.2) | 16 (80.0) | 65 (90.3) |
| Moderate | 1 (8.3) | 0 | 2 (8.3) | 0 | 2 (6.7) | 3 (5.8) | 4 (20.0) | 7 (9.7) |
| Severe | 0 | 0 | 0 | 0 | 0 | 0 | 0 | 0 |
| STEAEs reported[b] | 0 | 0 | 0 | 0 | 0 | 0 | 0 | 0 |
| Subjects with at least one STEAE[a] | 0 | 0 | 0 | 0 | 0 | 0 | 0 | 0 |
| Subject with at least one study drug-related STEAE[a] | 0 | 0 | 0 | 0 | 0 | 0 | 0 | 0 |
| Subjects with at least one TEAE leading to study discontinuation[a] | 0 | 0 | 0 | 0 | 0 | 0 | 0 | 0 |
| Deaths[a] | 0 | 0 | 0 | 0 | 0 | 0 | 0 | 0 |

AE: adverse event; N: number of subjects; n (%): number and percent of subjects included; SAE: serious adverse event; STEAE: serious treatment-emergent adverse event; TEAE: treatment-emergent adverse event
Notes:
Overall Active, Pooled Placebo and Overall columns include assessment counts not subject level counts. Possibly Related, Probably Related, Related, or Definitely Related categories are counted under Drug-Related.
[a]Percentages are based on the number of subjects in the Safety population in each treatment group.
[b]Percentages are based on the total number of treatment-emergent adverse events reported in each treatment group

TABLE 38

Treatment-Emergent Adverse Events Reported in Two or More Subjects Overall

| System Organ Class Preferred Term | Dexmedetomidine sublingual film | | | | | | Placebo (N = 14) n (%) | Overall (N = 42) n (%) |
|---|---|---|---|---|---|---|---|---|
| | Cohort 1 10 µg (N = 8) n (%) | Cohort 2 20 µg (N = 8) n (%) | Cohort 3 40 µg (N = 8) n (%) | Cohort 4 40 µg (N = 4) n (%) | Cohort 3 and Cohort 4 40 µg (N = 12) n (%) | Overall (N = 28) n (%) | | |
| Subjects with at least one TEAE | 6 (75.0) | 7 (87.5) | 8 (100.0) | 4 (100.0) | 12 (100.0) | 25 (89.3) | 10 (71.4) | 35 (83.3) |
| Nervous system disorders | 5 (62.5) | 7 (87.5) | 7 (87.5) | 2 (50.0) | 9 (75.0) | 21 (75.0) | 8 (57.1) | 29 (69.0) |
| Somnolence | 4 (50.0) | 6 (75.0) | 7 (87.5) | 2 (50.0) | 9 (75.0) | 19 (67.9) | 7 (50.0) | 26 (61.9) |
| Dizziness | 1 (12.5) | 1 (12.5) | 6 (75.0) | 0 | 6 (50.0) | 8 (28.6) | 2 (14.3) | 10 (23.8) |
| Headache | 1 (12.5) | 1 (12.5) | 0 | 0 | 0 | 2 (7.1) | 3 (21.4) | 5 (11.9) |
| Gastrointestinal disorders | 2 (25.0) | 1 (12.5) | 3 (37.5) | 1 (25.0) | 4 (33.3) | 7 (25.0) | 2 (14.3) | 9 (21.4) |
| Nausea | 1 (12.5) | 0 | 2 (25.0) | 0 | 2 (16.7) | 3 (10.7) | 0 | 3 (7.1) |
| Dry Mouth | 0 | 0 | 1 (12.5) | 1 (25.0) | 2 (16.7) | 2 (7.1) | 1 (7.1) | 3 (7.1) |
| Vomiting | 1 (12.5) | 0 | 1 (12.5) | 0 | 1 (8.3) | 2 (7.1) | 1 (7.1) | 3 (7.1) |
| General disorders and administration site conditions | 1 (12.5) | 0 | 2 (25.0) | 1 (25.0) | 3 (25.0) | 4 (14.3) | 1 (7.1) | 5 (11.9) |
| Fatigue | 1 (12.5) | 0 | 2 (25.0) | 0 | 2 (16.7) | 3 (10.7) | 0 | 3 (7.1) |

Conclusion: Overall, PK, PD and safety results presented in this study support further development of dexmedetomidine sublingual film for the acute treatment of agitation associated with dementia, schizophrenia, and bipolar disorders as a minimally invasive rapid-delivery dosage form of dexmedetomidine.

Example 8: Clinical Study of the Efficacy (Sedation and Anti-Agitation), Pharmacokinetics and Safety of Dexmedetomidine Infused Intravenously in Subjects Suffering from Schizophrenia A Key objective of the study was to determine the optimal intravenous (IV) dose of dexmedetomidine hydrochloride in the target population in terms of efficacy and safety to achieve arousable sedation (RASS of −1) which can be reversed by verbal stimulation. When this goal was achieved in each participant, the IV infusion of dexmedetomidine hydrochloride ceased. Another Key Objective of the study was to determine the reduction in the level of agitation, as determined by their PEC score, at the doses to achieve a RASS of −1.

In addition, the following Secondary Objectives were:
1. Determine how rapidly the drug can be administered up to the total dose needed to achieve RASS −1.
2. Determine how long the calming effect persists after discontinuation of study drug administration.
3. Determine whether any adverse effects on blood pressure, heart rate, or respiratory drive occurs before or coincident with the achievement of Primary Objective. Stopping rules for blood pressure and heart rate, indicating a clinically significant event, are:
   drop in systolic BP<90 mm of Hg.
   drop in diastolic BP<60 mm of Hg
   drop below 50 beats per minute Participants were provided written informed consent before any study related procedures were performed. All participants were screened for inclusion and exclusion criteria. The participants were admitted to the site at screening (Day −1), the day before the infusion. Baseline assessments were performed on Day −1, as well as on the day of infusion (Day 1). The participants were on Day 1 prepared for the infusion, infused for up to 3 hours and monitored for resolution of sedation and any decreases in blood pressure or heart rate which met stopping criteria. The participants were not discharged from the research unit until three hours after resolution of any reduction in the level of arousal (e.g., RASS −1) and/or resolution of any decrease in blood pressure or heart rate meeting stopping criteria. The Principal Investigator had discretion to keep the participant overnight at the site the evening of Day 1 for extended monitoring and then discharge home the participant on Day 2 if the Principal Investigator or designee determined that the participant has returned to their baseline state.

The study population included 14 participants, 10 active and 4 placebo. Patients 5, 7, 8 and 9 received placebo. Patients 1, 2, 3, 4, 11, 12, 14, 16, 17, 18 were infused with intravenous dexmedetomidine hydrochloride, starting at a rate of 0.2 mcg/kg/hr, and rising by 0.1 mcg/kg/hr every 30 minutes until stopping criteria were reached up or to a maximum duration of 3 hours (Table 39). Participants randomized to placebo received a matching intravenous infusion of placebo solution.

TABLE 39

Study Treatments

| Treatment | Formulation | Frequency |
|---|---|---|
| Dexmedetomidine hydrochloride | PRECEDEX ® | Continuous infusion, increment every 30 minutes |
| Placebo | Normal Saline | Continuous infusion |

Once the participant was drowsy (RASS −1), the infusion was stopped. The maximum total dose administered was 1.6 mcg/kg/hr, when either the desired level of sedation was achieved or the maximum allowable decrease in either systolic or diastolic blood pressure or heart rate occurred.

The participants were continuously monitored during the study by the site personnel, including monitoring blood pressure and heart rate. Intermittent electrocardiograms were taken from the start of the infusion through resolution of the sedation and/or any adverse effects on blood pressure or heart rate.

Whenever the above stopping criteria was met, the site stopped the infusion and the site continued to monitor the participant's vital signs every 15 minutes until the participant has reached their baseline parameters or in the judgment of the principal investigator the participant has reached a stable and acceptable level of blood pressure and heart rate. Return to baseline parameters is defined as BP falling within 15 mm of Hg of baseline reading prior to drug administration or HR falling within 10 beats per minute of baseline reading prior to drug administration.

In the event the investigator deemed the fall in blood pressure or heart rate to be clinically significant, suitable remedial drugs could be administered in addition to termination of the dexmedetomidine hydrochloride infusion, based on investigator's judgement.

Adverse events (AEs), including serious adverse events (SAEs), were assessed, recorded, and reported in accordance with FDA guidance. Should any SAE occur, the study would be stopped until a cause for the SAE was determined.

Efficacy Assessment:
(1) Richmond Agitation Sedation Scale (RASS): The desired endpoint was how rapidly drowsiness (RASS −1) could be achieved without causing changes in heart rate or blood pressure greater than that specified by the protocol. The study also monitored how long the participant remained at that level of sedation; sedation was considered resolved when the participant was awake and spontaneously responding.
(2) PANSS: Change from baseline for mildly agitated patients
(3) Clinical Global Impression of Improvement (CGI-I) (National Institute of Mental Health 1976) ranging from 1 (very much improved) to 7 (very much worse) compared with baseline. Each participant was rated, based on the severity of agitation, at 15 and 30 minutes for every dose infusion, at the endpoint, and at the time the participant returned to baseline (in terms of level of arousal). CGI-I focused on the severity of agitation rather than the severity of the illness.
(4) After the infusion was stopped, the participants were judged for the suitability for discharge by the principal investigator or designee as witnessed by a return to their baseline level of alertness and awareness with no impairment in balance, gait, and reaction time as determined by the principal investigator or designee.

Results
(A) Efficacy Study
RASS (Richmond Agitation-Sedation Scale)

Figure 16:
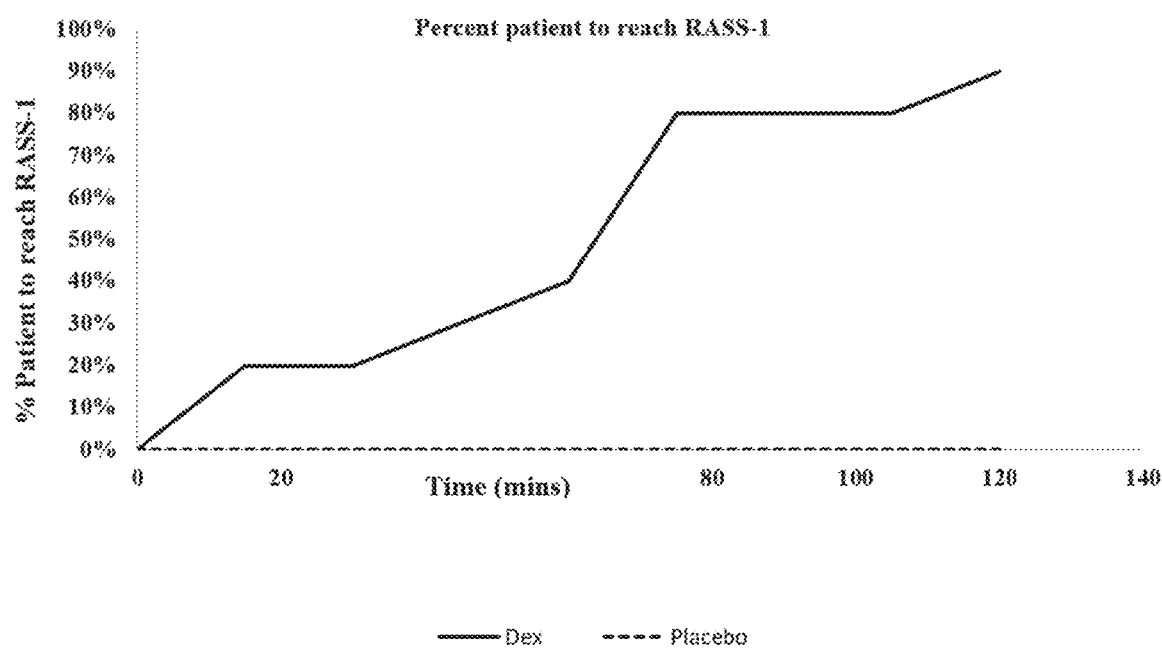
FIG. 16: depicts the percentage of schizophrenic patients achieving RASS −1 in the treatment arm (IV dexmedetomidine hydrochloride treated group) versus placebo group.

9 out of 10 patients in the treatment arm (subjects 1-3, 11, 12, 14, and 16-18) achieved a RASS score of at least −1, while no patients in the placebo arm (subjects 5, and 7-9) experienced meaningful sedation (see FIG. 16 and Table 40).

TABLE 40

Depicts the RASS score of Schizophrenia patients receiving infusion of dexmedetomidine hydrochloride and normal saline

| Infusion (minutes) | RASS values after infusion start Patient No. | | | | | | | | | | | | | |
|---|---|---|---|---|---|---|---|---|---|---|---|---|---|---|
| | 1 | 2 | 3 | 4 | 5 | 7 | 8 | 9 | 11 | 12 | 14 | 16 | 17 | 18 |
| | T | T | T | T | P | P | P | P | T | T | T | T | T | T |
| 0 | 1 | 3 | 1 | 1 | 1 | 1 | 1 | 1 | 1 | 1 | 1 | 1 | 1 | 0 |
| 15 | −2 | | | | | | | | | | | | | −1 |
| 30 | | 0 | 0 | 0 | 1 | 1 | 1 | 1 | 0 | 0 | 0 | 0 | 0 | |
| 45 | | | 0 | | | | | | | | | | −1 | |
| 60 | | 0 | −1 | 0 | 1 | 1 | 0 | 1 | 0 | 0 | 0 | 0 | | |
| 75 | | −1 | | | | | | | −1 | | −1 | −1 | | |
| 90 | | | | 0 | 1 | 0 | 0 | 1 | | 0 | | | | |
| 105 | | | | | | | | | | | | | | |
| 120 | | | | 0 | 0 | 0 | 0 | 1 | | −1 | | | | |
| 135 | | | | 0 | | | | | | | | | | |
| 150 | | | | | 0 | 0 | 0 | 1 | | | | | | |
| 165 | | | | | | | | | | | | | | |
| 180 | | | | | 0 | 0 | 0 | 1 | | | | | | |

T—treatment arm; P—placebo arm

PEC (PANSS Excitement Component)

Figure 17:
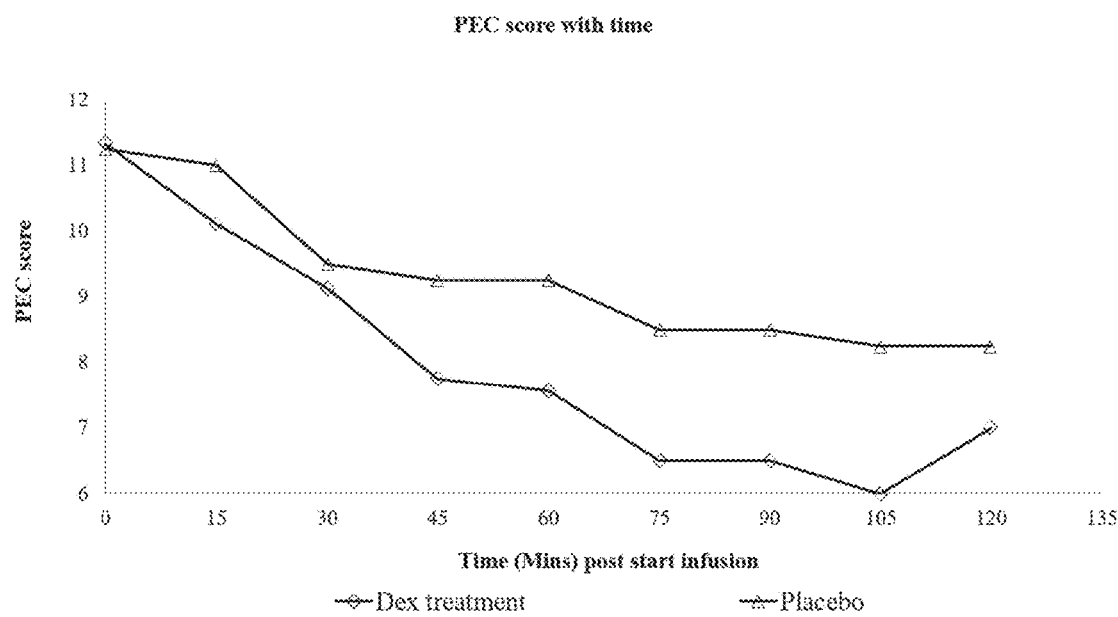
FIG. 17: depicts the mean drop in PEC score with time in schizophrenic patients in the treatment arm (IV dexmedetomidine hydrochloride treated group) versus placebo group.

9 out of 10 patients in the treatment arm (subjects 1-4, 11, 12, 14, 16 and 17) had agitation reduced to a minimum (as measured by a PEC score of 7 or below) (see Table 41 and FIG. 17).

TABLE 41

Depicts the PEC data of schizophrenia patients receiving infusion of dexmedetomidine and normal saline

| Time (Mins) | PEC values after infusion start Patient No. | | | | | | | | | | | | | |
|---|---|---|---|---|---|---|---|---|---|---|---|---|---|---|
| | 1 | 2 | 3 | 4 | 5 | 7 | 8 | 9 | 11 | 12 | 14 | 16 | 17 | 18 |
| | T | T | T | T | P | P | P | P | T | T | T | T | T | T |
| 0 | 9 | 16 | 12 | 9 | 11 | 12 | 9 | 13 | 13 | 13 | 10 | 10 | 10 | |
| 15 | 5 | 13 | 12 | 9 | 10 | 12 | 9 | 13 | 13 | 13 | 9 | 9 | 8 | |
| 30 | | 12 | 10 | 8 | 9 | 9 | 8 | 12 | 11 | 13 | 6 | 6 | 7 | |
| 45 | | 11 | 7 | 8 | 9 | 8 | 8 | 12 | 9 | 10 | 6 | 6 | 5 | |
| 60 | | 9 | 6 | 7 | 8 | 8 | 8 | 13 | 9 | 10 | 5 | 7 | | |
| 75 | 7 | | | 7 | 8 | 8 | 7 | 11 | 7 | 8 | 5 | 5 | | |
| 90 | | | | 7 | 7 | 9 | 7 | 11 | | 6 | | | | |
| 105 | | | | 7 | 8 | 8 | 7 | 10 | | 5 | | | | |
| 120 | | | | 7 | 8 | 8 | 7 | 10 | | | | | | |
| 135 | | | | 7 | 8 | 7 | 7 | 9 | | | | | | |
| 150 | | | | | 8 | 7 | 7 | 9 | | | | | | |
| 165 | | | | | 8 | 8 | 7 | 9 | | | | | | |
| 180 | | | | | 8 | 8 | 7 | 10 | | | | | | |

T—treatment arm; P—placebo arm (B) Pharmacokinetic Study: (PK Study)

Figure 18:
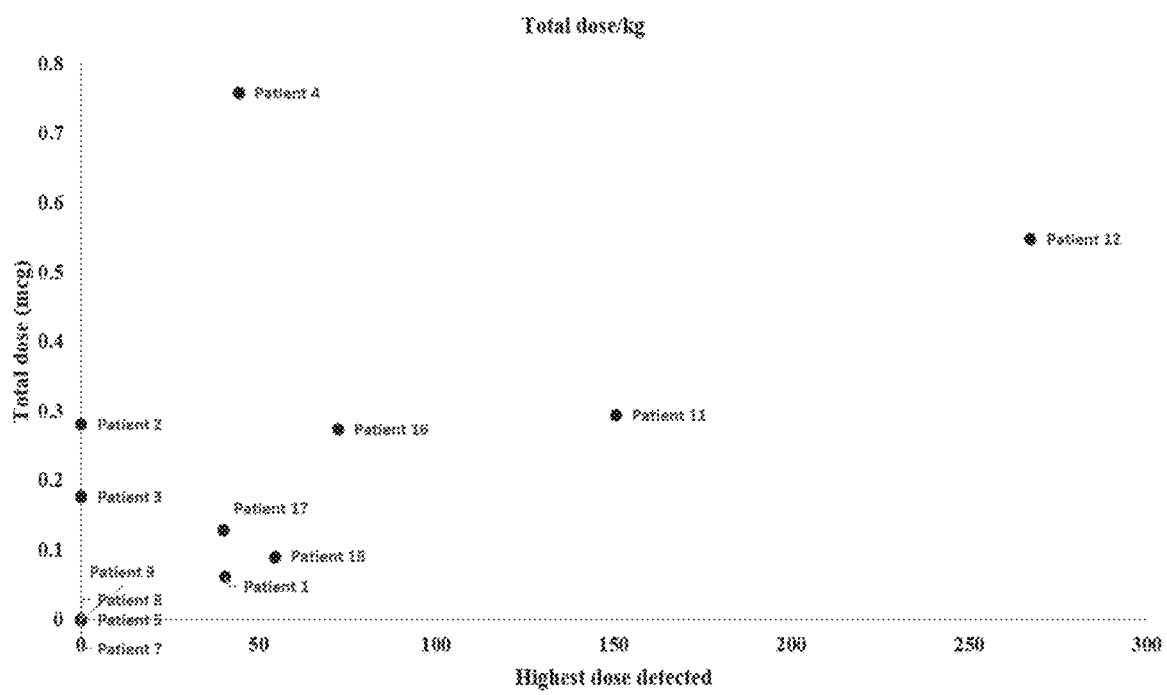
FIG. 18: depicts the maximum doses of IV dexmedetomidine hydrochloride received by schizophrenic patients for the treatment of agitation.
Figure 19:
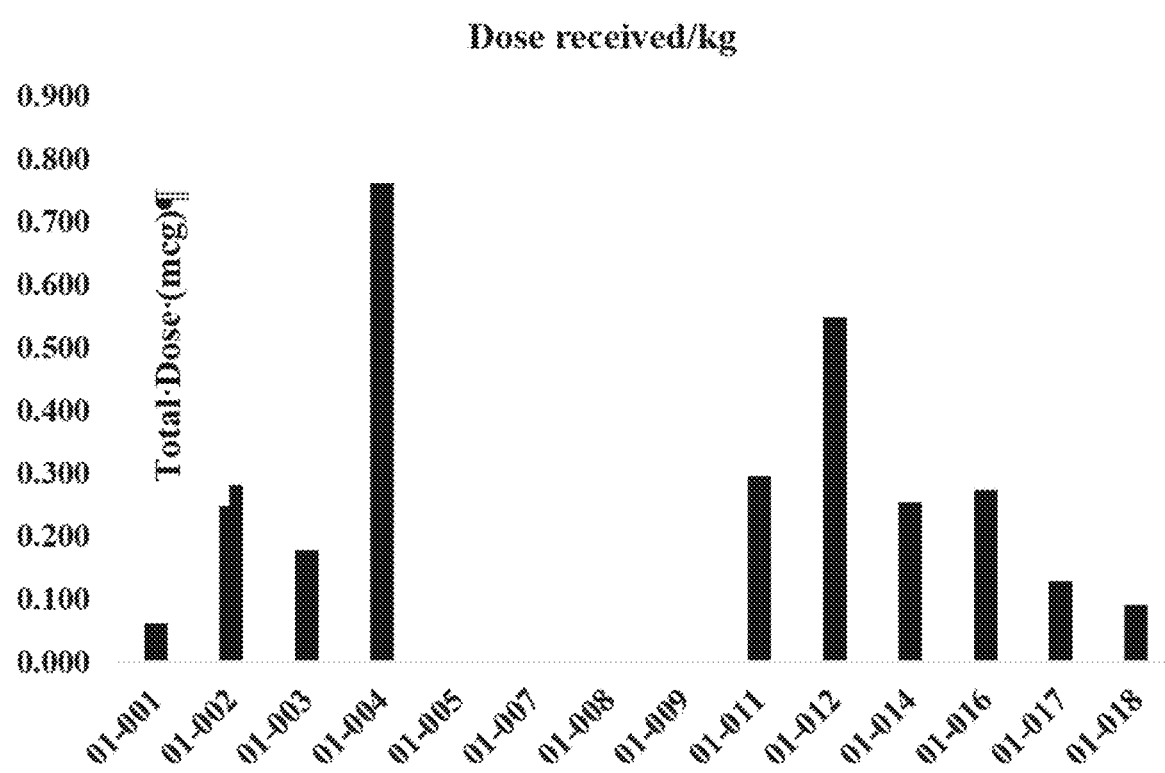
FIG. 19: depicts the total intravenous dose of dexmedetomidine hydrochloride received by schizophrenic patients for the treatment of agitation.
Figure 20:
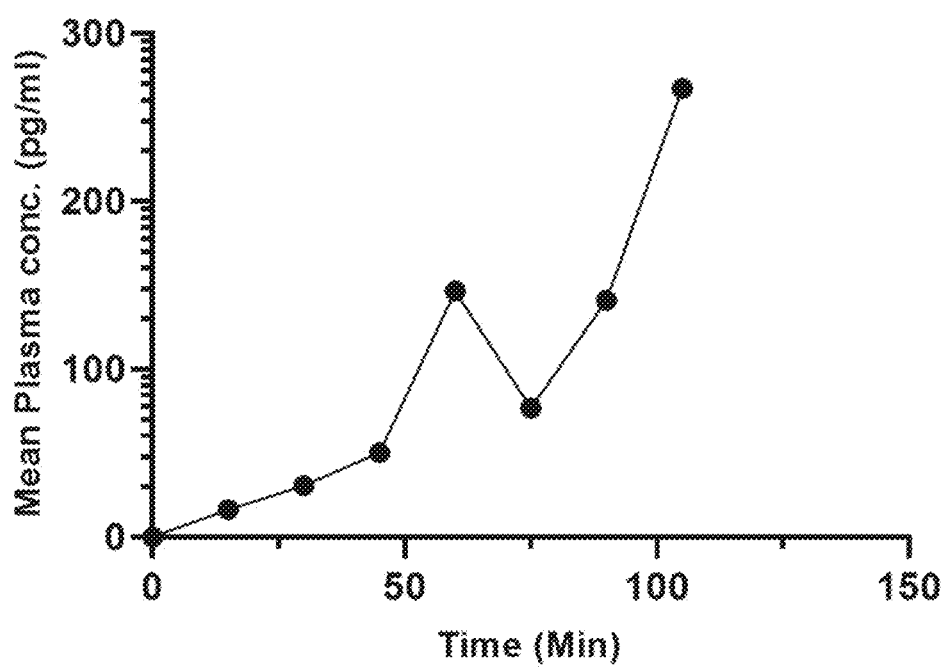
FIG. 20: depicts the mean plasma concentration (pg/ml) vs actual time in schizophrenic patients treated with dexmedetomidine hydrochloride.

The level of dexmedetomidine in the plasma of patients was also measured over the time of infusion. The results are tabulated in Table 42. The maximum dexmedetomidine concentrations in schizophrenic patients (Cm) ranged from about 22.45 µg/mL to about 406.3 µg/mL. Time to reach $C_{max}$ ranged from about 15 minutes to about 105 minutes. Mean infusion rate is 0.36 mcg/kg/hr with the maximum rate ranging from about 0.2 mcg/kg/hr to about 0.6 mcg/kg/hr (see FIGS. 18 to 20).

TABLE 42 depicts the plasma concentrations (pg/mL) of schizophrenia patients at different timepoints during the infusion of dexmedetomidine hydrochloride and normal saline

| Time (Mins) | Plasma level concentration (picogram/ml) | | | | | | | | | | | | | |
|---|---|---|---|---|---|---|---|---|---|---|---|---|---|---|
| | 1 | 2 | 3 | 4 | 5 | 7 | 8 | 9 | 11 | 12 | 14 | 16 | 17 | 18 |
| | T | T | T | T | P | P | P | P | T | T | T | T | T | T |
| 0 | BLQ | BLQ | | BLQ | BLQ | BLQ | BLQ | BLQ | BLQ | BLQ | BLQ | BLQ | BLQ | BLQ |
| 15 | 22.45 | | | BLQ | BLQ | BLQ | BLQ | BLQ | 41.01 | BLQ | BLQ | 2.56 | 15.87 | 48.36 |
| 30 | 14.72 | BLQ | BLQ | BLQ | BLQ | BLQ | BLQ | BLQ | 62.91 | 44.87 | 52.66 | 15.59 | BLQ | 54.53 |
| 45 | | | BLQ | BLQ | BLQ | BLQ | BLQ | BLQ | 124.07 | 50.51 | 46.53 | 41.17 | 39.93 | |
| 60 | | | | BLQ | BLQ | BLQ | BLQ | BLQ | 150.47 | 108.6 | 406.3 | 67.88 | | |
| 75 | | | | BLQ | BLQ | BLQ | BLQ | BLQ | | 158.54 | | 72.26 | | |
| 90 | | | | 44.3 | BLQ | BLQ | BLQ | BLQ | | 237.83 | | | | |
| 105 | | | | | BLQ | BLQ | BLQ | BLQ | | 267.3 | | | | |
| 120 | | | | | BLQ | BLQ | BLQ | BLQ | | | | | | |
| 135 | | | | | BLQ | BLQ | BLQ | BLQ | | | | | | |
| 150 | | | | | BLQ | BLQ | BLQ | BLQ | | | | | | |
| 165 | | | | | BLQ | BLQ | BLQ | BLQ | | | | | | |
| 180 | | | | | BLQ | BLQ | BLQ | BLQ | | | | | | |
| Total duration of infusion (Mins) | 19 | 75 | 60 | 149 | 180 | 180 | 180 | 179 | 68 | 103 | 64 | 66 | 36 | 30 |

*BLQ—below limit of quantification

T—Treatment; P—Placebo

Discussion: The administration of dexmedetomidine hydrochloride by the IV route produced a >=50% reduction in PEC score in a total of 7 of 10 subjects, with one subject (Patient 1) responding at a $C_{max}$ of 22 µg/mL. 5 of 10 subjects (Patients 1, 2, 3, 16 and 17) exhibited a 40% reduction in PEC score at a $C_{max}$ of =<72 µg/mL. The good response rates at these plasma exposure levels indicated that sublingual dexmedetomidine hydrochloride administration at similar or higher $C_{max}$ exposure levels achieved good anti-agitation effects. As demonstrated in Example 7 above, sublingual dexmedetomidine hydrochloride administered to healthy volunteers produced good plasma exposure levels at doses of 10, 20 and 40 micrograms, indicating that such doses were suitable for obtaining good anti-agitation effects (e.g. as measured by a reduction in PEC score) in agitated subjects, including subjects with schizophrenia, without also producing clinically meaningful detrimental effects on blood pressure and/or heart rate.

Example 9: A Phase III Multicenter, Randomized, Double-Blind, Placebo-Controlled Study to Determine Efficacy and Safety of Dexmedetomidine Sublingual Film in Agitation Associated with Schizophrenia Objectives:
Primary Objective To determine if a single dose of Dexmedetomidine sublingual film effectively reduced symptoms of acute agitation associated with schizophrenia, schizoaffective disorder or schizophreniform disorder assessed using the Positive and Negative Syndrome Scale-Excited Component (PEC) change from baseline as compared to placebo.
Key Secondary Objective.

To determine the earliest time where an effect on agitation was apparent as measured by the change from baseline in PEC total score in contrast with placebo.
Other exploratory objectives:
1. Overall clinical improvement after drug administration as measured by the Clinical Global Impression-Improvement Scale (CGI-1) score.
2. Agitation-Calmness Evaluation Scale (ACES) scores at 2, 4 and 8 hrs after dose administration.
3. Change from baseline in total PEC score over time measured from 10 min through 24 hrs after dosing.
4. PEC Responders and CGI-I Responders at 2 hours following dose of Dexmedetomidine sublingual film, compared with placebo:
   a. PEC responders were defined as those who achieve at least a 40% reduction in PEC total score from baseline at or before 2 hours post-dose.
   b. CGI-I responders were defined as subjects with a score of 1 or 2 on the CGI-I scale (the CGI-I non-responders were defined as subjects with scores from 3 to 7 at 2 hours).
5. Time to rescue medication during the entire 24 hrs Post-treatment Evaluation Period for subjects who received Dexmedetomidine sublingual film compared to placebo.
6. Proportion of subjects per treatment group who received rescue medication by 4 hrs and within 24 hrs after dosing.
7. Duration of calming effect as described by the change from baseline in PEC total score, and ACES score at 2, 4 and 8 hrs after dosing.
8. Describe effect on overall psychotic symptoms and subscales (PANSS total, positive, negative, and general psychopathology subscales)
9. Determine the safety profile of Dexmedetomidine sublingual film as measured by vital signs and treatment-emergent adverse event reports and vital signs.
10. Describe the overall tolerability in terms of adverse event reports and local site (oral/sublingual) tolerability of oral film.
11. Descriptive pharmacokinetics of Dexmedetomidine sublingual film in the patient population.
12. Determine patient acceptability, taste and likability of study medication using likert scales to capture subject's acceptability, opinion on taste and questions regarding likability.

Study Design: This was a randomized, double-blind, placebo-controlled Phase III study assessing efficacy, safety and tolerability of dexmedetomidine sublingual film dosing in adult (18-75 years old) males and females with acute agitation associated with schizophrenia, schizoaffective disorder, or schizophreniform disorder. This in-clinic study randomized subjects 1:1:1 to receive Dexmedetomidine sublingual film (180 µg or 120 µg dose of DEX) or matching placebo film. The randomization was be stratified by age; age <65 and age ≥65.

Eligible subjects (acutely agitated subjects with schizophrenia, schizoaffective, or schizophreniform disorder) might be identified in outpatient clinics, mental health, psychiatric or medical emergency services including medical/psychiatric observation units, or as newly admitted to a hospital setting for acute agitation or already hospitalized for chronic underlying conditions. Subjects were domiciled in a clinical research setting or hospitalized to remain under medical supervision while undergoing screening procedures to assess eligibility.

Upon confirmation of eligibility, subjects were randomized to receive either 180 µg or 120 µg Dexmedetomidine sublingual film or matching placebo. At the time of dosing, patients were instructed on how to take the investigational product sublingually, and that they should retain the investigational product in the sublingual cavity until dissolved. The patient was self-administered under the supervision of a trained staff member. If the patient was unable to self-administer, the event was recorded, and the subject's participation was concluded. In the event of persistent or recurrent agitation, investigators might chose to repeat dose at 90 µg or 60 µg (half of 180 µg or 120 µg film) after the 2-hour time point as measured by a PEC change from baseline <40% but in the absence of safety concerns. Patients could only be re-dosed if they were hemodynamically stable, not hypotensive (must be greater than 90/60 diastolic/systolic) and not bradycardic (must be greater than 60 bpm). Patients also could not be re-dosed if they were orthostatic (a drop of 20 points in either SBP or DBP) or if they were experiencing an AE that when assessed by the PI precludes redosing. The maximum number of repeat doses per subject was 2, during the 12 hours post first dose. Doses might not be administered sooner than 2 hours after a previous dose. If the PEC change from baseline was ≥40% repeat dosing was not allowed.

Participants were also be evaluated for local irritation around the area where the film was placed. Efficacy and safety assessments were conducted periodically before and after dosing. All efforts should be made to have the patient perform all assessments as per protocol. Vital Signs, pulse oximetry, and ECG with rhythm strip were measured as per schedule of assessments (Table 43), prior to any PK assessments. Participants were allowed water as desired 15 minutes after completion of dosing. Safety and tolerability assessments were conducted at various timepoints.

Any abnormal vital sign measurement, clinical laboratory test, physical examination finding, or ECG parameter deemed clinically significant by the investigator repeated, including test results obtained on the final study day or upon early termination. For any test abnormality deemed clinically significant, repeat analysis was performed during the follow-up period and until the value returns to baseline (or within normal limits) or the investigator deems the abnormality to be stable and no longer of clinical concern.

Approximately 4 mL of venous blood (to obtain a minimum of 1.2 mL plasma) was taken into K2-EDTA tubes at set time intervals for the determination of plasma concentrations of study drug (or Placebo). The PK plasma samples were collected within 10 min of the scheduled sampling time on Day 1.

Number of subjects (planned): Approximately 375 subjects were enrolled at up to 30 study sites in the United States.

Diagnosis and Main Criteria for Eligibility:

Inclusion Criteria:
(1) Male and female patients between the ages of 18 to 75 years, inclusive.
(2) Patients who had met DSM-5 criteria for schizophrenia, schizoaffective, or schizophreniform disorder.
(3) Patients who were judged to be clinically agitated at Baseline with a total score of ≥14 on the 5 items (poor impulse control, tension, hostility, uncooperativeness, and excitement) comprising the PANSS Excited Component (PEC).
(4) Patients who had a score of ≥4 on at least 1 of the 5 items on the PEC or PEC score at baseline
(5) Patients who read, understood and provided written informed consent.
(6) Patients who were in good general health prior to study participation as determined by a detailed medical history, physical examination, 12-lead ECG with rhythm strip, blood chemistry profile, hematology, urinalysis and in the opinion of the Principal Investigator.
(7) Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that might be used by the participant and/or his/her partner included abstinence, birth control pills or patches, diaphragm with spermicide, intrauterine device (IUD), condom with foam or spermicide, vaginal spermicidal suppository, surgical sterilization and progestin implant or injection. Prohibited methods included: the rhythm method, withdrawal, condoms alone, or diaphragm alone.

Exclusion Criteria:
(1) Patients with agitation caused by acute intoxication, including positive identification of alcohol by breathalyzer or drugs of abuse (with the exception of THC) during urine screening.
(2) Patients treated within 4 hours prior to study drug administration with benzodiazepines, other hypnotics or oral or short-acting intramuscular antipsychotics.
(3) Treatment with alpha-1 noradrenergic blockers (terazosin, doxazosin, tamsulosin, alfuzosin, or prazocin) or other prohibited medications.
(4) Patients with significant risk of suicide or homicide per the investigator's assessment, or any patient with an answer of "yes" to item 4 or 5 on the CSSRS.
(5) Female patients who had a positive pregnancy test at screening or are breastfeeding.
(6) Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
(7) History of syncope or other syncopal attacks, current evidence of hypovolemia, orthostatic hypotension (average of 1, 3 and 5 min measurements), a screening and baseline heart rate of <55 beats per minutes or systolic blood pressure <110 mmHg or diastolic BP<70 mmHg.
(8) Patients with laboratory or ECG abnormalities considered clinically significant by the investigator or qualified designee [Advanced heart block (second-degree or above atrioventricular block without pacemaker), diagnosis of Sick sinus syndrome] that would had clinical implications for the patient's participation in the study.
(9) Patients with serious or unstable medical illnesses. These include current hepatic (moderate severe hepatic impairment), renal, gastroenterologic, respiratory, cardiovascular (including ischemic heart disease, congestive heart failure), endocrinologic, or hematologic disease.
(10) Patients who had received an investigational drug within 30 days prior to the current agitation episode.
(11) Patients who were considered by the investigator, for any reason, to be an unsuitable candidate for receiving dexmedetomidine; e.g. patients with a history of allergic reactions to dexmedetomidine.

Study Treatments

Test Product, Dose, and Mode of Administration:

Dexmedetomidine hydrochloride was a thin film formulation of DEX for sublingual (SL) administration. Dosing delivers 180 µg or 120 µg of DEX sublingually. The product is a small, solid-dose film formulation, approximately 193.6 mm2 in area and 0.7 mm thick, designed to completely dissolve in the SL space within 1-3 minutes.

Reference Therapy, Dosage and Mode of Administration:

Matching placebo films was taken sublingually as described above.

Duration of Treatment: 1 day

Study Procedures

Subjects provided written informed consent before any study-related procedures were initiated, including the cessation of prohibited concomitant therapy.

The schedule of events performed during the study were provided in Table 43

TABLE 43

Schedule of Events

| | | Treatment Evaluation Day 1 | | | | | | | | | | |
|---|---|---|---|---|---|---|---|---|---|---|---|---|
| | Screening | Pre-Dose[1] | | | | | | | | | | |
| | | | Time point | | | | | | | | | |
| | | | Post Dose Time[1] | | | | | | | | | |
| Activity | Pre-treatment | −1 hr to time 0 | 10 min | 20 min | 30 min | 45 min | 1 hr | 1.5 hr | 2 hr | 4 hr | 6 hr | 8 hr |
| Informed Consent | X | | | | | | | | | | | |
| Medical History | X | | | | | | | | | | | |
| Demographics | X | | | | | | | | | | | |
| Weight | X | | | | | | | | | | | |
| Height | X | | | | | | | | | | | |
| BMI | X | | | | | | | | | | | |
| Alcohol breathalyzer | X | | | | | | | | | | | |
| MINI | X | | | | | | | | | | | |
| Physical Exam | | | | | | | | | | | | |
| Safety Labs[2] | X | | | | | | | | | | | |
| ECG with rhythm strip[3] | X | X | | | | | | | X | | | |
| Pulse oximetry | | X | | | X | | X | | X | X | | X |
| Resting vital signs[4] | X | X | | | X | | X | | X | X | X | X |
| Orthostatic vital signs[4] | X | X | | | | | | | X | X | | X |
| Admit to Unit | X | | | | | | | | | | | |
| Inclusion/Exclusion criteria | X | X | | | | | | | | | | |
| Randomization | | X | | | | | | | | | | |
| Study drug administration[10] | | X | | | | | | | | | | |
| PANSS[9] | | X | | | | | | | | | X | |
| PCRS[5] | X | X | | | | | | | X | | | |
| PEC[5] | X | X | X | X | X | X | X | X | X | X | X | X |
| ACES[5] | | X | | | | | | | X | X | | X |
| CGI-Severity[6] | X | X | | | | | | | | | | |
| CGI-Improvement[6] | | | | | | X | | X | X | X | | |
| C-SSRS | X | | | | | | | | | | | |
| Buccal (SL) assessment for local irritation[7] | | | | | | X | | | X | X | | |
| Likert scales | | | | X | | | | | | | | |
| Likability Question | | | | X | | | | | | | | |
| PK Sampling[8] | | | | | | | X | | | X | | X |
| Concomitant Medications | X | X | | | | | X | | | | | |
| Adverse Events | X | X | | | | | X | | | | | |

| | | Treatment Evaluation Day 2, 3, and 7 | | |
|---|---|---|---|---|
| | Screening | Day 2 Follow-Up (+1) | Day 3 Discharge | Day 7 (+2) |
| | | | Time point | |
| Activity | Pre-treatment | 24 hr (−9/+12 hr) | | End of Study |
| Informed Consent | X | | | |
| Medical History | X | | | |
| Demographics | X | | | |
| Weight | X | X | | |
| Height | X | | | |
| BMI | X | | | |
| Alcohol breathalyzer | X | | | |
| MINI | X | | | |
| Physical Exam | X | X | | |
| Safety Labs[2] | X | | X | X |
| ECG with rhythm strip[3] | X | X | | |
| Pulse oximetry | | | | |

TABLE 43-continued

Schedule of Events

| | | | | | |
|---|---|---|---|---|---|
| Resting vital signs[4] | X | X | X | | X |
| Orthostatic vital signs[4] | X | X | X | | X |
| Admit to Unit | X | | | | |
| Inclusion/Exclusion criteria | X | | | | |
| Randomization | | | | | |
| Study drug administration[10] | | | | | |
| PANSS[9] | | X | | | |
| PCRS[5] | X | X | | | |
| PEC[5] | X | X | | | |
| ACES[5] | | | | | |
| CGI-Severity[6] | X | | | | |
| CGI-Improvement[6] | | | | | |
| C-SSRS | X | X | | | |
| Buccal (SL) assessment for local irritation[7] | | X | | | |
| Likert scales | | | | | |
| Likability Question | | | | | |
| PK Sampling[8] | | | | | |
| Concomitant Medications | X | X | X | | X |
| Adverse Events | X | X | X | | X |

Notes to the Schedule of Events:
[1]Pre-dose assessments had a window of 60 minutes prior to dose with the exception of PEC and ACES which were performed within 15 minutes of dosing (15 to 0 min). All post-dose assessments had a window of −5/+15 minutes through the 1.5 hour assessments, −5/+25 minutes for the 2 hour assessments (with the exception of the PEC which will have a +/−5 minute window) and ±30 minutes for the 4, 6 and 8 hour assessments.
[2]Safety Labs were chemistry, hematology, urinalysis, UDS (local lab, only conducted at screening), alcohol breathalyzer (only conducted at screening), and urine pregnancy (only conducted at screening). Screening/enrollment labs: local labs drawn within 7 days prior to screening might suffice with the exception of urine drug screen. If results not available on the same day, a 'desktop' or non-CLIA test might be performed; to confirm, results from a CLIA-certified laboratory was recorded once available. Central Labs was performed on screening, Day 3 and Day 7.
[3]ECG for pre-dose did not need to be repeated if screening ECG was conducted on the day of dosing. ECGs collected following treatment were to be performed prior to PK assessments.
[4]Resting (recumbent) vital signs (SBP, DBP and HR) were taken upon having the subject recumbent for 5 min at Screening, Pre-dose and at 30 min, 1, 2, 4, 6, 8 and 24 hours post dose, as well as Day 3 and Day 7. Triplicate measurements performed in case of Systolic BP <90 mmHg, Diastolic BP <60 mmHg or Pulse <60 bpm. Orthostatic measurements (SBP, DBP, HR, respiratory rate and temperature) was taken upon having the subject stand, with measurements taken after 1, 3 and 5 minutes at Screening, Pre-dose, 2, 4, 8 and 24 hours post first dose, as well as Day 3 and Day 7.
[5]PEC was performed at Screening, Pre-dose (within 15 min prior to dose) and at 10, 20, 30, 45 min; 1, 1.5, 2, 4, 6, 8 and 24 hours post dose. The PCRS must be performed prior to PEC rating, when required. At 6 and 24 hrs the PEC rating must be performed before the PANSS interview. ACES was performed at Pre-dose (within 15 min of dose), 2, 4 and 8 hrs post dose.
[6]CGI-Severity was performed at Screening and pre-dose. CGI-Improvement was performed at 30 minutes, 1, 2 and 4 hours post dose.
[7]Buccal exam at 30 min, 2, 4 and 24hr post-dose for local irritation.
[8]PK blood samples were collected 1, 4, and 8 hr (while awake) after dose. A sample might not be collected if the Physician indicated in source documents that the patient was in a mental state that was not conducive to PK sample collection. Non-compliance or refusal of all or any PK draw was not exclusionary nor result in ET. Vital signs were to be done prior to PK sample draws, when performed at the same timepoints.
[9]Pre-dose PANSS might be administered at any time prior to dosing on the day of dosing and 6 and 24 hrs (−1/+2 hr) post-dose. At 6 and 24 hrs PANSS interview must be performed after PEC rating. The 6 hour and 24 hr PANSS was conducted with reference to the predose PANSS.
[10]The investigator might choose to re-dose the patient with half of a film after the 2 hour post-dose assessments are performed if the PEC change from baseline is <40%. Patients could be re-dosed up to 2 times during 12 hours post first dose. All assessments listed in this Schedule of Events at the 2 hour post first dose timepoint repeated at 2 hours post every re-dose.

Criteria for Evaluation:

Efficacy assessment: Assessment of Drug Effects on acute agitation was done by the Positive and Negative Syndrome Scale-Excited Component (PEC). The PEC comprises 5 items associated with agitation: poor impulse control, tension, hostility, uncooperativeness, and excitement; each scored 1 (minimum) to 7 (maximum). The PEC, the sum of these 5 subscales, thus ranges from 5 to 35.

Overall agitation and sedation were evaluated with the Agitation-Calmness Evaluation Scale (ACES), where 1 indicates marked agitation; 2—moderate agitation; 3—mild agitation; 4—normal behavior; 5—mild calmness; 6—moderate calmness; 7—marked calmness; 8—deep sleep; and 9—unarousable.

The overall clinical improvement in agitation in response to treatment was also be measured by the Clinical Global Impressions-Improvement (CGI-I). CGI-I scores range from 1 to 7: 0=not assessed (missing), 1=very much improved, 2=much improved, 3=minimally improved, 4=no change, 5=minimally worse, 6=much worse, 7=very much worse.

Safety and tolerability assessments: AEs, clinical laboratory tests, ECG with rhythm strip, pulse oximetry, and vital signs were monitored for tolerability assessment. All observed and volunteered AEs were recorded. The relationship of AEs to the study drug were graded as not related, unlikely/remotely related, possibly related, probably related or definitely related by the investigators. Vital signs including systolic blood pressure (SBP), diastolic blood pressure (DBP), and heart rate were monitored. The application site of the SL preparation (buccal mucosa) was inspected for any signs of local irritation Additional Assessments:

Demographics, Medical and Psychiatric History, psychotic symptoms (PANSS), Smoking history, Prior and Concomitant Medication, Physical Examination, Pregnancy Pharmacokinetics: A sparse PK sampling of plasma concentrations at specified timepoints were reported. A population PK/PD analysis of plasma concentration vs. clinical response was reported using a separate SAP and report. A graphical assessment of PK vs. vital signs and other potential PD parameters were included.

Statistical Analysis:
Efficacy Analyses

The primary efficacy endpoint of the study was the absolute change from baseline in the PEC total score at 120 min. The intent to treat population was analyzed and consist of all patients who took any study medication and who had both baseline and at least 1 efficacy assessment after dosing. The key secondary endpoints were: change from baseline in the PEC score at 90 min, 60 min, 45 min, 30 min, 20 min and 10 min. Other exploratory endpoints were same as listed under exploratory objectives.

Safety Analyses: Safety data analysis was conducted on all subjects receiving at least 1 dose of study drug. The number and percentage of subjects experiencing 1 or more AEs were summarized by treatment, relationship to study drug, and severity. AEs were coded using the Medical Dictionary for Regulatory Activities (Med DRA) terminology. Listings of subjects who experienced withdrawal due to an AE, serious AEs and/or death will be presented. Laboratory parameters were summarized by treatment using descriptive statistics and data listings of clinically significant abnormalities. Vital signs and ECG data were summarized by changes from baseline values using descriptive statistics.

Pharmacokinetic Analyses

Plasma concentrations and concentration-time data for dexmedetomidine were used to calculate PK parameters; these data and results were reported separately. All pharmacokinetic parameters were calculated using non-compartmental analysis using WinNonlin Version 5.2 or higher. Actual sampling times were used in all pharmacokinetic analyses. Per protocol times were used to calculate mean plasma concentrations for graphical displays. Other PK analyses were performed as appropriate.

Results Summary:
Demographics

The demographics and baseline characteristics is shown below in Table 44.

3. Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 2 dose cohorts (120 µg (N=129) and 180 µg (N=126)) and 126 placebo patients. Active patients in each of the 2 dose cohorts were compared to placebo patients. The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

Figure 21A:
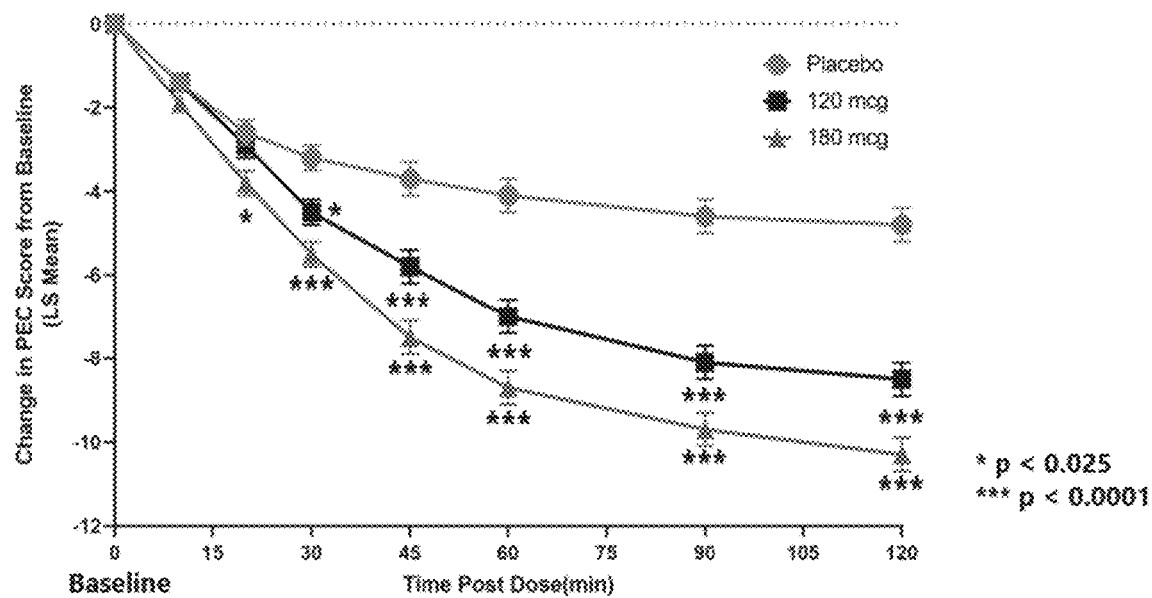
FIG. 21A: depicts change in PEC score from baseline in schizophrenia patients until 2 hours post-dose of 120 µg and 180 µg dexmedetomidine sublingual thin film (as exemplified in example 2) compared to placebo.
Figure 21B:
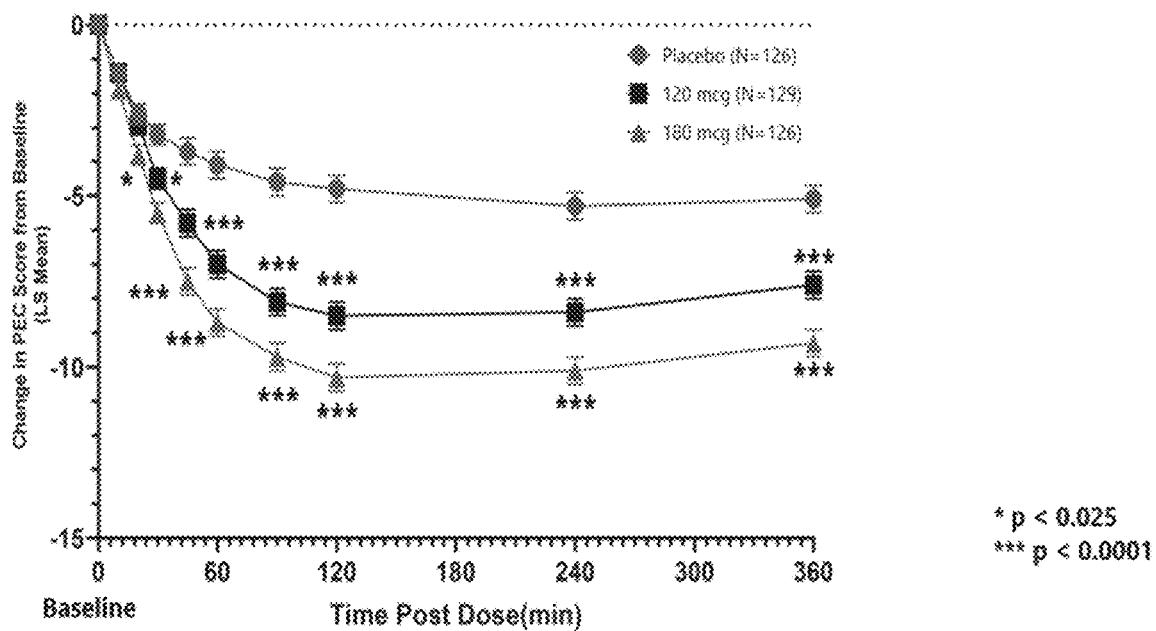
FIG. 21B: depicts change in PEC score from baseline in schizophrenia patients until 6 hours post-dose of 120 µg and 180 µg dexmedetomidine sublingual film (as exemplified in example 2) compared to placebo.

The efficacy of dexmedetomidine hydrochloride sublingual film as measured by PEC reduction is dose-responsive and robust. The decrease from baseline in PEC score in the 180 µg dose group showed significant response with a −10.3 mean change from baseline (CFB) total PEC score at 2 hours post dosing compared to placebo (Table 45 and FIGS. 21A and 21B). Mean changes from baseline were −8.5 points for the 120 µg treatment groups, compared to placebo (−4.8 Mean change). Additionally, as early onset of action is an important attribute for therapy in reducing agitation, the 180 µg group showed a statistically significant separation from placebo as early as 20 minutes post dosing (FIG. 21A and FIG. 21B). Further, the decrease from baseline in PEC score in the 180 µg and 120 µg dose groups showed significant responses at 6 hours post dosing compared to placebo (FIG. 21B).

PEC Responder Analyses: The proportion of treatment responders, defined as those with a 40% decrease from baseline in PEC total score at 2 hours post dose, was greatest in the 180 µg group (87% for 180 µg, 67% for 120 µg) as compared to placebo (34%) (TABLE 45). The durability of calming effects of the 180 µg dose was remarkably prolonged with a sustained statistically significant reduction in PEC evident after 24 hrs.

TABLE 44

Demographics

| | Dexmedetomidine Sublingual film | | Placebo (N = 126) | Overall (N = 381) |
|---|---|---|---|---|
| | 180 ug (N = 126) | 120 ug (N = 129) | | |
| Mean age (years) | 46.0 (11.91) | 45.7 (11.32) | 45.1 (11.13) | 45.6 (11.43) |
| Female N (%) | 44 (34.9) | 52 (40.3) | 44 (34.9) | 140 (36.7) |
| Race (% white/% non-white) | 16.7/83.3 | 25.6/74.4 | 16.7/83.3 | 19.7/80.3 |
| BMI | 32.53 (7.8) | 31.24 (7.6) | 32.56 (7.4) | 32.10 (7.6) |
| Diagnosis Schizophrenia | 85.70% | 87.60% | 80.20% | 84.50% |
| Schizophrenia | 14.30% | 12.40% | 19.80% | 15.50% |
| Baseline PEC means | 17.6 | 17.5 | 17.6 | NA |

TABLE 45

Summary of Change from Baseline at 2 hours in PANSS-PEC Total Score and Percent of Responders at 2 hours in the PEC Score by Treatment Group

| Endpoint (120 min) PEC Total score | N | Placebo | Dexmedetomidine Sublingual film | |
|---|---|---|---|---|
| | | | 120 μg (N = 126) | 180 μg (N = 126) |
| Change from Baseline (LSM) | N = 126 (180 μg) N = 129 (120 μg) | −4.8 | −8.5 *** | −10.3 *** |
| Response ° | 126 | 34% | 67% | 87% |

° Proportion achieving ≥ 40% PEC reduction; * p < 0.025; *** p < 0.0001

Secondary Efficacy Endpoints:

Changes in secondary efficacy measures (i.e., ACES and CGI-I scores) at 2 hours post-dose were consistent with the results for PEC total scores and were indicative of improvement in symptoms of agitation after treatment with dexmedetomidine sublingual film.

Figure 22:
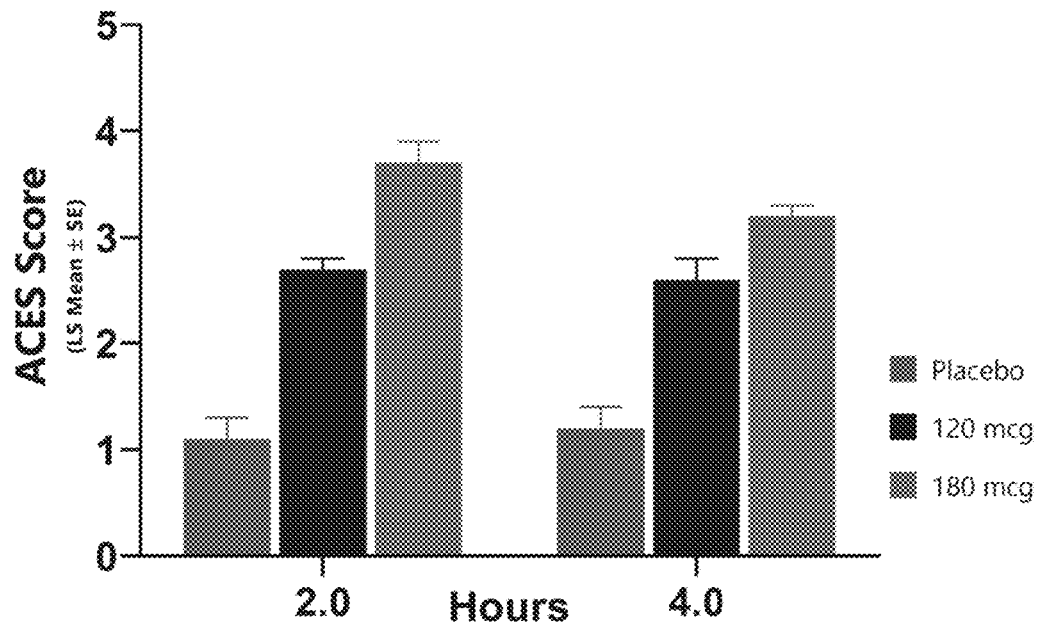
FIG. 22: depicts calming improvement in schizophrenia patients at 2 hours and 4 hours following administration of 120 µg (middle bar) and 180 µg dexmedetomidine (right bar) sublingual film (as exemplified in example 2) compared to placebo (left bar), as measured by Agitation and Calmness Evaluation Scale (ACES).

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in 120 μg and 180 μg (120 μg; p=0.0001) and (180 μg; p<0.0001). At 2 hours after dosing, subjects in the 120 μg and 180 μg treatment groups showed significantly greater improvements relative to placebo in ACES scores (+about 2.8 [P<0.0001] for 120 μg; +about 3.75 [P<0.0001] for 180 μg, compared to placebo of +about 1.0). The improvements at 4 hours post-dose were similar (+about 2.8 [P<0.0001] for 120 μg; +about 3.2 [P<0.0001] for 180 μg, compared to placebo of +about 1.0). (FIG. 22).

Figure 23:
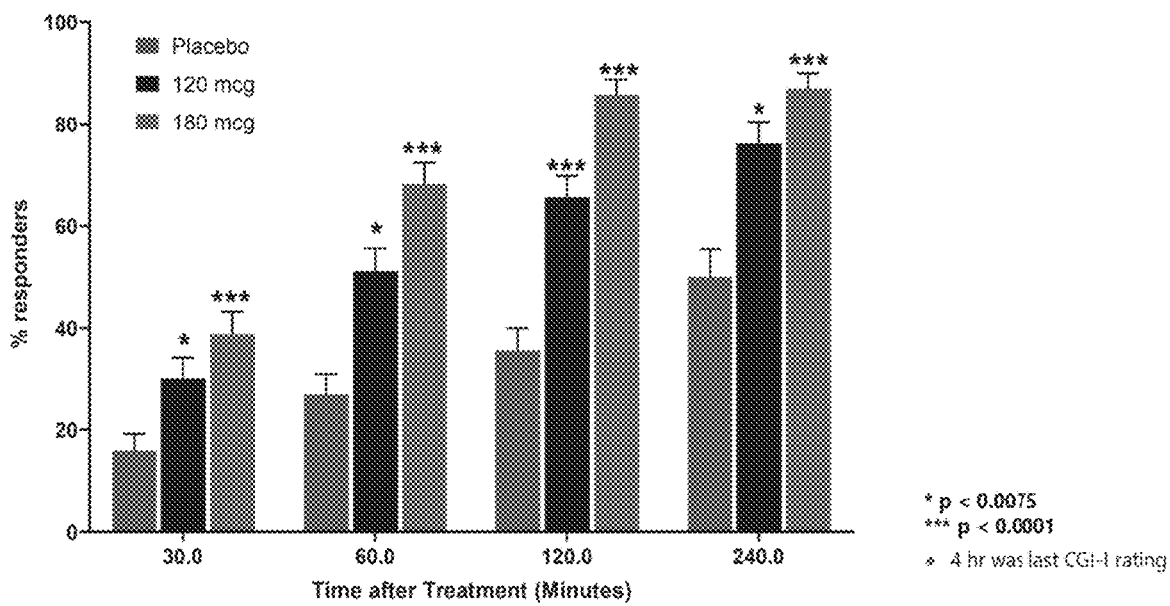
FIG. 23: depicts percent response in schizophrenia patients at 30 minutes, 60 minutes, 120 minutes and 240 minutes following administration of 120 µg (middle bar) and 180 µg dexmedetomidine (right bar) sublingual film (as exemplified in example 2) compared to placebo (left bar), as measured by Clinical Global Impression-Improvement (CGI).

CGI-scores: The percentage of subjects achieving CGI-I scores of 1 or 2 ('very much improved' or 'much improved') at 2 hours post-dose was significantly higher in the 120 μg group (about 65% [p<0.0001]) and in the 180 μg dose group (about 90% [p<0.0001]), compared with placebo (about 35%). Significant improvements were also observed at 30 minutes, 1 hour, and 4 hours after dosing for both treatment groups [in the 180 μg dose group (p<0.0001) and in the 120 μg dose group (p<0.0075)] (FIG. 23).

Conclusion: Dexmedetomidine sublingual film treatment significantly improved the severity of agitation from baseline as measured by PEC, CGI-I, and ACES scales in schizophrenia patients. The primary efficacy endpoint was met in 120 μg, and 180 μg treatment groups as there was significant improvements in PEC total scores from baseline at 2 hours post-dose with mean changes of −8.5 and −10.3 points, respectively, versus −4.8 for placebo. Reduction in agitation was observed as early as 20 minutes compared to placebo. Further, changes in secondary efficacy measures (ie, CGI-I and ACES scores) at 2 hours post-dose were consistent with the results for PEC total scores and were indicative of improvement in symptoms of agitation after treatment with Dexmedetomidine sublingual film.

Example 10: A Phase III Multicenter, Randomized, Double-Blind, Placebo-Controlled Study to Determine the Efficacy and Safety of Dexmedetomidine Hydrochloride Sublingual Film in Subjects with Agitation Associated with Bipolar Disorder (SERENITY II)

Objectives:
Primary Endpoint

The primary efficacy endpoint of the study was the absolute change from baseline in the PEC total score at 2 hours. The intent to treat population was analyzed and consists of all patients who took any study medication and who had both baseline and at least 1 efficacy assessment after dosing. Observations recorded after use of rescue medication were censored.

Key Secondary Endpoint Included:

The key secondary efficacy endpoint was the earliest time where an effect on agitation was apparent as measured by change from baseline PEC total score in contrast with placebo.

Exploratory Endpoints Included:

1. Overall clinical improvement after drug administration as measured by the Clinical Global Impression-Improvement Scale (CGI-I) score.
2. Agitation-Calmness Evaluation Scale (ACES) scores at 2, 4 and 8 hrs. after dose administration.
3. Change from baseline in total PEC score overtime measured from 10 min through 24 hrs. after dosing.
4. PEC Responders and CGI-I Responders at 2 hours following dose of dexmedetomidine hydrochloride, compared with placebo.
    a. PEC responders were defined as those who achieved at least a 40% reduction in PEC total score from baseline at or before 2 hours post-dose.
    b. CGI-I responders were defined as subjects with a score of 1 or 2 on the CGI-I scale (the CGI-I non-responders were defined as subjects with scores from 3 to 7 at 2 hours).
5. Time to rescue medication during the entire 24 hrs. Post-treatment Evaluation Period for subjects receiving dexmedetomidine hydrochloride compared to placebo.
6. Proportion of subjects per treatment group who received rescue medication by 4 hrs. and within 24 hrs. after dosing.
7. Duration of calming effect as described by the change from baseline in PEC total score, and ACES score at 2, 4 and 8 hrs. after dosing.
8. Determined the safety profile of dexmedetomidine hydrochloride as measured by vital signs and treatment-emergent adverse event reports.
9. Described the overall tolerability in terms of adverse event reports and local site (oral/sublingual) tolerability of oral film.
10. Descriptive pharmacokinetics of dexmedetomidine hydrochloride in the patient population.
11. Determined patient acceptability, taste and likability of study medication using Likert scales to capture subject's acceptability, opinion on taste and questions regarding likability.
12. Characterized the patient population utilizing the Young Mania Rating Scale (YMRS).

Study Design:

The study enrolled approximately 381 subjects randomized 1:1:1 to dose regimens of 180 μg, 120 μg dexmedetomidine hydrochloride, or placebo stratified by age <65 and age ≥65. The doses were selected based on the results of the prior Phase Ib clinical trial.

Male and female adults with acute agitation associated with bipolar I or II disorder were enrolled.

Eligible subjects (acutely agitated subjects with bipolar I or II disorder, generally hypomanic, manic or mixed episodes) may be identified in outpatient clinics, mental health, psychiatric or medical emergency services, including medical/psychiatric observation units, or as newly admitted to a hospital setting for acute agitation or already in hospital for chronic underlying conditions. Subjects were domiciled in a clinical research setting or hospitalized to remain under medical supervision while undergoing screening procedures to assessed eligibility.

Upon confirmation of eligibility, subjects were randomized to 180 μg dexmedetomidine hydrochloride sublingual film or 120 μg dexmedetomidine hydrochloride sublingual film or matching placebo. Efficacy and safety assessments were conducted periodically before and after dosing.

Vital signs, pulse oximetry and ECG with rhythm strip were measured as per schedule of assessments, prior to any PK assessments. Participants were allowed water as desired 15 minutes after completion of dosing. Safety and tolerability assessments were conducted at various timepoints. Please refer to the Table 46 for Schedule of events.

Any abnormal vital sign measurement, clinical laboratory test, physical examination finding, or ECG parameter deemed clinically significant by the investigator were repeated, including test results obtained on the final study day or upon early termination. For any test abnormality deemed clinically significant, repeat analysis performed during the follow-up period and until the value returns to baseline (or within normal limits) or the investigator deemed the abnormality to be stable and no longer of clinical concern.

Approximately 4 mL of venous blood (to obtain a minimum of 1.2 mL plasma) was taken into K2-EDTA tubes at set time intervals for the determination of plasma concentrations of study drug (or placebo). The PK plasma samples were collected within 10 min of the scheduled sampling time on Day 1. Blood samples were collected per Table 46 Schedule of Events.

Discussion of Study Design

This was a definitive study to support the safety and efficacy evaluation of dexmedetomidine hydrochloride sublingual film for the acute treatment of agitation in bipolar disorder. The study was designed to characterize the efficacy, safety and tolerability of dexmedetomidine hydrochloride sublingual film in agitation associated with bipolar disorder. A dose of dexmedetomidine hydrochloride was chosen based on results that showed rapid efficacy in a large proportion of subjects was well tolerated and had an acceptable safety profile. In the event of persistent or recurrent agitation, investigators might chose to administer an additional reduced dose of 90 μg or 60 μg (half of 180 μg or 120 μg film) after the 2-hour time point as measured by a PEC change from baseline ≤40%, but in the absence of safety concerns. Patients could only be re-dosed if they were hemodynamically stable, not hypotensive (must be greater than 90/60 systolic/diastolic) and not bradycardic (must be greater than 60 bpm). Patients also could not be re-dosed if they were orthostatic (a drop of >20 mm Hg systolic, or 10 mm Hg diastolic) or if they were experiencing an Adverse Event (AE) that in the assessment of the PI precludes re-dosing. The maximum number of repeat doses per subject is 2, during the 12 hours post-first dose. Doses might not be administered sooner than 2 hours after a previous dose. If the PEC change from baseline is ≥40%, repeat dosing was not allowed.

Placebo was chosen as a comparator to more accurately assess efficacy as well as safety and tolerability. The randomized, double-blind parallel-group design ensures the sponsor, all subjects, and study staff involved were shielded from treatment assignment and outcomes and therefore minimized any potential bias. The randomization ratio provided an additional element that ensured blinding by decreasing the odds of guessing treatment arms.

Diagnosis and Main Criteria for Eligibility:
Inclusion Criteria
1. Male and female patients between the ages of 18 to 75 years, inclusive.
2. Patients who had met DSM-5 criteria for bipolar I or II disorder, generally hypomanic, manic or mixed episodes.
3. Patients who were judged to be clinically agitated at Screening and Baseline with a total score of ≥14 on the 5 items (poor impulse control, tension, hostility, uncooperativeness, and excitement) comprising the PANSS Excited Component (PEC).
4. Patients who had a score of ≥4 on at least 1 of the 5 items on the PEC at Baseline.
5. Patients who read, understand and provided written informed consent.
6. Patients who were in good general health prior to study participation as determined by a detailed medical history, physical examination, 12-lead ECG with rhythm strip, blood chemistry profile, hematology, urinalysis, and in the opinion of the Principal Investigator.
7. Female participants, if of child-bearing potential and sexually active, and male participants, if sexually active with a partner of child-bearing potential, who agreed to use a medically acceptable and effective birth control method throughout the study and for one week following the end of the study. Medically acceptable methods of contraception that might be used by the participant and/or his/her partner include abstinence, birth control pills or patches, diaphragm with spermicide, intrauterine device (IUD), condom with foam or spermicide, vaginal spermicidal suppository, surgical sterilization, and progestin implant or injection. Prohibited methods include: the rhythm method, withdrawal, condoms alone, or diaphragm alone.

Exclusion Criteria
1. Patients with agitation caused by acute intoxication, including positive identification of alcohol by breathalyzer or drugs of abuse (with the exception of THC) during urine screening.
2. Use of benzodiazepines or other hypnotics or antipsychotic drugs in the 4 hours before study treatment.
3. Treatment with alpha-1 noradrenergic blockers (terazosin, doxazosin, tamsulosin, alfuzosin, or prazosin) or other prohibited medications.
4. Patients judged to be at serious risk of suicide must be excluded.
5. Female patients who had a positive pregnancy test at screening or are breastfeeding.
6. Patients who had hydrocephalus, seizure disorder, or history of significant head trauma, stroke, transient ischemic attack, subarachnoid bleeding, brain tumor, encephalopathy, meningitis, Parkinson's disease or focal neurological findings.
7. History of syncope or other syncopal attacks, current evidence of hypovolemia, orthostatic hypotension (average of 1, 3 and 5 min measurements), a screening and baseline heart rate of <55 beats per minutes or systolic blood pressure <110 mmHg or diastolic BP<70 mmHg.
8. Patients with laboratory or ECG abnormalities considered clinically significant by the investigator or qualified designee [Advanced heart block (second-degree or above atrioventricular block without pacemaker), diagnosis of Sick sinus syndrome] that would had clinical implications for the patient's participation in the study.
9. Patients with serious or unstable medical illnesses. These include current hepatic (moderate-severe hepatic impairment), renal, gastroenterologic, respiratory, cardiovascular (including ischemic heart disease, congestive heart failure), endocrinologic, or hematologic disease.
10. Patients who had received an investigational drug within 30 days prior to the current agitation episode.
11. Patients who were considered by the investigator, for any reason, to be an unsuitable candidate for receiving dexmedetomidine hydrochloride, e.g. patients with a history of allergic reactions to dexmedetomidine hydrochloride.

Study Treatments

Method of Assigning Subjects to Treatment Groups

Upon confirmation of eligibility, subjects were randomized to 180 µg dexmedetomidine hydrochloride film or 120 µg dexmedetomidine hydrochloride film or placebo. Randomization was 1:1:1 (180 µg or 120 µg dexmedetomidine hydrochloride or placebo and stratified by age <65, age ≥65) with 125 patients assigned to each arm by a permuted block design. Study randomization was computer generated.

Test Product, Dose, and Mode of Administration:

Dexmedetomidine hydrochloride was in a film formulation for sublingual (SL) administration. Dosing delivered 180 µg or 120 µg of dexmedetomidine hydrochloride sublingually. The product was a small, solid-dose film formulation, approximately 193.6 mm2 in area and 0.7 mm thick, designed to completely dissolve in the SL space within about 1-3 minutes.

Treatment Administration

At the time of dosing, patients were instructed on how to take dexmedetomidine hydrochloride film sublingually, and that they should retained the dexmedetomidine hydrochloride film in the sublingual cavity until dissolved. The patient self-administered under the supervision of a trained staff member. If the patient was unable to self-administer, the event was recorded, and the subject's participation was concluded.

In the event of persistent or recurrent agitation, investigators might choose to re-dose at 90 µg or 60 µg (dividing the 180 µg or 120 µg film in half) after the 2-hour time point as measured by a PEC change from baseline ≤40% but in the absence of safety concerns.

Study Procedures

Subjects provided written informed consent before any study-related procedures were initiated, including the cessation of concomitant therapy.

The schedule of events performed during the study was provided in Table 46.

TABLE 46

Schedule of Events

| | | Pre-Dose[1] | Treatment Evaluation Day 1 | | | | | | | | | |
|---|---|---|---|---|---|---|---|---|---|---|---|---|
| | Screening | | Time point | | | | | | | | | |
| | | | Post Dose Time! | | | | | | | | | |
| Activity | Pre-treatment | -1 hr to time 0 | 10 min | 20 min | 30 min | 45 min | 1 hr | 1.5 hr | 2 hr | 4 hr | 6 hr | 8 hr |
| Informed Consent | X | | | | | | | | | | | |
| Medical History | X | | | | | | | | | | | |
| Demographics | X | | | | | | | | | | | |
| Weight | X | | | | | | | | | | | |
| Height | X | | | | | | | | | | | |
| BMI | X | | | | | | | | | | | |
| Alcohol Breathalyzer | X | | | | | | | | | | | |
| MINI | X | | | | | | | | | | | |
| Physical Exam | X | | | | | | | | | | | |
| Safety Labs[2] | X | | | | | | | | | | | |
| ECG with rhythm strip[3] | X | X | | | | | | | X | | | |
| Pulse oximetry | | X | | | X | | X | | X | X | | X |
| Resting vital signs[4] | X | X | | | X | | X | | X | X | X | X |
| Orthostatic vital signs[4] | X | X | | | | | | | X | X | | X |
| Admit to Unit | X | | | | | | | | | | | |
| Inclusion/Exclusion criteria | X | X | | | | | | | | | | |
| Randomization | | X | | | | | | | | | | |
| Study drug administration[9] | | X | | | | | | | | | | |
| YMRS | | X | | | | | | | | | | |
| PCRS[5] | X | X | | | | | | | X | | | |
| PEC[5] | X | X | X | X | X | X | X | X | X | X | X | X |
| ACES[5] | | X | | | | | | | X | X | | X |
| CGI-Severity[6] | X | X | | | | | | | | | | |
| CGI-Improvement[6] | | | | | | X | | X | X | X | | |
| C-SSRS | X | X | | | | | | | | | | |
| Buccal (SL) assessment for local irritation[7] | | | | | | X | | | X | X | | |
| Likert Scales | | | | X | | | | | | | | |
| Likability Questions | | | | X | | | | | | | | |

TABLE 46-continued

Schedule of Events

| | | | Treatment Evaluation Day 1 | | | | | | | | |
|---|---|---|---|---|---|---|---|---|---|---|---|
| | Screening | Pre-Dose[1] | Time point | | | | | | | | |
| | | | Post Dose Time[1] | | | | | | | | |
| Activity | Pre-treatment | -1 hr to time 0 | 10 min | 20 min | 30 min | 45 min | 1 hr | 1.5 hr | 2 hr | 4 hr | 6 hr | 8 hr |
| Pharmacokinetic Sampling[8] | | | | | | | X | | X | | X |
| Concomitant Meds | X | X | | | | | X | | | | |
| Adverse Events | X | X | | | | | X | | | | |

| | | Treatment Evaluation Day 2, 3, and 7- Post Dose Time[1] | | |
|---|---|---|---|---|
| | Screening | Day 2 Follow-Up (+1) | Day 3 Discharge | Day 7 (+2) |
| | | Time point | | |
| Activity | Pre-treatment | 24 hr (−9/+12 hr) | | End of Study |
| Informed Consent | X | | | |
| Medical History | X | | | |
| Demographics | X | | | |
| Weight | X | X | | |
| Height | X | | | |
| BMI | X | | | |
| Alcohol Breathalyzer | X | | | |
| MINI | X | | | |
| Physical Exam | X | X | | |
| Safety Labs[2] | X | | X | X |
| ECG with rhythm strip[3] | X | X | | |
| Pulse oximetry | | | | |
| Resting vital signs[4] | X | X | X | X |
| Orthostatic vital signs[4] | X | X | X | X |
| Admit to Unit | X | | | |
| Inclusion/Exclusion criteria | X | | | |
| Randomization | | | | |
| Study drug administration[9] | | | | |
| YMRS | | X | | |
| PCRS[5] | X | X | | |
| PEC[5] | X | X | | |
| ACES[5] | | | | |
| CGI-Severity[6] | X | | | |
| CGI-Improvement[6] | | | | |
| C-SSRS | X | X | X | |
| Buccal (SL) assessment for local irritation[7] | | X | | |
| Likert Scales | | | | |
| Likability Questions | | | | |
| Pharmacokinetic Sampling[8] | | | | |

TABLE 46-continued

Schedule of Events

| | Screening | Pre-Dose[1] | Treatment Evaluation Day 1 | | | | | | | | | |
|---|---|---|---|---|---|---|---|---|---|---|---|---|
| | | | Time point | | | | | | | | | |
| | | | Post Dose Time! | | | | | | | | | |
| Activity | Pre-treatment | -1 hr to time 0 | 10 min | 20 min | 30 min | 45 min | 1 hr | 1.5 hr | 2 hr | 4 hr | 6 hr | 8 hr |
| Concomitant Meds | X | X | | | X | | | | X | | | |
| Adverse Events | X | X | | | X | | | | X | | | |

Notes to the Schedule of Events:

[1]Pre-dose assessments had a window of 60 minutes prior to dose with the exception of PEC and ACES which were performed within 15 minutes of dosing (15 to 0 min). All post-dose assessments had a window of −5/+15 minutes through the 1.5 hour assessments, −5/+25 minutes for the 2 hour assessments (with the exception of the PEC which had a +/−5 minute window) and ±30 minutes for the 4, 6 and 8 hour assessments and YMRS could be performed at any time.

[2]Safety Labs included chemistry, hematology, urinalysis, UDS (local lab, only conducted at screening), alcohol breathalyzer (only conducted at screening), and urine pregnancy (only conducted at screening). Screening/enrollment labs: local labs drawn within 7 days prior to screening might suffice with the exception of urine drug screen. If results not available on the same day, a 'desktop' or non-CLIA test might be performed; to confirm, results from a CLIA-certified laboratory should be recorded once available. Central Labs should be performed on Screening, Day 3 and Day 7.

[3]ECG for pre-dose does not need to be repeated if screening ECG was conducted on the day of dosing. ECGs collected following treatment were performed prior to PK assessments.

[4]Resting (recumbent) vital signs (SBP, DBP and HR) were taken upon having the subject recumbent for 5 min at Screening, Pre-dose and at 30 min, 1, 2, 4, 6, 8 and 24 hours post dose, as well as Day 3 and Day 7. Triplicate measurements were performed in ease of Systolic BP <90 mmHg, Diastolic BP <60 mmHg or Pulse <60 bpm. Orthostatic measurements (SBP, DBP, HR, respiratory rate) were taken upon having the subject stand, with measurements taken after 1, 3 and 5 minutes and temperature were taken at Screening, Pre-dose, 2, 4, 8 and 24 hours post first dose, as well as Day 3 and Day 7.

[5]PEC was performed at Screening, Pre-dose (within 15 min prior to dose) and at 10, 20, 30, 45 min; 1, 1.5, 2, 4, 6, 8 and 24 hours post dose. The PCRS must be performed prior to PEC rating, when required. ACES was performed at Pre-dose (within 15 min of dose), 2, 4 and 8 hrs post dose.

[6]CGI-Severity was performed at Screening and pre-dose. CGI-Improvement was performed at 30 minutes, 1, 2 and 4 hours post dose.

[7]Buccal examined at 30 min, 2, 4 and 24 hr post-dose for local irritation.

[8]PK blood samples were collected 1, 4, and 8 hr (while awake) after dose. A sample might not be collected if the Physician indicated in source documents that the patient was in a mental state that was not conducive to PK sample collection. Non-compliance or refusal of all or any PK draw was not exclusionary nor result in ET. Vital signs were to be done prior to PK sample draws, when performed at the same timepoints.

[9]The investigator might chose to re-dose the patient after the 2 hour post-dose assessments are performed if the PEC change from baseline is ≤40%. Patients could re-dosed after completing the 2 hour post first dose assessments. Repeat dosing administers half of a film. Patients could redosed twice in the 12 hour period post first dose. All assessments listed in this Schedule of Events at the 2 hour post first dose timepoint should be repeated at 2 hours post every re-dose. Assessments at 4, 6, or 8 hour post first dose that occur within 1 hour of a post re-dose assessment were not required to be performed.

Study Assessments

Efficacy

The effect of study drug was evaluated using several validated instruments as described below.

PANSS—Excitatory Component (PEC)

Agitation-Calmness Evaluation Scale (ACES)

CGI-S and CGI-I

Clinical Global Impression of Severity (CGI-S) was rated based upon the severity of agitation at screening and pre-dose (immediately prior to start of dosing).

Severity of illness was assessed based on following scale:
 0=Not assessed
 1=Not at all ill
 2=Borderline mentally ill
 3=Mildly ill
 4=Moderately ill
 5=Markedly ill
 6=Severely ill
 7=Among the most extremely ill subjects Drug response on agitation was evaluated by the Clinical Global Impressions-Improvement (CGI-I). It was performed at 30 minutes, 1, 2 and 4 hrs post dose. The CGI-I scores range from 1 to 7:
 0=not assessed (missing),
 1=very much improved,
 2=much improved,
 3=minimally improved,
 4=no change,
 5=minimally worse,
 6=much worse,
 7=very much worse Both CGI-I and CGI-S were focused on the severity of agitation rather than the severity of the overall illness of bipolar disorder.

Young Mania Rating Scale (YMRS)

The YMRS was an 11-item scale evaluating mania symptoms based on the patient's subjective report of their clinical condition. It was used to characterize the patient population enrolled in the study.

Placebo-Control Reminder Script (PCRS)

The Placebo-Control Reminder Script (PCRS)© Hassman and Cohen, 2019, Version 5.0 educates clinical trial participants of key causes of the placebo and nocebo effects, namely the tempering of participant study expectations, reminding subjects what a placebo is and how that relates to their reporting of symptoms and potential side effects, and explaining how interactions with research site staff differ from their experience with previous providers. To do this, the PCRS informs subjects that they were to be honest about their symptoms, site staff had no expectations of symptom improvement or worsening and was not disappointed if they feel better, worse or the same, and asked participants to explain in their own words its content to ensure comprehension. The PEC Rater was read the PCRS study source before administering the PEC to each subject at each visit (time point) listed on the study specific PCRS, typically taking about 2 minutes to read.

Likert Scales

After dosing with the study drug, subjects assessed their preference of the study medication by answering the statements "I like the taste of the medication" and "The medication is acceptable" using a five-level Likert scale as below:

Strongly disagree
Disagree
Neither agree nor disagree
Agree
Strongly agree

Drug Likability

Subjects responded to open ended questions regarding their experience. Additional comments about aftertaste, smell, dissolve time, etc. were asked as Yes/No questions with Yes responses prompting an explanation field.

Safety

Safety was assessed during the study by the monitoring and recording of AEs, clinical laboratory test results (hematology, biochemistry, and urinalysis), vital sign measurements (systolic and diastolic blood pressures, heart rate measured as pulse, respiratory rate, and temperature), ECG, and physical examination findings. Should a known safety issue be identified (e.g. a high incidence of severe hypotension or bradycardia in the active 180 μg dose arm or the 120 μg arm), the DSMB notified the sponsor. Should this occur, sponsor notified FDA, and sponsor might chose to continue dosing the patients at a lower dose.

Pharmacokinetics

Blood samples (4 ml) were collected per Table 46—Schedule of Events. For each subject, up to 3 blood samples (12 mL of blood) were collected during the study for PK analysis. In addition, approximately 30 mL of blood was collected at screening, approximately 15 mL of blood was collected at Day 3 Discharge, and approximately 15 mL of blood was collected at Day 7(+2) for clinical laboratory testing. The total volume of blood collected during the study was expected to be approximately 72 mL. For each subject, up to 3 blood samples (12 mL of blood) were collected during the study for PK analysis. In addition, approximately 30 mL of blood was collected at screening, approximately 15 mL of blood was collected at Day 3 Discharge, and approximately 15 mL of blood was collected at Day 7(+2) for clinical laboratory testing. The total volume of blood collected during the study was expected to be approximately 72 mL.

Statistical Analyses

Pharmacokinetic Analyses

Plasma concentrations and concentration-time data for dexmedetomidine were used to calculate PK parameters; these data and results were reported separately. Details regarding the analyses of PK data were described in a separate PK SAP. The separate SAP for the PK analyses was prepared and finalized prior to database lock.

Safety Analyses

All safety analyses were performed using the Safety Population. All subjects who received at least one dose of study drug were included in the population for safety analysis. Adverse events (AEs) were characterized by type, severity, seriousness, and relationship to treatment. Adverse events were coded by preferred term and system organ class using MedDRA version 20.0.

Efficacy Analyses

The primary efficacy endpoint of the study was the absolute change from baseline in the PEC total score at 120 min. The intent to treat population was analyzed and consist of all patients who took any study medication and who had both baseline and at least 1 efficacy assessment after dosing.

Results Summary:

Demographics

The demographics and baseline characteristics is shown below in Table 47.

TABLE 47

Demographics

| | Dexmedetomidine sublingual film | | | |
|---|---|---|---|---|
| | 180 μg (N = 126) | 120 μg (N = 129) | Placebo (N = 126) | Overall (N = 381) |
| Mean age (years) | 46.0 (11.91) | 45.7 (11.32) | 45.1 (11.13) | 45.6 (11.43) |
| Female N (%) | 44 (34.9) | 52 (40.3) | 44 (34.9) | 140 (36.7) |
| Race (% white/% non-white) | 38.9/61.1 | 44.4/55.6 | 39.7/60.3 | 41.0/59 |
| BMI | 32.53 (7.8) | 31.24 (7.6) | 32.56 (7.4) | 32.10 (7.6) |
| Diagnosis: Depressed | 22% | 16% | 21% | 20% |
| Diagnosis: Hypomania | 4% | 11% | 8% | 8% |
| Diagnosis: Mania | 47% | 46% | 50% | 47% |
| Diagnosis: Mixed Episodes | 24% | 21% | 17% | 21% |
| Diagnosis: Unspecified | 3% | 6% | 4% | 4% |
| Baseline PEC means | 18 | 18 | 17.9 | NA |

3. Efficacy

Dexmedetomidine sublingual film significantly improved the severity of agitation from baseline as measured by PEC, ACES scales and CGI-I scores. Key efficacy findings at 2 hours post-dose are presented below.

(a) Primary Efficacy Endpoint (PEC reduction): a reduction in the PEC score (PANSS or the Positive and Negative Syndrome Scale, Excitatory Component) for agitation was observed with rapid calming without excessive sedation at the clinical regulatory endpoint and at earlier time-points. The primary efficacy endpoint was the mean change from baseline in PEC total score at 2 hours (120 minutes) compared to placebo. There were 2 dose cohorts (120 μg (N=129) and 180 μg (N=126)) and 126 placebo patients. Active patients in each of the 2 dose cohorts were compared to placebo patients. The change from baseline in PEC at 2 hours for patients treated with dexmedetomidine sublingual film was compared with placebo using a mixed model repeated measures (MMRM) analysis, with baseline PEC, treatment group, time, the interaction between treatment groups and time, and the interaction between baseline PEC and time as covariates.

Figure 24A:
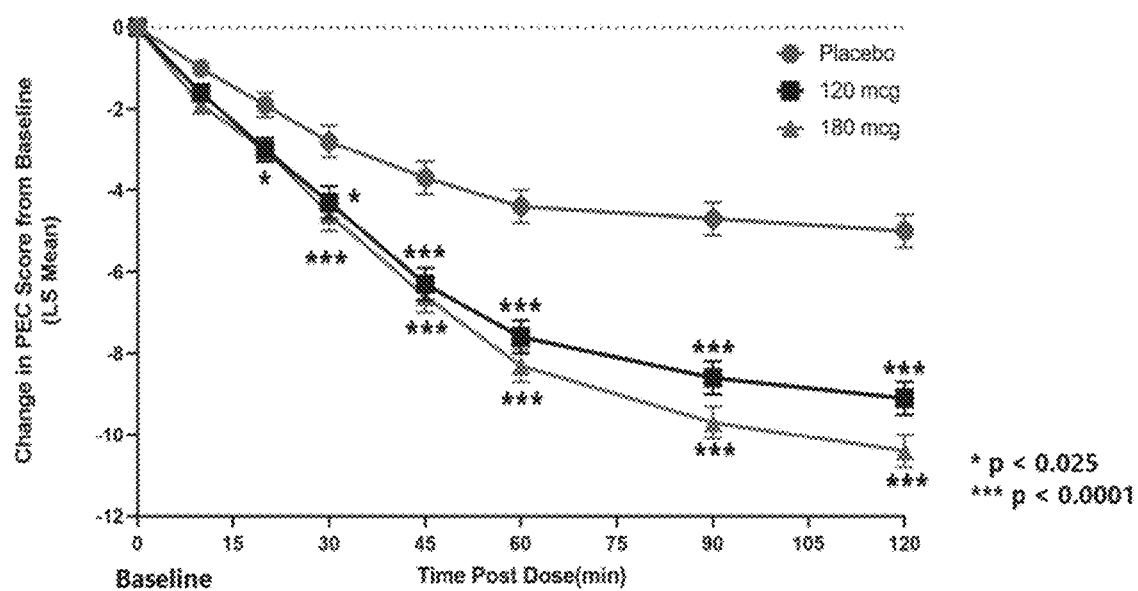
FIG. 24A: depicts change in PEC score from baseline in bipolar patients until 2 hours post-dose of 120 µg and 180 µg dexmedetomidine sublingual film (as exemplified in example 2) compared to placebo.
Figure 24B:
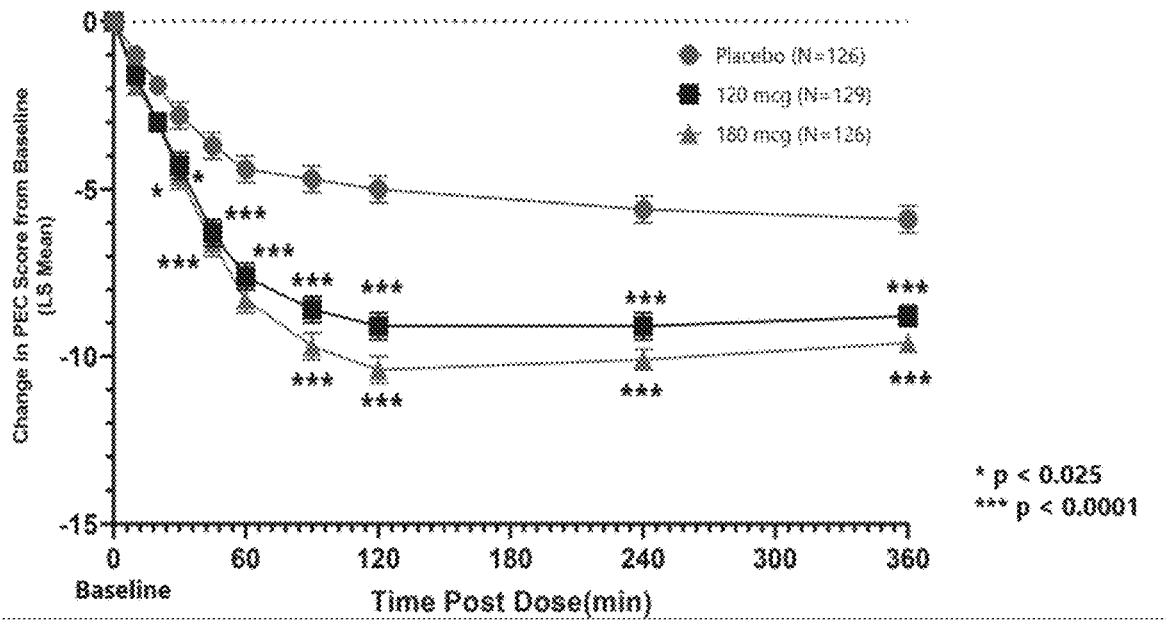
FIG. 24B: depicts change in PEC score from baseline in bipolar patients until 6 hours post-dose of 120 µg and 180 µg dexmedetomidine sublingual film (as exemplified in example 2) compared to placebo.

The efficacy of dexmedetomidine hydrochloride sublingual film as measured by PEC reduction is dose-responsive and robust. The decrease from baseline in PEC score in the 180 μg dose group showed significant response with a −10.4 mean change from baseline (CFB) total PEC score at 2 hours post dosing compared to placebo (Table 48 and FIG. 24A and FIG. 24.B). Mean changes from baseline were −9.1 points for the 120 μg treatment groups, compared to placebo (−5 Mean change). Additionally, as early onset of action is an important attribute for therapy in reducing agitation, the 180 μg group showed a statistically significant separation from placebo as early as 20 minutes post dosing (FIG. 24A and FIG. 24.B). Further, the decrease from baseline in PEC score in the 180 μg and 120 μg dose groups showed significant responses at 6 hours post dosing compared to placebo (FIG. 24B).

TABLE 48

Summary of Change from Baseline at 2 hours in PANSS-PEC Total Score and Percent of Responders at 2 hours in the PEC Score by Treatment Group

| Endpoint (120 min) | N | Placebo | Dexmedetomidine Sublingual film | |
|---|---|---|---|---|
| | | | 120 μg | 180 μg |
| PEC Total score Change from Baseline (LSM) | 126 (180 μg) 129 (120 μg) | −5.0 | −9.1 *** | −10.4 *** |
| Response ° | 126 | 37% | 69% | 85% |

° Proportion achieving ≥ 40% PEC reduction; * p < 0.025; *** p < 0.0001

PEC Responder Analyses: The proportion of treatment responders, defined as those with a 40% decrease from baseline in PEC total score at 2 hours post dose, was greatest in the 180 μg group (85% for 180 μg, 69% for 120 μg)) as compared to placebo (37%) (TABLE 48). The durability of calming effects of the 180 μg dose was remarkably prolonged with a sustained statistically significant reduction in PEC evident after 24 hrs.

Secondary Efficacy Endpoints:

Changes in secondary efficacy measures (i.e., ACES and CGI-I scores) at 2 hours post-dose were consistent with the results for PEC total scores and were indicative of improvement in symptoms of agitation after treatment with dexmedetomidine sublingual film.

Figure 25:
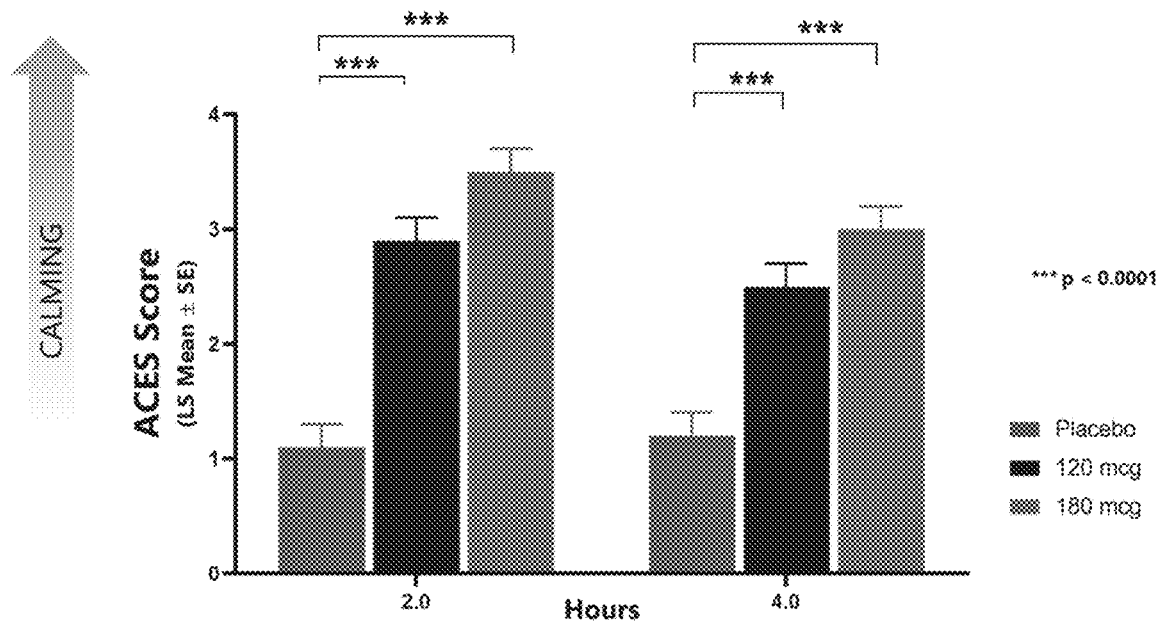
FIG. 25 depicts calming improvement in bipolar patients at 2 hours and 4 hours following administration of 120 µg (middle bar) and 180 µg dexmedetomidine (right bar) sublingual film (as exemplified in example 2) compared to placebo (left bar), as measured by Agitation and Calmness Evaluation Scale (ACES).

ACES scores: A secondary objective for this study was to evaluate the duration of calming effect of dexmedetomidine sublingual thin film drug utilizing the Agitation-Calmness Evaluation Scale (ACES) collected at pre-dose, 2 hr, and 4 hr after first dose. The ACES assessment was consistent with the analysis of the primary endpoint, and met statistically significance for calming as measured by ACES at two hours compared to placebo in 120 μg and 180 μg (120 μg: p<0.0001) and (180 μg; p<0.0001). At 2 hours after dosing, subjects in the 120 μg and 180 μg treatment groups showed significantly greater improvements relative to placebo in ACES scores (+about 3.0 [p<0.0001] for 120 μg; +about 3.7 [p<0.0001] for 180 μg, compared to placebo of +about 1.0. The improvements at 4 hours post-dose were similar (+about 2.8 [p<0.0001] for 120 μg; +about 3.2 [p<0.0001] for 180 μg, compared to placebo of +about 1.0). (FIG. 25).

Figure 26:
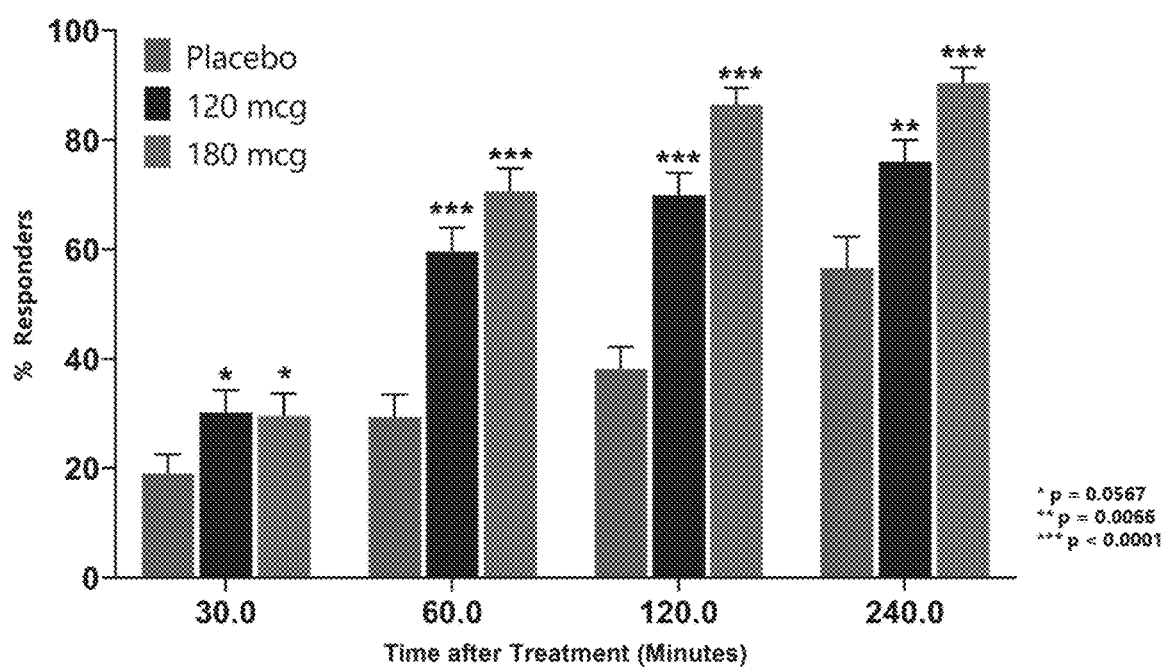
FIG. 26 depicts percent response in bipolar patients at 30 minutes, 60 minutes, 120 minutes and 240 minutes following administration of 120 µg (middle bar) and 180 µg dexmedetomidine (right bar) sublingual film (as exemplified in example 2) compared to placebo (left bar), as measured by Clinical Global Impression-Improvement (CGI).

CGI scores: The percentage of subjects achieving CGI-I scores of 1 or 2 ('very much improved' or 'much improved') at 2 hours post-dose was significantly higher in the 120 μg group (about 70/6 [p<0.0001]) and in the 180 μg dose group (about 90°/% [p<0.0001]), compared with placebo (about 38%). Significant improvements were also observed at 30 minutes, 1 hour, and 4 hours after dosing for both treatment groups (FIG. 26).

Safety and Tolerability:

Dexmedetomidine sublingual film (formulations of Example 2) was well tolerated in schizophrenia and bipolar I disorder patients and had a favourable safety profile in the treatment of subjects with agitation. An overview of subjects who experienced at least 1 treatment emergent adverse event (TEAE) by treatment group for the safety population is given in Tables 49.

TABLE 49

Summary of adverse events in Phase III trial (schizophrenia and bipolar I disorder patient

| Event | | Dexmedetomidine sublingual film | | Placebo (N = 252) |
|---|---|---|---|---|
| | | 180 μg N = (N = 252) | 120 μg (N = 255) | |
| Somnolence | Mild | 40 (15.9) | 43 (16.9) | 15 (6.0) |
| | Moderate | 16 (6.3) | 11 (4.3) | 1 (0.4) |
| Dizziness | Mild | 13 (5.2) | 7 (2.7) | 2 (0.8) |
| | Moderate | 2 (0.8) | 3 (1.2) | 0 |
| Hypotension | Mild | 10 (4.0) | 10 (3.9) | 0 |
| | Moderate | 3 (1.2) | 4 (1.6) | 0 |
| Orthostatic hypotension | Mild | 9 (3.6) | 7 (2.7) | 1 (0.4) |
| | Moderate | 4 (1.6) | 0 | 0 |
| Hypoaesthesia oral | | 12 (4.8) | 7 (2.7) | 1 (0.4) |
| Dry mouth | | 11 (4.4) | 19 (7.5) | 3 (1.2) |
| Nausea | | 7 (2.8) | 6 (2.4) | 4 (1.6) |
| Headache | | 6 (2.4) | 12 (4.7) | 12 (4.8) |
| Paraesthesia oral | | 6 (2.4) | 7 (2.7) | 1 (0.4) |

Conclusion: Dexmedetomidine sublingual film treatment significantly improved the severity of agitation from baseline as measured by PEC, CGI-I, and ACES scales in schizophrenia patients. The primary efficacy endpoint was met in 120 μg, and 180 μg treatment groups as there was significant improvements in PEC total scores from baseline at 2 hours post-dose with mean changes of −9.1 and −10.4 points, respectively, versus −5.0 for placebo. Reduction in agitation was observed as early as 20 minutes compared to placebo. Further, changes in secondary efficacy measures (ie, CGI-I and ACES scores) at 2 hours post-dose were consistent with the results for PEC total scores and were indicative of improvement in symptoms of agitation after treatment with Dexmedetomidine sublingual film Example 11

TABLE 50

Composition for a tablet formulation used for oromucosal delivery (with muco-adhesive properties)

| Ingredient(s) | Amount | % w/v |
|---|---|---|
| Dexmedetomidine hydrochloride | 180 μg (equivalent to dexmedetomidine) | 0.36% |
| Lactose Monohydrate | 44.27 mg | 88.54% |
| Hypromellose (or) Hydroxy propyl cellulose (or) Polyethylene oxide (or) Xanthan gum (or) Sodium alginate | 2.5 mg | 5.0% |
| Croscarmellose Sodium (or) sodium starch glycollate | 2.5 mg | 5.0% |
| Sucralose | 0.05 mg | 0.1% |
| Magnesium Stearate | 0.5 mg | 1.0% |
| Tablet weight | 50.0 mg | 100% |

Manufacturing Process:
1. Dexmedetomidine, binder (hypromellose (or) hydroxy propyl cellulose (or) polyethylene oxide (or) xanthan gum (or) sodium alginate) and sucralose are dissolved or dispersed in water to prepare a solution or dispersion.
2. Remaining ingredients except magnesium stearate are blended in a suitable mixer and sifted with the help of an appropriate sieve.
3. The blend obtained in step 2 is granulated using a suitable granulator.
4. Granules are dried in a suitable fluid bed dryer or any other suitable dryer and size appropriately in quadro-co-mill or multimill.
5. Granules are loaded into a suitable blender such as V-blender and lubricate with magnesium stearate.
6. The lubricated blend obtained in step 5 is compressed into tablets of specific dimensions using appropriate tooling.

TABLE 51

Composition for a tablet formulation used for buccal delivery (with muco-adhesive nature)

| Ingredient(s) | Amount | % w/v |
|---|---|---|
| Dexmedetomidine hydrochloride | 180 μg (equivalent to dexmedetomidine) | 0.36% |
| Lactose monohydrate | 43.77 | 87.54% |
| Hypromellose (or) Hydroxy propyl cellulose (or) Polyethylene oxide (or) Xanthan gum (or) Sodium alginate | 5.0 mg | 10.0% |
| Sucralose | 0.05 mg | 0.1% |
| Magnesium Stearate | 0.5 mg | 1.0% |
| Talc | 0.5 mg | 1.0% |
| Tablet weight | 50.0 mg | 100% |

Manufacturing Process:
1. Dexmedetomidine hydrochloride, binder (hypromellose (or) hydroxy propyl cellulose (or) polyethylene oxide (or) xanthan gum (or) sodium alginate) and sucralose are dissolved or dispersed in water to prepare a solution or dispersion.
2. Remaining ingredients except magnesium stearate and talc are blended in a suitable mixer and sifted with the help of an appropriate sieve.
3. The blend obtained in step 2 is granulated using a suitable granulator.
4. Granules are dried in a suitable fluid bed dryer or other dryer and size appropriately in quadro-co-mill or multimill.
5. Granules are loaded into a suitable blender such as V-blender and lubricated with magnesium stearate and talc.
6. The lubricated blend obtained in step 5 is compressed into tablets of specific dimensions using appropriate tooling.

TABLE 52

Composition for Dexmedetomidine hydrochloride spray formulation for sublingual delivery

| Ingredients | Amount | % w/v |
|---|---|---|
| Dexmedetomidine hydrochloride | 180 μg (equivalent to dexmedetomidine) | 0.18% |

TABLE 52-continued

Composition for Dexmedetomidine hydrochloride spray formulation for sublingual delivery

| Ingredients | Amount | % w/v |
|---|---|---|
| N-Methylpyrrolidone (or) Propylene Glycol (or) Polyethylene glycol (or) Glycerine | 10 μL | 10% |
| Ethanol | 5 μL | 5% |
| Sucralose | 0.1 mg | 0.1% |
| Peppermint Oil | 1 μL | 1.0% |
| Purified water | q.s. 100 μL | q.s. 100% |

Manufacturing Process:
1. The polymer (N-methylpyrrolidone (or) propylene glycol (or) polyethylene glycol) or glycerine is dissolved or dispersed in a part of the total water quantity.
2. Dexmedetomidine hydrochloride is mixed with rest of the excipients and the solution or dispersion obtained in step 1.
3. The final volume is made with water in a suitable vessel.
4. The resultant solution is filled into appropriate spray canisters using appropriate tooling such as metered nozzles.

TABLE 53

Composition for Dexmedetomidine hydrochloride drops formulation for sublingual delivery

| Ingredient(s) | Amount | % w/v |
|---|---|---|
| Dexmedetomidine hydrochloride | 180 μg (equivalent to dexmedetomidine) | 0.18% |
| Povidone or Hypromellose or Carbopol | 5 mg | 5.0% |
| N-Methylpyrrolidone (or) propylene glycol (or) polyethylene glycol (or) glycerine (or) ethanol | 10 μL | 10.0% |
| Sucralose | 0.1 mg | 0.1% |
| Peppermint oil | 1 μL | 1.0% |
| Purified water | q.s. 100 μL | q.s. 100% |

Manufacturing Process: Simple Mixing Process
1. The polymer (N-methylpyrrolidone (or) propylene glycol (or) polyethylene glycol) or Glycerine is dissolved or dispersed in a part of the total water quantity.
2. Dexmedetomidine hydrochloride is mixed with rest of the excipients and the solution or dispersion obtained in step 1.
3. The final volume is made with water in a suitable vessel.
4. The resultant solution is filled into appropriate pack or bottles.

TABLE 54

Composition for Dexmedetomidine hydrochloride gel formulation for sublingual delivery

| Ingredient(s) | Amount | % w/v |
|---|---|---|
| Dexmedetomidine | 180 μg | 0.18% |
| Carbopol or Hypromellose or HPC or CMC | 10 mg | 10.0% |

TABLE 54-continued

Composition for Dexmedetomidine hydrochloride gel formulation for sublingual delivery

| Ingredient(s) | Amount | % w/v |
| --- | --- | --- |
| N-Methylpyrrolidone (or) Propylene Glycol (or) Polyethylene glyol (or) Glycerine (or) Ethanol | 10 µL | 10.0% |
| Sucralose | 0.1 mg | 0.1% |
| Peppermint Oil | 1 µL | 1.0% |
| Purified water | q.s. 100 µL | q.s. 100% |

Manufacturing Process:
1. The polymer (N-methylpyrrolidone (or) propylene glycol (or) polyethylene glycol) or glycerine) is dissolved or dispersed in a part of the total water quantity.
2. Remaining ingredients are dissolved or dispersed in other part of the water.
3. Resultant solutions or dispersions of Step 1 and step 2 are mixed and final volume is made.
4. The resultant mixture of step 3 is packed into appropriate pack or containers

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

The invention claimed is:

1. A method of treating an agitation of a human subject in need thereof using an oromucosal formulation of dexmedetomidine or a pharmaceutically acceptable salt thereof, the method comprising:
administering a first dose of the oromucosal formulation of dexmedetomidine or a pharmaceutically acceptable salt thereof to the human subject, wherein the first dose is 60 mcg, 80 mcg, 90 mcg, 120 mcg, or 180 mcg of dexmedetomidine;
and, after at least two hours,
administering a second dose of the oromucosal formulation of dexmedetomidine or a pharmaceutically acceptable salt thereof to the human subject, and wherein the second dose is 40 mcg, 60 mcg, 80 mcg, 90 mcg, or 120 mcg of dexmedetomidine; and
wherein the human subject has a corrected QT interval using Fridericia's correction method (QTcF) of no greater than 450 msec for males and no greater than 470 msec for females.

2. The method of claim 1, wherein the initial dose is 60 mcg or 120 mcg.

3. The method of claim 1, wherein the second dose is 60 mcg or 120 mcg.

4. The method of claim 1, wherein the agitation is associated schizophrenia or bipolar disorders.

5. The method of claim 4, wherein the first dose is 120 mcg and the second dose is 120 mcg.

6. The method of claim 5, wherein the second dose is administered at least 4 hours after the first dose.

7. The method of claim 6, wherein the second dose is administered at least 6 hours after the first dose.

8. The method of claim 6, wherein the second dose is administered at least 8 hours after the first dose.

9. The method of claim 6, wherein the second dose is administered at least 10 hours after the first dose.

10. The method of claim 6, wherein the second dose is administered at least 12 hours after the first dose.

11. The method of claim 6, wherein the second dose is administered at least 14 hours after the first dose.

12. The method of claim 6, wherein the second dose is administered at least 16 hours after the first dose.

13. The method of claim 6, wherein the second dose is administered at least 18 hours after the first dose.

14. The method of claim 6, wherein the second dose is administered at least 20 hours after the first dose.

15. The method of claim 1, wherein the agitation is associated dementia.

16. The method of claim 15, wherein the first dose is 60 mcg and the second dose is 60 mcg.

17. The method of claim 16, wherein the second dose is administered at least 4 hours after the first dose.

18. The method of claim 17, wherein the second dose is administered at least 6 hours after the first dose.

19. The method of claim 17, wherein the second dose is administered at least 8 hours after the first dose.

20. The method of claim 17, wherein the second dose is administered at least 10 hours after the first dose.

21. The method of claim 17, wherein the second dose is administered at least 12 hours after the first dose.

22. The method of claim 17, wherein the second dose is administered at least 14 hours after the first dose.

23. The method of claim 17, wherein the second dose is administered at least 16 hours after the first dose.

24. The method of claim 17, wherein the second dose is administered at least 18 hours after the first dose.

25. The method of claim 17, wherein the second dose is administered at least 20 hours after the first dose.

* * * * *